US009388161B2

(12) United States Patent
Bair et al.

(10) Patent No.: US 9,388,161 B2
(45) Date of Patent: Jul. 12, 2016

(54) TETRAHYDROQUINOLINE COMPOSITIONS AS BET BROMODOMAIN INHIBITORS

(71) Applicant: Forma Therapeutics, Inc., Watertown, MA (US)

(72) Inventors: Kenneth W. Bair, Wellesley, MA (US); Torsten Herbertz, Stow, MA (US); Goss S. Kauffman, Ledyard, CT (US); Katherine J. Kayser-Bricker, Branford, CT (US); George P. Luke, Clinton, CT (US); Matthew W. Martin, Arlington, MA (US); David S. Millan, Watertown, MA (US); Shawn E. R. Schiller, Haverhill, MA (US); Adam C. Talbot, Guilford, CT (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 14/546,775

(22) Filed: Nov. 18, 2014

(65) Prior Publication Data

US 2015/0232445 A1 Aug. 20, 2015

Related U.S. Application Data

(60) Provisional application No. 62/054,811, filed on Sep. 24, 2014, provisional application No. 61/905,639, filed on Nov. 18, 2013.

(51) Int. Cl.
| | |
|---|---|
| *C07D 401/14* | (2006.01) |
| *A61K 31/4709* | (2006.01) |
| *C07D 401/04* | (2006.01) |
| *A61K 31/5377* | (2006.01) |
| *A61K 31/517* | (2006.01) |
| *C07D 487/04* | (2006.01) |
| *A61K 31/519* | (2006.01) |
| *A61K 45/06* | (2006.01) |

(52) U.S. Cl.
CPC .......... *C07D 401/04* (2013.01); *A61K 31/4709* (2013.01); *A61K 31/517* (2013.01); *A61K 31/519* (2013.01); *A61K 31/5377* (2013.01); *A61K 45/06* (2013.01); *C07D 401/14* (2013.01); *C07D 487/04* (2013.01)

(58) Field of Classification Search
CPC .. C07D 401/04; C07D 401/14; C07D 487/04; A61K 31/4709; A61K 31/5377; A61K 31/517; A61K 31/519; A61K 45/06
See application file for complete search history.

(56) References Cited

U.S. PATENT DOCUMENTS

| | | |
|---|---|---|
| 4,574,124 A | 3/1986 | Kabbe et al. |
| 5,063,230 A | 11/1991 | Pelletier et al. |
| 5,281,659 A | 1/1994 | Weaver et al. |
| 5,446,040 A | 8/1995 | Walter |
| 5,502,025 A | 3/1996 | Bussler |
| 5,530,021 A | 6/1996 | Yanagi et al. |
| 5,646,140 A | 7/1997 | Sugg et al. |
| 5,696,133 A | 12/1997 | Jones et al. |
| 5,739,129 A | 4/1998 | Aquino et al. |
| 5,780,464 A | 7/1998 | Sugg |
| 5,801,179 A | 9/1998 | Van Lommen et al. |
| 5,817,833 A | 10/1998 | Gaster |
| 5,889,022 A | 3/1999 | Gaster et al. |
| 5,910,495 A | 6/1999 | Hanley |
| 5,932,573 A | 8/1999 | Yuen |
| 6,048,873 A | 4/2000 | Vasudevan et al. |
| 6,262,074 B1 | 7/2001 | Otten et al. |
| 6,300,342 B1 | 10/2001 | Heckel et al. |
| 6,444,819 B1 | 9/2002 | Kover et al. |
| 6,479,436 B1 | 11/2002 | Otten et al. |
| 7,297,696 B2 | 11/2007 | Laborde et al. |
| 7,314,693 B2 | 1/2008 | Ikegami et al. |
| 7,442,693 B2 | 10/2008 | Szewczyk et al. |
| 7,446,103 B2 | 11/2008 | Best et al. |
| 7,741,317 B2 | 6/2010 | Chao et al. |
| 7,803,790 B2 | 9/2010 | Chong et al. |

(Continued)

FOREIGN PATENT DOCUMENTS

| | | |
|---|---|---|
| DE | 19838011 | 5/1999 |
| EP | 0198264 | 10/1986 |

(Continued)

OTHER PUBLICATIONS

Filippakopoulos, Nature Reviews: Drug Discovery, vol. 13, May 2014, 337-356.*
Berkovits, Curr TOp Dev Blol, 2013, 102:293-326.*
Muller, Expert Reviews in Molecular Medicine, vol. 13, e29, 1-21, Sep. 2011.*
Alsarraj et al., "Deletion of the Proline-Rich Region of the Murine Mesastasis Susceptability Gene Brd4 Promotes Epithelial-to-Mesenchymal Transition and Stem-Cell-Like Conversion" American Association for Cancer Research, pp. 3121-3122, Mar. 9, 2011.
Anand et al, BET Bromodomains Mediate Transcriptional Pause Release in Heart Failure Cell, Aug. 1, 2013; 154(3); 569-582.
Asangani, et al., "Therapeutic Targeting of BET Bromodomain Proteins in Castration-Resistant Prostate Cancer", Nature, Jun. 12, 2014; 510 (7504); 278-282.

(Continued)

*Primary Examiner* — D M Seaman
(74) *Attorney, Agent, or Firm* — Cooley LLP; J. Dean Farmer; Serge R. Banini

(57) ABSTRACT

The present invention relates to inhibitors of bromo and extra terminal (BET) bromodomains that are useful for the treatment of cancer, inflammatory diseases, diabetes, and obesity, having Formula I:

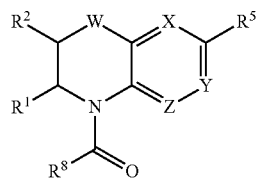

wherein W, X, Y, Z, $R^1$, $R^2$, $R^5$, and $R^8$ are as described herein.

44 Claims, No Drawings

(56) References Cited

U.S. PATENT DOCUMENTS

| | | | |
|---|---|---|---|
| 7,868,172 | B2 | 1/2011 | Schiemann et al. |
| 7,897,773 | B2 | 3/2011 | Aletru et al. |
| 7,902,236 | B2 | 3/2011 | Gomtsyan et al. |
| 7,928,238 | B2 | 4/2011 | Rano et al. |
| 7,947,834 | B2 | 5/2011 | Braun et al. |
| 7,972,987 | B2 | 7/2011 | Lee et al. |
| 8,017,601 | B2 | 9/2011 | Kim et al. |
| 8,022,294 | B2 | 9/2011 | Shigaki et al. |
| 8,101,662 | B2 | 1/2012 | Chandraratna |
| 8,288,377 | B2 | 10/2012 | Storck et al. |
| 8,357,717 | B2 | 1/2013 | Schunk et al. |
| 8,426,442 | B2 | 4/2013 | Hamlyn et al. |
| 8,476,308 | B2 | 7/2013 | Shi et al. |
| 8,536,221 | B2 | 9/2013 | Mortell et al. |
| 8,815,876 | B2 | 8/2014 | Neelamkavil et al. |
| 8,828,983 | B2 | 9/2014 | Quan et al. |
| 8,865,918 | B2 | 10/2014 | Zhi et al. |
| 8,895,050 | B2 | 11/2014 | Tachdjian et al. |
| 2007/0185055 | A1 | 8/2007 | Jiang et al. |
| 2008/0207588 | A1 | 8/2008 | Chu et al. |
| 2008/0319044 | A1 | 12/2008 | Didsbury et al. |
| 2009/0005344 | A1 | 1/2009 | Burns et al. |
| 2009/0036484 | A1 | 2/2009 | Bladh |
| 2009/0264384 | A1 | 10/2009 | Didsbury et al. |
| 2009/0324581 | A1 | 12/2009 | Machinaga et al. |
| 2010/0022515 | A1 | 1/2010 | Alper et al. |
| 2012/0022057 | A1 | 1/2012 | Zhou et al. |
| 2012/0165370 | A1 | 6/2012 | Tang et al. |
| 2014/0080788 | A1 | 3/2014 | Robl et al. |
| 2014/0142102 | A1 | 5/2014 | Fairfax et al. |

FOREIGN PATENT DOCUMENTS

| | | |
|---|---|---|
| EP | 0234036 | 9/1987 |
| EP | 0480902 | 4/1992 |
| EP | 0525111 | 6/1995 |
| EP | 0773929 | 6/1995 |
| HU | 9903186 | 2/2000 |
| IT | 1205963 | 4/1989 |
| JP | 03293673 | 12/1991 |
| JP | 2009114107 | 5/2009 |
| WO | WO 95/30675 | 11/1995 |
| WO | WO96/11940 | 4/1996 |
| WO | WO98/08818 | 3/1998 |
| WO | WO98/12192 | 3/1998 |
| WO | WO98/50346 | 11/1998 |
| WO | WO99/33798 | 8/1999 |
| WO | WO99/43670 | 9/1999 |
| WO | WO99/43672 | 9/1999 |
| WO | WO01/32610 | 5/2001 |
| WO | WO2004/072041 | 8/2004 |
| WO | WO2005/013949 | 2/2005 |
| WO | WO2005/066165 | 7/2005 |
| WO | WO2007/134169 | 11/2007 |
| WO | WO2008/032105 | 3/2008 |
| WO | WO2008/034650 | 3/2008 |
| WO | WO2009/087649 | 7/2009 |
| WO | WO2010/139967 | 12/2010 |
| WO | 2011/054843 * | 5/2011 |
| WO | 2011/054851 * | 5/2011 |
| WO | WO2012/137224 | 10/2012 |
| WO | WO2013/012723 | 1/2013 |
| WO | WO2013/036676 | 3/2013 |
| WO | WO2013/152687 | 10/2013 |
| WO | WO2013/184755 | 12/2013 |
| WO | WO2014/066435 | 5/2014 |

OTHER PUBLICATIONS

Baker et al., "BET Inhibitors induce apoptosis through a MYC independent mechanism and synergise with CDK inhibitors to kill osteosarcoma cells" Scientific Reports; pp. 1-14; May 6, 2015.

Bandopadhayay et al., "BET Bromodomain Inhibition of *MYC*-Amplified Medullblastoma" Clin Cancer Res; 20(4), pp. 912-925; Feb. 15, 2014.

Bandukwala et al., "Selective inhibition of CD4+ T-cell cytokine production and autoimmunity by BET protein and c-Myc inhibitors" 14532-14537 | PNAS | Sep. 4, 2012 | vol. 109 | No. 36.

Baratta et al., "An in-tumor genetic screen reveals that the BET bromodomain protein, BRD4, is a potential therapeutic target in ovarian carcinoma" PNAS | Jan. 6, 2015 | vol. 112 | No. 1 | 233.

Belkina et al., "Obesity genes and insulin resistance" Curr Opin Endocrinol Diabetes Obes. Oct. 2010; 17(5): 472-477.

Belkina et al., "BET Protein Function Is Required for Inflammation: Brd2 Genetic Disruption and BET Inhibitor JQ1 Impair Mouse Macrophage Inflammatory Response" *The Journal of Immunology*, 2013; 190:3670-3678.

Brown et al., NF-$^{K}$B Directs Dynamic Super Enhancer Formation in Inflammation and Atherogenesis Molecular Cell 56, 219-231, Oct. 23, 2014.

Boehm, et al., "BET bromodomain-targeting compounds reactivate HIV from latency via a Tat-independent mechanism" Cell Cycle 12:3, 452-462; Feb. 1, 2013.

Bolden, et al. "Inducible In Vivo Silencing of Brd4 Identifies Potential Toxicities of Sustained BET Protein Inhibition" *Cell Rep.* Sep. 25, 2014; 8(6): 1919-1929.

Ceribelli, et al., "Blockade of oncogenic IκB kinase activity in diffuse large B-cell lymphoma by bromodomain and extraterminal domain protein inhibitors" PNAS | Aug. 5, 2014 | vol. 111 | No. 31 | 11365-11370.

Chan et al., "BET bromodomain inhibition suppresses transcriptional responses to cytokine-Jak-STAT signaling in a gene-specific manner in human monocytes" Eur. J. Immunol. 2015. 45: 287-297.

Chang et al., "Phosphorylation of HPV-16 E2 at Serine 243 Enables Binding to Brd4 and Mitotic Chromosomes" PLOS ONE Oct. 2014 | vol. 9 | Issue 10.

Cheng et al., "Inhibition of BET Bromodomain Targets Genetically Diverse" Clin Cancer Res; 19(7); pp. 1748- 1759; Apr. 1, 2013.

Clifford, et al., "CXCL8 histone H3 acetylation is dysfunctional in airway smooth muscle in asthma: regulation by BET" *Am J Physiol Lung Cell Mol Physiol* 308: L962-L972, 2015.

Dawson et al., "Inhibition of BET recruitment to chromatin as an effective treatment for MLL-fusion leukaemia" 2 0 1 1 | vol. 000 | Nature | 1.

Delmore et al., "BET Bromodonain Inhibition as a Therapeutic Strategy to Target c-Myc", Cell 146, 1-14, Sep. 16, 2011.

Denis, Gerald V., "Bromodomain Coactivators in Cancer, Obesity, Type 2 Diabetes and Inflammation" Discov Med. Dec. 2010; 10(55): 489-499.

Fernandez et al., "Transformation resistance in a preature aging disorder identifies a tumor-protective function of BRD4" *Cell Rep.* Oct. 9, 2014; 9(1): 248-260.

Filippakopoulos et al., "Selective inhibition of BET bromodomaine" Nature, vol. 468, pp. 1067-1073; Dec. 2010.

French et al., "BRD4 Bromodomain Gene Rearrangement in Aggressive Carcinoma with Translocation", *American Journal of Pathology*, vol. 159, No. 6, Dec. 2001.

French et al., "BRD-NUT oncoproteins: a family of closely related nuclear proteins that block epithelial differentiation and maintain the growth of carcinoma cells" Oncogene (2008) 27, 2237-2242.

Helfer et al., "The Cellular Bromodomain Protein Brd4 has Multiple Functions in E2-Mediated Papillomavirus Transcription Activation" *Viruses* 2014, 6, 3228-3249.

Henssen et al., "BET bromodomain protein inhibition is a therapeutic option for medulloblastoma" Oncotarget, Nov. 2013; vol. 4, No. 11; pp. 2080-2095.

Hu et al. ," BRD4 Inhibitor Inhibits Colorectal Cancer Growth and Metastasis" *Int. J. Mol. Sci.* 2015, 16, 1928-1948.

Jahagirdar et al., "A novel BET bromodomain inhibitor, RVX-208, shows reduction of atherosclerosis in hyperlipidemic ApoE deficient mice" Atherosclerosis 236 (2014) 91-100.

Jiang et al., "Synergistic Reactivation of Latent HIV Expression by Ingenol-3-Angelate, PEP005, Targeted NF-κB Signaling in Combination with JQ1 Induced p-TEFb Activation" PLOS Pathogens; Jul. 30, 2015, pp. 1-27.

Khan et al., "Brd4 Is Essential for IL-1β-Induced Inflammation in Human Airway Epithelial Cells" PLOS ONE, Apr. 2014 | vol. 9 | Issue 4.

(56) References Cited

OTHER PUBLICATIONS

Knoechel et al., "An epigenetic mechanism of resistance to targeted therapy in Tcell acute lymphoblastic leukemia" *Nat Genet.* Apr. 2014; 46(4): 364-370.
Lamoureux et al., "Abstract A50: Selective inhibition of BET bromodomains epigenetic signaling interferes with the bone-associated tumor vicious cycle" The Journal of Cancer Research (1916-1930), 2015.
Lenhart et al., "Sensitivity of Small-Cell Lung Cancer to BET Inhibition is Mediated by Regulation of *ASCL1* Gene Expression", American Association for Cancer Research, Aug. 7, 2015.
Lin et al., "The EBNA1 Protein of Epstein-Barr Virus Functionally Interacts with Brd4" Journal of Virology, Dec. 2008, p. 12009-12019, vol. 82, No. 24.
Lockwood et al., "Sensitivity of human lung adenocarcinoma cell lines to targeted inhibition of BET epigenetic signaling proteins" 19408-19413 | PNAS | November 20, 2012 | vol. 109 | No. 47.
Matzuk et al., "Small-Molecule Inhibition of BRDT for Male Contraception" Cell 150, 673-684, Aug. 17, 2012.
Mele et al., "BET bromodomain inhibition suppresses $T_H17$-mediated pathology"JEM, pp. 2181-2193, Oct. 7, 2013.
Meng et al., "BET Inhibitor JQ1 Blocks Inflammation and Bone Destruction" *J Dent Res* 93(7) 2014.
Mertz ert al.,"Targeting MYC dependence in cancer by inhibiting BET bromodomains" PNAS Early Edition, pp. 1-6, Cancer Research Center, Aug. 30, 2011.
Nicodeme et al., "Suppression of inflammation by a synthetic histone mimic" Nature, Vol, 468, Dec. 2010; pp. 1119-1123.
Pastori et al., "BET bromodomain proteins are required for glioblastoma cell proliferation" Epigenetics 9:4, 611-620; Apr. 2014.
Patel et al.,"BET Bromodomain Inhibition Triggers Apoptosis of NF1-Associated Malignant Peripheral Nerve Sheath Tumors through Bim Induction" Cell Reports 6, 81-92, Jan. 16, 2014.
Perry et al., "BET Bromodomains Regulate Transforming Growth Factor-β-induced Proliferation and Cytokine Release in Asthmatic Airway Smooth Muscle" J Biol Chem. Apr. 3, 2015; 290(14): 9111-9121.
Puissante et al., "Targeting MYCN in Neuroblastoma by BET Bromodomain Inhibition" American Association for Cancer Research, pp. 308-324, Feb. 21, 2013.
Segura et al., "BRD4 Sustains Melanoma Proliferation and Represents a New Target for Epigenetic Therapy" Cancer Res; 73(20) Oct. 15, 2013.
Sengupta et al., "Disruption of BRD4 at H3K27Ac-enriched enhancer region correlates with decreased c-Myc expression in Merkel cell carcinoma" Epigenetics 10:6, 460-466; Jun. 2015.
Shi et al., "Disrupting the Interaction of BRD4 with Diacetylated Twist Suppresses Tumorigenesis in Basal-like Breast Cancer" Cancer Cell 25, 210-225, Feb. 10, 2014.
Smith et al., "Genome-wide siRNA screen identifies SMCX, EP400,and Brd4 as E2-dependent regulators of human papillomavirus oncogene expression" PNAS; vol. 107, No. 8, pp. 3752-3757, Feb. 2010.
Sun et al., "BET bromodomain inhibition suppresses graft-versus-host disease after allogeneic bone marrow transplantation in mice" Blood. Apr. 23, 2015; 125(17): 2724-2728.
Sun et al., "Synergistic activity of BET protein antagonist-based combinations in Mantle Cell Lymphoma cells sensitive or resistant to ibrutinib" American Society of Hematology, pp. 1-28, Aug. 17, 2015.
Tang et al. ,"Assessment of Brd4 Inhibition in Idiopathic Pulmonary Fibrosis Lung Fibroblasts and in Vivo Models of Lung Fibrosis" The American Journal of Pathology, vol. 183, No. 2, Aug. 2013.
Tang et al., "Epigenetic targeting of Hedgehog pathway transcriptional output through BET bromodomain inhibition" *Nat Med.* Jul. 2014; 20(7): 732-740.
Tang et al., "Assessment of Brd4 Inhibition in Idiopathic Pulmonary Fibrosis Lung Fibroblasts and in Vivo Models of Lung Fibrosis" The American Journal of Pathology, vol. 183, No. 2, Aug. 2013.
Wang et al., "*Brd2* disruption in mice causes severe obesity without Type 2 Diabetes" *Biochem J.* ; 425(1): 71-83.
Wang et al. "*Brd2* gene disruption causes 'metabolically healthy' obesity: Epigenetic and chromatin-based mechanisms that uncouple obesity from Type 2 diabetes" *Vitam Horm.* 2013 ; 91: 49-75.
Wienerroither et al., "Regulation of NO Synthesis, Local Inflammation, and Innate Immunity to Pathogens by BET Family Proteins" Molecular and Cellular Biology p. 415-427, Feb. 2014, vol. 34, No. 3.
Wong et al., "The bromodomain and extra-terminal inhibitor CPI203 enhances the antiproliferative effects of rapamycin on human neuroendocrine tumors" Cell Death and Disease (2014) 5.
Wyce et al., "Inhibition of BET bromodomain proteins as a therapeutic approach in prostate cancer", Ontarget, Dec. 2013, vol. 4, No. 12.
Yan et al., "Brornodornain 4 protein is a predictor of survival for urothelial carcinoma of bladder" int J Clin Exp Pathol 2014;7(7):4231-4238.
Zhang et al., "Targeting bromodomain-containing protein 4 (BRD4) benefits rheumatoid arthritis" Immunology Letters 166 (2015) 103-108.
Zou et al., "Brd4 maintains constitutively active NF-κB in cancer cells by binding to acetylated RelA", *Oncogene.* May 1, 2014; 33(18): 2395-2404.
Zuber et al., "RNAi screen identifies Brd4 as a therapeutic target in acute myeloid leukaemia", Nature, vol. 000, pp. 1-7, 2011.

\* cited by examiner

TETRAHYDROQUINOLINE COMPOSITIONS AS BET BROMODOMAIN INHIBITORS

RELATED APPLICATIONS

This application claims the benefit of, and priority to, U.S. Provisional Patent Application No. 61/905,639 filed on Nov. 18, 2013 and U.S. Provisional Patent Application No. 62/054,811 filed on Sep. 24, 2014. The entire contents of which are hereby incorporated by reference in their entirety.

FIELD OF THE INVENTION

The present invention is directed to inhibitors of the bromo and extra terminal (BET) family of bromodomains useful in the treatment of disease or disorders associated with the modulation of the bromo and extra terminal (BET) family of bromodomains. Specifically, the invention is concerned with compounds and compositions for inhibition of the bromo and extra terminal (BET) family of bromodomains, methods of treating, preventing, or ameliorating diseases or disorders associated with the inhibition of bromo and extra terminal (BET) family of bromodomains, and methods of synthesis of these compounds.

BACKGROUND OF THE INVENTION

The bromo and extra terminal (BET) family proteins contain four members in mammals, BRD2, BRD3, BRD4, and BRDT, with each of these containing two bromodomains (BRD): a conserved N-terminal bromodomain (bromodomain 1 [BD1]) and a C-terminal bromodomain (bromodomain 2 [BD2]). BET family proteins have been shown to have a critical role in cellular proliferation and cell cycle progression.

Bromodomain containing proteins are known to be involved in transcriptional regulation. In general, bromodomains are found in proteins that regulate chromatin structure and gene expression. The presence of these proteins is required for the systematic expression of various growth and antiapoptotic genes. Additionally, these proteins play a role in the omnipresent cell cycle progression, as many nuclear proteins have bromodomains that interact with chromatin such as histone acetyltransferases. Dysfunction of bromodomain containing proteins has been linked to the development of a number of diseases, particularly to the development of cancer. (Muller, S. Filippakopoulos, P. Knapp, S. (2011), Bromodomains as therapeutic targets. *Expert Rev. Mol. Med.* 13: e29). Bromodomains have also been implicated in inflammatory processes (Nicodeme et al, *Nature,* 2010, Vol. 468, pg. 1119).

BRD4 protein, as a gene product, contains 1362 amino acids. BRD4 BD1 is ~75-147; BRD4 BD2 is ~368-440; thus each is 73 residues long. For the purpose of biochemical screening, biophysics or X-ray crystallography, various protein constructs with additional N- and C-terminal residues added for both bromodomains are expressed and used. In addition, protein constructs with both bromodomains expressed within the same protein have also been used (~400 aa residues total).

The protein is comprised of four alpha helices, all left hand oriented, which is in stark contrast to the highly diverse sequential nature of the proteins. The helices ($\alpha_Z$, $\alpha_A$, $\alpha_C$, and $\alpha_B$) are arranged in such a way that the Z and A helices interact forming the long "ZA loop" and the C and B helices interact forming the short "BC loop." (Dhalluin C., Carlson J. E., Zeng L., He C., Aggarwal A. K., Zhou M. M. (1999), Structure and ligand of a histone acetyltransferase bromodomain. *Nature.* 399, 491-6.). These loops form hydrophobic pockets in the protein where the protein interacts with acetylated lysine residues. Mutagenesis studies suggest that tertiary contacts amongst the hydrophobic and aromatic residues between the two inter-helical loops contribute directly to the structural stability of the protein. ((Dhalluin C., Carlson J. E., Zeng L., He C., Aggarwal A. K., Zhou M. M. (1999), Structure and ligand of a histone acetyltransferase bromodomain. *Nature.* 399, 491-6.).

It has long been suggested that bromodomains play an important role on chromatin remodeling. In recent years, certain proteins of the double bromodomain family, including BRD2, BRD3, BRD4, and BRDT have been identified as major epigenetic regulators in human cancer. As such, these double bromodomains appear to play a particularly vital role in human cancer proliferation and differentiation. For example, BRD4 affects the breast cancer microenvironment and survival rates. (Crawford, N. P, Alsarraj, J., Lukes, L., Walker, R. C., Officewala, J. S., Yang, H. H., Lee, M. P., Ozato, K., Hunter, K. W. (2008), Bromodomain 4 Activation Predicts Breast Cancer Survival. *Proc. Natl. Acad. Sci. USA.* 105(17): 6380-6385.). BRD4 also plays a role in Kaposi's sarcoma and BRD2 factors in to some mixed lineage leukemias. (Guo, N., Faller, D. V., Denis, G. V., Activation-Induced Nuclear Translocation of RING3 (2001), *J. Cell Sci.* 113(17): 3085-3091.). In addition, genetic knockdown by RNAi or exposure of cells to BET inhibitors has resulted in significant transcriptional downregulation of MYC, a mutated version of which is found in many cancers. (Delmore J. E., Issa G. C., Lemieux M. E., Rahl, P. B., Shi J., Jacobs H. M. (2011), BET Bromodomain Inhibition as a Therapeutic Strategy to Target c-Myc. *Cell.* 146: 904-17.). Thus, inhibition of these interactions and exposure of cells to BET inhibitors results in a significant transcriptional downregulation. This, in turn, provides the medical community with a novel pharmacological strategy for the treatment of cancer.

The highly differentiated sequential nature of bromodomains has remained a severe obstacle in the discovery of potent and efficacious bromodomain inhibitors. (Dawson, M. A, Prinjha, R. K., Dittman, A. Giotopoulos, G. Bantcheff, M., Chan, W-I., Robson, S. C., Chung, C., Hopf, C., Savitski, M. M., Hutmacher, C., Gudgin, E., Lugo, D., Beinke, S., Chapman. T. D., Roberts, E. J., Soden. P. E., Auger, K. R., Mirguet, O., Doehner, K., Delwel, R., Burnett, A. K., Jeffrey, P., Drewes, G., Lee, K., Huntly, B. J. P. and Kouzarides, T. (2011), Inhibition of BET recruitment of chromatin as an effective treatment of MLL-fusion leukemia. *Nature.* 0: 1-5; Picaud, S., Da Costa, D. Thanasopoulou, A., Filippakopoulos, P., Fish, P., Philpott, M., Federov, O. Brennan, P., Bunnage, M. E., Owen, D. R., Bradner, J. E., Taniere, P., O'Sullivan, B., Muller, S, Schwaller, J., Stankovic, T., Knapp, S., PFI-1—A highly Selective Protein Interaction Inhibitor Targeting BET Bromodomains, *Cancer Res.,* 73(11), 2013, 3336-3346). As a result, there are currently no approved bromodomain inhibitors available on the market despite their well-recognized potential as anti-cancer therapeutic agents. For these reasons, there remains a considerable need for novel and potent small molecule modulators of BET bromodomains.

SUMMARY OF THE INVENTION

One aspect of the present invention relates to compounds of Formula I:

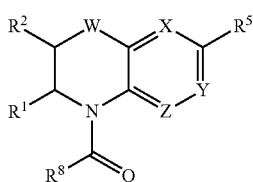

(I)

and pharmaceutically acceptable salts, enantiomers, hydrates, solvates, prodrugs, isomers, and tautomers thereof, wherein:

W is O, S, C(O), or $CHR^3$;
X is N or $CR^4$;
Y is N or $CR^6$;
Z is N or $CR^7$;
$R^1$ is hydrogen, $C_1$-$C_6$ alkyl, or $C_1$-$C_6$ haloalkyl;
$R^2$ is hydrogen or $NR^aR^b$;
$R^3$ is hydrogen, halogen, hydroxyl, $C_1$-$C_6$ alkyl, or $C_1$-$C_6$ haloalkyl;
$R^4$ is hydrogen, —$(CH_2)_nR^d$, —$O(CH_2)_nR^d$, —$N(CH_2)_nR^d$, —$O(CH_2)_nC(O)R^d$, or —$O(CH_2)_nS(O)_2R^d$;
$R^5$ and $R^6$ are each independently hydrogen, halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, heterocycloalkyl, cycloalkenyl, heterocycloalkenyl, aryl, heteroaryl, —$(C_1$-$C_6)$-alkylene-aryl, —$(C_1$-$C_6)$-alkylene-heteroaryl, —$(C_1$-$C_6)$-alkylene-heterocycloalkyl, —$(CR^aR^b)_nOR^c$, —$(CR^aR^b)_nR^c$, —$O(CR^aR^b)_nNR^aR^b$, —$NR^aR^b$, —$NR^aC(O)R^b$, —$NR^aS(O)_2R^b$, or $R^c$, wherein said alkyl, alkenyl, alkynyl, cycloalkyl, heterocycloalkyl, cycloalkenyl, heterocycloalkenyl, aryl, and heteroaryl are optionally substituted with one or more substituents independently selected from $R^a$, $R^b$, and $R^e$;
$R^7$ is hydrogen or halogen;
$R^8$ is $R^a$, —$OR^a$, —$NR^a$, or heterocycloalkyl;
$R^a$ and $R^b$ are each independently hydrogen, halogen, $C_1$-$C_6$ alkyl, cycloalkyl, or heterocycloalkyl, wherein $C_1$-$C_6$ alkyl, cycloalkyl, or heterocycloalkyl is optionally substituted with one or more $R^e$;
$R^c$ is —$NH_2$, OH, —$NH(C_1$-$C_6$ alkyl), —$O(CH_2)_nNR^aR^b$, —$NH(C_1$-$C_6$ alkoxy), —$(CH_2)_nR^a$, —$(CH_2)_nOR^a$, —$C(O)R^a$, —$C(O)OR^a$, —$C(O)NR^aR^b$, —$(CH_2)_nS(O)_2CH_3$, —$S(O)_2R^a$, —$S(O)_2NR^aR^b$, —$NR^a$—$S(O)_2R^b$, —$NHC(O)R^a$, $C_1$-$C_6$ alkyl, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, aryl, heteroaryl, cycloalkyl, heterocycloalkyl, halo, cyano, or oxo, wherein $C_1$-$C_6$ alkyl, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, aryl, heteroaryl, cycloalkyl, and heterocycloalkyl are optionally substituted with one or more $R^e$;
or two adjacent $R^c$ can combine with the carbons to which they are attached to form a carbocycle or heterocycle;
$R^d$ is hydrogen, $NH(C_1$-$C_6$ alkyl), $N(C_1$-$C_6$ alkyl)$_2$, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^e$;

$R^e$ is hydrogen, halogen, OH, $C_1$-$C_6$ alkyl, cycloalkyl, heterocycloalkyl, oxo, $C_1$-$C_6$ haloalkyl, $C_1$-$C_6$ haloalkoxy, $C_1$-$C_6$ alkoxy, or $S(O)_2(C_1$-$C_6$ alkyl); and
n is 0, 1, or 2.

Another aspect of the present invention relates to a pharmaceutical composition comprising a compound of Formula I, or a pharmaceutically acceptable salt, enantiomer, hydrate, solvate, prodrug, isomer, or tautomer thereof and a pharmaceutically acceptable carrier.

In another aspect, the present invention relates to a method of modulating one or more of BET-family bromodomains. The method comprises administering to a patient in need thereof a therapeutically effective amount of a compound of Formula I, or a pharmaceutically acceptable salt, enantiomer, hydrate, solvate, prodrug, isomer, or tautomer thereof Another aspect of the present invention relates to a method of inhibiting one or more of BET-family bromodomains. The method comprises administering to a patient in need thereof a therapeutically effective amount of a compound of Formula I, or a pharmaceutically acceptable salt, enantiomer, hydrate, solvate, prodrug, isomer, or tautomer thereof In another aspect, the present invention relates to a method of inhibiting one or more of BET-family bromodomains. The method comprises administering to a patient in need thereof a therapeutically effective amount of a pharmaceutical composition of Formula I.

Another aspect of the present invention relates to a method of treating, preventing, inhibiting, or eliminating a disease or disorder in a patient associated with the inhibition of one or more of BET-family bromodomains. The method comprises administering to a patient in need thereof a therapeutically effective amount of a compound of Formula I herein described, wherein the disease or disorder is selected from the group consisting of cancer, inflammatory disorders, irritable bowel syndrome, inflammatory bowel disease, rheumatoid arthritis, obesity and diabetes.

In another aspect, the present invention relates to a male contraceptive comprising a therapeutically effective amount of a compound of Formula I herein described.

The present invention provides inhibitors of BET domains that are therapeutic agents in the treatment of diseases such as cancer, inflammation, metabolic and neurological disorders, and infectious diseases.

DETAILED DESCRIPTION OF THE INVENTION

The present invention relates to compounds and compositions that are capable of modulating the activity the BET family bromodomains, e.g., BRD2, BRD3, BRD4, and BRDT bromodomains. The invention features methods of treating, preventing or ameliorating a disease or disorder associated with BET bromodomains by administering to a patient in need thereof a therapeutically effective amount of a compound of Formula (I), (II), (III), or (IV), or a pharmaceutically acceptable salt, enantiomer, hydrate, solvate, prodrug, isomer, or tautomer thereof. The methods of the present invention can be used in the treatment of a variety of BET bromodomain dependent diseases and disorders by inhibiting the activity of a BET bromodomains Inhibition of BET bromodomains provides a novel approach to the treatment, prevention, or amelioration of diseases including, but not limited to, cancer, inflammatory diseases, diabetes and obesity, and developing male contraceptives.

One aspect of the present invention relates to compounds of Formula I

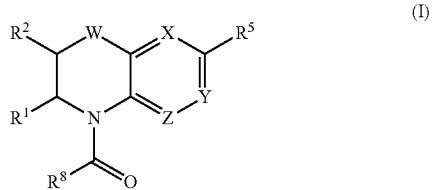

and pharmaceutically acceptable salts, enantiomers, hydrates, solvates, prodrugs, isomers, or tautomers thereof, wherein W, X, Y, Z, $R^1$, $R^2$, $R^3$, $R^4$, $R^5$, $R^6$, $R^7$, $R^8$, $R^a$, $R^b$, $R^c$, $R^d$, $R^e$ and n are as described above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

As used above, and throughout this disclosure, the following terms, unless otherwise indicated, shall be understood to have the following meanings. If a definition is missing, the conventional definition as known to one skilled in the art controls.

As used herein, the terms "including," "containing," and "comprising" are used in their open, non-limiting sense.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently A "patient" is a mammal, e.g., a human, mouse, rat, guinea pig, dog, cat, horse, cow, pig, or non-human primate, such as a monkey, chimpanzee, baboon or rhesus. "Patient" includes both human and animals.

The term "inhibitor" refers to a molecule such as a compound, a drug, enzyme, or a hormone that blocks or otherwise interferes with a particular biologic activity.

The term "bromodomain inhibitor" denotes a compound which inhibits binding of a bromodomain with its cognate acetylated proteins. In one embodiment the bromodomain inhibitor is a compound which inhibits the binding of any one or a combination of bromodomains to acetylated lysine residues. In a further embodiment the bromodomain inhibitor is a compound which inhibits the binding of a bromodomain to acetylated lysine residues on histones, particularly histones H3 and H4.

The term "BET family bromodomain inhibitor" or "inhibitor of bromodomain of the BET family proteins" means a compound that inhibits binding of BET (bromo and extra terminal) bromodomains BRD2 BD1, BRD2 BD2, BRD3 BD1, BRD3 BD2, BRD4 BD1, BRD4 BD2, BRDT BD1, or BRDT BD2. In one embodiment BET family bromodomain inhibitors are compounds according to Formulas I-IV. According to another embodiment, BET family bromodomain inhibitors are compounds selected from Table 1.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects. In the present case the active substance is the inhibitor of the bromodomains of the BET proteins.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" is used in this disclosure to mean, and is used interchangeably with, the terms disease, condition, or illness, unless otherwise indicated.

By using the terms "pharmaceutically acceptable" or "pharmacologically acceptable" it is intended to mean a material which is not biologically, or otherwise, undesirable—the material may be administered to an individual without causing any substantially undesirable biological effects or interacting in a deleterious manner with any of the components of the composition in which it is contained.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

The present invention also includes "prodrugs" of compounds of the invention. The term "prodrug" means a compound which is convertible in vivo by metabolic means (e.g., by hydrolysis) to a disclosed compound or active ingredient. Prodrugs can be prepared by techniques known to one skilled in the art. These techniques generally modify appropriate functional, e.g., a hydroxy, amino, carboxylic, etc., groups in a given compound. These modified functional groups, however, regenerate original functional groups by routine manipulation or in vivo. Examples of prodrugs include, but are not limited to esters (e.g., acetate, formate, and benzoate derivatives), carbamates (e.g., N,N-dimethylaminocarbonyl) of hydroxy or amino functional groups in compounds of the invention, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present invention may be delivered in prodrug form. Prodrugs, for instance, may be bioavailable by oral administration even when the parent drug is not. Thus, the present invention is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

The terms "administered", "administration", or "administering" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, or branched. As used herein, "lower alkyl" means an alkyl having from 1 to 6 carbon atoms.

As used herein, an "alkenyl" includes an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" includes an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As defined herein, an alkylene may also be a $C_1$-$C_6$ alkylene. An alkylene may further be a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The terms "trifluoromethyl", "sulfonyl", and "carboxyl" refers to $CF_3$, $S(O)_2$, and $C(O)OH$, respectively.

The term "hydroxyl" or "hydroxy" means an OH group;

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—$CH(OH)$—.

The term "alkoxy" as used herein refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Aralkyl" or "arylalkyl" means an a $C_1$-$C_6$ alkyl group, as defined herein above, substituted with an aryl ring containing from 3 to 24 ring atoms per ring. For example, arylalkyl groups herein described can have the following formula

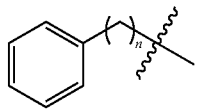

where n is an integer from 1 to 6. Non-limiting examples of suitable aralkyl groups include benzyl, 2-phenethyl and naphthalenylmethyl. The bond to the parent moiety is through the alkyl.

"Cycloalkylalkyl" means monocyclic saturated carbon rings containing 3-18 carbon atoms further substituted with $C_1$-$C_6$ alkyl groups. In general cycloalkylalkyl groups herein described display the following formula

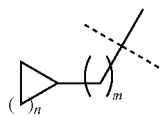

where m is an integer from 1 to 6 and n is an integer from 1 to 16.

"Heterocycloalkyl-alkyl" means an a $C_1$-$C_6$ alkyl group, as defined herein above, substituted with an heterocycloalkyl ring containing from 3 to 24 ring atoms per ring. For example, an heterocycloalkyl-alkyl group can have the following structure

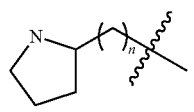

where n is an integer from 1 to 6. The bond to the parent moiety is through the alkyl.

"Heteroaryl alkyl" means an a $C_1$-$C_6$ alkyl group, as defined herein above, substituted with a heteroaryl ring containing from 5 to 24 ring atoms per ring. For example, a heteroarylalkyl group can have the following structure

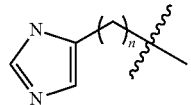

where n is an integer from 1 to 6. The bond to the parent moiety is through the alkyl.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "amino" as used herein means a substituent containing at least one nitrogen atom. Specifically, $NH_2$, —NH (alkyl) or alkylamino, —N(alkyl)$_2$ or dialkylamino, amide-, carbamide-, urea, and sulfamide substituents are included in the term "amino".

The term "(amino)alkoxy" or "aminoalkoxy" as used herein means an alkoxy group, as defined herein above, where the straight or branched chain saturated hydrocarbon of the alkoxy is substituted with one or more amino groups.

The term "aminoalkyl" or "amino(alkyl)" as used herein refers to an alkyl group, as defined herein, which is substituted one or more times with one or more amino groups.

The term "alkylamino" as used herein refers to an amino or NH2 group where one of the hydrogens has been replaced with an alkyl group, as defined herein above, i.e., —NH-alkyl. Example of alkylamino groups include, but are not limited to, methylamino (i.e., —$NHCH_3$), ethylamino, propylamino, iso-propylamino, n-butylamino, sec-butylamino, and tert-butylamino.

The term "dialkylamino" as used herein refers to an amino or $NH_2$ group where both of the hydrogens have been replaced with alkyl groups, as defined herein above, i.e., —N(alkyl)$_2$. The alkyl groups on the amino group can be the same ore different alkyl groups. Example of alkylamino groups include, but are not limited to, dimethylamino (i.e., —N($CH_3$)$_2$), diethylamino, dipropylamino, diiso-propylamino, di-n-butylamino, di-sec-butylamino, di-tert-butylamino, methyl(ethyl)amino, methyl(butylamino), etc.

The term "aryloxy" refers to an aryl ring as defined herein containing a terminal "O", i.e., Ar—O—, where Ar is aryl. Examples of aryloxy groups include, without limitation, phenoxy, biphenoxy, and naphtyloxy.

The term "methylenedioxy" as used herein means a functional group with the structural formula —O—$CH_2$—O— which is connected to the molecule by two chemical bonds via the oxygens.

As used herein, "alkoxyalkyl" means an alkyl group as defined herein further substituted with one or more alkoxy groups as defined herein, i.e., alkyl-O-alkyl-.

The term "(alkoxyalkyl)amino" as used herein means an amino group substituent having at least one alkoxyalkyl group as defined above and at least one amino group as defined above.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 18 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring.

As used herein, the term "cycloalkyl" refers to a saturated or partially saturated, monocyclic, fused or spiro polycyclic, carbocycle having from 3 to 18 carbon atoms per ring. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof As used herein, the term "heterocycloalkyl" refers to a saturated or partially saturated monocyclic, or fused or spiro, polycyclic, ring structure containing carbon and heteroatoms taken from oxygen, nitrogen, or sulfur and wherein there is not delocalized π-electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, homotropanyl, dihydrothiophen-2(3H)-onyl, tetrahydrothiophene 1,1-dioxide, 2,5-dihydro-1H-pyrrolyl, imidazolidin-2-one, pyrrolidin-2-one, dihydrofuran-2(3H)-one, 1,3-dioxolan-2-one, isothiazolidine 1,1-dioxide, 4,5-dihydro-1H-imidazolyl, 4,5-dihydrooxazolyl, oxiranyl, pyrazolidinyl, 4H-1,4-thiazinyl, thiomorpholinyl, 1,2,3,4-tetrahydropyridinyl, 1,2,3,4-tetrahydropyrazinyl, 1,3-oxazinan-2-one, tetrahydro-2H-thiopyran 1,1-dioxide, 7-oxabicyclo[2.2.1]heptanyl, 1,2-thiazepane 1,1-dioxide, octahydro-2H-quinolizinyl, 1,3-diazabicyclo[2.2.2]octanyl, 2,3-dihydrobenzo[b][1,4]dioxine, 3-azabicyclo[3.2.1]octanyl, 8-azaspiro[4.5]decane, 8-oxa-3-azabicyclo[3.2.1]octanyl, 2-azabicyclo[2.2.1]heptane, 2,8-diazaspiro[5.5]undecanyl, 2-azaspiro[5.5]undecanyl, 3-azaspiro[5.5]undecanyl, decahydroisoquinolinyl, 1-oxa-8-azaspiro[4.5]decanyl, 8-azabicyclo[3.2.1]octanyl, 1,4'-bipiperidinyl, azepanyl, 8-oxa-3-azabicyclo[3.2.1]octanyl, 3,4-dihydro-2H-benzo[b][1,4]oxazinyl, 5,6,7,8-tetrahydroimidazo[1,2-a]pyridinyl, 1,4-diazepanyl, phenoxathiinyl, benzo[d][1,3]dioxolyl, 2,3-dihydrobenzofuranyl, 2,3-dihydrobenzo[b][1,4]dioxinyl, 4-(piperidin-4-yl)morpholinyl, 3-azaspiro[5.5]undecanyl, decahydroquinolinyl, piperazin-2-one, 1-(pyrrolidin-2-ylmethyl)pyrrolidinyl, 1,3'-bipyrrolidinyl, and 6,7,8,9-tetrahydro-1H,5H-pyrazolo[1,2-a][1,2]diazepinyl.

Numerical ranges, as used herein, are intended to include sequential integers. For example, a range expressed as "from 0 to 4" would include 0, 1, 2, 3 and 4.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, oxo, -halogen, $C_1$-$C_6$ alkyl, $C_1$-$C_6$ alkoxy, $C_1$-$C_6$ haloalkyl, $C_1$-$C_6$ haloalkoxy, —O$C_1$-$C_6$ alkenyl, —O$C_1$-$C_6$ alkynyl, —$C_1$-$C_6$ alkenyl, —$C_1$-$C_6$ alkynyl, —OH, CN (cyano), —CH$_2$CN, —OP(O)(OH)$_2$, —C(O)OH, —OC(O)$C_1$-$C_6$ alkyl, —C(O)$C_1$-$C_6$ alkyl, —C(O)—$C_0$-$C_6$ alkylenyl-cycloalkyl, —C(O)—$C_0$-$C_6$ alkylenyl-heterocycloalkyl, —C(O)—$C_0$-$C_6$ alkylenyl-aryl, —C(O)—$C_0$-$C_6$ alkylenyl-heteroaryl, —OC(O)O$C_1$-$C_6$ alkyl, —NH$_2$, —NH($C_1$-$C_6$ alkyl), N($C_1$-$C_6$ alkyl)$_2$, —C(O)NH$_2$, —C(O)NH($C_1$-$C_6$ alkyl), —C(O)N($C_1$-$C_6$ alkyl)$_2$, —C(O)NH cycloalkyl, —C(O)N($C_1$-$C_6$ alkyl)cyclo alkyl, —C(O)NHheterocycloalkyl, —C(O)N($C_1$-$C_6$ alkyl)heterocycloalkyl, —C(O)NHaryl, —C(O)N($C_1$-$C_6$ alkyl)aryl, —C(O)NHheteroaryl, —C(O)N($C_1$-$C_6$ alkyl)heteroaryl, —S(O)$_2$—$C_1$-$C_6$ alkyl, —S(O)$_2$—$C_1$-$C_6$ haloalkyl, —S(O)$_2$-cycloalkyl, —S(O)$_2$-heterocycloalkyl, —S(O)$_2$-aryl, —S(O)$_2$-heteroaryl-$C_0$-$C_6$ alkylenyl-S(O)$_2$NH$_2$, —S(O)$_2$NH$C_1$-$C_6$ alkyl, —S(O)$_2$N($C_1$-$C_6$ alkyl)$_2$, —S(O)$_2$NHcycloalkyl, —S(O)$_2$NHheterocycloalkyl, —S(O)$_2$NHaryl, —S(O)$_2$NHhetereoaryl, —NHS(O)$_2$$C_1$-$C_6$ alkyl, —N($C_1$-$C_6$ alkyl)S(O)$_2$($C_1$-$C_6$ alkyl), —NHS(O)$_2$aryl, —N($C_1$-$C_6$ alkyl)S(O)$_2$ aryl, —NHS(O)$_2$ heteroaryl, —N($C_1$-$C_6$ alkyl)S(O)$_2$ heteroaryl, —NHS(O)$_2$ cycloalkyl, —N($C_1$-$C_6$ alkyl)S(O)$_2$ cycloalkyl, —NHS(O)$_2$ heterocycloalkyl, —N($C_1$-$C_6$ alkyl)S(O)$_2$ heterocycloalkyl, —N($C_1$-$C_6$ alkyl)S(O)$_2$ aryl, —$C_0$-$C_6$ alkylenyl-aryl, —$C_0$-$C_6$ alkylenyl-heteroaryl, —$C_0$-$C_6$ alkylenyl-cycloalkyl, —$C_0$-$C_6$ alkylenyl-heterocycloalkyl, —O-aryl, —NH-aryl, and N($C_1$-$C_6$ alkyl)aryl. The substituents can themselves be optionally substituted. When a multifunctional moiety is shown, the point of attachment to the core is indicated by a line, e.g., (cycloalkyloxy)alkyl-refers to alkyl being the point of attachment to the core while cycloalkyl is attached to alkyl via the oxy group. "Optionally substituted" also refers to "substituted" or "unsubstituted", with the meanings described above.

The term "oxy" as used herein refers to an "—O—" group.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I), (II), (III), or (IV) may have one or more asymmetric carbon atoms and may occur as racemates, racemic mixtures and as individual enantiomers or diastereomers.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

In another embodiment of the invention, the compounds of Formulae (I)-(IV) are enantiomers. In some embodiments the compounds are the (S)-enantiomer. In other embodiments the compounds are the (R)-enantiomer. In yet other embodiments, the compounds of Formula (I), (II), (III), or (IV) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the various Formulae, and salts, solvates, esters and prodrugs thereof, may exist in their tautomeric form (for example, as an amide or imino ether). All such tautomeric forms are contemplated herein as part of the present invention.

The compounds of the various Formulae may contain asymmetric or chiral centers, and, therefore, exist in different stereoisomeric forms. It is intended that all stereoisomeric forms of the compounds of the various Formulae as well as mixtures thereof, including racemic mixtures, form part of the present invention. In addition, the present invention embraces all geometric and positional isomers. For example, if a compound of the various Formulae incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulae may be atropisomers (e.g., substituted biaryls) and are considered as part of this invention. Enantiomers can also be separated by use of a chiral HPLC column.

It is also possible that the compounds of the various Formulae may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulae incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H (or D), $^3$H, $^{13}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the various Formulae (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

The compounds of Formulae I to IV may form salts which are also within the scope of this invention. Reference to a compound of the Formula herein is understood to include reference to salts thereof, unless otherwise indicated.

The present invention relates to compounds which are modulators of one or more bromodomains of the BET family. In one embodiment, the compounds of the present invention are inhibitors of one or more bromodomains of the BET family.

The invention is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof Compounds of the Invention The present invention relates to compounds, or pharmaceutically acceptable salts or isomers thereof, capable of modulating BET family bromodomains, including BRD2, BRD3, BRD4 and BRDT, which are useful for the treatment of diseases and disorders associated with modulation of BET family bromodomains. The invention further relates to compounds, or pharmaceutically acceptable salts or isomers thereof, which are useful for inhibiting BET family bromodomains.

Another aspect of the present invention is the provision of pharmaceutical compositions comprising therapeutically effective amounts of at least one compound of Formula I, II, III, or IV.

One aspect of the present invention relates to compounds of Formula I

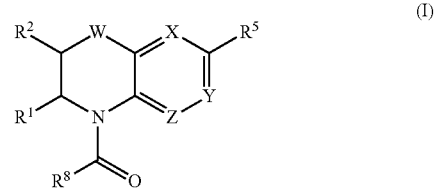

(I)

and pharmaceutically acceptable salts, enantiomers, hydrates, solvates, prodrugs, isomers, and tautomers thereof, wherein W, X, Y, Z, $R^1$, $R^2$, $R^3$, $R^4$, $R^5$, $R^6$, $R^7$, $R^8$, $R^a$, $R^b$, $R^c$, $R^d$, and n are as described above.

One embodiment of the invention relates to compounds of Formula II

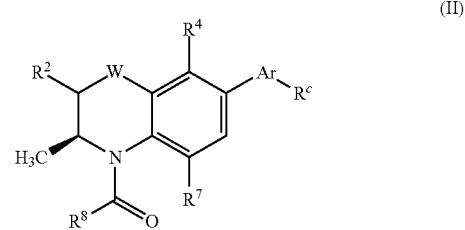

(II)

and pharmaceutically acceptable salts, enantiomers, hydrates, solvates, prodrugs, isomers, and tautomers thereof, wherein:
W is O, C(O), or CHR$^3$;
Ar is aryl or heteroaryl;
$R^2$ is hydrogen or NR$^a$R$^b$;
$R^3$ is hydrogen, hydroxy, or halo;
$R^4$ hydrogen, —O(CH$_2$)$_n$R$^d$, —O(CH$_2$)$_n$C(O)R$^d$, —O(CH$_2$)$_n$S(O)$_2$R$^d$ or —N(CH$_2$)$_n$R$^d$;
$R^7$ is hydrogen or halo;
$R^8$ is R$^a$, —OR$^a$, or heterocycloalkyl;
$R^a$ and $R^b$ are each independently hydrogen, C$_1$-C$_6$ alkyl, cycloalkyl, or heterocycloalkyl;
$R^c$ is R$^a$, —(CH$_2$)$_n$OR$^a$, —C(O)R$^a$, —C(O)OR$^a$, —C(O)NR$^a$R$^b$—S(O)$_2$R$^a$, halo, or oxo; and
n is 0, 1, or 2.
$R^d$ is hydrogen, NH(C$_1$-C$_6$ alkyl), N(C$_1$-C$_6$ alkyl)$_2$, C$_1$-C$_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from R$^a$, R$^b$, and R$^c$;
and n is 0, 1, or 2.

Another embodiment of the invention relates to compounds of Formula III

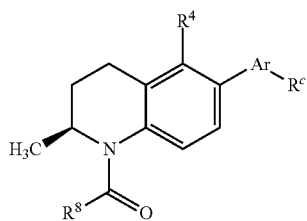

(III)

and pharmaceutically acceptable salts, enantiomers, hydrates, solvates, prodrugs, isomers, and tautomers thereof, wherein:

Ar is pyrazolyl or phenyl;

$R^4$ is hydrogen, $-O(CH_2)_nR^d$, $-O(CH_2)_nC(O)R^d$, or $-O(CH_2)_nS(O)_2R^d$;

$R^8$ is methyl, methoxy, or cyclopropyl;

$R^a$ and $R^b$ are each independently hydrogen or $C_1$-$C_6$ alkyl;

$R^c$ is $-(CH_2)_nR^a$, $-(CH_2)_nOR^a$, $-C(O)R^a$, $-C(O)OR^a$, $-C(O)NR^aR^b$, $-(CH_2)_nS(O)_2CH_3$, $-S(O)_2R^a$, $-S(O)_2NR^aR^b$, $C_1$-$C_6$ haloalkyl, $C_1$-$C_6$ haloalkoxy, cycloalkyl, heterocycloalkyl, halo, cyano, or oxo;

$R^d$ is hydrogen, $NH(C_1$-$C_6$ alkyl), $N(C_1$-$C_6$ alkyl)$_2$, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^c$; and n is 0, 1, or 2.

Another embodiment of the invention relates to compounds of Formula IV

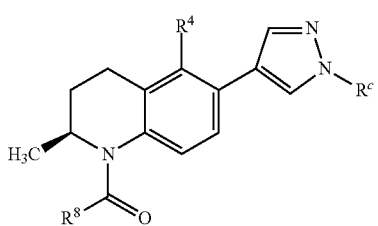

(IV)

and pharmaceutically acceptable salts, enantiomers, hydrates, solvates, prodrugs, isomers, and tautomers thereof, wherein:

$R^4$ is $-O(CH_2)_nR^d$, $-O(CH_2)_nC(O)R^d$, or $-O(CH_2)_nS(O)_2R^d$;

$R^8$ is alkyl, cycloalkyl, O-alkyl, or O-cycloalkyl $R^a$ and $R^b$ are each independently hydrogen or $C_1$-$C_6$ alkyl;

$R^c$ is $-(CH_2)_nR^a$, $-(CH_2)_nOR^a$, $-C(O)R^a$, $-C(O)OR^a$, $-C(O)NR^aR^b$$-S(O)_2R^a$, $-S(O)_2NR^aR^b$, $C_1$-$C_6$ haloalkyl, $C_1$-$C_6$ haloalkoxy, aryl, heteroaryl, cycloalkyl, heterocycloalkyl, halo, cyano, or oxo;

$R^d$ is hydrogen, $NH(C_1$-$C_6$ alkyl), $N(C_1$-$C_6$ alkyl)$_2$, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^c$; and n is 0, 1, or 2.

An aspect of the present invention concerns compounds which are, or can be, inhibitors of one or more bromodomains of the BET family.

An aspect of the present invention concerns the use of an inhibitor of BET family bromodomains for the preparation of a medicament used in the treatment, prevention, inhibition or elimination of tumors.

An aspect of the present invention concerns the use of an inhibitor of BET family bromodomains for the preparation of a medicament used in the treatment, prevention, inhibition or elimination of cancer.

An aspect of the present invention concerns the use of an inhibitor of BET family bromodomains for the preparation of a medicament used in treatment, prevention, inhibition or elimination of diseases associated with chronic autoimmune and inflammatory conditions.

An aspect of the present invention concerns the use of an inhibitor of BET family bromodomains for the preparation of a medicament used in treatment, prevention, inhibition or elimination of diseases associated with acute inflammatory conditions.

An aspect of the present invention concerns the use of an inhibitor of BET family bromodomains for the preparation of a medicament used in treatment, prevention, inhibition or elimination of diseases associated with systemic inflammatory response syndrome.

An aspect of the present invention concerns the use of an inhibitor of BET family bromodomains for the preparation of a medicament used in treatment, prevention, inhibition or elimination of diseases or disorders associated with virus, bacterial or fungal infections.

An aspect of the present invention concerns the use of an inhibitor of BET family bromodomains for the preparation of a medicament used in treatment, prevention, inhibition or elimination of diabetes or obesity.

An aspect of the present invention concerns the use of an inhibitor of BET family bromodomains for the preparation of a male contraceptive.

One embodiment of the present invention relates to compounds of Formula I, wherein X is $CR^4$ and Y and Z are CH.

Another embodiment of the present invention relates to compounds of Formula I, wherein W is $CHR^3$.

Another embodiment of the present invention relates to compounds of Formula II, wherein W is $CHR^3$.

Another embodiment of the present invention relates to compounds of Formula II, wherein Ar is pyrazole or phenyl.

Another embodiment of the present invention relates to compounds of Formula III, wherein Ar is pyrazole and $R^c$ is cycloalkyl or heterocycloalkyl.

Another aspect of the present invention relates to compounds of Formula III, wherein $R^c$ is cyclopropyl.

Yet another embodiment of the present invention is directed to compounds of Formula III, wherein Ar is phenyl, $R^c$ is $-(CH_2)_nS(O)_2CH_3$.

Another embodiment of the present invention is directed to compounds of Formula IV, wherein $R^c$ is cycloalkyl, or heterocycloalkyl.

Another embodiment of the present invention is directed to compounds of Formula IV, wherein $R^4$ is $-O(CH_2)_nR^c$.

Another embodiment of the present invention is directed to compounds of Formula IV, wherein $R^c$ is aryl, heteroaryl, or cycloalkyl.

In some embodiments of the present invention, W is CH. In another embodiment, W is CH. In yet another embodiment, W is CH and X is $CR_4$. In another embodiment, W is CH, X is $CR_4$ and Y is CH. In yet another embodiment, W is CH, X is $CR_4$, Y is CH, and Z is $CR^7$. In another embodiment, W is CH, X is $CR_4$, Y is CH, Z is $CR^7$, and $R^1$ is $C_1$-$C_6$ alkyl. In another embodiment, W is CH, X is $CR_4$, Y is CH, Z is $CR^7$, $R^1$ is $C_1$-$C_6$ alkyl and $R^2$ is H. In yet another embodiment, W is CH, X is $CR_4$, Y is CH, Z is $CR^7$, $R^1$ is $C_1$-$C_6$ alkyl, $R^2$ is H, and $R^8$ is $R^a$ or $OR^a$. In another embodiment, W is CH, X is $CR_4$, Y is CH, Z is $CR^7$, $R^1$ is $C_1$-$C_6$ alkyl, $R^2$ is H, $R^8$ is $R^a$ or $OR^a$, and $R^a$ is $C_1$-$C_6$ alkyl or cycloalkyl. In yet another embodiment, W is CH, X is $CR_4$, Y is CH, Z is $CR^7$, $R^1$ is $C_1$-$C_6$ alkyl, $R^2$ is H, $R^8$ is $R^a$ or $OR^a$, $R^a$ is $C_1$-$C_6$ alkyl or cycloalkyl, and $R^4$ is $OR^d$. In another embodiment, W is CH, X is $CR_4$, Y is CH, Z is $CR^7$, $R^1$ is $C_1$-$C_6$ alkyl, $R^2$ is H, $R^8$ is $R^a$ or $OR^a$, $R^a$ is $C_1$-$C_6$ alkyl or cycloalkyl, $R^4$ is $OR^d$, and $R^d$ is $C_1$-$C_6$ alkyl, $C_1$-$C_6$ haloalkyl, cycloalkyl, aryl, or heteroaryl optionally substituted with one or more preferred substituents. In yet another embodiment, W is CH, X is $CR_4$, Y is CH, Z is $CR^7$, $R^1$ is $C_1$-$C_6$ alkyl, $R^2$ is H, $R^8$ is $R^a$ or $OR^a$, $R^a$ is $C_1$-$C_6$ alkyl or cycloalkyl, $R^4$ is $OR^d$, $R^d$ is $C_1$-$C_6$ alkyl, $C_1$-$C_6$ haloalkyl, cycloalkyl, aryl, or heteroaryl optionally substituted with one or more preferred substituents, and $R^5$ is heteroaryl optionally substituted with one or more preferred substituents.

In some embodiments of the present invention, W is CH. In another embodiment, W is CH. In yet another embodiment, W is CH and X is $CR_4$. In another embodiment, W is CH, X is $CR_4$ and Y is CH. In yet another embodiment, W is CH, X is $CR_4$, Y is CH, and Z is CH or CF. In another embodiment, W is CH, X is $CR_4$, Y is CH, Z is CH or CF, and $R^1$ is methyl. In another embodiment, W is CH, X is $CR_4$, Y is CH, Z is CH or CF, $R^1$ is methyl and $R^2$ is H. In yet another embodiment, W is CH, X is $CR_4$, Y is CH, Z is CH or CF, $R^1$ is methyl, $R^2$ is H, and $R^8$ is $R^a$ or $OR^a$. In another embodiment, W is CH, X is $CR_4$, Y is CH, Z is CH or CF, $R^1$ is methyl, $R^2$ is H, $R^8$ is $R^a$ or $OR^a$, and $R^a$ is $C_1$-$C_6$ alkyl or cycloalkyl. In yet another embodiment, W is CH, X is $CR_4$, Y is CH, Z is CH or CF, $R^1$ is methyl, $R^2$ is H, $R^8$ is $R^a$ or $OR^a$, $R^a$ is $C_1$-$C_6$ alkyl or cycloalkyl, and $R^4$ is $OR^d$. In another embodiment, W is CH, X is $CR_4$, Y is CH, Z is CH or CF, $R^1$ is methyl, $R^2$ is H, $R^8$ is $R^a$ or $OR^a$, $R^a$ is $C_1$-$C_6$ alkyl or cycloalkyl, $R^4$ is $OR^d$, and $R^d$ is $C_1$-$C_6$ alkyl, $C_1$-$C_6$ haloalkyl, cycloalkyl, aryl, or heteroaryl optionally substituted with one or more preferred substituents. In yet another embodiment, W is CH, X is $CR_4$, Y is CH, Z is CH or CF, $R^1$ is methyl, $R^2$ is H, $R^8$ is $R^a$ or $OR^a$, $R^a$ is $C_1$-$C_6$ alkyl or cycloalkyl, $R^4$ is $OR^d$, $R^d$ is $C_1$-$C_6$ alkyl, $C_1$-$C_6$ haloalkyl, cycloalkyl, aryl, or heteroaryl optionally substituted with one or more preferred substituents, and $R^5$ is heteroaryl optionally substituted with one or more preferred substituents.

Another aspect of the present invention is a pharmaceutical composition comprising the compound of Formula I and a pharmaceutically acceptable carrier.

Another aspect of the present invention is a pharmaceutical composition comprising the compound of Formula I and a pharmaceutically acceptable carrier comprising therapeutically effective amounts of one or more additional therapeutic agents.

In some embodiment the present invention relates to a pharmaceutical composition comprising the compound of Formula I and a pharmaceutically acceptable carrier comprising therapeutically effective amounts of one or more additional therapeutic agents, wherein said additional therapeutic agents are selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methotrexate, temozolomide, cyclophosphamide, SCH 66336, tipifarnib, R115777, L778,123, BMS 214662, C225, GLEEVEC®, Intron®, Peg-Intron®, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, C225, Campath, leucovorin, dexamethasone, bicalutamide, carboplatin, chlorambucil, cisplatin, letrozole, megestrol, and valrubicin.

Another aspect of the present invention is directed to a method of inhibiting one or more of BET-family bromodomains in a patient comprising administering to the patient in need thereof an effective amount of the compound of Formula I.

Another aspect of the present invention is directed to a method of inhibiting one or more of BET-family bromodomains in a patient comprising administering to the patient in need thereof an effective amount of the pharmaceutical composition comprising the compound of Formula I and a pharmaceutically acceptable carrier.

Another aspect of the present invention is directed to a method of treating, preventing, inhibiting, or eliminating a disease or disorder associated with the activity of one or more BET-family bromodomains in a patient comprising administering to said patient in need thereof a therapeutically effective amount of the compound of Formula I.

One embodiment of the present invention relates a method of treating, preventing, inhibiting, or eliminating a disease or disorder associated with the activity of one or more BET-family bromodomains in a patient comprising administering to said patient in need thereof a therapeutically effective amount of the compound of Formula I, and further comprising administering to said patient in need thereof a therapeutically effective amount of another therapeutic agent.

Another embodiment of the present invention relates to a method of treating, preventing, inhibiting, or eliminating a disease or disorder associated with the activity of one or more BET-family bromodomains in a patient comprising administering to said patient in need thereof a therapeutically effective amount of the compound of Formula I, wherein said disease or disorder is selected from the group consisting of cancer, inflammatory disorders, irritable bowel syndrome, inflammatory bowel disease, rheumatoid arthritis, obesity, and diabetes.

Another aspect of the present invention is a male contraceptive comprising a therapeutically effective amount of at least one compound of Formula I.

Another aspect of the present invention is a male contraceptive comprising a therapeutically effective amount of at least one compound of Table 1.

The invention is further illustrated by the compounds shown in Table 1, with IUPAC nomenclature and the structures of the compounds. The table also provides reference to the method to make each compound as described below in the examples.

In another embodiment, illustrative compounds of the invention include:

methyl (2S)-6-(1-cyclopropyl-1H-pyrazol-4-yl)-5-{[3-(hydroxymethyl)oxetan-3-yl]methoxy}-2-methyl-1,2,3,4-tetrahydroquinoline-1-carboxylate;

methyl (2S)-5-(4-fluorophenoxy)-2-methyl-6-(1-{octahydrocyclopenta[c]pyrrol-5-yl}-1H-pyrazol-4-yl)-1,2,3,4-tetrahydroquinoline-1-carboxylate;

methyl (2S)-6-(1-cyclopropyl-1H-pyrazol-4-yl)-5-(3,3-difluorocyclobutoxy)-2-methyl-1,2,3,4-tetrahydroquinoline-1-carboxylate;

(2S)-1-cyclopropanecarbonyl-2-methyl-5-phenoxy-6-(1H-1,2,3-triazol-4-yl)-1,2,3,4-tetrahydroquinoline;

methyl (2S)-5-(azetidin-3-ylmethoxy)-6-(1-cyclopropyl-1H-pyrazol-4-yl)-2-methyl-1,2,3,4-tetrahydroquinoline-1-carboxylate;

methyl (2S)-5-(3-fluorophenoxy)-2-methyl-6-[1-(piperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-(2,2,2-trifluoroethoxy)-1,2,3,4-tetrahydroquinolin-1-yl]ethan-1-one;

methyl (2S)-5-(3-chlorophenoxy)-2-methyl-6-[1-(piperidin-4-yl)-1H-pyrazol-4-yl]-1,2,3,4-tetrahydroquinoline-1-carboxylate;

1-[(2S)-6-(1-cyclopropyl-1H-pyrazol-4-yl)-5-(2,2-difluoroethoxy)-2-methyl-1,2,3,4-tetrahydroquinolin-1-yl]ethan-1-one;

1-[(2S)-5-(4-fluorophenoxy)-2-methyl-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-(2,2-difluoropropoxy)-2-methyl-1,2,3,4-tetrahydroquinolin-1-yl]ethan-1-one;

1-[(2S)-5-(4-chlorophenoxy)-2-methyl-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-[(1,3-difluoropropan-2-yl)oxy]-2-methyl-1,2,3,4-tetrahydroquinolin-1-yl]ethan-1-one;

methyl (2S)-6-[1-(azetidin-3-yl)-1H-pyrazol-4-yl]-5-(3,4-difluorophenoxy)-2-methyl-1,2,3,4-tetrahydroquinoline-1-carboxylate;

1-[(2S)-6-(1-cyclopropyl-1H-pyrazol-4-yl)-5-(3-hydroxy-2,2-dimethylpropoxy)-2-methyl-1,2,3,4-tetrahydroquinolin-1-yl]ethan-1-one;

methyl (2S)-6-[1-(azetidin-3-yl)-1H-pyrazol-4-yl]-2-methyl-5-phenoxy-1,2,3,4-tetrahydroquinoline-1-carboxylate;

2-{[(2S)-1-acetyl-6-(1-cyclopropyl-1H-pyrazol-4-yl)-2-methyl-1,2,3,4-tetrahydroquinolin-5-yl]oxy}-2-methylpropanamide;

(2S)-1-cyclopropanecarbonyl-5-(2-methoxyphenoxy)-2-methyl-6-[1-(piperidin-4-yl)-1H-pyrazol-4-yl]-1,2,3,4-tetrahydroquinoline;

1-[(2S)-6-(1-cyclopropyl-1H-pyrazol-4-yl)-2-methyl-5-(3,3,3-trifluoropropoxy)-1,2,3,4-tetrahydroquinolin-1-yl]ethan-1-one;

(2S)-1-cyclopropanecarbonyl-5-(3-methoxyphenoxy)-2-methyl-6-[1-(piperidin-4-yl)-1H-pyrazol-4-yl]-1,2,3,4-tetrahydroquinoline;

1-(2-{[(2S)-1-acetyl-6-(1-cyclopropyl-1H-pyrazol-4-yl)-2-methyl-1,2,3,4-tetrahydroquinolin-5-yl]oxy}ethyl)pyrrolidin-2-one;

(2S)-1-cyclopropanecarbonyl-5-(4-methoxyphenoxy)-2-methyl-6-[1-(piperidin-4-yl)-1H-pyrazol-4-yl]-1,2,3,4-tetrahydroquinoline;

2-{[(2S)-1-acetyl-6-(1-cyclopropyl-1H-pyrazol-4-yl)-2-methyl-1,2,3,4-tetrahydroquinolin-5-yl]oxy}-1-(morpholin-4-yl)ethan-1-one;

methyl (2S)-5-(2-methoxyphenoxy)-2-methyl-6-[1-(piperidin-4-yl)-1H-pyrazol-4-yl]-1,2,3,4-tetrahydroquinoline-1-carboxylate;

2-(2-{[(2S)-1-acetyl-6-(1-cyclopropyl-1H-pyrazol-4-yl)-2-methyl-1,2,3,4-tetrahydroquinolin-5-yl]oxy}ethyl)-1λ⁶,2-thiazolidine-1,1-dione;

methyl (2S)-5-(3-methoxyphenoxy)-2-methyl-6-[1-(piperidin-4-yl)-1H-pyrazol-4-yl]-1,2,3,4-tetrahydroquinoline-1-carboxylate;

{[(2S)-1-acetyl-6-(1-cyclopropyl-1H-pyrazol-4-yl)-2-methyl-1,2,3,4-tetrahydroquinolin-5-yl]oxy}methanesulfonamide;

methyl (2S)-5-(4-methoxyphenoxy)-2-methyl-6-[1-(piperidin-4-yl)-1H-pyrazol-4-yl]-1,2,3,4-tetrahydroquinoline-1-carboxylate;

1-{[(2S)-1-acetyl-6-(1-cyclopropyl-1H-pyrazol-4-yl)-2-methyl-1,2,3,4-tetrahydroquinolin-5-yl]oxy}-N,N-dimethylmethanesulfonamide;

methyl (2S)-2-methyl-5-phenoxy-6-[1-(piperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-[2-(oxetan-3-yl)ethoxy]-1,2,3,4-tetrahydroquinolin-1-yl]ethan-1-one;

1-[(2S)-2-methyl-5-phenoxy-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-[(2,2-difluorocyclopropyl)methoxy]-2-methyl-1,2,3,4-tetrahydroquinolin-1-yl]ethan-1-one;

3-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;

1-[(2S)-6-(1-cyclopropyl-1H-pyrazol-4-yl)-5-{[3-(hydroxymethyl)oxetan-3-yl]methoxy}-2-methyl-1,2,3,4-tetrahydroquinolin-1-yl]ethan-1-one;

1-[(2S)-2-methyl-6-[1-(piperidin-4-yl)-1H-pyrazol-4-yl]-5-(pyridin-2-yloxy)-1,2,3,4-tetrahydroquinolin-1-yl]ethan-1-one;

1-[(2S)-6-(1-cyclopropyl-1H-pyrazol-4-yl)-5-[(3-fluorooxetan-3-yl)methoxy]-2-methyl-1,2,3,4-tetrahydroquinolin-1-yl]ethan-1-one;

1-[(2S)-5-(3-methoxyphenoxy)-2-methyl-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-(3,3-difluorocyclobutoxy)-2-methyl-1,2,3,4-tetrahydroquinolin-1-yl]ethan-1-one;

1-[(2S)-5-(azetidin-3-ylmethoxy)-6-(1-cyclopropyl-1H-pyrazol-4-yl)-2-methyl-1,2,3,4-tetrahydroquinolin-1-yl]ethan-1-one;

(2S)-5-cyclobutoxy-1-cyclopropanecarbonyl-2-methyl-6-(1-methyl-1H-1,2,3-triazol-4-yl)-1,2,3,4-tetrahydroquinoline;

(2S)-5-cyclobutoxy-1-cyclopropanecarbonyl-2-methyl-6-(1H-pyrazol-4-yl)-1,2,3,4-tetrahydroquinoline;

(2S)-5-cyclobutoxy-1-cyclopropanecarbonyl-2-methyl-6-(1-methyl-1H-pyrazol-4-yl)-1,2,3,4-tetrahydroquinoline;

(2S)-5-cyclobutoxy-1-cyclopropanecarbonyl-2-methyl-6-(1H-pyrazol-5-yl)-1,2,3,4-tetrahydroquinoline;

(2S)-5-cyclobutoxy-1-cyclopropanecarbonyl-2-methyl-6-(1-methyl-1H-imidazol-4-yl)-1,2,3,4-tetrahydroquinoline;

methyl (2S)-5-({1-[(tert-butoxy)carbonyl]azetidin-3-yl}oxy)-6-(1-cyclopropyl-1H-pyrazol-4-yl)-2-methyl-1,2,3,4-tetrahydroquinoline-1-carboxylate;

methyl (2S)-5-(azetidin-3-yloxy)-6-(1-cyclopropyl-1H-pyrazol-4-yl)-2-methyl-1,2,3,4-tetrahydroquinoline-1-carboxylate;

1-[(2S)-5-(azetidin-3-yloxy)-6-(1-cyclopropyl-1H-pyrazol-4-yl)-2-methyl-1,2,3,4-tetrahydroquinolin-1-yl]ethan-1-one;

methyl (2S)-5-cyclobutoxy-6-[1-(1,1-dioxo-1$\lambda^6$-thietan-3-yl)-1H-pyrazol-4-yl]-2-methyl-1,2,3,4-tetrahydroquinoline-1-carboxylate;

methyl (2S)-5-cyclobutoxy-6-[1-(1,1-dioxo-1$\lambda^6$-thian-3-yl)-1H-pyrazol-4-yl]-2-methyl-1,2,3,4-tetrahydroquinoline-1-carboxylate;

(2R)-2-{[(2S)-1-acetyl-6-(1-cyclopropyl-1H-pyrazol-4-yl)-2-methyl-1,2,3,4-tetrahydroquinolin-5-yl]oxy}-2-fluoroacetamide;

(2S)-2-{[(2S)-1-acetyl-6-(1-cyclopropyl-1H-pyrazol-4-yl)-2-methyl-1,2,3,4-tetrahydroquinolin-5-yl]oxy}-2-fluoroacetamide;

methyl (2S)-6-(1-cyclopropyl-1H-pyrazol-4-yl)-5-[(3-fluorooxetan-3-yl)methoxy]-2-methyl-1,2,3,4-tetrahydroquinoline-1-carboxylate;

2-{[(2S)-1-acetyl-6-(1-cyclopropyl-1H-pyrazol-4-yl)-2-methyl-1,2,3,4-tetrahydroquinolin-5-yl]oxy}-2,2-difluoroacetamide;

1-[(2S)-6-(1-cyclopropyl-1H-pyrazol-4-yl)-5-(2-fluoro-2-methylpropoxy)-2-methyl-1,2,3,4-tetrahydroquinolin-1-yl]ethan-1-one;

methyl (2S)-5-cyclobutoxy-2-methyl-6-[1-(oxan-4-yl)-1H-pyrazol-4-yl]-1,2,3,4-tetrahydroquinoline-1-carboxylate;

1-[(2S)-6-[1-(2-hydroxyethyl)-1H-pyrazol-4-yl]-2-methyl-5-propoxy-1,2,3,4-tetrahydroquinolin-1-yl]ethan-1-one;

2-{[(2S)-1-acetyl-6-[1-(2-hydroxyethyl)-1H-pyrazol-4-yl]-2-methyl-1,2,3,4-tetrahydroquinolin-5-yl]oxy}-N,N-dimethylacetamide;

methyl (2S)-5-[(dimethylcarbamoyl)methoxy]-6-[1-(2-hydroxyethyl)-1H-pyrazol-4-yl]-2-methyl-1,2,3,4-tetrahydroquinoline-1-carboxylate;

2-{[(2S)-1-acetyl-6-(1-cyclopropyl-1H-pyrazol-4-yl)-2-methyl-1,2,3,4-tetrahydroquinolin-5-yl]oxy}-N-ethylacetamide;

1-[(2S)-6-(1-cyclopropyl-1H-pyrazol-4-yl)-5-(2-fluoroethoxy)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}-N-cyclopropyl-N-methylacetamide;

2-{[(2S)-1-acetyl-6-(1-cyclopropyl-1H-pyrazol-4-yl)-2-methyl-1,2,3,4-tetrahydroquinolin-5-yl]oxy}-1-(azetidin-1-yl)ethan-1-one;

2-{[(2S)-1-acetyl-6-(1-cyclopropyl-1H-pyrazol-4-yl)-2-methyl-1,2,3,4-tetrahydroquinolin-5-yl]oxy}-1-(piperidin-1-yl)ethan-1-one;

methyl (2S)-6-(1-cyclopropyl-1H-pyrazol-4-yl)-2-methyl-5-(2,2,2-trifluoroethoxy)-1,2,3,4-tetrahydroquinoline-1-carboxylate;

methyl (2S)-6-(1-cyclopropyl-1H-pyrazol-4-yl)-5-(2,2-difluoroethoxy)-2-methyl-1,2,3,4-tetrahydroquinoline-1-carboxylate;

methyl (2S)-6-(1-cyclopropyl-1H-pyrazol-4-yl)-5-(2-fluoroethoxy)-2-methyl-1,2,3,4-tetrahydroquinoline-1-carboxylate;

methyl (2S)-6-(1-cyclopropyl-1H-pyrazol-4-yl)-5-(2,2-difluoropropoxy)-2-methyl-1,2,3,4-tetrahydroquinoline-1-carboxylate;

methyl (2S)-6-(1-cyclopropyl-1H-pyrazol-4-yl)-2-methyl-5-(3,3,3-trifluoropropoxy)-1,2,3,4-tetrahydroquinoline-1-carboxylate;

methyl (2S)-5-(carbamoyldifluoromethoxy)-6-(1-cyclopropyl-1H-pyrazol-4-yl)-2-methyl-1,2,3,4-tetrahydroquinoline-1-carboxylate;

methyl (2S)-6-(1-cyclopropyl-1H-pyrazol-4-yl)-5-[(1,3-difluoropropan-2-yl)oxy]-2-methyl-1,2,3,4-tetrahydroquinoline-1-carboxylate;

methyl (2S)-6-(1-cyclopropyl-1H-pyrazol-4-yl)-5-(2-fluoro-2-methylpropoxy)-2-methyl-1,2,3,4-tetrahydroquinoline-1-carboxylate;

methyl (2S)-6-(1-cyclopropyl-1H-pyrazol-4-yl)-5-(3-hydroxy-2,2-dimethylpropoxy)-2-methyl-1,2,3,4-tetrahydroquinoline-1-carboxylate;

methyl (2S)-5-(1-carbamoyl-1-methylethoxy)-6-(1-cyclopropyl-1H-pyrazol-4-yl)-2-methyl-1,2,3,4-tetrahydroquinoline-1-carboxylate;

methyl (2S)-5-[(R)-carbamoyl(fluoro)methoxy]-6-(1-cyclopropyl-1H-pyrazol-4-yl)-2-methyl-1,2,3,4-tetrahydroquinoline-1-carboxylate;

methyl (2S)-5-[(S)-carbamoyl(fluoro)methoxy]-6-(1-cyclopropyl-1H-pyrazol-4-yl)-2-methyl-1,2,3,4-tetrahydroquinoline-1-carboxylate;

methyl (2S)-6-(1-cyclopropyl-1H-pyrazol-4-yl)-5-[(ethylcarbamoyl)methoxy]-2-methyl-1,2,3,4-tetrahydroquinoline-1-carboxylate;

methyl (2S)-5-{[cyclopropyl(methyl)carbamoyl]methoxy}-6-(1-cyclopropyl-1H-pyrazol-4-yl)-2-methyl-1,2,3,4-tetrahydroquinoline-1-carboxylate;

methyl (2S)-5-[2-(azetidin-1-yl)-2-oxoethoxy]-6-(1-cyclopropyl-1H-pyrazol-4-yl)-2-methyl-1,2,3,4-tetrahydroquinoline-1-carboxylate;

methyl (2S)-6-(1-cyclopropyl-1H-pyrazol-4-yl)-2-methyl-5-[2-oxo-2-(piperidin-1-yl)ethoxy]-1,2,3,4-tetrahydroquinoline-1-carboxylate;

methyl (2S)-6-(1-cyclopropyl-1H-pyrazol-4-yl)-2-methyl-5-[2-(2-oxopyrrolidin-1-yl)ethoxy]-1,2,3,4-tetrahydroquinoline-1-carboxylate;

methyl (2S)-6-(1-cyclopropyl-1H-pyrazol-4-yl)-2-methyl-5-[2-(morpholin-4-yl)-2-oxoethoxy]-1,2,3,4-tetrahydroquinoline-1-carboxylate;

methyl (2S)-6-(1-cyclopropyl-1H-pyrazol-4-yl)-5-[2-(1,1-dioxo-1$\lambda^6$,2-thiazolidin-2-yl)ethoxy]-2-methyl-1,2,3,4-tetrahydroquinoline-1-carboxylate;

methyl (2S)-6-(1-cyclopropyl-1H-pyrazol-4-yl)-2-methyl-5-(sulfamoylmethoxy)-1,2,3,4-tetrahydroquinoline-1-carboxylate;

methyl (2S)-6-(1-cyclopropyl-1H-pyrazol-4-yl)-5-[(dimethylsulfamoyl)methoxy]-2-methyl-1,2,3,4-tetrahydroquinoline-1-carboxylate;

methyl (2S)-6-(1-cyclopropyl-1H-pyrazol-4-yl)-2-methyl-5-[2-(oxetan-3-yl)ethoxy]-1,2,3,4-tetrahydroquinoline-1-carboxylate;

methyl (2S)-6-(1-cyclopropyl-1H-pyrazol-4-yl)-5-[(2,2-difluorocyclopropyl)methoxy]-2-methyl-1,2,3,4-tetrahydroquinoline-1-carboxylate;

1-[(2S)-6-(1-cyclopropyl-1H-pyrazol-4-yl)-2-methyl-5-(quinazolin-2-yloxy)-1,2,3,4-tetrahydroquinolin-1-yl]ethan-1-one;

1-[(2S)-5-(1,3-benzoxazol-2-yloxy)-6-(1-cyclopropyl-1H-pyrazol-4-yl)-2-methyl-1,2,3,4-tetrahydroquinolin-1-yl]ethan-1-one;

1-[(2S)-5-(1,3-benzoxazol-2-yloxy)-2-methyl-6-[1-(oxetan-3-yl)-1H-pyrazol-4-yl]-1,2,3,4-tetrahydroquinolin-1-yl]ethan-1-one;

1-[(2S)-6-[1-(2-hydroxyethyl)-1H-pyrazol-4-yl]-2-methyl-5-(pyrimidin-2-yloxy)-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}pyridine-3-carboxamide;

1-[(2S)-6-(1-cyclopropyl-1H-pyrazol-4-yl)-2-methyl-5-{1H-pyrazolo[3,4-d]pyrimidin-6-yloxy}-1,2,3,4-tetrahydroquinolin-1-yl]ethan-1-one;

1-[(2S)-6-(1-cyclopropyl-1H-pyrazol-4-yl)-2-methyl-5-(1,3-thiazol-2-yloxy)-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}pyridine-3-carbonitrile;

1-[(2S)-6-(1-cyclopropyl-1H-pyrazol-4-yl)-2-methyl-5-{[4-(trifluoromethyl)pyrimidin-2-yl]oxy}-1,2,3,4-tetrahydroquinolin-1-yl]ethan-1-one;

1-[(2S)-6-(1-cyclopropyl-1H-pyrazol-4-yl)-2-methyl-5-{[3-(trifluoromethyl)pyridin-2-yl]oxy}-1,2,3,4-tetrahydroquinolin-1-yl]ethan-1-one;

1-[(2S)-5-[(3-chloropyridin-2-yl)oxy]-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(pyrazin-2-yloxy)-1,2,3,4-tetrahydroquinolin-1-yl]ethan-1-one;

1-[(2S)-6-(1-cyclopropyl-1H-pyrazol-4-yl)-2-methyl-5-(pyridin-2-yloxy)-1,2,3,4-tetrahydroquinolin-1-yl]ethan-1-one;

1-[(2S)-6-(1-cyclopropyl-1H-pyrazol-4-yl)-5-[(4,6-dimethylpyrimidin-2-yl)oxy]-2-methyl-1,2,3,4-tetrahydroquinolin-1-yl]ethan-1-one;

6-{[(2S)-1-acetyl-6-(1-cyclopropyl-1H-pyrazol-4-yl)-2-methyl-1,2,3,4-tetrahydroquinolin-5-yl]oxy}pyridazine-3-carbonitrile;

1-[(2S)-6-(1-cyclopropyl-1H-pyrazol-4-yl)-2-methyl-5-[(5-methylpyrimidin-2-yl)oxy]-1,2,3,4-tetrahydroquinolin-1-yl]ethan-1-one;

1-[(2S)-6-(1-cyclopropyl-1H-pyrazol-4-yl)-2-methyl-5-{[2-(trifluoromethyl)pyrimidin-4-yl]oxy}-1,2,3,4-tetrahydroquinolin-1-yl]ethan-1-one;

(2S)-5-cyclobutoxy-1-cyclopropanecarbonyl-2-methyl-6-[1-(piperidin-4-yl)-1H-pyrazol-4-yl]-1,2,3,4-tetrahydroquinoline;

(2S)-1-cyclopropanecarbonyl-2-methyl-6-[1-(piperidin-4-yl)-1H-pyrazol-4-yl]-5-propoxy-1,2,3,4-tetrahydroquinoline;

(2S)-6-[1-(azetidin-3-yl)-1H-pyrazol-4-yl]-5-cyclobutoxy-1-cyclopropanecarbonyl-2-methyl-1,2,3,4-tetrahydroquinoline;

(2S)-6-[1-(azetidin-3-yl)-1H-pyrazol-4-yl]-1-cyclopropanecarbonyl-2-methyl-5-propoxy-1,2,3,4-tetrahydroquinoline;

1-[(2S)-2-methyl-6-[1-(piperidin-4-yl)-1H-pyrazol-4-yl]-5-propoxy-1,2,3,4-tetrahydroquinolin-1-yl]ethan-1-one;

methyl (2S)-2-methyl-6-[1-(piperidin-4-yl)-1H-pyrazol-4-yl]-5-propoxy-1,2,3,4-tetrahydroquinoline-1-carboxylate;

methyl (2S)-5-cyclobutoxy-2-methyl-6-[1-(pyrrolidin-3-yl)-1H-pyrazol-4-yl]-1,2,3,4-tetrahydroquinoline-1-carboxylate;

methyl (2S)-5-cyclobutoxy-2-methyl-6-(1-{octahydrocyclopenta[c]pyrrol-5-yl}-1H-pyrazol-4-yl)-1,2,3,4-tetrahydroquinoline-1-carboxylate;

1-[6-(4-methanesulfonylphenyl)-2-methyl-5-phenoxy-1,2,3,4-tetrahydroquinolin-1-yl]ethan-1-one;

1-(2-methyl-5-phenoxy-1,2,3,4-tetrahydroquinolin-1-yl)ethan-1-one;

1-[(2S)-5-cyclopropoxy-6-(1-cyclopropyl-1H-pyrazol-4-yl)-2-methyl-1,2,3,4-tetrahydroquinolin-1-yl]ethan-1-one;

1-[(2S)-6-(5-methanesulfonylpyridin-2-yl)-2-methyl-5-propoxy-1,2,3,4-tetrahydroquinolin-1-yl]ethan-1-one;

N-{6-[(2S)-1-acetyl-2-methyl-5-propoxy-1,2,3,4-tetrahydroquinolin-6-yl]pyridin-3-yl}methanesulfonamide;

2-{[(2S)-1-acetyl-6-(5-methanesulfonylpyridin-2-yl)-2-methyl-1,2,3,4-tetrahydroquinolin-5-yl]oxy}-N,N-dimethylacetamide;

1-[(2S)-6-(1,3-benzoxazol-2-yl)-2-methyl-5-propoxy-1,2,3,4-tetrahydroquinolin-1-yl]ethan-1-one;

1-[(2S)-2-methyl-5-propoxy-6-{pyrazolo[1,5-a]pyridin-2-yl}-1,2,3,4-tetrahydroquinolin-1-yl]ethan-1-one;

1-[(2S)-6-{imidazo[1,2-a]pyridin-2-yl}-2-methyl-5-propoxy-1,2,3,4-tetrahydroquinolin-1-yl]ethan-1-one;

1-[(2S)-6-(1,3-benzothiazol-2-yl)-2-methyl-5-propoxy-1,2,3,4-tetrahydroquinolin-1-yl]ethan-1-one;

1-[(2S)-6-(1H-1,3-benzodiazol-2-yl)-2-methyl-5-propoxy-1,2,3,4-tetrahydroquinolin-1-yl]ethan-1-one;

(2S)-5-cyclobutoxy-1-cyclopropanecarbonyl-2-methyl-6-(5-methyl-1,3,4-thiadiazol-2-yl)-1,2,3,4-tetrahydroquinoline;

5-[(2S)-5-cyclobutoxy-1-cyclopropanecarbonyl-2-methyl-1,2,3,4-tetrahydroquinolin-6-yl]-1,3,4-thiadiazol-2-amine;

(2S)-5-cyclobutoxy-1-cyclopropanecarbonyl-2-methyl-6-(1H-1,2,3-triazol-4-yl)-1,2,3,4-tetrahydroquinoline;

methyl (2S)-5-(4-chloro-2-cyanophenoxy)-2-methyl-6-[1-(piperidin-4-yl)-1H-pyrazol-4-yl]-1,2,3,4-tetrahydroquinoline-1-carboxylate;

methyl (2S)-5-(2-cyano-4-fluorophenoxy)-2-methyl-6-[1-(piperidin-4-yl)-1H-pyrazol-4-yl]-1,2,3,4-tetrahydroquinoline-1-carboxylate;

methyl (2S)-5-(2-chloro-4-cyanophenoxy)-2-methyl-6-[1-(piperidin-4-yl)-1H-pyrazol-4-yl]-1,2,3,4-tetrahydroquinoline-1-carboxylate;

methyl (2S)-5-(4-cyano-2-fluorophenoxy)-2-methyl-6-[1-(piperidin-4-yl)-1H-pyrazol-4-yl]-1,2,3,4-tetrahydroquinoline-1-carboxylate 2-{[(2S)-1-acetyl-2-methyl-6-[1-(piperidin-4-yl)-1H-pyrazol-4-yl]-1,2,3,4-tetrahydroquinolin-5-yl]oxy}benzonitrile;

methyl (2S)-5-(2-cyanophenoxy)-2-methyl-6-[1-(piperidin-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(2-cyanophenoxy)-2-methyl-1,2,3,4-tetrahydroquinoline-1-carboxylate;

methyl (2S)-6-[1-(azetidin-3-yl)-1H-pyrazol-4-yl]-5-(2-cyano-3-fluorophenoxy)-2-methyl-1,2,3,4-tetrahydroquinoline-1-carboxylate;

4-{[(2S)-1-acetyl-2-methyl-6-[1-(piperidin-4-yl)-1H-pyrazol-4-yl]-1,2,3,4-tetrahydroquinolin-5-yl]oxy}benzonitrile;

1-[(2S)-2-methyl-6-[1-(piperidin-4-yl)-1H-pyrazol-4-yl]-5-{[3-(trifluoromethyl)pyridin-2-yl]oxy}-1,2,3,4-tetrahydroquinolin-1-yl]ethan-1-one;

1-[(2S)-5-[(3-chloropyridin-2-yl)oxy]-2-methyl-6-[1-(piperidin-4-yl)-1H-pyrazol-4-yl]-1,2,3,4-tetrahydroquinolin-1-yl]ethan-1-one;

2-{[(2S)-1-acetyl-2-methyl-6-[1-(piperidin-4-yl)-1H-pyrazol-4-yl]-1,2,3,4-tetrahydroquinolin-5-yl]oxy}pyridine-3-carbonitrile;

1-[(2S)-2-methyl-5-[(5-methylpyrimidin-2-yl)oxy]-6-[1-(piperidin-4-yl)-1H-pyrazol-4-yl]-1,2,3,4-tetrahydroquinolin-1-yl]ethan-1-one;

1-[(2S)-2-methyl-6-[1-(piperidin-4-yl)-1H-pyrazol-4-yl]-5-(pyrazin-2-yloxy)-1,2,3,4-tetrahydroquinolin-1-yl]ethan-1-one;

methyl (2S)-5-(4-cyanophenoxy)-2-methyl-6-[1-(piperidin-4-yl)-1H-pyrazol-4-yl]-1,2,3,4-tetrahydroquinoline-1-carboxylate;

methyl (2S)-5-[(3-cyanopyridin-2-yl)oxy]-2-methyl-6-[1-(piperidin-4-yl)-1H-pyrazol-4-yl]-1,2,3,4-tetrahydroquinoline-1-carboxylate;

methyl (2S)-5-(2-cyano-3-fluorophenoxy)-2-methyl-6-[1-(piperidin-4-yl)-1H-pyrazol-4-yl]-1,2,3,4-tetrahydroquinoline-1-carboxylate;

methyl (2S)-5-(3-chloro-2-cyanophenoxy)-2-methyl-6-[1-(piperidin-4-yl)-1H-pyrazol-4-yl]-1,2,3,4-tetrahydroquinoline-1-carboxylate;

2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;

2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}-6-fluorobenzonitrile;

4-{[(2S)-1-cyclopropanecarbonyl-2-methyl-6-[1-(piperidin-4-yl)-1H-pyrazol-4-yl]-1,2,3,4-tetrahydroquinolin-5-yl]oxy}-3-fluorobenzonitrile;

2-{[(2S)-1-acetyl-6-(1-cyclopropyl-1H-pyrazol-4-yl)-2-methyl-1,2,3,4-tetrahydroquinolin-5-yl]oxy}benzonitrile;

methyl (2S)-6-[1-(azetidin-3-yl)-1H-pyrazol-4-yl]-5-(3-chloro-4-fluorophenoxy)-2-methyl-1,2,3,4-tetrahydroquinoline-1-carboxylate;

4-{[(2S)-1-acetyl-2-methyl-6-[1-(piperidin-4-yl)-1H-pyrazol-4-yl]-1,2,3,4-tetrahydroquinolin-5-yl]oxy}benzamide;

1-[(2S)-5-(2-chlorophenoxy)-2-methyl-6-[1-(piperidin-4-yl)-1H-pyrazol-4-yl]-1,2,3,4-tetrahydroquinolin-1-yl]ethan-1-one;

methyl (2S)-5-(4-fluorophenoxy)-2-methyl-6-[1-(piperidin-4-yl)-1H-pyrazol-4-yl]-1,2,3,4-tetrahydroquinoline-1-carboxylate;

methyl (2S)-5-(4-chlorophenoxy)-2-methyl-6-[1-(piperidin-4-yl)-1H-pyrazol-4-yl]-1,2,3,4-tetrahydroquinoline-1-carboxylate;

methyl (2S)-5-(2-chlorophenoxy)-2-methyl-6-[1-(piperidin-4-yl)-1H-pyrazol-4-yl]-1,2,3,4-tetrahydroquinoline-1-carboxylate;

methyl (2S)-5-(4-carbamoylphenoxy)-2-methyl-6-[1-(piperidin-4-yl)-1H-pyrazol-4-yl]-1,2,3,4-tetrahydroquinoline-1-carboxylate;

methyl (2S)-5-(3-cyano-4-fluorophenoxy)-2-methyl-6-[1-(piperidin-4-yl)-1H-pyrazol-4-yl]-1,2,3,4-tetrahydroquinoline-1-carboxylate;

methyl (2S)-5-(3-chloro-4-fluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(4-fluorophenoxy)-2-methyl-6-[1-(piperidin-4-yl)-1H-pyrazol-4-yl]-1,2,3,4-tetrahydroquinoline;

(2S)-5-(2-chlorophenoxy)-1-cyclopropanecarbonyl-2-methyl-6-[1-(piperidin-4-yl)-1H-pyrazol-4-yl]-1,2,3,4-tetrahydroquinoline;

(2S)-5-(4-chlorophenoxy)-1-cyclopropanecarbonyl-2-methyl-6-[1-(piperidin-4-yl)-1H-pyrazol-4-yl]-1,2,3,4-tetrahydroquinoline;

4-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;

(2S)-1-cyclopropanecarbonyl-2-methyl-5-phenoxy-6-[1-(piperidin-4-yl)-1H-pyrazol-4-yl]-1,2,3,4-tetrahydroquinoline;

(2S)-5-(3-chloro-4-fluorophenoxy)-1-cyclopropanecarbonyl-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(4-fluorophenoxy)-2-methyl-1,2,3,4-tetrahydroquinoline;

(2S)-1-cyclopropanecarbonyl-5-(3-fluorophenoxy)-2-methyl-6-[1-(piperidin-4-yl)-1H-pyrazol-4-yl]-1,2,3,4-tetrahydroquinoline;

(2S)-1-cyclopropanecarbonyl-5-(3,4-difluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(3-fluorophenoxy)-2-methyl-1,2,3,4-tetrahydroquinoline;

(2S)-6-[1-(azetidin-3-yl)-1H-pyrazol-4-yl]-1-cyclopropanecarbonyl-5-(3,4-difluorophenoxy)-2-methyl-1,2,3,4-tetrahydroquinoline;

(2S)-6-[1-(azetidin-3-yl)-1H-pyrazol-4-yl]-1-cyclopropanecarbonyl-2-methyl-5-phenoxy-1,2,3,4-tetrahydroquinoline;

methyl (2S)-5-(3,4-difluorophenoxy)-2-methyl-6-[1-(piperidin-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(3-chlorophenoxy)-2-methyl-1,2,3,4-tetrahydroquinoline-1-carboxylate;

(2S)-6-[1-(azetidin-3-yl)-1H-pyrazol-4-yl]-5-(3-chlorophenoxy)-1-cyclopropanecarbonyl-2-methyl-1,2,3,4-tetrahydroquinoline;

(2S)-5-(3-chlorophenoxy)-1-cyclopropanecarbonyl-2-methyl-6-[1-(piperidin-4-yl)-1H-pyrazol-4-yl]-1,2,3,4-tetrahydroquinoline;

methyl (2S)-6-[1-(azetidin-3-yl)-1H-pyrazol-4-yl]-5-(3,5-difluorophenoxy)-2-methyl-1,2,3,4-tetrahydroquinoline-1-carboxylate;

(2S)-6-[1-(azetidin-3-yl)-1H-pyrazol-4-yl]-1-cyclopropanecarbonyl-5-(3,5-difluorophenoxy)-2-methyl-1,2,3,4-tetrahydroquinoline;

methyl (2S)-5-(3,5-difluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(3,5-difluorophenoxy)-2-methyl-6-[1-(piperidin-4-yl)-1H-pyrazol-4-yl]-1,2,3,4-tetrahydroquinoline;

5-[(2S)-1-cyclopropanecarbonyl-2-methyl-5-phenoxy-1,2,3,4-tetrahydroquinolin-6-yl]-1,3,4-thiadiazol-2-amine;

methyl (2S)-5-(4-fluorophenoxy)-2-methyl-6-[1-(pyrrolidin-3-yl)-1H-pyrazol-4-yl]-1,2,3,4-tetrahydroquinoline-1-carboxylate;

4-{[(2S)-1-acetyl-6-(1-cyclopropyl-1H-pyrazol-4-yl)-2-methyl-1,2,3,4-tetrahydroquinolin-5-yl]oxy}benzamide;

(2S)-1-cyclopropanecarbonyl-2-methyl-5-phenoxy-6-(1H-pyrazol-5-yl)-1,2,3,4-tetrahydroquinoline;

(2S)-1-cyclopropanecarbonyl-2-methyl-6-(1-methyl-1H-1,2,3-triazol-4-yl)-5-phenoxy-1,2,3,4-tetrahydroquinoline;

(2S)-1-cyclopropanecarbonyl-2-methyl-6-(5-methyl-1,3,4-thiadiazol-2-yl)-5-phenoxy-1,2,3,4-tetrahydroquinoline;

(2S)-1-cyclopropanecarbonyl-2-methyl-6-(1-methyl-1H-imidazol-4-yl)-5-phenoxy-1,2,3,4-tetrahydroquinoline;

methyl (2S)-6-[1-(1,1-dioxo-1$\lambda^6$-thian-3-yl)-1H-pyrazol-4-yl]-5-(4-fluorophenoxy)-2-methyl-1,2,3,4-tetrahydroquinoline-1-carboxylate;

methyl (2S)-6-[1-(1,1-dioxo-1λ⁶-thietan-3-yl)-1H-pyrazol-4-yl]-5-(4-fluorophenoxy)-2-methyl-1,2,3,4-tetrahydroquinoline-1-carboxylate;

(2S)-1-cyclopropanecarbonyl-2-methyl-6-(1-methyl-1H-pyrazol-4-yl)-5-phenoxy-1,2,3,4-tetrahydroquinoline;

1-[(2S)-6-(1-cyclopropyl-1H-pyrazol-4-yl)-5-(4-fluorophenoxy)-2-methyl-1,2,3,4-tetrahydroquinolin-1-yl]ethan-1-one;

1-[(2S)-5-(4-chlorophenoxy)-6-(1-cyclopropyl-1H-pyrazol-4-yl)-2-methyl-1,2,3,4-tetrahydroquinolin-1-yl]ethan-1-one;

methyl (2S)-6-(1-cyclopropyl-1H-pyrazol-4-yl)-5-(2-fluorophenoxy)-2-methyl-1,2,3,4-tetrahydroquinoline-1-carboxylate;

1-[(2S)-6-(1-cyclopropyl-1H-pyrazol-4-yl)-5-(2-fluorophenoxy)-2-methyl-1,2,3,4-tetrahydroquinolin-1-yl]ethan-1-one;

(2S)-1-cyclopropanecarbonyl-2-methyl-5-phenoxy-6-(1H-pyrazol-4-yl)-1,2,3,4-tetrahydroquinoline;

3-{4-[(2S)-1-cyclopropanecarbonyl-5-(4-fluorophenoxy)-2-methyl-1,2,3,4-tetrahydroquinolin-6-yl]-1H-pyrazol-1-yl}-1λ⁶-thietane-1,1-dione;

3-{4-[(2S)-1-cyclopropanecarbonyl-2-methyl-5-phenoxy-1,2,3,4-tetrahydroquinolin-6-yl]-1H-pyrazol-1-yl}-1λ⁶-thietane-1,1-dione;

1-[(2S)-5-(2-chlorophenoxy)-6-(1-cyclopropyl-1H-pyrazol-4-yl)-2-methyl-1,2,3,4-tetrahydroquinolin-1-yl]ethan-1-one;

methyl (2S)-6-(1-cyclopropyl-1H-pyrazol-4-yl)-5-(4-fluorophenoxy)-2-methyl-1,2,3,4-tetrahydroquinoline-1-carboxylate;

methyl (2S)-5-(4-cyanophenoxy)-6-(1-cyclopropyl-1H-pyrazol-4-yl)-2-methyl-1,2,3,4-tetrahydroquinoline-1-carboxylate;

methyl (2S)-5-(4-chlorophenoxy)-6-(1-cyclopropyl-1H-pyrazol-4-yl)-2-methyl-1,2,3,4-tetrahydroquinoline-1-carboxylate;

methyl (2S)-5-(2-chlorophenoxy)-6-(1-cyclopropyl-1H-pyrazol-4-yl)-2-methyl-1,2,3,4-tetrahydroquinoline-1-carboxylate;

methyl (2S)-5-(4-carbamoylphenoxy)-6-(1-cyclopropyl-1H-pyrazol-4-yl)-2-methyl-1,2,3,4-tetrahydroquinoline-1-carboxylate;

4-{[(2S)-1-acetyl-6-(1-cyclopropyl-1H-pyrazol-4-yl)-2-methyl-1,2,3,4-tetrahydroquinolin-5-yl]oxy}benzonitrile;

methyl (2S)-5-(4-chloro-2-cyanophenoxy)-2-methyl-6-[1-(1-methylpiperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-{[1-(propan-2-yl)azetidin-3-yl]oxy}-1,2,3,4-tetrahydroquinolin-1-yl]ethan-1-one;

2-{[(2S)-1-acetyl-2-methyl-6-[1-(1-methylpiperidin-4-yl)-1H-pyrazol-4-yl]-1,2,3,4-tetrahydroquinolin-5-yl]oxy}benzonitrile;

methyl (2S)-5-cyclobutoxy-2-methyl-6-[1-(1-methylpyrrolidin-3-yl)-1H-pyrazol-4-yl]-1,2,3,4-tetrahydroquinoline-1-carboxylate;

methyl (2S)-5-cyclobutoxy-2-methyl-6-(1-{2-methyl-octahydrocyclopenta[c]pyrrol-5-yl}-1H-pyrazol-4-yl)-1,2,3,4-tetrahydroquinoline-1-carboxylate;

methyl (2S)-5-(4-fluorophenoxy)-2-methyl-6-[1-(1-methylpyrrolidin-3-yl)-1H-pyrazol-4-yl]-1,2,3,4-tetrahydroquinoline-1-carboxylate;

methyl (2S)-5-(4-fluorophenoxy)-2-methyl-6-(1-{2-methyl-octahydrocyclopenta[c]pyrrol-5-yl}-1H-pyrazol-4-yl)-1,2,3,4-tetrahydroquinoline-1-carboxylate;

methyl (2S)-6-(1-cyclopropyl-1H-pyrazol-4-yl)-5-[(1-ethylazetidin-3-yl)oxy]-2-methyl-1,2,3,4-tetrahydroquinoline-1-carboxylate;

methyl (2S)-6-(1-cyclopropyl-1H-pyrazol-4-yl)-2-methyl-5-{[1-(propan-2-yl)azetidin-3-yl]oxy}-1,2,3,4-tetrahydroquinoline-1-carboxylate;

1-[(2S)-6-(1-cyclopropyl-1H-pyrazol-4-yl)-5-[(1-ethylazetidin-3-yl)oxy]-2-methyl-1,2,3,4-tetrahydroquinolin-1-yl]ethan-1-one;

1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one;

1-[(2S)-6-(1-cyclopropyl-1H-pyrazol-4-yl)-2-methyl-5-[(6-methylpyridin-2-yl)oxy]-1,2,3,4-tetrahydroquinolin-1-yl]ethan-1-one;

1-[(2S)-6-(1-cyclopropyl-1H-pyrazol-4-yl)-5-(isoquinolin-1-yloxy)-2-methyl-1,2,3,4-tetrahydroquinolin-1-yl]ethan-1-one;

1-[(2S)-5-(2-fluorophenoxy)-2-methyl-6-[1-(piperidin-4-yl)-1H-pyrazol-4-yl]-1,2,3,4-tetrahydroquinolin-1-yl]ethan-1-one;

methyl (2S)-5-(2-fluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2-fluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2-fluorophenoxy)-2-methyl-1,2,3,4-tetrahydroquinoline;

methyl (2S)-6-[1-(azetidin-3-yl)-1H-pyrazol-4-yl]-5-(2-fluorophenoxy)-2-methyl-1,2,3,4-tetrahydroquinoline-1-carboxylate;

methyl (2S)-5-(2,4-difluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2,4-difluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2,4-difluorophenoxy)-2-methyl-1,2,3,4-tetrahydroquinoline;

methyl (2S)-6-[1-(azetidin-3-yl)-1H-pyrazol-4-yl]-5-(2,4-difluorophenoxy)-2-methyl-1,2,3,4-tetrahydroquinoline-1-carboxylate;

(2S)-1-cyclopropanecarbonyl-5-(2,3-difluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2,3-difluorophenoxy)-2-methyl-1,2,3,4-tetrahydroquinoline;

methyl (2S)-5-(2,3-difluorophenoxy)-2-methyl-6-[1-(piperidin-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(2,3-difluorophenoxy)-2-methyl-1,2,3,4-tetrahydroquinoline-1-carboxylate;

methyl (2S)-6-[1-(azetidin-3-yl)-1H-pyrazol-4-yl]-5-(2,5-difluorophenoxy)-2-methyl-1,2,3,4-tetrahydroquinoline-1-carboxylate;

(2S)-6-[1-(azetidin-3-yl)-1H-pyrazol-4-yl]-1-cyclopropanecarbonyl-5-(2,5-difluorophenoxy)-2-methyl-1,2,3,4-tetrahydroquinoline;

methyl (2S)-5-(2,5-difluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2,5-difluorophenoxy)-2-methyl-6-[1-(piperidin-4-yl)-1H-pyrazol-4-yl]-1,2,3,4-tetrahydroquinoline;

1-[(2S)-5-(3,4-difluorophenoxy)-2-methyl-6-[1-(piperidin-4-yl)-1H-pyrazol-4-yl]-1,2,3,4-tetrahydroquinolin-1-yl]ethan-1-one;

1-[(2S)-5-(2,5-difluorophenoxy)-2-methyl-6-[1-(piperidin-4-yl)-1H-pyrazol-4-yl]-1,2,3,4-tetrahydroquinolin-1-yl]ethan-1-one 1-[(2S)-5-{[(E)-2-chloro ethenyl]oxy}-6-(1-cyclopropyl-1H-pyrazol-4-yl)-2-methyl-1,2,3,4-tetrahydroquinolin-1-yl]ethan-1-one;

(2S)-5-cyclobutoxy-1-cyclopropanecarbonyl-2-methyl-6-{1H,2H,3H-pyrazolo[1,5-a]imidazol-7-yl]-1,2,3,4-tetrahydroquinoline;

(2S)-5-cyclobutoxy-1-cyclopropanecarbonyl-6-{1-methanesulfonyl-1H,2H,3H-pyrazolo[1,5-a]imidazol-7-yl}-2-methyl-1,2,3,4-tetrahydroquinoline;

methyl (2S)-5-cyclobutoxy-6-[2-(4-hydroxypiperidin-4-yl)-1,3-thiazol-4-yl]-2-methyl-1,2,3,4-tetrahydroquinoline-1-carboxylate;

methyl (2S)-5-cyclobutoxy-6-[2-(4-fluoropiperidin-4-yl)-1,3-thiazol-4-yl]-2-methyl-1,2,3,4-tetrahydroquinoline-1-carboxylate;

methyl (2S)-5-(4-fluorophenoxy)-2-methyl-6-[1-(1-methylazetidin-3-yl)-1H-pyrazol-4-yl]-1,2,3,4-tetrahydroquinoline-1-carboxylate;

methyl (2S)-5-(4-fluorophenoxy)-2-methyl-6-[1-(1-methylpiperidin-4-yl)-1H-pyrazol-4-yl]-1,2,3,4-tetrahydroquinoline-1-carboxylate;

methyl (2S)-5-cyclobutoxy-2-methyl-6-(1-[1-methylazetidin-3-yl]-1H-pyrazol-4-yl]-1,2,3,4-tetrahydroquinoline-1-carboxylate;

methyl (2S)-5-cyclobutoxy-2-methyl-6-[1-(1-methylpiperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-[(3-methylpyridin-2-yl)oxy]-1,2,3,4-tetrahydroquinolin-1-yl]ethan-1-one;

1-[(2S)-6-(1-cyclopropyl-1H-pyrazol-4-yl)-2-methyl-5-[(5-methylpyridin-2-yl)oxy]-1,2,3,4-tetrahydroquinolin-1-yl]ethan-1-one;

1-[(2S)-5-[(5-chloropyridin-2-yl)oxy]-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(7H-purin-2-yloxy)-1,2,3,4-tetrahydroquinolin-1-yl]ethan-1-one;

methyl (2S)-5-cyclobutoxy-6-[1-(3-methoxypiperidin-4-yl)-1H-pyrazol-4-yl]-2-methyl-1,2,3,4-tetrahydroquinoline-1-carboxylate;

methyl (2S)-5-(4-fluorophenoxy)-6-[1-(3-methoxypiperidin-4-yl)-1H-pyrazol-4-yl]-2-methyl-1,2,3,4-tetrahydroquinoline-1-carboxylate;

methyl (2S)-5-cyclobutoxy-6-[1-(3-methoxy-1-methylpiperidin-4-yl)-1H-pyrazol-4-yl]-2-methyl-1,2,3,4-tetrahydroquinoline-1-carboxylate;

methyl (2S)-5-(4-fluorophenoxy)-6-[1-(3-methoxy-1-methylpiperidin-4-yl)-1H-pyrazol-4-yl]-2-methyl-1,2,3,4-tetrahydroquinoline-1-carboxylate;

3-{4-[(2S)-1-cyclopropanecarbonyl-2-methyl-5-phenoxy-1,2,3,4-tetrahydroquinolin-6-yl]-1H-pyrazol-1-yl}-1$\lambda^6$-thiane-1,1-dione;

3-{4-[(2S)-1-cyclopropanecarbonyl-5-(4-fluorophenoxy)-2-methyl-1,2,3,4-tetrahydroquinolin-6-yl]-1H-pyrazol-1-yl}-1$\lambda^6$-thiane-1,1-dione;

methyl (2S)-5-cyclobutoxy-2-methyl-6-[1-(2-oxopiperidin-4-yl)-1H-pyrazol-4-yl]-1,2,3,4-tetrahydroquinoline-1-carboxylate;

methyl (2S)-5-(4-fluorophenoxy)-2-methyl-6-[1-(2-oxopiperidin-4-yl)-1H-pyrazol-4-yl]-1,2,3,4-tetrahydroquinoline-1-carboxylate;

methyl (2S)-5-(4-fluorophenoxy)-2-methyl-6-{1-[(2S)-2-methylazetidin-3-yl]-1H-pyrazol-4-yl}-1,2,3,4-tetrahydroquinoline-1-carboxylate;

methyl (2S)-5-cyclobutoxy-2-methyl-6-{1-[(2S)-2-methylazetidin-3-yl]-1H-pyrazol-4-yl}-1,2,3,4-tetrahydroquinoline-1-carboxylate;

N-{4-[(2S)-5-cyclobutoxy-1-cyclopropanecarbonyl-2-methyl-1,2,3,4-tetrahydroquinolin-6-yl]-1-cyclopropyl-1H-pyrazol-5-yl}methanesulfonamide;

N-{4-[(2S)-5-cyclobutoxy-1-cyclopropanecarbonyl-2-methyl-1,2,3,4-tetrahydroquinolin-6-yl]-1-cyclopropyl-1H-pyrazol-5-yl}acetamide;

methyl (2S)-5-cyclobutoxy-6-[1-(3-hydroxycyclobutyl)-1H-pyrazol-4-yl]-2-methyl-1,2,3,4-tetrahydroquinoline-1-carboxylate;

methyl (2S)-5-cyclobutoxy-2-methyl-6-[2-(piperidin-4-yl)-1H-imidazol-4-yl]-1,2,3,4-tetrahydroquinoline-1-carboxylate;

methyl (2S)-5-cyclobutoxy-2-methyl-6-[1-methyl-2-(piperidin-4-yl)-1H-imidazol-4-yl]-1,2,3,4-tetrahydroquinoline-1-carboxylate;

2-{[(2S)-1-acetyl-2-methyl-6-[1-(oxetan-3-yl)-1H-pyrazol-4-yl]-1,2,3,4-tetrahydroquinolin-5-yl]oxy}-N-methylacetamide;

1-[(2S)-2-methyl-5-(1,2-oxazol-5-ylmethoxy)-6-[1-(oxetan-3-yl)-1H-pyrazol-4-yl]-1,2,3,4-tetrahydroquinolin-1-yl]ethan-1-one;

N-(2-{[(2S)-1-acetyl-2-methyl-6-[1-(oxetan-3-yl)-1H-pyrazol-4-yl]-1,2,3,4-tetrahydroquinolin-5-yl]oxy}ethyl)methanesulfonamide;

1-[(2S)-6-(1-cyclopropyl-1H-pyrazol-4-yl)-2-methyl-5-(1,2-oxazol-5-ylmethoxy)-1,2,3,4-tetrahydroquinolin-1-yl]ethan-1-one;

N-(2-{[(2S)-1-acetyl-6-(1-cyclopropyl-1H-pyrazol-4-yl)-2-methyl-1,2,3,4-tetrahydroquinolin-5-yl]oxy}ethyl)methanesulfonamide;

2-{[(2S)-1-acetyl-6-(1-cyclopropyl-1H-pyrazol-4-yl)-2-methyl-1,2,3,4-tetrahydroquinolin-5-yl]oxy}-N-methylacetamide;

1-[(2S)-6-(1-cyclopropyl-1H-pyrazol-4-yl)-2-methyl-5-(oxetan-3-yloxy)-1,2,3,4-tetrahydroquinolin-1-yl]ethan-1-one;

1-[(2S)-5-(cyclopentylmethoxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-5-[2-(dimethylamino)ethoxy]-2-methyl-1,2,3,4-tetrahydroquinolin-1-yl]ethan-1-one;

1-[(2S)-6-(1-cyclopropyl-1H-pyrazol-4-yl)-2-methyl-5-propoxy-1,2,3,4-tetrahydroquinolin-1-yl]ethan-1-one;

1-[(2S)-6-(1-cyclopropyl-1H-pyrazol-4-yl)-2-methyl-5-(propan-2-yloxy)-1,2,3,4-tetrahydroquinolin-1-yl]ethan-1-one;

1-[(2S)-5-cyclobutoxy-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-5-(cyclopropylmethoxy)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}acetamide;

1-[(2S)-5-(cyclobutylmethoxy)-6-(1-cyclopropyl-1H-pyrazol-4-yl)-2-methyl-1,2,3,4-tetrahydroquinolin-1-yl]ethan-1-one;

1-[(2S)-5-(benzyloxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(2-methylpropoxy)-1,2,3,4-tetrahydroquinolin-1-yl]ethan-1-one;

1-[(2S)-6-(1-cyclopropyl-1H-pyrazol-4-yl)-2-methyl-5-[(3-methyloxetan-3-yl)methoxy]-1,2,3,4-tetrahydroquinolin-1-yl]ethan-1-one;

1-[(2S)-5-(cyclopentyloxy)-6-(1-cyclopropyl-1H-pyrazol-4-yl)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}acetonitrile;

1-[(2S)-6-(1-cyclopropyl-1H-pyrazol-4-yl)-5-(2-methoxyethoxy)-2-methyl-1,2,3,4-tetrahydroquinolin-1-yl]ethan-1-one;

1-[(2S)-6-(1-cyclopropyl-1H-pyrazol-4-yl)-2-methyl-5-(pyridin-3-ylmethoxy)-1,2,3,4-tetrahydroquinolin-1-yl]ethan-1-one;

1-[(2S)-6-(1-cyclopropyl-1H-pyrazol-4-yl)-2-methyl-5-(oxan-4-ylmethoxy)-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}-N,N-dimethylacetamide;

1-[(2S)-5-(cyclohexylmethoxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(pyridin-2-ylmethoxy)-1,2,3,4-tetrahydroquinolin-1-yl]ethan-1-one;

1-[(2S)-6-(1-cyclopropyl-1H-pyrazol-4-yl)-5-methoxy-2-methyl-1,2,3,4-tetrahydroquinolin-1-yl]ethan-1-one;

1-[(2S)-6-(1-cyclopropyl-1H-pyrazol-4-yl)-2-methyl-5-[(1-methyl-1H-pyrazol-3-yl)methoxy]-1,2,3,4-tetrahydroquinolin-1-yl]ethan-1-one;

1-[(2S)-6-(1-cyclopropyl-1H-pyrazol-4-yl)-2-methyl-5-(1,3-thiazol-5-ylmethoxy)-1,2,3,4-tetrahydroquinolin-1-yl]ethan-1-one;

1-[(2S)-6-[1-(2-methanesulfonylethyl)-1H-pyrazol-4-yl]-2-methyl-5-propoxy-1,2,3,4-tetrahydroquinolin-1-yl]ethan-1-one;

1-[(2S)-6-[1-(2-hydroxy-2-methylpropyl)-1H-pyrazol-4-yl]-2-methyl-5-propoxy-1,2,3,4-tetrahydroquinolin-1-yl]ethan-1-one;

1-[(2S)-5-cyclobutoxy-6-[1-(2-methanesulfonylethyl)-1H-pyrazol-4-yl]-2-methyl-1,2,3,4-tetrahydroquinolin-1-yl]ethan-1-one;

1-[(2S)-5-cyclobutoxy-6-[1-(2-hydroxy-2-methylpropyl)-1H-pyrazol-4-yl]-2-methyl-1,2,3,4-tetrahydroquinolin-1-yl]ethan-1-one;

1-[(2S)-5-cyclobutoxy-6-[1-(2-hydroxyethyl)-1H-pyrazol-4-yl]-2-methyl-1,2,3,4-tetrahydroquinolin-1-yl]ethan-1-one;

1-[(2S)-5-cyclobutoxy-2-methyl-6-[1-(piperidin-4-yl)-1H-pyrazol-4-yl]-1,2,3,4-tetrahydroquinolin-1-yl]ethan-1-one;

1-[(2S)-6-[1-(2-methanesulfonylethyl)-1H-pyrazol-4-yl]-2-methyl-5-(oxan-4-ylmethoxy)-1,2,3,4-tetrahydroquinolin-1-yl]ethan-1-one;

1-[(2S)-6-[1-(2-hydroxy-2-methylpropyl)-1H-pyrazol-4-yl]-2-methyl-5-(oxan-4-ylmethoxy)-1,2,3,4-tetrahydroquinolin-1-yl]ethan-1-one;

1-[(2S)-6-[1-(2-hydroxyethyl)-1H-pyrazol-4-yl]-2-methyl-5-(oxan-4-ylmethoxy)-1,2,3,4-tetrahydroquinolin-1-yl]ethan-1-one;

1-[(2S)-2-methyl-5-(oxan-4-ylmethoxy)-6-[1-(piperidin-4-yl)-1H-pyrazol-4-yl]-1,2,3,4-tetrahydroquinolin-1-yl]ethan-1-one;

2-{[(2S)-1-acetyl-6-[1-(2-methanesulfonylethyl)-1H-pyrazol-4-yl]-2-methyl-1,2,3,4-tetrahydroquinolin-5-yl]oxy}-N,N-dimethylacetamide;

2-{[(2S)-1-acetyl-6-[1-(2-hydroxy-2-methylpropyl)-1H-pyrazol-4-yl]-2-methyl-1,2,3,4-tetrahydroquinolin-5-yl]oxy}-N,N-dimethylacetamide;

2-{[(2S)-1-acetyl-2-methyl-6-[1-(piperidin-4-yl)-1H-pyrazol-4-yl]-1,2,3,4-tetrahydroquinolin-5-yl]oxy}-N,N-dimethylacetamide;

1-[(2S)-6-[1-(2-methanesulfonylethyl)-1H-pyrazol-4-yl]-2-methyl-5-(2-methylpropoxy)-1,2,3,4-tetrahydroquinolin-1-yl]ethan-1-one;

1-[(2S)-6-[1-(2-hydroxy-2-methylpropyl)-1H-pyrazol-4-yl]-2-methyl-5-(2-methylpropoxy)-1,2,3,4-tetrahydroquinolin-1-yl]ethan-1-one;

1-[(2S)-6-[1-(2-hydroxyethyl)-1H-pyrazol-4-yl]-2-methyl-5-(2-methylpropoxy)-1,2,3,4-tetrahydroquinolin-1-yl]ethan-1-one;

1-[(2S)-2-methyl-5-(2-methylpropoxy)-6-[1-(piperidin-4-yl)-1H-pyrazol-4-yl]-1,2,3,4-tetrahydroquinolin-1-yl]ethan-1-one;

1-[(2S)-5-(cyclopentylmethoxy)-6-[1-(2-methanesulfonylethyl)-1H-pyrazol-4-yl]-2-methyl-1,2,3,4-tetrahydroquinolin-1-yl]ethan-1-one;

1-[(2S)-5-(cyclopentylmethoxy)-6-[1-(2-hydroxy-2-methylpropyl)-1H-pyrazol-4-yl]-2-methyl-1,2,3,4-tetrahydroquinolin-1-yl]ethan-1-one;

1-[(2S)-5-(cyclopentylmethoxy)-6-[1-(2-hydroxyethyl)-1H-pyrazol-4-yl]-2-methyl-1,2,3,4-tetrahydroquinolin-1-yl]ethan-1-one;

1-[(2S)-5-(cyclopentylmethoxy)-2-methyl-6-[1-(piperidin-4-yl)-1H-pyrazol-4-yl]-1,2,3,4-tetrahydroquinolin-1-yl]ethan-1-one;

2-{[(2S)-1-acetyl-6-[1-(2-methanesulfonylethyl)-1H-pyrazol-4-yl]-2-methyl-1,2,3,4-tetrahydroquinolin-5-yl]oxy}-1-(pyrrolidin-1-yl)ethan-1-one;

2-{[(2S)-1-acetyl-6-[1-(2-hydroxy-2-methylpropyl)-1H-pyrazol-4-yl]-2-methyl-1,2,3,4-tetrahydroquinolin-5-yl]oxy}-1-(pyrrolidin-1-yl)ethan-1-one;

2-{[(2S)-1-acetyl-6-[1-(2-hydroxyethyl)-1H-pyrazol-4-yl]-2-methyl-1,2,3,4-tetrahydroquinolin-5-yl]oxy}-1-(pyrrolidin-1-yl)ethan-1-one;

2-{[(2S)-1-acetyl-2-methyl-6-[1-(piperidin-4-yl)-1H-pyrazol-4-yl]-1,2,3,4-tetrahydroquinolin-5-yl]oxy}-1-(pyrrolidin-1-yl)ethan-1-one;

(5R)-5-({[(2S)-1-acetyl-6-[1-(2-methanesulfonylethyl)-1H-pyrazol-4-yl]-2-methyl-1,2,3,4-tetrahydroquinolin-5-yl]oxy}methyl)pyrrolidin-2-one;

(5R)-5-({[(2S)-1-acetyl-6-[1-(2-hydroxy-2-methylpropyl)-1H-pyrazol-4-yl]-2-methyl-1,2,3,4-tetrahydroquinolin-5-yl]oxy}methyl)pyrrolidin-2-one;

(5R)-5-({[(2S)-1-acetyl-6-[1-(2-hydroxyethyl)-1H-pyrazol-4-yl]-2-methyl-1,2,3,4-tetrahydroquinolin-5-yl]oxy}methyl)pyrrolidin-2-one;

(5R)-5-({[(2S)-1-acetyl-2-methyl-6-[1-(piperidin-4-yl)-1H-pyrazol-4-yl]-1,2,3,4-tetrahydroquinolin-5-yl]oxy}methyl)pyrrolidin-2-one;

N-(2-{[(2S)-1-acetyl-6-[1-(2-methanesulfonylethyl)-1H-pyrazol-4-yl]-2-methyl-1,2,3,4-tetrahydroquinolin-5-yl]oxy}ethyl)-N-methylmethanesulfonamide;

N-(2-{[(2S)-1-acetyl-6-[1-(2-hydroxy-2-methylpropyl)-1H-pyrazol-4-yl]-2-methyl-1,2,3,4-tetrahydroquinolin-5-yl]oxy}ethyl)-N-methylmethanesulfonamide;

N-(2-{[(2S)-1-acetyl-6-[1-(2-hydroxyethyl)-1H-pyrazol-4-yl]-2-methyl-1,2,3,4-tetrahydroquinolin-5-yl]oxy}ethyl)-N-methylmethanesulfonamide;

N-(2-{[(2S)-1-acetyl-2-methyl-6-[1-(piperidin-4-yl)-1H-pyrazol-4-yl]-1,2,3,4-tetrahydroquinolin-5-yl]oxy}ethyl)-N-methylmethanesulfonamide;

1-[(2S)-6-[1-(2-hydroxyethyl)-1H-pyrazol-4-yl]-2-methyl-5-[(3S)-pyrrolidin-3-ylmethoxy]-1,2,3,4-tetrahydroquinolin-1-yl]ethan-1-one;

methyl (2S)-6-[1-(2-methanesulfonylethyl)-1H-pyrazol-4-yl]-2-methyl-5-propoxy-1,2,3,4-tetrahydroquinoline-1-carboxylate;

methyl (2S)-6-[1-(2-hydroxy-2-methylpropyl)-1H-pyrazol-4-yl]-2-methyl-5-propoxy-1,2,3,4-tetrahydroquinoline-1-carboxylate;

methyl (2S)-6-[1-(2-hydroxyethyl)-1H-pyrazol-4-yl]-2-methyl-5-propoxy-1,2,3,4-tetrahydroquinoline-1-carboxylate;

methyl (2S)-5-cyclobutoxy-6-[1-(2-methanesulfonylethyl)-1H-pyrazol-4-yl]-2-methyl-1,2,3,4-tetrahydroquinoline-1-carboxylate;

methyl (2S)-5-cyclobutoxy-6-[1-(2-hydroxy-2-methylpropyl)-1H-pyrazol-4-yl]-2-methyl-1,2,3,4-tetrahydroquinoline-1-carboxylate;

methyl (2S)-5-cyclobutoxy-6-[1-(2-hydroxyethyl)-1H-pyrazol-4-yl]-2-methyl-1,2,3,4-tetrahydroquinoline-1-carboxylate;

methyl (2S)-5-cyclobutoxy-2-methyl-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-(oxan-4-ylmethoxy)-1,2,3,4-tetrahydroquinoline-1-carboxylate;

methyl (2S)-6-[1-(2-hydroxy-2-methylpropyl)-1H-pyrazol-4-yl]-2-methyl-5-(oxan-4-ylmethoxy)-1,2,3,4-tetrahydroquinoline-1-carboxylate;

methyl (2S)-6-[1-(2-hydroxyethyl)-1H-pyrazol-4-yl]-2-methyl-5-(oxan-4-ylmethoxy)-1,2,3,4-tetrahydroquinoline-1-carboxylate;

methyl (2S)-2-methyl-5-(oxan-4-ylmethoxy)-6-[1-(piperidin-4-yl)-1H-pyrazol-4-yl]-1,2,3,4-tetrahydroquinoline-1-carboxylate;

methyl (2S)-5-[(dimethylcarbamoyl)methoxy]-6-[1-(2-methanesulfonylethyl)-1H-pyrazol-4-yl]-2-methyl-1,2,3,4-tetrahydroquinoline-1-carboxylate;

methyl (2S)-5-[(dimethylcarbamoyl)methoxy]-6-[1-(2-hydroxy-2-methylpropyl)-1H-pyrazol-4-yl]-2-methyl-1,2,3,4-tetrahydroquinoline-1-carboxylate;

methyl (2S)-5-[(dimethylcarbamoyl)methoxy]-2-methyl-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-(2-methylpropoxy)-1,2,3,4-tetrahydroquinoline-1-carboxylate;

methyl (2S)-6-[1-(2-hydroxy-2-methylpropyl)-1H-pyrazol-4-yl]-2-methyl-5-(2-methylpropoxy)-1,2,3,4-tetrahydroquinoline-1-carboxylate;

methyl (2S)-6-[1-(2-hydroxyethyl)-1H-pyrazol-4-yl]-2-methyl-5-(2-methylpropoxy)-1,2,3,4-tetrahydroquinoline-1-carboxylate;

methyl (2S)-2-methyl-5-(2-methylpropoxy)-6-[1-(piperidin-4-yl)-1H-pyrazol-4-yl]-1,2,3,4-tetrahydroquinoline-1-carboxylate;

methyl (2S)-5-(cyclopentylmethoxy)-6-[1-(2-methanesulfonylethyl)-1H-pyrazol-4-yl]-2-methyl-1,2,3,4-tetrahydroquinoline-1-carboxylate;

methyl (2S)-5-(cyclopentylmethoxy)-6-[1-(2-hydroxy-2-methylpropyl)-1H-pyrazol-4-yl]-2-methyl-1,2,3,4-tetrahydroquinoline-1-carboxylate;

methyl (2S)-5-(cyclopentylmethoxy)-6-[1-(2-hydroxyethyl)-1H-pyrazol-4-yl]-2-methyl-1,2,3,4-tetrahydroquinoline-1-carboxylate;

methyl (2S)-5-(cyclopentylmethoxy)-2-methyl-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-6-[1-(2-hydroxyethyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-2-methyl-5-[2-oxo-2-(pyrrolidin-1-yl)ethoxy]-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-6-[1-(2-hydroxy-2-methylpropyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-6-[1-(2-hydroxyethyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-2-methyl-5-{[(2R)-5-oxopyrrolidin-2-yl]methoxy}-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[2-(N-methylmethanesulfonamido)ethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[2-(N-methylmethanesulfonamido)ethoxy]-1,2,3,4-tetrahydroquinoline-1-carboxylate;

methyl (2S)-6-[1-(2-hydroxyethyl)-1H-pyrazol-4-yl]-2-methyl-5-[2-(N-methylmethanesulfonamido)ethoxy]-1,2,3,4-tetrahydroquinoline-1-carboxylate;

methyl (2S)-2-methyl-5-[2-(N-methylmethanesulfonamido)ethoxy]-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[(3S)-pyrrolidin-3-ylmethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[(3S)-pyrrolidin-3-ylmethoxy]-1,2,3,4-tetrahydroquinoline-1-carboxylate;

methyl (2S)-6-[1-(2-hydroxyethyl)-1H-pyrazol-4-yl]-2-methyl-5-[(3S)-pyrrolidin-3-ylmethoxy]-1,2,3,4-tetrahydroquinoline-1-carboxylate;

methyl (2S)-2-methyl-6-[1-(piperidin-4-yl)-1H-pyrazol-4-yl]-5-[(3S)-pyrrolidin-3-ylmethoxy]-1,2,3,4-tetrahydroquinoline-1-carboxylate;

1-[(2S)-6-(1-cyclopropyl-1H-pyrazol-4-yl)-2-methyl-5-[(5-methyl-1,3-oxazol-2-yl)methoxy]-1,2,3,4-tetrahydroquinolin-1-yl]ethan-1-one;

1-[(2S)-6-(1-cyclopropyl-1H-pyrazol-4-yl)-2-methyl-5-(pyridin-4-ylmethoxy)-1,2,3,4-tetrahydroquinolin-1-yl]ethan-1-one;

1-[(2S)-5-(1,3-benzoxazol-2-ylmethoxy)-6-(1-cyclopropyl-1H-pyrazol-4-yl)-2-methyl-1,2,3,4-tetrahydroquinolin-1-yl]ethan-1-one;
1-[(2S)-6-(4-methanesulfonylphenyl)-2-methyl-5-propoxy-1,2,3,4-tetrahydroquinolin-1-yl]ethan-1-one;
2-{[(2S)-1-acetyl-6-(4-methanesulfonylphenyl)-2-methyl-1,2,3,4-tetrahydroquinolin-5-yl]oxy}-N,N-dimethylacetamide;
1-[(2S)-6-[4-(ethanesulfonyl)phenyl]-2-methyl-5-propoxy-1,2,3,4-tetrahydroquinolin-1-yl]ethan-1-one;
2-{[(2S)-1-acetyl-6-[4-(ethanesulfonyl)phenyl]-2-methyl-1,2,3,4-tetrahydroquinolin-5-yl]oxy}-N,N-dimethylacetamide;
1-[(2S)-6-{4-[2-(dimethylamino)ethoxy]phenyl}-2-methyl-5-propoxy-1,2,3,4-tetrahydroquinolin-1-yl]ethan-1-one;
2-{[(2S)-1-acetyl-6-{4-[2-(dimethylamino)ethoxy]phenyl}-2-methyl-1,2,3,4-tetrahydroquinolin-5-yl]oxy}-N,N-dimethylacetamide;
1-[(2S)-2-methyl-6-[3-(morpholine-4-carbonyl)phenyl]-5-propoxy-1,2,3,4-tetrahydroquinolin-1-yl]ethan-1-one;
2-{[(2S)-1-acetyl-2-methyl-6-[3-(morpholine-4-carbonyl)phenyl]-1,2,3,4-tetrahydroquinolin-5-yl]oxy}-N,N-dimethylacetamide;
N-{3-[(2S)-1-acetyl-2-methyl-5-propoxy-1,2,3,4-tetrahydroquinolin-6-yl]phenyl}methanesulfonamide;
2-{[(2S)-1-acetyl-6-(3-methanesulfonamidophenyl)-2-methyl-1,2,3,4-tetrahydroquinolin-5-yl]oxy}-N,N-dimethylacetamide;
1-[(2S)-6-(3-methanesulfonylphenyl)-2-methyl-5-propoxy-1,2,3,4-tetrahydroquinolin-1-yl]ethan-1-one;
2-{[(2S)-1-acetyl-6-(3-methanesulfonylphenyl)-2-methyl-1,2,3,4-tetrahydroquinolin-5-yl]oxy}-N,N-dimethylacetamide;
N-{4-[(2S)-1-acetyl-2-methyl-5-propoxy-1,2,3,4-tetrahydroquinolin-6-yl]phenyl}methanesulfonamide;
2-{[(2S)-1-acetyl-6-(4-methanesulfonamidophenyl)-2-methyl-1,2,3,4-tetrahydroquinolin-5-yl]oxy}-N,N-dimethylacetamide;
1-[(2S)-2-methyl-6-[4-(morpholine-4-carbonyl)phenyl]-5-propoxy-1,2,3,4-tetrahydroquinolin-1-yl]ethan-1-one;
2-{[(2S)-1-acetyl-2-methyl-6-[4-(morpholine-4-carbonyl)phenyl]-1,2,3,4-tetrahydroquinolin-5-yl]oxy}-N,N-dimethylacetamide;
2-{4-[(2S)-1-acetyl-2-methyl-5-propoxy-1,2,3,4-tetrahydroquinolin-6-yl]phenyl}-1$\lambda^6$,2-thiazolidine-1,1-dione;
2-{[(2S)-1-acetyl-6-[4-(1,1-dioxo-1$\lambda^6$,2-thiazolidin-2-yl)phenyl]-2-methyl-1,2,3,4-tetrahydroquinolin-5-yl]oxy}-N,N-dimethylacetamide;
1-[(2S)-6-(1-methanesulfonyl-2,3-dihydro-1H-indol-5-yl)-2-methyl-5-propoxy-1,2,3,4-tetrahydroquinolin-1-yl]ethan-1-one;
2-{[(2S)-1-acetyl-6-(1-methanesulfonyl-2,3-dihydro-1H-indol-5-yl)-2-methyl-1,2,3,4-tetrahydroquinolin-5-yl]oxy}-N,N-dimethylacetamide;
N-{4-[(2S)-1-acetyl-2-methyl-5-propoxy-1,2,3,4-tetrahydroquinolin-6-yl]phenyl}-N-methylmethanesulfonamide;
2-{[(2S)-1-acetyl-2-methyl-6-[4-(N-methylmethanesulfonamido)phenyl]-1,2,3,4-tetrahydroquinolin-5-yl]oxy}-N,N-dimethylacetamide;
1-[(2S)-6-(1-benzofuran-2-yl)-2-methyl-5-propoxy-1,2,3,4-tetrahydroquinolin-1-yl]ethan-1-one;
1-[(2S)-6-(1H-indol-2-yl)-2-methyl-5-propoxy-1,2,3,4-tetrahydroquinolin-1-yl]ethan-1-one;
methyl (2S)-6-[1-(azetidin-3-yl)-1H-pyrazol-4-yl]-5-cyclobutoxy-2-methyl-1,2,3,4-tetrahydroquinoline-1-carboxylate;
methyl (2S)-6-[1-(azetidin-3-yl)-1H-pyrazol-4-yl]-2-methyl-5-propoxy-1,2,3,4-tetrahydroquinoline-1-carboxylate;
(2S)-5-cyclobutoxy-1-cyclopropanecarbonyl-2-methyl-6-[1-(oxan-4-yl)-1H-pyrazol-4-yl]-1,2,3,4-tetrahydroquinoline;
3-{4-[(2S)-5-cyclobutoxy-1-cyclopropanecarbonyl-2-methyl-1,2,3,4-tetrahydroquinolin-6-yl]-1H-pyrazol-1-yl}-1$\lambda^6$-thiane-1,1-dione;
3-{4-[(2S)-5-cyclobutoxy-1-cyclopropanecarbonyl-2-methyl-1,2,3,4-tetrahydroquinolin-6-yl]-1H-pyrazol-1-yl}-1$\lambda^6$-thietane-1,1-dione;
1-[(2S)-5-[(5-fluoropyrimidin-2-yl)oxy]-2-methyl-6-[1-(piperidin-4-yl)-1H-pyrazol-4-yl]-1,2,3,4-tetrahydroquinolin-1-yl]ethan-1-one;
1-[(2S)-2-methyl-6-[1-(piperidin-4-yl)-1H-pyrazol-4-yl]-5-{[5-(trifluoromethyl)pyridin-2-yl]oxy}-1,2,3,4-tetrahydroquinolin-1-yl]ethan-1-one;
1-[(2S)-2-methyl-6-[1-(piperidin-4-yl)-1H-pyrazol-4-yl]-5-(pyrimidin-2-yloxy)-1,2,3,4-tetrahydroquinolin-1-yl]ethan-1-one;
1-[(2S)-2-methyl-6-[1-(piperidin-4-yl)-1H-pyrazol-4-yl]-5-{[4-(trifluoromethyl)pyrimidin-2-yl]oxy}-1,2,3,4-tetrahydroquinolin-1-yl]ethan-1-one;
1-[(2S)-2-methyl-6-[1-(piperidin-4-yl)-1H-pyrazol-4-yl]-5-{[2-(trifluoromethyl)pyrimidin-4-yl]oxy}-1,2,3,4-tetrahydroquinolin-1-yl]ethan-1-one;
1-[(2S)-2-methyl-5-{[6-(morpholin-4-yl)pyrimidin-4-yl]oxy}-6-[1-(piperidin-4-yl)-1H-pyrazol-4-yl]-1,2,3,4-tetrahydroquinolin-1-yl]ethan-1-one;
1-[(2S)-5-[(6-cyclopropylpyrimidin-4-yl)oxy]-2-methyl-6-[1-(piperidin-4-yl)-1H-pyrazol-4-yl]-1,2,3,4-tetrahydroquinolin-1-yl]ethan-1-one;
1-[(2S)-5-[(5-cyclopropylpyrimidin-2-yl)oxy]-2-methyl-6-[1-(piperidin-4-yl)-1H-pyrazol-4-yl]-1,2,3,4-tetrahydroquinolin-1-yl]ethan-1-one;
1-[(2S)-2-methyl-6-[1-(piperidin-4-yl)-1H-pyrazol-4-yl]-5-{[5-(trifluoromethyl)pyrimidin-2-yl]oxy}-1,2,3,4-tetrahydroquinolin-1-yl]ethan-1-one;
2-{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxamide;
1-[(2S)-5-{[3-fluoro-5-(trifluoromethyl)pyridin-2-yl]oxy}-2-methyl-6-[1-(piperidin-4-yl)-1H-pyrazol-4-yl]-1,2,3,4-tetrahydroquinolin-1-yl]ethan-1-one;
methyl 6-{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxylate;
6-{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxamide;
methyl (2S)-2-methyl-6-[1-(piperidin-4-yl)-1H-pyrazol-4-yl]-5-{[5-(trifluoromethyl)pyridin-2-yl]oxy}-1,2,3,4-tetrahydroquinoline-1-carboxylate;
methyl (2S)-2-methyl-6-[1-(piperidin-4-yl)-1H-pyrazol-4-yl]-5-(pyrimidin-2-yloxy)-1,2,3,4-tetrahydroquinoline-1-carboxylate;
methyl (2S)-2-methyl-6-[1-(piperidin-4-yl)-1H-pyrazol-4-yl]-5-(pyrazin-2-yloxy)-1,2,3,4-tetrahydroquinoline-1-carboxylate;
methyl (2S)-2-methyl-6-[1-(piperidin-4-yl)-1H-pyrazol-4-yl]-5-{[3-(trifluoromethyl)pyridin-2-yl]oxy}-1,2,3,4-tetrahydroquinoline-1-carboxylate;
methyl (2S)-2-methyl-6-[1-(piperidin-4-yl)-1H-pyrazol-4-yl]-5-{[4-(trifluoromethyl)pyrimidin-2-yl]oxy}-1,2,3,4-tetrahydroquinoline-1-carboxylate;

methyl (2S)-2-methyl-6-[1-(piperidin-4-yl)-1H-pyrazol-4-yl]-5-{[2-(trifluoromethyl)pyrimidin-4-yl]oxy}-1,2,3,4-tetrahydroquinoline-1-carboxylate;
methyl (2S)-2-methyl-5-{[6-(morpholin-4-yl)pyrimidin-4-yl]oxy}-6-[1-(piperidin-4-yl)-1H-pyrazol-4-yl]-1,2,3,4-tetrahydroquinoline-1-carboxylate;
methyl (2S)-5-[(6-cyclopropylpyrimidin-4-yl)oxy]-2-methyl-6-[1-(piperidin-4-yl)-1H-pyrazol-4-yl]-1,2,3,4-tetrahydroquinoline-1-carboxylate;
methyl (2S)-5-[(5-cyclopropylpyrimidin-2-yl)oxy]-2-methyl-6-[1-(piperidin-4-yl)-1H-pyrazol-4-yl]-1,2,3,4-tetrahydroquinoline-1-carboxylate;
methyl (2S)-5-[(5-fluoropyrimidin-2-yl)oxy]-2-methyl-6-[1-(piperidin-4-yl)-1H-pyrazol-4-yl]-1,2,3,4-tetrahydroquinoline-1-carboxylate;
methyl (2S)-2-methyl-6-[1-(piperidin-4-yl)-1H-pyrazol-4-yl]-5-{[5-(trifluoromethyl)pyrimidin-2-yl]oxy}-1,2,3,4-tetrahydroquinoline-1-carboxylate;
methyl (2S)-2-methyl-5-[(5-methylpyrimidin-2-yl)oxy]-6-[1-(piperidin-4-yl)-1H-pyrazol-4-yl]-1,2,3,4-tetrahydroquinoline-1-carboxylate;
methyl (2S)-5-{[3-fluoro-5-(trifluoromethyl)pyridin-2-yl]oxy}-2-methyl-6-[1-(piperidin-4-yl)-1H-pyrazol-4-yl]-1,2,3,4-tetrahydroquinoline-1-carboxylate;
methyl (2S)-5-{[5-(methoxycarbonyl)pyridin-2-yl]oxy}-2-methyl-6-[1-(piperidin-4-yl)-1H-pyrazol-4-yl]-1,2,3,4-tetrahydroquinoline-1-carboxylate;
methyl (2S)-5-[(5-carbamoylpyridin-2-yl)oxy]-2-methyl-6-[1-(piperidin-4-yl)-1H-pyrazol-4-yl]-1,2,3,4-tetrahydroquinoline-1-carboxylate;
(2S)-1-cyclopropanecarbonyl-2-methyl-6-[1-(piperidin-4-yl)-1H-pyrazol-4-yl]-5-{[3-(trifluoromethyl)pyridin-2-yl]oxy}-1,2,3,4-tetrahydroquinoline;
2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}pyridine-3-carbonitrile;
(2S)-1-cyclopropanecarbonyl-2-methyl-6-[1-(piperidin-4-yl)-1H-pyrazol-4-yl]-5-{[5-(trifluoromethyl)pyridin-2-yl]oxy}-1,2,3,4-tetrahydroquinoline;
1-[(2S)-6-[1-(2-hydroxyethyl)-1H-pyrazol-4-yl]-2-methyl-5-{[5-(trifluoromethyl)pyrimidin-2-yl]oxy}-1,2,3,4-tetrahydroquinolin-1-yl]ethan-1-one;
1-[(2S)-5-[(5-fluoropyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-5-[(4,6-dimethylpyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-6-[1-(2-hydroxyethyl)-1H-pyrazol-4-yl]-2-methyl-5-{[5-(propan-2-yl)pyrimidin-2-yl]oxy}-1,2,3,4-tetrahydroquinolin-1-yl]ethan-1-one;
1-[(2S)-6-[1-(2-hydroxyethyl)-1H-pyrazol-4-yl]-2-methyl-5-[(5-methoxypyrimidin-2-yl)oxy]-1,2,3,4-tetrahydroquinolin-1-yl]ethan-1-one;
1-[(2S)-5-[(5-cyclopropylpyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-(1-methane sulfonyl-2,3-dihydro-1H-indol-5-yl)-2-methyl-1,2,3,4-tetrahydroquinolin-1-yl]ethan-1-one;
1-[(2S)-5-[(5-fluoropyrimidin-2-yl)oxy]-6-(4-methanesulfonylphenyl)-2-methyl-1,2,3,4-tetrahydroquinolin-1-yl]ethan-1-one;
1-[(2S)-5-[(5-fluoropyrimidin-2-yl)oxy]-6-[1-(2-methane sulfonylethyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-[1-(2-hydroxy-2-methylpropyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-[1-(1-hydroxy-2-methylpropan-2-yl)-1H-pyrazol-4-yl]-2-methyl-1,2,3,4-tetrahydroquinolin-1-yl]ethan-1-one;
2-{4-[(2S)-1-acetyl-5-[(5-fluoropyrimidin-2-yl)oxy]-2-methyl-1,2,3,4-tetrahydroquinolin-6-yl]phenyl}-1$\lambda^6$,2-thiazolidine-1,1-dione;
methyl (2S)-6-[1-(2-methane sulfonylethyl)-1H-pyrazol-4-yl]-2-methyl-5-{[5-(trifluoromethyl)pyridin-2-yl]oxy}-1,2,3,4-tetrahydroquinoline-1-carboxylate;
methyl (2S)-6-[1-(2-hydroxy-2-methylpropyl)-1H-pyrazol-4-yl]-2-methyl-5-{[5-(trifluoromethyl)pyridin-2-yl]oxy}-1,2,3,4-tetrahydroquinoline-1-carboxylate;
methyl (2S)-6-[1-(2-hydroxyethyl)-1H-pyrazol-4-yl]-2-methyl-5-{[5-(trifluoromethyl)pyridin-2-yl]oxy}-1,2,3,4-tetrahydroquinoline-1-carboxylate;
methyl (2S)-6-(1-cyclopropyl-1H-pyrazol-4-yl)-2-methyl-5-{[5-(trifluoromethyl)pyridin-2-yl]oxy}-1,2,3,4-tetrahydroquinoline-1-carboxylate;
methyl (2S)-6-[1-(2-methanesulfonylethyl)-1H-pyrazol-4-yl]-2-methyl-5-(pyrazin-2-yloxy)-1,2,3,4-tetrahydroquinoline-1-carboxylate;
methyl (2S)-6-[1-(2-hydroxy-2-methylpropyl)-1H-pyrazol-4-yl]-2-methyl-5-(pyrazin-2-yloxy)-1,2,3,4-tetrahydroquinoline-1-carboxylate;
methyl (2S)-6-[1-(2-hydroxyethyl)-1H-pyrazol-4-yl]-2-methyl-5-(pyrazin-2-yloxy)-1,2,3,4-tetrahydroquinoline-1-carboxylate;
methyl (2S)-6-(1-cyclopropyl-1H-pyrazol-4-yl)-2-methyl-5-(pyrazin-2-yloxy)-1,2,3,4-tetrahydroquinoline-1-carboxylate;
methyl (2S)-6-[1-(2-methanesulfonylethyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-[1-(2-hydroxy-2-methylpropyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-[1-(2-hydroxyethyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-(1-cyclopropyl-1H-pyrazol-4-yl)-2-methyl-5-{[3-(trifluoromethyl)pyridin-2-yl]oxy}-1,2,3,4-tetrahydroquinoline-1-carboxylate;
methyl (2S)-5-[(3-cyanopyridin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(3-cyanopyridin-2-yl)oxy]-6-[1-(2-hydroxy-2-methylpropyl)-1H-pyrazol-4-yl]-2-methyl-1,2,3,4-tetrahydroquinoline-1-carboxylate;
methyl (2S)-5-[(3-cyanopyridin-2-yl)oxy]-6-[1-(2-hydroxyethyl)-1H-pyrazol-4-yl]-2-methyl-1,2,3,4-tetrahydroquinoline-1-carboxylate;
methyl (2S)-5-[(3-cyanopyridin-2-yl)oxy]-6-(1-cyclopropyl-1H-pyrazol-4-yl)-2-methyl-1,2,3,4-tetrahydroquinoline-1-carboxylate;
methyl (2S)-5-[(5-cyclopropylpyrimidin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(5-cyclopropylpyrimidin-2-yl)oxy]-6-[1-(2-hydroxy-2-methylpropyl)-1H-pyrazol-4-yl]-2-methyl-1,2,3,4-tetrahydroquinoline-1-carboxylate;
methyl (2S)-5-[(5-cyclopropylpyrimidin-2-yl)oxy]-6-[1-(2-hydroxyethyl)-1H-pyrazol-4-yl]-2-methyl-1,2,3,4-tetrahydroquinoline-1-carboxylate;

methyl (2S)-6-(1-cyclopropyl-1H-pyrazol-4-yl)-5-[(5-cyclopropylpyrimidin-2-yl)oxy]-2-methyl-1,2,3,4-tetrahydroquinoline-1-carboxylate;

methyl (2S)-5-[(5-fluoropyrimidin-2-yl)oxy]-6-[1-(2-methanesulfonylethyl)-1H-pyrazol-4-yl]-2-methyl-1,2,3,4-tetrahydroquinoline-1-carboxylate;

methyl (2S)-5-[(5-fluoropyrimidin-2-yl)oxy]-6-[1-(2-hydroxy-2-methylpropyl)-1H-pyrazol-4-yl]-2-methyl-1,2,3,4-tetrahydroquinoline-1-carboxylate;

methyl (2S)-5-[(5-fluoropyrimidin-2-yl)oxy]-6-[1-(2-hydroxyethyl)-1H-pyrazol-4-yl]-2-methyl-1,2,3,4-tetrahydroquinoline-1-carboxylate;

methyl (2S)-6-(1-cyclopropyl-1H-pyrazol-4-yl)-5-[(5-fluoropyrimidin-2-yl)oxy]-2-methyl-1,2,3,4-tetrahydroquinoline-1-carboxylate;

methyl (2S)-6-[1-(2-methanesulfonylethyl)-1H-pyrazol-4-yl]-2-methyl-5-{[5-(trifluoromethyl)pyrimidin-2-yl]oxy}-1,2,3,4-tetrahydroquinoline-1-carboxylate;

methyl (2S)-6-[1-(2-hydroxy-2-methylpropyl)-1H-pyrazol-4-yl]-2-methyl-5-{[5-(trifluoromethyl)pyrimidin-2-yl]oxy}-1,2,3,4-tetrahydroquinoline-1-carboxylate;

methyl (2S)-6-[1-(2-hydroxyethyl)-1H-pyrazol-4-yl]-2-methyl-5-{[5-(trifluoromethyl)pyrimidin-2-yl]oxy}-1,2,3,4-tetrahydroquinoline-1-carboxylate;

methyl (2S)-6-(1-cyclopropyl-1H-pyrazol-4-yl)-2-methyl-5-{[5-(trifluoromethyl)pyrimidin-2-yl]oxy}-1,2,3,4-tetrahydroquinoline-1-carboxylate;

methyl (2S)-6-[1-(2-methanesulfonylethyl)-1H-pyrazol-4-yl]-2-methyl-5-[(5-methylpyrimidin-2-yl)oxy]-1,2,3,4-tetrahydroquinoline-1-carboxylate;

methyl (2S)-6-[1-(2-hydroxy-2-methylpropyl)-1H-pyrazol-4-yl]-2-methyl-5-[(5-methylpyrimidin-2-yl)oxy]-1,2,3,4-tetrahydroquinoline-1-carboxylate;

methyl (2S)-6-[1-(2-hydroxyethyl)-1H-pyrazol-4-yl]-2-methyl-5-[(5-methylpyrimidin-2-yl)oxy]-1,2,3,4-tetrahydroquinoline-1-carboxylate;

methyl (2S)-6-(1-cyclopropyl-1H-pyrazol-4-yl)-2-methyl-5-[(5-methylpyrimidin-2-yl)oxy]-1,2,3,4-tetrahydroquinoline-1-carboxylate;

methyl (2S)-5-[(3-carbamoylpyridin-2-yl)oxy]-6-[1-(2-methanesulfonylethyl)-1H-pyrazol-4-yl]-2-methyl-1,2,3,4-tetrahydroquinoline-1-carboxylate;

methyl (2S)-5-[(3-carbamoylpyridin-2-yl)oxy]-6-(1-cyclopropyl-1H-pyrazol-4-yl)-2-methyl-1,2,3,4-tetrahydroquinoline-1-carboxylate;

methyl (2S)-5-{[3-fluoro-5-(trifluoromethyl)pyridin-2-yl]oxy}-6-[1-(2-methanesulfonylethyl)-1H-pyrazol-4-yl]-2-methyl-1,2,3,4-tetrahydroquinoline-1-carboxylate;

methyl (2S)-5-{[3-fluoro-5-(trifluoromethyl)pyridin-2-yl]oxy}-6-[1-(2-hydroxy-2-methylpropyl)-1H-pyrazol-4-yl]-2-methyl-1,2,3,4-tetrahydroquinoline-1-carboxylate;

methyl (2S)-5-{[3-fluoro-5-(trifluoromethyl)pyridin-2-yl]oxy}-6-[1-(2-hydroxyethyl)-1H-pyrazol-4-yl]-2-methyl-1,2,3,4-tetrahydroquinoline-1-carboxylate;

methyl (2S)-6-(1-cyclopropyl-1H-pyrazol-4-yl)-5-{[3-fluoro-5-(trifluoromethyl)pyridin-2-yl]oxy}-2-methyl-1,2,3,4-tetrahydroquinoline-1-carboxylate;

methyl (2S)-5-(4-fluorophenoxy)-2-methyl-6-[1-(oxan-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(4-fluorophenoxy)-2-methyl-1,2,3,4-tetrahydroquinoline-1-carboxylate;

1-[(2S)-6-(1-cyclopropyl-1H-pyrazol-4-yl)-2-methyl-5-phenoxy-1,2,3,4-tetrahydroquinolin-1-yl]ethan-1-one;

4-{[(2S)-1-acetyl-6-(1-cyclopropyl-1H-pyrazol-4-yl)-2-methyl-1,2,3,4-tetrahydroquinolin-5-yl]oxy}-N,N-dimethylbenzamide;

methyl (2S)-5-(3-cyanophenoxy)-2-methyl-6-[1-(piperidin-4-yl)-1H-pyrazol-4-yl]-1,2,3,4-tetrahydroquinoline-1-carboxylate;

1-[6-(1-cyclopropyl-1H-pyrazol-4-yl)-2-methyl-5-phenoxy-1,2,3,4-tetrahydroquinolin-1-yl]ethan-1-one;

1-cyclopropanecarbonyl-6-(1-cyclopropyl-1H-pyrazol-4-yl)-2-methyl-5-phenoxy-1,2,3,4-tetrahydroquinoline;

methyl 6-(1-cyclopropyl-1H-pyrazol-4-yl)-2-methyl-5-phenoxy-1,2,3,4-tetrahydroquinoline-1-carboxylate;

1-[(2S)-2-methyl-6-[1-(oxetan-3-yl)-1H-pyrazol-4-yl]-5-[(3R)-pyrrolidin-3-ylmethoxy]-1,2,3,4-tetrahydroquinolin-1-yl]ethan-1-one;

1-[(2S)-2-methyl-6-[1-(oxetan-3-yl)-1H-pyrazol-4-yl]-5-[(3S)-pyrrolidin-3-ylmethoxy]-1,2,3,4-tetrahydroquinolin-1-yl]ethan-1-one;

1-[(2S)-6-(1-cyclopropyl-1H-pyrazol-4-yl)-2-methyl-5-[(3R)-pyrrolidin-3-ylmethoxy]-1,2,3,4-tetrahydroquinolin-1-yl]ethan-1-one;

1-[(2S)-6-(1-cyclopropyl-1H-pyrazol-4-yl)-2-methyl-5-[(3S)-pyrrolidin-3-ylmethoxy]-1,2,3,4-tetrahydroquinolin-1-yl]ethan-1-one;

1-[(2S)-6-[1-(2-hydroxy-2-methylpropyl)-1H-pyrazol-4-yl]-2-methyl-5-[(3S)-pyrrolidin-3-ylmethoxy]-1,2,3,4-tetrahydroquinolin-1-yl]ethan-1-one;

1-[(2S)-2-methyl-5-propoxy-1,2,3,4-tetrahydroquinolin-1-yl]ethan-1-one;

2-{[(2S)-1-acetyl-2-methyl-1,2,3,4-tetrahydroquinolin-5-yl]oxy}-N,N-dimethylacetamide;

1-[(2S)-5-(cyclopentylmethoxy)-2-methyl-1,2,3,4-tetrahydroquinolin-1-yl]ethan-1-one;

1-[(2S)-6-(1-cyclopropyl-1H-pyrazol-4-yl)-2-methyl-5-({1-[(1E)-prop-1-en-1-yl]-1H-1,3-benzodiazol-2-yl}oxy)-1,2,3,4-tetrahydroquinolin-1-yl]ethan-1-one;

1-[(2S)-6-(1-cyclopropyl-1H-pyrazol-4-yl)-2-methyl-5-({1-[(1Z)-prop-1-en-1-yl]-1H-1,3-benzodiazol-2-yl}oxy)-1,2,3,4-tetrahydroquinolin-1-yl]ethan-1-one;

methyl (2S)-5-cyclobutoxy-2-methyl-6-[1-methyl-2-(piperazin-1-yl)-1H-imidazol-4-yl]-1,2,3,4-tetrahydroquinoline-1-carboxylate;

methyl (2S)-5-cyclobutoxy-2-methyl-6-[2-(piperazin-1-yl)-1,3-thiazol-4-yl]-1,2,3,4-tetrahydroquinoline-1-carboxylate;

methyl (2S)-5-cyclobutoxy-6-[2-(3-hydroxyazetidin-1-yl)-1,3-thiazol-4-yl]-2-methyl-1,2,3,4-tetrahydroquinoline-1-carboxylate;

(2S)-5-cyclobutoxy-1-cyclopropanecarbonyl-2-methyl-6-(1,2-oxazol-4-yl)-1,2,3,4-tetrahydroquinoline;

(2S)-1-cyclopropanecarbonyl-2-methyl-6-(1,2-oxazol-4-yl)-5-phenoxy-1,2,3,4-tetrahydroquinoline;

(2S)-5-cyclobutoxy-1-cyclopropanecarbonyl-8-fluoro-2-methyl-6-[1-(piperidin-4-yl)-1H-pyrazol-4-yl]-1,2,3,4-tetrahydroquinoline;

(2S)-5-cyclobutoxy-1-cyclopropanecarbonyl-6-(1-cyclopropyl-1H-pyrazol-4-yl)-8-fluoro-2-methyl-1,2,3,4-tetrahydroquinoline;

(2S)-5-cyclobutoxy-1-cyclopropanecarbonyl-8-fluoro-2-methyl-6-(1H-pyrazol-4-yl)-1,2,3,4-tetrahydroquinoline;

methyl (2S)-5-cyclobutoxy-8-fluoro-2-methyl-6-[1-(piperidin-4-yl)-1H-pyrazol-4-yl]-1,2,3,4-tetrahydroquinoline-1-carboxylate;

methyl (2S)-5-cyclobutoxy-6-(1-cyclopropyl-1H-pyrazol-4-yl)-8-fluoro-2-methyl-1,2,3,4-tetrahydroquinoline-1-carboxylate;

methyl (2S)-5-cyclobutoxy-8-fluoro-2-methyl-6-(1H-pyrazol-4-yl)-1,2,3,4-tetrahydroquinoline-1-carboxylate;
1-[(2S)-5-cyclobutoxy-8-fluoro-2-methyl-6-[1-(piperidin-4-yl)-1H-pyrazol-4-yl]-1,2,3,4-tetrahydroquinolin-1-yl]ethan-1-one;
1-[(2S)-5-cyclobutoxy-6-(1-cyclopropyl-1H-pyrazol-4-yl)-8-fluoro-2-methyl-1,2,3,4-tetrahydroquinolin-1-yl]ethan-1-one;
1-[(2S)-5-cyclobutoxy-8-fluoro-2-methyl-6-(1H-pyrazol-4-yl)-1,2,3,4-tetrahydroquinolin-1-yl]ethan-1-one;
(2S)-1-cyclopropanecarbonyl-8-fluoro-2-methyl-5-phenoxy-6-[1-(piperidin-4-yl)-1H-pyrazol-4-yl]-1,2,3,4-tetrahydroquinoline;
(2S)-1-cyclopropanecarbonyl-6-(1-cyclopropyl-1H-pyrazol-4-yl)-8-fluoro-2-methyl-5-phenoxy-1,2,3,4-tetrahydroquinoline;
(2S)-1-cyclopropanecarbonyl-8-fluoro-2-methyl-5-phenoxy-6-(1H-pyrazol-4-yl)-1,2,3,4-tetrahydroquinoline;
methyl (2S)-8-fluoro-2-methyl-5-phenoxy-6-[1-(piperidin-4-yl)-1H-pyrazol-4-yl]-1,2,3,4-tetrahydroquinoline-1-carboxylate;
methyl (2S)-6-(1-cyclopropyl-1H-pyrazol-4-yl)-8-fluoro-2-methyl-5-phenoxy-1,2,3,4-tetrahydroquinoline-1-carboxylate;
methyl (2S)-8-fluoro-2-methyl-5-phenoxy-6-(1H-pyrazol-4-yl)-1,2,3,4-tetrahydroquinoline-1-carboxylate;
1-[(2S)-8-fluoro-2-methyl-5-phenoxy-6-[1-(piperidin-4-yl)-1H-pyrazol-4-yl]-1,2,3,4-tetrahydroquinolin-1-yl]ethan-1-one;
1-[(2S)-6-(1-cyclopropyl-1H-pyrazol-4-yl)-8-fluoro-2-methyl-5-phenoxy-1,2,3,4-tetrahydroquinolin-1-yl]ethan-1-one;
1-[(2S)-8-fluoro-2-methyl-5-phenoxy-6-(1H-pyrazol-4-yl)-1,2,3,4-tetrahydroquinolin-1-yl]ethan-1-one;
1-[(2S)-5-cyclobutoxy-7,8-difluoro-2-methyl-6-[1-(piperidin-4-yl)-1H-pyrazol-4-yl]-1,2,3,4-tetrahydroquinolin-1-yl]ethan-1-one;
1-[(2S)-5-cyclobutoxy-6-(1-cyclopropyl-1H-pyrazol-4-yl)-7,8-difluoro-2-methyl-1,2,3,4-tetrahydroquinolin-1-yl]ethan-1-one;
(2S)-5-cyclobutoxy-1-cyclopropanecarbonyl-2-methyl-6-(1H-pyrazol-1-yl)-1,2,3,4-tetrahydroquinoline;
(2S)-5-cyclobutoxy-1-cyclopropanecarbonyl-2-methyl-6-(2H-1,2,3-triazol-2-yl)-1,2,3,4-tetrahydroquinoline;
(2S)-1-cyclopropanecarbonyl-2-methyl-5-phenoxy-6-(1H-pyrazol-1-yl)-1,2,3,4-tetrahydroquinoline;
(2S)-1-cyclopropanecarbonyl-2-methyl-5-phenoxy-6-(2H-1,2,3-triazol-2-yl)-1,2,3,4-tetrahydroquinoline;
(2S)-5-cyclobutoxy-1-cyclopropanecarbonyl-2-methyl-6-[1-(piperidin-4-yl)-1H-pyrazol-3-yl]-1,2,3,4-tetrahydroquinoline;
(2S)-5-cyclobutoxy-1-cyclopropanecarbonyl-2-methyl-6-[1-(piperidin-4-yl)-1H-pyrazol-5-yl]-1,2,3,4-tetrahydroquinoline;
(2S)-5-cyclobutoxy-1-cyclopropanecarbonyl-2-methyl-6-[2-(piperidin-4-yl)-2H-1,2,3-triazol-4-yl]-1,2,3,4-tetrahydroquinoline;
(2S)-5-cyclobutoxy-1-cyclopropanecarbonyl-2-methyl-6-[1-(piperidin-4-yl)-1H-1,2,3-triazol-4-yl]-1,2,3,4-tetrahydroquinoline;
(2S)-5-cyclobutoxy-1-cyclopropanecarbonyl-2-methyl-6-[5-(piperidin-4-yl)-1H-imidazol-2-yl]-1,2,3,4-tetrahydroquinoline;
(2S)-1-cyclopropanecarbonyl-2-methyl-5-phenoxy-6-[1-(piperidin-4-yl)-1H-pyrazol-3-yl]-1,2,3,4-tetrahydroquinoline;
(2S)-1-cyclopropanecarbonyl-2-methyl-5-phenoxy-6-[1-(piperidin-4-yl)-1H-pyrazol-5-yl]-1,2,3,4-tetrahydroquinoline;
(2S)-1-cyclopropanecarbonyl-2-methyl-5-phenoxy-6-[2-(piperidin-4-yl)-2H-1,2,3-triazol-4-yl]-1,2,3,4-tetrahydroquinoline;
(2S)-1-cyclopropanecarbonyl-2-methyl-5-phenoxy-6-[1-(piperidin-4-yl)-1H-1,2,3-triazol-4-yl]-1,2,3,4-tetrahydroquinoline;
(2S)-1-cyclopropanecarbonyl-2-methyl-5-phenoxy-6-[5-(piperidin-4-yl)-1H-imidazol-2-yl]-1,2,3,4-tetrahydroquinoline;
(2S)-5-cyclobutoxy-1-cyclopropanecarbonyl-8-fluoro-2-methyl-6-(1-methyl-1H-1,2,3-triazol-4-yl)-1,2,3,4-tetrahydroquinoline;
(2S)-1-cyclopropanecarbonyl-8-fluoro-2-methyl-6-(1-methyl-1H-1,2,3-triazol-4-yl)-5-phenoxy-1,2,3,4-tetrahydroquinoline;
methyl (2S)-5-cyclobutoxy-8-fluoro-2-methyl-6-(1-methyl-1H-1,2,3-triazol-4-yl)-1,2,3,4-tetrahydroquinoline-1-carboxylate;
methyl (2S)-8-fluoro-2-methyl-6-(1-methyl-1H-1,2,3-triazol-4-yl)-5-phenoxy-1,2,3,4-tetrahydroquinoline-1-carboxylate;
1-[(2S)-5-cyclobutoxy-8-fluoro-2-methyl-6-(1-methyl-1H-1,2,3-triazol-4-yl)-1,2,3,4-tetrahydroquinolin-1-yl]ethan-1-one;
1-[(2S)-8-fluoro-2-methyl-6-(1-methyl-1H-1,2,3-triazol-4-yl)-5-phenoxy-1,2,3,4-tetrahydroquinolin-1-yl]ethan-1-one;
(2S)-1-cyclopropanecarbonyl-2-methyl-5-[(6-methylpyridin-2-yl)oxy]-6-[1-(piperidin-4-yl)-1H-pyrazol-4-yl]-1,2,3,4-tetrahydroquinoline;
(2S)-1-cyclopropanecarbonyl-5-[(2,6-dimethylpyridin-3-yl)oxy]-2-methyl-6-[1-(piperidin-4-yl)-1H-pyrazol-4-yl]-1,2,3,4-tetrahydroquinoline;
(2S)-1-cyclopropanecarbonyl-5-[(2,6-dimethylpyridin-4-yl)oxy]-2-methyl-6-[1-(piperidin-4-yl)-1H-pyrazol-4-yl]-1,2,3,4-tetrahydroquinoline;
(2S)-5-[(6-chloropyridin-2-yl)oxy]-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-2-methyl-6-[1-(piperidin-4-yl)-1H-pyrazol-4-yl]-5-(pyridin-2-yloxy)-1,2,3,4-tetrahydroquinoline;
(2S)-1-cyclopropanecarbonyl-5-[(6-fluoropyridin-2-yl)oxy]-2-methyl-6-[1-(piperidin-4-yl)-1H-pyrazol-4-yl]-1,2,3,4-tetrahydroquinoline;
methyl (2S)-2-methyl-5-[(6-methylpyridin-2-yl)oxy]-6-[1-(piperidin-4-yl)-1H-pyrazol-4-yl]-1,2,3,4-tetrahydroquinoline-1-carboxylate;
methyl (2S)-2-methyl-6-[1-(piperidin-4-yl)-1H-pyrazol-4-yl]-5-(pyridin-2-yloxy)-1,2,3,4-tetrahydroquinoline-1-carboxylate;
1-[(2S)-2-methyl-5-[(6-methylpyridin-2-yl)oxy]-6-[1-(piperidin-4-yl)-1H-pyrazol-4-yl]-1,2,3,4-tetrahydroquinolin-1-yl]ethan-1-one;
(2S)-1-cyclopropanecarbonyl-2-methyl-6-[4-(morpholin-4-yl)-1H-pyrazol-1-yl]-5-phenoxy-1,2,3,4-tetrahydroquinoline;
(2S)-1-cyclopropanecarbonyl-2-methyl-5-phenoxy-6-[4-(piperazin-1-yl)-1H-pyrazol-1-yl]-1,2,3,4-tetrahydroquinoline;
(2S)-1-cyclopropanecarbonyl-2-methyl-5-phenoxy-6-[4-(piperidin-4-yl)-1H-pyrazol-1-yl]-1,2,3,4-tetrahydroquinoline;

methyl (2S)-2-methyl-6-[4-(morpholin-4-yl)-1H-pyrazol-1-yl]-5-phenoxy-1,2,3,4-tetrahydroquinoline-1-carboxylate;
methyl (2S)-2-methyl-5-phenoxy-6-[4-(piperazin-1-yl)-1H-pyrazol-1-yl]-1,2,3,4-tetrahydroquinoline-1-carboxylate;
(2S)-1-cyclopropanecarbonyl-2-methyl-5-phenoxy-1,2,3,4-tetrahydroquinoline-6-carbonitrile;
(2S)-1-cyclopropanecarbonyl-6-ethynyl-2-methyl-5-phenoxy-1,2,3,4-tetrahydroquinoline;
(2S)-1-cyclopropanecarbonyl-2-methyl-5-phenoxy-6-(prop-1-yn-1-yl)-1,2,3,4-tetrahydroquinoline;
methyl (2S)-6-cyano-2-methyl-5-phenoxy-1,2,3,4-tetrahydroquinoline-1-carboxylate;
methyl (2S)-6-ethynyl-2-methyl-5-phenoxy-1,2,3,4-tetrahydroquinoline-1-carboxylate;
methyl (2S)-6-[2-(azetidin-3-yl)-1,3-thiazol-4-yl]-5-cyclobutoxy-2-methyl-1,2,3,4-tetrahydroquinoline-1-carboxylate;
methyl (2S)-5-cyclobutoxy-6-[2-(3-fluoroazetidin-3-yl)-1,3-thiazol-4-yl]-2-methyl-1,2,3,4-tetrahydroquinoline-1-carboxylate;
methyl (2S)-5-cyclobutoxy-6-[2-(3-hydroxyazetidin-3-yl)-1,3-thiazol-4-yl]-2-methyl-1,2,3,4-tetrahydroquinoline-1-carboxylate;
methyl (2S)-5-cyclobutoxy-6-[2-(3-methoxyazetidin-3-yl)-1,3-thiazol-4-yl]-2-methyl-1,2,3,4-tetrahydroquinoline-1-carboxylate;
methyl (2S)-6-(2-carbamoyl-1,3-thiazol-4-yl)-5-cyclobutoxy-2-methyl-1,2,3,4-tetrahydroquinoline-1-carboxylate;
methyl (2S)-5-cyclobutoxy-2-methyl-6-[2-(methylcarbamoyl)-1,3-thiazol-4-yl]-1,2,3,4-tetrahydroquinoline-1-carboxylate;
methyl (2S)-5-cyclobutoxy-6-(2-acetamido-1,3-thiazol-4-yl)-2-methyl-1,2,3,4-tetrahydroquinoline-1-carboxylate;
(2S)-1-cyclopropanecarbonyl-6-cyclopropyl-2-methyl-5-phenoxy-1,2,3,4-tetrahydroquinoline;
methyl (2S)-6-cyclopropyl-2-methyl-5-phenoxy-1,2,3,4-tetrahydroquinoline-1-carboxylate;
(2S)-1-cyclopropanecarbonyl-8-fluoro-5-(3-methoxyphenoxy)-2-methyl-6-[1-(piperidin-4-yl)-1H-pyrazol-4-yl]-1,2,3,4-tetrahydroquinoline;
methyl (2S)-2-methyl-6-(1-methyl-1H-1,2,3-triazol-4-yl)-5-phenoxy-1,2,3,4-tetrahydroquinoline-1-carboxylate;
1-[(2S)-2-methyl-6-(1-methyl-1H-1,2,3-triazol-4-yl)-5-phenoxy-1,2,3,4-tetrahydroquinolin-1-yl]ethan-1-one;
(2S)-1-cyclopropanecarbonyl-5-(3-methoxyphenoxy)-2-methyl-6-(1-methyl-1H-1,2,3-triazol-4-yl)-1,2,3,4-tetrahydroquinoline;
(2S)-1-cyclopropanecarbonyl-5-(2,5-difluorophenoxy)-2-methyl-6-(1-methyl-1H-1,2,3-triazol-4-yl)-1,2,3,4-tetrahydroquinoline;
(2S)-1-cyclopropanecarbonyl-5-(3,4-difluorophenoxy)-2-methyl-6-(1-methyl-1H-1,2,3-triazol-4-yl)-1,2,3,4-tetrahydroquinoline;
2-{[(2S)-1-cyclopropanecarbonyl-2-methyl-6-(1-methyl-1H-1,2,3-triazol-4-yl)-1,2,3,4-tetrahydroquinolin-5-yl]oxy}benzonitrile;
(2S)-1-cyclopropanecarbonyl-5-(3-fluorophenoxy)-2-methyl-6-(1-methyl-1H-1,2,3-triazol-4-yl)-1,2,3,4-tetrahydroquinoline;
(2S)-1-cyclopropanecarbonyl-5-(2-fluorophenoxy)-2-methyl-6-(1-methyl-1H-1,2,3-triazol-4-yl)-1,2,3,4-tetrahydroquinoline;
(2S)-1-cyclopropanecarbonyl-5-(4-fluorophenoxy)-2-methyl-6-(1-methyl-1H-1,2,3-triazol-4-yl)-1,2,3,4-tetrahydroquinoline;
(2S)-1-cyclopropanecarbonyl-5-[(6-methoxypyridin-2-yl)oxy]-2-methyl-6-[1-(piperidin-4-yl)-1H-pyrazol-4-yl]-1,2,3,4-tetrahydroquinoline;
methyl (2S)-5-[(6-methoxypyridin-2-yl)oxy]-2-methyl-6-[1-(piperidin-4-yl)-1H-pyrazol-4-yl]-1,2,3,4-tetrahydroquinoline-1-carboxylate;
1-[(2S)-5-[(6-methoxypyridin-2-yl)oxy]-2-methyl-6-[1-(piperidin-4-yl)-1H-pyrazol-4-yl]-1,2,3,4-tetrahydroquinolin-1-yl]ethan-1-one;
methyl (2S)-5-cyclobutoxy-6-[1-(1,1-dioxo-1$\lambda^6$-thian-4-yl)-1H-pyrazol-4-yl]-2-methyl-1,2,3,4-tetrahydroquinoline-1-carboxylate;
4-{4-[(2S)-5-cyclobutoxy-1-cyclopropanecarbonyl-2-methyl-1,2,3,4-tetrahydroquinolin-6-yl]-1H-pyrazol-1-yl}-1$\lambda^6$-thiane-1,1-dione;
1-[(2S)-6-(1-acetylpiperidin-4-yl)-2-methyl-5-propoxy-1,2,3,4-tetrahydroquinolin-1-yl]ethan-1-one;
1-[(2S)-6-(1-methanesulfonylpiperidin-4-yl)-2-methyl-5-propoxy-1,2,3,4-tetrahydroquinolin-1-yl]ethan-1-one;
tert-butyl 4-[(2S)-1-acetyl-2-methyl-5-propoxy-1,2,3,4-tetrahydroquinolin-6-yl]-1,2,3,6-tetrahydropyridine-1-carboxylate;
1-[(2S)-2-methyl-6-(piperidin-4-yl)-5-propoxy-1,2,3,4-tetrahydroquinolin-1-yl]ethan-1-one;
4-[(2S)-1-acetyl-2-methyl-5-propoxy-1,2,3,4-tetrahydroquinolin-6-yl]-N-ethylpiperidine-1-carboxamide;
methyl 4-[(2S)-1-acetyl-2-methyl-5-propoxy-1,2,3,4-tetrahydroquinolin-6-yl]piperidine-1-carboxylate;
1-[(2S)-6-(1-ethylpiperidin-4-yl)-2-methyl-5-propoxy-1,2,3,4-tetrahydroquinolin-1-yl]ethan-1-one;
1-[(2S)-2-methyl-5-(phenylamino)-6-[1-(piperidin-4-yl)-1H-pyrazol-4-yl]-1,2,3,4-tetrahydroquinolin-1-yl]ethan-1-one;
methyl (2S)-5-cyclobutoxy-6-{1-[(3S,4R)-3-fluoropiperidin-4-yl]-1H-pyrazol-4-yl}-2-methyl-1,2,3,4-tetrahydroquinoline-1-carboxylate;
methyl (2S)-5-cyclobutoxy-6-{1-[(3R,4S)-3-fluoropiperidin-4-yl]-1H-pyrazol-4-yl}-2-methyl-1,2,3,4-tetrahydroquinoline-1-carboxylate;
methyl (2S)-5-cyclobutoxy-6-{1-[(3S,4S)-3-fluoropiperidin-4-yl]-1H-pyrazol-4-yl}-2-methyl-1,2,3,4-tetrahydroquinoline-1-carboxylate;
methyl (2S)-5-(4-fluorophenoxy)-6-{1-[(3S,4S)-3-fluoropiperidin-4-yl]-1H-pyrazol-4-yl}-2-methyl-1,2,3,4-tetrahydroquinoline-1-carboxylate;
methyl (2S)-5-(4-fluorophenoxy)-6-{1-[(3S,4R)-3-fluoropiperidin-4-yl]-1H-pyrazol-4-yl}-2-methyl-1,2,3,4-tetrahydroquinoline-1-carboxylate;
methyl (2S)-5-(4-fluorophenoxy)-6-{1-[(3R,4S)-3-fluoropiperidin-4-yl]-1H-pyrazol-4-yl}-2-methyl-1,2,3,4-tetrahydroquinoline-1-carboxylate;
methyl (2S)-5-cyclobutoxy-6-{1-[(3R,4R)-3-fluoropiperidin-4-yl]-1H-pyrazol-4-yl}-2-methyl-1,2,3,4-tetrahydroquinoline-1-carboxylate;
methyl (2S)-5-(4-fluorophenoxy)-6-{1-[(3R,4R)-3-fluoropiperidin-4-yl]-1H-pyrazol-4-yl}-2-methyl-1,2,3,4-tetrahydroquinoline-1-carboxylate;
methyl (2S)-5-cyclobutoxy-2-methyl-6-[1-(2-methylpiperidin-4-yl)-1H-pyrazol-4-yl]-1,2,3,4-tetrahydroquinoline-1-carboxylate;
methyl (2S)-5-cyclobutoxy-2-methyl-6-[1-(2-methylpiperidin-4-yl)-1H-pyrazol-4-yl]-1,2,3,4-tetrahydroquinoline-1-carboxylate;
(2S)-5-cyclobutoxy-1-cyclopropanecarbonyl-6-{1-[(3S,4R)-3-fluoropiperidin-4-yl]-1H-pyrazol-4-yl}-2-methyl-1,2,3,4-tetrahydroquinoline;

methyl (2S)-5-cyclobutoxy-6-[5-fluoro-1-(piperidin-4-yl)-1H-pyrazol-4-yl]-2-methyl-1,2,3,4-tetrahydroquinoline-1-carboxylate;
methyl (2S)-5-cyclobutoxy-6-{1-[(3R*,4S*)-4-fluoropyrrolidin-3-yl]-1H-pyrazol-4-yl}-2-methyl-1,2,3,4-tetrahydroquinoline-1-carboxylate; and
(2S)-5-cyclobutoxy-1-cyclopropanecarbonyl-6-{1-[(3R*,4S*)-4-fluoropiperidin-3-yl]-1H-pyrazol-4-yl}-2-methyl-1,2,3,4-tetrahydroquinoline.

In another embodiment, suitable compounds of the invention include:
methyl (2S)-2-methyl-6-[1-(piperidin-4-yl)-1H-pyrazol-4-yl]-5-propoxy-1,2,3,4-tetrahydroquinoline-1-carboxylate;
methyl (2S)-5-cyclobutoxy-2-methyl-6-[1-(piperidin-4-yl)-1H-pyrazol-4-yl]-1,2,3,4-tetrahydroquinoline-1-carboxylate;
1-[(2S)-6-(1-cyclopropyl-1H-pyrazol-4-yl)-5-(2-fluoro-2-methylpropoxy)-2-methyl-1,2,3,4-tetrahydroquinolin-1-yl]ethan-1-one;
2-{[(2S)-1-acetyl-6-(1-cyclopropyl-1H-pyrazol-4-yl)-2-methyl-1,2,3,4-tetrahydroquinolin-5-yl]oxy}benzonitrile;
2-{[(2S)-1-acetyl-2-methyl-6-[1-(piperidin-4-yl)-1H-pyrazol-4-yl]-1,2,3,4-tetrahydroquinolin-5-yl]oxy}benzonitrile;
1-[(2S)-5-(4-fluorophenoxy)-2-methyl-6-[1-(piperidin-4-yl)-1H-pyrazol-4-yl]-1,2,3,4-tetrahydroquinolin-1-yl]ethan-1-one;
1-[(2S)-5-(4-chlorophenoxy)-2-methyl-6-[1-(piperidin-4-yl)-1H-pyrazol-4-yl]-1,2,3,4-tetrahydroquinolin-1-yl]ethan-1-one;
1-[(2S)-5-(2-chlorophenoxy)-2-methyl-6-[1-(piperidin-4-yl)-1H-pyrazol-4-yl]-1,2,3,4-tetrahydroquinolin-1-yl]ethan-1-one;
1-[(2S)-2-methyl-5-phenoxy-6-[1-(piperidin-4-yl)-1H-pyrazol-4-yl]-1,2,3,4-tetrahydroquinolin-1-yl]ethan-1-one;
methyl (2S)-5-(4-methoxyphenoxy)-2-methyl-6-[1-(piperidin-4-yl)-1H-pyrazol-4-yl]-1,2,3,4-tetrahydroquinoline-1-carboxylate;
methyl (2S)-2-methyl-5-phenoxy-6-[1-(piperidin-4-yl)-1H-pyrazol-4-yl]-1,2,3,4-tetrahydroquinoline-1-carboxylate;
methyl (2S)-5-(2-methoxyphenoxy)-2-methyl-6-[1-(piperidin-4-yl)-1H-pyrazol-4-yl]-1,2,3,4-tetrahydroquinoline-1-carboxylate;
methyl (2S)-5-(3-fluorophenoxy)-2-methyl-6-[1-(piperidin-4-yl)-1H-pyrazol-4-yl]-1,2,3,4-tetrahydroquinoline-1-carboxylate;
methyl (2S)-5-(3-chlorophenoxy)-2-methyl-6-[1-(piperidin-4-yl)-1H-pyrazol-4-yl]-1,2,3,4-tetrahydroquinoline-1-carboxylate;
methyl (2S)-5-(3-cyanophenoxy)-2-methyl-6-[1-(piperidin-4-yl)-1H-pyrazol-4-yl]-1,2,3,4-tetrahydroquinoline-1-carboxylate;
1-[(2S)-6-(1-cyclopropyl-1H-pyrazol-4-yl)-5-(2-fluorophenoxy)-2-methyl-1,2,3,4-tetrahydroquinolin-1-yl]ethan-1-one;
methyl (2S)-5-(4-fluorophenoxy)-2-methyl-6-[1-(piperidin-4-yl)-1H-pyrazol-4-yl]-1,2,3,4-tetrahydroquinoline-1-carboxylate;
(2S)-5-cyclobutoxy-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(4-fluorophenoxy)-2-methyl-6-[1-(piperidin-4-yl)-1H-pyrazol-4-yl]-1,2,3,4-tetrahydroquinoline;
1-[(2S)-5-(2-fluorophenoxy)-2-methyl-6-[1-(piperidin-4-yl)-1H-pyrazol-4-yl]-1,2,3,4-tetrahydroquinolin-1-yl]ethan-1-one;
1-[(2S)-5-[(5-chloropyridin-2-yl)oxy]-6-(1-cyclopropyl-1H-pyrazol-4-yl)-2-methyl-1,2,3,4-tetrahydroquinolin-1-yl]ethan-1-one;
methyl (2S)-5-(2-cyano-3-fluorophenoxy)-2-methyl-6-[1-(piperidin-4-yl)-1H-pyrazol-4-yl]-1,2,3,4-tetrahydroquinoline-1-carboxylate;
methyl (2S)-5-(3-chloro-4-fluorophenoxy)-2-methyl-6-[1-(piperidin-4-yl)-1H-pyrazol-4-yl]-1,2,3,4-tetrahydroquinoline-1-carboxylate;
methyl (2S)-5-cyclobutoxy-2-methyl-6-[1-(oxan-4-yl)-1H-pyrazol-4-yl]-1,2,3,4-tetrahydroquinoline-1-carboxylate;
methyl (2S)-5-cyclobutoxy-6-{1-[(3S,4R)-3-fluoropiperidin-4-yl]-1H-pyrazol-4-yl}-2-methyl-1,2,3,4-tetrahydroquinoline-1-carboxylate;
1-[(2S)-6-(1-cyclopropyl-1H-pyrazol-4-yl)-2-methyl-5-[(6-methylpyridin-2-yl)oxy]-1,2,3,4-tetrahydroquinolin-1-yl]ethan-1-one;
(2S)-5-(4-chlorophenoxy)-1-cyclopropanecarbonyl-2-methyl-6-[1-(piperidin-4-yl)-1H-pyrazol-4-yl]-1,2,3,4-tetrahydroquinoline;
4-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;
(2S)-1-cyclopropanecarbonyl-2-methyl-5-phenoxy-6-[1-(piperidin-4-yl)-1H-pyrazol-4-yl]-1,2,3,4-tetrahydroquinoline;
2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;
methyl (2S)-6-[1-(1,1-dioxo-1$\lambda^6$-thietan-3-yl)-1H-pyrazol-4-yl]-5-(4-fluorophenoxy)-2-methyl-1,2,3,4-tetrahydroquinoline-1-carboxylate;
(2S)-5-(3-chloro-4-fluorophenoxy)-1-cyclopropanecarbonyl-2-methyl-6-[1-(piperidin-4-yl)-1H-pyrazol-4-yl]-1,2,3,4-tetrahydroquinoline;
(2S)-6-[1-(azetidin-3-yl)-1H-pyrazol-4-yl]-1-cyclopropanecarbonyl-5-(4-fluorophenoxy)-2-methyl-1,2,3,4-tetrahydroquinoline;
(2S)-1-cyclopropanecarbonyl-5-(2-fluorophenoxy)-2-methyl-6-[1-(piperidin-4-yl)-1H-pyrazol-4-yl]-1,2,3,4-tetrahydroquinoline;
(2S)-5-(2-chlorophenoxy)-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(3-fluorophenoxy)-2-methyl-6-[1-(piperidin-4-yl)-1H-pyrazol-4-yl]-1,2,3,4-tetrahydroquinoline;
(2S)-1-cyclopropanecarbonyl-5-(3,4-difluorophenoxy)-2-methyl-6-[1-(piperidin-4-yl)-1H-pyrazol-4-yl]-1,2,3,4-tetrahydroquinoline;
methyl (2S)-5-(3,4-difluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(2,4-difluorophenoxy)-2-methyl-6-[1-(piperidin-4-yl)-1H-pyrazol-4-yl]-1,2,3,4-tetrahydroquinoline;
(2S)-1-cyclopropanecarbonyl-2-methyl-6-(1-methyl-1H-1,2,3-triazol-4-yl)-5-phenoxy-1,2,3,4-tetrahydroquinoline;
(2S)-1-cyclopropanecarbonyl-2-methyl-5-phenoxy-6-(1H-pyrazol-4-yl)-1,2,3,4-tetrahydroquinoline;
(2S)-1-cyclopropanecarbonyl-2-methyl-6-(1-methyl-1H-imidazol-4-yl)-5-phenoxy-1,2,3,4-tetrahydroquinoline;

(2S)-5-(3-chlorophenoxy)-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(2,5-difluorophenoxy)-2-methyl-6-[1-(piperidin-4-yl)-1H-pyrazol-4-yl]-1,2,3,4-tetrahydroquinoline;
methyl (2S)-5-(3,5-difluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(3,5-difluorophenoxy)-2-methyl-6-[1-(piperidin-4-yl)-1H-pyrazol-4-yl]-1,2,3,4-tetrahydroquinoline;
(2S)-1-cyclopropanecarbonyl-5-(3-methoxyphenoxy)-2-methyl-6-[1-(piperidin-4-yl)-1H-pyrazol-4-yl]-1,2,3,4-tetrahydroquinoline;
(2S)-5-cyclobutoxy-1-cyclopropanecarbonyl-6-{1-[(3S,4R)-3-fluoropiperidin-4-yl]-1H-pyrazol-4-yl}-2-methyl-1,2,3,4-tetrahydroquinoline;
(2S)-1-cyclopropanecarbonyl-5-(2-methoxyphenoxy)-2-methyl-6-[1-(piperidin-4-yl)-1H-pyrazol-4-yl]-1,2,3,4-tetrahydroquinoline;
methyl (2S)-5-(3-methoxyphenoxy)-2-methyl-6-[1-(piperidin-4-yl)-1H-pyrazol-4-yl]-1,2,3,4-tetrahydroquinoline-1-carboxylate;
3-{4-[(2S)-1-cyclopropanecarbonyl-5-(4-fluorophenoxy)-2-methyl-1,2,3,4-tetrahydroquinolin-6-yl]-1H-pyrazol-1-yl}-1$1^6$-thietane-1,1-dione;
3-{4-[(2S)-1-cyclopropanecarbonyl-5-(4-fluorophenoxy)-2-methyl-1,2,3,4-tetrahydroquinolin-6-yl]-1H-pyrazol-1-yl}-1$1^6$-thiane-1,1-dione;
(2S)-1-cyclopropanecarbonyl-5-(4-methoxyphenoxy)-2-methyl-6-[1-(piperidin-4-yl)-1H-pyrazol-4-yl]-1,2,3,4-tetrahydroquinoline;
(2S)-1-cyclopropanecarbonyl-8-fluoro-2-methyl-5-phenoxy-6-[1-(piperidin-4-yl)-1H-pyrazol-4-yl]-1,2,3,4-tetrahydroquinoline;
methyl (2S)-5-cyclobutoxy-8-fluoro-2-methyl-6-[1-(piperidin-4-yl)-1H-pyrazol-4-yl]-1,2,3,4-tetrahydroquinoline-1-carboxylate;
methyl (2S)-8-fluoro-2-methyl-5-phenoxy-6-[1-(piperidin-4-yl)-1H-pyrazol-4-yl]-1,2,3,4-tetrahydroquinoline-1-carboxylate; and 1-[(2S)-8-fluoro-2-methyl-5-phenoxy-6-[1-(piperidin-4-yl)-1H-pyrazol-4-yl]-1,2,3,4-tetrahydroquinolin-1-yl]ethan-1-one.

Method of Synthesizing the Compounds

The compounds of the present invention may be made by a variety of methods, including standard chemistry. Suitable synthetic routes are depicted in the Schemes given below.

The compounds of the present invention, i.e., compounds of Formulae (I)-(IV), or a pharmaceutically acceptable salt, enantiomer, hydrate, solvate, prodrug, isomer, or tautomer thereof, may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formulae (I)-(IV).

Those skilled in the art will recognize if a stereocenter exists in the compounds of Formulae (I)-(IV). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Illustrative methods include but are not limited to those methods described below. Compounds of the present invention can be synthesized by following the steps outlined in General Schemes 1 and 2, which comprise different sequences of assembling intermediates. Starting materials are either commercially available or made by known procedures in the reported literature or as illustrated.

Scheme 1

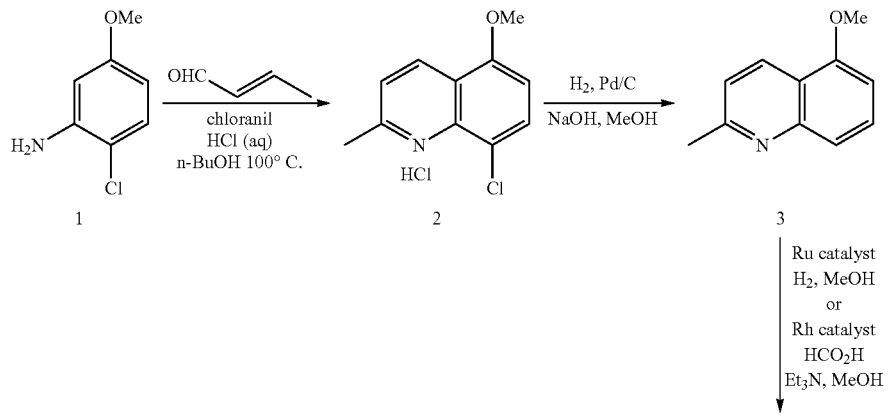

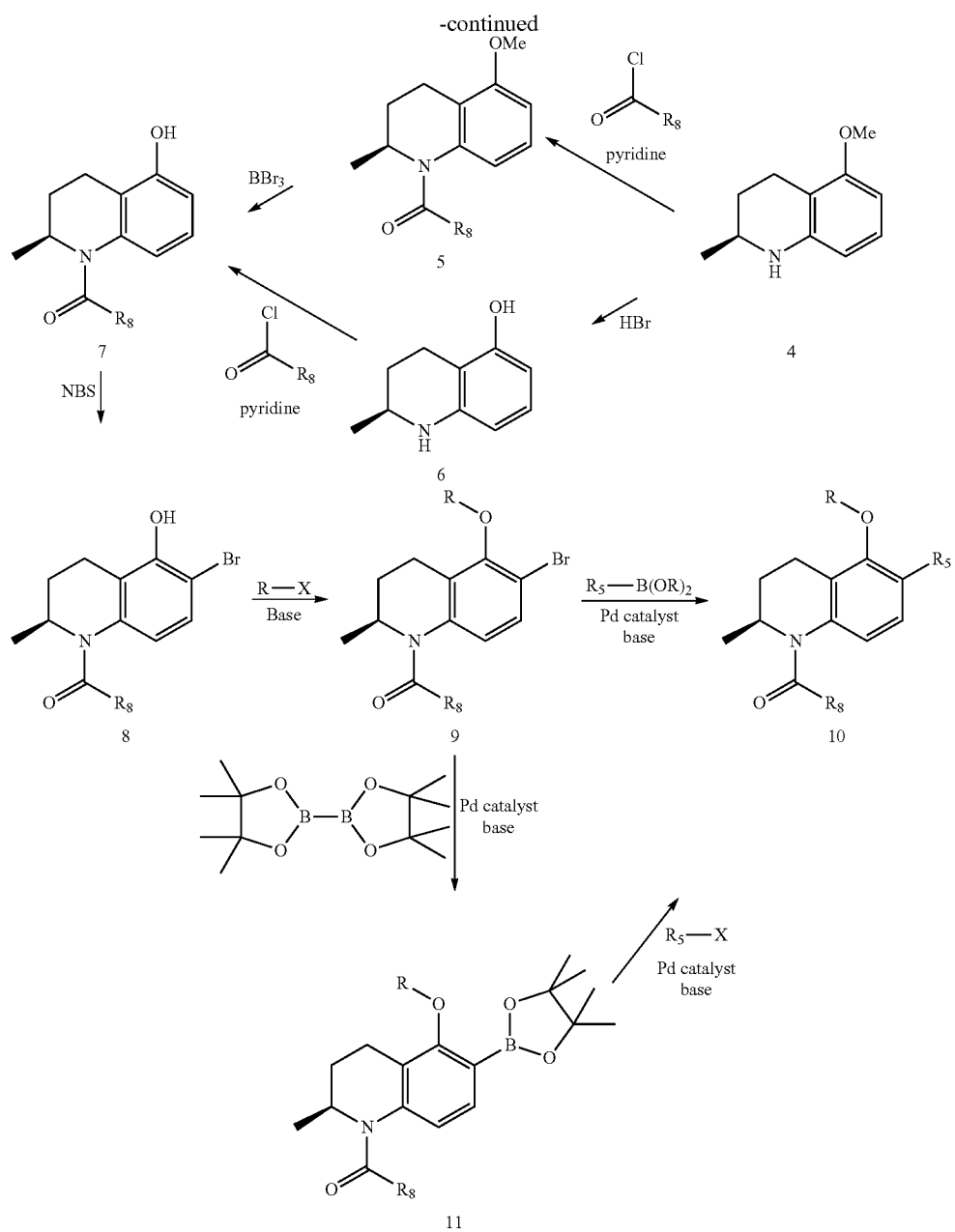

wherein $R_5$ and $R_8$ are as defined above.

The substituted tetrahydroquinolines (10) described herein can be prepared according to the general procedures outlined in Scheme 1. Oxidative cyclization of 2-chloro-5-methoxyaniline and crotonaldehyde, using chloranil as the oxidant, affords methoxyquinoline 2 as its hydrochloride salt. Catalytic hydrogenation in the presence of base reductively removes the chlorine to provide 3 in good yield. Catalytic asymmetric hydrogenation of 3 with a chiral ruthenium (II) complex at high pressure provides the desired tetrahydroquinoline 4 in excellent yield. Alternatively, tetrahydroquinoline 4 can be accessed via an asymmetric transfer hydrogenation of 3 using a chiral rhodium (II) complex. Conversion of 4 to phenol 7 can be accomplished via one of two routes. Acylation of 4 with an acid chloride or chloroformate and demethylation with boron tribromide yields affords 7. Phenol 7 can also be accessed via demethylation with hydrobromic acid followed by acylation with an acid chloride or chloroformate. Regioselective bromination of 7 with N-bromosuccinimide provides 8 as the major product. Nucleophilic aromatic substitution or alkylation with the appropriate aryl or alkyl halide, respectively, yields 9. Aryl bromide 9 can be converted to the desired tetrahydroquinoline 10 via a palladium-catalyzed Suzuki cross-coupling using the appropriate boronic acid or ester. Alternatively, aryl bromide 9 can be converted to boronic ester 11 via a palladium-catalyzed cross-coupling with bis(pinacolato)diboron. Subsequent palladium-catalyzed Suzuki cross-coupling with the appropriate aryl halide affords the desired tetrahydroquinoline 10.

Scheme 2

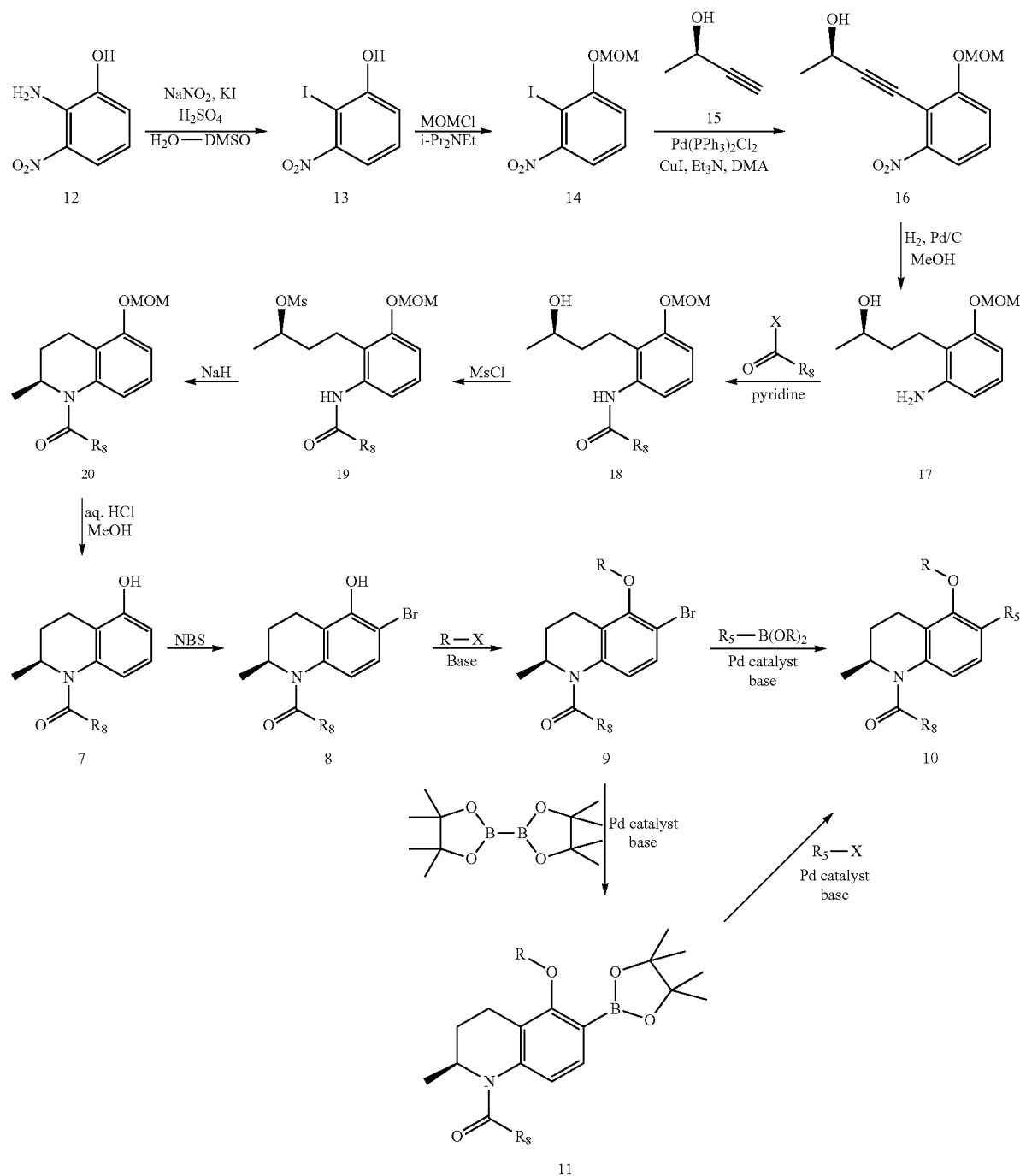

wherein $R_5$ and $R_8$ are as defined above.

Alternatively, tetrahydroquinolines (10) can be prepared according to the procedures outlined in Scheme 2. Iodophenol 13 is available via diazotization of 2-amino-3-nitrophenol (12) with sodium nitrate in the presence of sulfuric acid, followed by the addition of potassium iodide. Protection of the phenol with methoxymethylchloride provides intermediate 14 which can undergo a palladium-catalyzed Sonagashira coupling with (R)-but-3-yn-2-ol to afford 16. Palladium-catalyzed hydrogenation of the triple bond in 16 yields 17 which can be acylated with the appropriate acid chloride, anhydride, or chloroformate to provide 18. Treatment of 18 with methanesulfonyl chloride followed by the reaction with sodium hydride leads to intramolecular cyclization affording tetrahydroquinoline 20. Removal of the methoxymethyl group yields phenol 7, which can be converted to intermediate 8 via regioselective bromination with N-bromosuccinimide. Nucleophilic aromatic substitution or alkylation with the appropriate aryl or alkyl halide, respectively, yields 9. Aryl bromide 9 can be converted to the desired tetrahydroquinoline 10 via a palladium-catalyzed Suzuki cross-coupling using the appropriate boronic acid or ester. Alternatively, aryl bromide 9 can be converted to boronic ester 11 via a palladium-catalyzed cross-coupling with bis(pinacolato)diboron. Subsequent palladium-catalyzed Suzuki cross-coupling with the appropriate aryl halide affords the desired tetrahydroquinoline 10.

Methods of Using the Disclosed Compounds

One aspect of the present invention relates to a method of modulating one or more of BET family bromodomains, comprising administering to a patient in need thereof a therapeutically effective amount of a compound of Formulae (I), (II), (III), or (IV).

Another aspect of the present invention relates to a method of inhibiting one or more of BET-family bromodomains, comprising administering to a patient in need thereof a therapeutically effective amount of a compound of Formulae (I), (II), (III), or (IV).

In another aspect, the present invention relates to a method of inhibiting one or more of BET-family bromodomains, comprising administering to a patient in need thereof a therapeutically effective amount of the pharmaceutical composition of Formula (I), (II), (III), or (IV).

Another aspect of the present invention relates to a method of treating, preventing, inhibiting, or eliminating a disease or disorder in a patient associated with the inhibition of one or more of BET-family bromodomains, the method comprising administering a therapeutically effective amount of a compound of Formulae (I), (II), (III), or (IV). In one embodiment, the disease or disorder is selected from the group consisting of cancer, inflammatory disorders, irritable bowel syndrome, inflammatory bowel disease, rheumatoid arthritis, obesity and diabetes.

The present invention also relates to the use of an inhibitor of BET family bromodomains for the preparation of a medicament used in the treatment, prevention, inhibition or elimination of a disease or disorder mediated by BET family bromodomains, wherein the medicament comprises a compound of Formulae (I), (II), (III), or (IV).

In another aspect, the present invention the present invention relates to a method for the manufacture of a medicament for treating, preventing, inhibiting, or eliminating a disease or disorder mediated by BET family bromodomains, wherein the medicament comprises a compound of Formulae (I), (II), (III), or (IV).

Another aspect of the present invention relates to a pharmaceutical composition for use in a method for treating a disease or disorder mediated by BET family bromodomains, wherein the pharmaceutical composition comprises a compound of Formulae (I), (II), (III), or (IV).

In yet another aspect, the present invention relates to a compound for use in a method for treating a disease or disorder mediated by BET family bromodomains, wherein the compound comprises a compound of Formulae (I), (II), (III), or (IV).

The present invention also relates to the use of an inhibitor of BET family bromodomains for the preparation of a medicament used in the treatment, prevention, inhibition or elimination of tumors, wherein the medicament comprises a compound of Formulae (I), (II), (III), or (IV).

The present invention further relates to the use of an inhibitor of BET family bromodomains for the preparation of a medicament used in the treatment, prevention, inhibition or elimination of cancer, wherein the medicament comprises a compound of Formulae (I), (II), (III), or (IV).

In one embodiment, the present invention relates to the use of an inhibitor of BET family bromodomains for the preparation of a medicament used in treatment, prevention, inhibition or elimination of diseases associated with chronic autoimmune, inflammatory conditions, acute inflammatory conditions, systemic inflammatory response syndrome, virus, bacterial, or fungal infections, diabetes, and/or obesity. In one embodiment, the medicament prepared comprises a compound of Formulae (I), (II), (III), or (IV), or a pharmaceutically acceptable salt, enantiomer, hydrate, solvate, prodrug, isomer, or tautomer thereof. In another embodiment, the present invention relates to the use of an inhibitor of BET family bromodomains for the preparation of a male contraceptive, wherein the inhibitor comprises a compound of Formulae (I), (II), (III), or (IV).

Another embodiment of the present invention relates to a compound of Formulae (I), (II), (III), or (IV), or a pharmaceutically acceptable salt, enantiomer, hydrate, solvate, prodrug, isomer, or tautomer thereof, or a pharmaceutical composition comprising a compound of the present invention, or a pharmaceutically acceptable salt, enantiomer, hydrate, solvate, prodrug, isomer, or tautomer thereof, and a pharmaceutically acceptable carrier which provides, upon administration to a human, a decrease in tumor burden and/or metastases. The pharmaceutical composition can be administered by oral means or other suitable means.

In another embodiment, the present invention relates to a compound of Formula (I), (II), (III), or (IV) or a pharmaceutical composition comprising a compound of the present invention and a pharmaceutically acceptable carrier used for the treatment of cancers including but not limited to cervix, colon, breast, lung, and stomach cancers; hematologic cancer, such as but not limited to leukaemia, lymphoma and multiple myeloma; midline carcinomas, mesenchymal, hepatic, renal and neurological tumors; and melanoma, squamous cell carcinoma and cutaneous T-cell lymphoma.

In another embodiment, the present invention relates to a compound of Formulae (I), (II), (III), or (IV) or a pharmaceutical composition comprising a compound of the present invention and a pharmaceutically acceptable carrier used for the treatment of a variety of diseases or disorders related to systemic or tissue inflammation, inflammatory responses to infection or hypoxia, cellular activation and proliferation, lipid metabolism, fibrosis and in the prevention and treatment of viral infections. In one embodiment, the pharmaceutical composition is used.

Another embodiment of the present invention relates to a compound of Formula (I), (II), (III), or (IV) or a pharmaceutical composition comprising a compound of the present invention and a pharmaceutically acceptable carrier used for the treatment of a variety of chronic and inflammatory conditions, including but not limited to rheumatoid arthritis, osteoarthritis, acute gout, psoriasis, systemic lupus erythematosus, multiple sclerosis, Crohn's disease, ulcerative colitis, asthma, chronic obstructive airways disease, pneumonitis, myocarditis, pericarditis, myositis, eczema, dermatitis, alopecia, vitiligo, bullous skin disease, nephrititis, vasculitis, atherosclerosis, Alzheimer's disease, depression, Sjogren's syndrome, siloadenitis, central retinal vein occlusion, branched retinal vein occlusion, Irvine-Gass syndrome, parafoveal telangiectasis, retinitis pigmentosa, pars planitis, birdshot retinochoroidopathy, epiretinal membrane, cystic macular edema, maculopathies, vitreomacular traction syndromes, retinal detachment, neuroretinitis, idiopathic macular edema, retinitis, dry eye, vernal keratoconjuctivitis, atopic keratoconjuctivitis, anterior uveitis, pan uveitis, posterior uveitis, uveitis-associated macular edema, scleritis, diabetic retinopathy, diabetic macular edema, age-related macular dystrophy, hepatitis, pancreatitis, primary biliary cirrhosis, sclerosing cholangitis, Addison's disease, hypophysitis, thyroiditis, type I diabetes and acute rejection of transplanted organisms.

In another embodiment, the present invention relates to a compound of Formula (I), (II), (III), or (IV) or a pharmaceutical composition comprising a compound of the present invention and a pharmaceutically acceptable carrier used for the treatment of a variety of acute inflammatory conditions such as acute gout, giant cell arteritis, nephritis including lupus nephritis, vasculitis with organ involvement such as glomerulonephritis, vasculitis including giant cell arteritis, Wegner's granulomatosis, Polyarteritis nodosa, Becet's disease, Kawasaki disease, Takayasu's arteritis, pyoderma gangrenosum, vasculitis with organ involvement and acute rejection of transplanted organs.

Another embodiment of the present invention relates to a compound of Formula (I), (II), (III), or (IV) or a pharmaceutical composition comprising a compound of the present invention and a pharmaceutically acceptable carrier used for the treatment of a variety of diseases or disorders which involve inflammatory responses to infections with bacteria, viruses, fungi, parasites or their toxins, such as but not limited to sepsis, sepsis syndrome, septic shock, endotoxaemia, systemic inflammatory response syndrome, multi organ dysfunction syndrome, toxic shock syndrome, acute lung injury, acute respiratory distress syndrome, acute renal failure, fulmiant hepatitis, burns, acute pancreatitis, post-surgical syndromes, sarcoidosis, Herxheimer reactions, encephalitis, myelitis, meningitis, malaria, systemic inflammatory responses associated with viral infections, such as but not limited to influenza, herpes zoster, herpes simplex and coronavirus.

In another embodiment, the present invention relates to a compound of Formulae (I), (II), (III), or (IV) or a pharmaceutical composition comprising a compound of the present invention and a pharmaceutically acceptable carrier used for the treatment of a variety of conditions associated with ischaemia reperfusion injury such as myocardial infarction, cerebro-vascular ischaemia, acute coronary syndromes, renal reperfusion injury, organ transplantation, coronary artery bypass procedures, cardio-, pulmonary and bypass procedures, pulmonary, renal, hepatitic, gastrointestinal or peripheral limb embolism.

Another embodiment of the present invention relates to a compound of Formulae (I), (II), (III), or (IV) or a pharmaceutical composition comprising a compound of the present invention and a pharmaceutically acceptable carrier used for treatment of a variety of disorders of lipid metabolisms such as hypercholesterolemia, atherosclerosis and Alzheimer disease.

In another embodiment, the present invention relates to a compound of Formulae (I), (II), (III), or (IV) or a pharmaceutical composition comprising a compound of the present invention and a pharmaceutically acceptable carrier used for the treatment of a variety of fibrotic conditions such as, but not limited to idiopathic pulmonary fibrosis, renal fibrosis, post-operative structure, keloid scar formation, scleroma and cardial fibrosis.

Another embodiment of the present invention relates to a compound of Formulae (I), (II), (III), or (IV) or a pharmaceutical composition comprising a compound of the present invention used for the treatment of a variety of viral infections such as, but not limited to herpes virus, human papilloma virus, adenovirus, poxvirus, and DNA viruses in general.

In another embodiment, the present invention relates to a compound of Formulae (I), (II), (III), or (IV) or a pharmaceutical composition comprising a compound of the present invention and a pharmaceutically acceptable carrier used for the treatment of a variety of conditions such as non-malignant melanoma, actinic keratosis, basal cell melanoma, in situ melanoma, squamous cell carcinoma and cutaneous T-cell lymphoma.

Another embodiment of the present invention relates to a compound of Formulae (I), (II), (III), or (IV) or a pharmaceutical composition comprising a compound of the present invention and a pharmaceutically acceptable carrier used for the treatment of obesity.

In another embodiment, the present invention relates to a compound of Formulae (I), (II), (III), or (IV) or a pharmaceutical composition comprising a pharmaceutically acceptable compound of the present invention and a pharmaceutically acceptable carrier used for male contraceptive.

Another embodiment of the present invention relates to a method of treating a disease associated with systemic inflammatory response syndrome, such as but not limited to sepsis, burns, pancreatitis, major trauma, hemorrhage and ischaemia, the method comprising administering a compound of Formulae (I), (II), (III), or (IV).

In another embodiment, the present invention relates to a method to reduce incidence of SIRS, onset of shock, multiorgan dysfunction syndrome, acute lung injury, acute renal hepatic, cardiac and gastrointestinal injury at the point of diagnosis by administering a compound of Formulae (I), (II), (III), or (IV).

Another embodiment of the present invention relates to a method to reduce incidence of sepsis, hemorrhage, tissue damage, and multiple organ dysfunction before surgery or any procedure with high risk of sepsis, the method comprising administering a compound of Formulae (I), (II), (III), or (IV).

The disclosed compounds of the invention can be administered in effective amounts to treat or prevent a disorder and/or prevent the development thereof in subjects.

The present invention also relates to a pharmaceutical composition comprising a compound of Formulae (I), (II), (III), or (IV) and a pharmaceutically acceptable carrier. The pharmaceutical acceptable carrier may further include an excipient, diluent, additive, or surfactant.

The compounds or pharmaceutical compositions of the invention may be administered via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or compositions can be in solid, semisolid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the present invention relates to a method of preparing a pharmaceutical composition of the present invention by mixing at least one pharmaceutically acceptable compound of the present invention, and, optionally, one or more pharmaceutically acceptable carriers, additives, or excipients.

In another embodiment, the present invention relates to a method of preparing a pharmaceutical composition of the present invention by mixing at least one pharmaceutically acceptable compound of the present invention and one or more additional therapeutic agents.

According to one embodiment of the invention, the additional therapeutic agents may be selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methotrexate, temozolomide, cyclophosphamide, SCH 66336, tipifarnib (Zarnestra®), R115777, L778,123, BMS 214662, Iressa®, Tarceva®, C225, GLEEVEC®, Intron®, Peg-Intron®, aromatase combinations, ara-C, adriamycin, Cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, C225, Campath, leucovorin, dexamethasone, bicalutamide, carboplatin, letrozole, megestrol, and valrubicin.

The dosage forms of the present invention, may contain a mixture of one or more compounds of this invention, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (WV), preferably about 0.5% (WV). Suitable, but non-limiting, examples of stabilizing additives include gum acacia, gelatin, methyl cellulose, polyethylene glycol, carboxylic acids and salts thereof, and polylysine. In one embodiment, the stabilizing additives are gum acacia, gelatin and methyl cellulose.

Examples of pharmaceutical excipients and additives include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octaacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate sodium formaldehyde sulfoxylate sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate ethylcellulose, gelatin, pharmaceutical glaze, hydroxypropyl cellulose, hydroxypropyl methylcellulose, hydroxypropyl methylcellulose phthalate methacrylic acid copolymer, methylcellulose, polyethylene glycol, polyvinyl acetate phthalate shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and diglycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present invention.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

For preparing pharmaceutical compositions from the compounds described in this disclosure inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

If formulated as a fixed dose, such combination products employ the compounds of this invention within the dosage range described herein, or as known to those skilled in the art.

Since the compounds of this invention are intended for use in pharmaceutical compositions a skilled artisan will understand that they can be provided in substantially pure forms for example, at least 60% pure, more suitably at least 75% pure, preferably at least 85% pure and most preferably at least 98% pure (w/w).

The pharmaceutical preparation may be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, from about 1 mg to about 500 mg, from about 1 mg to about 250 mg, or from about 1 mg to about 25 mg, according to the particular application.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. A typical recommended daily dosage regimen for oral administration can range from about 1 mg/day to about 500 mg/day or 1 mg/day to 200 mg/day, in two to four divided doses.

The compounds of Formulae I through IV can form salts which are also within the scope of this invention. Reference to a compound of the Formula herein is understood to include reference to salts thereof, unless otherwise indicated.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The synthetic schemes are presented for the synthesis of certain compounds herein disclosed. The process and results for the assays testing BET family bromodomain inhibition and effects on a cancer cell line proliferation are also described.

Definitions used in the following Schemes and elsewhere herein are:
Ac$_2$O acetic anhydride
Boc tert-butoxycarbonyl
DCE 1,2-dichloro ethane
DCM dichloromethane or methylene chloride
DIPEA N,N-diisopropylethylamine
DMAP 4-(dimethylamino)pyridine
DMF N,N-dimethylformamide
DMSO dimethylsulfoxide
DPPA diphenylphosphoryl azide
dppf bis(diphenylphosphino)ferrocene
Et$_3$N triethylamine
EtOAc ethyl acetate
EtOH ethanol
h hours
HATU 2-(3H-[1,2,3]triazolo[4,5-b]pyridin-3-yl)-1,1,3,3-tetramethylisouronium hexafluorophosphate
HCl hydrogen chloride
HPLC high performance liquid chromatography
(i-Pr)$_2$NEt N,N-diisopropylethylamine
LCMS liquid chromatography/mass spectrometry
K$_2$CO$_3$ potassium carbonate
MS mass spectrometry
NBS N-bromosuccinimide
Ph$_3$P triphenylphosphine
PhCHO benzaldehyde
Pd$_2$(dba)$_3$ tris(dibenzylideneacetone)dipalladium
p-TsOH para-toluenesulfonic acid
rt room temperature
TFAA trifluoroacetic anhydride
THF tetrahydrofuran
XPhos 2-dicyclohexylphosphino-2',4',6'-triisopropylbiphenyl Materials Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C$_{18}$ 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Example 1

Intermediate 1—(2S)-5-methoxy-2-methyl-1,2,3,4-tetrahydroquinoline

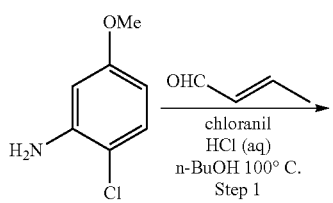

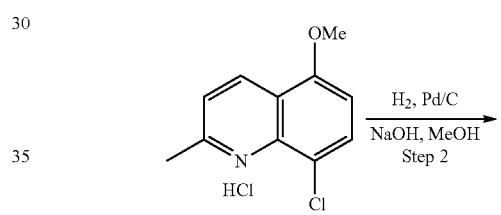

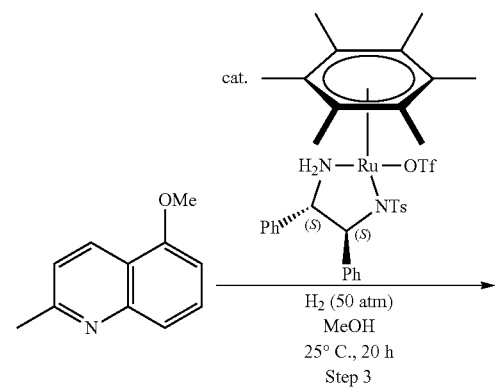

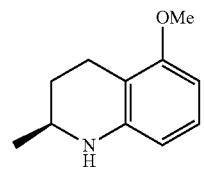

Intermediate 1

Step 1. 8-chloro-5-methoxy-2-methylquinoline hydrochloride

A 1000-mL 3-necked round-bottom flask was charged with 2-chloro-5-methoxyaniline (50 g, 317 mmol), n-butanol (120 mL), concentrated hydrochloric acid (37%, 90 mL), and chloranil (tetrachloro-1,4-benzoquinone) (78 g, 317 mmol). The resulting solution stirred for 1 h at 100° C. in an oil bath. A solution of (E)-crotonaldehyde (28.9 mL, 349 mmol) in n-butanol (50 mL) was added dropwise over 1 h. The resulting solution stirred for 1 h at 100° C. in an oil bath and was then cooled to 70° C. Tetrahydrofuran (650 mL) was added, and the reaction mixture stirred for 1 h at 70° C. and was then cooled to 0° C. The resulting precipitate was held at 0-5° C. for 1 h. The mixture was filtered, the solids were washed with cold (ca. 0° C.) THF (2×350 mL), and then dried in an oven to afford 8-chloro-5-methoxy-2-methylquinoline hydrochloride (83.0 g, 74%) as a yellow solid. MS (ES, m/z): 208 [M+H]$^+$

Step 2. 5-methoxy-2-methylquinoline

A 1000-mL round-bottom flask was charged with 8-chloro-5-methoxy-2-methylquinoline hydrochloride (50.0 g, 204.8 mmol), methanol (300 mL), aqueous sodium hydroxide solution (3 M, 205 mL), and 10% palladium on active carbon (25 g). The system was purged with hydrogen gas, and the resulting mixture was stirred under a hydrogen atmosphere for 3 h at room temperature. The reaction mixture was filtered through a pad of Celite and concentrated under vacuum to remove most of methanol. The resulting solution was extracted with ethyl acetate (2×2000 mL). The organic layers were combined, dried over anhydrous sodium sulfate, filtered, and concentrated under vacuum. The residue was purified via column chromatography on silica gel (gradient elution with 0-20% ethyl acetate/petroleum ether) to afford 5-methoxy-2-methylquinoline (36 g, 63%) as a yellow solid. MS (ES, m/z): 174 [M+H]$^+$

Step 3. (2S)-5-methoxy-2-methyl-1,2,3,4-tetrahydroquinoline (Intermediate 1)

A 30-mL glass-lined stainless steel reactor with a magnetic stirring bar was charged with 5-methoxy-2-methylquinoline (4.0 g, 23.1 mmol), Ru(OTf)(η6-hexamethylbenzene)((S,S)-TsDPEN)([N-[(1S,2S)-2-(amino-κN)-1,2-diphenylethyl]-4-methylbenzenesulfonamidato-κN][(1,2,3,4,5,6-η)-1,2,3,4,5,6-hexamethylbenzene](1,1,1-trifluoromethanesulfonato-κO)-ruthenium, prepared according to the procedure in *J. Am. Chem. Soc.* 2011, 133, 9878-9891) (0.100 g, 0.13 mmol) and methanol (10 mL). The reactor was closed and hydrogen gas was initially introduced in at a pressure of 50 atm, before being reduced to 1 atm. After this procedure was repeated three times, the reactor was pressurized with hydrogen to 50 atm. The resulting mixture was stirred under this hydrogen pressure for 24 h at room temperature. After carefully releasing the hydrogen, the reaction mixture was concentrated under vacuum. The residue was purified via column chromatography on silica gel (gradient elution with 0-20% ethyl acetate/petroleum ether) to afford (2S)-5-methoxy-2-methyl-1,2,3,4-tetrahydroquinoline (4.0 g, 98%, >99% ee) as yellow oil. MS (ES, m/z): 178 [M+H]$^+$

Example 2

Intermediate 1—HCl salt. (2S)-5-methoxy-2-methyl-1,2,3,4-tetrahydroquinoline hydrochloride

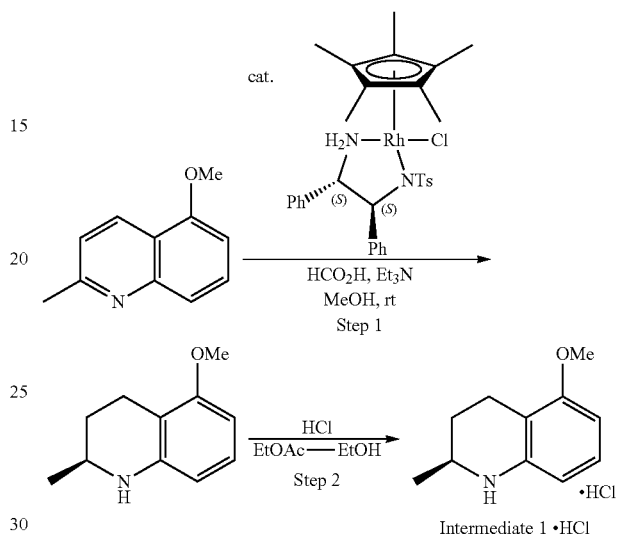

Step 1. (2S)-5-methoxy-2-methyl-1,2,3,4-tetrahydroquinoline

A three-necked, 2-L round bottomed flask equipped with an overhead stirrer, thermocouple, and nitrogen inlet was charged with methanol (1350 mL) and formic acid (51.8 mL, 1350 mmol). The flask was lowered into an ice-water bath and when the internal temperature reached 13° C., triethylamine (75 mL, 540 mmol) was slowly added, causing the internal temperature to rise to 21° C. Next, 5-methoxy-2-methylquinoline (58.47 g, 338 mmol) was added in one portion, and the resulting solution was cooled to 0° C. Finally, Cp*RhCl[(S,S)-TsDPEN]([N-[(1S,2S)-2-(amino-κN)-1,2-diphenylethyl]-4-methylbenzenesulfonamidato-κN]chloro[(1,2,3,4,5-η)-1,2,3,4,5-pentamethyl-2,4-cyclopentadien-1-yl]rhodium, prepared according to the procedure in *Org. Lett.* 1999, 1, 841) (2.157 g, 3.38 mmol) was added in one portion. The ice bath was left in place and allowed to slowly expire. After 22 h (internal temperature=17° C.), additional formic acid (12.95 mL, 338 mmol) was added to the reaction mixture. The dark solution stirred at room temperature for 4 days. After a total of 5 days, the solution was concentrated under reduced pressure. The concentrated reaction mixture was re-dissolved in ethyl acetate (ca. 750 mL) and washed twice with saturated aqueous sodium bicarbonate solution (250 mL, then 100 mL), and finally with 5% aqueous sodium chloride solution (100 mL). The ethyl acetate extract was then concentrated under reduced pressure to afford 64.7 g of a dark syrup. Chiral HPLC analysis showed the material to have an enantiopurity of 97.2:2.8 e.r. (94.4% ee). (Chiral HPLC method: Column: ODH; Method: ODH 98% Hexane 2% IPA; UV:254, Flow: 0.5 mL/min). The crude (S)-5-methoxy-2-methyl-1,2,3,4-tetrahydroquinoline (59.8 g, 338 mmol, 100% yield) was used without further purification in the salt formation (assumed 100% yield). MS (ES, m/z): 178 [M+H]+

Step 2. (2S)-5-methoxy-2-methyl-1,2,3,4-tetrahydroquinoline hydrochloride (Intermediate 1·HCl salt)

A three-necked, 500-mL round-bottomed flask equipped with a magnetic stir bar and thermocouple was charged with ethanol (160 mL), and the solution was cooled to 0° C. Acetyl chloride (26.4 mL, 372 mmol) was slowly added over 45 min, maintaining the internal temperature below 8° C. The ice bath was removed and the HCl solution (~2 M) was allowed to warm for about 30 min (internal temperature=15° C.).

A three-necked, 1-L round-bottomed flask equipped with an overhead stirrer, thermocouple, and nitrogen inlet was charged with a solution of crude (S)-5-methoxy-2-methyl-1,2,3,4-tetrahydroquinoline (59.9 g, 338 mmol) in ethyl acetate (600 mL). To this solution was then added the freshly prepared HCl solution (ca. 2 M in ethanol, 86 mL, 372 mmol) at 17° C. As the HCl solution was being added, the mixture initially became cloudy but then became a clear solution upon complete addition. The internal temperature rose to 26° C. The clear solution was stirred at ambient temperature, and after 10-15 min, a granular precipitate formed. The slurry was stirred at ambient temperature for 4.5 h, then filtered on a glass, 600-mL Buchner funnel. The flask and solids were rinsed with fresh ethyl acetate, filtered, and dried on the filter under suction and a positive pressure of nitrogen to afford (S)-5-methoxy-2-methyl-1,2,3,4-tetrahydroquinoline hydrochloride (64.43 g, 89%) as a cream-colored, free-flowing, granular solid. Chiral HPLC analysis showed the salt to have an enantiopurity of 98.9:1.1 e.r. (97.8% ee). (Chiral HPLC method: Column: ODH; Method: ODH 98% Hexane 2% IPA; UV:254, Flow: 0.5 mL/min). MS (ES, m/z): 178 [M+H]+

Example 3

Intermediate 2—(2S)-6-bromo-1-cyclopropanecarbonyl-2-methyl-1,2,3,4-tetrahydroquinolin-5-ol

Step 1a. (2S)-1-cyclopropanecarbonyl-5-methoxy-2-methyl-1,2,3,4-tetrahydroquinoline A 1000-mL 3-necked round-bottom flask was charged with (2S)-5-methoxy-2-methyl-1,2,3,4-tetrahydroquinoline (47.41 g, 267.5 mmol), dichloromethane (500 mL), and pyridine (38 mL). Cyclopropanecarbonyl chloride (28.4 g, 271.7 mmol) was added dropwise with stirring at 0° C., and the resulting solution stirred for 3 h at 0° C. The reaction mixture was poured into 400 mL of water/ice, and then washed with 2 N hydrochloric acid (1×100 mL) and brine (3×300 mL), dried over anhydrous sodium sulfate, filtered, and concentrated under vacuum. The residue was purified via column chromatography on silica gel (eluting with 0-15% ethyl acetate/petroleum ether) to afford (2S)-1-cyclopropanecarbonyl-5-methoxy-2-methyl-1,2,3,4-tetrahydroquinoline (64.6 g, 98%) as a yellow solid. MS (ES, m/z): 246 [M+H]+

Step 2a. (2S)-1-cyclopropanecarbonyl-2-methyl-1,2,3,4-tetrahydroquinolin-5-ol A 1000-mL round-bottom flask was charged with (2S)-1-cyclopropanecarbonyl-5-methoxy-2-methyl-1,2,3,4-tetrahydroquinoline (15.0 g, 61.2 mmol) and dichloromethane (300 mL). A solution of boron tribromide (1 M in dichloromethane, 308 mL, 308 mmol) was added dropwise at 0° C., and the resulting solution stirred for 1 h at 0° C. The reaction mixture was then poured into 500 mL of water/ice and extracted with dichloromethane (2×500 mL). The combined organic layers were dried over anhydrous sodium sulfate, filtered, and concentrated under vacuum. The residue was purified via column chromatography on silica gel (eluting with 0-80% ethyl acetate/petroleum ether) to afford (2S)-1-cyclopropanecarbonyl-2-methyl-1,2,3,4-tetrahydroquinolin-5-ol (9.4 g, 66%) as an off-white solid. MS (ES, m/z): 232 [M+H]+

Step 1b. (S)-2-methyl-1,2,3,4-tetrahydroquinolin-5-ol hydrobromide

A 500-mL round bottomed flask equipped with a heating mantle and an overhead stirrer was charged with (S)-5-methoxy-2-methyl-1,2,3,4-tetrahydroquinoline hydrochloride (20

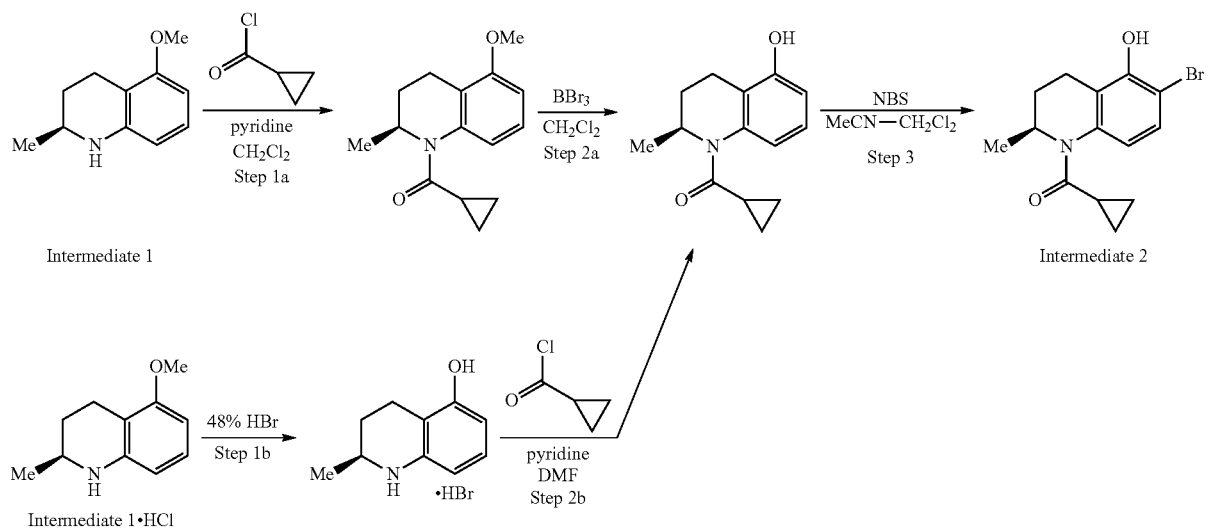

g, 94 mmol) followed by hydrobromic acid (48%, 154 mL, 1361 mmol). The mixture was heated to 100° C., and the reaction readily proceeded with loss of bromomethane through an uncooled reflux condenser. After 1 h, solids precipitated from the solution. The reaction was complete after 10 h at 100° C. and allowed to cool to ambient temperature while stirring overnight. The reaction mixture was placed in an ice bath and stirred for 2 h at 0-5° C. The resulting white slurry was filtered and the pot and solids were washed with 20 mL of ice cold water. The filter cake was dried on a Buchner funnel under nitrogen blanket to afford (S)-2-methyl-1,2,3,4-tetrahydroquinolin-5-ol hydrobromide (21.71 g, 95%) as a white powder. MS (ES, m/z): 164 [M+H]$^+$ Step 2b. (2S)-1-cyclopropanecarbonyl-2-methyl-1,2,3,4-tetrahydroquinolin-5-ol A 1000-mL round bottomed flask fitted with a nitrogen inlet, overhead stirrer, addition funnel, and thermocouple, was charged with (S)-2-methyl-1,2,3,4-tetrahydroquinolin-5-ol hydrobromide (20 g, 82 mmol), followed by anhydrous DMF (109 mL), and pyridine (19.8 mL, 246 mmol). Cyclopropanecarbonyl chloride (7.43 mL, 82 mmol) was added dropwise over 30 minutes while holding temperature below 20° C. with a cool water bath. Following completion of the addition, the reaction mixture was stirred for 1.5 h at ambient temperature. The pot was cooled to 0° C. in an ice bath and 0.29 M aqueous HCl solution (315 mL) was added dropwise over 15 minutes. The slurry was stirred for 90 minutes in the ice bath before being filtered. The pot and filter cake were washed with 25 mL of ice water. The filter cake was dried under nitrogen on a Buchner funnel to afford (2S)-1-cyclopropanecarbonyl-2-methyl-1,2,3,4-tetrahydroquinolin-5-ol (17.16 g, 91%) as an off-white powder. MS (ES, m/z): 232 [M+H]$^+$ Step 3. (2S)-6-bromo-1-cyclopropanecarbonyl-2-methyl-1,2,3,4-tetrahydroquinolin-5-ol (Intermediate 2)

Into a 1000-mL 3-necked round-bottom flask purged and maintained with an inert atmosphere of nitrogen, was placed (2S)-1-cyclopropanecarbonyl-2-methyl-1,2,3,4-tetrahydroquinolin-5-ol (4.0 g, 17.3 mmol) in acetonitrile (600 mL) and dichloromethane (150 mL). The solution was cooled to −10° C., and a solution of N-bromosuccinimide (3.08 g, 17.3 mmol) in acetonitrile (50 mL) was added dropwise over 3 h. The resulting solution stirred for 30 minutes at −10° C., and was then concentrated under vacuum. The residue was purified via column chromatography on silica gel (eluting with 0-20% ethyl acetate/petroleum ether) to afford (2S)-6-bromo-1-cyclopropanecarbonyl-2-methyl-1,2,3,4-tetrahydroquinolin-5-ol (3.6 g, 68%) as a light yellow solid. MS: (ES, m/z): 310, 312 [M+H]$^+$ Example 4

Intermediate 3. (S)-1-(6-bromo-5-hydroxy-2-methyl-3,4-dihydroquinolin-1(2H)-yl)ethanone

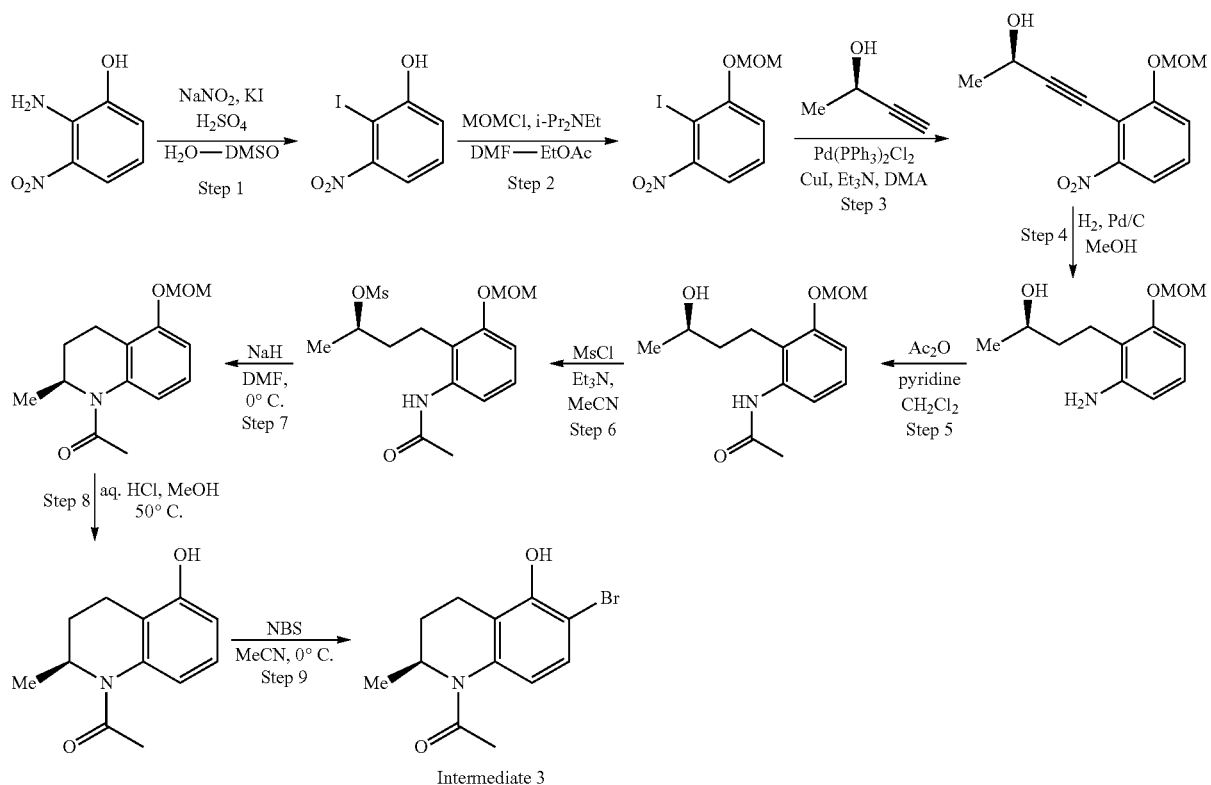

Intermediate 3

Step 1. 2-iodo-3-nitrophenol

A 1-L, three-necked, round bottomed flask equipped with an overhead stirrer, thermocouple, and nitrogen inlet was charged with 2-amino-3-nitrophenol (17.5 g, 114 mmol), DMSO (280 mL), and 30% sulfuric acid (280 mL, 1575 mmol). The dark red-orange solution was heated to 50° C. After 45 min, heating was discontinued, and the solution was cooled to 3° C. (once the solution reached 13° C., a precipitate formed). Next, a solution of sodium nitrite (10.97 g, 159 mmol) in water (35 mL) was slowly added to the slurry while maintaining the internal temperature below 5° C.; the addition took ca. 5-7 min. The solution was stirred at 0° C. After 1 h, a solution of potassium iodide (52.8 g, 318 mmol) in water (105 mL) was slowly added over a 5 min period. After 1 h, the ice bath was removed, and the reaction mixture was allowed to warm to room temperature and stirred for 20 h. The reaction mixture was then extracted with methyl tert-butyl ether (1×800 mL and 1×400 mL). The combined methyl tert-butyl ether extracts were washed with 20% aqueous sodium thiosulfate solution (2×200 mL) followed by 5% aqueous sodium chloride solution (2×200 mL). The organic extract was concentrated under reduced pressure. Toluene (200 mL) was added and then removed under reduced pressure to afford 2-iodo-3-nitrophenol (30.2 g, 100%) as a brown powder. $^1$H NMR (400 MHz, CDCl$_3$): δ 7.44 (dd, J=8.0, 1.5 Hz, 1H), 7.37 (t, J=8.0 Hz, 1H), 7.24 (dd, J=8.0, 1.5 Hz, 1H), 5.97 (br, 1H) ppm.

Step 2. 2-iodo-1-(methoxymethoxy)-3-nitrobenzene

A 200-mL round bottomed flask equipped with a magnetic stir bar was charged with ethyl acetate (37 mL), dimethoxymethane (12.25 mL, 137 mmol), and zinc acetate (2.51 mg, 0.014 mmol). Next, acetyl chloride (9.73 mL, 137 mmol) was slowly added over a 20 min period. The solution was stirred at room temperature for 2 h. This chloromethyl methyl ether solution was then added to a solution of 2-iodo-3-nitrophenol (30.2 g, 114 mmol) in N,N-dimethylformamide (170 mL). The resulting solution was cooled to 0° C. and slowly treated with diisopropylethylamine (49.8 mL, 285 mmol) over a 20 min period. The ice bath was left in place, and the reaction mixture stirred overnight as the ice bath slowly expired. The reaction mixture was then diluted with ethyl acetate and partitioned between water (340 mL) and ethyl acetate (500 mL). The organic layer was separated and washed with half-saturated aqueous sodium bicarbonate solution (1×340 mL) and 5% aqueous sodium chloride solution (1×340 mL, then 1×200 mL). The organic layer was then concentrated under reduced pressure to afford a dark brown syrup (33.6 g), which crystallized upon standing. The crude product was dissolved in a small amount of dichloromethane and purified by filtration through a pad of silica gel (14 cm(d)×6 cm(h), eluting with 3:2 hexanes-dichloromethane) to afford 2-iodo-1-(methoxymethoxy)-3-nitrobenzene (30.2 g, 86%) as a pale yellow solid. $^1$H NMR (400 MHz, CDCl$_3$): δ 7.39 (t, J=8.1 Hz, 1H), 7.34 (dd, J=8.0, 1.6 Hz, 1H), 7.25 (dd, J=8.1, 1.6 Hz, 1H), 5.30 (s, 2H), 3.52 (s, 3H) ppm.

Step 3. (R)-4-(2-(methoxymethoxy)-6-nitrophenyl)but-3-yn-2-ol

A two-necked, 100-mL round bottomed flask equipped with a magnetic stir bar was charged with 2-iodo-1-(methoxymethoxy)-3-nitrobenzene (5.0 g, 16.18 mmol), copper(I) iodide (0.154 g, 0.809 mmol), bis(triphenylphosphine)palladium(II) chloride (0.284 g, 0.404 mmol), N,N-dimethylacetamide (25 mL), and triethylamine (9.02 mL, 64.7 mmol). Nitrogen was bubbled through the dark orange solution for several minutes and then (R)-but-3-yn-2-ol (1.33 mL, 17.0 mmol) was added, which caused the solution to lighten in color considerably. The solution was then heated to 70° C. for 10 h, at which point heating was discontinued and the reaction mixture allowed to cool to rt. After stirring at rt for 10 h, the reaction mixture was diluted with isopropyl acetate and washed with water (50 mL), saturated aqueous ammonium chloride solution (50 mL), and 5% aqueous sodium chloride solution (2×50 mL). The organic layer was concentrated under reduced pressure to afford a dark brown syrup (4.7 g). The crude product was purified by flash chromatography on silica gel (eluting with 2:1 hexanes-ethyl acetate, then 3:2 hexanes-ethyl acetate, and finally 1:1 hexanes-ethyl acetate) to afford (R)-4-(2-(methoxymethoxy)-6-nitrophenyl)but-3-yn-2-ol (2.1 g, 52%). MS (ESI, pos. ion) m/z 274 [M+23]$^+$.

Step 4. (R)-4-(2-amino-6-(methoxymethoxy)phenyl)butan-2-ol

A 400-mL Parr bottle charged with (R)-4-(2-(methoxymethoxy)-6-nitrophenyl)but-3-yn-2-ol (2.9 g, 11.54 mmol), methanol (58 mL), and 10% palladium on carbon (50% water, 1.228 g, 0.577 mmol) was pressurized to 39 psig with hydrogen and then shaken. Hydrogen was quickly consumed, and within 15 min, the pressure had dropped to 0 psig. The bottle was re-pressurized to 39 psig and shaking was continued. The pressure dropped to ca. 20 psig over the next 15 min and stabilized. The bottle was re-pressurized to 34 psig and held there with continued shaking for 2 h. The mixture was flushed with nitrogen, and then filtered through a pad of Celite. The bottle and catalyst were rinsed with methanol, and the filtrate concentrated under reduced pressure. Toluene was added and the mixture was concentrated to afford (R)-4-(2-amino-6-(methoxymethoxy)phenyl)butan-2-ol (2.60 g, 100%) as a dark yellow syrup which was used without further purification. MS (ESI, pos. ion) m/z 248 [M+23]$^+$.

Step 5. (R)—N-(2-(3-hydroxybutyl)-3-(methoxymethoxy)phenyl)acetamide

A solution of crude (R)-4-(2-amino-6-(methoxymethoxy)phenyl)butan-2-ol (2.60 g, 11.54 mmol) and pyridine (2.80 mL, 34.6 mmol) in dichloromethane (52 mL) was cooled to 0° C. and treated with acetic anhydride (1.14 mL, 12.1 mmol). The ice bath was removed and the reaction mixture stirred at room temperature. After 45 min, the solution was washed with 5% aqueous sodium chloride solution (2×20 mL) and then concentrated under reduced pressure. Toluene (ca. 100 mL) was added and the mixture was concentrated. The residue was purified by column chromatography on silica gel (gradient elution with 25-100% ethyl acetate-hexanes) to afford (R)—N-(2-(3-hydroxybutyl)-3-(methoxymethoxy)phenyl)acetamide (2.7 g, 88%) as a pale yellow syrup. MS (ESI, pos. ion) m/z 290 [M+23]$^+$.

Step 6. (R)-4-(2-acetamido-6-(methoxymethoxy)phenyl)butan-2-yl methanesulfonate

A solution of (R)—N-(2-(3-hydroxybutyl)-3-(methoxymethoxy)phenyl)acetamide (4.0 g, 14.96 mmol) in acetonitrile (40 mL) was treated with triethylamine (3.13 mL, 22.44 mmol) and cooled to 0° C. Methanesulfonyl chloride (1.46 mL, 18.7 mmol) was slowly added and a precipitate formed immediately. The slurry was stirred at 0° C. After 3 h, the reaction mixture was diluted with ethyl acetate and poured into 5% aqueous sodium chloride solution (50 mL). The layers were separated, and the organic layer washed with additional 5% aqueous sodium chloride solution (40 mL). The combined aqueous layers were extracted with ethyl acetate, and the combined organic layers were concentrated under reduced pressure. The residue was dissolved in toluene (50-75 mL), which was then removed under reduced pressure to afford (R)-4-(2-acetamido-6-(methoxymethoxy)phenyl)butan-2-yl methanesulfonate (5.17 g, 100%) as an amber syrup. The crude was used without further purification. MS (ESI, pos. ion) m/z 250 [M−95].$^+$.

Step 7. (S)-1-(5-(methoxymethoxy)-2-methyl-3,4-dihydroquinolin-1(2H)-yl)ethanone (R)-4-(2-Acetamido-6-(methoxymethoxy)phenyl)butan-2-yl methanesulfonate (3.39 g, 9.8 mmol) was dissolved in N,N-dimethylformamide (34 mL). The solution was cooled to 0° C., and sodium hydride (60% in mineral oil, 0.510 g, 12.74 mmol) was added in one portion. The ice bath was removed and the reaction mixture stirred at room temperature. After 2 h, the reaction mixture was cooled to 0° C. with an ice bath and slowly diluted with water (40 mL). The mixture was extracted with ethyl acetate. The organic layer was separated and washed with 5% aqueous sodium chloride solution (2×40 mL). The combined aqueous layers were extracted with ethyl acetate, and the combined organic extracts were concentrated under reduced pressure to afford a dark amber syrup (3.9 g). The crude product was purified via column chromatography on silica gel (eluting with 2:1 hexanes-ethyl acetate, followed by 3:2 hexanes-ethyl acetate) to afford (S)-1-(5-(methoxymethoxy)-2-methyl-3,4-dihydroquinolin-1(2H)-yl)ethanone (1.74 g, 71%) as a dark yellow-orange syrup. MS (ESI, pos. ion) m/z 250 [M+1]$^+$.

Step 8. (S)-1-(5-hydroxy-2-methyl-3,4-dihydroquinolin-1(2H)-yl)ethanone

A solution of (S)-1-(5-(methoxymethoxy)-2-methyl-3,4-dihydroquinolin-1(2H)-yl)ethanone (1.6 g, 6.42 mmol) in methanol (16 mL) was treated with concentrated hydrochloric acid (1.0 mL, 12.8 mmol) at rt. The solution was heated to 50° C. for 90 min. Heating was discontinued, and the solution was allowed to slowly cool to room temperature overnight. Methanol was removed under reduced pressure and the residue was partitioned between dichloromethane and water. The aqueous layer was separated and extracted with dichloromethane. The combined organic extracts were concentrated under reduced pressure. The residue was dissolved in acetonitrile (ca. 20-30 mL), and then concentrated under reduced pressure to afford (S)-1-(5-hydroxy-2-methyl-3,4-dihydroquinolin-1(2H)-yl)ethanone (1.23 g, 93%) as an off-white to tan solid. MS (ESI, pos. ion) m/z 206 [M+1]$^+$.

Step 9. (S)-1-(6-bromo-5-hydroxy-2-methyl-3,4-dihydroquinolin-1(2H)-yl)ethanone (Intermediate 3)

A solution of (S)-1-(5-hydroxy-2-methyl-3,4-dihydroquinolin-1(2H)-yl)ethanone (1.2 g, 5.85 mmol) in acetonitrile (24 mL) was cooled to 0° C. and treated with N-bromosuccinimide (1.041 g, 5.85 mmol) in one portion. The solution turned dark yellow-orange in color initially, then faded to a pale orange color over the next 10-15 min. After 30 min, the solution was concentrated under reduced pressure. The crude product was purified by column chromatography on silica gel (eluting with 8:1 dichloromethane-ethyl acetate followed by 7:1 dichloromethane-ethyl acetate) to afford (S)-1-(6-bromo-5-hydroxy-2-methyl-3,4-dihydroquinolin-1 (2H)-yl)ethanone (1.37 g, 82%). MS (ESI, pos. ion) m/z 284, 286 [M+1]$^+$.

Intermediate 3 could also be synthesized from (2S)-5-methoxy-2-methyl-1,2,3,4-tetrahydroquinoline following the procedure used for the synthesis of (2S)-6-bromo-1-cyclopropanecarbonyl-2-methyl-1,2,3,4-tetrahydroquinolin-5-ol, substituting acetyl chloride for cyclopropanecarbonyl chloride. MS: (ES, m/z): 284, 286 [M+H]$^+$

Example 5

Intermediate 4. Methyl (S)-6-bromo-5-hydroxy-2-methyl-3,4-dihydroquinoline-1(2H)-carboxylate

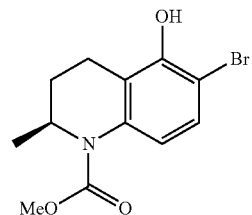 [SMILES: COC(=O)N1c2ccc(Br)c(O)c2CC[C@@H]1C]

Methyl (S)-6-bromo-5-hydroxy-2-methyl-3,4-dihydroquinoline-1(2H)-carboxylate was synthesized following the procedure for (5)-1-(6-bromo-5-hydroxy-2-methyl-3,4-dihydroquinolin-1(2H)-yl)ethanone substituting methyl chloroformate for acetyl chloride in Step 5 or from (2S)-5-methoxy-2-methyl-1,2,3,4-tetrahydroquinoline following the procedure used for the synthesis of (2S)-6-bromo-1-cyclopropanecarbonyl-2-methyl-1,2,3,4-tetrahydroquinolin-5-ol, substituting methyl chloroformate for cyclopropanecarbonyl chloride. MS: (ES, m/z): 300, 302 [M+H]$^+$

Example 6

Intermediates 5 and 6. rac-2-methyl-5-phenoxy-1,2,3,4-tetrahydroquinoline (5) and rac-6-bromo-2-methyl-5-phenoxy-1,2,3,4-tetrahydroquinoline (6)

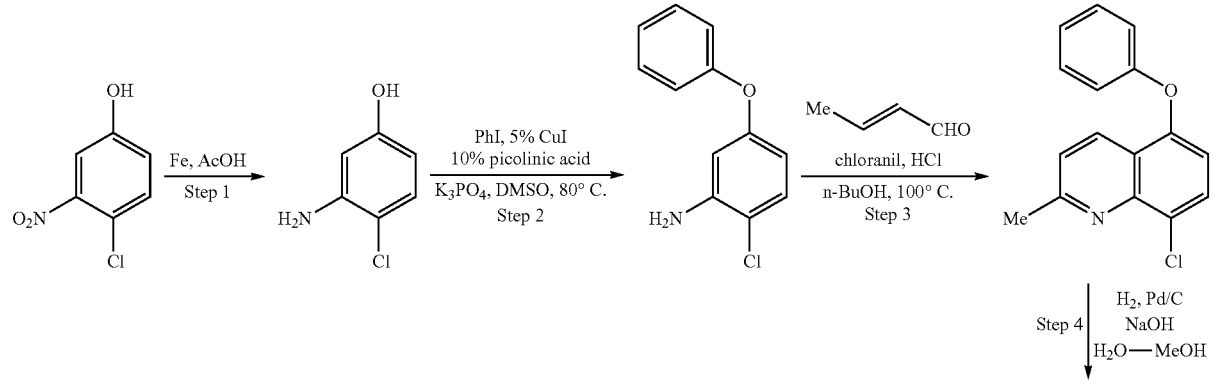

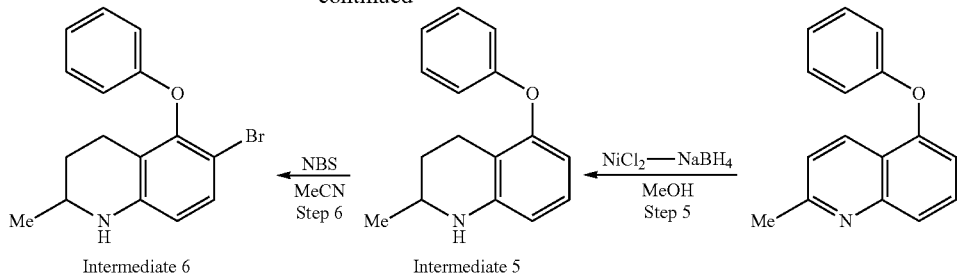

Step 1. 3-amino-4-chlorophenol

A 100-mL round bottomed flask equipped with a magnetic stir bar was charged with 4-chloro-3-nitrophenol (6.0 g, 34.6 mmol) and acetic acid (60 mL). Iron powder (325 mesh) (19.31 g, 346 mmol) was added, and the mixture was heated at 100° C. for 30 min. The mixture was cooled to room temperature and diluted with water (40 mL). The mixture was then filtered through a pad of Celite and rinsed with water. The filtrate was then extracted with ethyl acetate, and the combined extracts were concentrated under reduced pressure. Heptane (ca. 100 mL) was added to the filtrate and then removed under reduced pressure in order to remove residual acetic acid and water. This was repeated. The residue was dissolved in acetonitrile and concentrated under reduced pressure. The resulting solid was suspended in heptane and concentrated under reduced pressure to afford 3-amino-4-chlorophenol (4.38 g, 88%) as a pale purple/amber solid. MS (ESI, pos. ion) m/z 144 [M+1].

Step 2. 2-chloro-5-phenoxyaniline

A heat gun-dried 100-mL round bottomed flask equipped with a magnetic stir bar was charged with potassium phosphate (5.91 g, 27.9 mmol), picolinic acid (0.171 g, 1.393 mmol), copper(I) iodide (0.133 g, 0.697 mmol), 3-amino-4-chlorophenol (2.0 g, 13.93 mmol), dimethylsulfoxide (27.9 mL), and iodobenzene (3.41 g, 16.72 mmol). The resulting mixture was heated to 80° C. After 15 h, the reaction mixture was subjected to an aqueous workup to afford the crude product, which was then purified by flash chromatography to afford pure 2-chloro-5-phenoxyaniline (2.61 g, 85%). MS (ESI, pos. ion) m/z 220 [M+1].

Step 3. 8-chloro-2-methyl-5-phenoxyquinoline

A 50-mL round bottomed flask equipped with a magnetic stir bar was charged with 2-chloro-5-phenoxyaniline (1.25 g, 5.69 mmol), chloranil (1.399 g, 5.69 mmol), n-butanol (5 mL), and concentrated hydrochloric acid (1.61 mL, 19.3 mmol). The mixture was heated to 100° C. and then a solution of (E)-but-2-enal (0.566 mL, 6.83 mmol) in n-butanol (2 mL) was slowly added over 5 min. The mixture turned a dark amber/brown solution. After 45 min, heating was discontinued. After cooling, the solution was diluted with THF (30 mL). The solution was then concentrated under reduced pressure to remove the THF. Ethyl acetate was added and a precipitate formed. The slurry was stirred for 15 min and then filtered. The solids were rinsed with ethyl acetate and dried to yield 1.9 g of a dark yellow-brown solid. This material was suspended in 25 mL of 1 N aqueous sodium hydroxide solution, and the slurry was stirred rapidly for 30 min and then filtered. The solids were thoroughly rinsed with water and dried to afford 8-chloro-2-methyl-5-phenoxyquinoline (0.95 g, 62%) as an off-white solid. MS (ESI, pos. ion) m/z 270 [M+1].

Step 4. 2-methyl-5-phenoxyquinoline

A Parr bottle was charged with 8-chloro-2-methyl-5-phenoxyquinoline (0.93 g, 3.45 mmol), methanol (20 mL), and 3 M aqueous sodium hydroxide solution (3.79 mL, 11.38 mmol). The bottle was flushed with nitrogen, and 10% palladium on carbon (0.5 g, 0.470 mmol) was added. The mixture was then shaken under an atmosphere of hydrogen (30 psig). After 4.5 h, the mixture was filtered through a pad of Celite. The bottle and filter pad were rinsed with methanol. The filtrate was concentrated under reduced pressure. The residue was then partitioned between ethyl acetate and 5% aqueous sodium chloride solution (25 mL). The layers were separated, and the organic layer washed again with 5% aqueous sodium chloride solution (25 mL). The aqueous washes were extracted once with ethyl acetate, and the combined extracts were concentrated to afford crude 2-methyl-5-phenoxyquinoline (0.82 g, 101%) as a pale yellow-orange syrup which was used without further purification. MS (ESI, pos. ion) m/z 236 [M+1].

Step 5. rac-2-methyl-5-phenoxy-1,2,3,4-tetrahydroquinoline (Intermediate 5)

A glass, screw-cap vial equipped with a magnetic stir bar was charged with 2-methyl-5-phenoxyquinoline (0.05 g, 0.213 mmol), methanol (1 mL), and nickel(II) chloride (4.96 mg, 0.038 mmol). Sodium borohydride (0.032 g, 0.850 mmol) was added portion-wise over 30 sec at rt. The reaction mixture turned dark purple (almost black), and an exotherm was observed. After 10 min, the reaction mixture was concentrated under a stream of nitrogen. The residue was then treated with 1 N aqueous sodium hydroxide solution (1 mL) and dichloromethane (2-3 mL). The resulting emulsion was filtered through a pad of Celite and washed with ethyl acetate. The filtrate was concentrated to afford rac-2-methyl-5-phenoxy-1,2,3,4-tetrahydroquinoline (0.051 g) as a pale yellow syrup. The crude product was carried forward without further purification. MS (ESI, pos. ion) m/z 240 [M+1].

Step 6. rac-6-bromo-2-methyl-5-phenoxy-1,2,3,4-tetrahydroquinoline (Intermediate 6)

A 50-mL round bottomed flask equipped with a magnetic stir bar and thermocouple was charged with rac-2-methyl-5-phenoxy-1,2,3,4-tetrahydroquinoline (0.574 g, 2.399 mmol) and acetonitrile (11.5 mL). The solution was cooled to 0° C., and N-bromosuccinimide (0.427 g, 2.399 mmol) was added in one portion. The solution turned yellow, and the internal temperature rose to 5° C. before falling back to 0° C. After 10 min, additional N-bromosuccinimide (0.021 g, 0.120 mmol) was added. After an additional 10 min, the reaction mixture was removed from the ice bath and concentrated under reduced pressure. The residue was then partitioned between ethyl acetate and 10% aqueous sodium carbonate solution. The layers were separated, and the ethyl acetate layer was washed with 5% aqueous sodium chloride solution (10 mL) and concentrated to a yellow oil (0.81 g). The crude product was purified by column chromatography on silica gel (eluting with 12:1 hexanes-ethyl acetate followed by 10:1 hexanes-ethyl acetate) to afford rac-6-bromo-2-methyl-5-phenoxy-1,2,3,4-tetrahydroquinoline (0.60, 79%) as a colorless syrup. MS (ESI, pos. ion) m/z 318, 320 [M+1].

Example 7

Intermediate 7—3-(4-(4,4,5,5-tetramethyl-1,3,2-dioxaborolan-2-yl)-1H-pyrazol-1-yl)thietane 1,1-dioxide

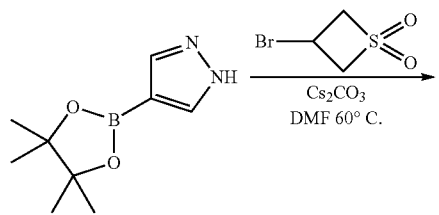

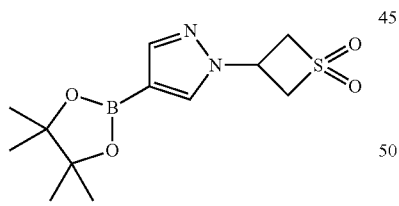

A 100-mL round bottomed flask was charged with 4-(4,4,5,5-tetramethyl-1,3,2-dioxaborolan-2-yl)-1H-pyrazole (0.942 g, 4.85 mmol), N,N-dimethylformamide (20 mL) and cesium carbonate (3.16 g, 9.71 mmol). 3-Bromothietane 1,1-dioxide (0.925 g, 5.00 mmol) was added, and the reaction stirred at 60° C. overnight. The reaction mixture was cooled to room temperature and then partitioned between ethyl acetate and water. The aqueous phase was separated and extracted with ethyl acetate. The combined organic phases were washed with water and brine and concentrated to afford an oil. This material was purified via column chromatography on silica gel (eluting with 1:5 ethyl acetate-hexanes) to afford 3-(4-(4,4,5,5-tetramethyl-1,3,2-dioxaborolan-2-yl)-1H-pyrazol-1-yl)thietane 1,1-dioxide (0.172 g, 12% yield) as a white solid. MS (ESI, pos. ion) m/z 299 [M+H]+.

Example 8

Intermediate 8—3-(4-(4,4,5,5-tetramethyl-1,3,2-dioxaborolan-2-yl)-1H-pyrazol-1-yl)tetrahydro-2H-thiopyran 1,1-dioxide

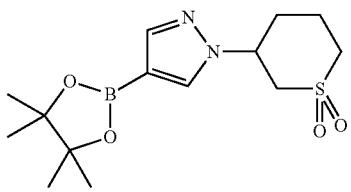 [SMILES: CC1(C)OB(c2cnn(C3CCCS(=O)(=O)C3)c2)OC1(C)C]

3-(4-(4,4,5,5-Tetramethyl-1,3,2-dioxaborolan-2-yl)-1H-pyrazol-1-yl)tetrahydro-2H-thiopyran 1,1-dioxide was synthesized from 4-(4,4,5,5-tetramethyl-1,3,2-dioxaborolan-2-yl)-1H-pyrazole and 4-bromotetrahydro-2H-thiopyran 1,1-dioxide according to the procedure outlined above for 3-(4-(4,4,5,5-tetramethyl-1,3,2-dioxaborolan-2-yl)-1H-pyrazol-1-yl)thietane 1,1-dioxide (Intermediate 7). $^{13}$C NMR (400 MHz, CDCl$_3$) δ ppm 20.85 (s, 1C), 24.75 (s, 1C), 24.77 (s, 4C), 31.38 (s, 1C), 50.50 (s, 1C), 56.62 (s, 1C), 57.33 (s, 1C), 83.50 (s, 2C), 134.95 (s, 1C), 146.21 (s, 1C). MS (ESI, pos. ion) m/z 327 [M+H]+.

Example 9

Intermediate 9—8-fluoro-5-methoxy-2-methylquinoline

8-Fluoro-5-methoxy-2-methylquinoline was synthesized from 2-fluoro-5-methoxyaniline (30.0 g, 213 mmol) according to the procedures described above for 8-chloro-5-methoxy-2-methylquinoline hydrochloride (Intermediate 1, Step 1) with the following change: The hydrochloride salt was dissolved in dichloromethane (400 mL) and the pH of the resulting solution was adjusted to 8-9 with saturated aqueous potassium carbonate solution. The resulting mixture was extracted with dichloromethane, and the combined organic layers were dried over anhydrous sodium sulfate, filtered, and concentrated under vacuum. The residue was purified via column chromatography on silica gel (eluting with 20% ethyl acetate-petroleum ether) to afford 8-fluoro-5-methoxy-2-methylquinoline (25.2 g, 62%) as a yellow solid. MS (ESI, pos. ion) m/z 192 [M+H]+.

Example 10

Intermediate 10—(S)-8-fluoro-5-methoxy-2-methyl-1,2,3,4-tetrahydroquinoline

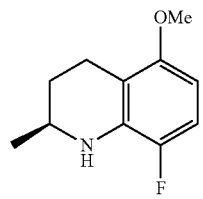

(S)-8-Fluoro-5-methoxy-2-methyl-1,2,3,4-tetrahydroquinoline was synthesized from 8-fluoro-5-methoxy-2-methylquinoline according to the procedures described above for (2S)-5-methoxy-2-methyl-1,2,3,4-tetrahydroquinoline (Intermediate 1). MS (ESI, pos. ion) m/z 196 [M+H]+.

Example 11

Intermediate 11—(S)-(6-bromo-8-fluoro-5-hydroxy-2-methyl-3,4-dihydroquinolin-1(2H)-yl)(cyclopropyl)methanone

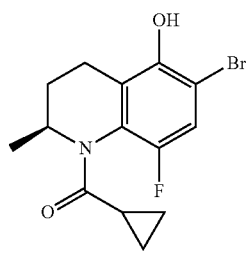 [SMILES: C[C@H]1CCc2c(O)c(Br)cc(F)c2N1C(=O)C1CC1]

(S)-(6-Bromo-8-fluoro-5-hydroxy-2-methyl-3,4-dihydroquinolin-1 (2H)-yl)(cyclopropyl)methanone was synthesized from (S)-8-fluoro-5-methoxy-2-methyl-1,2,3,4-tetrahydroquinoline according to the procedures described above for (2S)-6-bromo-1-cyclopropanecarbonyl-2-methyl-1,2,3,4-tetrahydroquinolin-5-ol (Intermediate 2, Steps 1a, 2a, and 3). MS (ESI, pos. ion) m/z 328, 330 [M+H]+.

The following intermediates were prepared according to the procedure described above for Intermediate 11:

Example 12

Intermediate 12—(S)-1-(6-bromo-8-fluoro-5-hydroxy-2-methyl-3,4-dihydroquinolin-1(2H)-yl)ethanone

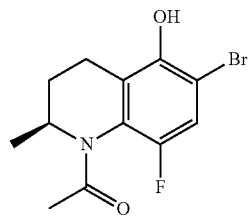 [SMILES: CC(=O)N1c2c(F)cc(Br)c(O)c2CC[C@@H]1C]

MS (ESI, pos. ion) m/z 302, 304 [M+H]+.

Example 13

Intermediate 13—(S)-methyl 6-bromo-8-fluoro-5-hydroxy-2-methyl-3,4-dihydroquinoline-1(2H)-carboxylate

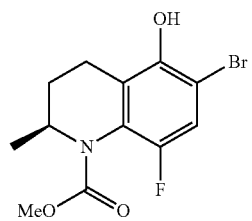 [SMILES: COC(=O)N1c2c(F)cc(Br)c(O)c2CC[C@@H]1C]

MS (ESI, pos. ion) m/z 318, 320 [M+H]+.

Example 14

Intermediate 14—(S)-1-(6-bromo-5-cyclobutoxy-7,8-difluoro-2-methyl-3,4-dihydroquinolin-1(2H)-yl)ethanone

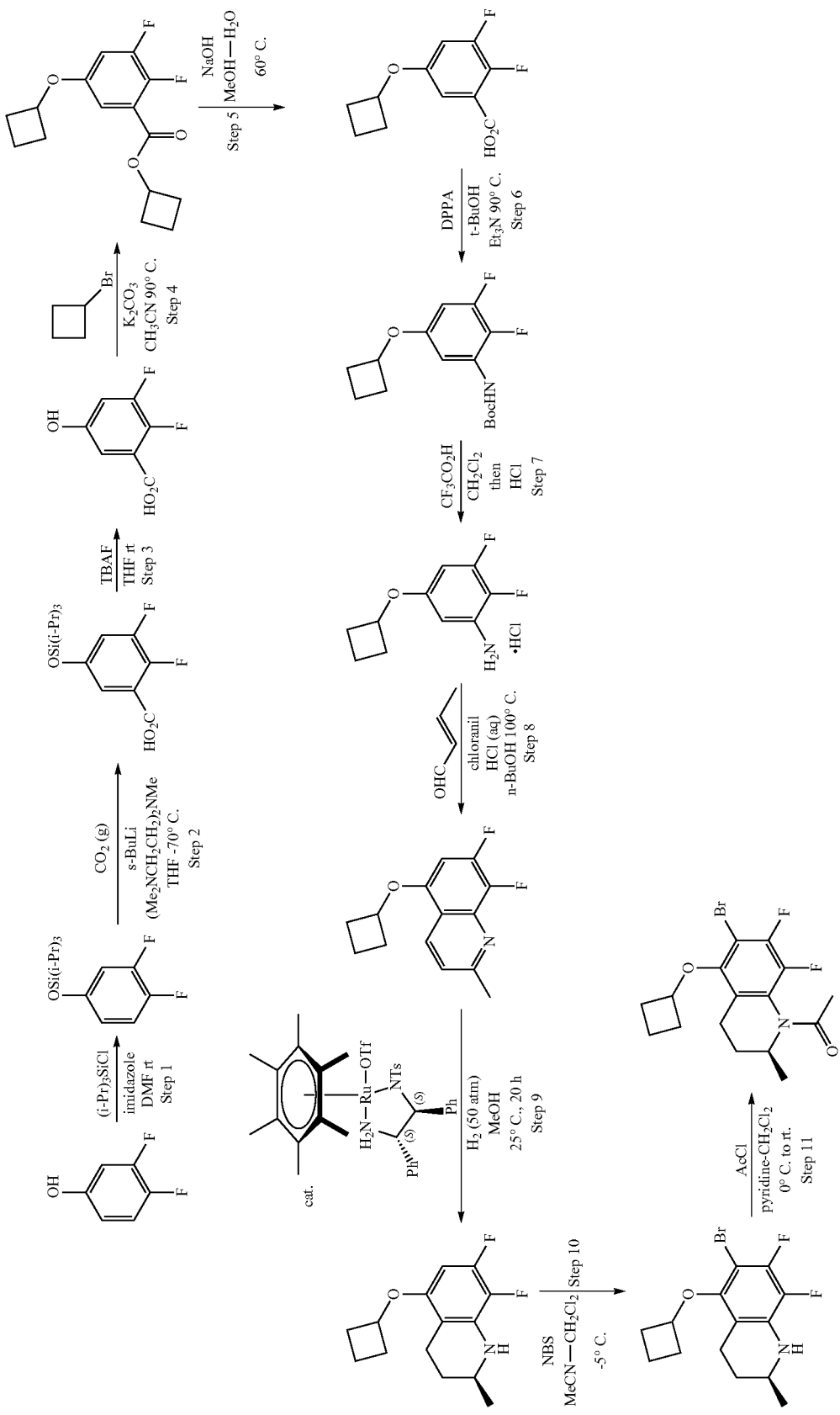

Step 1. (3,4-difluorophenoxy)triisopropylsilane

Triisopropylsilyl chloride (166 mL, 961.5 mmol) was slowly added to a mixture of 3,4-difluorophenol (125 g, 961.5 mmol) and imidazole (65.4 g, 961.5 mmol) in N,N-dimethylformamide (500 mL), and the resulting solution stirred overnight at room temperature. The reaction mixture was diluted with water (1500 mL) and extracted with dichloromethane (3×300 mL). The combined organic layers washed with water (3×200 mL) and brine (2×200 mL), dried over anhydrous sodium sulfate, filtered, and concentrated under vacuum. The residue was purified via column chromatography on silica gel (eluting with petroleum ether) to afford (3,4-difluorophenoxy)triisopropylsilane (220 g, 80%) as a colorless oil.

Step 2. 2,3-difluoro-5-(triisopropylsilyloxy)benzoic acid

A solution of N,N,N',N'',N''-pentamethyldiethylenetriamine (60.4 g, 349.1 mmol) in tetrahydrofuran (480 mL) was cooled to −70° C., and s-butyllithium (1.25 M in cyclohexane, 335 mL, 419 mmol) was added over 10 min. (3,4-Difluorophenoxy)triisopropylsilane (99.85 g, 349.1 mmol) was added dropwise over 1 h, and the resulting mixture stirred for 2 at −70° C. Carbon dioxide was bubbled into the solution, and the resulting mixture stirred for 5 h at −70° C. and then 2 h at room temperature. The reaction mixture was then poured into water (200 mL), and the pH was adjusted to 5 with 2 N hydrochloric acid. The resulting mixture was extracted with ethyl acetate (3×500 mL), and the combined organic layers were washed with brine (200 mL), dried over anhydrous sodium sulfate, filtered, and concentrated to afford 2,3-difluoro-5-(triisopropylsilyloxy)benzoic acid (99.1 g, 86%) as a light yellow solid. MS (ESI, neg. anion) m/z 329 [M−H]$^-$.

Step 3. 2,3-difluoro-5-hydroxybenzoic acid

Tetrabutylammonium fluoride trihydrate (191 g, 731.8 mmol) was added in portions to a solution of 2,3-difluoro-5-(triisopropylsilyloxy)benzoic acid (99.13 g, 300.0 mmol) in tetrahydrofuran (500 mL), and the resulting mixture stirred overnight at room temperature. The reaction mixture was poured into water (1000 mL) and extracted with ethyl acetate (2×500 mL). The combined organic layers were washed with brine (2×500 mL), dried over anhydrous sodium sulfate, filtered, and concentrated under vacuum to afford 2,3-difluoro-5-hydroxybenzoic acid (50 g, 95%) as a light yellow solid. MS (ESI, neg. anion) m/z 173 [M−H]$^-$.

Step 4. cyclobutyl 5-cyclobutoxy-2,3-difluorobenzoate

Bromocyclobutane (150 g, 1.12 mol) was added to a mixture of 2,3-difluoro-5-hydroxybenzoic acid (50 g, 287 mmol), and potassium carbonate (230 g, 1.67 mol) in acetonitrile (1500 mL), and the resulting mixture stirred overnight at 90° C. The reaction mixture was cooled to room temperature, filtered, and concentrated under vacuum. The residue was purified via column chromatography on silica gel (eluting with petroleum ether) to afford cyclobutyl 5-cyclobutoxy-2,3-difluorobenzoate (49 g, 60%) as a yellow green solid. MS (ESI, pos. ion) m/z 283 [M+H]$^+$.

Step 5. 5-cyclobutoxy-2,3-difluorobenzoic acid

A mixture of cyclobutyl 5-cyclobutoxy-2,3-difluorobenzoate (49 g, 174 mmol), ethanol (300 mL), sodium hydroxide (20 g, 500 mmol) and water (300 mL) stirred at 60° C. overnight. The mixture was cooled to room temperature and extracted with petroleum ether (2×100 mL). The pH of the aqueous layer was adjusted to 5 with 6 M hydrochloric acid, and then it was extracted ethyl acetate (3×300 mL). The combined ethyl acetate layers were washed with brine, dried over anhydrous sodium sulfate, filtered, and concentrated to afford 5-cyclobutoxy-2,3-difluorobenzoic acid (38 g, 96%) as a white solid. MS (ESI, neg. anion) m/z 227 [M−H]$^-$.

Step 6. tert-butyl 5-cyclobutoxy-2,3-difluorophenylcarbamate

A solution of 5-cyclobutoxy-2,3-difluorobenzoic acid (38 g, 148 mmol), t-butanol (280 mL), triethylamine (21.4 mL, 154 mmol) and diphenylphosphoryl azide (33.2 mL, 154 mmol) stirred overnight at 90° C. The reaction mixture was cooled to room temperature and concentrated. The residue was dissolved dichloromethane (200 mL), washed with 1 M sodium hydroxide (2×100 mL) and brine (2×50 mL), dried over anhydrous sodium sulfate, filtered, and concentrated. The residue was purified via column chromatography on silica gel (eluting with 5% ethyl acetate/petroleum ether) to afford tert-butyl 5-cyclobutoxy-2,3-difluorophenylcarbamate (32 g, 76%) as a white solid. MS (ESI, pos. ion) m/z 230 [M+H]$^+$.

Step 7. 5-cyclobutoxy-2,3-difluoroaniline hydrogen chloride

Trifluoroacetic acid (70 mL) was added to a solution of tert-butyl 5-cyclobutoxy-2,3-difluorophenylcarbamate (32 g, 107 mmol) in dichloromethane (320 mL), and the resulting solution stirred overnight at room temperature. The reaction solution was concentrated, and the residue was dissolved in dichloromethane (500 mL). A solution of HCl (4 M in 1,4-dioxane, 120 mL) was slowly added with stirring. The resulting mixture was concentrated and poured into ethyl ether (480 mL). The resulting precipitate was filtered, and the filter cake was dried under reduced pressure to afford 5-cyclobutoxy-2,3-difluoroaniline hydrogen chloride (21 g, 89%) as a light yellow solid. MS (ESI, pos. ion) m/z 200 [M+H]$^+$.

Step 8. 5-cyclobutoxy-7,8-difluoro-2-methylquinoline hydrochloride

A mixture of 5-cyclobutoxy-2,3-difluorobenzenamine hydrogen chloride (9.9 g, 42.1 mmol), concentrated hydrochloric acid (36 mL), chloranil (12.32 g, 49.8 mmol) in n-butanol (60 mL) stirred for 1 h at 100° C. (E)-Crotonaldehyde (19.8 mL, 239 mmol) was added dropwise, and the resulting solution stirred for 1 h at 100° C. and was then cooled to 70° C. Tetrahydrofuran (600 mL) was added, and the mixture stirred for another 30 min at 70° C. The reaction mixture was cooled to room temperature and concentrated under vacuum. The residue was poured into water (300 mL) and the pH of the mixture was adjusted to 7-8 with saturated aqueous potassium carbonate solution. The resulting mixture was extracted with ethyl acetate (3×300 mL), and the combined organic layers were dried over anhydrous sodium sulfate, filtered, and concentrated under vacuum. The residue was purified via column chromatography on silica gel (eluting with 25% ethyl acetate/petroleum ether) to afford 5-cyclobutoxy-7,8-difluoro-2-methylquinoline hydrochloride (6 g, 57%) as a yellow solid. MS (ESI, pos. ion) m/z 250 [M+H]$^+$.

Step 9. (S)-5-cyclobutoxy-7,8-difluoro-2-methyl-1,2,3,4-tetrahydroquinoline

A 30-mL glass-lined stainless steel reactor was charged with 5-cyclobutoxy-7,8-difluoro-2-methylquinoline (4.2 g, 16.9 mmol), Cp*Ru(OTf)[(S,S)-TsDPEN](0.100 g, 0.13 mmol) and methanol (10 mL). The reactor was closed and hydrogen was introduced in at a pressure of 50 atm, before being reduced to 1 atm. After this procedure was repeated three times, the reactor was pressurized with hydrogen to 50 atm. The resulting mixture was stirred under this hydrogen pressure for 24 h at room temperature. After carefully releasing the hydrogen, the reaction mixture was concentrated under vacuum. The residue purified via column chromatography on silica gel (eluting with 25% ethyl acetate/petroleum ether) to afford (S)-5-cyclobutoxy-7,8-difluoro-2-methyl-1,2,3,4-tetrahydroquinoline (1.4 g, 33%, 87% ee) as colorless oil.

MS (ESI, pos. ion) m/z 254 [M+H]$^+$.

Step 10. (S)-6-bromo-5-cyclobutoxy-7,8-difluoro-2-methyl-1,2,3,4-tetrahydroquinoline A solution of N-bromosuccinimide (0.703 g, 3.95 mmol) in acetonitrile (10 mL) was added dropwise to a −5° C. solution of (S)-5-cyclobutoxy-7,8-difluoro-2-methyl-1,2,3,4-tetrahydroquinoline (1.0 g, 3.95 mmol) in acetonitrile (80 mL) and dichloromethane (15 mL), and the resulting solution stirred for 4 h at −5° C. The reaction mixture was concentrated under vacuum. The residue was purified via column chromatography on silica gel (eluting with 50% ethyl acetate/petroleum ether) to afford (S)-6-bromo-5-cyclobutoxy-7,8-difluoro-2-methyl-1,2,3,4-tetrahydroquinoline (1.05 g, 81%) as a yellow solid. MS (ESI, pos. ion) m/z 332, 334 [M+H]$^+$.

Step 11. (S)-1-(6-bromo-5-cyclobutoxy-7,8-difluoro-2-methyl-3,4-dihydroquinolin-1(2H)-yl)ethanone Acetyl chloride (0.21 mL, 3.02 mmol) was added dropwise to a 0° C. solution of (S)-6-bromo-5-cyclobutoxy-7,8-difluoro-2-methyl-1,2,3,4-tetrahydroquinoline (1.0 g, 3.02 mmol) in dichloromethane (20 mL) and pyridine (0.6 mL), and the resulting solution was allowed to stir and warm to room temperature overnight. The reaction mixture was diluted with dichloromethane (40 mL), washed with 1 N hydrochloric acid (40 mL) and brine (40 mL), dried over anhydrous sodium sulfate, filtered, and concentrated to afford (S)-1-(6-bromo-5-cyclobutoxy-7,8-difluoro-2-methyl-3,4-dihydroquinolin-1(2H)-yl)ethanone (1.19 g, 99%) as yellow oil. MS (ESI, pos. ion) m/z 374, 376 [M+H]$^+$.

Example 15

Intermediate 15—tert-butyl 4-(4-bromo-1H-imidazol-2-yl)piperidine-1-carboxylate

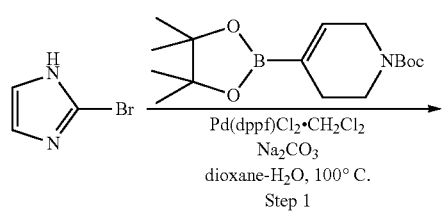

Pd(dppf)Cl$_2$·CH$_2$Cl$_2$
Na$_2$CO$_3$
dioxane-H$_2$O, 100° C.
Step 1

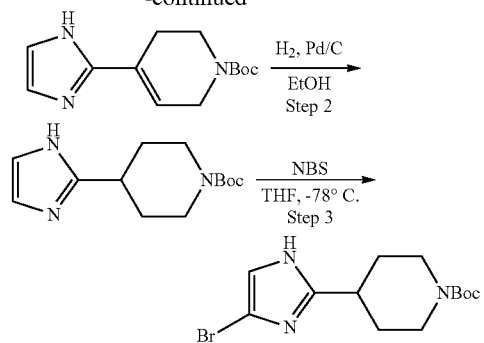

Step 1. tert-butyl 4-(1H-imidazol-2-yl)-5,6-dihydropyridine-1(2H)-carboxylate A mixture of 2-bromo-1H-imidazole (1.2 g, 8.16 mmol), tert-butyl 4-(4,4,5,5-tetramethyl-1,3,2-dioxaborolan-2-yl)-5,6-dihydropyridine-1(2H)-carboxylate (3.0 g, 9.70 mmol), sodium carbonate (2.1 g, 19.8 mmol), and [1,1′-bis(diphenylphosphino)ferrocene]dichloropalladium(II) dichloromethane adduct (0.120 g, 0.16 mmol) in 1,4-dioxane (30 mL) and water (10 mL) stirred overnight at 100° C. The reaction mixture was cooled to room temperature, poured into ethyl acetate (100 mL), washed with water (30 mL) and brine (30 mL), dried over anhydrous sodium sulfate, filtered, and concentrated under vacuum. The residue was purified via column chromatography on silica gel (eluting with 25% ethyl acetate-petroleum ether) to afford tert-butyl 4-(1H-imidazol-2-yl)-5,6-dihydropyridine-1(2H)-carboxylate (0.300 g, 15%) as a light yellow solid. MS (ESI, pos. ion) m/z 250 [M+H]$^+$.

Step 2. tert-butyl 4-(1H-imidazol-2-yl)piperidine-1-carboxylate

Palladium on carbon (10 wt %, 0.100 g) was added to a solution tert-butyl 4-(1H-imidazol-2-yl)-5,6-dihydropyridine-1(2H)-carboxylate (0.300 g, 1.20 mmol) in ethanol (20 mL), and the mixture stirred under a hydrogen atmosphere at room temperature for 2 h. The reaction mixture was filtered, and the filtrate was concentrated under vacuum to afford tert-butyl 4-(1H-imidazol-2-yl)piperidine-1-carboxylate (0.300 g, 99%) as an off-white solid. MS (ESI, pos. ion) m/z 252 [M+H]$^+$.

Step 3. tert-butyl 4-(4-bromo-1H-imidazol-2-yl)piperidine-1-carboxylate

A 100-mL round-bottom flask was charged with tert-butyl 4-(1H-imidazol-2-yl)piperidine-1-carboxylate (0.300 g, 1.19 mmol) and tetrahydrofuran (10 mL), and the solution was cooled to −78. N-Bromosuccinimide (0.185 g, 1.04 mmol) was added, and the resulting solution stirred at −78° C. for 2 h. The reaction mixture was poured into water (10 mL) and extracted with ethyl acetate (3×20 mL). The combined organic layers were washed with brine (10 mL), dried over anhydrous sodium sulfate, filtered, and concentrated under vacuum. The residue was purified via column chromatography on silica gel (eluting with 2:1, ethyl acetate/petroleum ether) to afford tert-butyl 4-(4-bromo-1H-imidazol-2-yl)piperidine-1-carboxylate (0.26 g, 66%) as a white solid. MS (ESI, pos. ion) m/z 330, 332 [M+H]⁺.

Example 16

Intermediate 16—tert-butyl 4-(4-bromo-1-methyl-1H-imidazol-2-yl)piperidine-1-carboxylate

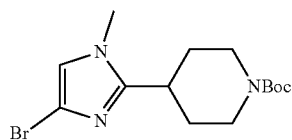 [SMILES: Cn1cc(Br)nc1C1CCN(C(=O)OC(C)(C)C)CC1]

tert-Butyl 4-(4-bromo-1-methyl-1H-imidazol-2-yl)piperidine-1-carboxylate was synthesized according to the procedure described above for tert-butyl 4-(1H-imidazol-2-yl)piperidine-1-carboxylate (Intermediate 15), substituting 2-bromo-1-methyl-1H-imidazole for 2-bromo-1H-imidazole in Step 1. MS (ESI, pos. ion) m/z 264 [M+H]⁺.

Example 17

Intermediates 17 and 18—tert-butyl 4-(3-bromo-1H-pyrazol-1-yl)piperidine-1-carboxylate (Intermediate 17) and tert-butyl 4-(5-bromo-1H-pyrazol-1-yl)piperidine-1-carboxylate (Intermediate 18)

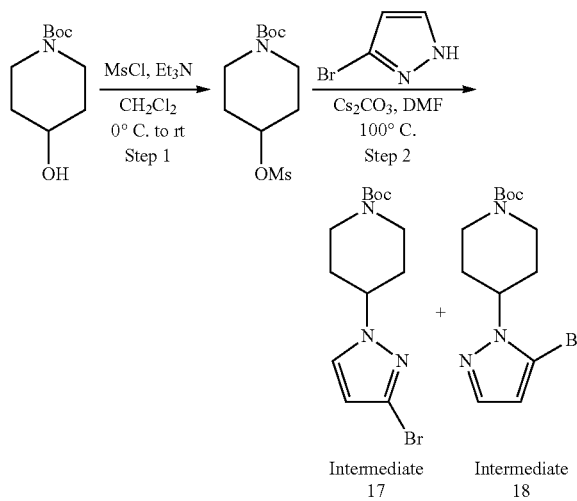

Step 1. tert-butyl 4-(methylsulfonyloxy)piperidine-1-carboxylate

Methanesulfonyl chloride (2.90 mL, 37.6 mmol) was added to a 0° C. solution of tert-butyl 4-hydroxypiperidine-1-carboxylate (5.00 g, 24.8 mmol) and triethyl amine (10.4 mL, 74.65 mmol) in dichloromethane (50 mL), and the resulting solution stirred for 1 h at room temperature. The reaction mixture was diluted with dichloromethane (200 mL), washed with water (2×50 mL), dried over anhydrous sodium sulfate, filtered, and concentrated to afford tert-butyl 4-(methylsulfonyloxy)piperidine-1-carboxylate (7.00 g, 99%) as a yellow solid. MS (ESI, pos. ion) m/z 280 [M+H]⁺.

Step 2. tert-butyl 4-(3-bromo-1H-pyrazol-1-yl)piperidine-1-carboxylate (Intermediate 17) and tert-butyl 4-(5-bromo-1H-pyrazol-1-yl)piperidine-1-carboxylate (Intermediate 18)

A mixture of tert-butyl 4-(methylsulfonyloxy)piperidine-1-carboxylate (0.837 g, 3.00 mmol), 3-bromo-1H-pyrazole (0.441 g, 3.02 mmol), and cesium carbonate (2.94 g, 9.02 mmol) in DMF (10 mL) stirred for 5 h at 100° C. The reaction mixture was cooled to room temperature and poured ethyl acetate (50 mL). The mixture was washed with water (3×10 mL), dried over anhydrous sodium sulfate, filtered, and concentrated under vacuum. The residue purified via column chromatography on silica gel (eluting with 10% dichloromethane/methanol to afford tert-butyl 4-(3-bromo-1H-pyrazol-1-yl)piperidine-1-carboxylate (0.25 g, 25%) as a white solid. MS (ESI, pos. ion) m/z 330, 332 [M+H]⁺.

tert-butyl 4-(5-bromo-1H-pyrazol-1-yl)piperidine-1-carboxylate (0.150 g, 15%) was also obtained as a white solid. MS (ESI, pos. ion) m/z 330, 332 [M+H]⁺.

Example 18

Intermediates 19 and 20—tert-butyl 4-(4-bromo-2H-1,2,3-triazol-2-yl)piperidine-1-carboxylate (Intermediate 19) and tert-butyl 4-(4-bromo-1H-1,2,3-triazol-1-yl)piperidine-1-carboxylate (Intermediate 20)

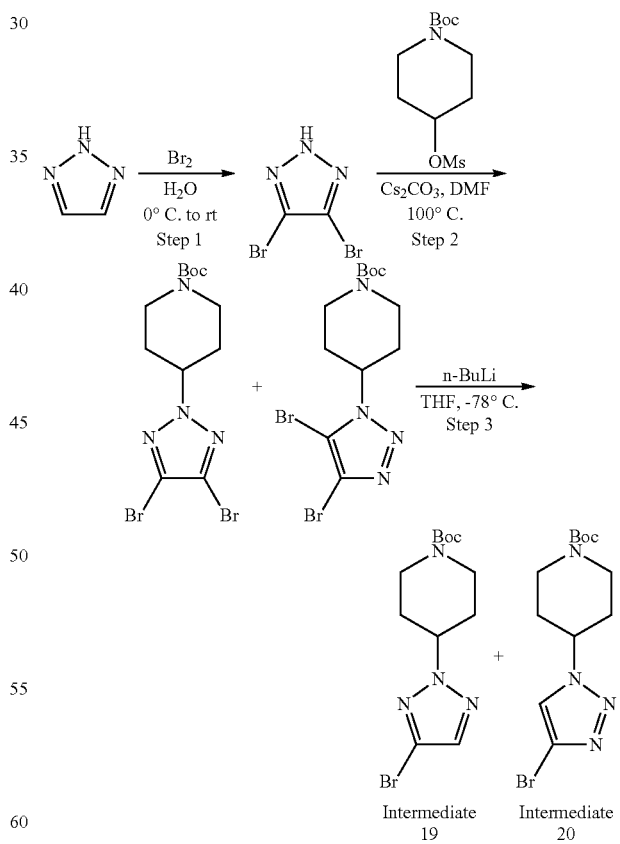

Step 1. 4,5-dibromo-2H-1,2,3-triazole

Bromine (11.59 g, 73.35 mmol) was added dropwise to a 0° C. solution of 2H-1,2,3-triazole (5.00 g, 72.46 mmol) in water (50 mL), and the resulting solution was allowed to warm to room temperature and stir overnight. The precipitate was collected by filtration and dried to afford 4,5-dibromo-2H-1,2,3-triazole (8.00 g, 49%) as a white solid. MS (ESI, pos. ion) m/z 228, 226, 230 [M+H]+.

Step 2. tert-butyl 4-(4,5-dibromo-2H-1,2,3-triazol-2-yl)piperidine-1-carboxylate and tert-butyl 4-(4,5-dibromo-1H-1,2,3-triazol-1-yl)piperidine-1-carboxylate A mixture of 4,5-dibromo-2H-1,2,3-triazole (2.27 g, 10.08 mmol), tert-butyl 4-(methylsulfonyloxy)piperidine-1-carboxylate (2.79 g, 10.00 mmol), and cesium carbonate (9.75 g, 29.91 mmol) in N,N-dimethylformamide (50 mL) stirred overnight at 100° C. The reaction mixture was cooled to room temperature, poured into water (100 mL) and extracted with ethyl acetate (2×100 mL). The combined organic layers were washed with brine (100 mL), dried over anhydrous sodium sulfate, filtered, and concentrated to afford a mixture of tert-butyl 4-(4,5-dibromo-2H-1,2,3-triazol-2-yl)piperidine-1-carboxylate and tert-butyl 4-(4,5-dibromo-1H-1,2,3-triazol-1-yl)piperidine-1-carboxylate (4.00 g, 97%) as a yellow oil. MS (ESI, pos. ion) m/z 411, 409, 413 [M+H]+.

Step 3. tert-butyl 4-(4-bromo-2H-1,2,3-triazol-2-yl)piperidine-1-carboxylate (Intermediate 19) and tert-butyl 4-(4-bromo-1H-1,2,3-triazol-1-yl)piperidine-1-carboxylate (Intermediate 20)

n-Butyllithium (2.5 M in hexanes, 2.92 mL, 7.30 mmol) was added dropwise to a −78° C. solution containing a mixture of tert-butyl 4-(4,5-dibromo-2H-1,2,3-triazol-2-yl)piperidine-1-carboxylate and tert-butyl 4-(4,5-dibromo-1H-1,2,3-triazol-1-yl)piperidine-1-carboxylate (3.00 g, 7.35 mmol) in tetrahydrofuran (20 mL). The resulting solution stirred for 1 hour at −78° C., and then the reaction mixture was poured into saturated aqueous ammonium chloride solution (20 mL). The aqueous phase was separated and extracted with ethyl acetate (3×20 mL), and the combined organic layers were dried over anhydrous sodium sulfate, filtered, and concentrated under vacuum. The residue was purified via column chromatography on silica gel (eluting with 2:1, ethyl acetate/petroleum ether) to afford tert-butyl 4-(4-bromo-2H-1,2,3-triazol-2-yl)piperidine-1-carboxylate (0. 800 g, 33%) as a colorless oil. MS (ESI, pos. ion) m/z 331, 333 [M+H]+.

tert-Butyl 4-(4-bromo-1H-1,2,3-triazol-1-yl)piperidine-1-carboxylate (0.500 g, 20%) was also obtained as a colorless oil. MS (ESI, pos. ion) m/z 331, 333 [M+H]+.

Example 19

Intermediate 21—tert-butyl 3-(4-bromothiazol-2-yl)azetidine-1-carboxylate

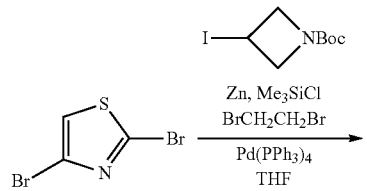

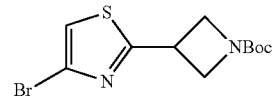

1,2-Dibromoethane (0.084 mL, 0.97 mmol) was added to a mixture of zinc powder (0.520 g, 8.13 mmol) in tetrahydrofuran (2 mL), and the resulting mixture was stirred for 10 min at 80° C. and was then cooled to room temperature. A solution of chlorotrimethylsilane (0.115 mL, 1.22 mmol) in tetrahydrofuran (1 mL) was added dropwise with stirring, and the resulting mixture stirred for 45 min at room temperature. A solution of tert-butyl 3-iodoazetidine-1-carboxylate (1.74 g, 6.15 mmol) in tetrahydrofuran (2 mL) was added, and the resulting mixture stirred for 2 h at room temperature. A solution of 2,4-dibromothiazole (0.744 g, 3.09 mmol) in tetrahydrofuran (1 mL) and tetrakis(triphenylphosphine)palladium (O) (0.354 g, 0.31 mmol) were added, and the resulting mixture stirred overnight at room temperature. The reaction mixture was poured into water (10 mL) and extracted with ethyl acetate (3×10 mL). The combined organic layers were dried over anhydrous sodium sulfate, filtered, and concentrated under vacuum. The residue was purified via column chromatography on silica gel (eluting with 1:2, ethyl acetate/petroleum ether) to afford tert-butyl 3-(4-bromothiazol-2-yl)azetidine-1-carboxylate (0.151 g, 8%) of as yellow oil. MS (ESI, pos. ion) m/z 319, 321 [M+H]+.

Example 20

Intermediate 22—tert-butyl 3-(4-bromothiazol-2-yl)-3-hydroxyazetidine-1-carboxylate

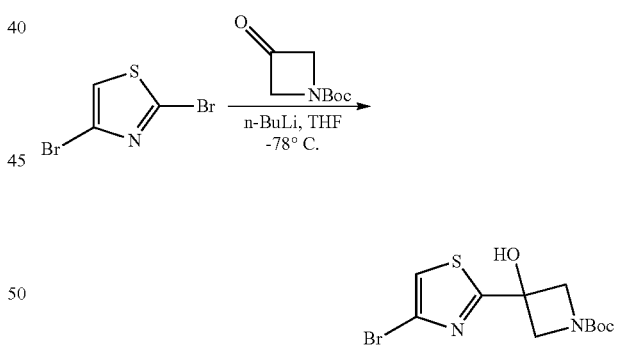

n-Butyllithium (1.6 M in THF, 6.3 mL, 10.1 mmol) was added dropwise to a −78° C. solution of 2,4-dibromothiazole (2.00 g, 8.30 mmol) in tetrahydrofuran (50 mL), and the mixture stirred at −78° C. for 1 h. A solution of tert-butyl 3-oxoazetidine-1-carboxylate (2.83 g, 16.55 mmol) in tetrahydrofuran (5 mL) was added, and the resulting mixture stirred for 1 h at room temperature. The reaction mixture was poured into saturated aqueous ammonium chloride solution (50 mL) and extracted with dichloromethane (3×50 mL). The combined organic layers were dried over anhydrous sodium sulfate, filtered, and concentrated under vacuum. The residue was purified via column chromatography on silica gel (eluting with 20% with ethyl acetate/petroleum ether) to afford tert-butyl 3-(4-bromothiazol-2-yl)-3-hydroxyazetidine-1-carboxylate (0.890 g, 32%) as a white solid. MS (ESI, pos. ion) m/z 335, 337 [M+H]⁺.

Example 21

Intermediate 23—N-(4-bromothiazol-2-yl)acetamide

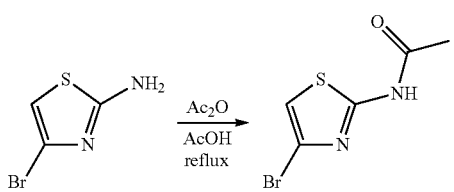

A solution of 4-bromothiazol-2-amine (0.500 g, 2.81 mmol), acetic anhydride (0.43 mL, 4.50 mmol) and acetic acid (5 mL) was refluxed for 2 h. The reaction mixture was cooled to room temperature and concentrated under vacuum. The residue was purified via column chromatography on silica gel (eluting with 25% ethyl acetate-petroleum ether) to afford N-(4-bromothiazol-2-yl)acetamide (0.300 g, 49%) as a white solid. MS (ESI, pos. ion) m/z 221, 223 [M+H]⁺.

Example 22

Intermediate 24—N-(4-bromothiazol-2-yl)acetamide

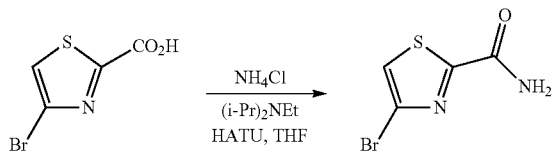 [SMILES: O=C(O)c1nc(Br)cs1 ; "NH4Cl" ; NC(=O)c1nc(Br)cs1]

Into a 100-mL round-bottom flask, was placed 4-bromothiazole-2-carboxylic acid (800 mg, 3.86 mmol, 1.00 equiv), DIEA (1.03 g, 7.92 mmol, 2.00 equiv), tetrahydrofuran (50 mL), —NH₄Cl (424 mg, 8.00 mmol, 2.07 equiv) and HATU (1.82 g, 4.80 mmol, 1.24 equiv). The resulting mixture was stirred for 24 h at 25° C. The reaction mixture was concentrated under vacuum, dissolved in 25 mL of ethyl acetate, washed with 3×5 mL of water, 5 mL of brine, dried over anhydrous sodium sulfate and concentrated under vacuum. The residue was applied onto a silica gel column with ethyl acetate/petroleum ether (11). This resulted in 500 mg (63%) of 4-bromothiazole-2-carboxamide as a white solid. MS (ESI, pos. ion) m/z 207, 209 [M+H]⁺.

Example 23

Intermediate 25—4-bromo-N-methylthiazole-2-carboxamide

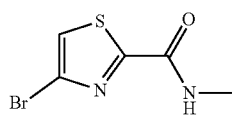

4-Bromo-N-methylthiazole-2-carboxamide was synthesized according to the procedure described above for N-(4-bromothiazol-2-yl)acetamide (Intermediate 24), substituting methyl amine for ammonium chloride. MS (ESI, pos. ion) m/z 221, 223 [M+H]⁺.

Example 24

(S)-1-(6-(1-(2-hydroxyethyl)-1H-pyrazol-4-yl)-2-methyl-5-propoxy-3,4-dihydroquinolin-1(2H)-yl)ethanone (I-1)

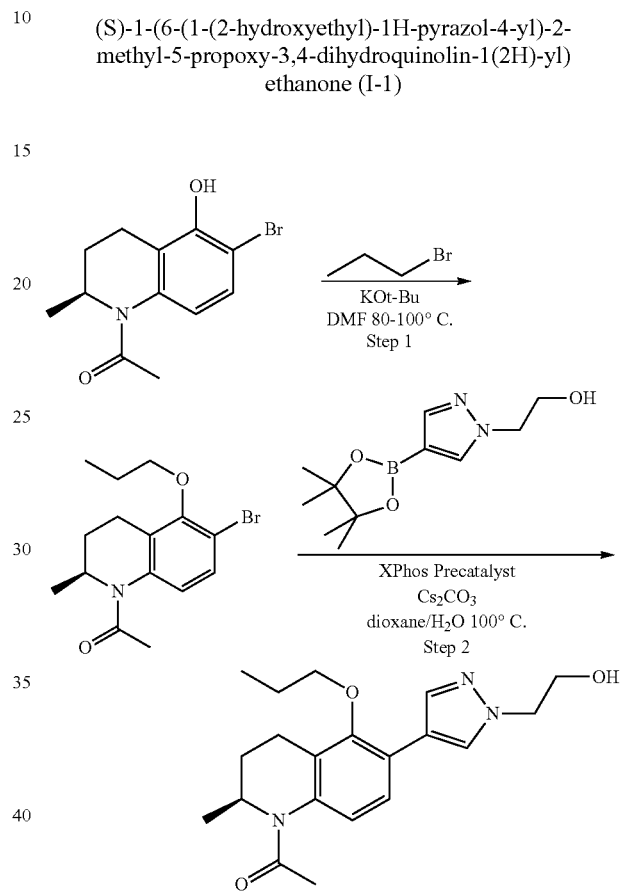

Step 1. (S)-1-(6-bromo-2-methyl-5-propoxy-3,4-dihydroquinolin-1(2H)-yl)ethanone

A mixture of (S)-1-(6-bromo-5-hydroxy-2-methyl-3,4-dihydroquinolin-1 (2H)-yl)ethanone (0.150 g, 0.528 mmol), 1-bromopropane (0.24 mL, 2.64 mmol), and potassium tert-butoxide (0.296 g, 2.64 mmol) in N,N-dimethylformamide (3.0 mL) was heated at 80° C. After 24 h, a second portion of 1-bromopropane (0.24 mL, 2.64 mmol) and potassium tert-butoxide (0.296 g, 2.64 mmol) was added and the mixture was heated at 100° C. for 24 h. The reaction mixture was cooled to rt and water was added. The mixture was extracted with dichloromethane and the combined organic phases were washed with water and brine, dried over anhydrous sodium sulfate, filtered, and concentrated to afford a yellow oil. This material was purified via column chromatography on silica gel (Biotage 25 g column, gradient elution with 50-100% ethyl acetate-hexane) to afford (S)-1-(6-bromo-2-methyl-5-propoxy-3,4-dihydroquinolin-1(2H)-yl)ethanone (0.100 g, 58%) as a colorless oil. MS (ESI, pos. ion) m/z 326, 328 [M+H]⁺.

Step 2. (S)-1-(6-(1-(2-hydroxyethyl)-1H-pyrazol-4-yl)-2-methyl-5-propoxy-3,4-dihydroquinolin-1(2H)-yl)ethanone A mixture of (S)-1-(6-bromo-2-methyl-5-propoxy-3,4-dihydroquinolin-1(2H)-yl)ethanone (0.050 g, 0.153 mmol), 2-(4-(4,4,5,5-tetramethyl-1,3,2-dioxaborolan-2-yl)-1H-pyrazol-1-yl)ethanol (0.055 g, 0.230 mmol), chloro(2-dicyclohexylphosphino-2',4',6'-tri-i-propyl-1,1'-biphenyl)(2'-amino-1,1'-biphenyl-2-yl) palladium(II) (XPhos 2nd generation precatalyst) (0.012 g, 0.015 mmol), and cesium carbonate (0.150 g, 0.460 mmol) in 1,4-dioxane (2.0 mL) and water (0.40 mL) was heated in the microwave at 100° C. for 2.5 h. The reaction mixture was filtered through Celite and concentrated to afford an orange oil. This material was purified via column chromatography on silica gel (Biotage 25 g column, gradient elution with 50-100% ethyl acetate-hexane followed by 10% methanol-ethyl acetate) to afford (S)-1-(6-(1-(2-hydroxyethyl)-1H-pyrazol-4-yl)-2-methyl-5-propoxy-3,4-dihydroquinolin-1(2H)-yl)ethanone (0.047 g, 86%) as an off-white solid. $^1$H NMR (300 MHz, DMSO-d$_6$) δ ppm 0.97 (t, J=7.48 Hz, 3H), 1.03 (d, J=6.45 Hz, 3H), 1.23 (m, 1H), 1.64-1.80 (m, 2H), 2.07 (s, 3H), 2.18-2.38 (m, 2H), 2.75-2.90 (m, 1H), 3.50-3.65 (m, 2H), 3.68-3.80 (m, 2H), 4.17 (t, J=5.57 Hz, 2H), 4.62 (m, 1H), 4.84-4.94 (m, 1H), 7.12 (br d, J=8.21 Hz, 1H), 7.38 (d, J=8.50 Hz, 1H), 7.85 (s, 1H), 8.09 (s, 1H). MS (ESI, pos. ion) m/z 358 [M+H]$^+$. The following examples were made according to the procedure outlined for Example 24:

(S)-2-(1-acetyl-6-(1-(2-hydroxyethyl)-1H-pyrazol-4-yl)-2-methyl-1,2,3,4-tetrahydroquinolin-5-yloxy)-N,N-dimethylacetamide (I-2)

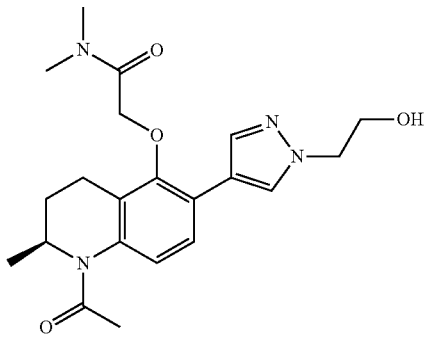 [SMILES: CC(=O)N1c2ccc(-c3cnn(CCO)c3)c(OCC(=O)N(C)C)c2CC[C@@H]1C]

$^1$H NMR (300 MHz, DMSO-d$_6$) δ ppm 0.98-1.09 (m, 3H), 1.29 (m, 1H), 2.08 (s, 3H), 2.18-2.40 (m, 1H), 2.75-2.90 (m, 2H), 2.81 (s, 3H), 2.84 (s, 3H), 3.63-3.78 (m, 2H), 4.05-4.18 (m, 2H), 4.22-4.48 (m, 2H), 4.61 (m, 1H), 4.82-4.95 (m, 1H), 7.15 (br d, J=8.50 Hz, 1H), 7.43 (d, J=8.50 Hz, 1H), 7.93 (s, 1H), 8.21 (s, 1H). MS (ESI, pos. ion) m/z 401 [M+H]$^+$.

(S)-methyl 5-(2-(dimethylamino)-2-oxoethoxy)-6-(1-(2-hydroxyethyl)-1H-pyrazol-4-yl)-2-methyl-3,4-dihydroquinoline-1(2H)-carboxylate (I-3)

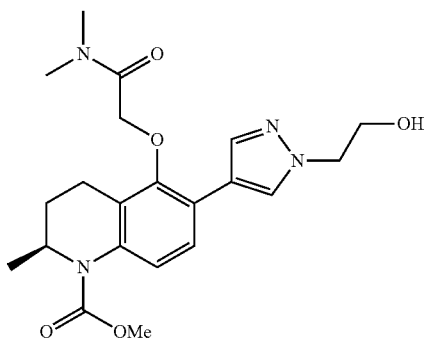 [SMILES: COC(=O)N1c2ccc(-c3cnn(CCO)c3)c(OCC(=O)N(C)C)c2CC[C@@H]1C]

$^1$H NMR (300 MHz, DMSO-d$_6$) δ ppm 1.03-1.12 (m, 3H), 1.48 (td, J=13.12, 6.89 Hz, 1H), 2.09 (td, J=13.63, 5.28 Hz, 1H), 2.70-2.82 (m, 2H), 2.80 (s, 3H), 2.84 (s, 3H), 3.67 (s, 3H), 3.72 (q, J=5.77 Hz, 2H), 4.11 (t, J=5.57 Hz, 2H), 4.35 (q, J=13.88 Hz, 2H), 4.42-4.56 (m, 1H), 4.88 (t, J=5.28 Hz, 1H), 7.23-7.34 (m, 1H), 7.35-7.45 (m, 1H), 7.90 (s, 1H), 8.18 (s, 1H). MS (ESI, pos. ion) m/z 417 [M+H]$^+$.

(S)-2-(1-acetyl-6-(1-cyclopropyl-1H-pyrazol-4-yl)-2-methyl-1,2,3,4-tetrahydroquinolin-5-yloxy)-N-ethylacetamide (I-4)

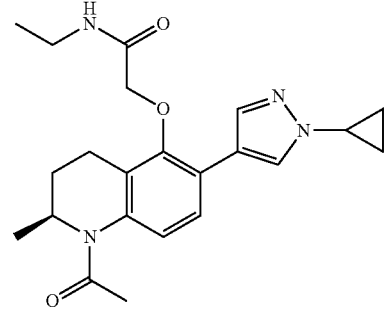 [SMILES: CCNC(=O)COc1c(-c2cnn(C3CC3)c2)ccc2c1CC[C@H](C)N2C(C)=O]

$^1$H NMR (300 MHz, CD$_3$OD) δ ppm 1.01-1.15 (m, 7H), 1.22 (t, J=7.20 Hz, 3H), 1.29-1.42 (m, 1H), 2.17 (s, 3H), 2.31-2.45 (m, 2H), 2.91-3.01 (m, 1H), 3.35-3.43 (m, 3H), 3.65-3.72 (m, 1H), 4.07 (d, J=14.40 Hz, 1H), 4.15 (d, J=14.40

Hz, 1H), 4.71-4.81 (m, 1H), 7.08-7.15 (m, 1H), 7.43 (d, J=8.40 Hz, 1H), 7.89 (s, 1H), 8.12 (s, 1H). MS (ESI, pos. ion) m/z 397 [M+H]⁺.

(S)-1-(6-(1-cyclopropyl-1H-pyrazol-4-yl)-5-(2-fluoroethoxy)-2-methyl-3,4-dihydroquinolin-1(2H)-yl)ethanone (I-5)

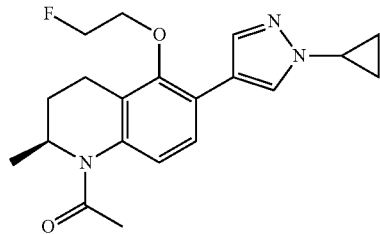 [SMILES: CC(=O)N1c2ccc(-c3cnn(C4CC4)c3)c(OCCF)c2CC[C@@H]1C]

¹H NMR (300 MHz, CD₃OD) δ ppm 1.01-1.15 (m, 7H), 1.21-1.39 (m, 1H), 2.15 (s, 3H), 2.22-2.43 (m, 2H), 2.95-2.07 (m, 1H), 3.63-3.71 (m, 1H), 3.81-4.01 (m, 2H), 4.50-4.62 (m, 1H), 4.67-4.78 (m, 2H), 7.02-7.13 (m, 1H), 7.45 (d, J=8.40 Hz, 1H), 7.89 (s, 1H), 8.12 (s, 1H). MS (ESI, pos. ion) m/z 358 [M+H]⁺.

(S)-2-(1-acetyl-6-(1-cyclopropyl-1H-pyrazol-4-yl)-2-methyl-1,2,3,4-tetrahydroquinolin-5-yloxy)-N-cyclopropyl-N-methylacetamide (I-6)

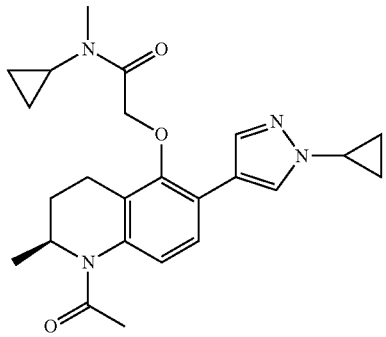 [SMILES: CC(=O)N1c2ccc(-c3cnn(C4CC4)c3)c(OCC(=O)N(C)C3CC3)c2CC[C@@H]1C]

¹H NMR (400 MHz, CD₃OD) δ ppm 0.55-0.65 (m, 2H), 0.72-0.78 (m, 2H), 1.05-1.15 (m, 7H), 1.23-1.41 (m, 1H), 2.19 (s, 3H), 2.30-2.42 (m, 2H), 2.51-2.59 (m, 1H), 2.98 (s, 3H), 2.95-3.08 (m, 1H), 3.65-3.72 (m, 1H), 4.55 (d, J=14.80 Hz, 1H), 4.64 (d, J=14.80 Hz, 1H), 4.71-4.83 (m, 1H), 7.05-7.20 (m, 1H), 7.47 (d, J=8.40 Hz, 1H), 7.91 (s, 1H), 8.21 (s, 1H). MS (ESI, pos. ion) m/z 423 [M+H]⁺.

(S)-2-(1-acetyl-6-(1-cyclopropyl-1H-pyrazol-4-yl)-2-methyl-1,2,3,4-tetrahydroquinolin-5-yloxy)-1-(azetidin-1-yl)ethanone (I-7)

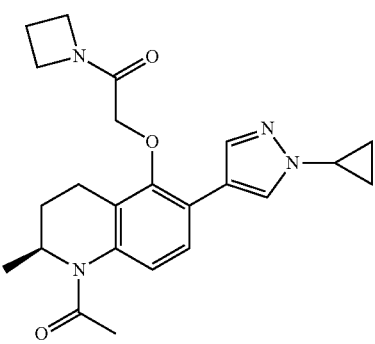 [SMILES: CC(=O)N1c2ccc(-c3cnn(C4CC4)c3)c(OCC(=O)N3CCC3)c2CC[C@@H]1C]

¹H NMR (300 MHz, CD₃OD) δ ppm 1.02-1.15 (m, 7H), 1.24-1.43 (m, 1H), 2.16 (s, 3H), 2.24-2.43 (m, 4H), 2.90-3.05 (m, 1H), 3.65-3.75 (m, 1H), 4.01-4.25 (m, 6H), 4.65-4.82 (m, 1H), 7.05-7.15 (m, 1H), 7.45 (d, J=8.10 Hz, 1H), 7.89 (s, 1H), 8.19 (s, 1H). MS (ESI, pos. ion) m/z 409 [M+H]⁺.

(S)-2-(1-acetyl-6-(1-cyclopropyl-1H-pyrazol-4-yl)-2-methyl-1,2,3,4-tetrahydroquinolin-5-yloxy)-1-(piperidin-1-yl)ethanone (I-8)

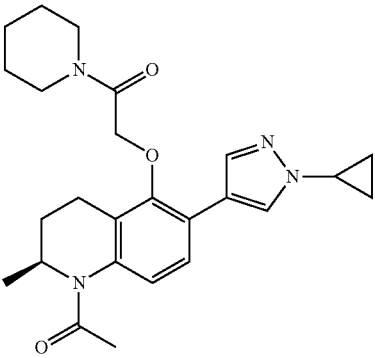 [SMILES: CC(=O)N1c2ccc(-c3cnn(C4CC4)c3)c(OCC(=O)N3CCCCC3)c2CC[C@@H]1C]

¹H NMR (300 MHz, CD₃OD) δ ppm 1.01-1.18 (m, 7H), 1.21-1.53 (m, 3H), 1.55-1.73 (m, 4H), 2.18 (s, 3H), 2.30-2.47 (m, 2H), 2.94-3.05 (m, 1H), 3.21-3.38 (m, 2H), 3.58-3.65 (m, 2H), 3.66-3.74 (m, 1H), 4.39 (d, J=14.10 Hz, 1H), 4.50 (d, J=14.10 Hz, 1H), 4.73-4.85 (m, 1H), 7.09-7.17 (m, 1H), 7.48 (d, J=8.40 Hz, 1H), 7.92 (s, 1H), 8.21 (s, 1H). MS (ESI, pos. ion) m/z 437 [M+H]⁺.

(S)-methyl 6-(1-cyclopropyl-1H-pyrazol-4-yl)-2-methyl-5-(2,2,2-trifluoroethoxy)-3,4-dihydroquinoline-1(2H)-carboxylate (I-9)

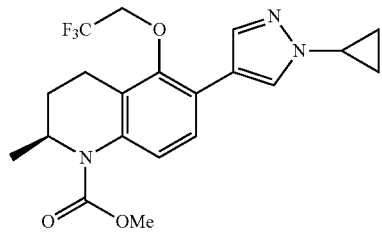 [SMILES: COC(=O)N1c2ccc(-c3cnn(C4CC4)c3)c(OCC(F)(F)F)c2CC[C@@H]1C]

¹H NMR (300 MHz, CD₃OD) δ ppm 1.01-1.19 (m, 7H), 1.49-1.68 (m, 1H), 2.14-2.28 (m, 1H), 2.50-2.63 (m, 1H), 2.87-3.01 (m, 1H), 3.65-3.78 (m, 1H), 3.78 (s, 3H), 4.01-4.18 (m, 2H), 4.55-4.68 (m, 1H), 7.37 (q, d=8.70 Hz, 2H), 7.83 (s, 1H), 8.02 (s, 1H). MS (ESI, pos. ion) m/z 410 [M+H]⁺.

(S)-methyl 6-(1-cyclopropyl-1H-pyrazol-4-yl)-5-(2,2-difluoroethoxy)-2-methyl-3,4-dihydroquinoline-1(2H)-carboxylate (I-10)

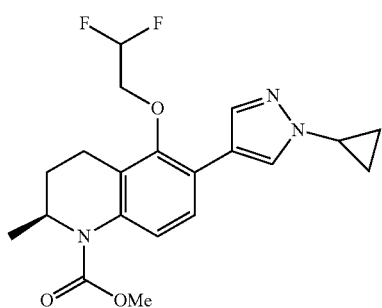 [SMILES: COC(=O)N1c2ccc(-c3cnn(C4CC4)c3)c(OCC(F)F)c2CC[C@@H]1C]

¹H NMR (400 MHz, CD₃OD) δ ppm 1.01-1.20 (m, 7H), 1.50-1.62 (m, 1H), 2.20-2.28 (m, 1H), 2.49-2.59 (m, 1H), 2.91-3.01 (m, 1H), 3.67-3.72 (m, 1H), 3.79 (s, 3H), 3.79-3.91 (m, 2H), 4.55-4.62 (m, 1H), 6.10 (tt, J=54.80, 3.60 Hz, 1H), 7.37 (s, 2H), 7.86 (s, 1H), 8.04 (s, 1H). MS (ESI, pos. ion) m/z 392 [M+H]⁺.

(S)-methyl 6-(1-cyclopropyl-1H-pyrazol-4-yl)-5-(2-fluoroethoxy)-2-methyl-3,4-dihydroquinoline-1(2H)-carboxylate (I-11)

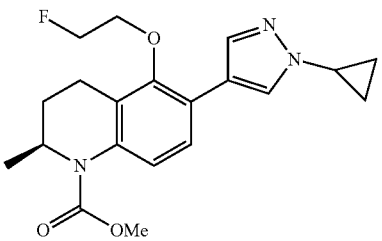 [SMILES: COC(=O)N1c2ccc(-c3cnn(C4CC4)c3)c(OCCF)c2CC[C@@H]1C]

¹H NMR (400 MHz, CD₃OD) δ ppm 1.01-1.15 (m, 4H), 1.18 (d, J=6.80 Hz, 3H), 1.47-1.58 (m, 1H), 2.18-2.25 (m, 1H), 2.48-2.58 (m, 1H), 2.90-2.99 (m, 1H), 3.63-3.71 (m, 1H), 3.78 (s, 3H), 3.81-3.87 (m, 1H), 3.90-3.94 (m, 1H0, 4.51-4.62 (m, 2H), 4.68-4.73 (m, 1H), 7.33 (d, J=8.40 Hz, 1H), 7.38 (d, J=8.80 Hz, 1H), 7.88 (s, 1H), 8.11 (s, 1H). MS (ESI, pos. ion) m/z 374 [M+H]⁺.

(S)-methyl 6-(1-cyclopropyl-1H-pyrazol-4-yl)-5-(2,2-difluoropropoxy)-2-methyl-3,4-dihydroquinoline-1(2H)-carboxylate (I-12)

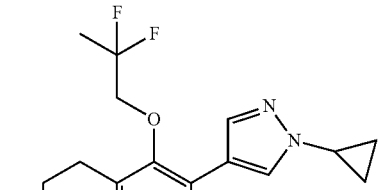

¹H NMR (300 MHz, CD₃OD) δ ppm 1.02-1.19 (m, 7H), 1.51-1.62 (m, 1H), 1.77 (t, J=18.90 Hz, 3H), 2.15-2.25 (m, 1H), 2.51-2.68 (m, 1H), 2.89-3.01 (m, 1H), 3.65-3.71 (m, 1H), 3.75-3.85 (m, 5H), 4.55-4.65 (m, 1H), 7.36-7.37 (m, 2H), 7.86 (s, 1H), 8.06 (s, 1H). MS (ESI, pos. ion) m/z 406 [M+H]⁺.

(S)-methyl 6-(1-cyclopropyl-1H-pyrazol-4-yl)-2-methyl-5-(3,3,3-trifluoropropoxy)-3,4-dihydroquinoline-1(2H)-carboxylate (I-13)

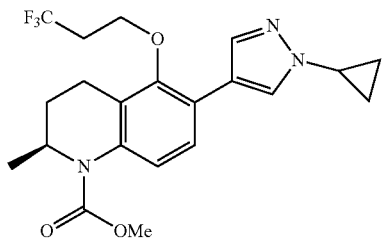 [SMILES: COC(=O)N1c2ccc(-c3cnn(C4CC4)c3)c(OCCC(F)(F)F)c2CC[C@@H]1C]

¹H NMR (300 MHz, CD₃OD) δ ppm 1.01-1.19 (m, 7H), 1.48-1.61 (m, 1H), 2.15-2.27 (m, 1H), 2.48-2.72 (m, 3H), 2.85-2.95 (m, 1H), 3.65-3.72 (m, 1H), 3.72-3.83 (m, 5H), 4.58-4.62 (m, 1H), 7.28-7.34 (m, 2H), 7.82 (s, 1H), 8.01 (s, 1H). MS (ESI, pos. ion) m/z 424 [M+H]⁺.

(S)-methyl 5-(2-amino-1,1-difluoro-2-oxoethoxy)-6-(1-cyclopropyl-1H-pyrazol-4-yl)-2-methyl-3,4-dihydroquinoline-1(2H)-carboxylate (I-14)

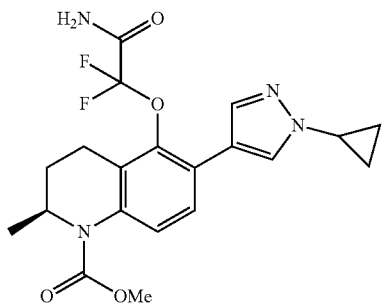

¹H NMR (300 MHz, CD₃OD) δ ppm 0.98-1.21 (m, 7H), 1.25-1.39 (m, 1H), 2.21-2.45 (m, 2H), 2.91-3.04 (m, 1H), 3.61-3.68 (m, 1H), 3.77 (s, 3H), 4.41-4.52 (m, 1H), 7.37-7.41 (m, 2H), 7.79 (s, 1H), 8.05 (s, 1H). MS (ESI, pos. ion) m/z 421 [M+H]⁺.

(S)-methyl 6-(1-cyclopropyl-1H-pyrazol-4-yl)-5-(1,3-difluoropropan-2-yloxy)-2-methyl-3,4-dihydroquinoline-1(2H)-carboxylate (I-15)

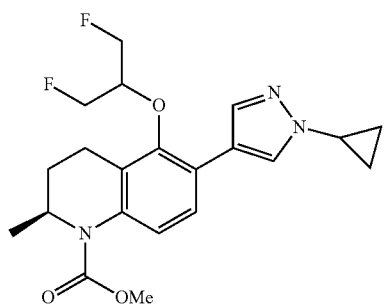 [SMILES: COC(=O)N1c2ccc(-c3cnn(C4CC4)c3)c(OC(CF)CF)c2CC[C@@H]1C]

¹H NMR (300 MHz, CD₃OD) δ ppm 0.98-1.15 (m, 4H), 1.18 (d, J=6.60 Hz, 3H), 1.35-1.45 (m, 1H), 2.20-2.31 (m, 1H), 2.35-2.47 (m, 1H), 2.95-3.03 (m, 1H), 3.62-3.69 (m, 1H), 3.69 (s, 3H), 4.05-4.25 (m, 1H), 4.29-4.33 (m, 1H), 4.45-4.52 (m, 3H), 4.61-4.63 (m, 1H), 7.31 (s, 2H), 7.78 (s, 1H), 7.99 (s, 1H). MS (ESI, pos. ion) m/z 406 [M+H]⁺.

(S)-methyl 6-(1-cyclopropyl-1H-pyrazol-4-yl)-5-(2-fluoro-2-methylpropoxy)-2-methyl-3,4-dihydroquinoline-1(2H)-carboxylate (I-16)

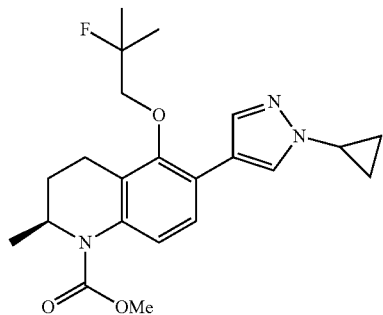 [SMILES: COC(=O)N1c2ccc(-c3cnn(C4CC4)c3)c(OCC(C)(C)F)c2CC[C@@H]1C]

¹H NMR (300 MHz, CD₃OD) δ ppm 0.98-1.18 (m, 7H), 1.37-1.62 (m, 7H), 2.11-2.23 (m, 1H), 2.48-2.59 (m, 1H), 2.87-2.99 (m, 1H), 3.57 (s, 1H), 3.58-3.71 (m, 2H), 3.77 (s, 3H), 4.52-4.62 (m, 1H), 7.28-7.29 (m, 2H), 7.86 (s, 1H), 8.09 (s, 1H). MS (ESI, pos. ion) m/z 402 [M+H]⁺.

(S)-methyl 6-(1-cyclopropyl-1H-pyrazol-4-yl)-5-(3-hydroxy-2,2-dimethylpropoxy)-2-methyl-3,4-dihydroquinoline-1(2H)-carboxylate (I-17)

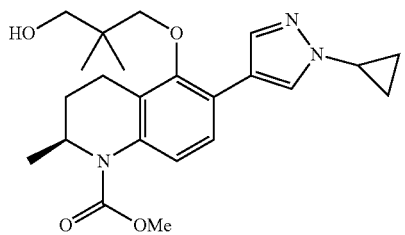 [SMILES: COC(=O)N1c2ccc(-c3cnn(C4CC4)c3)c(OCC(C)(C)CO)c2CC[C@@H]1C]

¹H NMR (300 MHz, CD₃OD) δ ppm 0.99 (s, 6H), 1.01-1.18 (m, 7H), 1.45-1.61 (m, 1H), 2.17-2.23 (m, 1H), 2.47-2.57 (m, 1H), 2.91-3.01 (m, 1H), 3.30-3.45 (m, 4H), 3.60-3.71 (m, 1H), 3.77 (s, 3H), 4.51-4.62 (m, 1H), 7.19-7.30 (m, 2H), 7.76 (s, 1H), 7.98 (s, 1H). MS (ESI, pos. ion) m/z 414 [M+H]⁺.

(S)-methyl 5-(1-amino-2-methyl-1-oxopropan-2-yloxy)-6-(1-cyclopropyl-1H-pyrazol-4-yl)-2-methyl-3,4-dihydroquinoline-1(2H)-carboxylate (I-18)

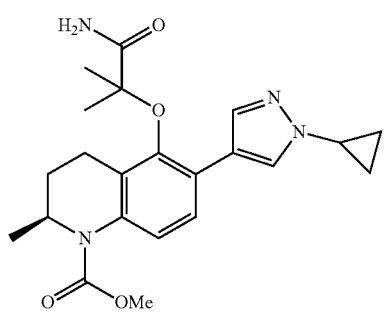 [SMILES: COC(=O)N1c2ccc(-c3cnn(C4CC4)c3)c(OC(C)(C)C(N)=O)c2CC[C@@H]1C]

¹H NMR (300 MHz, CD₃OD) δ ppm 0.98-1.38 (m, 14H), 2.20-2.39 (m, 2H), 2.92-3.03 (m, 1H), 3.63-3.72 (m, 1H), 3.77 (s, 3H), 4.38-4.52 (m, 1H), 7.18-7.28 (m, 2H), 7.72 (s, 1H), 7.96 (s, 1H). MS (ESI, pos. ion) m/z 413 [M+H]⁺.

(S)-methyl 5-((R)-2-amino-1-fluoro-2-oxoethoxy)-6-(1-cyclopropyl-1H-pyrazol-4-yl)-2-methyl-3,4-dihydroquinoline-1(2H)-carboxylate (I-19)

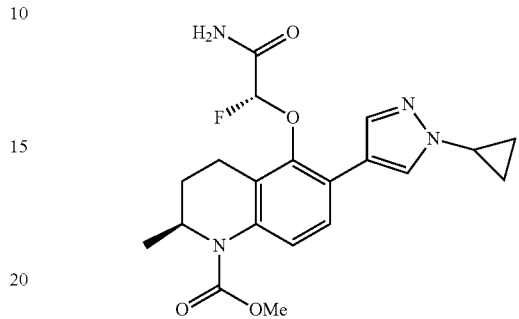

¹H NMR (300 MHz, CD₃OD) δ ppm 1.01-1.34 (m, 7H), 1.42-1.58 (m, 1H), 2.15-2.29 (m, 1H), 2.48-2.62 (m, 1H), 2.95-3.09 (m, 1H), 3.59-3.71 (m, 1H), 3.79 (s, 3H), 4.52-4.63 (m, 1H), 5.41 (d, J=61.20 Hz, 1H), 7.38 (d, J=8.70 Hz, 1H), 7.45 (d, J=8.70 Hz, 1H), 7.83 (s, 1H), 8.08 (s, 1H). MS (ESI, pos. ion) m/z 403 [M+H]⁺. Stereochemistry of fluorine tentatively assigned.

(S)-methyl 5-((S)-2-amino-1-fluoro-2-oxoethoxy)-6-(1-cyclopropyl-1H-pyrazol-4-yl)-2-methyl-3,4-dihydroquinoline-1(2H)-carboxylate (I-20)

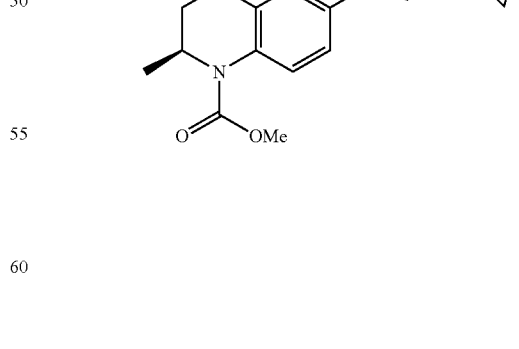

¹H NMR (300 MHz, CD₃OD) δ ppm 1.03-1.1.35 (m, 7H), 1.45-1.55 (m, 1H), 2.17-2.24 (m, 1H), 2.49-2.72 (m, 1H), 3.01-3.12 (m, 1H), 3.68-3.73 (m, 1H), 3.80 (s, 3H), 4.55-4.65 (m, 1H), 5.49 (d, J=61.50 Hz, 1H), 7.41 (d, J=8.40 Hz, 1H), 7.47 (d, J=8.70 Hz, 1H), 7.84 (s, 1H), 8.09 (s, 1H). MS (ESI, pos. ion) m/z 403 [M+H]+. Stereochemistry of fluorine tentatively assigned.

(S)-methyl 6-(1-cyclopropyl-1H-pyrazol-4-yl)-5-(2-(ethylamino)-2-oxoethoxy)-2-methyl-3,4-dihydroquinoline-1(2H)-carboxylate (I-21)

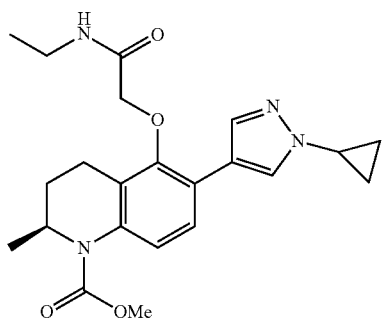 [SMILES: CCNC(=O)COc1c(-c2cnn(C3CC3)c2)ccc2c1CC[C@H](C)N2C(=O)OC]

<sup>1</sup>H NMR (300 MHz, CD<sub>3</sub>OD) δ ppm 1.01-1.27 (m, 10H), 1.55-1.65 (m, 1H), 2.15-2.23 (m, 1H), 2.58-2.68 (m, 1H), 2.83-2.93 (m, 1H), 3.29-3.38 (m, 2H), 3.65-3.71 (m, 1H), 3.78 (s, 3H), 4.08 (s, 2H), 4.55-4.65 (m, 1H), 7.35-7.42 (m, 2H), 7.86 (s, 1H), 8.09 (s, 1H). MS (ESI, pos. ion) m/z 413 [M+H]+.

(S)-methyl 5-(2-(cyclopropyl)methyl)amino)-2-oxoethoxy)-6-(1-cyclopropyl-1H-pyrazol-4-yl)-2-methyl-3,4-dihydroquinoline-1(2H)-carboxylate (I-22)

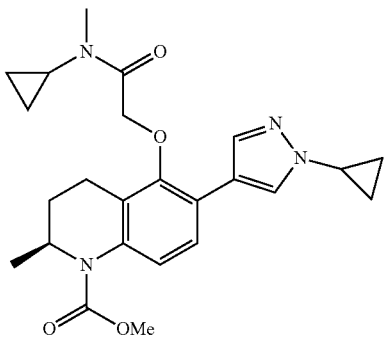 [SMILES: COC(=O)N1c2ccc(-c3cnn(C4CC4)c3)c(OCC(=O)N(C)C3CC3)c2CC[C@@H]1C]

$^1$H NMR (300 MHz, CD$_3$OD) δ ppm 0.48-0.62 (m, 2H), 0.65-0.83 (m, 2H), 1.01-1.09 (m, 4H), 1.17 (d, J=6.30 Hz, 3H), 1.48-1.62 (m, 1H), 2.15-2.25 (m, 1H), 2.28-2.63 (m, 2H), 2.78-3.01 (m, 4H), 3.65-3.72 (m, 1H), 3.77 (s, 3H), 4.049-4.63 (m, 3H), 7.31-7.41 (m, 2H), 7.87 (s, 1H), 8.12 (s, 1H). MS (ESI, pos. ion) m/z 439 [M+H]+.

(S)-methyl 5-(2-(azetidin-1-yl)-2-oxoethoxy)-6-(1-cyclopropyl-1H-pyrazol-4-yl)-2-methyl-3,4-dihydroquinoline-1(2H)-carboxylate (I-23)

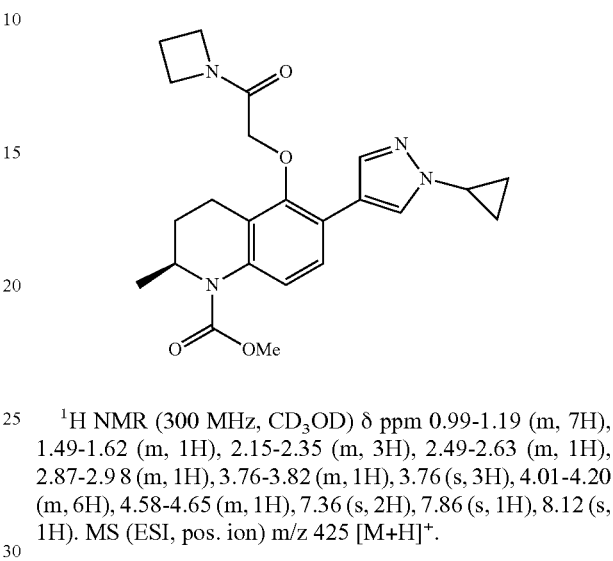

$^1$H NMR (300 MHz, CD$_3$OD) δ ppm 0.99-1.19 (m, 7H), 1.49-1.62 (m, 1H), 2.15-2.35 (m, 3H), 2.49-2.63 (m, 1H), 2.87-2.98 (m, 1H), 3.76-3.82 (m, 1H), 3.76 (s, 3H), 4.01-4.20 (m, 6H), 4.58-4.65 (m, 1H), 7.36 (s, 2H), 7.86 (s, 1H), 8.12 (s, 1H). MS (ESI, pos. ion) m/z 425 [M+H]+.

(S)-methyl 6-(1-cyclopropyl-1H-pyrazol-4-yl)-2-methyl-5-(2-oxo-2-(piperidin-1-yl)ethoxy)-3,4-dihydroquinoline-1(2H)-carboxylate (I-24)

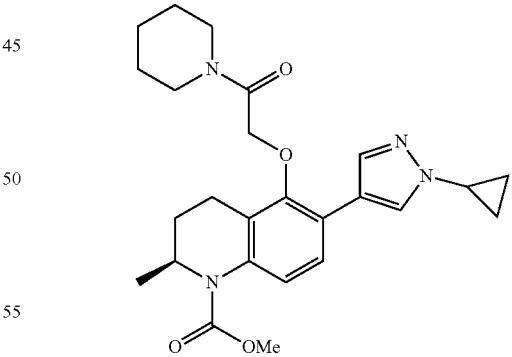

$^1$H NMR (300 MHz, CD$_3$OD) δ ppm 0.99-1.12 (m, 4H), 1.17 (d, J=6.60 Hz, 3H), 1.38-1.72 (m, 7H), 2.10-2.23 (m, 1H), 2.49-2.62 (m, 1H), 2.85-2.99 (m, 1H), 3.17-3.21 (m, 2H), 3.55-3.60 (m, 2H), 3.61-3.68 (m, 1H), 3.76 (s, 3H), 4.38

(q, J=14.10 Hz, 2H), 4.51-4.62 (m, 1H), 7.36 (s, 2H), 7.86 (s, 1H), 8.12 (s, 1H). MS (ESI, pos. ion) m/z 453 [M+H]⁺.

(S)-methyl 6-(1-cyclopropyl-1H-pyrazol-4-yl)-2-methyl-5-(2-(2-oxopyrrolidin-1-yl)ethoxy)-3,4-dihydroquinoline-1(2H)-carboxylate (I-25)

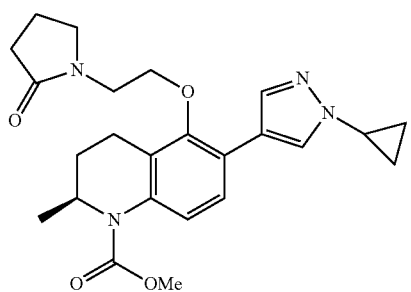 [SMILES: COC(=O)N1c2ccc(-c3cnn(C4CC4)c3)c(OCCN3CCCC3=O)c2CC[C@@H]1C]

$^1$H NMR (300 MHz, CD$_3$OD) δ ppm 1.01-1.19 (m, 7H), 1.48-1.62 (m, 1H), 2.03-2.25 (m, 3H), 2.40-2.58 (m, 3H), 2.80-2.91 (m, 1H), 3.50-3.61 (m, 4H), 3.68-3.79 (m, 6H), 4.55-4.65 (m, 1H), 7.25-7.32 (m, 2H), 7.80 (s, 1H), 8.03 (s, 1H). MS (ESI, pos. ion) m/z 439 [M+H]⁺.

(S)-methyl 6-(1-cyclopropyl-1H-pyrazol-4-yl)-2-methyl-5-(2-morpholino-2-oxoethoxy)-3,4-dihydroquinoline-1(2H)-carboxylate (I-26)

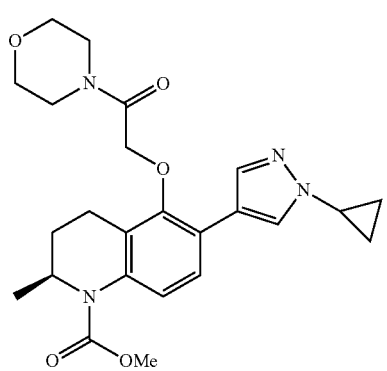 [SMILES: COC(=O)N1c2ccc(-c3cnn(C4CC4)c3)c(OCC(=O)N3CCOCC3)c2CC[C@@H]1C]

$^1$H NMR (300 MHz, CD$_3$OD) δ ppm 1.01-1.12 (m, 4H), 1.18 (d, J=6.40 Hz, 3H), 1.52-1.63 (m, 1H), 2.17-2.23 (m, 1H), 2.50-2.65 (m, 1H), 2.89-3.01 (m, 1H), 3.53-3.73 (m, 7H), 3.78 (s, 3H), 4.31-4.45 (m, 2H), 4.58-4.63 (m, 1H), 7.30-7.38 (m, 2H), 7.88 (s, 1H), 8.15 (s, 1H). MS (ESI, pos. ion) m/z 455 [M+H]⁺.

methyl (2S)-6-(1-cyclopropyl-1H-pyrazol-4-yl)-5-[2-(1,1-dioxo-1λ⁶,2-thiazolidin-2-yl)ethoxy]-2-methyl-1,2,3,4-tetrahydroquinoline-1-carboxylate (I-27)

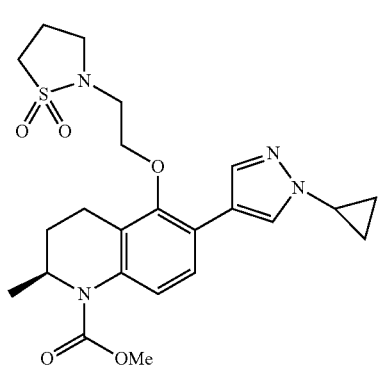 [SMILES: COC(=O)N1c2ccc(-c3cnn(C4CC4)c3)c(OCCN3CCCS3(=O)=O)c2CC[C@@H]1C]

$^1$H NMR (300 MHz, CD$_3$OD) δ ppm 1.01-1.19 (m, 7H), 1.48-1.49 (m, 1H), 2.15-2.23 (m, 1H), 2.30-2.41 (m, 2H), 2.48-2.58 (m, 1H), 2.89-3.01 (m, 1H), 3.18-3.22 (m, 2H), 3.35-3.41 (m, 4H), 3.63-3.79 (m, 6H), 4.52-4.62 (m, 1H), 7.32 (s, 2H), 7.87 (s, 1H), 8.09 (s, 1H). MS (ESI, pos. ion) m/z 475 [M+H]⁺.

(S)-methyl 6-(1-cyclopropyl-1H-pyrazol-4-yl)-2-methyl-5-(sulfamoylmethoxy)-3,4-dihydroquinoline-1(2H)-carboxylate (I-28)

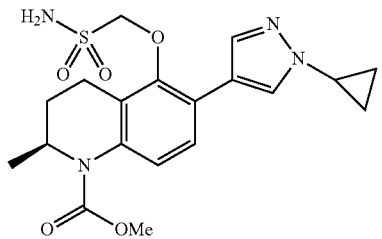 [SMILES: COC(=O)N1c2ccc(-c3cnn(C4CC4)c3)c(OCS(N)(=O)=O)c2CC[C@@H]1C]

$^1$H NMR (300 MHz, CD$_3$OD) δ ppm 0.99-1.09 (m, 2H), 1.11-1.19 (m, 5H), 1.49-1.62 (m, 1H), 2.15-2.25 (m, 1H), 2.52-2.68 (m, 1H), 2.99-2.3.12 (m, 1H), 3.61-3.70 (m, 1H), 3.78 (s, 3H), 4.50-4.63 (m, 3H), 7.39 (s, 2H), 7.89 (s, 1H), 8.20 (s, 1H). MS (ESI, pos. ion) m/z 421 [M+H]⁺.

(S)-methyl 6-(1-cyclopropyl-1H-pyrazol-4-yl)-5-((N,N-dimethylsulfamoyl)methoxy)-2-methyl-3,4-dihydroquinoline-1(2H)-carboxylate (I-29)

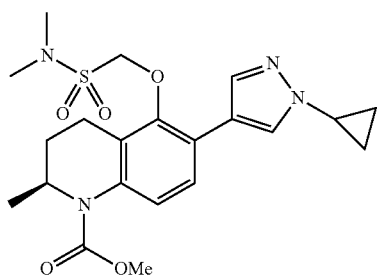 [SMILES: COC(=O)N1c2ccc(-c3cnn(C4CC4)c3)c(OCS(=O)(=O)N(C)C)c2CC[C@@H]1C]

$^1$H NMR (300 MHz, CD$_3$OD) δ ppm 0.98-1.19 (m, 7H), 1.52-1.63 (m, 1H), 2.15-2.25 (m, 1H), 2.55-2.73 (m, 1H), 2.88-3.02 (m, 7H), 3.60-3.72 (m, 1H), 3.77 (s, 3H), 4.50-4.67 (m, 3H), 7.34 (d, J=8.70 Hz, 1H), 7.41 (d, J=8.70 Hz, 1H), 7.85 (s, 1H), 8.12 (s, 1H). MS (ESI, pos. ion) m/z 449 [M+H]⁺.

(S)-methyl 6-(1-cyclopropyl-1H-pyrazol-4-yl)-2-methyl-5-(2-(oxetan-3-yl)ethoxy)-3,4-dihydroquinoline-1(2H)-carboxylate (I-30)

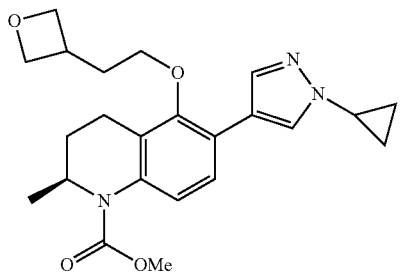 [SMILES: COC(=O)N1c2ccc(-c3cnn(C4CC4)c3)c(OCCC3COC3)c2CC[C@@H]1C]

$^1$H NMR (300 MHz, CD$_3$OD) δ ppm 1.01-1.19 (m, 7H), 1.45-1.69 (m, 1H), 2.03-2.21 (m, 3H), 2.38-2.53 (m, 1H), 2.75-2.89 (m, 1H), 3.15-3.20 (m, 1H), 3.47-3.58 (m, 2H), 3.65-3.73 (m, 1H), 3.76 (s, 3H), 4.40-4.48 (m, 2H), 4.49-4.62 (m, 1H), 4.78-4.83 (m, 2H), 7.21-7.31 (m, 2H), 7.80 (s, 1H), 7.99 (s, 1H). MS (ESI, pos. ion) m/z 412 [M+H]⁺.

(2S)-methyl 6-(1-cyclopropyl-1H-pyrazol-4-yl)-5-((2,2-difluorocyclopropyl)methoxy)-2-methyl-3,4-dihydroquinoline-1(2H)-carboxylate (I-31)

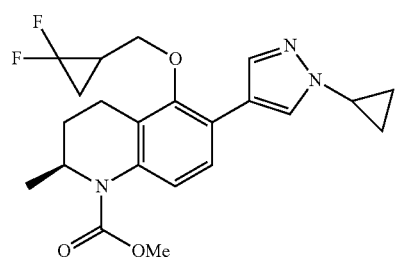 [SMILES: COC(=O)N1c2ccc(-c3cnn(C4CC4)c3)c(OCC3CC3(F)F)c2CC[C@@H]1C]

$^1$H NMR (300 MHz, CD$_3$OD) δ ppm 1.01-1.19 (m, 8H), 1.45-1.58 (m, 2H), 1.90-2.05 (m, 1H), 2.18-2.25 (m, 1H), 2.45-2.55 (m, 1H), 2.88-2.99 (m, 1H), 3.57-3.71 (m, 2H), 3.77 (s, 3H), 3.78-3.83 (m, 1H), 4.50-4.61 (m, 1H), 7.32 (s, 2H), 7.84 (s, 1H), 8.02 (s, 1H). MS (ESI, pos. ion) m/z 418 [M+H]⁺.

(S)-methyl 6-(1-cyclopropyl-1H-pyrazol-4-yl)-5-((3-(hydroxymethyl)oxetan-3-yl)methoxy)-2-methyl-3,4-dihydroquinoline-1(2H)-carboxylate (I-32)

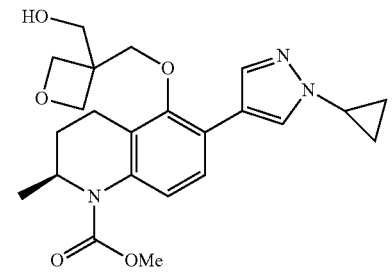 [SMILES: COC(=O)N1c2ccc(-c3cnn(C4CC4)c3)c(OCC3(CO)COC3)c2CC[C@@H]1C]

$^1$H NMR (300 MHz, CD$_3$OD) δ ppm 1.01-1.17 (m, 7H), 1.45-1.55 (m, 1H), 2.15-2.25 (m, 1H), 2.48-2.62 (m, 1H), 2.88-2.99 (m, 1H), 3.67-3.72 (m, 1H), 3.75-3.85 (m, 7H), 4.45-4.63 (m, 5H), 7.25 (d, J=8.40 Hz, 1H), 7.33 (d, J=8.70 Hz, 1H), 7.73 (s, 1H), 7.93 (s, 1H). MS (ESI, pos. ion) m/z 428 [M+H]⁺.

(S)-methyl 6-(1-cyclopropyl-1H-pyrazol-4-yl)-5-(3,3-difluorocyclobutoxy)-2-methyl-3,4-dihydroquinoline-1(2H)-carboxylate (I-33)

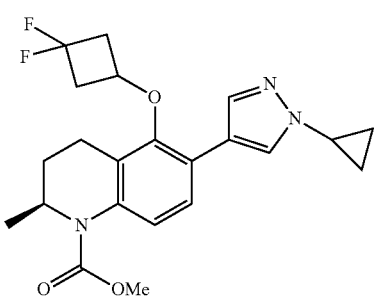 [SMILES: COC(=O)N1c2ccc(-c3cnn(C4CC4)c3)c(OC3CC(F)(F)C3)c2CC[C@@H]1C]

$^1$H NMR (400 MHz, CD$_3$OD) δ ppm 1.02-1.19 (m, 7H), 1.38-1.48 (m, 1H), 2.25-2.31 (m, 1H), 2.39-2.48 (m, 1H), 2.53-2.82 (m, 4H), 2.89-2.95 (m, 1H), 3.68-3.73 (m, 1H), 3.78 (s, 3H), 4.21-4.30 (m, 1H), 4.48-4.58 (m, 1H), 7.30 (s, 2H), 7.79 (s, 1H), 7.99 (s, 1H). MS (ESI, pos. ion) m/z 418 [M+H]⁺.

tert-butyl (S)-4-(1-acetyl-2-methyl-5-propoxy-1,2,3,4-tetrahydroquinolin-6-yl)-3,6-dihydropyridine-1(2H)-carboxylate (I-34)

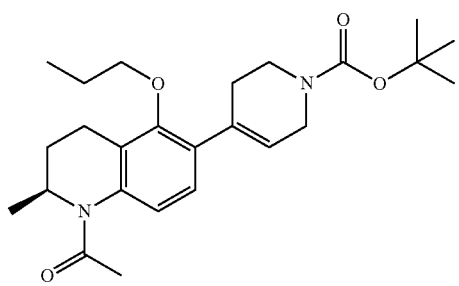 [SMILES: CCCOc1c(C2=CCN(C(=O)OC(C)(C)C)CC2)ccc2c1CC[C@H](C)N2C(C)=O]

$^1$H NMR (300 MHz, DMSO-d6) δ ppm 0.94 (t, 3H), 1.00 (d, 3H), 1.20-1.30 (m, 2H), 1.40 (s, 9H), 1.59-1.69 (m, 2H), 2.05 (s, 3H), 2.16-2.32 (m, 2H), 2.36-2.44 (m, 2H), 2.70-2.81 (m, 1H), 3.49 (d, 2H), 3.53-3.67 (m, 2H), 3.94 (t, 2H), 5.82 (m, 1H), 6.98 (d, 1H), 7.07 (d, 1H). MS (ESI, pos. ion) m/z 429 [M+H]⁺.

(S)-1-(6-(1-cyclopropyl-1H-pyrazol-4-yl)-2-methyl-5-(2,2,2-trifluoroethoxy)-3,4-dihydroquinolin-1(2H)-yl)ethanone (I-35)

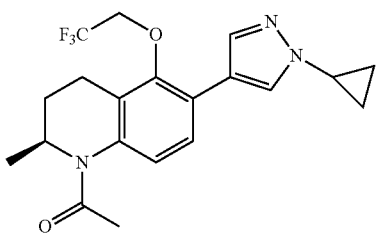 [SMILES: CC(=O)N1c2ccc(-c3cnn(C4CC4)c3)c(OCC(F)(F)F)c2CC[C@@H]1C]

$^1$H NMR (300 MHz, CD$_3$OD) δ ppm 1.01-1.18 (m, 7H), 1.21-1.42 (m, 1H), 2.16 (s, 3H), 2.28-2.32 (m, 2H), 2.95-3.05 (m, 1H), 3.65-3.75 (m, 1H), 4.01-4.21 (m, 2H), 4.68-4.83 (m, 1H), 7.10-7.20 (m, 1H), 7.43 (d, J=8.10 Hz, 1H), 7.85 (s, 1H), 8.05 (s, 1H). MS (ESI, pos. ion) m/z 394 [M+H]⁺.

(S)-1-(6-(1-cyclopropyl-1H-pyrazol-4-yl)-5-(2,2-difluoroethoxy)-2-methyl-3,4-dihydroquinolin-1(2H)-yl)ethanone (I-36)

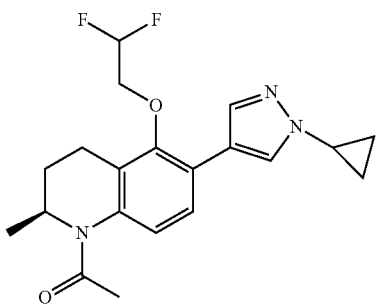 [SMILES: CC(=O)N1c2ccc(-c3cnn(C4CC4)c3)c(OCC(F)F)c2CC[C@@H]1C]

$^1$H NMR (300 MHz, CD$_3$OD) δ ppm 1.01-1.20 (m, 7H), 1.28-1.43 (m, 1H), 2.18 (s, 3H), 2.28-2.35 (m, 2H), 2.95-3.05 (m, 1H), 3.65-3.75 (m, 1H), 3.85-4.01 (m, 2H), 4.61 (s, 1H), 4.69-4.82 (m, 1H), 6.13 (tt, J=54.60, 3.30 Hz, 1H), 7.05-7.15

(m, 1H), 7.46 (d, J=8.40 Hz, 1H), 7.90 (s, 1H), 8.11 (s, 1H). MS (ESI, pos. ion) m/z 376 [M+H]⁺.

(S)-1-(6-(1-cyclopropyl-1H-pyrazol-4-yl)-5-(2,2-difluoropropoxy)-2-methyl-3,4-dihydroquinolin-1(2H)-yl)ethanone (I-37)

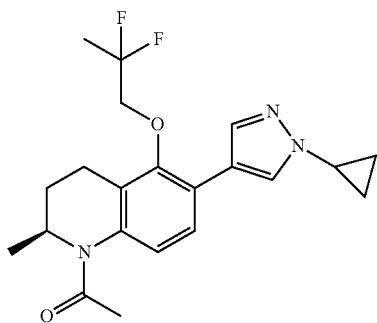 [SMILES: CC(=O)N1c2ccc(-c3cnn(C4CC4)c3)c(OCC(C)(F)F)c2CC[C@@H]1C]

¹H NMR (400 MHz, CD₃OD) δ ppm 1.01-1.18 (m, 7H), 1.25-1.40 (m, 1H), 1.77 (t, J=18.80 Hz, 3H), 2.18 (s, 3H), 2.30-2.42 (m, 2H), 2.95-3.05 (m, 1H), 3.68-3.89 (m, 3H), 4.70-4.82 (m, 1H), 7.05-7.18 (m, 1H), 7.44 (d, J=8.40 Hz, 1H), 7.88 (s, 1H), 8.10 (s, 1H). MS (ESI, pos. ion) m/z 390 [M+H]⁺.

(S)-1-(6-(1-cyclopropyl-1H-pyrazol-4-yl)-5-(1,3-difluoropropan-2-yloxy)-2-methyl-3,4-dihydroquinolin-1(2H)-yl)ethanone (I-38)

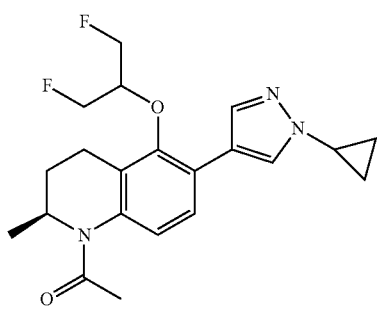 [SMILES: CC(=O)N1c2ccc(-c3cnn(C4CC4)c3)c(OC(CF)CF)c2CC[C@@H]1C]

¹H NMR (300 MHz, CD₃OD) δ ppm 0.98-1.30 (m, 8H), 2.15 (s, 3H), 2.25-2.49 (m, 2H), 3.05-3.12 (m, 1H), 3.65-3.72 (m, 1H), 4.10-4.32 (m, 2H), 4.47-4.54 (m, 2H), 4.65-4.80 (m, 2H), 7.05-7.15 (m, 1H), 7.40 (d, J=8.10 Hz, 1H), 7.92 (s, 1H), 8.02 (s, 1H). MS (ESI, pos. ion) m/z 390 [M+H]⁺.

(S)-1-(6-(1-cyclopropyl-1H-pyrazol-4-yl)-5-(3-hydroxy-2,2-dimethylpropoxy)-2-methyl-3,4-dihydroquinolin-1(2H)-yl)ethanone (I-39)

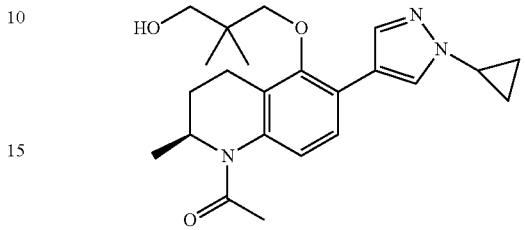

¹H NMR (400 MHz, CD₃OD) δ ppm 0.99 (s, 6H), 1.05-1.25 (m, 7H), 1.23-1.35 (m, 1H), 2.17 (s, 3H), 2.23-2.38 (m, 2H), 3.01-3.13 (m, 1H), 3.40-3.48 (m, 4H), 3.65-3.75 (m, 1H), 4.70-4.83 (m, 1H), 7.01-7.09 (m, 1H), 7.35 (d, J=8.00 Hz, 1H), 7.81 (s, 1H), 8.04 (s, 1H). MS (ESI, pos. ion) m/z 398 [M+H]⁺.

(S)-2-(1-acetyl-6-(1-cyclopropyl-1H-pyrazol-4-yl)-2-methyl-1,2,3,4-tetrahydroquinolin-5-yloxy)-2-methylpropanamide (I-40)

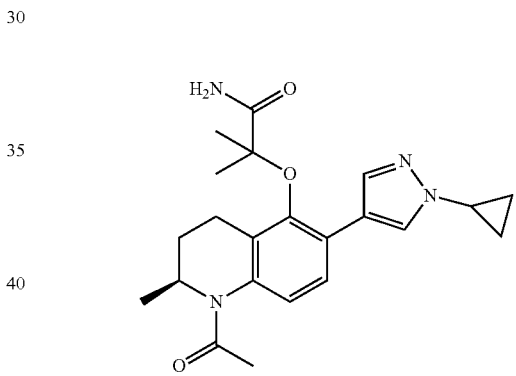

¹H NMR (300 MHz, CD₃OD) δ ppm 0.98-1.20 (m, 11H), 1.30 (s, 3H), 2.05-2.30 (m, 4H), 2.33-2.45 (m, 1H), 3.01-3.12 (m, 1H), 3.65-3.72 (m, 1H), 4.60-4.72 (m, 1H), 7.05-7.12 (m, 1H), 7.33 (d, J=8.10 Hz, 1H), 7.77 (s, 1H), 8.02 (s, 1H). MS (ESI, pos. ion) m/z 397 [M+H]⁺.

(S)-1-(6-(1-cyclopropyl-1H-pyrazol-4-yl)-2-methyl-5-(3,3,3-trifluoropropoxy)-3,4-dihydroquinolin-1(2H)-yl)ethanone (I-41)

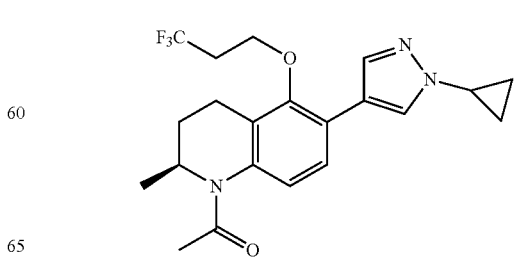

$^1$H NMR (400 MHz, CDCl$_3$) δ ppm 1.07-1.18 (m, 7H), 1.31-1.37 (m, 1H), 2.18 (s, 2H), 2.38-2.41 (m, 2H), 2.61-2.72 (m, 2H), 2.97-3.02 (m, 1H), 3.69-3.75 (m, 1H), 3.82-3.92 (m, 2H), 4.78 (s, 1H), 7.14 (s, 1H), 7.41 (d, J=8.00 Hz, 1H), 7.87 (s, 1H), 8.10 (s, 1H). MS (ESI, pos. ion) m/z 408 [M+H]$^+$.

(S)-1-(2-(1-acetyl-6-(1-cyclopropyl-1H-pyrazol-4-yl)-2-methyl-1,2,3,4-tetrahydroquinolin-5-yloxy)ethyl)pyrrolidin-2-one (I-42)

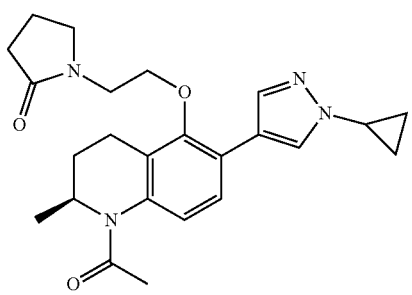 [SMILES: CC(=O)N1c2ccc(-c3cnn(C4CC4)c3)c(OCCN3CCCC3=O)c2CC[C@@H]1C]

$^1$H NMR (300 MHz, CD$_3$OD) δ ppm 1.01-1.19 (m, 7H), 1.25-1.39 (m, 1H), 2.01-2.19 (m, 5H), 2.27-2.48 (m, 4H), 2.85-2.95 (m, 1H), 3.55-3.68 (m, 4H), 3.59-3.84 (m, 3H), 4.65-4.78 (m, 1H), 7.01-7.12 (m, 1H), 7.37 (d, J=8.40 Hz, 1H), 7.83 (s, 1H), 8.09 (s, 1H). MS (ESI, pos. ion) m/z 423 [M+H]$^+$.

(S)-2-(1-acetyl-6-(1-cyclopropyl-1H-pyrazol-4-yl)-2-methyl-1,2,3,4-tetrahydroquinolin-5-yloxy)-1-morpholinoethanone (I-43)

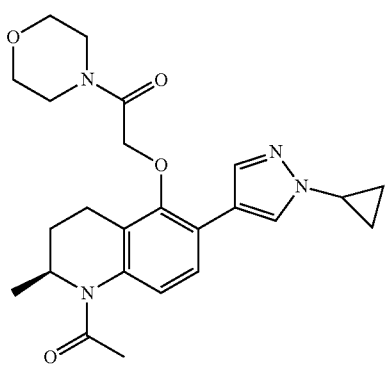 [SMILES: CC(=O)N1c2ccc(-c3cnn(C4CC4)c3)c(OCC(=O)N3CCOCC3)c2CC[C@@H]1C]

$^1$H NMR (300 MHz, CD$_3$OD) δ ppm 1.01-1.15 (m, 7H), 1.15-1.45 (m, 1H), 2.16 (s, 3H), 2.30-2.43 (m, 2H), 2.90-3.05 (m, 1H), 3.50-3.80 (m, 7H), 4.35-4.55 (m, 2H), 4.68-4.84 (m, 1H), 7.05-7.15 (m, 1H), 7.46 (d, J=8.40 Hz, 1H), 7.90 (s, 1H), 8.19 (s, 1H). MS (ESI, pos. ion) m/z 439 [M+H]$^+$.

2-(2-{[(2S)-1-acetyl-6-(1-cyclopropyl-1H-pyrazol-4-yl)-2-methyl-1,2,3,4-tetrahydroquinolin-5-yl]oxy}ethyl)-1λ$^6$,2-thiazolidine-1,1-dione (I-44)

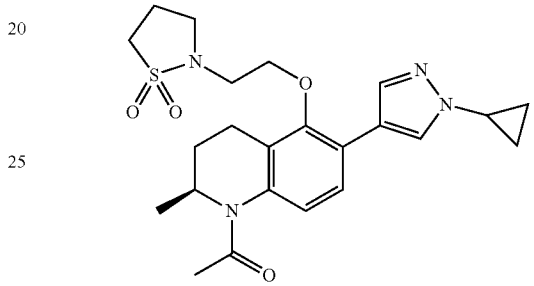

$^1$H NMR (300 MHz, CD$_3$OD) δ ppm 1.01-1.19 (m, 7H), 1.25-1.35 (m, 1H), 2.16 (s, 3H), 2.28-2.45 (m, 4H), 2.98-3.05 (m, 1H), 3.22 (t, J=7.80 Hz, 2H), 3.28-3.42 (m, 4H), 3.68-3.86 (m, 3H), 4.70-4.83 (m, 1H), 7.05-7.12 (m, 1H), 7.41 (d, J=8.40 Hz, 1H), 7.91 (s, 1H), 8.12 (s, 1H). MS (ESI, pos. ion) m/z 459 [M+H]$^+$.

(S)-(1-acetyl-6-(1-cyclopropyl-1H-pyrazol-4-yl)-2-methyl-1,2,3,4-tetrahydroquinolin-5-yloxy)methanesulfonamide (I-45)

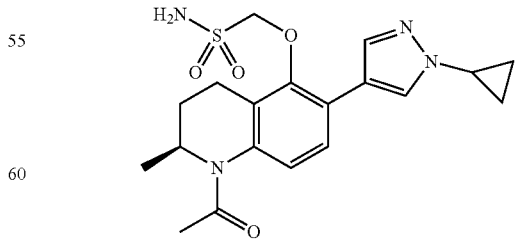

$^1$H NMR (400 MHz, CD$_3$OD) δ ppm 1.01-1.25 (m, 7H), 1.30-1.45 (m, 1H), 2.18 (s, 3H), 2.30-2.45 (m, 2H), 3.10-3.20 (m, 1H), 3.68-3.72 (m, 1H), 4.58-4.68 (m, 2H), 4.70-4.85 (m, 1H), 7.10-7.20 (m, 1H), 7.47 (d, J=8.40 Hz, 1H), 7.93 (s, 1H), 8.21 (s, 1H). MS (ESI, pos. ion) m/z 405 [M+H]+.

(S)-(1-acetyl-6-(1-cyclopropyl-1H-pyrazol-4-yl)-2-methyl-1,2,3,4-tetrahydroquinolin-5-yloxy)-N,N-dimethylmethanesulfonamide (I-46)

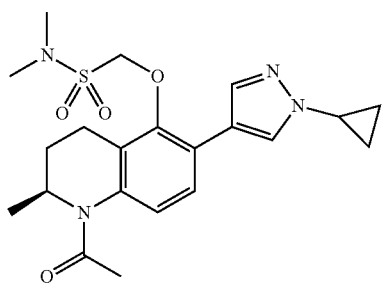 [SMILES: CC(=O)N1c2ccc(-c3cnn(C4CC4)c3)c(OCS(=O)(=O)N(C)C)c2CC[C@@H]1C]

¹H NMR (400 MHz, CD₃OD) δ ppm 1.03-1.23 (m, 7H), 1.34-1.52 (m, 1H), 2.18 (s, 3H), 2.30-2.52 (m, 2H), 3.00 (s, 6H), 3.05-3.15 (m, 1H), 3.68-3.74 (m, 1H), 4.67 (d, J=10.80 Hz, 1H), 4.72-4.79 (m, 2H), 7.10-7.20 (m, 1H), 7.45 (d, J=8.40 Hz, 1H), 7.91 (s, 1H), 8.22 (s, 1H). MS (ESI, pos. ion) m/z 433 [M+H]+.

(S)-1-(6-(1-cyclopropyl-1H-pyrazol-4-yl)-2-methyl-5-(2-(oxetan-3-yl)ethoxy)-3,4-dihydroquinolin-1(2H)-yl)ethanone (I-47)

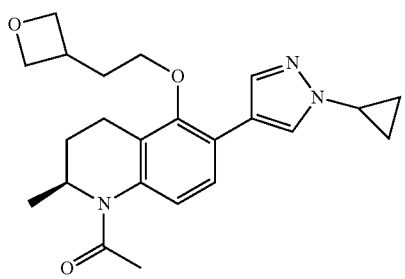 [SMILES: CC(=O)N1c2ccc(-c3cnn(C4CC4)c3)c(OCCC3COC3)c2CC[C@@H]1C]

¹H NMR (300 MHz, CD₃OD) δ ppm 1.05-1.15 (m, 7H), 1.21-1.37 (m, 1H), 2.05-2.15 (m, 5H), 2.25-2.42 (m, 2H), 2.82-2.95 (m, 1H), 3.18-3.30 (m, 1H), 3.55-3.78 (m, 3H), 4.46 (t, J=6.30 Hz, 2H), 4.65-4.83 (m, 2H), 4.83-4.89 (m, 1H), 7.01-7.11 (m, 1H), 7.37 (d, J=8.40 Hz, 1H), 7.84 (s, 1H), 8.05 (s, 1H). MS (ESI, pos. ion) m/z 396 [M+H]+.

1-((S)-6-(1-cyclopropyl-1H-pyrazol-4-yl)-5-((2,2-difluorocyclopropyl)methoxy)-2-methyl-3,4-dihydroquinolin-1(2H)-yl)ethanone (I-48)

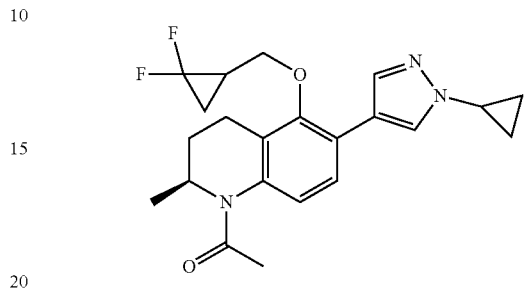

¹H NMR (400 MHz, CD₃OD) δ ppm 1.01-1.15 (m, 8H), 1.21-1.35 (m, 1H), 1.45-1.55 (m, 1H), 1.90-2.05 (m, 1H), 2.16 (s, 3H), 2.25-2.45 (m, 2H), 2.95-3.05 (m, 1H), 3.58-3.75 (m, 2H), 3.85-3.99 (m, 1H), 4.67-4.82 (m, 1H), 7.05-7.12 (m, 1H), 7.42 (d, J=8.40 Hz, 1H), 7.89 (s, 1H), 8.10 (s, 1H). MS (ESI, pos. ion) m/z 402 [M+H]+.

(S)-1-(6-(1-cyclopropyl-1H-pyrazol-4-yl)-5-((3-(hydroxymethyl)oxetan-3-yl)methoxy)-2-methyl-3,4-dihydroquinolin-1(2H)-yl)ethanone (I-49)

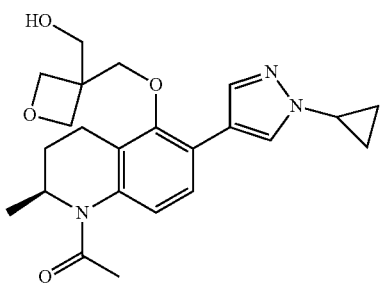 [SMILES: CC(=O)N1c2ccc(-c3cnn(C4CC4)c3)c(OCC3(CO)COC3)c2CC[C@@H]1C]

¹H NMR (300 MHz, CD₃OD) δ ppm 1.01-1.19 (m, 7H), 1.15-1.42 (m, 1H), 2.17 (s, 3H), 2.28-2.45 (m, 2H), 2.95-3.05 (m, 1H), 3.68-3.75 (m, 1H), 3.79-3.95 (m, 4H), 4.45-4.57 (m, 4H), 4.68-4.82 (m, 1H), 7.05-7.12 (m, 1H), 7.35 (d, J=8.40 Hz, 1H), 7.77 (s, 1H), 7.99 (s, 1H). MS (ESI, pos. ion) m/z 412 [M+H]⁺.

(S)-1-(6-(1-cyclopropyl-1H-pyrazol-4-yl)-5-((3-fluorooxetan-3-yl)methoxy)-2-methyl-3,4-dihydroquinolin-1(2H)-yl)ethanone (I-50)

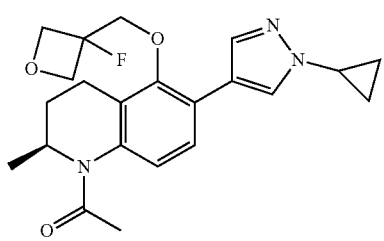 [SMILES: CC(=O)N1c2ccc(-c3cnn(C4CC4)c3)c(OCC3(F)COC3)c2CC[C@@H]1C]

$^1$H NMR (300 MHz, CD$_3$OD) δ ppm 0.99-1.15 (m, 7H), 1.25-1.41 (m, 1H), 2.16 (s, 3H), 2.28-2.45 (m, 2H), 2.95-3.05 (m, 1H), 3.65-3.75 (m, 1H), 3.99-4.25 (m, 2H), 4.55-4.85 (m, 5H), 7.05-7.15 (m, 1H), 7.41 (d, J=8.70 Hz, 1H), 7.84 (s, 1H), 8.05 (s, 1H). MS (ESI, pos. ion) m/z 400 [M+H]⁺.

(S)-1-(6-(1-cyclopropyl-1H-pyrazol-4-yl)-5-(3,3-difluorocyclobutoxy)-2-methyl-3,4-dihydroquinolin-1(2H)-yl)ethanone (I-51)

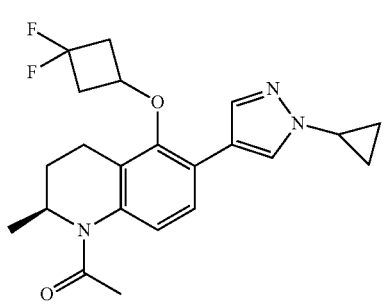 [SMILES: CC(=O)N1c2ccc(-c3cnn(C4CC4)c3)c(OC3CC(F)(F)C3)c2CC[C@@H]1C]

$^1$H NMR (300 MHz, CD$_3$OD) δ ppm 1.01-1.15 (m, 7H), 1.15-1.25 (m, 1H), 2.15 (s, 3H), 2.20-2.48 (m, 2H), 2.55-2.89 (m, 4H), 2.91-3.01 (m, 1H), 3.68-3.75 (m, 1H), 4.25-4.35 (m, 1H), 4.65-4.80 (m, 1H), 7.05-7.11 (m, 1H), 7.38 (d, J=8.40 Hz, 1H), 7.82 (s, 1H), 8.05 (s, 1H). MS (ESI, pos. ion) m/z 402 [M+H]⁺.

(S)-1-(5-(azetidin-3-ylmethoxy)-6-(1-cyclopropyl-1H-pyrazol-4-yl)-2-methyl-3,4-dihydroquinolin-1(2H)-yl)ethanone (I-52)

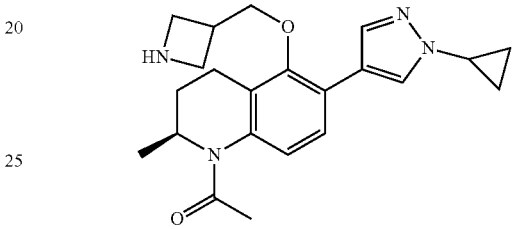

$^1$H NMR (300 MHz, CD$_3$OD) δ ppm 1.00-1.15 (m, 7H), 1.21-1.39 (m, 1H), 2.16 (s, 3H), 2.25-2.45 (m, 2H), 2.75-3.10 (m, 3H), 3.48-3.65 (m, 2H), 3.70-3.95 (m, 4H), 4.69-4.85 (m, 1H), 7.05-7.11 (m, 1H), 7.37 (d, J=8.40 Hz, 1H), 7.82 (s, 1H), 8.03 (s, 1H). MS (ESI, pos. ion) m/z 381 [M+H]⁺.

(S)-(5-cyclobutoxy-2-methyl-6-(1-methyl-1H-1,2,3-triazol-4-yl)-3,4-dihydroquinolin-1(2H)-yl)(cyclopropyl)methanone (I-53)

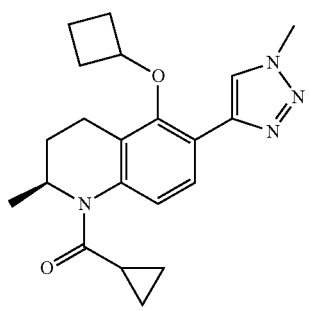 [SMILES: C[C@H]1CCc2c(ccc(-c3cn(C)nn3)c2OC2CCC2)N1C(=O)C1CC1]

$^1$H NMR (300 MHz, CDCl$_3$) δ ppm 0.65-0.67 (m, 1H), 0.81-0.92 (m, 1H), 0.93-1.03 (m, 1H), 1.13 (d, J=6.60 Hz, 3H), 1.23-1.32 (m, 1H), 1.33-1.42 (m, 1H), 1.60-1.70 (m, 1H), 1.83-1.87 (m, 2H), 2.03-2.26 (m, 4H), 2.27-2.44 (m, 2H), 2.91-3.07 (m, 1H), 4.05-4.28 (m, 4H), 4.68-4.82 (m, 1H), 7.15-7.28 (m, 1H), 7.92-8.08 (m, 2H). MS (ESI, pos. ion) m/z 367 [M+H]⁺.

(S)-(5-cyclobutoxy-2-methyl-6-(1H-pyrazol-4-yl)-3,4-dihydroquinolin-1(2H)-yl)(cyclopropyl)methanone (I-54)

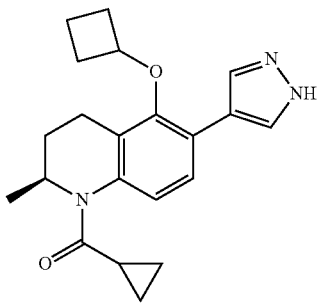 [SMILES: C[C@H]1CCc2c(ccc(-c3cn[nH]c3)c2OC2CCC2)N1C(=O)C1CC1]

¹H NMR (300 MHz, CD₃OD) δ ppm 0.55-0.65 (m, 1H), 0.72-0.89 (m, 2H), 1.13 (d, J=6.60 Hz, 4H), 1.13-1.40 (m, 2H), 1.41-1.70 (m, 1H), 1.71-1.90 (m, 1H), 1.90-1.93 (m, 4H), 2.14-2.39 (m, 2H), 2.90-3.02 (m, 1H), 3.99-4.16 (m, 1H), 4.55-4.65 (m, 1H), 7.05 (d, J=8.10 Hz, 1H), 7.31 (d, J=8.10 Hz, 1H), 7.88 (s, 1H). MS (ESI, pos. ion) m/z 352 [M+H]⁺.

(S)-(5-cyclobutoxy-2-methyl-6-(1-methyl-1H-pyrazol-4-yl)-3,4-dihydroquinolin-1(2H)-yl)(cyclopropyl)methanone (I-55)

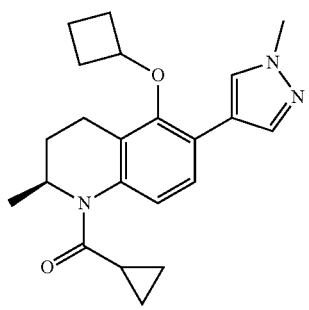 [SMILES: C[C@H]1CCc2c(ccc(-c3cnn(C)c3)c2OC2CCC2)N1C(=O)C1CC1]

¹H NMR (300 MHz, CD₃OD) δ ppm 0.65-0.79 (m, 1H), 0.85-1.01 (m, 2H), 1.13 (d, J=6.60 Hz, 4H), 1.25-1.51 (m, 2H), 1.51-1.76 (m, 1H), 1.85-2.01 (m, 1H), 2.01-2.57 (m, 6H), 2.99-3.15 (m, 1H), 3.85-3.04 (m, 3H), 4.12-4.31 (m, 1H), 4.61-4.79 (m, 1H), 7.15 (d, J=8.10 Hz, 1H), 7.39 (d, J=8.10 Hz, 1H), 7.86 (s, 1H), 7.99 (s, 1H). MS (ESI, pos. ion) m/z 367 [M+H]⁺.

(S)-(5-cyclobutoxy-2-methyl-6-(1H-pyrazol-5-yl)-3,4-dihydroquinolin-1(2H)-yl)(cyclopropyl)methanone (I-56)

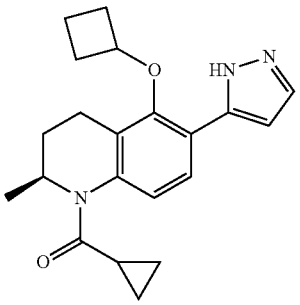 [SMILES: C[C@H]1CCc2c(ccc(-c3ccn[nH]3)c2OC2CCC2)N1C(=O)C1CC1]

¹H NMR (300 MHz, CD₃OD) δ ppm 0.61-0.85 (m, 1H), 0.85-1.03 (m, 2H), 1.15 (d, J=6.60 Hz, 4H), 1.25-1.51 (m, 2H), 1.51-1.80 (m, 1H), 1.81-2.28 (m, 5H), 2.29-2.60 (m, 2H), 2.99-3.20 (m, 1H), 4.06-4.29 (m, 1H), 4.68-4.82 (m, 1H), 7.15 (br s, 1H), 7.04-7.32 (m, 1H), 7.61 (br s, 2H). MS (ESI, pos. ion) m/z 352 [M+H]⁺.

(S)-(5-cyclobutoxy-2-methyl-6-(1-methyl-1H-imidazol-4-yl)-3,4-dihydroquinolin-1(2H)-yl)(cyclopropyl)methanone (I-57)

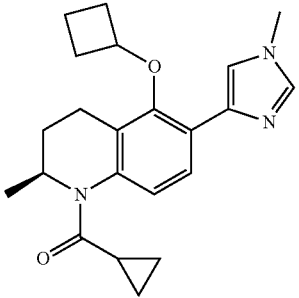 [SMILES: C[C@H]1CCc2c(ccc(-c3cn(C)cn3)c2OC2CCC2)N1C(=O)C1CC1]

¹H NMR (400 MHz, CD₃OD) δ ppm 0.63-0.78 (m, 1H), 0.87-0.98 (m, 2H), 1.29 (d, J=13.20 Hz, 4H), 1.25-1.36 (m, 1H), 1.37-1.51 (m, 1H), 1.61-1.77 (m, 1H), 1.84-1.96 (m, 1H), 2.05-2.49 (m, 6H), 2.99-3.13 (m, 1H), 3.81 (s, 3H), 4.13-4.35 (m, 1H), 4.62-4.77 (m, 1H), 7.17 (d, J=8.40 Hz, 1H), 7.70 (s, 1H), 7.64-7.76 (m, 2H). MS (ESI, pos. ion) m/z 366 [M+H]⁺.

(S)-methyl 5-(1-(tert-butoxycarbonyl)azetidin-3-yloxy)-6-(1-cyclopropyl-1H-pyrazol-4-yl)-2-methyl-3,4-dihydroquinoline-1(2H)-carboxylate (I-58)

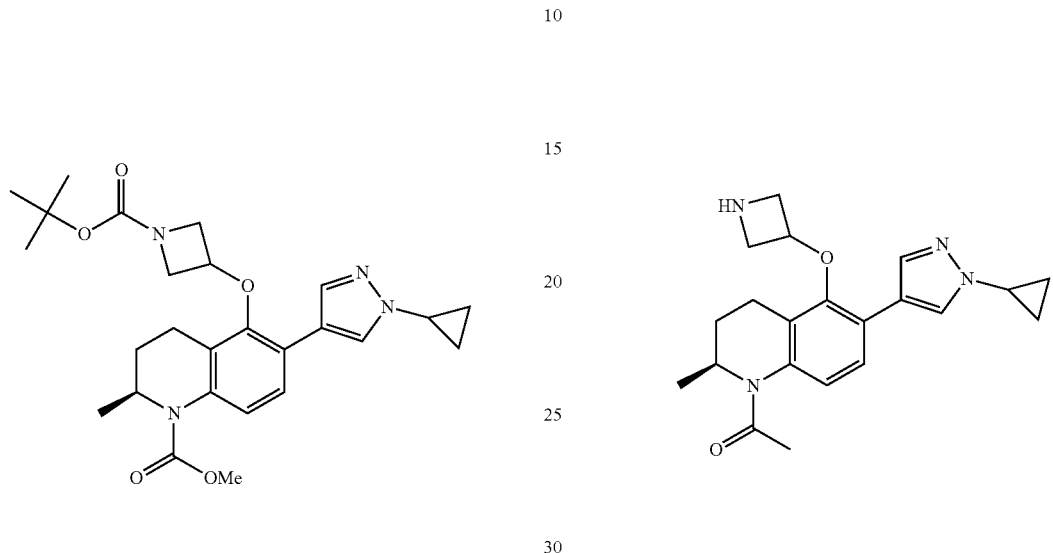

$^1$H NMR (300 MHz, CD$_3$OD) δ ppm 1.05-1.21 (m, 7H), 1.39-1.55 (m, 10H), 2.18-2.28 (m, 1H), 2.40-2.53 (m, 1H), 2.85-2.95 (m, 1H), 3.68-3.75 (m, 1H), 3.79 (s, 3H), 3.78-4.05 (m, 4H), 4.50-4.65 (m, 2H), 7.28-7.30 (m, 2H), 7.80 (s, 1H), 8.03 (s, 1H). MS (ESI, pos. ion) m/z 483 [M+H]⁺.

(S)-methyl 5-(azetidin-3-yloxy)-6-(1-cyclopropyl-1H-pyrazol-4-yl)-2-methyl-3,4-dihydroquinoline-1(2H)-carboxylate (I-59)

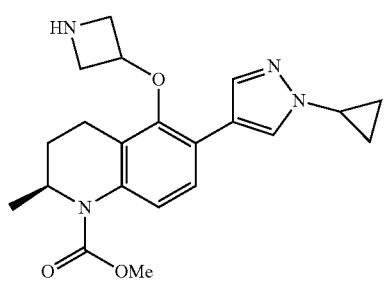 [SMILES: COC(=O)N1c2ccc(-c3cnn(C4CC4)c3)c(OC3CNC3)c2CC[C@@H]1C]

(S)-Methyl 5-(azetidin-3-yloxy)-6-(1-cyclopropyl-1H-pyrazol-4-yl)-2-methyl-3,4-dihydroquinoline-1(2H)-carboxylate was prepared by treating a solution of (S)-methyl 5-(1-(tert-butoxycarbonyl)azetidin-3-yloxy)-6-(1-cyclopropyl-1H-pyrazol-4-yl)-2-methyl-3,4-dihydroquinoline-1(2H)-carboxylate in dichloromethane with trifluoroacetic acid according to the procedure outlined in Example 5-1, Step 3. $^1$H NMR (300 MHz, CD$_3$OD) δ ppm 1.01-1.15 (m, 7H), 1.40-1.58 (m, 1H), 2.15-2.25 (m, 1H), 2.35-2.50 (m, 1H), 2.80-2.92 (m, 1H), 3.40-3.59 (m, 2H), 3.60-3.81 (m, 6H), 4.43-4.62 (m, 2H), 7.21-7.32 (m, 2H), 7.75 (s, 1H), 7.95 (s, 1H). MS (ESI, pos. ion) m/z 383 [M+H]⁺.

(S)-1-(5-(azetidin-3-yloxy)-6-(1-cyclopropyl-1H-pyrazol-4-yl)-2-methyl-3,4-dihydroquinolin-1(2H)-yl)ethanone (I-60)

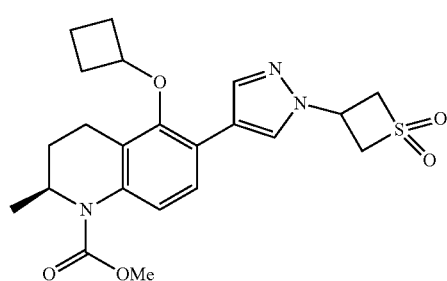 [SMILES: COC(=O)N1c2ccc(-c3cnn(C4CS(=O)(=O)C4)c3)c(OC3CCC3)c2CC[C@@H]1C]

(S)-1-(5-(Azetidin-3-yloxy)-6-(1-cyclopropyl-1H-pyrazol-4-yl)-2-methyl-3,4-dihydroquinolin-1(2H)-yl)ethanone was prepared from tert-butyl (S)-3-((1-acetyl-6-(1-cyclopropyl-1H-pyrazol-4-yl)-2-methyl-1,2,3,4-tetrahydroquinolin-5-yl)oxy)azetidine-1-carboxylate as outlined above for Examples 1-58 and 1-59. $^1$H NMR (400 MHz, CD$_3$OD) δ ppm 0.85-1.05 (m, 7H), 1.10-1.25 (m, 1H), 2.04 (s, 3H), 2.05-2.35 (m, 2H), 2.78-2.88 (m, 1H), 3.34-3.48 (m, 2H), 3.55-3.75 (m, 3H), 4.35-4.45 (m, 1H), 4.55-4.65 (m, 1H), 6.85-7.05 (m, 1H), 7.25 (d, J=8.40 Hz, 1H), 7.69 (s, 1H), 7.97 (s, 1H). MS (ESI, pos. ion) m/z 367 [M+H]⁺.

Methyl (S)-5-cyclobutoxy-6-(1-(1,1-dioxidothietan-3-yl)-1H-pyrazol-4-yl)-2-methyl-3,4-dihydroquinoline-1(2H)-carboxylate (I-61)

MS (ESI, pos. ion) m/z 446 [M+H]⁺.

Methyl (2S)-5-cyclobutoxy-6-(1-(1,1-dioxidotetrahydro-2H-thiopyran-3-yl)-1H-pyrazol-4-yl)-2-methyl-3,4-dihydroquinoline-1(2H)-carboxylate (I-62)

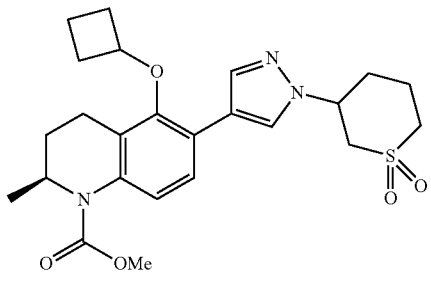 [SMILES: COC(=O)N1c2ccc(-c3cnn(C4CCCS(=O)(=O)C4)c3)c(OC3CCC3)c2CC[C@@H]1C]

MS (ESI, pos. ion) m/z 474 [M+H]⁺.

(R)-2-((S)-1-acetyl-6-(1-cyclopropyl-1H-pyrazol-4-yl)-2-methyl-1,2,3,4-tetrahydroquinolin-5-yloxy)-2-fluoroacetamide (I-63)

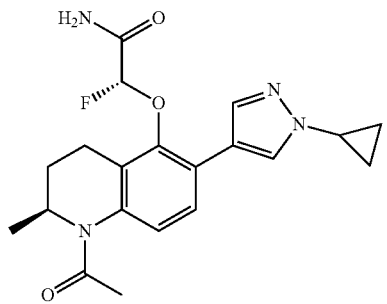

¹H NMR (300 MHz, CD₃OD) δ ppm 1.03-1.30 (m, 7H), 1.32-1.38 (m, 2H), 2.17 (s, 3H), 2.35-2.42 (m, 2H), 3.08-3.17 (m, 1H), 3.65-3.72 (m, 1H), 4.75-4.77 (m, 1H), 5.42-5.63 (m, 1H), 7.22-7.24 (m, 1H), 7.47-7.50 (m, 1H), 7.86 (s, 1H), 8.15 (s, 1H). MS (ESI, pos. ion) m/z 387 [M+H]⁺. Stereochemistry arbitrarily assigned.

2-((S)-1-acetyl-6-(1-cyclopropyl-1H-pyrazol-4-yl)-2-methyl-1,2,3,4-tetrahydroquinolin-5-yloxy)-2-fluoroacetamide (I-64)

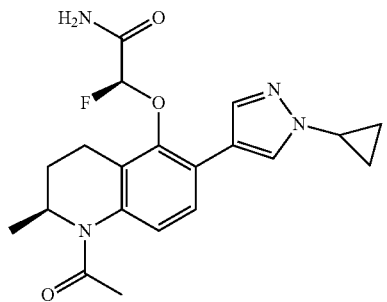 [SMILES: CC(=O)N1c2ccc(-c3cnn(C4CC4)c3)c(O[C@@H](F)C(N)=O)c2CC[C@@H]1C]

¹H NMR (300 MHz, CD₃OD) δ ppm 1.00-1.21 (m, 7H), 1.21-1.40 (m, 2H), 2.17 (s, 3H), 2.25-2.45 (m, 2H), 3.03-3.19 (m, 1H), 3.65-3.72 (m, 1H), 4.68-4.84 (m, 1H), 5.53 (d, J=61.20 Hz, 1H), 7.15-7.25 (m, 1H), 7.49 (d, J=8.40 Hz, 1H), 7.86 (s, 1H), 8.11 (s, 1H). MS (ESI, pos. ion) m/z 387 [M+H]⁺. Stereochemistry arbitrarily assigned.

(S)-methyl 6-(1-cyclopropyl-1H-pyrazol-4-yl)-5-((3-fluorooxetan-3-yl)methoxy)-2-methyl-3,4-dihydroquinoline-1(2H)-carboxylate (I-65)

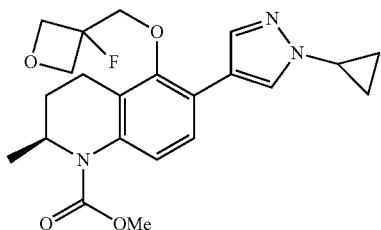 [SMILES: COC(=O)N1c2ccc(-c3cnn(C4CC4)c3)c(OCC3(F)COC3)c2CC[C@@H]1C]

¹H NMR (300 MHz, CD₃OD) δ ppm 1.05-1.23 (m, 7H), 1.41-1.71 (m, 1H), 2.12-2.38 (m, 1H), 2.47-2.70 (m, 1H), 2.81-3.05 (m, 1H), 3.65-3.73 (m, 1H), 3.78 (s, 3H), 3.96-4.19 (m, 2H), 4.55-4.83 (m, 5H), 7.28-7.41 (m, 2H), 7.82 (s, 1H), 8.05 (s, 1H). MS (ESI, pos. ion) m/z 416 [M+H]⁺.

(S)-2-(1-acetyl-6-(1-cyclopropyl-1H-pyrazol-4-yl)-2-methyl-1,2,3,4-tetrahydroquinolin-5-yloxy)-2,2-difluoroacetamide (I-66)

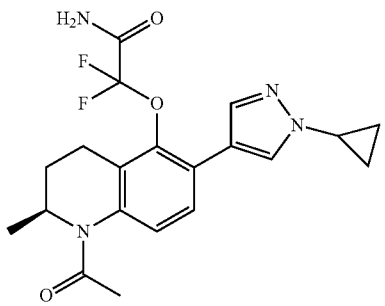 [SMILES: CC(=O)N1c2ccc(-c3cnn(C4CC4)c3)c(OC(F)(F)C(N)=O)c2CC[C@@H]1C]

¹H NMR (400 MHz, CDCl₃) δ ppm 0.93-1.19 (m, 8H), 2.06 (s, 3H), 2.16-2.22 (m, 1H), 2.30-2.37 (m, 1H), 2.95-2.98

(m, 1H), 3.55-3.61 (m, 1H), 4.61-4.77 (m, 1H), 7.18 (s, 1H), 7.41 (d, J=8.00 Hz, 1H), 7.74 (s, 1H), 8.05 (s, 1H). MS (ESI, pos. ion) m/z 405 [M+H]+.

(S)-1-(6-(1-cyclopropyl-1H-pyrazol-4-yl)-5-(2-fluoro-2-methylpropoxy)-2-methyl-3,4-dihydro-quinolin-1(2H)-yl)ethanone (I-67)

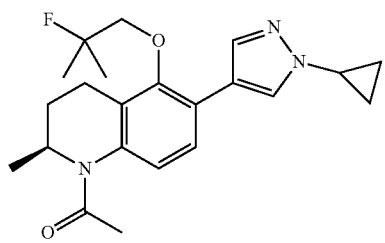 [SMILES: CC(=O)N1c2ccc(-c3cnn(C4CC4)c3)c(OCC(C)(C)F)c2CC[C@@H]1C]

¹H NMR (300 MHz, CDCl₃) δ ppm 1.04-1.17 (m, 7H), 1.24-1.53 (m, 7H), 2.17 (s, 3H), 2.21-2.35 (m, 2H), 2.96-3.01 (m, 1H), 3.57-3.64 (m, 3H), 4.75-4.85 (m, 1H), 6.91-6.98 (m, 1H), 7.30-7.33 (m, 1H), 7.81 (s, 1H), 7.99 (s, 1H). MS (ESI, pos. ion) m/z 386 [M+H]+.

(S)-methyl 5-cyclobutoxy-2-methyl-6-(1-(tetrahydro-2H-pyran-4-yl)-1H-pyrazol-4-yl)-3,4-dihydroquinoline-1(2H)-carboxylate (I-68)

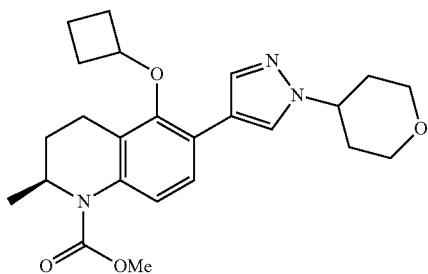 [SMILES: COC(=O)N1c2ccc(-c3cnn(C4CCOCC4)c3)c(OC3CCC3)c2CC[C@@H]1C]

¹H NMR (300 MHz, CD₃OD) δ ppm 1.17 (d, J=6.30 Hz, 3H), 1.25-1.50 (m, 2H), 1.55-1.67 (m, 1H), 2.05-2.21 (m, 8H), 2.22-2.29 (m, 1H), 2.35-2.49 (m, 1H), 2.91-3.01 (m, 1H), 3.52-3.66 (m, 2H), 3.77 (s, 3H), 4.05-4.21 (m, 3H), 4.42-4.61 (m, 2H), 7.25-7.36 (m, 2H), 7.84 (s, 1H), 8.07 (s, 1H). MS (ESI, pos. ion) m/z 426 [M+H]+.

(S)-(5-cyclobutoxy-6-(1-cyclopropyl-1H-pyrazol-4-yl)-8-fluoro-2-methyl-3,4-dihydroquinolin-1(2H)-yl)(cyclopropyl)methanone (I-69)

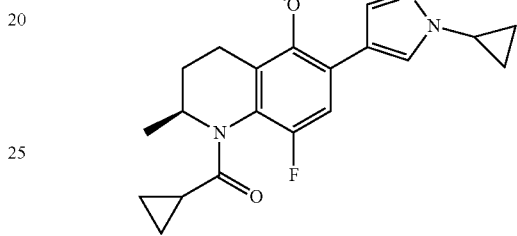

¹H NMR (400 MHz, CD₃OD) δ ppm 0.62-0.71 (m, 1H), 0.85-1.03 (m, 3H), 1.08-1.20 (m, 8H), 1.37-1.48 (m, 1H), 1.59-1.71 (m, 2H), 2.10-2.31 (m, 5H), 2.41-2.51 (m, 1H), 3.07-3.13 (m, 1H), 3.69-3.78 (m, 1H), 4.10-4.22 (m, 1H), 4.68-4.75 (m, 1H), 7.28 (d, J=10.80 Hz, 1H), 7.90 (s, 1H), 8.12 (s, 1H). MS (ESI, pos. ion) m/z 410 [M+H]+.

(S)-(5-cyclobutoxy-8-fluoro-2-methyl-6-(1H-pyrazol-4-yl)-3,4-dihydroquinolin-1(2H)-yl)(cyclopropyl)methanone (I-70)

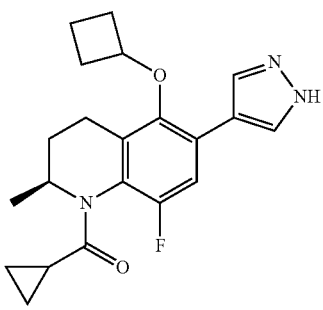 [SMILES: C[C@H]1CCc2c(OC3CCC3)c(-c3cn[nH]c3)cc(F)c2N1C(=O)C1CC1]

¹H NMR (400 MHz, DMSO-d₆) δ ppm 0.55-0.89 (m, 4H), 0.99-1.18 (m, 4H), 1.26-1.35 (m, 1H), 1.48-1.61 (m, 2H), 1.99-2.41 (m, 6H), 2.90-3.01 (m, 1H), 4.09-4.13 (m, 1H), 4.55-4.65 (m, 1H), 7.43 (d, J=10.80 Hz, 1H), 7.92-8.21 (m, 2H). MS (ESI, pos. ion) m/z 370 [M+H]⁺.

(S)-methyl 5-cyclobutoxy-6-(1-cyclopropyl-1H-pyrazol-4-yl)-8-fluoro-2-methyl-3,4-dihydroquinoline-1(2H)-carboxylate (I-71)

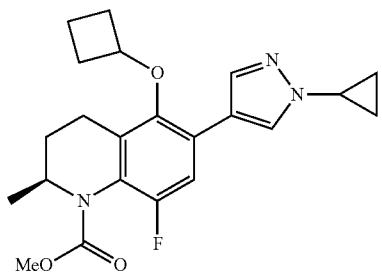 [SMILES: COC(=O)N1c2c(F)cc(-c3cnn(C4CC4)c3)c(OC3CCC3)c2CC[C@@H]1C]

$^1$H NMR (400 MHz, CD$_3$OD) δ ppm 1.08-1.20 (m, 7H), 1.22-1.41 (m, 2H), 1.60-1.71 (m, 1H), 2.05-2.20 (m, 4H), 2.25-2.42 (m, 2H), 2.96-3.05 (m, 1H), 3.67-3.80 (m, 4H), 4.11-4.19 (m, 1H), 4.38-4.49 (m, 1H), 7.14 (d, J=11.20 Hz, 1H), 7.85 (s, 1H), 8.06 (s, 1H). MS (ESI, pos. ion) m/z 400 [M+H]⁺.

(S)-methyl 5-cyclobutoxy-8-fluoro-2-methyl-6-(1H-pyrazol-4-yl)-3,4-dihydroquinoline-1(2H)-carboxylate (I-72)

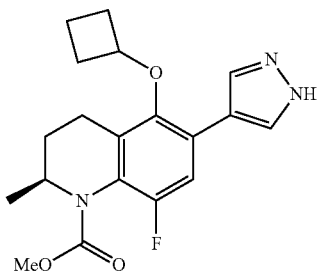 [SMILES: COC(=O)N1c2c(F)cc(-c3cn[nH]c3)c(OC3CCC3)c2CC[C@@H]1C]

$^1$H NMR (300 MHz, CD$_3$OD) δ ppm 1.17 (d, J=6.30 Hz, 3H), 1.25-1.35 (m, 2H), 1.55-1.65 (m, 1H), 2.01-2.18 (m, 4H), 2.23-2.41 (m, 2H), 2.95-3.07 (m, 1H), 3.74 (s, 3H), 4.07-4.15 (m, 1H), 4.39-4.45 (m, 1H), 7.15 (d, J=14.40 Hz, 1H), 8.00 (s, 2H). MS (ESI, pos. ion) m/z 360 [M+H]⁺.

(S)-1-(5-cyclobutoxy-6-(1-cyclopropyl-1H-pyrazol-4-yl)-8-fluoro-2-methyl-3,4-dihydroquinolin-1(2H)-yl)ethanone (I-73)

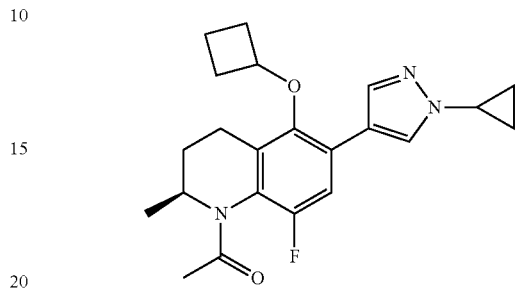

$^1$H NMR (400 MHz, CD$_3$OD) δ ppm 1.10-1.18 (m, 8H), 1.35-1.45 (m, 1H), 1.59-1.70 (m, 1H), 1.95-2.25 (m, 8H), 2.42-2.51 (m, 1H), 3.05-3.11 (m, 1H), 3.70-3.78 (m, 1H), 4.15-4.20 (m, 1H), 4.70-4.80 (m, 1H), 7.29 (d, J=11.20 Hz, 1H), 7.90 (s, 1H), 8.12 (s, 1H). MS (ESI, pos. ion) m/z 384 [M+H]⁺.

(S)-1-(5-cyclobutoxy-8-fluoro-2-methyl-6-(1H-pyrazol-4-yl)-3,4-dihydroquinolin-1(2H)-yl)ethanone (I-74)

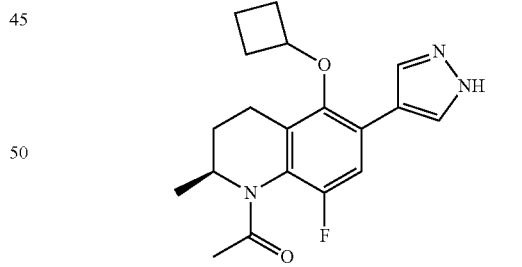

$^1$H NMR (400 MHz, CD$_3$OD) δ ppm 1.10-1.18 (m, 4H), 1.35-1.45 (m, 1H), 1.59-1.70 (m, 1H), 2.05-2.25 (m, 8H), 2.42-2.51 (m, 1H), 3.05-3.11 (m, 1H), 4.15-4.20 (m, 1H), 4.70-4.80 (m, 1H), 7.31 (d, J=11.20 Hz, 1H), 8.05 (br s, 2H). MS (ESI, pos. ion) m/z 344 [M+H]+.

(S)-1-(5-cyclobutoxy-6-(1-cyclopropyl-1H-pyrazol-4-yl)-7,8-difluoro-2-methyl-3,4-dihydroquinolin-1(2H)-yl)ethanone (I-75)

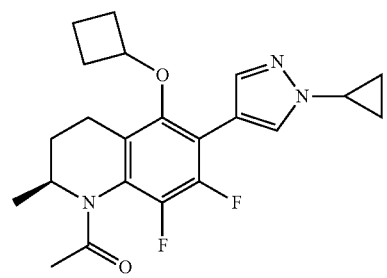 [SMILES: CC(=O)N1c2c(F)c(F)c(-c3cnn(C4CC4)c3)c(OC3CCC3)c2CC[C@@H]1C]

(S)-1-(5-cyclobutoxy-6-(1-cyclopropyl-1H-pyrazol-4-yl)-7,8-difluoro-2-methyl-3,4-dihydroquinolin-1(2H)-yl)ethanone was synthesized from (S)-1-(6-bromo-5-cyclobutoxy-7,8-difluoro-2-methyl-3,4-dihydroquinolin-1(2H)-yl)ethanone according to the procedure described above in Step 2 of the synthesis of (S)-1-(6-(1-(2-hydroxyethyl)-1H-pyrazol-4-yl)-2-methyl-5-propoxy-3,4-dihydroquinolin-1(2H)-yl)ethanone (Example 24). ¹H NMR (300 MHz, CD₃OD) δ ppm 1.11-1.18 (m, 9H), 1.56-1.68 (m, 1H), 1.98-2.47 (m, 9H), 2.94-3.08 (m, 1H), 3.70-3.81 (m, 1H), 4.09-4.20 (m, 1H), 4.73-4.81 (m, 1H), 7.86 (s, 1H), 8.12 (s, 1H). MS (ESI, pos. ion) m/z 402 [M+H]+.

(S)-methyl 5-(azetidin-3-ylmethoxy)-6-(1-cyclopropyl-1H-pyrazol-4-yl)-2-methyl-3,4-dihydroquinoline-1(2H)-carboxylate (I-76)

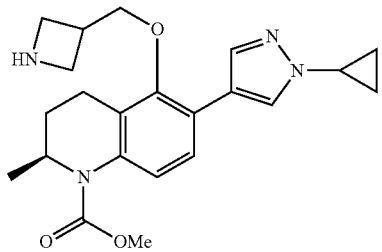 [SMILES: COC(=O)N1c2ccc(-c3cnn(C4CC4)c3)c(OCC3CNC3)c2CC[C@@H]1C]

¹H NMR (300 MHz, CD₃OD) δ ppm 1.01-1.21 (m, 6H), 1.48-1.68 (m, 1H), 2.18-2.28 (m, 1H), 2.48-2.63 (m, 1H), 2.83-2.99 (m, 1H), 3.65-3.99 (m, 9H), 4.55-4.68 (m, 1H), 7.25-7.35 (m, 2H), 7.81 (s, 1H), 8.01 (s, 1H). MS (ESI, pos. ion) m/z 397 [M+H]+.

Example 25

(S)-1-(6-(1-cyclopropyl-1H-pyrazol-4-yl)-2-methyl-5-(quinazolin-2-yloxy)-3,4-dihydroquinolin-1(2H)-yl)ethanone. (I-77)

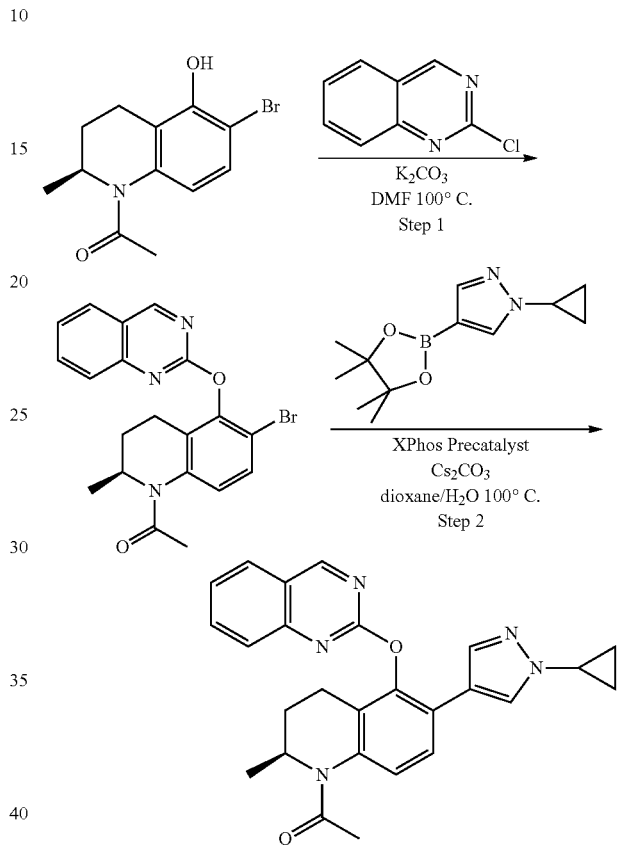

Step 1. (S)-1-(6-bromo-2-methyl-5-(quinazolin-2-yloxy)-3,4-dihydroquinolin-1(2H)-yl)ethanone A mixture of (S)-1-(6-bromo-5-hydroxy-2-methyl-3,4-dihydroquinolin-1(2H)-yl)ethanone (0.025 g, 0.088 mmol), 2-chloroquinazoline (0.017 g, 0.106 mmol), and potassium carbonate (0.024 g, 0.176 mmol) in N,N-dimethylformamide (1.0 mL) was stirred in the microwave at 100° C. for 4 h. The reaction mixture was cooled to room temperature and water was added. The mixture was extracted with dichloromethane and the combined organic phases were washed with water and brine, dried over anhydrous sodium sulfate, filtered, and concentrated to afford a yellow oil. This material was purified via column chromatography on silica gel (Biotage 10 g column, gradient elution with 50-100% ethyl acetate-hexane) to afford (S)-1-(6-bromo-2-methyl-5-(quinazolin-2-yloxy)-3,4-dihydroquinolin-1(2H)-yl)ethanone (0.023 g, 63%). MS (ESI, pos. ion) m/z 412, 414 [M+H]+.

Step 2. (S)-1-(6-(1-cyclopropyl-1H-pyrazol-4-yl)-2-methyl-5-(quinazolin-2-yloxy)-3,4-dihydroquinolin-1(2H)-yl)ethanone A mixture of (S)-1-(6-bromo-2-methyl-5-(quinazolin-2-yloxy)-3,4-dihydroquinolin-1(2H)-yl)ethanone (0.025 g, 0.061 mmol), 1-cyclopropyl-4-(4,4,5,5-tetramethyl-1,3,2-dioxaborolan-2-yl)-1H-pyrazole (0.017 g, 0.073 mmol), chloro (2-dicyclohexylphosphino-2',4',6'-tri-i-propyl-1,1'-biphenyl)(2'-amino-1,1'-biphenyl-2-yl) palladium(II) (XPhos 2nd generation precatalyst) (2.4 mg, 0.003 mmol), and cesium carbonate (0.059 g, 0.182 mmol) in 1,4-dioxane (2.0 mL) and water (0.40 mL) was heated at 100° C. for 2 h. The reaction mixture was filtered through Celite and concentrated to afford an orange oil. This material was purified via column chromatography on silica gel (Biotage 25 g column, gradient elution with 25-100% ethyl acetate-hexane) to afford (S)-1-(6-(1-cyclopropyl-1H-pyrazol-4-yl)-2-methyl-5-(quinazolin-2-yloxy)-3,4-dihydroquinolin-1(2H)-yl)ethanone (0.012 g, 45%) as a white solid. MS (ESI, pos. ion) m/z 440. $^1$H NMR (300 MHz, DMSO-d$_6$) δ ppm 0.81-0.91 (m, 5H), 1.07 (d, J=6.74 Hz, 3H), 1.47 (m, 1H), 2.03 (br dd, J=13.34, 6.89 Hz, 1H), 2.18 (s, 3H), 2.44 (m, 1H), 3.55-3.67 (m, 1H), 4.63 (m, 1H), 7.41 (br s, 1H), 7.51-7.70 (m, 3H), 7.72 (s, 1H), 7.91 (ddd, J=8.50, 7.04, 1.47 Hz, 1H), 8.06 (s, 1H), 8.10 (d, J=8.21 Hz, 1H), 9.54 (s, 1H). MS (ESI, pos. ion) m/z 440 [M+H]$^+$.

The following examples were made according to the procedure described above for Example 25:

(S)-1-(5-(benzo[d]oxazol-2-yloxy)-6-(1-cyclopropyl-1H-pyrazol-4-yl)-2-methyl-3,4-dihydroquinolin-1(2H)-yl)ethanone (I-78)

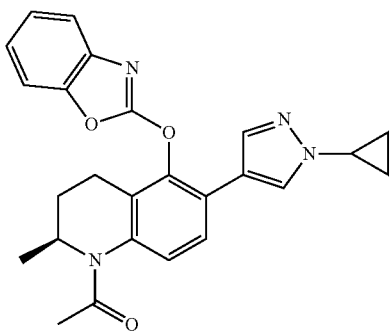 [SMILES: CC(=O)N1c2ccc(-c3cnn(C4CC4)c3)c(Oc3nc4ccccc4o3)c2CC[C@@H]1C]

MS (ESI, pos. ion) m/z 429 [M+H]$^+$.

(S)-1-(5-(benzo[d]oxazol-2-yloxy)-2-methyl-6-(1-(oxetan-3-yl)-1H-pyrazol-4-yl)-3,4-dihydroquinolin-1(2H)-yl)ethanone (I-79)

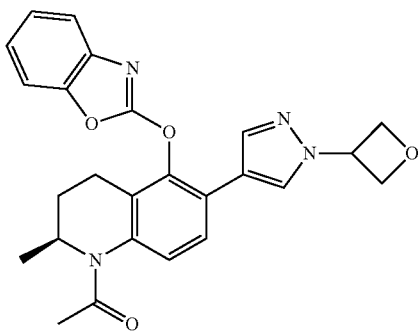 [SMILES: CC(=O)N1c2ccc(-c3cnn(C4COC4)c3)c(Oc3nc4ccccc4o3)c2CC[C@@H]1C]

MS (ESI, pos. ion) m/z 445 [M+H]$^+$.

(S)-1-(6-(1-(2-hydroxyethyl)-1H-pyrazol-4-yl)-2-methyl-5-(pyrimidin-2-yloxy)-3,4-dihydroquinolin-1(2H)-yl)ethanone (I-80)

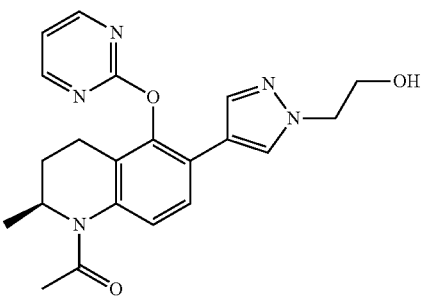 [SMILES: CC(=O)N1c2ccc(-c3cnn(CCO)c3)c(Oc3ncccn3)c2CC[C@@H]1C]

$^1$H NMR (300 MHz, DMSO-d$_6$) δ ppm 1.04 (d, J=6.45 Hz, 3H), 1.42 (m, 1H), 1.93-2.10 (m, 1H), 2.16 (s, 3H), 2.28 (m, 1H), 2.40 (br t, J=7.18 Hz, 1H), 3.64 (q, J=5.47 Hz, 2H), 4.05 (t, J=5.72 Hz, 2H), 4.64 (m, 1H), 4.83 (t, J=5.28 Hz, 1H), 7.21 (t, J=4.84 Hz, 1H), 7.38 (br s, 1H), 7.52 (d, J=8.50 Hz, 1H), 7.70 (s, 1H), 7.94 (s, 1H), 8.60 (d, J=4.69 Hz, 2H). MS (ESI, pos. ion) m/z 394 [M+H]$^+$.

(S)-2-(1-acetyl-6-(1-cyclopropyl-1H-pyrazol-4-yl)-2-methyl-1,2,3,4-tetrahydroquinolin-5-yloxy)nicotinamide (I-81)

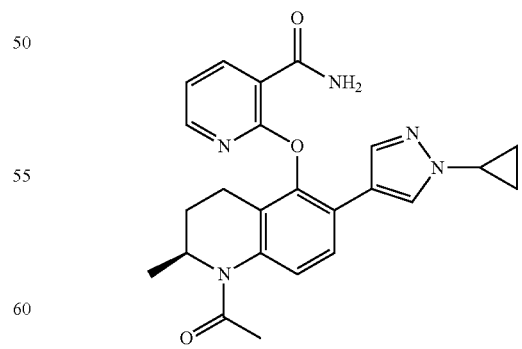

$^1$H NMR (400 MHz, CD$_3$OD) δ ppm 0.91-1.01 (m, 4H), 1.16 (d, J=6.40 Hz, 3H), 1.35-1.55 (m, 1H), 2.05-2.35 (m, 4H), 2.37-2.55 (m, 1H), 2.70-2.85 (m, 1H), 3.51-3.59 (m, 1H), 4.70-4.85 (m, 1H), 7.11-7.18 (m, 1H), 7.20-7.35 (m, 1H), 7.53 (d, J=8.40 Hz, 1H), 7.32 (s, 1H), 7.96 (s, 1H), 8.01-8.09 (m, 1H), 8.35-8.39 (m, 1H). MS (ESI, pos. ion) m/z 432 [M+H]+.

(S)-1-(5-(1H-pyrazolo[3,4-d]pyrimidin-6-yloxy)-6-(1-cyclopropyl-1H-pyrazol-4-yl)-2-methyl-3,4-dihydroquinolin-1(2H)-yl)ethanone (I-82)

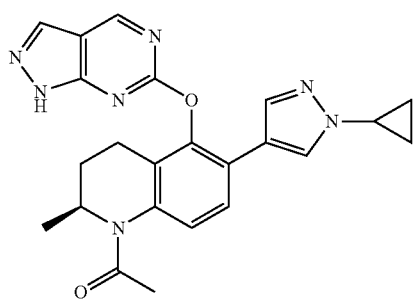 [SMILES: CC(=O)N1c2ccc(-c3cnn(C4CC4)c3)c(Oc3ncc4cn[nH]c4n3)c2CC[C@@H]1C]

¹H NMR (400 MHz, CD3OD) δ ppm 0.90-1.01 (m, 4H), 1.18 (d, J=6.40 Hz, 3H), 1.35-1.52 (m, 1H), 2.15-2.45 (m, 5H), 2.60-2.72 (m, 1H), 3.52-3.59 (m, 1H), 4.73-4.85 (m, 1H), 7.25-7.35 (m, 1H), 7.57 (d, J=8.40 Hz, 1H), 7.78 (s, 1H), 7.99 (s, 1H), 8.19 (s, 1H), 9.05 (s, 1H). MS (ESI, pos. ion) m/z 430 [M+H]+.

(S)-1-(6-(1-cyclopropyl-1H-pyrazol-4-yl)-2-methyl-5-(thiazol-2-yloxy)-3,4-dihydroquinolin-1(2H)-yl)ethanone (I-83)

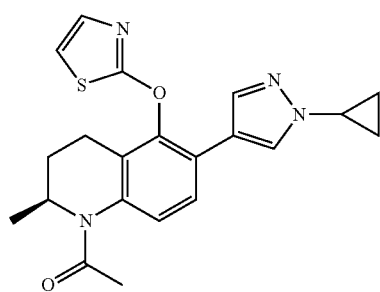 [SMILES: CC(=O)N1c2ccc(-c3cnn(C4CC4)c3)c(Oc3nccs3)c2CC[C@@H]1C]

¹H NMR (300 MHz, CD₃OD) δ ppm 0.98-1.05 (m, 4H), 1.15 (d, J=6.60 Hz, 3H), 1.39-1.53 (m, 1H), 2.15-2.45 (m, 5H), 2.70-2.82 (m, 1H), 3.58-3.65 (m, 1H), 4.70-4.85 (m, 1H), 6.95 (d, J=4.20 Hz, 1H), 7.18 (d, J=4.20 Hz, 1H), 7.30-

7.45 (m, 1H), 7.60 (d, J=8.40 Hz, 1H), 7.79 (s, 1H), 7.99 (s, 1H). MS (ESI, pos. ion) m/z 395 [M+H]+.

(S)-2-(1-acetyl-6-(1-cyclopropyl-1H-pyrazol-4-yl)-2-methyl-1,2,3,4-tetrahydroquinolin-5-yloxy)nicotinonitrile (I-84)

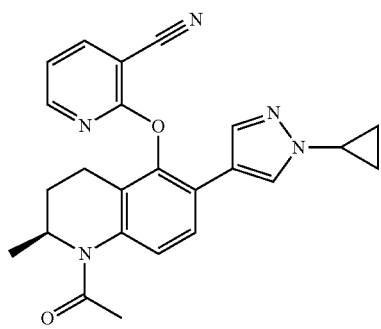 [SMILES: CC(=O)N1c2ccc(-c3cnn(C4CC4)c3)c(Oc3ncccc3C#N)c2CC[C@@H]1C]

¹H NMR (300 MHz, CD₃OD) δ ppm 0.95-1.02 (m, 4H), 1.15 (d, J=6.60 Hz, 3H), 1.35-1.52 (m, 1H), 2.15-2.38 (m, 5H), 2.51-2.63 (m, 1H), 3.53-3.63 (m, 1H), 4.70-4.85 (m, 1H), 7.15-7.19 (m, 1H), 7.25-7.35 (m, 1H), 7.51 (d, J=8.40 Hz, 1H), 7.70 (s, 1H), 7.92 (s, 1H), 8.15-8.25 (m, 2H). MS (ESI, pos. ion) m/z 414 [M+H]+.

(S)-1-(6-(1-cyclopropyl-1H-pyrazol-4-yl)-2-methyl-5-(4-(trifluoromethyl)pyrimidin-2-yloxy)-3,4-dihydroquinolin-1(2H)-yl)ethanone (I-85)

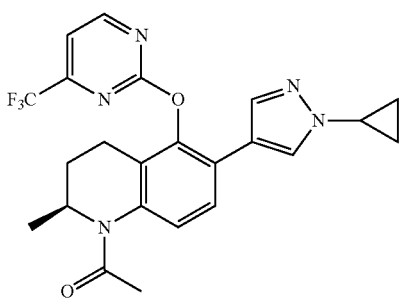 [SMILES: CC(=O)N1c2ccc(-c3cnn(C4CC4)c3)c(Oc3nccc(C(F)(F)F)n3)c2CC[C@@H]1C]

¹H NMR (300 MHz, CD₃OD) δ ppm 0.95-1.05 (m, 4H), 1.16 (d, J=6.60 Hz, 3H), 1.40-1.5 8(m, 1H), 2.15-2.45 (m, 5H), 2.55-2.65 (m, 1H), 3.55-3.65 (m, 1H), 4.70-4.85 (m, 1H), 7.25-7.35 (m, 1H), 7.53-7.60 (m, 2H), 7.76 (s, 1H), 7.99 (s, 1H), 8.85 (d, J=5.10 Hz, 1H). MS (ESI, pos. ion) m/z 458 [M+H]⁺.

(S)-1-(6-(1-cyclopropyl-1H-pyrazol-4-yl)-2-methyl-5-(3-(trifluoromethyl)pyridin-2-yloxy)-3,4-dihydroquinolin-1(2H)-yl)ethanone (I-86)

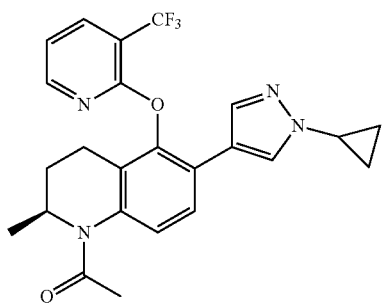

¹H NMR (300 MHz, CD₃OD) δ ppm 0.89-1.01 (m, 4H), 1.05-1.15 (m, 3H), 1.20-1.45 (m, 1H), 1.95-2.25 (m, 5H), 2.75-2.89 (m, 1H), 3.49-3.60 (m, 1H), 4.70-4.85 (m, 1H), 7.11-7.19 (m, 1H), 7.20-7.35 (m, 1H), 7.54 (d, J=8.40 Hz, 1H), 7.68 (s, 1H), 7.84 (s, 1H), 8.09-8.19 (m, 2H). MS (ESI, pos. ion) m/z 457 [M+H]⁺.

(S)-1-(5-(3-chloropyridin-2-yloxy)-6-(1-cyclopropyl-1H-pyrazol-4-yl)-2-methyl-3,4-dihydroquinolin-1(2H)-yl)ethanone (I-87)

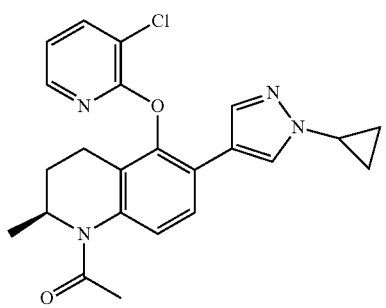 [SMILES: CC(=O)N1c2ccc(-c3cnn(C4CC4)c3)c(Oc3ncccc3Cl)c2CC[C@@H]1C]

¹H NMR (300 MHz, CD₃OD) δ ppm 0.95-1.05 (m, 4H), 1.16 (d, J=6.60 Hz, 3H), 1.35-1.60 (m, 1H), 2.10-2.30 (m, 5H), 2.50-2.63 (m, 1H), 3.55-3.60 (m, 1H), 4.70-4.89 (m, 1H), 6.95-7.09 (m, 1H), 7.25-7.35 (m, 1H), 7.54 (d, J=8.40

Hz, 1H), 7.78 (s, 1H), 7.82-7.89 (m, 1H), 7.91-7.99 (m, 2H). MS (ESI, pos. ion) m/z 423 [M+H]⁺.

(S)-1-(6-(1-cyclopropyl-1H-pyrazol-4-yl)-2-methyl-5-(pyrazin-2-yloxy)-3,4-dihydroquinolin-1(2H)-yl)ethanone (I-88)

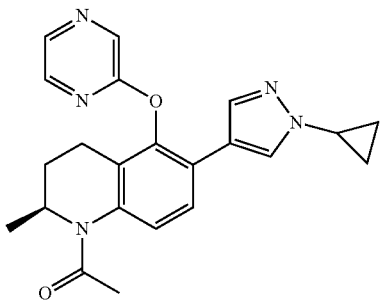 [SMILES: CC(=O)N1c2ccc(-c3cnn(C4CC4)c3)c(Oc3cnccn3)c2CC[C@@H]1C]

¹H NMR (300 MHz, CD₃OD) δ ppm 0.95-1.01 (m, 4H), 1.14 (d, J=5.40 Hz, 3H), 1.30-1.48 (m, 1H), 2.10-2.40 (m, 5H), 2.55-2.68 (m, 1H), 3.50-3.65 (m, 1H), 4.68-4.85 (m, 1H), 7.20-7.35 (m, 1H), 7.52 (d, J=8.40 Hz, 1H), 7.69 (s, 1H), 7.92 (s, 1H), 7.99-8.03 (m, 1H), 8.22 (d, J=2.70 Hz, 1H), 8.50 (d, J=1.20 Hz, 1H). MS (ESI, pos. ion) m/z 390 [M+H]⁺.

(S)-1-(6-(1-cyclopropyl-1H-pyrazol-4-yl)-2-methyl-5-(pyridin-2-yloxy)-3,4-dihydroquinolin-1(2H)-yl)ethanone (I-89)

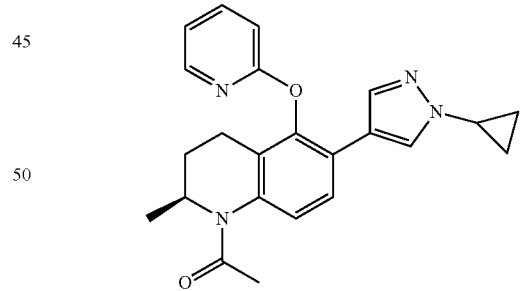

¹H NMR (300 MHz, CD₃OD) δ ppm 0.95-1.05 (m, 4H), 1.16 (d, J=6.60 Hz, 3H), 1.32-1.50 (m, 1H0, 2.10-2.32 (m, 5H), 2.55-2.72 (m, 1H), 3.55-3.65 (m, 1H), 4.72-4.90 (m, 1H), 6.94 (d, J=8.10 Hz, 1H0, 7.02-7.10 (m, 1H), 7.32 (br s, 1H), 7.58 (d, J=8.40 Hz, 1H), 7.74 (s, 1H), 7.75-7.85 (m, 1H), 7.93 (s, 1H), 8.05-8.09 (m, 1H). MS (ESI, pos. ion) m/z 389 [M+H]⁺.

(S)-1-(6-(1-cyclopropyl-1H-pyrazol-4-yl)-5-(4,6-dimethylpyrimidin-2-yloxy)-2-methyl-3,4-dihydroquinolin-1(2H)-yl)ethanone (I-90)

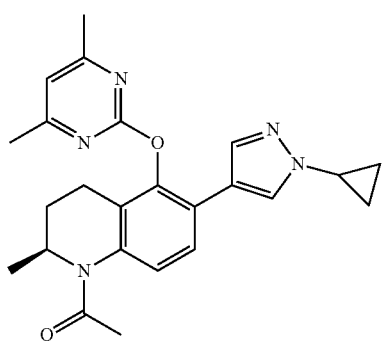 [SMILES: CC(=O)N1c2ccc(-c3cnn(C4CC4)c3)c(Oc3nc(C)cc(C)n3)c2CC[C@@H]1C]

¹H NMR (300 MHz, CD₃OD) δ ppm 0.95-1.01 (m, 4H), 1.14 (d, J=6.30 Hz, 3H), 1.30-1.49 (m, 1H), 2.10-2.35 (m, 11H), 2.52-2.65 (m, 1H), 3.55-3.65 (m, 1H), 4.70-4.85 (m, 1H), 6.93 (s, 1H), 7.20-7.35 (m, 1H), 7.54 (d, J=8.10 Hz, 1H), 7.75 (s, 1H), 7.96 (s, 1H). MS (ESI, pos. ion) m/z 418 [M+H]⁺.

(S)-6-(1-acetyl-6-(1-cyclopropyl-1H-pyrazol-4-yl)-2-methyl-1,2,3,4-tetrahydroquinolin-5-yloxy)pyridazine-3-carbonitrile (I-91)

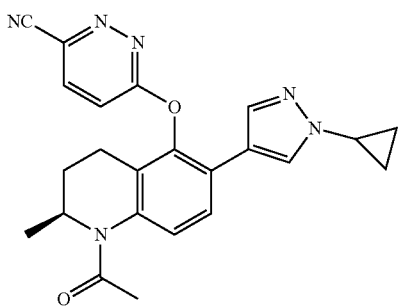 [SMILES: CC(=O)N1c2ccc(-c3cnn(C4CC4)c3)c(Oc3ccc(C#N)nn3)c2CC[C@@H]1C]

¹H NMR (300 MHz, CD₃OD) δ ppm 0.95-1.01 (m, 4H), 1.15 (d, J=6.60 Hz, 3H), 1.45 (br s, 1H), 2.15-2.32 (m, 5H), 2.55-2.72 (m, 1H), 3.52-3.69 (m, 1H), 4.75-4.90 (m, 1H), 7.39 (br s, 1H), 7.54 (d, J=8.10 Hz, 1H), 7.62-7.69 (m, 2H), 7.92 (s, 1H), 8.12 (d, J=9.30 Hz, 1H). MS (ESI, pos. ion) m/z 415 [M+H]⁺.

(S)-1-(6-(1-cyclopropyl-1H-pyrazol-4-yl)-2-methyl-5-(5-methylpyrimidin-2-yloxy)-3,4-dihydroquinolin-1(2H)-yl)ethanone (I-92)

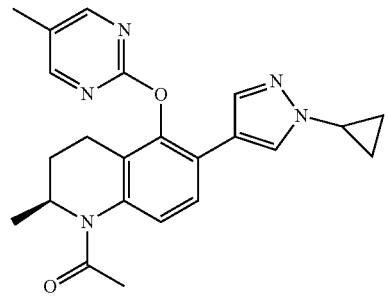

¹H NMR (400 MHz, CDCl₃) δ ppm 0.90-0.92 (m, 4H), 1.04 (d, J=6.40 Hz, 3H), 1.35 (m, 1H), 2.07-2.14 (m, 8H), 2.49-2.55 (m, 1H), 3.45-3.51 (m, 1H), 4.68 (m, 1H), 7.19 (m, 1H), 7.44 (d, J=8.40 Hz, 1H), 7.64 (s, 1H), 7.84 (s, 1H), 8.27 (d, J=4.80 Hz, 2H). MS (ESI, pos. ion) m/z 404 [M+H]⁺.

(S)-1-(6-(1-cyclopropyl-1H-pyrazol-4-yl)-2-methyl-5-(2-(trifluoromethyl)pyrimidin-4-yloxy)-3,4-dihydroquinolin-1(2H)-yl)ethanone (I-93)

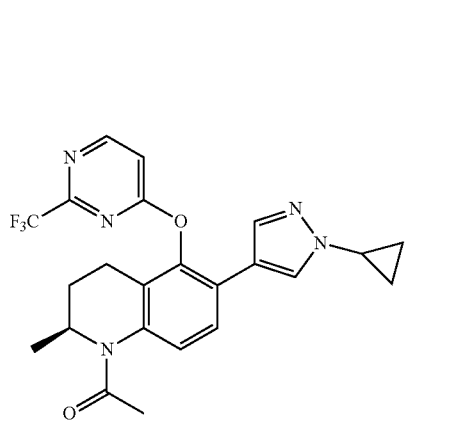 [SMILES: CC(=O)N1c2ccc(-c3cnn(C4CC4)c3)c(Oc3ccnc(C(F)(F)F)n3)c2CC[C@@H]1C]

¹H NMR (400 MHz, CD₃OD) δ ppm 1.02 (s, 4H), 1.15 (s, 3H), 1.49 (s, 1H), 2.19-2.38 (m, 5H), 2.52-2.63 (m, 1H), 3.55-3.63 (m, 1H), 4.76-4.82 (m, 1H), 7.29-7.49 (m, 2H), 7.56 (d, J=8.40 Hz, 1H), 7.70 (s, 1H), 7.94 (s, 1H), 8.78 (s, 1H). MS (ESI, pos. ion) m/z 458 [M+H]⁺.

The following examples were made according to the procedure described above for Example 25, with the following changes: (1) In Step 2, tert-butyl 4-(4-(4,4,5,5-tetramethyl-1,3,2-dioxaborolan-2-yl)-1H-pyrazol-1-yl)piperidine-1-carboxylate was used instead of 1-cyclopropyl-4-(4,4,5,5-tetramethyl-1,3,2-dioxaborolan-2-yl)-1H-pyrazole (2) The Boc group was removed according to the procedure described below in Step 3 of Example 27.

(S)-(5-(6-chloropyridin-2-yloxy)-2-methyl-6-(1-(piperidin-4-yl)-1H-pyrazol-4-yl)-3,4-dihydroquinolin-1(2H)-yl)(cyclopropyl)methanone (I-94)

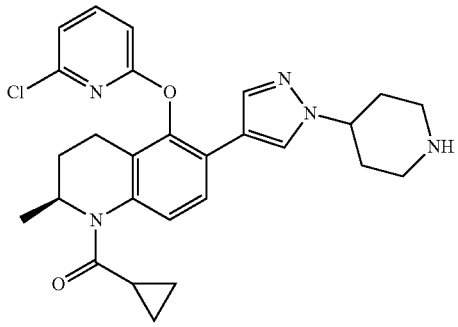 [SMILES: C[C@H]1CCc2c(ccc(-c3cnn(C4CCNCC4)c3)c2Oc2cccc(Cl)n2)N1C(=O)C1CC1]

¹H NMR (300 MHz, CD₃OD) δ ppm 0.73-0.82 (m, 1H), 0.91-1.02 (m, 2H), 1.12-1.21 (m, 4H), 1.45-1.53 (m, 1H), 1.85-2.00 (m, 2H), 2.00 (s, 3H), 2.22-2.41 (m, 2H), 2.63-2.71 (m, 1H), 2.72-2.82 (m, 2H), 3.16-3.24 (m, 2H), 4.22-4.31 (m, 1H), 4.71-4.85 (m, 1H), 6.87 (d, J=8.10 Hz, 1H), 7.07 (d, J=7.50 Hz, 1H), 7.39 (d, J=8.40 Hz, 1H), 7.57 (d, J=8.40 Hz, 1H), 7.73-7.77 (m, 2H), 7.96 (s, 1H). MS (ESI, pos. ion) m/z 492 [M+H]⁺.

(S)-cyclopropyl(2-methyl-6-(1-(piperidin-4-yl)-1H-pyrazol-4-yl)-5-(pyridin-2-yloxy)-3,4-dihydroquinolin-1(2H)-yl)methanone (I-95)

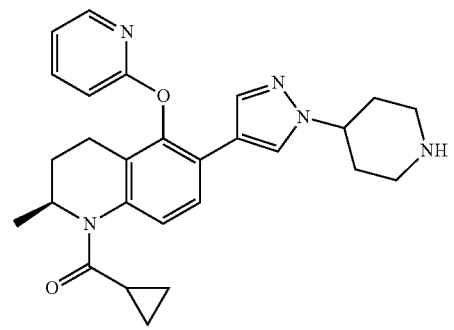 [SMILES: C[C@H]1CCc2c(ccc(-c3cnn(C4CCNCC4)c3)c2Oc2ccccn2)N1C(=O)C1CC1]

¹H NMR (300 MHz, CD₃OD) δ ppm 0.73-0.82 (m, 1H), 0.89-1.01 (m, 2H), 1.12-1.24 (m, 4H), 1.41-1.51 (m, 1H), 2.05-2.37 (m, 7H), 2.62-2.71 (m, 1H), 3.14-3.22 (m, 2H), 3.50-3.64 (m, 2H), 4.45-4.55 (m, 1H), 4.78-4.85 (m, 1H), 6.92 (d, J=8.40 Hz, 1H), 7.04-7.09 (m, 1H), 7.39 (d, J=8.40 Hz, 1H), 7.59 (d, J=8.40 Hz, 1H), 7.77-7.81 (m, 2H), 7.96 (s, 1H), 8.05 (t, J=3.60 Hz, 1H). MS (ESI, pos. ion) m/z 458 [M+H]⁺.

(S)-methyl 2-methyl-6-(1-(piperidin-4-yl)-1H-pyrazol-4-yl)-5-(pyridin-2-yloxy)-3,4-dihydroquinoline-1(2H)-carboxylate (I-96)

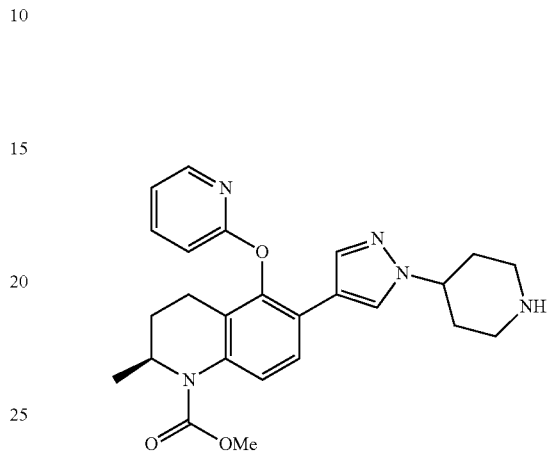

¹H NMR (300 MHz, CD₃OD) δ ppm 1.16 (d, J=6.90 Hz, 3H), 1.25-1.33 (m, 1H), 1.54-1.64 (m, 1H), 1.73-1.90 (m, 2H), 1.95-2.15 (m, 3H), 2.40-2.50 (m, 1H), 2.53-2.76 (m, 3H), 3.09-3.16 (m, 2H), 3.81 (s, 3H), 4.15-4.24 (m, 1H), 4.60-4.71 (m, 1H), 6.83 (d, J=8.40 Hz, 1H), 7.01-7.09 (m, 1H), 7.47-7.61 (m, 2H), 7.70-7.80 (m, 2H), 7.89 (s, 1H), 8.06 (m, 1H). MS (ESI, pos. ion) m/z 448 [M+H]⁺.

(S)-cyclopropyl(5-(6-fluoropyridin-2-yloxy)-2-methyl-6-(1-(piperidin-4-yl)-1H-pyrazol-4-yl)-3,4-dihydroquinolin-1(2H)-yl)methanone (I-97)

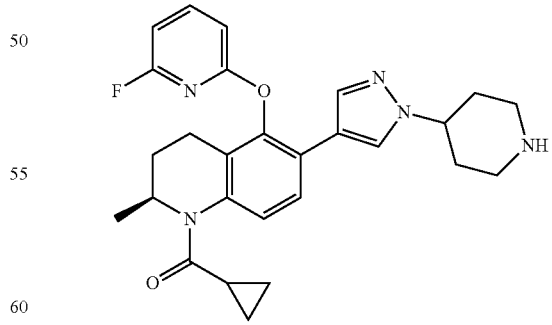

¹H NMR (400 MHz, CD₃OD) δ ppm 0.67-0.74 (m, 1H), 0.81-0.92 (m, 2H), 1.02-1.08 (m, 4H), 1.42-1.49 (m, 1H), 1.62-1.71 (m, 2H), 1.82-1.95 (m, 3H), 2.05-2.16 (m, 1H), 2.05-2.16 (m, 1H), 2.27-2.34 (m, 2H), 2.46-2.58 (m, 3H), 2.95-3.05 (m, 2H), 4.05-4.16 (m, 1H), 4.66-4.74 (m, 1H), 6.78-6.81 (m, 1H), 6.95-7.00 (m, 1H), 7.33-7.37 (m, 1H), 7.66 (s, 1H), 7.96-8.05 (m, 2H). MS (ESI, pos. ion) m/z 476 [M+H]+.

Example 26

(S)-cyclopropyl(5-(6-methoxypyridin-2-yloxy)-2-methyl-6-(1-(piperidin-4-yl)-1H-pyrazol-4-yl)-3,4-dihydroquinolin-1(2H)-yl)methanone (I-98)

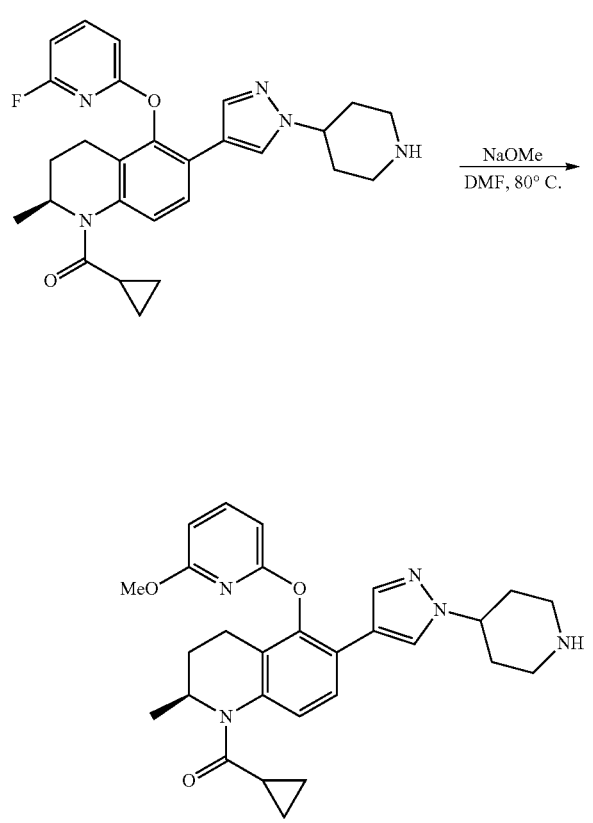

A mixture of (S)-cyclopropyl(5-(6-fluoropyridin-2-yloxy)-2-methyl-6-(1-(piperidin-4-yl)-1H-pyrazol-4-yl)-3,4-dihydroquinolin-1(2H)-yl)methanone (0.024 g, 0.05 mmol), and sodium methoxide (0.015 g, 0.28 mmol) in N,N-dimethylformamide (1 mL) stirred overnight at 80° C. The reaction mixture was cooled to room temperature, diluted with ethyl acetate (15 mL), washed with brine (2×5 mL), dried over anhydrous sodium sulfate, filtered, and concentrated under vacuum. The residue was purified by preparative-HPLC with the following conditions (Waters I): Column, SunFire Prep C18, 5 um, 19×100 mm; mobile phase, water (0.05% ammonium bicarbonate) and acetonitrile (16% to 34% acetonitrile in 10 min, flow rate: 20 mL/min); Detector, UV 220&254 nm. This afforded (S)-cyclopropyl(5-(6-methoxypyridin-2-yloxy)-2-methyl-6-(1-(piperidin-4-yl)-1H-pyrazol-4-yl)-3,4-dihydroquinolin-1(2H)-yl)methanone (0.0033 g, 13%) as a white solid. $^1$H NMR (400 MHz, CD$_3$OD) δ ppm 0.79-0.87 (m, 1H), 0.91-1.00 (m, 2H), 1.10-1.18 (m, 4H), 1.39-1.49 (m, 1H), 1.79-1.84 (m, 2H), 1.97-2.09 (m, 3H), 2.18-2.41 (m, 2H), 2.62-2.79 (m, 3H), 3.12-3.19 (m, 2H), 3.62 (s, 3H), 4.15-4.27 (m, 1H), 4.72-4.89 (m, 1H), 6.41 (t, J=8.00 Hz, 2H), 7.36 (d, J=8.40 Hz, 1H), 7.55-7.65 (m, 2H), 7.79 (s, 1H), 7.96 (s, 1H). MS (ESI, pos. ion) m/z 488 [M+H]+.

Example 27

(2S)-5-cyclobutoxy-1-cyclopropanecarbonyl-2-methyl-6-[1-(piperidin-4-yl)-1H-pyrazol-4-yl]-1,2,3,4-tetrahydroquinoline (I-99)

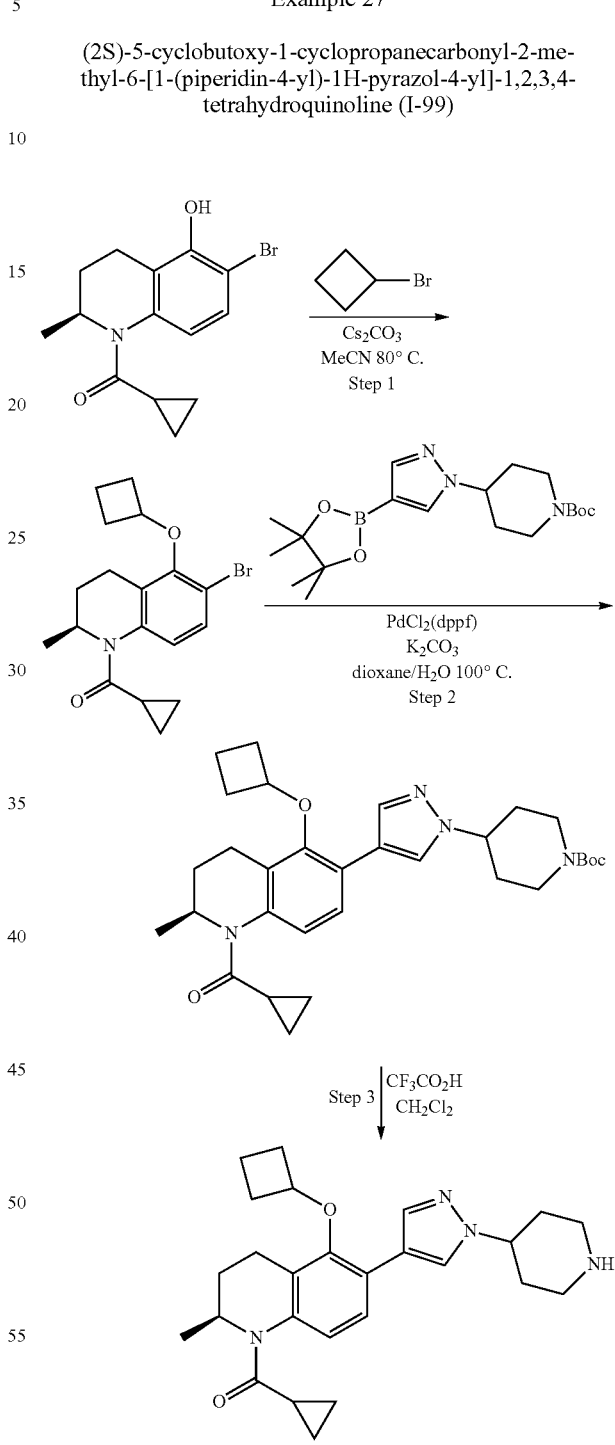

Step 1. (2S)-6-bromo-5-cyclobutoxy-1-cyclopropanecarbonyl-2-methyl-1,2,3,4-tetrahydroquinoline A 250-mL round-bottom flask was charged with (2S)-6-bromo-1-cyclopropanecarbonyl-2-methyl-1,2,3,4-tetrahydroquinolin-5-ol (2.00 g, 6.45 mmol), bromocyclobutane (1.81 mL, 2.60 g, 19.3 mmol), cesium carbonate (6.3 g, 19.34 mmol) and acetonitrile (100 mL). The resulting mixture was stirred for 6 h at 80° C. The reaction mixture was filtered through a pad of Celite and concentrated under vacuum. The residue was purified via column chromatography on silica gel (gradient elution with 0-10% ethyl acetate-petroleum ether) to afford (2S)-6-bromo-5-cyclobutoxy-1-cyclopropanecarbonyl-2-methyl-1,2,3,4-tetrahydroquinoline (2.00 g, 85%) as a colorless oil. MS (ES, m/z): 364, 366 [M+H]$^+$ Step 2. (S)-tert-butyl 4-(4-(5-cyclobutoxy-1-(cyclopropanecarbonyl)-2-methyl-1,2,3,4-tetrahydroquinolin-6-yl)-1H-pyrazol-1-yl)piperidine-1-carboxylate A 250-mL round-bottom flask was purged and maintained with an inert atmosphere of nitrogen, and charged with (2S)-6-bromo-5-cyclobutoxy-1-cyclopropanecarbonyl-2-methyl-1,2,3,4-tetrahydroquinoline (2.0 g, 5.5 mmol), tert-butyl 4-[4-(tetramethyl-1,3,2-dioxaborolan-2-yl)-1H-pyrazol-1-yl]piperidine-1-carboxylate (2.5 g, 6.63 mmol), [1,1'-bis(diphenylphosphino)ferrocene]dichloropalladium(II) dichloromethane adduct (0.45 g, 0.55 mmol), potassium carbonate (2.3 g, 16.64 mmol), 1,4-dioxane (50 mL) and water (5 mL). The resulting mixture stirred overnight at 100° C. The reaction mixture was cooled to room temperature and then filtered through a pad of Celite. The filtrate was concentrated, and the residue was purified via column chromatography on silica gel (gradient elution with 0-30% ethyl acetate-petroleum ether) to afford (S)-tert-butyl 4-(4-(5-cyclobutoxy-1-(cyclopropanecarbonyl)-2-methyl-1,2,3,4-tetrahydroquinolin-6-yl)-1H-pyrazol-1-yl)piperidine-1-carboxylate (2.2 g, 75%) as a light yellow solid. MS (ES, m/z): 535 [M+H]$^+$ Step 3. (2S)-5-cyclobutoxy-1-cyclopropanecarbonyl-2-methyl-6-[1-(piperidin-4-yl)-1H-pyrazol-4-yl]-1,2,3,4-tetrahydroquinoline Trifluoroacetic acid (0.5 mL, 6.49 mmol) was added to a 0° C. solution of (S)-tert-butyl 4-(4-(5-cyclobutoxy-1-(cyclopropanecarbonyl)-2-methyl-1,2,3,4-tetrahydroquinolin-6-yl)-1H-pyrazol-1-yl)piperidine-1-carboxylate (0.032 g, 0.060 mmol) in dichloromethane (2.0 mL). The ice bath was removed, and the mixture stirred at rt for 1.5 h. The reaction mixture was concentrated, and the residue was partitioned between dichloromethane and saturated aqueous sodium bicarbonate solution. The layers were separated and the organic phase was washed with brine, dried over anhydrous sodium sulfate, filtered, and concentrated to afford (S)-(5-cyclobutoxy-2-methyl-6-(1-(piperidin-4-yl)-1H-pyrazol-4-yl)-3,4-dihydroquinolin-1(2H)-yl)(cyclopropyl)methanone (0.022 g, 85%) as an off-white solid. $^1$H NMR (300 MHz, CHLOROFORM-d) δ ppm 0.57-0.71 (m, 1H), 0.78-0.91 (m, 1H), 0.92-1.04 (m, 1H), 1.13 (d, J=6.45 Hz, 3H), 1.19-1.45 (m, 3H), 1.53-1.71 (m, 2H), 1.79-2.42 (m, 11H), 2.74-2.92 (m, 2H), 2.94-3.09 (m, 1H), 3.30 (br d, J=12.61 Hz, 2H), 4.04-4.21 (m, 1H), 4.28 (ddt, J=11.43, 7.62, 3.96, 3.96 Hz, 1H), 4.66-4.84 (m, 1H), 7.12 (d, J=8.21 Hz, 1H), 7.28 (d, J=8.21 Hz, 1H), 7.81 (s, 1H), 7.88 (s, 1H). MS (ESI, pos. ion) m/z 435 [M+H]$^+$.

The following examples were made according to the procedure outlined for Example 27:

(S)-cyclopropyl(2-methyl-6-(1-(piperidin-4-yl)-1H-pyrazol-4-yl)-5-propoxy-3,4-dihydroquinolin-1(2H)-yl)methanone (I-100)

$^1$H NMR (300 MHz, CD$_3$OD) δ ppm 0.65-0.778 (m, 1H), 0.85-0.99 (m, 2H), 1.01-1.19 (m, 7H), 1.25-1.42 (m, 1H), 1.70-1.82 (m, 2H), 1.85-2.05 (m, 3H), 2.10-2.21 (m, 2H), 2.30-2.49 (m, 2H), 2.75-2.89 (m, 2H), 2.95-3.07 (m, 1H), 3.17-3.20 (m, 2H), 3.58-3.72 (m, 2H), 4.28-4.42 (m, 1H), 4.70-4.83 (m, 1H), 7.19 (d, J=8.10 Hz, 1H), 7.44 (d, J=8.10 Hz, 1H), 7.93 (s, 1H), 8.12 (s, 1H). MS (ESI, pos. ion) m/z 423 [M+H]$^+$ (S)-(6-(1-(azetidin-3-yl)-1H-pyrazol-4-yl)-5-cyclobutoxy-2-methyl-3,4-dihydroquinolin-1(2H)-yl)(cyclopropyl)methanone (I-101)

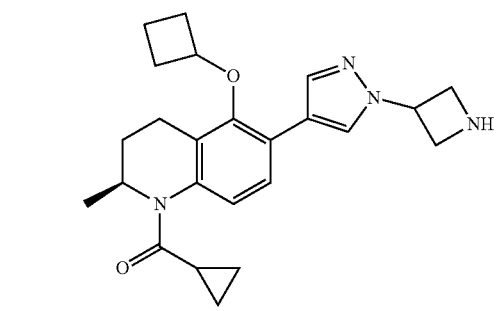 [SMILES: C[C@H]1CCc2c(ccc(-c3cnn(C4CNC4)c3)c2OC2CCC2)N1C(=O)C1CC1]

$^1$H NMR (300 MHz, CD$_3$OD) 0.65-0.75 (m, 1H), 0.85-0.95 (m, 2H), 1.05-1.15 (m, 4H), 1.20-1.40 (m, 2H), 1.50-1.70 (m, 1H), 1.80-1.95 (m, 1H), 2.01-2.45 (m, 6H), 2.95-3.05 (m, 1H), 3.92-4.01 (m, 2H), 4.10-4.25 (m, 3H), 4.65-

4.75 (m, 1H), 5.25-5.40 (m, 1H), 7.15 (d, J=8.10 Hz, 1H), 7.40 (d, J=8.70 Hz, 1H), 7.96 (s, 1H), 8.14 (s, 1H). MS (ESI, pos. ion) m/z 407 [M+H]+.

(S)-(6-(1-(azetidin-3-yl)-1H-pyrazol-4-yl)-2-methyl-5-propoxy-3,4-dihydroquinolin-1(2H)-yl)(cyclopropyl)methanone (I-102)

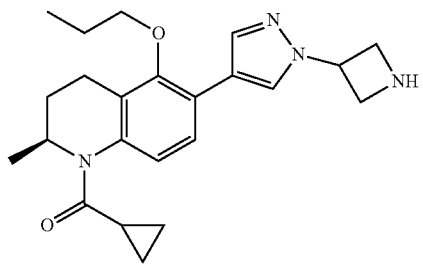 [SMILES: CCCOc1c(-c2cnn(C3CNC3)c2)ccc2c1CC[C@H](C)N2C(=O)C1CC1]

(S)-(6-(1-(azetidin-3-yl)-1H-pyrazol-4-yl)-2-methyl-5-propoxy-3,4-dihydroquinolin-1(2H)-yl)(cyclopropyl)methanone (I-102)

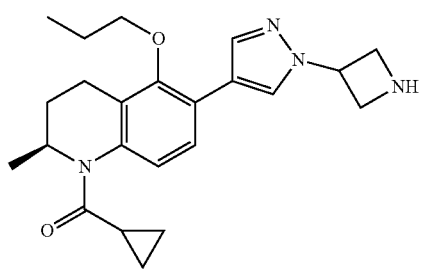 [SMILES: CCCOc1c(-c2cnn(C3CNC3)c2)ccc2c1CC[C@H](C)N2C(=O)C1CC1]

¹H NMR (300 MHz, CD₃OD) δ ppm 0.60-0.75 (m, 1H), 0.85-0.95 (m, 2H), 1.00-1.08 (m, 3H), 1.10-1.18 (m, 4H), 1.25-1.38 (m, 1H), 1.70-1.80 (m, 2H), 1.85-1.95 (m, 1H), 2.30-2.45 (m, 2H), 2.90-3.05 (m, 1H), 3.55-2.75 (m, 2H), 3.95-4.05 (m, 2H), 4.15-4.25 (m, 2H), 4.65-4.75 (m, 1H), 5.28-5.38 (m, 1H), 7.17 (d, J=8.40 Hz, 1H), 7.43 (d, J=8.40 Hz, 1H), 8.00 (s, 1H), 8.15 (s, 1H). MS (ESI, pos. ion) m/z 395 [M+H]+.

(S)-(5-cyclobutoxy-8-fluoro-2-methyl-6-(1-(piperidin-4-yl)-1H-pyrazol-4-yl)-3,4-dihydroquinolin-1(2H)-yl)(cyclopropyl)methanone (I-103)

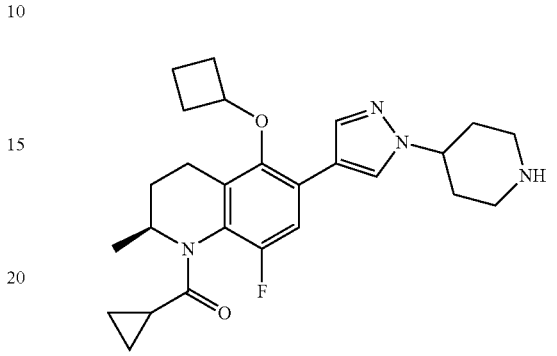

¹H NMR (400 MHz, DMSO-d6) δ ppm 0.56-0.90 (m, 4H), 0.99-1.17 (m, 4H), 1.25-1.34 (m, 1H), 1.47-1.59 (m, 2H), 1.74-1.81 (m, 2H), 1.95-2.28 (m, 7H), 2.31-2.41 (m, 1H), 2.55-2.61 (m, 2H), 2.85-2.93 (m, 1H), 3.02-3.09 (m, 2H), 4.05-4.24 (m, 2H), 4.56-4.67 (m, 1H), 7.42 (d, J=10.0 Hz, 1H), 7.90 (s, 1H), 8.18 (s, 1H). MS (ESI, pos. ion) m/z 453 [M+H]+.

Example 28

(S)-1-(2-methyl-6-(1-(piperidin-4-yl)-1H-pyrazol-4-yl)-5-propoxy-3,4-dihydroquinolin-1(2H)-yl)ethanone (I-104)

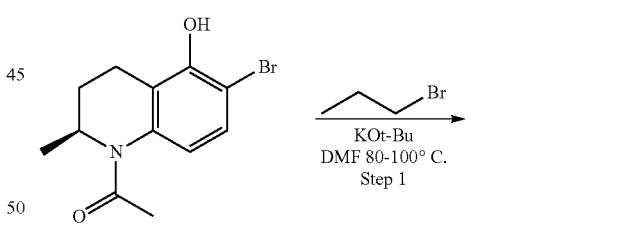

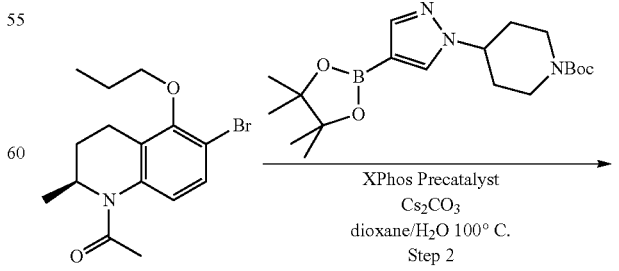

-continued

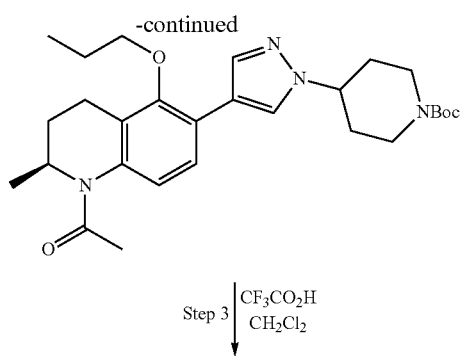

Step 3 | CF₃CO₂H
CH₂Cl₂

Step 1. (S)-1-(6-bromo-2-methyl-5-propoxy-3,4-dihydroquinolin-1(2H)-yl)ethanone A mixture of (S)-1-(6-bromo-5-hydroxy-2-methyl-3,4-dihydroquinolin-1(2H)-yl)ethanone (0.150 g, 0.528 mmol), 1-bromopropane (0.240 mL, 2.64 mmol), and potassium tert-butoxide (0.296 g, 2.64 mmol) in DMF (3.0 mL) was heated at 80° C. After 24 h, additional 1-bromopropane (0.240 mL, 2.64 mmol) was added and mixture stirred at 70° C. for 16 h. The reaction was incomplete, so 1-bromopropane (0.240 mL, 2.64 mmol) and potassium tert-butoxide (0.296 g, 2.64 mmol) were added, and the mixture was stirred at 100° C. After 24 h, the reaction mixture was cooled to rt and water was added. The mixture was extracted with dichloromethane and the combined organic phases were washed with water and brine, dried over anhydrous sodium sulfate, filtered, and concentrated to afford a yellow oil. This material was purified via column chromatography on silica gel (Biotage 25 g column, gradient elution with 50-100% ethyl acetate-hexane) to afford (S)-1-(6-bromo-2-methyl-5-propoxy-3,4-dihydroquinolin-1(2H)-yl)ethanone (0.100 g, 58%) as a colorless oil. MS (ESI, pos. ion) m/z 326, 328 [M+H]⁺

Step 2. (S)-tert-butyl 4-(4-(1-acetyl-2-methyl-5-propoxy-1,2,3,4-tetrahydroquinolin-6-yl)-1H-pyrazol-1-yl)piperidine-1-carboxylate A mixture of (S)-1-(6-bromo-2-methyl-5-propoxy-3,4-dihydroquinolin-1(2H)-yl)ethanone (0.050 g, 0.153 mmol), tert-butyl 4-(4-(4,4,5,5-tetramethyl-1,3,2-dioxaborolan-2-yl)-1H-pyrazol-1-yl)piperidine-1-carboxylate (0.058 g, 0.153 mmol), chloro(2-dicyclohexylphosphino-2',4',6'-tri-i-propyl-1,1'-biphenyl)(2'-amino-1,1'-biphenyl-2-yl) palladium(II) (XPhos 2nd generation precatalyst) (0.012 g, 0.015 mmol), and cesium carbonate (0.150 g, 0.460 mmol) in 1,4-dioxane (2.0 mL) and water (0.40 mL) was heated in the microwave at 100° C. for 2.5 h. The reaction mixture was filtered through Celite and concentrated to afford an orange oil. This material was purified via column chromatography on silica gel (Biotage 25 g column, gradient elution with 50-100% ethyl acetate-hexane) to afford (S)-tert-butyl 4-(4-(1-acetyl-2-methyl-5-propoxy-1,2,3,4-tetrahydroquinolin-6-yl)-1H-pyrazol-1-yl)piperidine-1-carboxylate (0.063 g, 83%) as an off-white solid. MS (ESI, pos. ion) m/z 497 [M+H]⁺

Step 3. (S)-1-(2-methyl-6-(1-(piperidin-4-yl)-1H-pyrazol-4-yl)-5-propoxy-3,4-dihydroquinolin-1(2H)-yl)ethanone Trifluoroacetic acid (0.5 mL, 6.49 mmol) was added to a solution of (S)-tert-butyl 4-(4-(1-acetyl-2-methyl-5-propoxy-1,2,3,4-tetrahydroquinolin-6-yl)-1H-pyrazol-1-yl)piperidine-1-carboxylate (0.063 g, 0.127 mmol) in dichloromethane (2.0 mL) and the reaction mixture stirred at rt for 1.5 h. The reaction mixture was concentrated and the residue was partitioned between dichloromethane and saturated aqueous sodium bicarbonate solution. The organic phase was separated, dried over anhydrous sodium sulfate, filtered, and concentrated to afford (S)-1-(2-methyl-6-(1-(piperidin-4-yl)-1H-pyrazol-4-yl)-5-propoxy-3,4-dihydroquinolin-1(2H)-yl)ethanone (0.045 g, 89%) as a tan solid. ¹H NMR (300 MHz, DMSO-d₆) δ ppm 0.91-1.12 (m, 6H), 1.18-1.37 (m, 1H), 1.57-1.88 (m, 5H), 1.97 (br d, J=10.26 Hz, 2H), 2.07 (s, 3H), 2.16-2.40 (m, 2H), 2.53-2.66 (m, 2H), 2.73-2.89 (m, 1H), 3.03 (br d, J=12.61 Hz, 2H), 3.46-3.65 (m, 2H), 4.09-4.30 (m, 1H), 4.62 (br d, J=5.86 Hz, 1H), 7.11 (br d, J=8.21 Hz, 1H), 7.38 (d, J=8.21 Hz, 1H), 7.84 (s, 1H), 8.09 (s, 1H). MS (ESI, pos. ion) m/z 397 [M+H]⁺.

The following examples were made according to the procedure outlined for Example 28:

(S)-1-(5-cyclobutoxy-8-fluoro-2-methyl-6-(1-(piperidin-4-yl)-1H-pyrazol-4-yl)-3,4-dihydroquinolin-1(2H)-yl)ethanone (I-105)

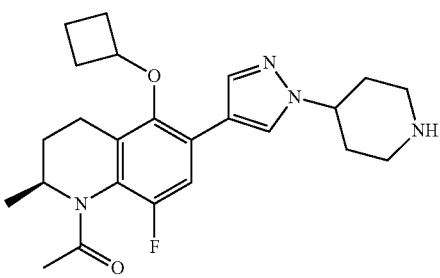 [SMILES: CC(=O)N1c2c(F)cc(-c3cnn(C4CCNCC4)c3)c(OC3CCC3)c2CC[C@@H]1C]

¹H NMR (400 MHz, CD₃OD) δ ppm 0.93-1.17 (m, 4H), 1.27-1.41 (m, 1H), 1.55-1.68 (m, 1H), 1.92-2.48 (m, 13H), 2.70-2.83 (m, 2H), 3.02-3.10 (m, 1H), 3.10-3.22 (m, 2H), 4.05-4.18 (m, 1H), 4.25-4.43 (m, 1H), 4.70-4.88 (m, 1H), 7.15-7.35 (m, 1H), 7.90 (s, 1H), 8.13 (s, 1H). MS (ESI, pos. ion) m/z 427 [M+H]⁺.

(S)-1-(5-cyclobutoxy-7,8-difluoro-2-methyl-6-(1-(piperidin-4-yl)-1H-pyrazol-4-yl)-3,4-dihydroquinolin-1(2H)-yl)ethanone (I-106)

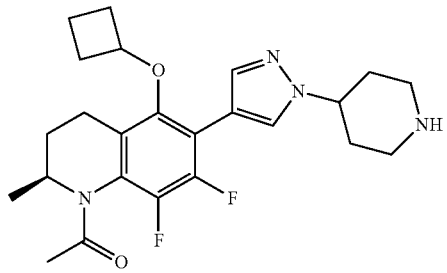 [SMILES: CC(=O)N1c2c(F)c(F)c(-c3cnn(C4CCNCC4)c3)c(OC3CCC3)c2CC[C@@H]1C]

(S)-1-(5-cyclobutoxy-7,8-difluoro-2-methyl-6-(1-(piperidin-4-yl)-1H-pyrazol-4-yl)-3,4-dihydroquinolin-1(2H)-yl)ethanone was synthesized from (S)-1-(6-bromo-5-cyclobutoxy-7,8-difluoro-2-methyl-3,4-dihydroquinolin-1(2H)-yl)ethanone according to the procedures described above in Steps 2 and 3 of the synthesis of (S)-1-(2-methyl-6-(1-(piperidin-4-yl)-1H-pyrazol-4-yl)-5-propoxy-3,4-dihydroquinolin-1(2H)-yl)ethanone (Example 4-1). ¹H NMR (300 MHz, CD₃OD) δ ppm 1.12-1.28 (m, 4H), 1.30-1.41 (m, 1H), 1.56-1.68 (m, 1H), 1.98-2.20 (m, 11H), 2.32-2.49 (m, 2H), 2.75-2.88 (m, 2H), 2.99-3.10 (m, 1H), 3.21-3.25 (m, 2H), 4.17-4.20 (m, 1H), 4.35-4.45 (m, 1H), 4.75-4.82 (m, 1H), 7.91 (s, 1H), 8.12 (s, 1H). MS (ESI, pos. ion) m/z 445 [M+H]⁺.

Example 29

(S)-methyl 2-methyl-6-(1-(piperidin-4-yl)-1H-pyrazol-4-yl)-5-propoxy-3,4-dihydroquinoline-1(2H)-carboxylate (I-107)

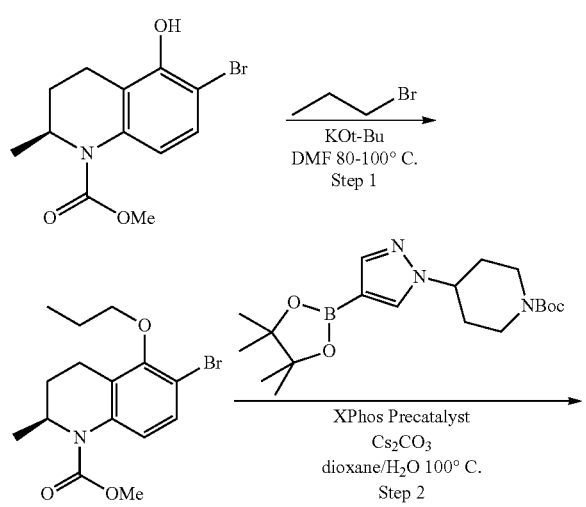

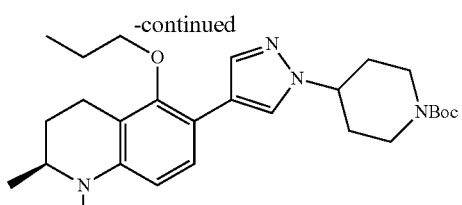

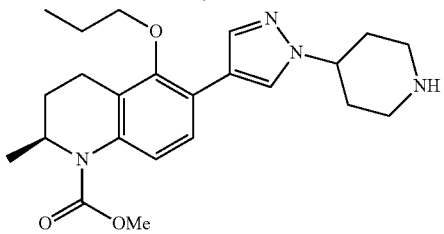

Step 1. (S)-methyl 6-bromo-2-methyl-5-propoxy-3,4-dihydroquinoline-1(2H)-carboxylate A mixture of (S)-methyl 6-bromo-5-hydroxy-2-methyl-3,4-dihydroquinoline-1(2H)-carboxylate (0.110 g, 0.366 mmol), 1-bromopropane (0.166 mL, 1.832 mmol), and potassium tert-butoxide (0.103 g, 0.916 mmol) in DMF (3.0 mL) was heated in a sealed tube at 100° C. After 24 h, additional 1-bromopropane (0.166 mL, 1.832 mmol) and potassium tert-butoxide (0.103 g, 0.916 mmol) were added and the mixture was heated in a sealed tube at 100° C. for 24 h. The reaction mixture was cooled to rt and water was added. The mixture was extracted with dichloromethane and the combined organic phases were washed with water and brine, dried over anhydrous sodium sulfate, filtered, and concentrated to afford a yellow oil. This material was purified via column chromatography on silica gel (Biotage 25 g column, gradient elution with 0-25% ethyl acetate-hexane) to afford (S)-methyl 6-bromo-2-methyl-5-propoxy-3,4-dihydroquinoline-1(2H)-carboxylate (0.120 g, 96%) as a colorless oil. MS (ESI, pos. ion) m/z 342, 344 [M+H]⁺.

Step 2. (S)-methyl 6-(1-(1-(tert-butoxycarbonyl)piperidin-4-yl)-1H-pyrazol-4-yl)-2-methyl-5-propoxy-3,4-dihydroquinoline-1(2H)-carboxylate A mixture of (S)-methyl 6-bromo-2-methyl-5-propoxy-3,4-dihydroquinoline-1(2H)-carboxylate (0.060 g, 0.175 mmol), tert-butyl 4-(4-(4,4,5,5-tetramethyl-1,3,2-dioxaborolan-2-yl)-1H-pyrazol-1-yl)piperidine-1-carboxylate (0.066 g, 0.175 mmol), chloro(2-dicyclohexylphosphino-2',4',6'-tri-i-propyl-1,1'-biphenyl)(2'-amino-1,1'-biphenyl-2-yl) palladium(II) (XPhos 2nd generation precatalyst) (0.014 g, 0.018 mmol), and cesium carbonate (0.171 g, 0.526 mmol) in 1,4-dioxane (2.0 mL) and water (0.40 mL) was heated in the microwave at 100° C. for 5 h. The reaction mixture was filtered through Celite and concentrated to afford an orange oil. This material was purified via column chromatography on silica gel (Biotage 25 g column, gradient elution with 0-50% ethyl acetate-hexane) to afford (S)-methyl 6-(1-(1-(tert-butoxycarbonyl)piperidin-4-yl)-1H-pyrazol-4-yl)-2-methyl-5- propoxy-3,4-dihydroquinoline-1(2H)-carboxylate (0.090 g, 100%) as a colorless oil. MS (ESI, pos. ion) m/z 513 [M+H]+.

Step 3. (S)-methyl 2-methyl-6-(1-(piperidin-4-yl)-1H-pyrazol-4-yl)-5-propoxy-3,4-dihydroquinoline-1(2H)-carboxylate Trifluoroacetic acid (0.5 mL, 6.49 mmol) was added to a solution of (S)-methyl 6-(1-(1-(tert-butoxycarbonyl)piperidin-4-yl)-1H-pyrazol-4-yl)-2-methyl-5-propoxy-3,4-dihydroquinoline-1(2H)-carboxylate (0.090 g, 0.176 mmol) in dichloromethane (2.0 mL) and the reaction mixture stirred at rt for 1 h. The reaction mixture was concentrated and the residue was partitioned between dichloromethane and saturated aqueous sodium bicarbonate solution. The organic phase was separated, dried over anhydrous sodium sulfate, filtered, and concentrated to afford (S)-methyl 2-methyl-6-(1-(piperidin-4-yl)-1H-pyrazol-4-yl)-5-propoxy-3,4-dihydroquinoline-1(2H)-carboxylate (0.070 g, 97%) as an off-white solid. $^1$H NMR (300 MHz, DMSO-$d_6$) δ ppm 0.97 (t, J=7.48 Hz, 3H), 1.05-1.13 (m, 3H), 1.48 (dq, J=13.05, 6.50 Hz, 1H), 1.63-1.87 (m, 5H), 1.88-2.03 (m, 2H), 2.05-2.19 (m, 2H), 2.53-2.66 (m, 2H), 2.72-2.90 (m, 1H), 3.04 (br d, J=12.61 Hz, 2H), 3.54 (br t, J=6.60 Hz, 2H), 3.67 (s, 3H), 4.11-4.32 (m, 1H), 4.37-4.57 (m, 1H), 7.21-7.31 (m, 1H), 7.31-7.40 (m, 1H), 7.81 (s, 1H), 8.06 (s, 1H). MS (ESI, pos. ion) m/z 413 [M+H]+. MS (ESI, pos. ion) m/z 413 [M+H]+.

Example 30

(2S)-methyl 5-cyclobutoxy-2-methyl-6-(1-(pyrrolidin-3-yl)-1H-pyrazol-4-yl)-3,4-dihydroquinoline-1(2H)-carboxylate (I-108)

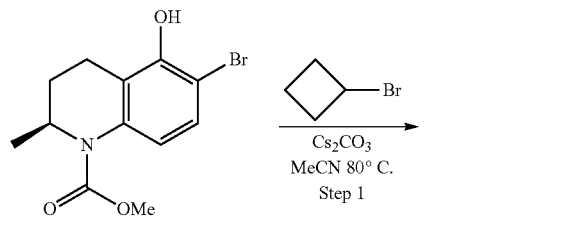

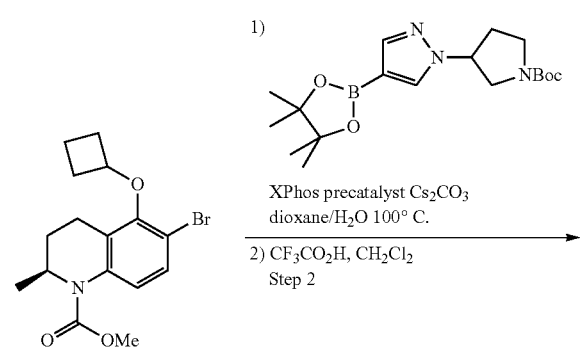

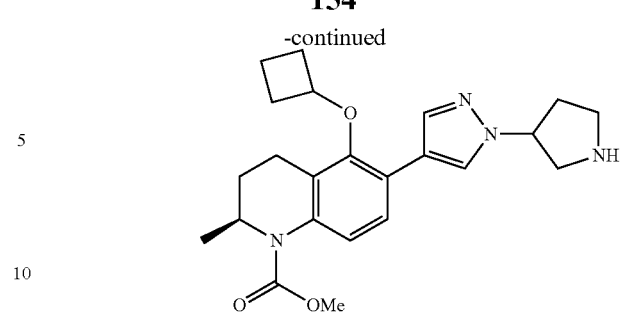

Step 1. Methyl (S)-6-bromo-5-hydroxy-2-methyl-3,4-dihydroquinoline-1(2H)-carboxylate A 100-mL round-bottom was charged with methyl (2S)-6-bromo-5-hydroxy-2-methyl-1,2,3,4-tetrahydroquinoline-1-carboxylate (600 mg, 2.00 mmol), bromocyclobutane (807 mg, 5.98 mmol), acetonitrile (30 mL), and cesium carbonate (1.96 g, 6.00 mmol). The mixture stirred for 6 h at 80° C. in an oil bath. After cooling to room temperature, the reaction mixture was poured into 10 mL of water and the layers were separated. The aqueous layer was extracted with ethyl acetate (3×15 mL). The combined organic layers were dried over anhydrous sodium sulfate, filtered, and concentrated under vacuum. The residue was purified via column chromatography on silica gel (eluting with 8:1, ethyl acetate/petroleum ether) to afford methyl (S)-6-bromo-5-hydroxy-2-methyl-3,4-dihydroquinoline-1(2H)-carboxylate (0.67 g, 95%) as colorless oil. MS (ESI, pos. ion) m/z 354, 356 [M+H]+.

Step 2. (2S)-methyl 5-cyclobutoxy-2-methyl-6-(1-(pyrrolidin-3-yl)-1H-pyrazol-4-yl)-3,4-dihydroquinoline-1(2H)-carboxylate (2S)-methyl 5-cyclobutoxy-2-methyl-6-(1-(pyrrolidin-3-yl)-1H-pyrazol-4-yl)-3,4-dihydroquinoline-1(2H)-carboxylate was synthesized from (S)-6-bromo-5-hydroxy-2-methyl-3,4-dihydroquinoline-1(2H)-carboxylate and tert-butyl 3-(4-(4,4,5,5-tetramethyl-1,3,2-dioxaborolan-2-yl)-1H-pyrazol-1-yl)pyrrolidine-1-carboxylate according to the procedures outlined above in Steps 2 and 3 for Example 29. $^1$H NMR (400 MHz, CD$_3$OD) δ ppm 1.17 (d, J=6.40 Hz, 3H), 1.25-1.65 (m, 3H), 1.98-2.30 (m, 6H), 2.31-2.45 (m, 2H), 2.85-3.08 (m, 2H), 3.20-3.35 (m, 3H), 3.79 (s, 3H), 4.10-4.15 (m, 1H), 4.49-4.55 (m, 1H), 4.90-5.05 (m, 1H), 7.20-7.32 (m, 2H), 7.86 (s, 1H), 8.05 (s, 1H). MS (ESI, pos. ion) m/z 411 [M+H]+.

The following examples were made according to the procedure outlined for Example 30:

(2S)-methyl 5-cyclobutoxy-2-methyl-6-(1-(octahydrocyclopenta[c]pyrrol-5-yl)-1H-pyrazol-4-yl)-3,4-dihydroquinoline-1(2H)-carboxylate (I-109)

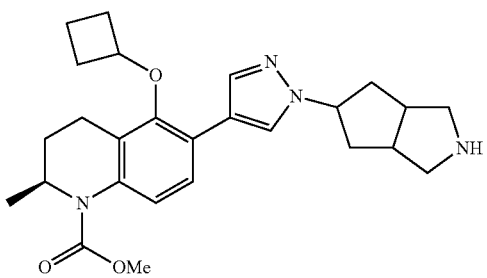 [SMILES: COC(=O)N1c2ccc(-c3cnn(C4CC5CNCC5C4)c3)c(OC3CCC3)c2CC[C@@H]1C]

$^1$H NMR (300 MHz, CD$_3$OD) δ ppm 1.17 (d, J=6.30 Hz, 3H), 1.20-1.52 (m, 2H), 1.55-1.75 (m, 1H), 1.95-2.30 (m, 7H), 2.35-2.50 (m, 3H), 2.85-3.00 (m, 1H), 3.05-3.20 (m, 4H), 3.50-3.62 (m, 2H), 3.77 (s, 1H), 4.05-4.15 (m, 1H), 4.45-4.55 (m, 1H), 4.85-5.00 (m, 1H), 7.20-7.30 (m, 2H), 7.85 (s, 1H), 8.01 (s, 1H). MS (ESI, pos. ion) m/z 451 [M+H]$^+$.

(S)-methyl 5-cyclobutoxy-8-fluoro-2-methyl-6-(1-(piperidin-4-yl)-1H-pyrazol-4-yl)-3,4-dihydroquinoline-1(2H)-carboxylate (I-110)

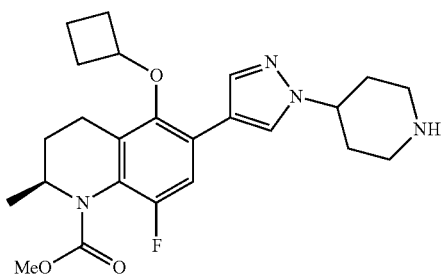 [SMILES: COC(=O)N1c2c(F)cc(-c3cnn(C4CCNCC4)c3)c(OC3CCC3)c2CC[C@@H]1C]

$^1$H NMR (300 MHz, CD$_3$OD) δ ppm 1.14 (d, J=6.60 Hz, 3H), 1.21-1.38 (m, 2H), 1.55-1.61 (m, 1H), 1.90-2.16 (m, 8H), 2.35-2.40 (m, 2H), 2.71-2.79 (m, 2H), 2.95-3.15 (m, 1H), 3.15-3.22 (m, 2H), 3.71 (s, 3H), 4.05-4.16 (m, 1H), 4.25-4.43 (m, 2H), 7.11 (d, J=11.40 Hz, 1H), 7.83 (s, 1H), 8.05 (s, 1H). MS (ESI, pos. ion) m/z 443 [M+H]$^+$.

Example 31 rac-1-(2-methyl-6-(4-(methylsulfonyl)phenyl)-5-phenoxy-3,4-dihydroquinolin-1(2H)-yl)ethanone (I-111)

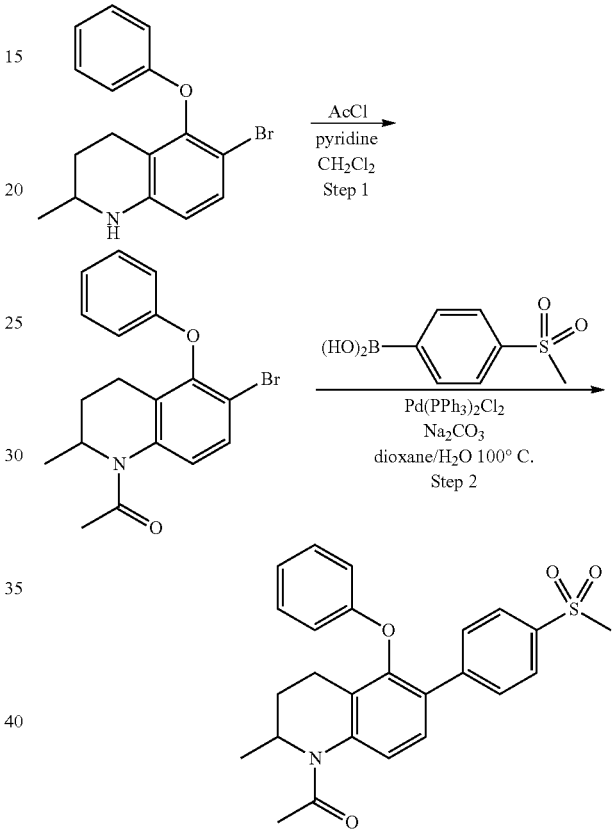

Step 1. rac-1-(6-bromo-2-methyl-5-phenoxy-3,4-dihydroquinolin-1(2H)-yl)ethanone

A solution of rac-6-bromo-2-methyl-5-phenoxy-1,2,3,4-tetrahydroquinoline (0.022 g, 0.069 mmol) in dichloromethane (1 mL), and pyridine (0.017 mL, 0.207 mmol) was cooled to 0° C. and treated with acetyl chloride (5.41 μL, 0.076 mmol). The reaction mixture was then stirred at rt. After 10 min, additional acetyl chloride (3.93 μL, 0.055 mmol) was added and stirring was continued at rt. After 75 min, the reaction mixture was diluted with dichloromethane and washed with 1 N aqueous hydrochloric acid solution (2×0.5 mL) and 5% aqueous sodium chloride solution (0.5 mL). The dichloromethane layer was concentrated to afford crude rac-1-(6-bromo-2-methyl-5-phenoxy-3,4-dihydroquinolin-1 (2H)-yl)ethanone (0.024 g, 96%) as a nearly colorless gum that solidified upon standing. The crude product was used without further purification. MS (ESI, pos. ion) m/z 360, 362 [M+H]$^+$.

Step 2. rac-1-(2-methyl-6-(4-(methylsulfonyl)phenyl)-5-phenoxy-3,4-dihydroquinolin-1(2H)-yl)ethanone A screw-cap vial equipped with a magnetic stir bar was charged with rac-1-(6-bromo-2-methyl-5-phenoxy-3,4-dihydroquinolin-1(2H)-yl)ethanone (0.024 g, 0.067 mmol), 4-(methylsulfonyl)phenylboronic acid (0.020 g, 0.100 mmol), 1,4-dioxane (0.67 mL), 1.0 M aqueous sodium bicarbonate (0.200 mL, 0.200 mmol), and bis(triphenylphosphine) palladium(II) chloride (4.7 mg, 6.7 µmol). The vial was flushed with nitrogen and then capped. The reaction mixture was then heated to 80° C. for 3 h and then cooled to room temperature. The reaction mixture was diluted with 5% aqueous sodium chloride solution (0.5 mL) and ethyl acetate. The layers were separated, and the aqueous layer was extracted with ethyl acetate. The combined extracts were concentrated under reduced pressure to afford a dark brown residue, which was then purified by preparative thin layer chromatography (1×1000 micron plate; eluting with 3:2 ethyl acetate-hexanes). The major band was isolated (26 mg) and further purified by preparative HPLC to afford rac-1-(2-methyl-6-(4-(methylsulfonyl)phenyl)-5-phenoxy-3,4-dihydroquinolin-1(2H)-yl)ethanone. $^1$H NMR (400 MHz, CDCl$_3$) δ ppm 1.17 (d, J=6.60 Hz, 3H), 1.45 (br s, 1H), 2.07-2.24 (m, 1H), 2.27 (s, 3H), 2.29-2.37 (m, 1H), 2.71 (dt, J=16.13, 6.42 Hz, 1H), 3.01 (s, 3H), 4.79 (br s, 1H), 6.59-6.69 (m, 2H), 6.82-6.95 (m, 1H), 7.15 (t, J=7.70 Hz, 2H), 7.32 (br d, J=7.33 Hz, 2H), 7.65 (d, J=8.43 Hz, 2H), 7.84 (d, J=8.43 Hz, 2H). MS (ESI, pos. ion) m/z 436 [M+H]$^+$.

Example 32 rac-1-(2-methyl-5-phenoxy-3,4-dihydroquinolin-1(2H)-yl)ethanone (I-112)

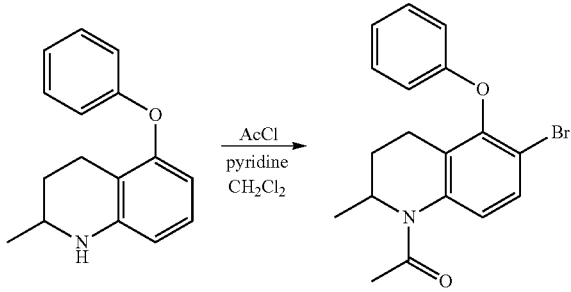 [SMILES: "AcCl" ; CC1CCc2c(cccc2Oc2ccccc2)N1 ; CC(=O)N1c2ccc(Br)c(Oc3ccccc3)c2CCC1C]

A glass, screw-cap vial equipped with a magnetic stir bar was charged with a solution of rac-2-methyl-5-phenoxy-1,2,3,4-tetrahydroquinoline (0.050 g, 0.21 mmol) in dichloromethane (1 mL) and pyridine (0.051 mL, 0.630 mmol). The solution was cooled to 0° C. and acetyl chloride (0.015 mL, 0.210 mmol) was added. The ice bath was removed and the reaction mixture stirred at rt. After 10 min, the reaction mixture was diluted with dichloromethane and washed with 1 N aqueous hydrochloric acid solution (2×1 mL) followed by 5% aqueous sodium chloride solution (1 mL). The organic layer was concentrated to a yellow oil, which crystallized upon standing. The crude product was purified by preparative thin layer chromatography (1×1000 micron plate, eluting with 2:1 hexanes-ethyl acetate) to yield 1-(2-methyl-5-phenoxy-3,4-dihydroquinolin-1(2H)-yl)ethanone (0.0189 g, 32%) as a nearly colorless oil. $^1$H NMR (400 MHz, CDCl$_3$) δ ppm 1.13 (d, J=6.60 Hz, 3 H), 1.36-1.55 (m, 1H), 2.11-2.27 (m, 4H), 2.36 (br s, 1H), 2.85 (dt, J=16.04, 6.09 Hz, 1H), 4.88 (br s, 1H), 6.76 (d, J=8.80 Hz, 1H), 6.89-6.96 (m, 2H), 6.96-7.04 (m, 1H), 7.04-7.11 (m, 1H), 7.12-7.19 (m, 1H), 7.29-7.37 (m, 2H). MS (ESI, pos. ion) m/z 282 [M+H]$^+$.

Example 33

(S)-1-(5-cyclopropoxy-6-(1-cyclopropyl-1H-pyrazol-4-yl)-2-methyl-3,4-dihydroquinolin-1(2H)-yl)ethanone (I-113)

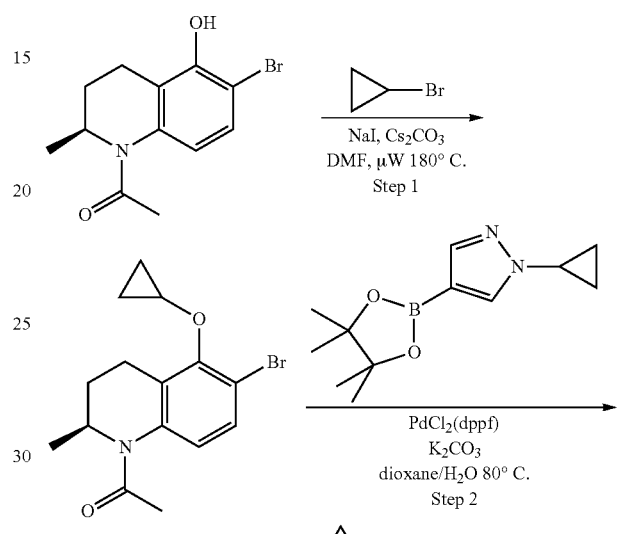

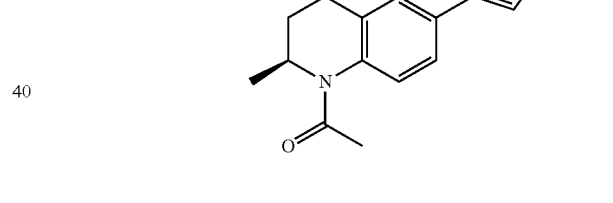

Step 1. (S)-1-(6-bromo-5-cyclopropoxy-2-methyl-3,4-dihydroquinolin-1(2H)-yl)ethanone A solution of (S)-1-(6-bromo-5-hydroxy-2-methyl-3,4-dihydroquinolin-1(2H)-yl)ethanone (17.05 mg, 0.06 mmol) in DMF (500 µL) was added to a microwave reaction vial equipped with a magnetic stir bar. Bromocyclopropane (150 µL, 1.87 mmol), sodium iodide (8.99 mg, 0.060 mmol) and cesium carbonate (98 mg, 0.300 mmol) were then added and the reaction was sealed. The reaction was heated in the microwave at 180° C. for 6 h. The mixture was diluted with ethyl acetate and washed with brine. The organic layer was dried over anhydrous sodium sulfate, filtered, and concentrated to afford (S)-1-(6-bromo-5-cyclopropoxy-2-methyl-3,4-dihydroquinolin-1(2H)-yl)ethanone (0.019 g, 100%) which was used without further purification. MS (ESI, pos. ion) m/z 324, 326 [M+H]$^+$.

Step 2. (S)-1-(5-cyclopropoxy-6-(1-cyclopropyl-1H-pyrazol-4-yl)-2-methyl-3,4-dihydroquinolin-1(2H)-yl)ethanone A 1.5 mL reaction vial was charged with (S)-1-(6-bromo-5-cyclopropoxy-2-methyl-3,4-dihydroquinolin-1(2H)-yl)

ethanone (0.019 g, 0.06 mmol) and 1,4-dioxane (50 μL). 1-cyclopropyl-4-(4,4,5,5-tetramethyl-1,3,2-dioxaborolan-2-yl)-1H-pyrazole (0.2 M solution in 1,4-dioxane, 540 μL, 0.108 mmol) and potassium carbonate (1 M solution in water, 180 μL, 0.18 mmol) were added, and the reaction mixture was purged with nitrogen. [1,1'-Bis(diphenylphosphino)ferrocene]dichloropalladium(II) dichloromethane adduct (0.02 M solution in 1,2-dichloroethane, 300 μL, 0.006 mmol) was added, and the reaction was purged with nitrogen and heated to 80° C. on a heater shaker overnight. The reaction was diluted with ethyl acetate and washed with 1 N aqueous sodium hydroxide solution. The aqueous layer was separated and washed with ethyl acetate, and the combined organic layers were concentrated under a stream of nitrogen. The crude product was purified by mass triggered preparatory HPLC. The product-containing fractions were combined and concentrated in a Genevac to afford (S)-1-(5-cyclopropoxy-6-(1-cyclopropyl-1H-pyrazol-4-yl)-2-methyl-3,4-dihydroquinolin-1 (2H)-yl)ethanone (0.0039 g, 19%). MS (ESI, pos. ion) m/z 352 [M+H]⁺.

Example 34

(S)-1-(2-methyl-6-(5-(methylsulfonyl)pyridin-2-yl)-5-propoxy-3,4-dihydroquinolin-1(2H)-yl)ethanone (I-114)

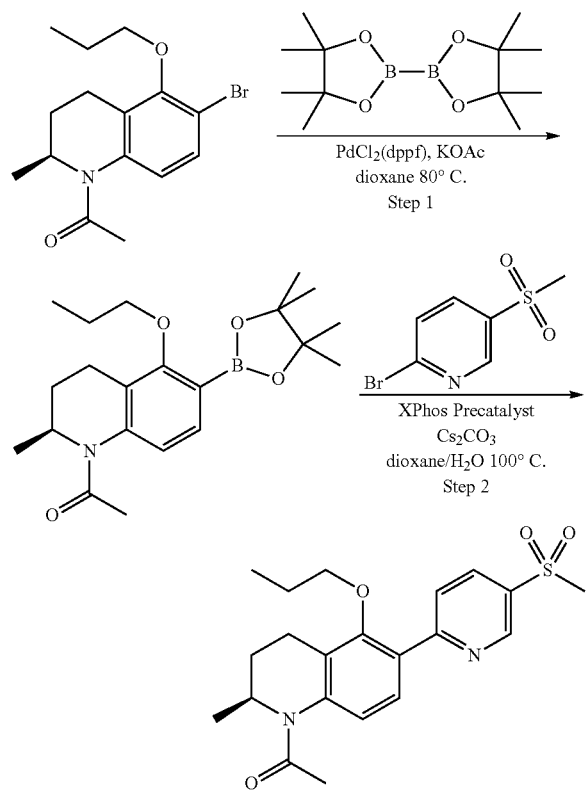

Step 1. (S)-1-(2-methyl-5-propoxy-6-(4,4,5,5-tetramethyl-1,3,2-dioxaborolan-2-yl)-3,4-dihydroquinolin-1(2H)-yl)ethanone A mixture of (S)-1-(6-bromo-2-methyl-5-propoxy-3,4-dihydroquinolin-1(2H)-yl)ethanone (0.127 g, 0.389 mmol), bis(pinacolato)diboron (0.109 g, 0.428 mmol), potassium acetate (0.096 g, 0.973 mmol) and [1,1'-bis(diphenylphosphino)ferrocene]dichloropalladium(II), complex with dichloromethane (0.028 g, 0.039 mmol) in 1,4-dioxane (3.0 mL) was heated at 80° C. After 24 h, additional portions of [1,1'-bis(diphenylphosphino)ferrocene]dichloropalladium (II), complex with dichloromethane (0.028 g, 0.039 mmol), bis(pinacolato)diboron (0.109 g, 0.428 mmol), and potassium acetate (0.096 g, 0.973 mmol) were added and the mixture was heated at 100° C. for 4 h. The reaction mixture was cooled to rt and filtered through Celite to afford a dark brown oil. This material was purified via column chromatography on silica gel (Biotage 25 g column, gradient elution with 25-50% ethyl acetate-hexane) to afford (S)-1-(2-methyl-5-propoxy-6-(4,4,5,5-tetramethyl-1,3,2-dioxaborolan-2-yl)-3,4-dihydroquinolin-1(2H)-yl)ethanone (0.110 g, 76%) as a colorless oil. MS (ESI, pos. ion) m/z 374 [M+H]⁺.

Step 2. (S)-1-(2-methyl-6-(5-(methylsulfonyl)pyridin-2-yl)-5-propoxy-3,4-dihydroquinolin-1(2H)-yl)ethanone A mixture of (S)-1-(2-methyl-5-propoxy-6-(4,4,5,5-tetramethyl-1,3,2-dioxaborolan-2-yl)-3,4-dihydroquinolin-1(2H)-yl)ethanone (0.055 g, 0.147 mmol), 2-bromo-5-(methylsulfonyl)pyridine (0.037 g, 0.155 mmol), XPhos Precatalyst 2nd Generation (0.012 g, 0.015 mmol), and cesium carbonate (0.144 g, 0.442 mmol) in 1,4-dioxane (2.0 mL) and water (0.40 mL) was heated in the microwave at 100° C. for 1.5 h. The reaction mixture was filtered through Celite and concentrated to afford an orange oil. This material was purified via column chromatography on silica gel (Biotage 25 g column, gradient elution with 25-100% ethyl acetate-hexane) to afford (S)-1-(2-methyl-6-(5-(methylsulfonyl)pyridin-2-yl)-5-propoxy-3,4-dihydroquinolin-1(2H)-yl)ethanone (0.016 g, 27%) as a tan solid. ¹H NMR (300 MHz, DMSO-d₆) δ ppm 0.85 (t, J=7.33 Hz, 3H), 1.07 (d, J=6.45 Hz, 3H), 1.32-1.50 (m, 2H), 1.56 (dt, J=14.07, 7.04 Hz, 2H), 2.14 (s, 3H), 2.19-2.33 (m, 1H), 2.79-2.94 (m, 1H), 3.37 (s, 3H), 3.50 (td, J=6.30, 2.64 Hz, 2H), 4.51-4.75 (m, 1H), 7.33 (br d, J=8.50 Hz, 1H), 7.64 (d, J=8.50 Hz, 1H), 8.08-8.21 (m, 1H), 8.36 (dd, J=8.50, 2.35 Hz, 1H), 9.14 (d, J=2.05 Hz, 1H). MS (ESI, pos. ion) m/z 403 [M+H]⁺.

Example 35

(S)—N-(6-(1-acetyl-2-methyl-5-propoxy-1,2,3,4-tetrahydroquinolin-6-yl)pyridin-3-yl)methanesulfonamide (I-115)

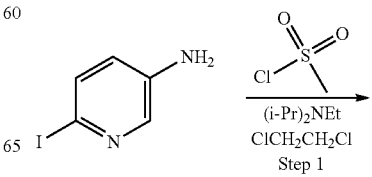

-continued

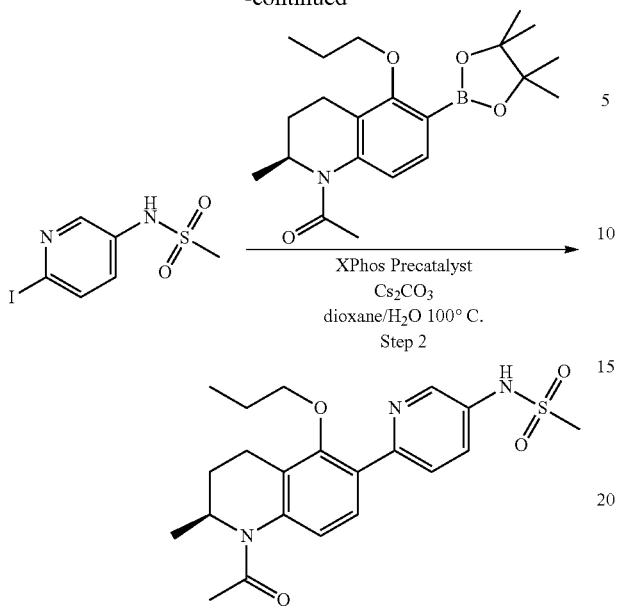

XPhos Precatalyst
Cs₂CO₃
dioxane/H₂O 100° C.
Step 2

Step 1. N-(6-iodopyridin-3-yl)methanesulfonamide

N,N-Diisopropylethylamine (0.992 mL, 5.68 mmol) was added to a solution of 6-iodopyridin-3-amine (0.500 g, 2.273 mmol) and methanesulfonyl chloride (0.186 mL, 2.386 mmol) in 1,2-dichloroethane (10.0 mL), and the mixture stirred at 50° C. for 2.5 h. The reaction mixture was concentrated to afford a brown oil which was dissolved in 1,4-dioxane (5.0 mL) and water (1.0 mL). Potassium hydroxide (0.128 g, 2.273 mmol) was added and the mixture stirred at 80° C. for 4 h. The reaction mixture was cooled to room temperature and then partitioned between dichloromethane and water. The aqueous phase was separated and extracted with dichloromethane. The combined organic phases were washed with brine, dried over anhydrous sodium sulfate, filtered and concentrated to afford a brown oil. This material was purified via column chromatography on silica gel (Biotage 25 g column, gradient elution with 0-50% ethyl acetate-hexane) to afford N-(6-iodopyridin-3-yl)methanesulfonamide (0.537 g, 79%) as a tan solid. MS (ESI, pos. ion) m/z 299 [M+H]⁺.

Step 2. (S)—N-(6-(1-acetyl-2-methyl-5-propoxy-1,2,3,4-tetrahydroquinolin-6-yl)pyridin-3-yl)methanesulfonamide A mixture of (S)-1-(2-methyl-5-propoxy-6-(4,4,5,5-tetramethyl-1,3,2-dioxaborolan-2-yl)-3,4-dihydroquinolin-1(2H)-yl)ethanone (0.055 g, 0.147 mmol), N-(6-iodopyridin-3-yl)methanesulfonamide (0.046 g, 0.155 mmol), XPhos Precatalyst 2nd Generation (0.012 g, 0.015 mmol), and cesium carbonate (0.144 g, 0.442 mmol) in 1,4-dioxane (2.0 mL) and water (0.40 mL) was heated in the microwave at 100° C. for 1.5 h. The reaction mixture was filtered through Celite and concentrated to afford an orange oil. This material was purified via column chromatography on silica gel (Biotage 25 g column, gradient elution with 25-100% ethyl acetate-hexane) to afford (S)—N-(6-(1-acetyl-2-methyl-5-propoxy-1,2,3,4-tetrahydroquinolin-6-yl)pyridin-3-yl)methanesulfonamide (0.007 g, 11%) as an off-white solid. ¹H NMR (300 MHz, CDCl₃) δ ppm 0.79-0.85 (m, 3H), 1.08 (d, J=6.45 Hz, 3H), 1.17-1.55 (m, 3H), 2.12 (s, 3H), 2.20-2.41 (m, 2H), 2.82-3.01 (m, 1H), 3.04 (s, 3H), 3.28-3.59 (m, 2H), 4.76 (br s, 1H), 6.64-6.86 (m, 1H), 6.98 (br s, 1H), 7.52 (d, J=8.21 Hz, 1H), 7.68 (dd, J=8.79, 2.64 Hz, 1H), 7.87 (d, J=8.50 Hz, 1H), 8.47 (d, J=2.64 Hz, 1H). MS (ESI, pos. ion) m/z 418 [M+H]⁺.

The following examples were made according to the procedure outlined for Example 34:

(S)-2-(1-acetyl-2-methyl-6-(5-(methylsulfonyl)pyridin-2-yl)-1,2,3,4-tetrahydroquinolin-5-yloxy)-N,N-dimethylacetamide (I-116)

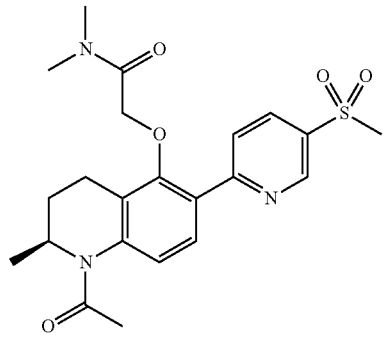

¹H NMR (300 MHz, CDCl₃) δ ppm 1.09 (d, J=6.74 Hz, 3H), 2.07-2.20 (m, 3H), 2.20-2.42 (m, 2H), 2.73 (s, 3H), 2.83-2.94 (m, 3H), 2.94-3.07 (m, 1H), 3.11 (s, 3H), 4.03 (dt, J=19.35, 6.89 Hz, 1H), 4.20-4.30 (m, 2H), 4.61-4.82 (m, 1H), 7.00-7.17 (m, 1H), 7.63 (d, J=8.50 Hz, 1H), 8.15-8.20 (m, 2H), 9.06-9.22 (m, 1H). MS (ESI, pos. ion) m/z 446 [M+H]⁺.

(S)-1-(6-(benzo[d]oxazol-2-yl)-2-methyl-5-propoxy-3,4-dihydroquinolin-1(2H)-yl)ethanone (I-117)

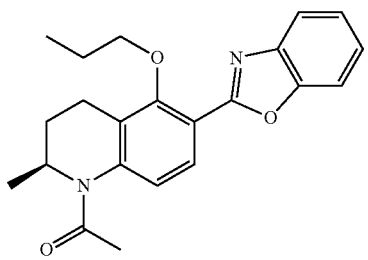 [SMILES: CCCOc1c(-c2nc3ccccc3o2)ccc2c1CC[C@H](C)N2C(C)=O]

¹H NMR (300 MHz, DMSO-d₆) δ ppm 1.01 (t, J=7.48 Hz, 3H), 1.08 (d, J=6.45 Hz, 3H), 1.38-1.58 (m, 2H), 1.79 (dq, J=14.14, 7.01 Hz, 2H), 2.17 (s, 3H), 2.20-2.32 (m, 1H), 2.77-3.01 (m, 1H), 3.84 (t, J=6.30 Hz, 2H), 4.52-4.74 (m, 1H), 7.36-7.45 (m, 3H), 7.71-7.85 (m, 2H), 7.92 (d, J=8.50 Hz, 1H). MS (ESI, pos. ion) m/z 365 [M+H]+.

(S)-1-(2-methyl-5-propoxy-6-(pyrazolo[1,5-a]pyridin-2-yl)-3,4-dihydroquinolin-1(2H)-yl)ethanone (I-118)

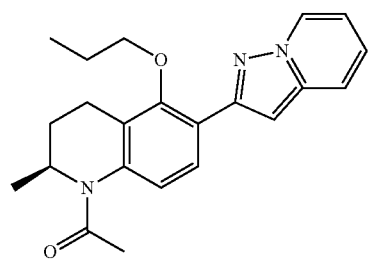

¹H NMR (300 MHz, DMSO-d₆) δ ppm 0.73 (t, J=7.33 Hz, 3H), 1.03-1.10 (m, 6H), 1.32-1.51 (m, 3H), 2.12 (s, 3H), 2.20-2.45 (m, 2H), 2.89 (dt, J=15.32, 5.09 Hz, 1H), 3.36-3.43 (m, 1H), 3.94 (s, 1H), 4.55-4.72 (m, 1H), 6.93 (t, J=6.89 Hz, 1H), 7.18-7.30 (m, 2H), 7.33 (d, J=8.21 Hz, 1H), 7.73 (d, J=8.79 Hz, 1H), 8.24 (s, 1H), 8.71 (dd, J=7.04, 0.88 Hz, 1H). MS (ESI, pos. ion) m/z 364 [M+H]+.

(S)-1-(6-(imidazo[1,2-a]pyridin-2-yl)-2-methyl-5-propoxy-3,4-dihydroquinolin-1(2H)-yl)ethanone (I-119)

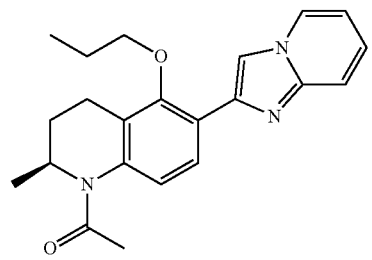 [SMILES: CCCOc1c(-c2cn3ccccc3n2)ccc2c1CC[C@H](C)N2C(C)=O]

¹H NMR (300 MHz, DMSO-d₆) δ ppm 0.98-1.08 (m, 6H), 1.21-1.56 (m, 1H), 1.78-1.96 (m, 2H), 2.10 (s, 3H), 2.21-2.44 (m, 2H), 2.79-3.00 (m, 1H), 3.60-3.78 (m, 2H), 4.44-4.76 (m, 1H), 6.88 (t, J=6.74 Hz, 1H), 7.16-7.30 (m, 2H), 7.56 (d, J=9.09 Hz, 1H), 8.04 (d, J=8.50 Hz, 1H), 8.35 (s, 1H), 8.65 (d, J=6.74 Hz, 1H). MS (ESI, pos. ion) m/z 364 [M+H]+.

(S)-1-(6-(benzo[d]thiazol-2-yl)-2-methyl-5-propoxy-3,4-dihydroquinolin-1(2H)-yl)ethanone (I-120)

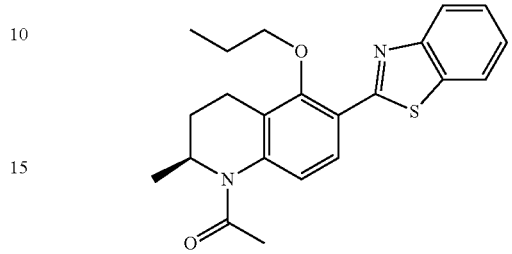

¹H NMR (300 MHz, DMSO-d₆) δ ppm 1.01-1.15 (m, 6H), 1.43 (m, 2H), 1.82-2.04 (m, 2H), 2.15 (s, 3H), 2.29 (br dd, J=12.46, 6.01 Hz, 1H), 2.82-2.98 (m, 1H), 3.84 (br t, J=6.45 Hz, 2H), 4.53-4.70 (m, 1H), 7.31-7.49 (m, 2H), 7.49-7.61 (m, 1H), 8.05 (d, J=7.92 Hz, 1H), 8.16 (t, J=9.09 Hz, 2H). MS (ESI, pos. ion) m/z 381 [M+H]+.

(S)-1-(6-(1H-benzo[d]imidazol-2-yl)-2-methyl-5-propoxy-3,4-dihydroquinolin-1(2H)-yl)ethanone (I-121)

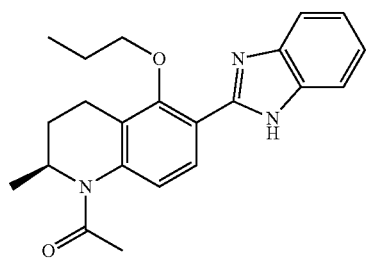 [SMILES: CCCOc1c(-c2nc3ccccc3[nH]2)ccc2c1CC[C@H](C)N2C(C)=O]

¹H NMR (300 MHz, DMSO-d₆) δ ppm 0.88 (t, J=7.33 Hz, 3H), 1.07 (d, J=6.45 Hz, 3H), 1.36-1.52 (m, 2H), 1.57-1.79 (m, 2H), 2.15 (s, 3H), 2.22-2.38 (m, 1H), 2.90 (dt, J=15.83, 5.86 Hz, 1H), 3.50-3.72 (m, 2H), 4.52-4.78 (m, 1H), 7.10-7.25 (m, 2H), 7.33 (br d, J=8.21 Hz, 1H), 7.51-7.60 (m, 1H), 7.61-7.70 (m, 1H), 7.83 (d, J=8.50 Hz, 1H), 12.30 (s, 1H). MS (ESI, pos. ion) m/z 364 [M+H]+.

(S)-(5-cyclobutoxy-2-methyl-6-(5-methyl-1,3,4-thiadiazol-2-yl)-3,4-dihydroquinolin-1(2H)-yl)(cyclopropyl)methanone (I-122)

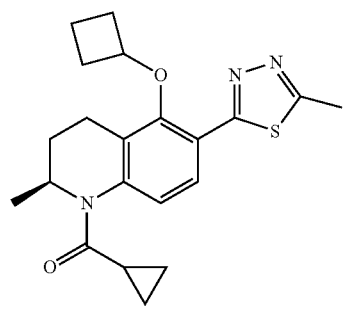

¹H NMR (400 MHz, CD₃OD) δ ppm 0.65-0.83 (m, 1H), 0.85-1.06 (m, 2H), 1.11-1.22 (m, 4H), 1.23-1.38 (m, 1H), 1.41-1.53 (m, 1H), 1.53-1.69 (m, 1H), 1.81-1.94 (m, 1H), 2.15-2.51 (m, 6H), 2.84 (s, 3H), 2.95-2.13 (m, 1H), 4.32-4.51 (m, 1H), 4.60-4.79 (m, 1H), 7.33 (d, J=8.40 Hz, 1H), 7.85-8.12 (m, 1H). MS (ESI, pos. ion) m/z 384 [M+H]+.

(S)-(5-cyclobutoxy-6-(isoxazol-4-yl)-2-methyl-3,4-dihydroquinolin-1(2H)-yl)(cyclopropyl)methanone (I-123)

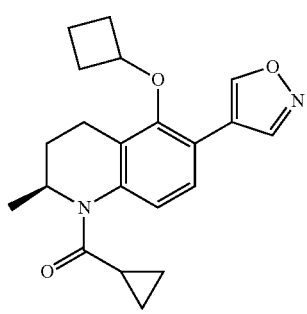 [SMILES: C[C@H]1CCc2c(ccc(-c3cnoc3)c2OC2CCC2)N1C(=O)C1CC1]

¹H NMR (400 MHz, CD₃OD) δ ppm 0.66-0.72 (m, 1H), 0.76-0.71 (m, 2H), 0.98-1.08 (m, 4H), 1.15-1.33 (m, 2H), 1.50-1.58 (m, 1H), 1.74-1.81 (m, 1H), 1.96-2.03 (m, 2H), 2.03-2.14 (m, 2H), 2.14-2.33 (m, 2H), 2.89-2.94 (m, 1H), 4.10-4.16 (m, 1H), 4.52-4.63 (m, 1H), 7.11 (d, J=8.40 Hz, 1H), 7.35 (d, J=8.40 Hz, 1H), 8.73 (s, 1H), 8.96 (s, 1H). MS (ESI, pos. ion) m/z 353 [M+H]+.

(S)-(5-cyclobutoxy-8-fluoro-2-methyl-6-(1-methyl-1H-1,2,3-triazol-4-yl)-3,4-dihydroquinolin-1(2H)-yl)(cyclopropyl)methanone (I-124)

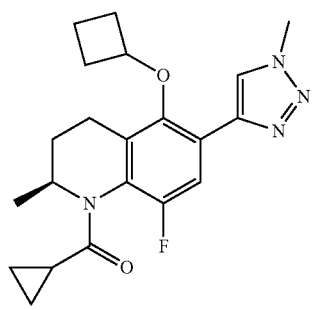 [SMILES: C[C@H]1CCc2c(OC3CCC3)c(-c3cn(C)nn3)cc(F)c2N1C(=O)C1CC1]

¹H NMR (400 MHz, CD₃OD) δ ppm 0.76-0.85 (m, 1H), 0.91-1.03 (m, 3H), 1.04-1.30 (m, 4H), 1.35-1.47 (m, 1H), 1.61-1.72 (m, 2H), 2.13-2.36 (m, 5H), 2.46-2.55 (m, 1H), 3.05-3.13 (m, 2H), 4.20-4.27 (m, 4H), 4.69-4.78 (m, 1H), 7.69 (d, J=8.40 Hz, 1H), 8.38 (s, 1H). MS (ESI, pos. ion) m/z 385 [M+H]+.

(S)-methyl 5-cyclobutoxy-8-fluoro-2-methyl-6-(1-methyl-1H-1,2,3-triazol-4-yl)-3,4-dihydroquinoline-1(2H)-carboxylate (I-125)

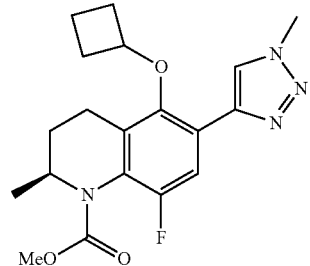 [SMILES: COC(=O)N1c2c(F)cc(-c3cn(C)nn3)c(OC3CCC3)c2CC[C@@H]1C]

¹H NMR (400 MHz, CDCl₃) δ ppm 1.21-1.25 (m, 3H), 1.25-1.34 (m, 4H), 1.60-1.70 (m, 1H), 2.05-2.20 (m, 4H), 2.26-2.41 (m, 1H), 3.79 (s, 3H), 4.13-4.14 (m, 1H), 4.17 (s, 3H), 4.42-4.53 (m, 1H), 7.8 (s, 1H), 8.0 (s, 1H). MS (ESI, pos. ion) m/z 375 [M+H]+.

(S)-1-(5-cyclobutoxy-8-fluoro-2-methyl-6-(1-methyl-1H-1,2,3-triazol-4-yl)-3,4-dihydroquinolin-1(2H)-yl)ethanone (I-126)

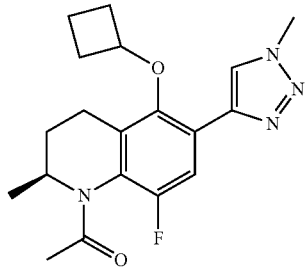 [SMILES: CC(=O)N1c2c(F)cc(-c3cn(C)nn3)c(OC3CCC3)c2CC[C@@H]1C]

¹H NMR (300 MHz, CD₃OD) δ ppm 1.11-1.25 (m, 4H), 1.31-1.45 (m, 1H), 1.55-1.71 (m, 1H), 1.98-2.55 (m, 9H), 2.97-3.10 (m, 1H), 4.20-4.37 (m, 4H), 4.71-4.83 (m, 1H), 7.69 (d, J=11.10 Hz, 1H), 8.37 (s, 1H). MS (ESI, pos. ion) m/z 359 [M+H]+.

(S)-(6-(5-amino-1,3,4-thiadiazol-2-yl)-5-cyclobutoxy-2-methyl-3,4-dihydroquinolin-1(2H)-yl)(cyclopropyl)methanone (I-127)

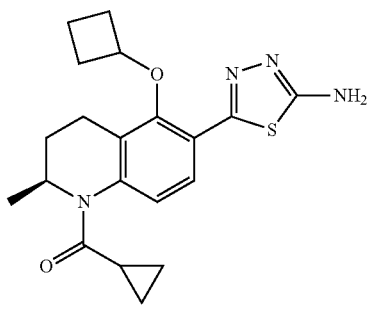 [SMILES: C[C@H]1CCc2c(ccc(-c3nnc(N)s3)c2OC2CCC2)N1C(=O)C1CC1]

For (S)-(6-(5-amino-1,3,4-thiadiazol-2-yl)-5-cyclobutoxy-2-methyl-3,4-dihydroquinolin-1(2H)-yl)(cyclopropyl)methanone, tert-butyl (5-bromo-1,3,4-thiadiazol-2-yl)carbamate was used as the aryl bromide source. The Boc-group was removed as outlined in Example 29, Step 3. ¹H NMR (400 MHz, CD₃OD) δ ppm 0.65-0.80 (m, 1H), 0.87-1.01 (m, 2H), 1.09-1.19 (m, 4H), 1.21-1.39 (m, 1H), 1.42-1.59 (m, 1H), 1.68-1.79 (m, 1H), 1.82-1.96 (m, 1H), 2.15-2.53 (m, 6H), 2.97-3.10 (m, 1H), 4.32-4.54 (m, 1H), 4.60-4.75 (m, 1H), 7.27 (d, J=8.40 Hz, 1H), 7.82-7.94 (m, 1H). MS (ESI, pos. ion) m/z 385 [M+H]+.

(S)-(5-cyclobutoxy-2-methyl-6-(1H-1,2,3-triazol-4-yl)-3,4-dihydroquinolin-1(2H)-yl)(cyclopropyl)methanone (I-128)

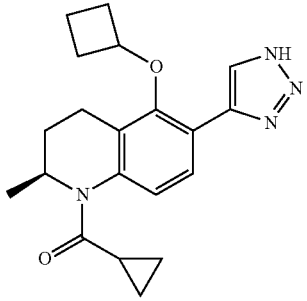 [SMILES: C[C@H]1CCc2c(ccc(-c3c[nH]nn3)c2OC2CCC2)N1C(=O)C1CC1]

For (S)-(5-cyclobutoxy-2-methyl-6-(1H-1,2,3-triazol-4-yl)-3,4-dihydroquinolin-1(2H)-yl)(cyclopropyl)methanone, 1-benzyl-4-bromo-1H-1,2,3-triazole was used as the aryl bromide source. The benzyl group was removed using the hydrogenation conditions outlined above for Intermediate 1, Step 2. ¹H NMR (300 MHz, CD₃OD) δ ppm 0.65-0.80 (m, 1H), 0.87-0.99 (m, 2H), 1.13 (d, J=6.60 Hz, 4H), 1.27-1.39 (m, 2H), 1.53-1.73 (m, 1H), 1.82-1.97 (m, 1H), 2.01-2.23 (m, 4H), 2.27-2.44 (m, 2H), 2.99-3.16 (m, 1H), 4.05-4.28 (m, 4H), 4.65-4.81 (m, 1H), 7.24 (d, J=7.80 Hz, 1H), 7.72 (d, J=8.40 Hz, 1H), 8.15 (s, 1H). MS (ESI, pos. ion) m/z 353 [M+H]+.

(S)-methyl-6-(2-carbamoylthiazol-4-yl)-5-cyclobutoxy-2-methyl-3,4-dihydroquinoline-1(2H)-carboxylate (I-129)

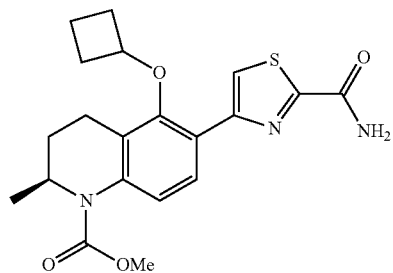 [SMILES: COC(=O)N1c2ccc(-c3csc(C(N)=O)n3)c(OC3CCC3)c2CC[C@@H]1C]

¹H NMR (300 MHz, CDCl₃) δ ppm 1.19 (d, J=6.60 Hz, 3H), 1.21-1.32 (m, 2H), 1.46-1.56 (m, 1H), 2.01-2.16 (m, 4H), 2.18-2.27 (m, 1H), 2.86-3.00 (m, 1H), 3.80 (s, 3H), 4.05-4.13 (m, 1H), 4.55-4.63 (m, 1H), 5.58-5.63 (m, 1H), 7.41 (d, J=8.70 Hz, 1H), 7.74 (d, J=8.70 Hz, 1H), 8.03 (s, 1H). MS (ESI, pos. ion) m/z 402 [M+H]⁺.

(S)-methyl 5-cyclobutoxy-2-methyl-6-(2-(methylcarbamoyl)thiazol-4-yl)-3,4-dihydroquinoline-1(2H)-carboxylate (I-130)

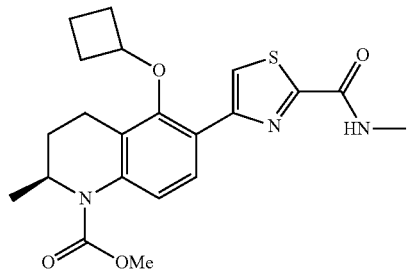

$^1$H NMR (300 MHz, CDCl$_3$) δ ppm 1.16-1.31 (m, 5H), 1.45-1.59 (m, 2H), 1.98-2.11 (m, 4H), 2.15-2.28 (m, 1H), 2.45-2.55 (m, 1H), 2.90-2.99 (m, 1H), 3.06 (d, J=5.40 Hz, 3H), 3.80 (s, 3H), 4.05-4.14 (m, 1H), 4.55-4.65 (m, 1H), 7.41 (d, J=8.70 Hz, 1H), 7.72 (d, J=8.70 Hz, 1H), 7.96 (s, 1H). MS (ESI, pos. ion) m/z 416 [M+H]⁺.

(S)-methyl 6-(2-acetamidothiazol-4-yl)-5-cyclobutoxy-2-methyl-3,4-dihydroquinoline-1(2H)-carboxylate (I-131)

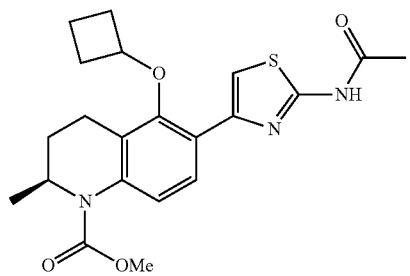 [SMILES: COC(=O)N1c2ccc(-c3csc(NC(C)=O)n3)c(OC3CCC3)c2CC[C@@H]1C]

$^1$H NMR (400 MHz, CDCl$_3$) δ ppm 1.17 (d, J=6.40 Hz, 3H), 1.25-1.36 (m, 1H), 1.45-1.66 (m, 1H), 1.67-1.75 (m, 1H), 1.92-1.95 (m 3H), 1.97-2.13 (m, 4H), 2.16-2.26 (m, 1H), 2.45-2.51 (m, 1H), 2.90-3.00 (m, 1H), 3.79 (s, 3H), 4.13-4.15 (m, 1H), 4.55-4.62 (m, 1H), 7.31-7.37 (m, 2H), 7.54-7.57 (m, 1H), 11.6 (br s, 1H). MS (ESI, pos. ion) m/z 416 [M+H]⁺.

Example 36

(S)-methyl 5-(4-chloro-2-cyanophenoxy)-2-methyl-6-(1-(piperidin-4-yl)-1H-pyrazol-4-yl)-3,4-dihydroquinoline-1(2H)-carboxylate (I-132)

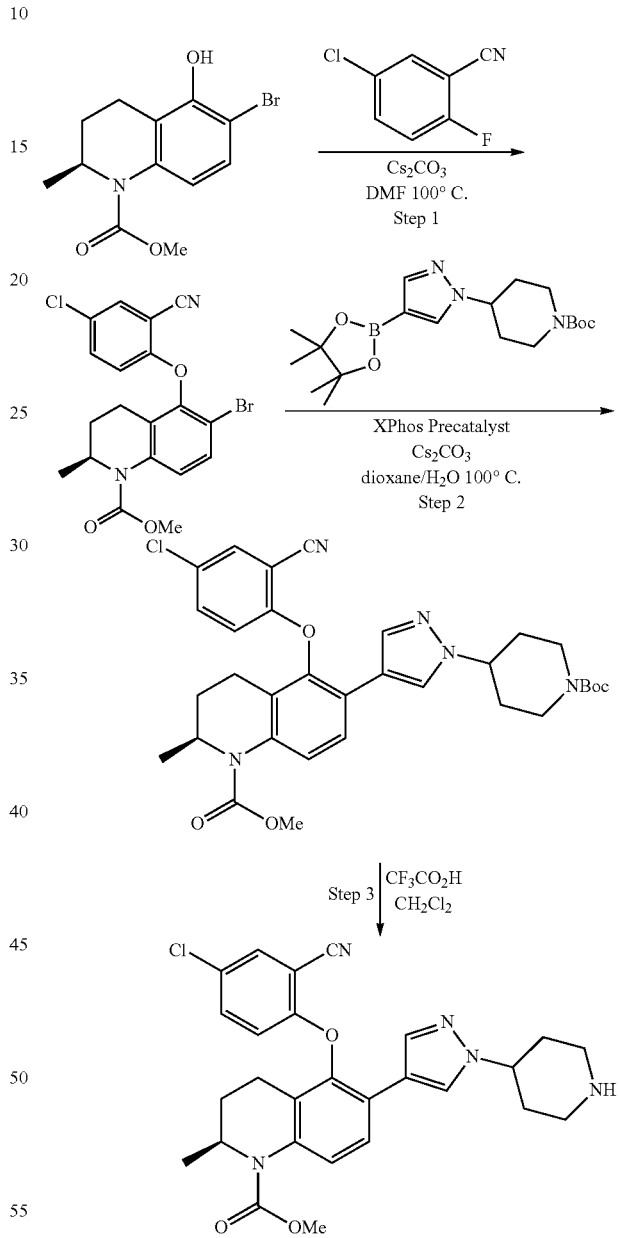

Step 1. (S)-methyl 6-bromo-5-(4-chloro-2-cyanophenoxy)-2-methyl-3,4-dihydroquinoline-1(2H)-carboxylate A mixture of (S)-methyl 6-bromo-5-hydroxy-2-methyl-3,4-dihydroquinoline-1(2H)-carboxylate (0.050 g, 0.167 mmol), 5-chloro-2-fluorobenzonitrile (0.065 g, 0.416 mmol), and cesium carbonate (0.136 g, 0.416 mmol) in DMF (2.0 mL) was heated at 100° C. for 16 h. The reaction mixture was cooled to room temperature and water was added. The mixture was partitioned between ethyl acetate and water. The aqueous phase was separated and extracted with ethyl acetate. The combined organic phases were washed with brine, dried over anhydrous sodium sulfate, filtered, and concentrated to afford a brown oil. This material was purified via column chromatography on silica gel (Biotage 25 g column, gradient elution with 0-25% ethyl acetate-hexane) to afford (S)-methyl 6-bromo-5-(4-chloro-2-cyanophenoxy)-2-methyl-3,4-dihydroquinoline-1(2H)-carboxylate (0.068 g, 94%) as an off-white solid. MS (ESI, pos. ion) m/z 435, 437 [M+H]+.

Step 2. (S)-methyl 6-(1-(1-(tert-butoxycarbonyl) piperidin-4-yl)-1H-pyrazol-4-yl)-5-(4-chloro-2-cyanophenoxy)-2-methyl-3,4-dihydroquinoline-1(2H)-carboxylate A mixture of (S)-methyl 6-bromo-5-(4-chloro-2-cyanophenoxy)-2-methyl-3,4-dihydroquinoline-1(2H)-carboxylate (0.068 g, 0.156 mmol), tert-butyl 4-(4-(4,4,5,5-tetramethyl-1,3,2-dioxaborolan-2-yl)-1H-pyrazol-1-yl)piperidine-1-carboxylate (0.065 g, 0.172 mmol), XPhos Precatalyst 2nd Generation (0.012 g, 0.016 mmol), and cesium carbonate (0.153 g, 0.468 mmol) in dioxane (2.0 mL) and water (0.400 mL) was heated in the microwave at 100° C. for 2 h. The reaction mixture was filtered through Celite and concentrated to afford an orange oil. This material was purified via column chromatography on silica gel (Biotage 25 g column, gradient elution with 25-50% ethyl acetate-hexane) to afford (S)-methyl 6-(1-(1-(tert-butoxycarbonyl)piperidin-4-yl)-1H-pyrazol-4-yl)-5-(4-chloro-2-cyanophenoxy)-2-methyl-3,4-dihydroquinoline-1(2H)-carboxylate (0.057 g, 60%) as an off-white solid. MS (ESI, pos. ion) m/z 606 [M+H]+.

Step 3. (S)-methyl 5-(4-chloro-2-cyanophenoxy)-2-methyl-6-(1-(piperidin-4-yl)-1H-pyrazol-4-yl)-3,4-dihydroquinoline-1(2H)-carboxylate Trifluoroacetic acid (0.5 mL, 6.49 mmol) was added to a solution of (S)-methyl 6-(1-(1-(tert-butoxycarbonyl)piperidin-4-yl)-1H-pyrazol-4-yl)-5-(4-chloro-2-cyanophenoxy)-2-methyl-3,4-dihydroquinoline-1(2H)-carboxylate (0.057 g, 0.094 mmol) in dichloromethane (2.0 mL) and the reaction mixture stirred at rt for 1.5 h. The reaction mixture was concentrated and the residue was partitioned between dichloromethane and saturated aqueous sodium bicarbonate solution. The organic phase was separated, dried over anhydrous sodium sulfate, filtered, and concentrated to afford (S)-methyl 5-(4-chloro-2-cyanophenoxy)-2-methyl-6-(1-(piperidin-4-yl)-1H-pyrazol-4-yl)-3,4-dihydroquinoline-1(2H)-carboxylate (0.041 g, 86%) as an off-white solid. 1H NMR (300 MHz, DMSO-d6) δ ppm 1.01-1.09 (m, 4H), 1.49-1.79 (m, 4H), 1.80-2.07 (m, 4H), 2.52-2.63 (m, 2H), 2.99 (br d, J=12.31 Hz, 2H), 3.72 (s, 3H), 4.03-4.23 (m, 1H), 4.45-4.70 (m, 1H), 6.44 (br d, J=9.09 Hz, 1H), 7.47-7.64 (m, 3H), 7.67 (s, 1H), 7.95 (s, 1H), 8.10 (d, J=2.35 Hz, 1H). MS (ESI, pos. ion) m/z 506 [M+H]+.

The following examples were made according to the procedure outlined for Example 36:

(S)-methyl 5-(2-cyano-4-fluorophenoxy)-2-methyl-6-(1-(piperidin-4-yl)-1H-pyrazol-4-yl)-3,4-dihydroquinoline-1(2H)-carboxylate (I-133)

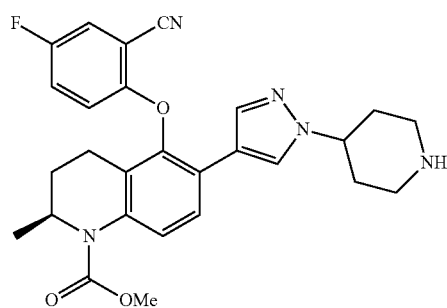 [SMILES: COC(=O)N1c2ccc(-c3cnn(C4CCNCC4)c3)c(Oc3ccc(F)cc3C#N)c2CC[C@@H]1C]

1H NMR (300 MHz, DMSO-d6) δ ppm 1.00-1.12 (m, 4H), 1.48-1.79 (m, 4H), 1.79-2.05 (m, 4H), 2.51-2.61 (m, 2H), 2.98 (br d, J=12.31 Hz, 2H), 3.72 (s, 3H), 3.99-4.23 (m, 1H), 4.38-4.67 (m, 1H), 6.43 (br d, J=5.28 Hz, 1H), 7.37 (td, J=8.79, 3.22 Hz, 1H), 7.54-7.70 (m, 3H), 7.89-7.98 (m, 2H). MS (ESI, pos. ion) m/z 490 [M+H]+.

(S)-methyl 5-(2-chloro-4-cyanophenoxy)-2-methyl-6-(1-(piperidin-4-yl)-1H-pyrazol-4-yl)-3,4-dihydroquinoline-1(2H)-carboxylate (I-134)

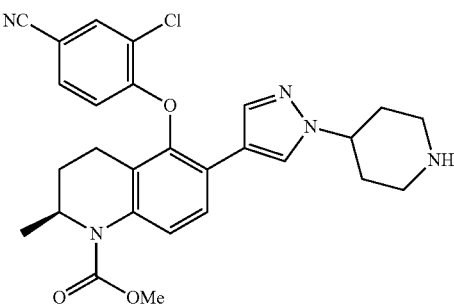

1H NMR (300 MHz, DMSO-d6) δ ppm 1.06 (br d, J=1.76 Hz, 4H), 1.43-1.75 (m, 4H), 1.77-2.08 (m, 4H), 2.52-2.68 (m, 2H), 2.98 (br d, J=12.02 Hz, 2H), 3.72 (s, 3H), 4.09 (br t, J=12.02 Hz, 1H), 4.44-4.73 (m, 1H), 6.27-6.66 (m, 1H), 7.50-7.65 (m, 3H), 7.67 (s, 1H), 7.95 (s, 1H), 8.22 (s, 1H). MS (ESI, pos. ion) m/z 506 [M+H]⁺.

(S)-methyl 5-(4-cyano-2-fluorophenoxy)-2-methyl-6-(1-(piperidin-4-yl)-1H-pyrazol-4-yl)-3,4-dihydroquinoline-1(2H)-carboxylate (I-135)

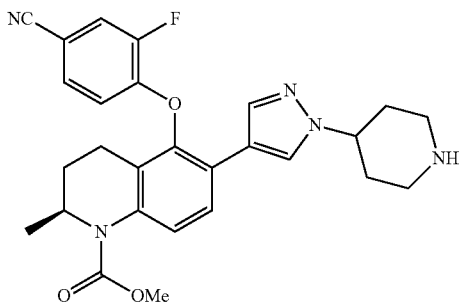 [SMILES: COC(=O)N1c2ccc(-c3cnn(C4CCNCC4)c3)c(Oc3ccc(C#N)cc3F)c2CC[C@@H]1C]

¹H NMR (300 MHz, DMSO-d₆) δ ppm 1.00-1.12 (m, 4H), 1.50-1.76 (m, 4H), 1.79-2.09 (m, 4H), 2.47-2.64 (m, 2H), 2.99 (br d, J=12.61 Hz, 2H), 3.72 (s, 3H), 4.01-4.21 (m, 1H), 4.44-4.70 (m, 1H), 6.52 (ᵇʳ t, J=8.65 Hz, 1H), 7.37-7.71 (m, 4H), 7.94 (s, 1H), 8.05 (br d, J=11.14 Hz, 1H). MS (ESI, pos. ion) m/z 490 [M+H]⁺.

(S)-2-(1-acetyl-2-methyl-6-(1-(piperidin-4-yl)-1H-pyrazol-4-yl)-1,2,3,4-tetrahydroquinolin-5-yloxy)benzonitrile (I-136)

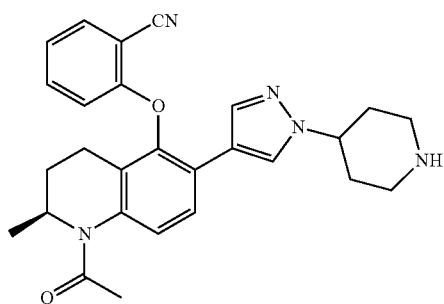 [SMILES: CC(=O)N1c2ccc(-c3cnn(C4CCNCC4)c3)c(Oc3ccccc3C#N)c2CC[C@@H]1C]

¹H NMR (300 MHz, CD₃OD) δ ppm 1.16 (d, J=6.60 Hz, 3H), 1.47 (br s, 1H), 1.78-1.93 (m, 2H), 2.01-2.09 (m, 2H), 2.15-2.35 (m, 5H), 2.55-2.83 (m, 3H), 3.10-3.21 (m, 2H), 4.18-4.32 (m, 1H), 4.78 (br s, 1H), 6.50 (d, J=8.10 Hz, 1H), 7.11 (t, J=7.80 Hz, 1H), 7.35-7.50 (m, 2H), 7.61 (d, J=8.40 Hz, 1H), 7.71-7.79 (m, 2H), 7.99 (s, 1H). MS (ESI, pos. ion) m/z 456 [M+H]⁺.

methyl (S)-5-(2-cyanophenoxy)-2-methyl-6-(1-(piperidin-4-yl)-1H-pyrazol-4-yl)-3,4-dihydroquinoline-1(2H)-carboxylate (I-137)

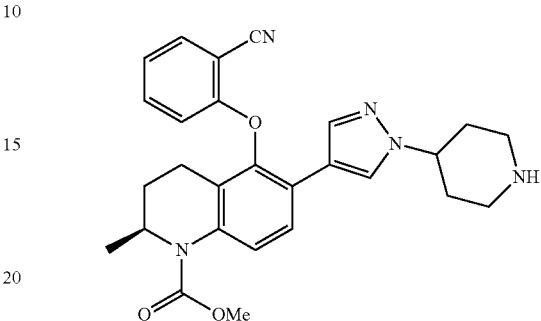

¹H NMR (400 ᴹᴴᶻ, CD₃OD) δ ppm 1.06 (d, J=6.40 Hz, 3H), 1.48-1.55 (m, 1H), 1.65-1.74 (m, 1H), 1.85-2.05 (m, 3H), 2.20-2.85 (m, 4H), 2.95-3.05 (m, 2H), 3.72 (s, 3H), 4.05-4.15 (m, 1H), 4.50-4.60 (m, 1H), 6.30-6.40 (m, 1H), 6.93-6.99 (m, 1H), 7.23-7.30 (m, 1H), 7.43 (d, J=8.80 Hz, 1H), 7.50-7.60 (m, 1H), 7.59-7.65 (m, 2H), 7.79 (s, 1H). MS (ESI, pos. ion) m/z 472 [M+H]⁺.

(S)-methyl 6-(1-(azetidin-3-yl)-1H-pyrazol-4-yl)-5-(2-cyanophenoxy)-2-methyl-3,4-dihydroquinoline-1(2H)-carboxylate (I-138)

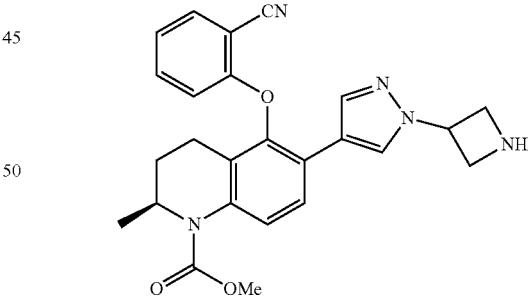

¹H NMR (300 MHz, DMSO-d₆) δ ppm 1.00 (br d, J=6.45 Hz, 3H), 1.39-1.62 (m, 2H), 1.83-2.00 (m, 2H), 3.29-3.51 (m, 2H), 3.55-3.63 (m, 1H), 3.66 (s, 3H), 3.70-3.82 (m, 1H), 4.52 (m, 1H), 4.80 (br d, J=7.04 Hz, 1H), 4.95-5.16 (m, 1H), 6.37 (br d, J=8.50 Hz, 1H), 6.94-7.20 (m, 1H), 7.42 (q, J=7.⁵² Hz, 1H), 7.55 (m, 2H), 7.65-7.75 (m, 1H), 7.75-7.90 (m, 1H), 7.93-8.12 (m, 1H). MS (ESI, pos. ion) m/z 444 [M+H]+.

(S)-methyl 6-(1-(azetidin-3-yl)-1H-pyrazol-4-yl)-5-(2-cyano-3-fluorophenoxy)-2-methyl-3,4-dihydroquinoline-1(2H)-carboxylate (I-139)

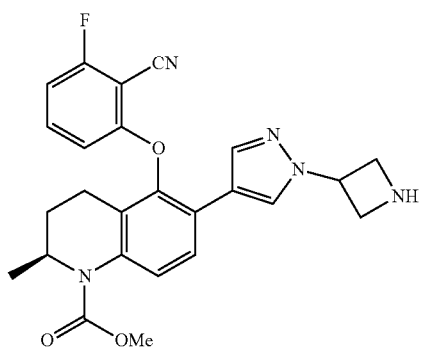 [SMILES: COC(=O)N1c2ccc(-c3cnn(C4CNC4)c3)c(Oc3cccc(F)c3C#N)c2CC[C@@H]1C]

$^1$H NMR (300 MHz, DMSO-d$_6$) δ ppm 1.00 (br d, J=5.86 Hz, 3H), 1.45-1.67 (m, 2H), 1.81-1.99 (m, 2H), 3.29-3.51 (m, 2H), 3.66 (s, 3H), 3.73-4.02 (m, 2H), 4.40-4.65 (m, 1H), 4.82 (m, 1H), 4.98-5.27 (m, 1H), 6.25 (br d, J=7.33 Hz, 1H), 7.08 (br t, J=8.79 Hz, 1H), 7.38-7.64 (m, 3H), 7.72 (br d, J=6.16 Hz, 1H), 7.89-8.10 (m, 1H). MS (ESI, pos. ion) m/z 462 [M+H]+.

(S)-4-(1-acetyl-2-methyl-6-(1-(piperidin-4-yl)-1H-pyrazol-4-yl)-1,2,3,4-tetrahydroquinolin-5-yloxy)benzonitrile (I-140)

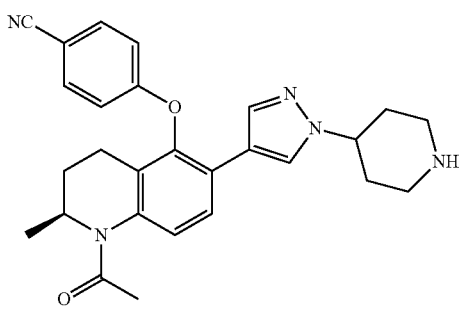 [SMILES: CC(=O)N1c2ccc(-c3cnn(C4CCNCC4)c3)c(Oc3ccc(C#N)cc3)c2CC[C@@H]1C]

$^1$H NMR (300 MHz, CD$_3$OD) δ ppm 1.15 (d, J=6.60 Hz, 3H), 1.20-1.45 (m, 1H), 1.80-1.95 (m, 2H), 1.97-2.05 (m, 2H), 2.10-2.25 (m, 5H), 2.52-2.69 (m, 1H), 2.72-2.82 (m, 2H), 3.20 (d, J=12.90 Hz, 2H), 4.15-4.25 (m, 1H), 4.65-4.82 (m, 1H), 6.93 (d, J=8.70 Hz, 2H), 7.38 (br s, 1H), 7.62 (t, J=9.00 Hz, 3H), 7.75 (s, 1H), 7.93 (s, 1H). MS (ESI, pos. ion) m/z 456 [M+H]+.

(S)-1-(2-methyl-6-(1-(piperidin-4-yl)-1H-pyrazol-4-yl)-5-(3-(trifluoromethyl)pyridin-2-yloxy)-3,4-dihydroquinolin-1(2H)-yl)ethanone (I-141)

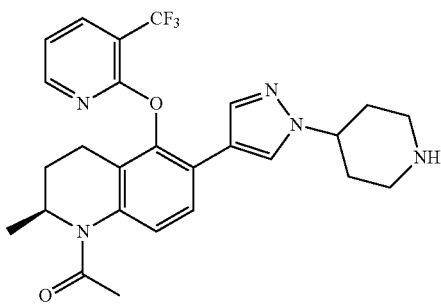 [SMILES: CC(=O)N1c2ccc(-c3cnn(C4CCNCC4)c3)c(Oc3ncccc3C(F)(F)F)c2CC[C@@H]1C]

$^1$H NMR (400 MHz, CD$_3$OD) δ ppm 1.15 (s, 3H), 1.20-1.50 (m, 1H), 1.72-1.87 (m, 2H), 1.95-2.05 (m, 2H), 2.07-2.45 (m, 6H), 2.65-2.75 (m, 2H), 3.05-3.15 (m, 2H), 4.10-4.22 (m, 1H), 4.79 (br s, 1H), 7.15-7.37 (m, 2H), 7.56 (d, J=8.40 Hz, 1H), 7.71 (s, 1H), 7.86 (s, 1H), 8.12-8.19 (m, 2H). MS (ESI, pos. ion) m/z 500 [M+H]+.

(S)-1-(5-(3-chloropyridin-2-yloxy)-2-methyl-6-(1-(piperidin-4-yl)-1H-pyrazol-4-yl)-3,4-dihydroquinolin-1(2H)-yl)ethanone (I-142)

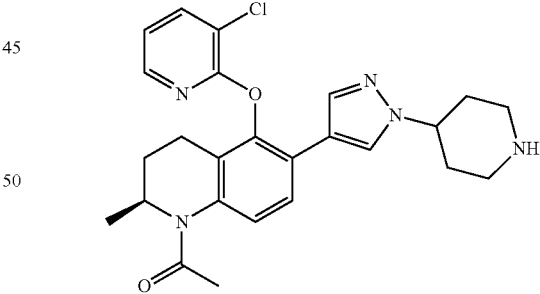

$^1$H NMR (300 MHz, CD$_3$OD) δ ppm 1.16 (d, J=6.60 Hz, 3H), 1.45 (br s, 1H), 1.75-1.92 (m, 2H), 1.97-2.10 (m, 2H), 2.15-2.32 (m, 5H), 2.50-2.70 (m, 1H), 2.69-2.78 (m, 2H), 3.08-3.15 (m, 2H), 4.08-4.21 (m, 1H), 4.72-4.91 (m, 1H), 6.95-7.05 (m, 1H), 7.25-7.35 (m, 1H), 7.55 (d, J=8.10 Hz, 1H), 7.77 (s, 1H), 7.85-7.95 (m, 2H), 7.96 (s, 1H). MS (ESI, pos. ion) m/z 466 [M+H]+.

(S)-2-(1-acetyl-2-methyl-6-(1-(piperidin-4-yl)-1H-pyrazol-4-yl)-1,2,3,4-tetrahydroquinolin-5-yloxy)nicotinonitrile (I-143)

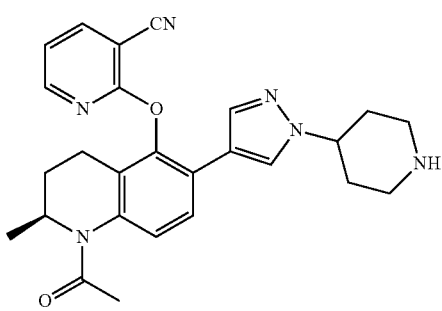 [SMILES: CC(=O)N1c2ccc(-c3cnn(C4CCNCC4)c3)c(Oc3ncccc3C#N)c2CC[C@@H]1C]

$^1$H NMR (400 MHz, CD$_3$OD) δ ppm 1.17 (d, J=6.80 Hz, 3H), 1.38-1.55 (m, 1H), 1.79-1.92 (m, 2H), 1.98-2.09 (m, 2H), 2.15-2.41 (m, 5H), 2.52-2.70 (m, 1H), 2.70-2.79 (m, 2H), 3.10-3.18 (m, 2H), 4.18-4.28 (m, 1H), 4.70-4.85 (m, 1H), 7.12-7.18 (m, 1H), 7.20-7.39 (m, 1H), 7.53 (d, J=8.40 Hz, 1H), 7.74 (s, 1H), 7.95 (s, 1H), 8.11-8.22 (m, 2H). MS (ESI, pos. ion) m/z 457 [M+H]+.

(S)-1-(2-methyl-5-(5-methylpyrimidin-2-yloxy)-6-(1-(piperidin-4-yl)-1H-pyrazol-4-yl)-3,4-dihydroquinolin-1(2H)-yl)ethanone (I-144)

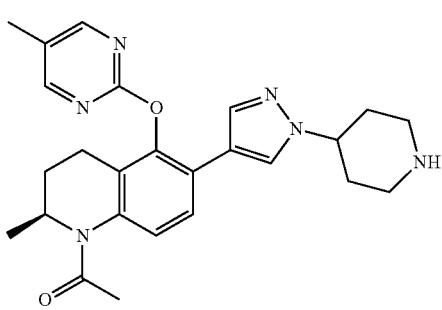 [SMILES: CC(=O)N1c2ccc(-c3cnn(C4CCNCC4)c3)c(Oc3ncc(C)cn3)c2CC[C@@H]1C]

$^1$H NMR (400 MHz, CD$_3$OD) δ ppm 1.02 (d, J=6.80 Hz, 3H), 1.25-1.35 (m, 1H), 1.65-1.78 (m, 2H), 1.85-95 (m, 2H), 2.01-2.21 (m, 8H), 2.45-2.65 (m, 3H), 2.98-3.059 (m, 2H), 4.05-4.12 (m, 1H), 4.58-4.75 (m, 1H), 7.05-7.20 (m, 1H), 7.43 (d, J=8.40 Hz, 1H), 7.66 (s, 1H), 7.87 (s, 1H), 8.27 (s, 2H). MS (ESI, pos. ion) m/z 447 [M+H]+.

(S)-1-(2-methyl-6-(1-(piperidin-4-yl)-1H-pyrazol-4-yl)-5-(pyrazin-2-yloxy)-3,4-dihydroquinolin-1(2H)-yl)ethanone (I-145)

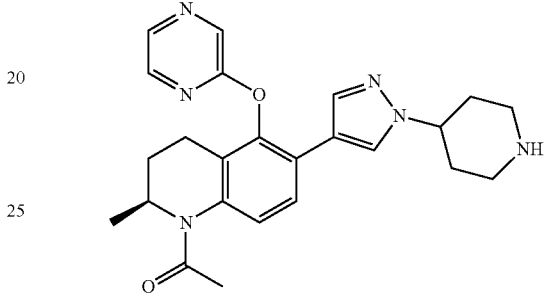

$^1$H NMR (400 MHz, CD$_3$OD) δ ppm 1.05 (d, J=6.40 Hz, 3H), 1.20-1.45 (m, 1H), 1.65-1.80 (m, 2H), 1.82-1.89 (m, 2H), 2.05-2.25 (m, 5H), 2.48-2.65 (m, 3H), 2.95-3.05 (m, 2H), 4.05-4.15 (m, 1H), 4.60-4.78 (m, 1H), 7.10-7.25 (m, 1H), 7.43 (d, J=8.40 Hz, 1H), 7.61 (s, 1H), 7.84 (s, 1H), 7.92 (s, 1H), 8.10 (d, J=2.80 Hz, 1H), 8.38 (s, 1H). MS (ESI, pos. ion) m/z 433 [M+H]+.

(S)-methyl 5-(4-cyanophenoxy)-2-methyl-6-(1-(piperidin-4-yl)-1H-pyrazol-4-yl)-3,4-dihydroquinoline-1(2H)-carboxylate (I-146)

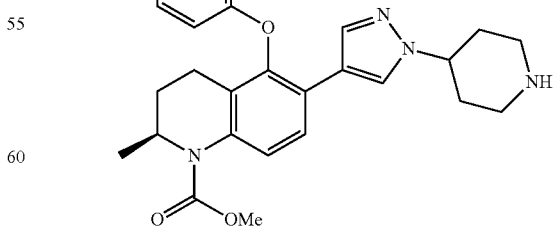

$^1$H NMR (300 MHz, CD$_3$OD) δ ppm 1.17 (d, J=6.30 Hz, 3H), 1.52-1.65 (m, 1H), 1.75-1.95 (m, 2H), 1.97-2.15 (m, 3H), 2.38-2.48 (m, 1H), 2.55-2.78 (m, 3H), 3.08-3.15 (m, 2H), 3.83 (s, 1H), 4.15-4.29 (m, 1H), 4.65-4.72 (m, 1H), 6.89-6.99 (m, 2H), 7.53-7.70 (m, 5H), 7.92 (s, 1H). MS (ESI, pos. ion) m/z 472 [M+H]⁺.

(S)-methyl 5-(3-cyanopyridin-2-yloxy)-2-methyl-6-(1-(piperidin-4-yl)-1H-pyrazol-4-yl)-3,4-dihydro-quinoline-1(2H)-carboxylate (I-147)

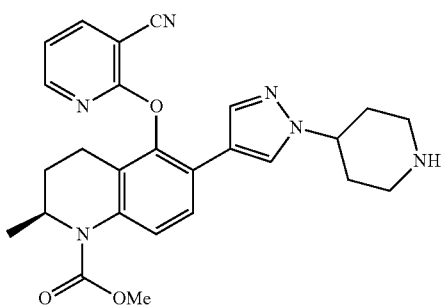 [SMILES: COC(=O)N1c2ccc(-c3cnn(C4CCNCC4)c3)c(Oc3ncccc3C#N)c2CC[C@@H]1C]

¹H NMR (400 MHz, CD₃OD) δ ppm 1.18 (d, J=6.80 Hz, 3H), 1.59-1.68 (m, 1H), 1.80-1.95 (m, 2H), 1.99-2.15 (m, 3H), 2.30-2.70 (br m, 2H), 2.70-2.80 (m, 2H), 3.10-3.19 (m, 2H), 3.83 (s, 3H), 4.15-4.25 (m, 1H), 4.65-4.71 (m, 1H), 7.11-7.15 (m, 1H), 7.45 (d, J=8.80 Hz, 1H), 7.61 (d, J=8.80 Hz, 1H), 7.71 (s, 1H), 7.91 (s, 1H), 8.12-8.21 (m, 2H). MS (ESI, pos. ion) m/z 473 [M+H]⁺.

(S)-methyl 5-(2-cyano-3-fluorophenoxy)-2-methyl-6-(1-(piperidin-4-yl)-1H-pyrazol-4-yl)-3,4-dihydro-quinoline-1(2H)-carboxylate (I-148)

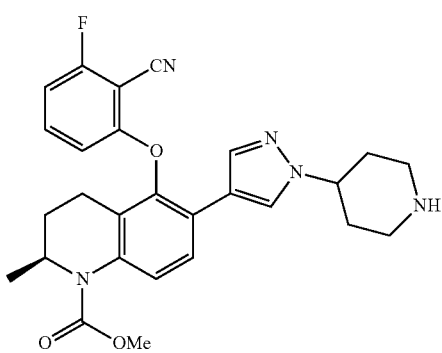 [SMILES: COC(=O)N1c2ccc(-c3cnn(C4CCNCC4)c3)c(Oc3cccc(F)c3C#N)c2CC[C@@H]1C]

¹H NMR (300 MHz, CD₃OD) δ ppm 1.19 (d, J=6.60 Hz, 3H), 1.58-1.72 (m, 1H), 1.78-1.99 (m, 2H), 1.98-2.15 (m, 3H), 2.68-2.82 (m, 2H), 3.07-3.19 (m, 2H), 4.20-4.30 (m, 1H), 4.60-4.75 (m, 1H), 6.25-6.35 (m, 1H), 6.96 (t, J=8.40 Hz, 1H), 7.39-7.55 (m, 2H), 7.65-7.71 (m, 1H), 7.76 (s, 1H), 7.95 (s, 1H). MS (ESI, pos. ion) m/z 490 [M+H]⁺.

(S)-methyl 5-(3-chloro-2-cyanophenoxy)-2-methyl-6-(1-(piperidin-4-yl)-1H-pyrazol-4-yl)-3,4-dihydro-quinoline-1(2H)-carboxylate (I-149)

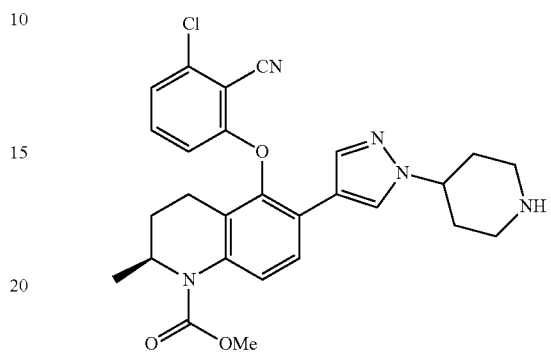

¹H NMR (300 MHz, CD₃OD) δ ppm 1.05-1.20 (m, 3H), 1.58-1.72 (m, 1H), 1.79-1.95 (m, 2H), 1.98-2.15 (m, 3H), 2.20-2.70 (br s, 1H), 2.65-2.80 (m, 3H), 3.05-3.15 (m, 2H), 3.82 (s, 3H), 4.15-4.25 (m, 1H), 4.60-4.75 (m, 1H), 6.30-6.50 (m, 1H), 7.20 (d, J=8.10 Hz, 1H), 7.38 (t, J=8.40 Hz, 1H), 7.52 (d, J=8.70 Hz, 1H), 7.60-7.75 (m, 2H), 7.93 (s, 1H). MS (ESI, pos. ion) m/z 506 [M+H]⁺.

(S)-2-(1-(cyclopropanecarbonyl)-2-methyl-6-(1-(piperidin-4-yl)-1H-pyrazol-4-yl)-1,2,3,4-tetrahydro-quinolin-5-yloxy)benzonitrile (I-150)

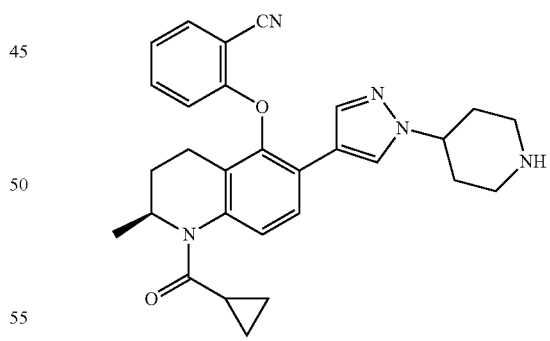

¹H NMR (300 MHz, CD₃OD) δ ppm 0.75-0.90 (m, 1H), 0.95-1.05 (m, 2H), 1.15-1.30 (m, 4H), 1.45-1.65 (m, 1H), 1.81-1.99 (m, 2H), 2.01-2.13 (m, 3H), 2.20-2.60 (m, 2H), 2.65-2.82 (m, 3H), 3.10-3.21 (m, 2H), 4.20-4.35 (m, 1H), 4.80-4.95 (m, 1H), 6.50-6.64 (m, 1H), 7.18 (t, J=7.50 Hz, 1H), 7.45-7.55 (m, 2H), 7.67 (d, J=8.40 Hz, 1H), 7.78-7.82 (m, 2H), 8.03 (s, 1H). MS (ESI, pos. ion) m/z 483 [M+H]⁺.

(S)-2-(1-(cyclopropanecarbonyl)-2-methyl-6-(1-(piperidin-4-yl)-1H-pyrazol-4-yl)-1,2,3,4-tetrahydro-quinolin-5-yloxy)-6-fluorobenzonitrile (I-151)

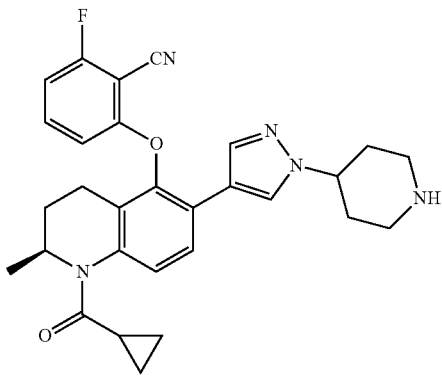 [SMILES: C[C@H]1CCc2c(ccc(-c3cnn(C4CCNCC4)c3)c2Oc2cccc(F)c2C#N)N1C(=O)C1CC1]

¹H NMR (400 MHz, CD₃OD) δ ppm 0.75-0.82 (m, 1H), 0.85-1.01 (m, 2H), 1.10-1.21 (m, 4H), 1.45-1.60 (m, 1H), 1.79-1.92 (m, 2H), 1.95-2.10 (m, 3H), 2.15-2.30 (m, 1H), 2.30-2.50 (m, 1H), 2.65-2.79 (m, 3H), 3.08-3.19 (m, 2H), 4.15-4.30 (m, 1H), 4.78-4.90 (m, 1H), 6.30-6.40 (m, 1H), 6.90-7.00 (m, 1H), 7.40-7.50 (m, 2H), 7.62 (d, J=8.40 Hz, 1H), 7.78 (s, 1H), 7.98 (s, 1H). MS (ESI, pos. ion) m/z 500 [M+H]⁺.

(S)-4-(1-(cyclopropanecarbonyl)-2-methyl-6-(1-(piperidin-4-yl)-1H-pyrazol-4-yl)-1,2,3,4-tetrahydro-quinolin-5-yloxy)-3-fluorobenzonitrile (I-152)

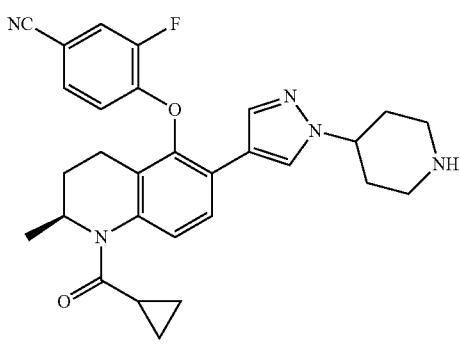 [SMILES: C[C@H]1CCc2c(ccc(-c3cnn(C4CCNCC4)c3)c2Oc2ccc(C#N)cc2F)N1C(=O)C1CC1]

¹H NMR (400 MHz, CD₃OD) δ ppm 0.65-0.70 (m, 1H), 0.78-0.92 (m, 2H), 0.99-1.11 (m, 4H), 1.30-1.42 (m, 1H), 1.65-1.80 (m, 2H), 1.85-1.95 (m, 3H), 2.08-2.19 (m, 1H), 2.20-2.30 (m, 1H), 2.50-2.65 (m, 3H), 2.95-3.05 (m, 2H), 4.05-4.15 (m, 1H), 4.65-4.75 (m, 1H), 6.51 (t, J=8.40 Hz, 1H), 7.24 (d, J=8.80 Hz, 1H), 7.36 (d, J=8.40 Hz, 1H), 7.51 (d, J=8.40 Hz, 1H), 7.60-7.70 (m, 2H), 7.80 (s, 1H). MS (ESI, pos. ion) m/z 500 [M+H]⁺.

(S)-2-(1-acetyl-6-(1-cyclopropyl-1H-pyrazol-4-yl)-2-methyl-1,2,3,4-tetrahydroquinolin-5-yloxy)benzonitrile (I-153)

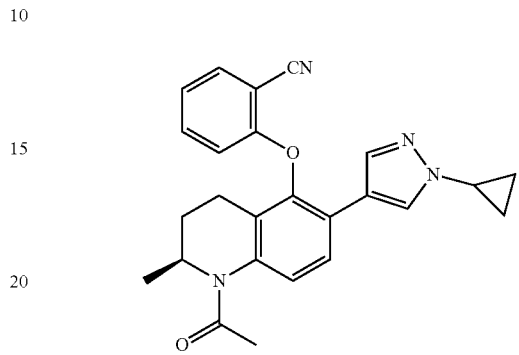

(S)-2-(1-acetyl-6-(1-cyclopropyl-1H-pyrazol-4-yl)-2-methyl-1,2,3,4-tetrahydroquinolin-5-yloxy)benzonitrile was synthesized according to the procedures described above for Example 36, with the following changes: (1) in Step 2, 1-cyclopropyl-4-(4,4,5,5-tetramethyl-1,3,2-dioxaborolan-2-yl)-1H-pyrazole was used in place of tert-butyl 4-(4-(4,4,5,5-tetramethyl-1,3,2-dioxaborolan-2-yl)-1H-pyrazol-1-yl)piperidine-1-carboxylate (3) Step 3 (removal of the Boc-protecting group) was eliminated. ¹H NMR (300 MHz, CD₃OD) δ ppm 0.92-1.05 (m, 4H), 1.16 (d, J=6.30 Hz, 3H), 1.35-1.52 (m, 1H), 2.10-2.40 (m, 5H), 2.58-2.80 (m, 1H), 3.55-3.65 (m, 1H), 4.68-4.89 (m, 1H), 6.40-6.55 (m, 1H), 7.05-7.15 (m, 1H), 7.30-7.52 (m, 2H), 7.55-7.65 (m, 1H), 7.70-7.80 (m, 2H), 7.96 (s, 1H). MS (ESI, pos. ion) m/z 413 [M+H]⁺.

Example 37

(S)-2-(1-(cyclopropanecarbonyl)-2-methyl-6-(1-methyl-1H-1,2,3-triazol-4-yl)-1,2,3,4-tetrahydro-quinolin-5-yloxy)benzonitrile (I-154)

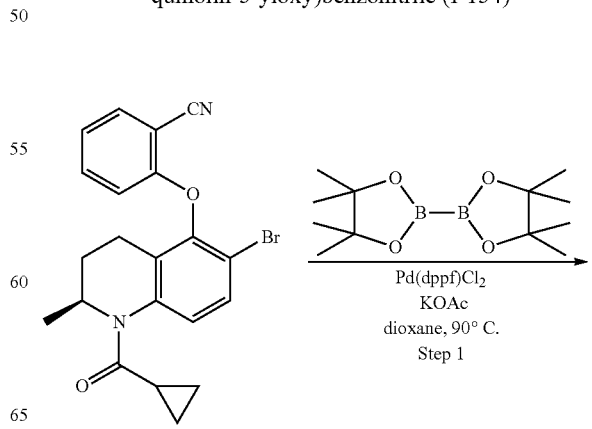

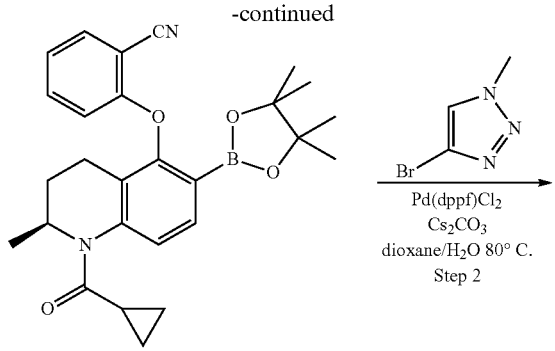

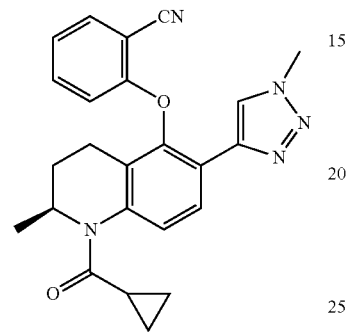

Step 1. (S)-2-(1-(cyclopropanecarbonyl)-2-methyl-6-(4,4,5,5-tetramethyl-1,3,2-dioxaborolan-2-yl)-1,2,3,4-tetrahydroquinolin-5-yloxy)benzonitrile A mixture of (S)-2-(6-bromo-1-(cyclopropanecarbonyl)-2-methyl-1,2,3,4-tetrahydroquinolin-5-yloxy)benzonitrile (0.70 g, 0.17 mmol, 1.00 equiv), bis(pinacolato)diboron (0.216 g, 0.85 mmol), [1,1'-bis(diphenylphosphino)ferrocene]dichloropalladium(II) dichloromethane adduct (0.015 g, 0.02 mmol), potassium acetate (0.042 g, 0.43 mmol) in 1,4-dioxane (10 mL) was stirred overnight at 90° C. The mixture was cooled to room temperature, diluted with ethyl acetate (50 mL), washed with water (20 mL) and brine (20 mL), dried over anhydrous sodium sulfate, filtered, and concentrated under vacuum. The residue was purified via column chromatography on silica gel (eluting with 25% ethyl acetate-petroleum ether) to afford (S)-2-(1-(cyclopropanecarbonyl)-2-methyl-6-(4,4,5,5-tetramethyl-1,3,2-dioxaborolan-2-yl)-1,2,3,4-tetrahydroquinolin-5-yloxy)benzonitrile (0.050 g, 64%) as yellow oil. MS (ESI, pos. ion) m/z 459 [M+H]$^+$.

Step 2. (S)-2-(1-(cyclopropanecarbonyl)-2-methyl-6-(1-methyl-1H-1,2,3-triazol-4-yl)-1,2,3,4-tetrahydroquinolin-5-yloxy)benzonitrile A mixture of (S)-2-(1-(cyclopropanecarbonyl)-2-methyl-6-(4,4,5,5-tetramethyl-1,3,2-dioxaborolan-2-yl)-1,2,3,4-tetrahydroquinolin-5-yloxy)benzonitrile (0.050 g, 0.11 mmol), 4-bromo-1-methyl-1H-1,2,3-triazole (0.025 g, 0.15 mmol), cesium carbonate (0.110 g, 0.34 mmol), [1,1'-bis(diphenylphosphino)ferrocene]dichloropalladium(II) dichloromethane adduct (0.10 g, 0.01 mmol) in 1,4-dioxane (10 mL) and water (3 mL) was stirred overnight at 80° C. The reaction mixture was cooled to room temperature and filtered through a short pad of Celite. The filtrate was concentrated and purified via preparative thin layer chromatography (eluting with 25% ethyl acetate-petroleum ether) to afford (S)-2-(1-(cyclopropanecarbonyl)-2-methyl-6-(1-methyl-1H-1,2,3-triazol-4-yl)-1,2,3,4-tetrahydroquinolin-5-yloxy)

benzonitrile (0.006 g, 13%) as a white solid. MS (ESI, pos. ion) m/z 414 [M+H]$^+$. $^1$H NMR (400 MHz, CD$_3$OD) δ ppm 0.75-0.82 (m, 1H), 0.88-1.05 (m, 2H), 1.15-1.25 (m, 3H), 1.28-1.35 (m, 1H), 1.45-1.55 (m, 1H), 1.97-2.05 (m, 1H), 2.15-2.25 (m, 1H), 2.27-2.45 (m, 1H), 2.60-2.75 (m, 1H), 4.09 (s, 3H), 4.75-4.85 (m, 1H), 6.58 (d, J=8.40 Hz, 1H), 7.17 (t, J=8.00 Hz, 1H), 7.45-7.51 (m, 1H), 7.57 (d, J=8.40 Hz, 1H), 7.78 (d, J=1.20 Hz, 1H), 8.03-8.07 (m, 2H). MS (ESI, pos. ion) m/z 414 [M+H]$^+$.

Example 38

(S)-4-(1-acetyl-2-methyl-6-(1-(piperidin-4-yl)-1H-pyrazol-4-yl)-1,2,3,4-tetrahydroquinolin-5-yloxy)benzamide (I-155)

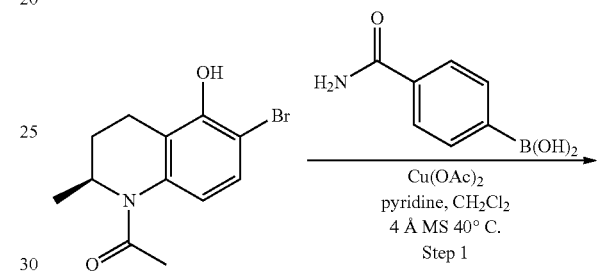

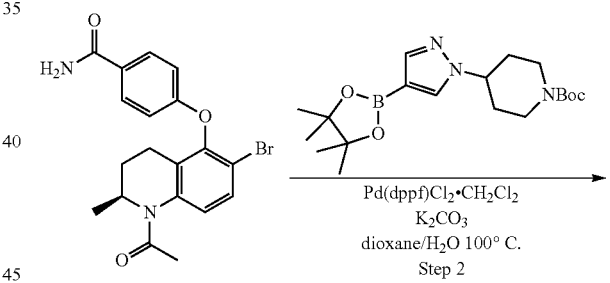

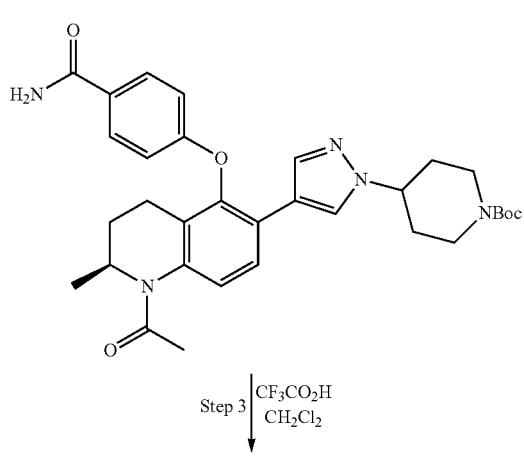

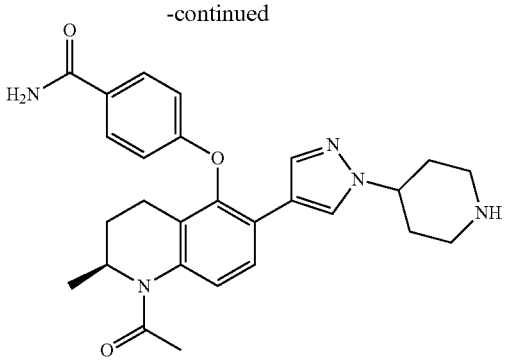

Step 1. 4-[[(2S)-1-acetyl-6-bromo-2-methyl-1,2,3,4-tetrahydroquinolin-5-yl]oxy]benzamide A 100-mL round-bottom flask equipped with a balloon filled with air was charged with 1-[(2S)-6-bromo-5-hydroxy-2-methyl-1,2,3,4-tetrahydroquinolin-1-yl]ethan-1-one (0.300 g, 1.06 mmol), (4-carbamoylphenyl)boronic acid (0.437 g, 2.65 mmol), copper acetate (0.386 g, 2.12 mmol), pyridine (1 mL), dichloromethane (40 mL), and 4 Å molecular sieves (4.0 g). The resulting mixture stirred for 3 days at room temperature. The reaction mixture was filtered through a pad of Celite, and the filtrate was concentrated under vacuum. The residue was purified by preparative thin layer chromatography (eluting with 20-25% ethyl acetate-petroleum ether) to afford 4-[[(2S)-1-acetyl-6-bromo-2-methyl-1,2,3,4-tetrahydroquinolin-5-yl]oxy]benzamide (0.148 g, 35%) as a yellow oil. MS (ESI, pos. ion) m/z 403, 405 [M+H]$^+$.

Step 2. tert-butyl 4-[4-[(2S)-1-acetyl-5-(4-carbamoylphenoxy)-2-methyl-1,2,3,4-tetrahydroquinolin-6-yl]-1H-pyrazol-1-yl]piperidine-1-carboxylate A mixture of 4-[[(2S)-1-acetyl-6-bromo-2-methyl-1,2,3,4-tetrahydroquinolin-5-yl]oxy]benzamide (0.080 g, 0.20 mmol), tert-butyl 4-[4-(tetramethyl-1,3,2-dioxaborolan-2-yl)-1H-pyrazol-1-yl]piperidine-1-carboxylate (0.090 g, 0.24 mmol), potassium carbonate (0.082 g, 0.59 mmol), and [1,1'-bis(diphenylphosphino)ferrocene]dichloropalladium(II) dichloromethane adduct (0.016 g, 0.02 mmol) in 1,4-dioxane (20 mL) and water (2 mL) stirred overnight at 100° C. The reaction mixture was cooled to room temperature, filtered through a pad of Celite, and concentrated under vacuum. The residue was purified via preparative thin layer chromatography (eluting with 50% ethyl acetate-petroleum ether) to afford tert-butyl 4-[4-[(2S)-1-acetyl-5-(4-carbamoylphenoxy)-2-methyl-1,2,3,4-tetrahydroquinolin-6-yl]-1H-pyrazol-1-yl]piperidine-1-carboxylate (0.080 g, 70%) as a yellow oil. MS (ESI, pos. ion) m/z 574 [M+H]$^+$.

Step 3. (S)-4-(1-acetyl-2-methyl-6-(1-(piperidin-4-yl)-1H-pyrazol-4-yl)-1,2,3,4-tetrahydroquinolin-5-yloxy)benzamide Trifluoroacetic acid (3.5 mL) was added to a solution of tert-butyl 4-[4-[(2S)-1-acetyl-5-(4-carbamoylphenoxy)-2-methyl-1,2,3,4-tetrahydroquinolin-6-yl]-1H-pyrazol-1-yl]piperidine-1-carboxylate (0.080 g, 0.14 mmol) in dichloromethane (30 mL). The reaction mixture stirred for 2 h at room temperature and was then concentrated under vacuum. The residue was dissolved in dichloromethane (50 mL), washed with saturated aqueous potassium carbonate solution (3×20 mL) and brine (20 mL), dried over anhydrous sodium sulfate, filtered, and concentrated under vacuum. The residue was purified by preparative-HPLC with the following conditions (Prep-HPLC-12): Column, XBridge Prep C18 OBD Column, 19×150 mm 5 um 13 nm; mobile phase: water (0.05% ammonium bicarbonate) and acetonitrile (20% to 95% acetonitrile in 18 min, flow rate: 20 mL/min); Detector, UV 254/220 nm. This afforded 4-[[(2S)-1-acetyl-2-methyl-6-[1-(piperidin-4-yl)-1H-pyrazol-4-yl]-1,2,3,4-tetrahydroquinolin-5-yl]oxy]benzamide (0.033 g, 50%) as an off-white solid.

$^1$H NMR (300 MHz, CD$_3$OD) δ ppm 1.15 (d, J=6.60 Hz, 3H), 1.25-1.45 (m, 1H), 1.72-1.92 (m, 2H), 1.95-2.05 (m, 2H), 2.15-2.40 (m, 5H), 2.60-2.80 (m, 3H), 3.05-3.15 (m, 2H), 4.15-4.25 (m, 1H), 4.79 (br s, 1H), 6.87 (d, J=8.70 Hz, 2H), 7.38 (br s, 1H), 7.64 (d, J=8.70 Hz, 1H), 7.75-7.89 (m, 3H), 7.96 (s, 1H). MS (ESI, pos. ion) m/z 474 [M+H]$^+$.

The following examples were made according to the procedure outlined for Example 38:

(S)-1-(5-(3-methoxyphenoxy)-2-methyl-6-(1-(piperidin-4-yl)-1H-pyrazol-4-yl)-3,4-dihydroquinolin-1(2H)-yl)ethanone (I-156)

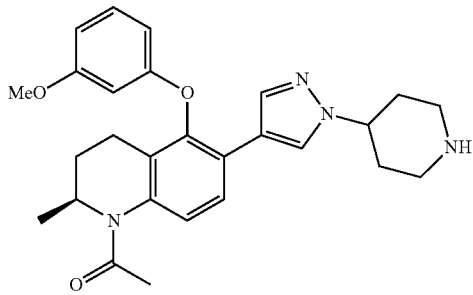 [SMILES: COc1cccc(Oc2c(-c3cnn(C4CCNCC4)c3)ccc3c2CC[C@H](C)N3C(C)=O)c1]

$^1$H NMR (300 MHz, CD$_3$OD) δ ppm 1.11 (d, J=6.60 Hz, 3H), 1.22-1.42 (m, 1H), 1.75-1.89 (m, 2H), 1.98-2.08 (m, 2H), 2.23 (s, 3H), 2.14-2.35 (m, 2H), 2.64-2.79 (m, 3H), 3.09-3.18 (m, 2H), 3.72 (s, 3H), 4.15-4.25 (m, 1H), 4.68-4.83 (m, 1H), 6.28-35 (m, 2H), 6.52-6.57 (m, 1H), 7.14 (t, J=8.10 Hz, 1H), 7.20-7.35 (m, 1H), 7.61 (d, J=8.40 Hz, 1H), 7.80 (s, 1H), 7.96 (s, 1H). MS (ESI, pos. ion) m/z 461 [M+H]$^+$.

(S)-1-(5-(2-chlorophenoxy)-2-methyl-6-(1-(piperidin-4-yl)-1H-pyrazol-4-yl)-3,4-dihydroquinolin-1(2H)-yl)ethanone (I-157)

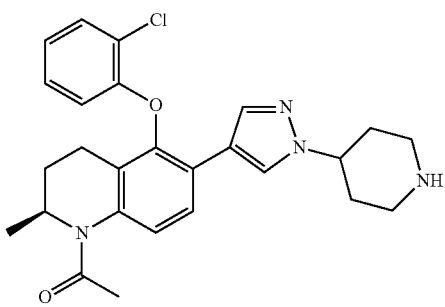 [SMILES: CC(=O)N1c2ccc(-c3cnn(C4CCNCC4)c3)c(Oc3ccccc3Cl)c2CC[C@@H]1C]

¹H NMR (400 MHz, CD₃OD) δ ppm 1.16 (d, J=6.80 Hz, 3H), 1.30-1.45 (m, 1H), 1.75-1.89 (m, 2H), 1.95-2.05 (m, 2H), 2.15-2.35 (m, 5H), 2.55-2.79 (m, 3H), 3.09-3.15 (m, 2H), 4.12-4.22 (m, 1H), 4.78 (br s, 1H), 6.30-6.35 (m, 1H), 6.89-6.97 (m, 1H), 6.99-7.05 (m, 1H), 7.37 (br s, 1H), 7.42-7.49 (m, 1H), 7.64 (d, J=8.40 Hz, 1H), 7.83 (s, 1H), 8.01 (s, 1H). MS (ESI, pos. ion) m/z 465 [M+H]⁺.

(S)-methyl 5-(4-fluorophenoxy)-2-methyl-6-(1-(piperidin-4-yl)-1H-pyrazol-4-yl)-3,4-dihydroquinoline-1(2H)-carboxylate (I-158)

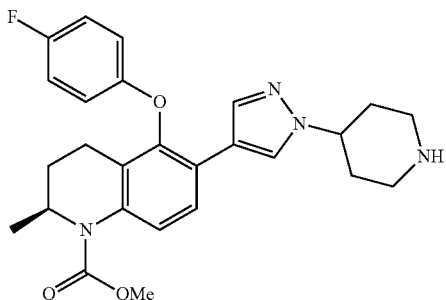 [SMILES: COC(=O)N1c2ccc(-c3cnn(C4CCNCC4)c3)c(Oc3ccc(F)cc3)c2CC[C@@H]1C]

¹H NMR (300 MHz, CD₃OD) δ ppm 1.14 (d, J=6.60 Hz, 3H), 1.48-1.62 (m, 1H), 1.75-1.91 (m, 2H), 1.95-2.15 (m, 3H), 2.35-2.45 (m, 1H), 2.55-2.78 (m, 3H), 3.09-3.18 (m, 2H), 4.15-4.25 (m, 1H), 4.55-4.68 (m, 1H), 6.68-6.78 (m, 2H), 6.91-7.02 (m, 2H), 7.49-7.52 (m, 2H), 7.76 (s, 1H), 7.92 (s, 1H). MS (ESI, pos. ion) m/z 465 [M+H]⁺.

(S)-methyl 5-(4-chlorophenoxy)-2-methyl-6-(1-(piperidin-4-yl)-1H-pyrazol-4-yl)-3,4-dihydroquinoline-1(2H)-carboxylate (I-159)

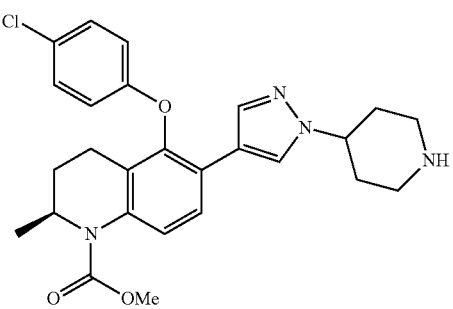 [SMILES: COC(=O)N1c2ccc(-c3cnn(C4CCNCC4)c3)c(Oc3ccc(Cl)cc3)c2CC[C@@H]1C]

¹H NMR (300 MHz, CD₃OD) δ ppm 1.15 (d, J=6.60 Hz, 3H), 1.50-1.62 (m, 1H), 1.75-1.92 (m, 2H), 1.97-2.15 (m, 3H), 2.35-2.48 (m, 1H), 2.52-2.82 (m, 3H), 3.09-3.18 (m, 2H), 4.15-4.25 (m, 1H), 4.55-4.72 (m, 1H), 6.77 (d, J=8.70 Hz, 2H), 7.24 (d, J=9.00 Hz, 2H), 7.45-7.55 (m, 2H), 7.77 (s, 1H), 7.92 (s, 1H). MS (ESI, pos. ion) m/z 481 [M+H]⁺.

(S)-methyl 5-(2-chlorophenoxy)-2-methyl-6-(1-(piperidin-4-yl)-1H-pyrazol-4-yl)-3,4-dihydroquinoline-1(2H)-carboxylate (I-160)

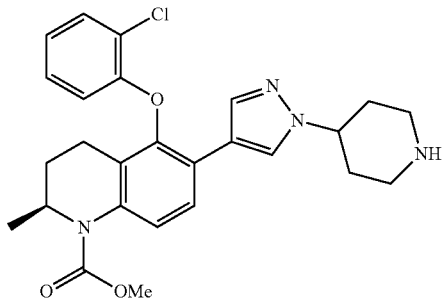 [SMILES: COC(=O)N1c2ccc(-c3cnn(C4CCNCC4)c3)c(Oc3ccccc3Cl)c2CC[C@@H]1C]

¹H NMR (300 MHz, CD₃OD) δ ppm 1.15 (d, J=6.60 Hz, 3H), 1.52-1.68 (m, 1H), 1.72-1.92 (m, 2H), 1.95-2.15 (m, 4H), 2.65-2.80 (m, 3H), 3.05-3.18 (m, 2H), 3.81 (s, 3H), 4.12-4.25 (m, 1H), 4.55-4.75 (m, 1H), 6.28-6.35 (m, 1H), 6.85-6.95 (m, 1H), 6.95-7.05 (m, 1H), 7.42-7.65 (m, 3H), 7.79 (s, 1H), 7.96 (s, 1H). MS (ESI, pos. ion) m/z 481 [M+H]⁺.

(S)-methyl 5-(4-carbamoylphenoxy)-2-methyl-6-(1-(piperidin-4-yl)-1H-pyrazol-4-yl)-3,4-dihydroquinoline-1(2H)-carboxylate (I-161)

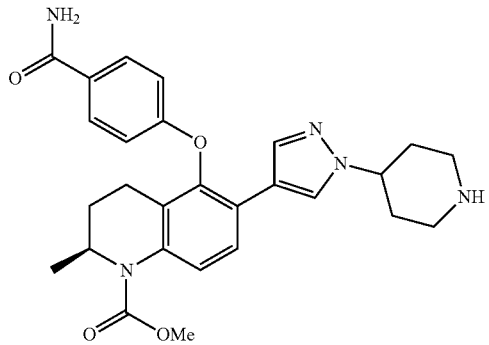 [SMILES: COC(=O)N1c2ccc(-c3cnn(C4CCNCC4)c3)c(Oc3ccc(C(N)=O)cc3)c2CC[C@@H]1C]

¹H NMR (400 MHz, CD₃OD) δ ppm 1.16 (d, J=6.40 Hz, 3H), 1.52-1.62 (m, 1H), 1.83-1.95 (m, 2H), 1.99-2.13 (m, 3H), 2.42-2.49 (m, 1H), 2.55-2.65 (m, 1H), 2.78-2.85 (m, 2H), 3.15-3.22 (m, 2H), 3.83 (s, 3H), 4.19-4.25 (m, 1H), 4.62-4.65 (m, 1H), 6.84 (d, J=8.80 Hz, 2H), 7.50-7.60 (m, 2H), 7.75-7.82 (m, 3H), 7.91 (s, 1H). MS (ESI, pos. ion) m/z 490 [M+H]+.

(S)-methyl 5-(3-cyano-4-fluorophenoxy)-2-methyl-6-(1-(piperidin-4-yl)-1H-pyrazol-4-yl)-3,4-dihydro-quinoline-1(2H)-carboxylate (I-162)

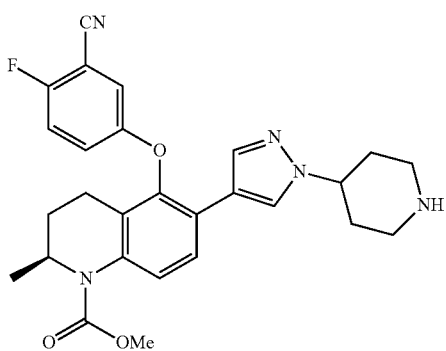

¹H NMR (400 MHz, CD₃OD) δ ppm 1.16 (d, J=6.80 Hz, 3H), 1.55-1.65 (m, 1H), 1.80-1.98 (m, 2H), 1.99-2.12 (m, 3H), 2.39-2.48 (m, 1H), 2.60-2.80 (m, 3H), 3.10-3.20 (m, 2H), 3.82 (s, 3H), 4.19-4.30 (m, 1H), 4.60-4.70 (m, 1H), 7.05-7.22 (m, 3H), 7.50-7.62 (m, 2H), 7.75 (s, 1H), 7.94 (s, 1H). MS (ESI, pos. ion) m/z 490 [M+H]+.

(S)-methyl 5-(3-chloro-4-fluorophenoxy)-2-methyl-6-(1-(piperidin-4-yl)-1H-pyrazol-4-yl)-3,4-dihydro-quinoline-1(2H)-carboxylate (I-163)

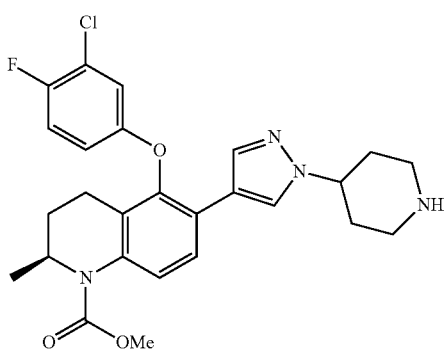 [SMILES: COC(=O)N1c2ccc(-c3cnn(C4CCNCC4)c3)c(Oc3ccc(F)c(Cl)c3)c2CC[C@@H]1C]

¹H NMR (300 MHz, CD₃OD) δ ppm 1.17 (d, J=6.60 Hz, 3H), 1.52-1.65 (m, 1H), 1.78-1.95 (m, 2H0, 1.97-2.15 (m, 3H), 2.38-2.45 (m, 1H), 2.58-2.79 (m, 3H), 3.09-3.15 (m, 2H), 3.83 (s, 3H), 4.15-4.30 (m, 1H), 4.60-4.72 (m, 1H), 6.68-6.72 (m, 1H), 6.85-6.89 (m, 1H), 7.13 (t, J=9.00 Hz, 1H), 7.52-7.63 (m, 2H), 7.76 (s, 1H), 7.95 (s, 1H). MS (ESI, pos. ion) m/z 499 [M+H]+.

(S)-cyclopropyl(5-(4-fluorophenoxy)-2-methyl-6-(1-(piperidin-4-yl)-1H-pyrazol-4-yl)-3,4-dihydroquinolin-1(2H)-yl)methanone (I-164)

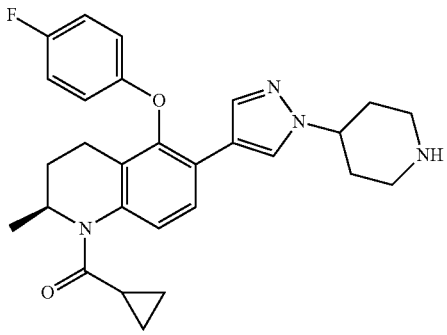 [SMILES: C[C@H]1CCc2c(ccc(-c3cnn(C4CCNCC4)c3)c2Oc2ccc(F)cc2)N1C(=O)C1CC1]

¹H NMR (400 MHz, CD₃OD) δ ppm 0.65-0.8 2 (m, 1H), 0.85-1.01 (m, 2H), 1.01-1.19 (m, 4H), 1.30-1.45 (m, 1H), 1.75-1.90 (m, 2H), 1.90-2.05 (m, 3H), 2.09-2.35 (m, 2H), 2.60-2.80 (m, 3H), 3.05-3.20 (m, 2H), 4.11-4.28 (m, 1H), 4.70-4.82 (m, 1H), 6.79 (s, 1H), 6.90-7.03 (m, 2H), 7.39 (d, J=8.00 Hz, 1H), 7.62 (d, J=8.00 Hz, 1H), 7.79 (s, 1H), 7.96 (s, 1H). MS (ESI, pos. ion) m/z 475 [M+H]+.

(S)-(5-(2-chlorophenoxy)-2-methyl-6-(1-(piperidin-4-yl)-1H-pyrazol-4-yl)-3,4-dihydroquinolin-1(2H)-yl)(cyclopropyl)methanone (I-165)

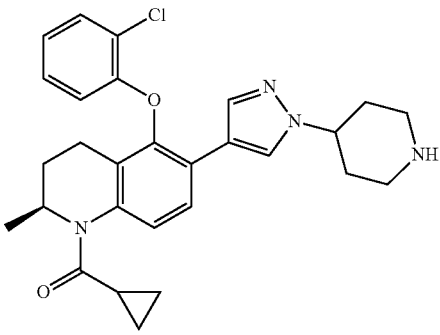 [SMILES: C[C@H]1CCc2c(ccc(-c3cnn(C4CCNCC4)c3)c2Oc2ccccc2Cl)N1C(=O)C1CC1]

¹H NMR (400 MHz, CD₃OD) δ ppm 0.72-0.82 (m, 1H), 0.90-1.05 (m, 2H), 1.10-1.25 (m, 4H), 1.40-1.50 (m, 1H), 1.78-1.95 (m, 2H), 1.95-2.10 (m, 3H), 2.20-2.40 (m, 2H), 2.70-2.90 (m, 3H), 3.10-3.18 (m, 2H), 4.15-4.25 (m, 1H), 4.75-4.85 (m, 1H), 6.35-6.42 (m, 1H), 6.90-6.98 (m, 1H), 7.01-7.09 (m, 1H), 7.40-7.50 (m, 2H), 7.65 (d, J=8.40 Hz, 1H), 7.84 (s, 1H), 8.01 (s, 1H). MS (ESI, pos. ion) m/z 491 [M+H]⁺.

(S)-(5-(4-chlorophenoxy)-2-methyl-6-(1-(piperidin-4-yl)-1H-pyrazol-4-yl)-3,4-dihydroquinolin-1(2H)-yl)(cyclopropyl)methanone (I-166)

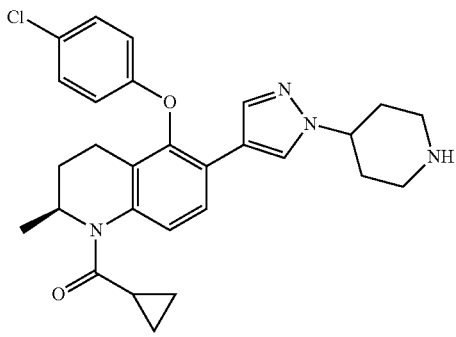 [SMILES: C[C@H]1CCc2c(ccc(-c3cnn(C4CCNCC4)c3)c2Oc2ccc(Cl)cc2)N1C(=O)C1CC1]

¹H NMR (400 MHz, CD₃OD) δ ppm 0.72-0.80 (m, 1H), 0.85-1.05 (m, 2H), 1.10-1.19 (m, 4H), 1.35-1.45 (m, 1H), 1.75-1.90 (m, 2H), 1.95-2.05 (m, 3H), 2.15-2.35 (m, 2H), 2.65-2.79 (m, 3H), 3.10-3.20 (m, 2H), 4.15-4.30 (m, 1H), 4.75-4.85 (m, 1H), 6.80 (dd, J=10.80, 2.00 Hz, 2H), 7.26 (dd, J=10.80, 2.00 Hz, 2H), 7.40 (d, J=8.40 Hz, 1H), 7.63 (d, J=8.40 Hz, 1H), 7.79 (s, 1H), 7.96 (s, 1H). MS (ESI, pos. ion) m/z 491 [M+H]⁺.

(S)-4-(1-(cyclopropanecarbonyl)-2-methyl-6-1-(piperidin-4-yl)-1H-pyrazol-4-yl)-1,2,3,4-tetrahydroquinolin-5-yloxy)benzonitrile (I-167)

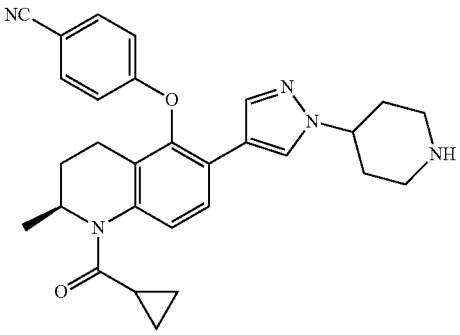 [SMILES: C[C@H]1CCc2c(ccc(-c3cnn(C4CCNCC4)c3)c2Oc2ccc(C#N)cc2)N1C(=O)C1CC1]

¹H NMR (300 MHz, CD₃OD) δ ppm 0.69-0.80 (m, 1H), 0.83-1.01 (m, 2H), 1.09-1.22 (m, 4H), 1.30-1.50 (m, 1H), 1.70-1.90 (m, 2H), 1.90-2.01 (m, 3H), 2.11-2.35 (m, 2H), 2.60-2.75 (m, 3H), 3.03-3.12 (m, 2H), 4.10-4.25 (m, 1H), 4.70-4.85 (m, 1H), 6.95 (d, J=8.70 Hz, 2H), 7.41 (d, J=8.40 Hz, 2H), 7.55-7.68 (m, 3H), 7.73 (s, 1H), 7.92 (s, 1H). MS (ESI, pos. ion) m/z 491 [M+H]⁺.

(S)-cyclopropyl(2-methyl-5-phenoxy-6-(1-(piperidin-4-yl)-1H-pyrazol-4-yl)-3,4-dihydroquinolin-1(2H)-yl)methanone (I-168)

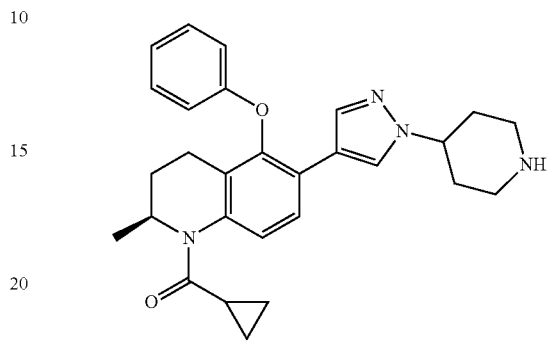

¹H NMR (400 MHz, CD₃OD) δ ppm 0.75-0.80 (m, 1H), 0.90-1.01 (m, 2H), 1.10-1.20 (m, 4H), 1.32-1.45 (m, 1H), 1.75-1.92 (m, 2H), 1.95-2.05 (m, 3H), 2.15-2.35 (m, 2H), 2.65-2.75 (m, 3H), 3.05-3.15 (m, 2H), 4.10-4.25 (m, 1H), 4.70-4.82 (m, 1H), 6.80 (d, J=8.00 Hz, 2H), 6.98 (t, J=7.20 Hz, 1H), 7.28 (t, J=8.00 Hz, 2H), 7.39 (d, J=8.40 Hz, 1H), 7.80 (s, 1H), 7.98 (s, 1H). MS (ESI, pos. ion) m/z 457 [M+H]⁺.

(S)-(5-(3-chloro-4-fluorophenoxy)-2-methyl-6-(1-(piperidin-4-yl)-1H-pyrazol-4-yl)-3,4-dihydroquinolin-1(2H)-yl)(cyclopropyl)methanone (I-169)

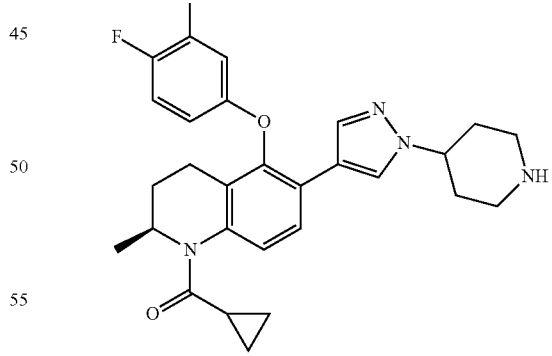

¹H NMR (400 MHz, CD₃OD) δ ppm 0.62-0.72 (m, 1H), 0.78-0.90 (m, 2H), 0.98-1.10 (m, 4H), 1.25-1.35 (m, 1H), 1.68-1.80 (m, 2H), 1.85-1.95 (m, 3H), 2.09-2.25 (m, 2H), 2.55-2.70 (m, 3H), 2.95-3.05 (m, 2H), 4.05-4.15 (m, 1H), 4.65-4.75 (m, 1H), 6.55-6.65 (m, 1H), 6.75-6.85 (m, 1H), 7.03 (t, J=8.80 Hz, 1H), 7.31 (d, J=8.40 Hz, 1H), 7.51 (d, J=8.40 Hz, 1H), 7.67 (s, 1H), 7.83 (s, 1H). MS (ESI, pos. ion) m/z 509 [M+H]⁺.

(S)-(6-(1-(azetidin-3-yl)-1H-pyrazol-4-yl)-5-(4-fluorophenoxy)-2-methyl-3,4-dihydroquinolin-1(2H)-yl)(cyclopropyl)methanone (I-170)

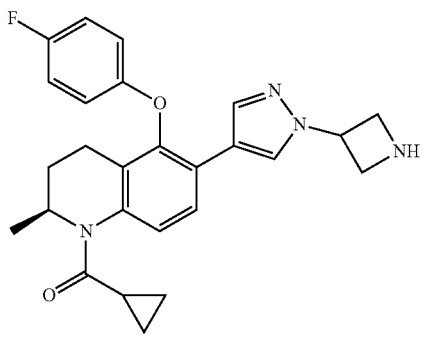 [SMILES: C[C@H]1CCc2c(ccc(-c3cnn(C4CNC4)c3)c2Oc2ccc(F)cc2)N1C(=O)C1CC1]

¹H NMR (400 MHz, CD₃OD) δ ppm 0.58-0.70 (m, 1H), 0.78-0.92 (m, 2H), 0.95-1.10 (m, 4H), 1.20-1.30 (m, 1H), 1.80-1.90 (m, 1H), 2.05-2.18 (m, 2H), 2.55-2.65 (m, 1H), 3.75-3.85 (m, 2H), 3.88-3.95 (m, 2H), 4.60-4.70 (m, 1H), 5.01-5.12 (m, 1H), 6.65-6.70 (m, 2H), 6.85-6.90 (m, 2H), 7.28 (d, J=8.40 Hz, 1H), 7.51 (d, J=8.40 Hz, 1H), 7.77 (s, 1H), 7.93 (s, 1H). MS (ESI, pos. ion) m/z 447 [M+H]⁺.

(S)-cyclopropyl(5-(3-fluorophenoxy)-2-methyl-6-(1-(piperidin-4-yl)-1H-pyrazol-4-yl)-3,4-dihydroquinolin-1(2H)-yl)methanone (I-171)

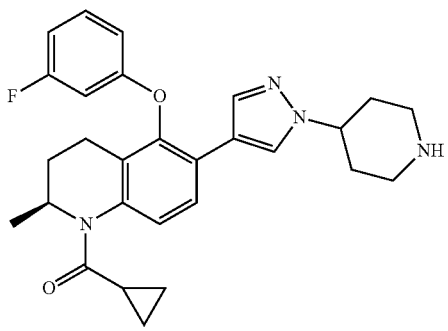 [SMILES: C[C@H]1CCc2c(ccc(-c3cnn(C4CCNCC4)c3)c2Oc2cccc(F)c2)N1C(=O)C1CC1]

¹H NMR (400 MHz, CD₃OD) δ ppm 0.62-0.72 (m, 1H), 0.78-0.90 (m, 2H), 0.95-1.10 (m, 4H), 1.20-1.35 (m, 1H), 1.68-1.80 (m, 2H), 1.85-1.95 (m, 3H), 2.05-2.25 (m, 2H), 2.55-2.70 (m, 3H), 2.95-3.10 (m, 2H), 4.05-4.15 (m, 1H), 4.65-4.70 (m, 1H), 6.40-6.52 (m, 2H), 6.55-6.65 (m, 1H), 7.10-7.15 (m, 1H), 7.30 (d, J=8.40 Hz, 1H), 7.52 (d, J=8.40 Hz, 1H), 7.69 (s, 1H), 7.85 (s, 1H). MS (ESI, pos. ion) m/z 475 [M+H]⁺.

(S)-cyclopropyl(5-(3,4-difluorophenoxy)-2-methyl-6-(1-(piperidin-4-yl)-1H-pyrazol-4-yl)-3,4-dihydroquinolin-1(2H)-yl)methanone (I-172)

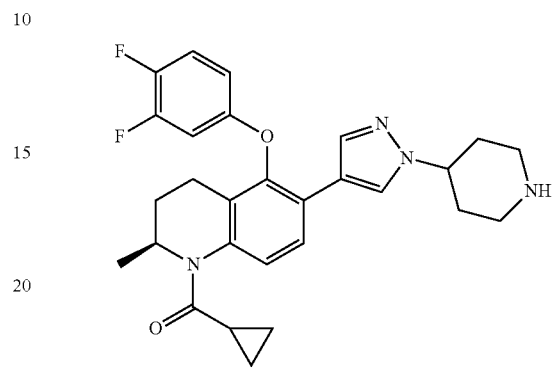

¹H NMR (400 MHz, CD₃OD) δ ppm 0.65-0.70 (m, 1H), 0.75-0.90 (m, 2H), 0.95-1.10 (m, 4H), 1.25-1.35 (m, 1H), 1.65-1.80 (m, 2H), 1.85-1.95 (m, 3H), 2.05-2.25 (m, 2H), 2.55-2.65 (m, 3H), 2.95-3.05 (m, 2H), 4.05-4.18 (m, 1H), 4.65-4.75 (m, 1H), 6.40-6.50 (m, 1H), 6.55-6.70 (m, 1H), 6.95-7.10 (m, 1H), 7.30 (d, J=8.40 Hz, 1H), 7.51 (d, J=8.40 Hz, 1H), 7.68 (s, 1H), 7.86 (s, 1H). MS (ESI, pos. ion) m/z 493 [M+H]⁺.

(S)-(6-(1-(azetidin-3-yl)-1H-pyrazol-4-yl)-5-(3-fluorophenoxy)-2-methyl-3,4-dihydroquinolin-1(2H)-yl)(cyclopropyl)methanone (I-173)

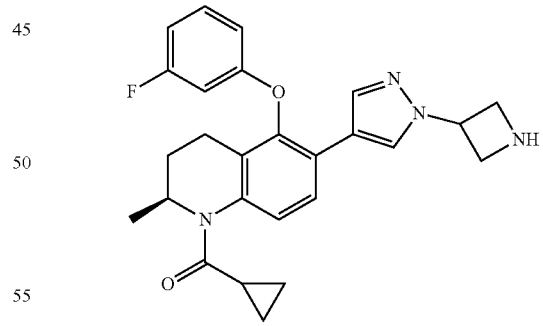

¹H NMR (400 MHz, CD₃OD) δ ppm 0.65-0.72 (m, 1H), 0.75-0.90 (m, 2H), 0.95-1.10 (m, 4H), 1.20-1.35 (m, 1H), 1.85-1.95 (m, 1H), 2.05-2.25 (m, 2H), 2.55-2.65 (m, 1H), 3.55-3.70 (m, 1H), 3.75-3.85 (m, 1H), 3.90-3.98 (m, 1H), 4.65-4.72 (m, 1H), 5.05-5.12 (m, 1H), 6.40-6.50 (m, 2H), 6.55-6.70 (m, 1H), 7.05-7.15 (m, 1H), 7.25-7.30 (m, 1H), 7.53 (d, J=8.40 Hz, 1H), 7.70-7.79 (m, 1H), 7.90-8.00 (m, 1H). MS (ESI, pos. ion) m/z 447 [M+H]+.

(S)-(6-(1-(azetidin-3-yl)-1H-pyrazol-4-yl)-5-(3,4-difluorophenoxy)-2-methyl-3,4-dihydroquinolin-1(2H)-yl)(cyclopropyl)methanone (I-174)

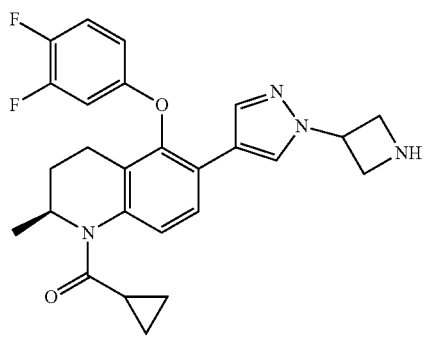 [SMILES: C[C@H]1CCc2c(ccc(-c3cnn(C4CNC4)c3)c2Oc2ccc(F)c(F)c2)N1C(=O)C1CC1]

¹H NMR (400 MHz, CD₃OD) δ ppm 0.60-0.70 (m, 1H), 0.75-0.90 (m, 2H), 0.95-1.10 (m, 4H), 1.20-1.35 (m, 1H), 1.85-1.90 (m, 1H), 2.05-2.22 (m, 2H), 2.55-2.62 (m, 1H), 3.75-3.85 (m, 2H), 3.92-3.98 (m, 2H), 4.65-4.70 (m, 1H), 5.05-5.15 (m, 1H), 6.40-6.50 (m, 1H), 6.60-6.68 (m, 1H), 6.95-7.05 (m, 1H), 7.30 (d, J=8.40 Hz, 1H), 7.52 (d, J=8.00 Hz, 1H), 7.77 (s, 1H), 7.93 (s, 1H). MS (ESI, pos. ion) m/z 465 [M+H]+.

(S)-(6-(1-(azetidin-3-yl)-1H-pyrazol-4-yl)-2-methyl-5-phenoxy-3,4-dihydroquinolin-1(2H)-yl)(cyclopropyl)methanone (I-175)

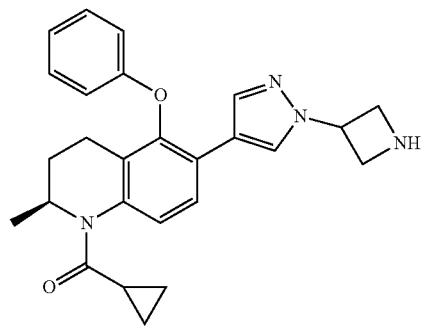 [SMILES: C[C@H]1CCc2c(ccc(-c3cnn(C4CNC4)c3)c2Oc2ccccc2)N1C(=O)C1CC1]

¹H NMR (400 MHz, CD₃OD) δ ppm 0.75-0.80 (m, 1H), 0.85-1.02 (m, 2H), 1.10-1.20 (m, 4H), 1.30-1.40 (m, 1H), 1.92-2.02 (m, 1H), 2.12-2.32 (m, 2H), 2.65-2.75 (m, 1H), 4.48 (d, J=7.60, 4H), 4.75-4.81 (m, 1H), 5.30-41 (m, 1H), 6.75-6.82 (m, 2H), 6.95-7.01 (m, 1H), 7.23-7.29 (m, 2H), 7.40 (d, J=8.40 Hz, 1H), 7.64 (d, J=8.40 Hz, 1H), 7.98 (s, 1H), 8.03 (s, 1H). MS (ESI, pos. ion) m/z 429 [M+H]+.

(S)-methyl 5-(3,4-difluorophenoxy)-2-methyl-6-(1-(piperidin-4-yl)-1H-pyrazol-4-yl)-3,4-dihydroquinoline-1(2H)-carboxylate (I-176)

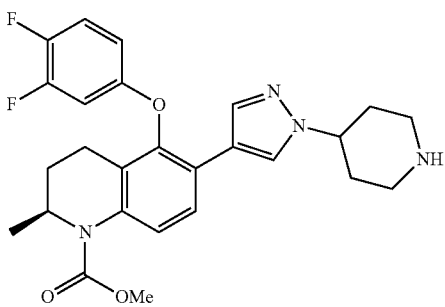 [SMILES: COC(=O)N1c2ccc(-c3cnn(C4CCNCC4)c3)c(Oc3ccc(F)c(F)c3)c2CC[C@@H]1C]

¹H NMR (400 MHz, CD₃OD) δ ppm 1.04 (d, J=6.40 Hz, 3H), 1.45-1.52 (m, 1H), 1.68-1.82 (m, 2H), 1.87-2.02 (m, 3H), 2.25-2.35 (m, 1H), 2.45-2.70 (m, 3H), 3.00-3.10 (m, 2H), 3.70 (s, 3H), 4.05-4.15 (m, 1H), 4.48-4.55 (m, 1H), 6.35-6.42 (m, 1H), 6.55-6.65 (m, 1H), 6.95-7.05 (m, 1H), 7.45-7.55 (m, 2H), 7.65 (s, 1H), 7.80 (s, 1H). MS (ESI, pos. ion) m/z 483 [M+H]+.

(S)-methyl 6-(1-(azetidin-3-yl)-1H-pyrazol-4-yl)-5-(3-chlorophenoxy)-2-methyl-3,4-dihydroquinoline-1(2H)-carboxylate (I-177)

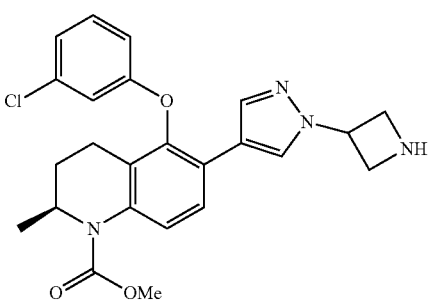 [SMILES: COC(=O)N1c2ccc(-c3cnn(C4CNC4)c3)c(Oc3cccc(Cl)c3)c2CC[C@@H]1C]

¹H NMR (300 MHz, DMSO-d6) δ ppm 1.06 (d, J=6.60 Hz, 3H), 1.46-1.67 (m, 1H), 1.89-2.09 (m, 1H), 2.37-2.48 (m, 2H), 3.60-3.90 (m, 7H), 4.45-4.70 (m, 1H), 5.03-5.20 (m, 1H), 6.59-6.64 (m, 1H), 6.86 (s, 1H), 6.95-7.11 (m, 1H), 7.21-7.33 (m, 1H), 7.58 (s, 2H), 7.78 (s, 1H), 8.14 (s, 1H). MS (ESI, pos. ion) m/z 453 [M+H]⁺.

(S)-(6-(1-(azetidin-3-yl)-1H-pyrazol-4-yl)-5-(3-chlorophenoxy)-2-methyl-3,4-dihydroquinolin-1(2H)-yl)(cyclopropyl)methanone (I-178)

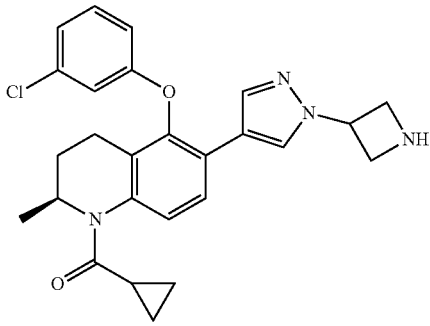 [SMILES: C[C@H]1CCc2c(ccc(-c3cnn(C4CNC4)c3)c2Oc2cccc(Cl)c2)N1C(=O)C1CC1]

¹H NMR (400 MHz, CD₃OD) δ ppm 0.59-0.75 (m, 1H), 0.76-0.99 (m, 2H), 0.99-1.14 (m, 4H), 1.14-1.41 (m, 1H), 1.80-1.99 (m, 1H), 2.02-2.31 (m, 2H), 2.58-2.69 (m, 1H), 3.48-3.71 (m, 1H), 3.77-3.98 (m, 1H), 3.98-4.07 (m, 1H), 4.58-4.71 (m, 1H), 4.82-4.90 (m, 1H), 5.00-5.22 (m, 1H), 6.55-6.67 (m, 1H), 6.67-6.80 (m, 1H), 6.80-6.97 (m, 1H), 7.13-7.22 (m, 1H), 7.23-7.39 (m, 1H), 7.42-7.49 (m, 1H), 7.53-7.62 (m, 1H), 7.62-7.80 (m, 1H), 7.85-8.08 (m, 1H). MS (ESI, pos. ion) m/z 463 [M+H]⁺.

(S)-(5-(3-chlorophenoxy)-2-methyl-6-(1-(piperidin-4-yl)-1H-pyrazol-4-yl)-3,4-dihydroquinolin-1(2H)-yl)(cyclopropyl)methanone (I-179)

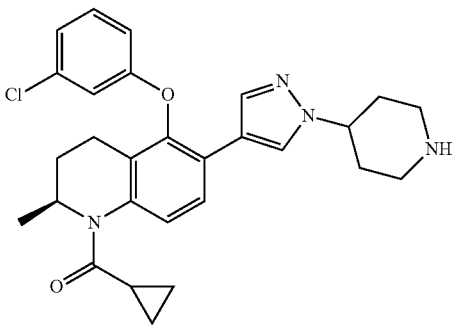 [SMILES: C[C@H]1CCc2c(ccc(-c3cnn(C4CCNCC4)c3)c2Oc2cccc(Cl)c2)N1C(=O)C1CC1]

¹H NMR (400 MHz, CD₃OD) δ ppm 0.69-0.84 (m, 1H), 0.90-1.09 (m, 2H), 1.10-1.26 (m, 4H), 1.37-1.52 (m, 1H), 1.80-1.95 (m, 2H), 1.98-2.11 (m, 3H), 2.18-2.39 (m, 1H), 2.39-2.43 (m, 1H), 2.68-2.84 (m, 3H), 3.17-3.22 (m, 2H), 4.14-4.34 (m, 1H), 4.70-4.89 (m, 1H), 6.62-6.78 (m, 1H), 6.80-6.85 (m, 1H), 6.93-7.07 (m, 1H), 7.14-7.30 (m, 1H), 7.34-7.46 (m, 1H), 7.55-7.66 (m, 1H), 7.79 (s, 1H), 8.00 (s, 1H). MS (ESI, pos. ion) m/z 491 [M+H]⁺.

(S)-methyl 6-(1-(azetidin-3-yl)-1H-pyrazol-4-yl)-5-(3,5-difluorophenoxy)-2-methyl-3,4-dihydroquinoline-1(2H)-carboxylate (I-180)

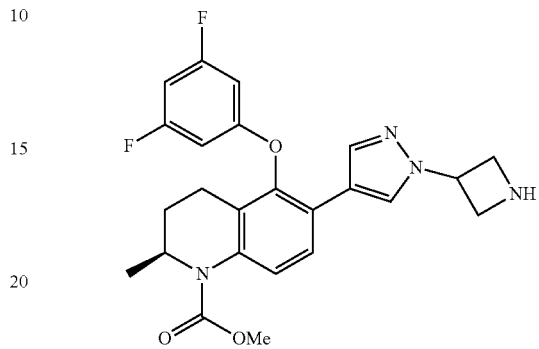

¹H NMR (300 MHz, CD₃OD) δ ppm 1.16 (d, J=6.30 Hz, 3H), 1.55-1.69 (m, 1H), 2.06-2.18 (m, 1H), 2.41-2.55 (m, 1H), 2.62-2.75 (m, 1H), 3.82 (s, 3H), 3.90-4.01 (m, 2H), 4.01-4.15 (m, 1H), 4.64-4.75 (m, 1H), 5.21-5.31 (m, 1H), 6.39 (d, J=8.40 Hz, 2H), 6.54-6.63 (m, 1H), 7.55-7.65 (m, 2H), 7.86 (s, 1H), 8.04 (s, 1H). MS (ESI, pos. ion) m/z 455 [M+H]⁺.

(S)-(6-(1-(azetidin-3-yl)-1H-pyrazol-4-yl)-5-(3,5-difluorophenoxy)-2-methyl-3,4-dihydroquinolin-1(2H)-yl)(cyclopropyl)methanone (I-181)

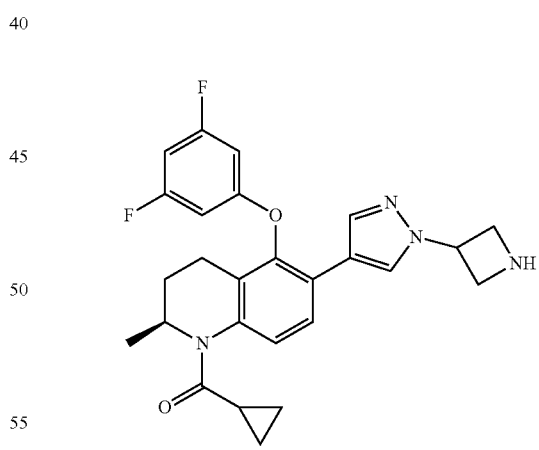

¹H NMR (400 MHz, CD₃OD) δ ppm 0.78-0.81 (m, 1H), 0.95-1.00 (m, 2H), 1.13-1.20 (m, 4H), 1.40-1.53 (m, 1H), 2.01-2.08 (m, 1H), 2.22-2.27 (m, 1H), 2.29-2.38 (m, 1H), 2.69-2.74 (m, 1H), 3.85-3.94 (m, 2H), 4.04-4.08 (m, 2H), 4.75-4.84 (m, 1H), 5.22-5.28 (m, 1H), 6.41-6.48 (m, 2H), 6.53-6.63 (m, 1H), 7.44 (d, J=8.40 Hz, 1H), 7.63 (d, J=8.40 Hz, 1H), 7.88 (s, 1H), 8.07 (s, 1H). MS (ESI, pos. ion) m/z 465 [M+H]⁺.

(S)-methyl 5-(3,5-difluorophenoxy)-2-methyl-6-(1-(piperidin-4-yl)-1H-pyrazol-4-yl)-3,4-dihydroquinoline-1(2H)-carboxylate (I-182)

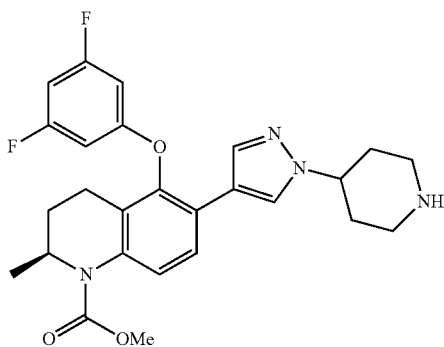 [SMILES: COC(=O)N1c2ccc(-c3cnn(C4CCNCC4)c3)c(Oc3cc(F)cc(F)c3)c2CC[C@@H]1C]

¹H NMR (400 MHz, CD₃OD) δ ppm 1.17 (m, 3H), 1.56-1.67 (m, 1H), 185-1.97 (m, 2H), 2.01-2.11 (m, 2H), 2.11-2.18 (m, 1H), 2.43-2.52 (m, 1H), 2.62-2.69 (m, 1H), 2.71-2.82 (m, 2H), 3.14-3.12 (m, 2H), 3.83 (s, 3H), 4.22-4.33 (m, 1H), 4.75-4.84 (m, 1H), 6.41-6.48 (m, 2H), 6.53-6.63 (m, 1H), 7.54-7.57 (m, 1H), 7.63-7.65 (m, 1H), 7.77 (s, 1H), 7.96 (s, 1H). MS (ESI, pos. ion) m/z 483 [M+H]⁺.

(S)-cyclopropyl(5-(3,5-difluorophenoxy)-2-methyl-6-(1-(piperidin-4-yl)-1H-pyrazol-4-yl)-3,4-dihydroquinolin-1(2H)-yl)methanone (I-183)

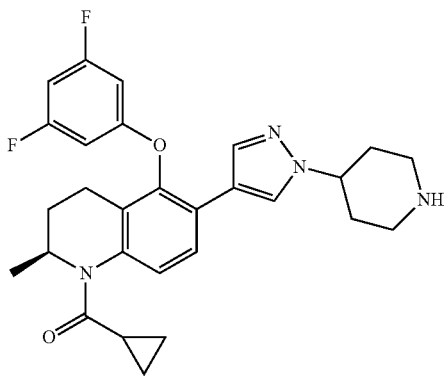 [SMILES: C[C@H]1CCc2c(ccc(-c3cnn(C4CCNCC4)c3)c2Oc2cc(F)cc(F)c2)N1C(=O)C1CC1]

¹H NMR (300 MHz, CD₃OD) δ ppm 0.76-7.84 (m, 1H), 0.91-1.03 (m, 2H), 1.11-1.21 (m, 4H), 1.41-1.52 (m, 1H), 1.87-2.11 (m, 5H), 2.22-2.41 (m, 2H), 3.20-3.28 (m, 2H), 6.39-6.46 (m, 2H), 6.53-6.63 (m, 1H), 7.43 (d, J=8.40 Hz, 1H), 7.63 (d, J=8.70 Hz, 1H), 7.80 (s, 1H), 8.00 (s, 1H). MS (ESI, pos. ion) m/z 493 [M+H]⁺.

(S)-(6-(5-amino-1,3,4-thiadiazol-2-yl)-2-methyl-5-phenoxy-3,4-dihydroquinolin-1(2H)-yl)(cyclopropyl)methanone (I-184)

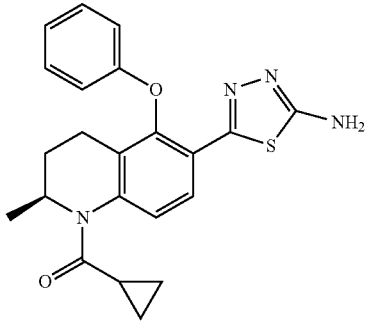 [SMILES: C[C@H]1CCc2c(ccc(-c3nnc(N)s3)c2Oc2ccccc2)N1C(=O)C1CC1]

¹H NMR (400 MHz, CD₃OD) δ ppm 0.79-0.88 (m, 1H), 0.92-1.09 (m, 2H), 1.11-1.25 (m, 4H), 1.38-1.49 (m, 1H), 1.96-2.08 (m, 1H), 2.14-2.24 (m, 1H), 2.24-2.35 (m, 1H), 2.62-2.73 (m, 1H), 4.73-4.82 (m, 1H), 6.75-6.89 (m, 2H), 6.97-7.12 (m, 1H), 7.20-7.37 (m, 2H), 7.42-7.53 (m, 1H), 8.08-8.19 (m, 1H). MS (ESI, pos. ion) m/z 407 [M+H]⁺.

(2S)-methyl 5-(4-fluorophenoxy)-2-methyl-6-(1-(pyrrolidin-3-yl)-1H-pyrazol-4-yl)-3,4-dihydroquinoline-1(2H)-carboxylate (I-185)

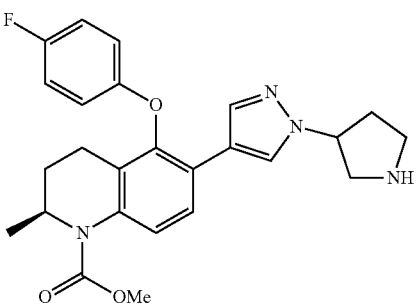 [SMILES: COC(=O)N1c2ccc(-c3cnn(C4CCNC4)c3)c(Oc3ccc(F)cc3)c2CC[C@@H]1C]

¹H NMR (400 MHz, CD₃OD) δ ppm 1.15 (d, J=6.40 Hz, 3H), 1.48-1.52 (m, 1H), 2.01-2.11 (m, 2H), 2.20-2.30 (m, 1H), 2.38-2.45 (m, 1H), 2.55-2.70 (m, 1H), 2.90-3.01 (m, 1H), 3.02-3.25 (m, 3H), 3.82 (s, 3H), 4.60-4.70 (m, 1H), 4.80-4.95 (m, 1H), 6.68-6.75 (m, 2H), 6.91-7.00 (m, 2H), 7.50-7.58 (m, 2H), 7.78 (s, 1H), 7.92 (s, 1H). MS (ESI, pos. ion) m/z 451 [M+H]⁺.

(2S)-methyl 5-(4-fluorophenoxy)-2-methyl-6-(1-(octahydrocyclopenta[c]pyrrol-5-yl)-1H-pyrazol-4-yl)-3,4-dihydroquinoline-1(2H)-carboxylate (I-186)

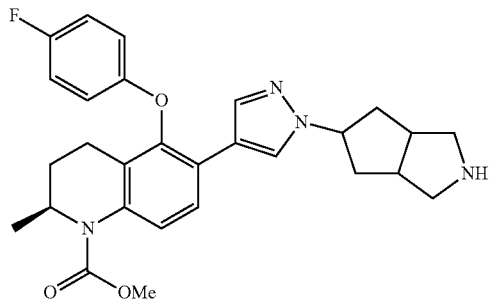 [SMILES: COC(=O)N1c2ccc(-c3cnn(C4CC5CNCC5C4)c3)c(Oc3ccc(F)cc3)c2CC[C@@H]1C]

¹H NMR (300 MHz, CD₃OD) δ ppm 1.14 (d, J=6.60 Hz, 3H), 1.48-1.62 (m, 1H), 1.79-1.90 (m, 2H), 1.98-2.10 (m, 1H), 2.15-2.25 (m, 2H), 2.35-2.45 (m, 1H), 2.58-2.70 (m, 5H), 2.95-3.05 (m, 2H), 3.80 (s, 3H), 4.58-4.80 (m, 2H), 6.68-6.72 (m, 2H), 6.93-7.02 (m, 2H), 7.50-7.60 (m, 2H), 7.76 (s, 1H), 7.89 (s, 1H). MS (ESI, pos. ion) m/z 491 [M+H]⁺.

(S)-cyclopropyl(2-methyl-5-phenoxy-6-(1H-1,2,3-triazol-4-yl)-3,4-dihydroquinolin-1(2H)-yl)methanone (I-187)

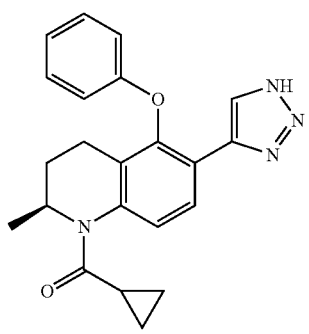 [SMILES: C[C@H]1CCc2c(ccc(-c3c[nH]nn3)c2Oc2ccccc2)N1C(=O)C1CC1]

For (S)-cyclopropyl(2-methyl-5-phenoxy-6-(1H-1,2,3-triazol-4-yl)-3,4-dihydroquinolin-1(2H)-yl)methanone, 1-benzyl-4-bromo-1H-1,2,3-triazole was used as the aryl bromide source. The benzyl group was removed using the hydrogenation conditions outlined above for Intermediate 1, Step 2. ¹H NMR (400 MHz, CD₃OD) δ ppm 0.75-0.87 (m, 1H), 0.91-1.03 (m, 2H), 1.11-1.22 (m, 4H), 1.39-1.52 (m, 1H), 1.95-2.08 (m, 1H), 2.17-2.29 (m, 1H), 2.29-2.38 (m, 1H), 2.66-2.82 (m, 1H), 4.73-4.88 (m, 1H), 6.71-6.89 (m, 2H), 6.96-7.22 (m, 1H), 7.21-7.38 (m, 2H), 7.44-7.53 (m, 1H), 8.03 (s, 1H), 8.03-8.14 (m, 1H). MS (ESI, pos. ion) m/z 375 [M+H]⁺.

Methyl (S)-5-(3-fluorophenoxy)-2-methyl-6-(1-(piperidin-4-yl)-1H-pyrazol-4-yl)-3,4-dihydroquinoline-1(2H)-carboxylate (I-188)

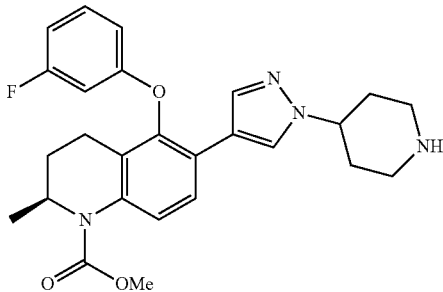 [SMILES: COC(=O)N1c2ccc(-c3cnn(C4CCNCC4)c3)c(Oc3cccc(F)c3)c2CC[C@@H]1C]

MS (ESI, pos. ion) m/z 465 [M+H]⁺.

Methyl (S)-5-(3-chlorophenoxy)-2-methyl-6-(1-(piperidin-4-yl)-1H-pyrazol-4-yl)-3,4-dihydroquinoline-1(2H)-carboxylate (I-189)

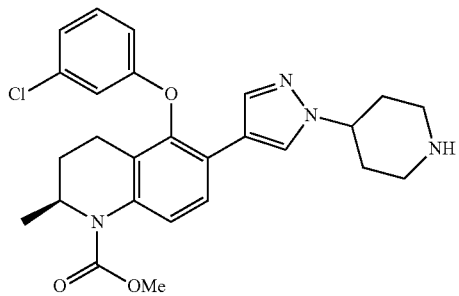 [SMILES: COC(=O)N1c2ccc(-c3cnn(C4CCNCC4)c3)c(Oc3cccc(Cl)c3)c2CC[C@@H]1C]

MS (ESI, pos. ion) m/z 481 [M+H]⁺.

(S)-1-(5-(4-fluorophenoxy)-2-methyl-6-(1-(piperidin-4-yl)-1H-pyrazol-4-yl)-3,4-dihydroquinolin-1(2H)-yl)ethanone (I-190)

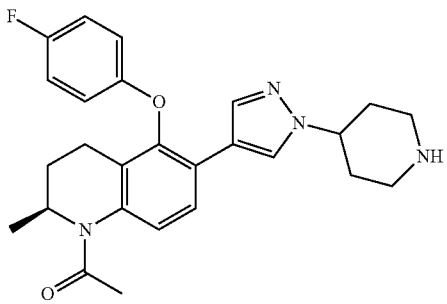 [SMILES: CC(=O)N1c2ccc(-c3cnn(C4CCNCC4)c3)c(Oc3ccc(F)cc3)c2CC[C@@H]1C]

¹H NMR (300 MHz, CD₃OD) δ ppm 1.10-1.15 (m, 3H), 1.30-1.43 (m, 1H), 1.76-1.86 (m, 2H), 1.94-2.10 (m, 2H), 2.20-2.35 (m, 5H), 2.63-2.76 (m, 3H), 3.06-3.18 (m, 2H), 4.15-4.26 (m, 1H), 4.69-4.81 (m, 1H), 6.70-6.78 (m, 2H), 6.97-7.03 (m, 2H), 7.30 (br s, 1H), 7.61 (d, J=8.40 Hz, 1H), 7.78 (s, 1H), 7.95 (s, 1H). MS (ESI, pos. ion) m/z 449 [M+H]$^+$.

(S)-1-(5-(4-chlorophenoxy)-2-methyl-6-(1-(piperidin-4-yl)-1H-pyrazol-4-yl)-3,4-dihydroquinolin-1(2H)-yl)ethanone (I-191)

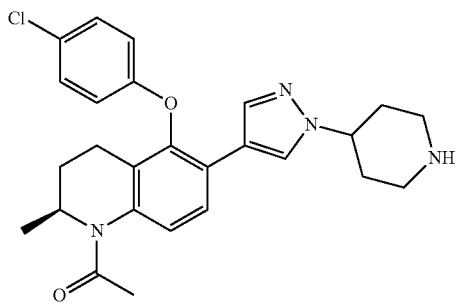 [SMILES: CC(=O)N1c2ccc(-c3cnn(C4CCNCC4)c3)c(Oc3ccc(Cl)cc3)c2CC[C@@H]1C]

$^1$H NMR (300 MHz, CD$_3$OD) δ ppm 1.13 (d, J=6.30 Hz, 3H), 1.35-1.51 (m, 1H), 1.75-1.90 (m, 2H), 1.95-2.10 (m, 2H), 2.15-2.33 (m, 5H), 2.63-2.77 (m, 3H), 3.08-3.15 (m, 2H), 4.15-4.27 (m, 1H), 4.68-4.81 (m, 1H), 6.73-6.80 (m, 2H), 7.20-7.39 (m, 3H), 7.59-7.63 (m, 1H), 7.78 (s, 1H), 7.95 (s, 1H). MS (ESI, pos. ion) m/z 465 [M+H]$^+$.

(S)-methyl 6-(1-(azetidin-3-yl)-1H-pyrazol-4-yl)-5-(3,4-difluorophenoxy)-2-methyl-3,4-dihydroquinoline-1(2H)-carboxylate (I-192)

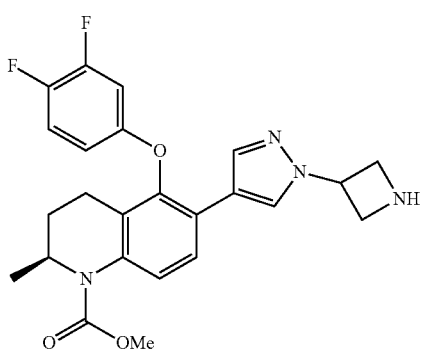 [SMILES: COC(=O)N1c2ccc(-c3cnn(C4CNC4)c3)c(Oc3ccc(F)c(F)c3)c2CC[C@@H]1C]

$^1$H NMR (400 MHz, CD$_3$OD) δ ppm 1.04 (d, J=6.80 Hz, 3H), 1.41-1.48 (m, 1H), 1.93-2.02 (m, 1H), 2.29-2.36 (m, 1H), 2.51-2.57 (m, 1H), 3.70 (s, 3H), 3.77-3.82 (m, 2H), 3.93-3.99 (m, 2H), 4.50-4.60 (m, 1H), 5.08-5.16 (m, 1H), 6.40-6.45 (m, 1H), 6.55-6.64 (m, 1H), 6.95-7.07 (m, 1H), 7.40-7.51 (m, 2H), 7.74 (s, 1H), 7.91 (s, 1H). MS (ESI, pos. ion) m/z 455 [M+H]$^+$.

(S)-methyl 6-(1-(azetidin-3-yl)-1H-pyrazol-4-yl)-2-methyl-5-phenoxy-3,4-dihydroquinoline-1(2H)-carboxylate (I-193)

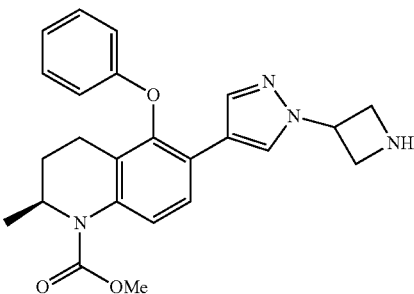 [SMILES: COC(=O)N1c2ccc(-c3cnn(C4CNC4)c3)c(Oc3ccccc3)c2CC[C@@H]1C]

$^1$H NMR (400 MHz, CD$_3$OD) δ ppm 1.03 (d, J=6.80 Hz, 3H), 1.38-1.48 (m, 1H), 1.91-2.01 (m, 1H), 2.35-2.48 (m, 1H), 2.49-2.58 (m, 1H), 3.70 (s, 3H), 3.73-3.82 (m, 2H), 2.85-2.95 (m, 2H), 4.43-4.53 (m, 1H), 5.05-5.13 (m, 1H), 6.65 (d, J=8.80 Hz, 2H), 6.84-6.89 (m, 1H), 7.12-7.18 (m, 2H), 7.47 (s, 1H), 7.91 (s, 1H), 7.74 (s, 1H). MS (ESI, pos. ion) m/z 419 [M+H]$^+$.

(S)-cyclopropyl(5-(2-methoxyphenoxy)-2-methyl-6-(1-(piperidin-4-yl)-1H-pyrazol-4-yl)-3,4-dihydroquinolin-1(2H)-yl)methanone (I-194)

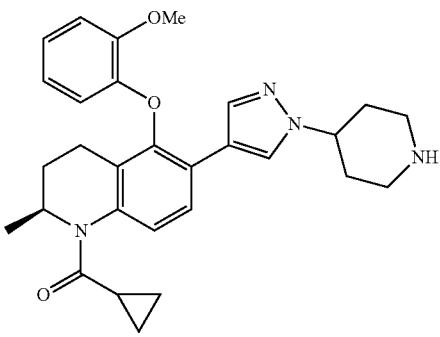 [SMILES: COc1ccccc1Oc1c(-c2cnn(C3CCNCC3)c2)ccc2c1CC[C@H](C)N2C(=O)C1CC1]

$^1$H NMR (400 MHz, CD$_3$OD) δ ppm 0.75-0.81 (m, 1H), 0.92-1.02 (m, 2H), 1.14-1.22 (m, 4H), 1.39-1.49 (m, 1H), 1.77-1.88 (m, 2H), 2.01-2.09 (m, 3H), 2.21-2.35 (m, 2H), 2.69-2.79 (m, 3H), 3.14-3.19 (m, 2H), 4.02 (s, 3H), 4.15-4.25 (m, 1H), 4.75-4.84 (m, 1H), 6.30 (d, J=3.60 Hz, 1H), 6.69-6.73 (m, 1H), 6.94-6.98 (m, 1H), 7.11-7.15 (m, 1H), 7.38 (d, J=6.30 Hz, 1H), 7.65 (d, J=6.30 Hz, 1H), 7.86 (s, 1H), 8.05 (s, 1H). MS (ESI, pos. ion) m/z 487 [M+H]+.

(S)-cyclopropyl(5-(3-methoxyphenoxy)-2-methyl-6-(1-(piperidin-4-yl)-1H-pyrazol-4-yl)-3,4-dihydroquinolin-1(2H)-yl)methanone (I-195)

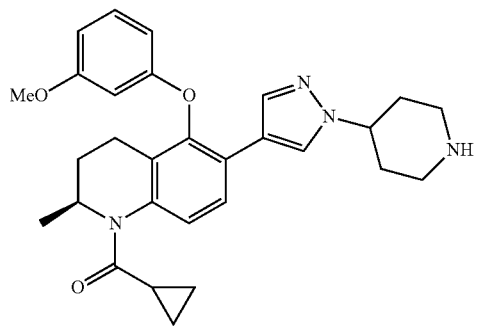 [SMILES: COc1cccc(Oc2c(-c3cnn(C4CCNCC4)c3)ccc3c2CC[C@H](C)N3C(=O)C2CC2)c1]

$^1$H NMR (400 MHz, CD$_3$OD) δ ppm 0.78-0.85 (m, 1H), 0.83-1.01 (m, 2H), 1.12-1.21 (m, 4H), 1.38-1.46 (m, 1H), 1.85-1.95 (m, 2H), 1.97-2.09 (m, 3H), 2.20-2.47 (m, 2H), 2.69-2.81 (m, 3H), 3.15-3.20 (m, 2H), 3.74 (s, 3H), 4.21-4.31 (m, 1H), 4.75-4.85 (m, 1H), 6.33-6.38 (m, 2H), 6.55-6.58 (m, 1H), 7.15-7.19 (m, 1H), 7.37-7.41 (m, 1H), 7.64-7.68 (m, 1H), 7.81 (s, 1H), 7.96 (s, 1H). MS (ESI, pos. ion) m/z 487 [M+H]+.

(S)-cyclopropyl(5-(4-methoxyphenoxy)-2-methyl-6-(1-(piperidin-4-yl)-1H-pyrazol-4-yl)-3,4-dihydroquinolin-1(2H)-yl)methanone (I-196)

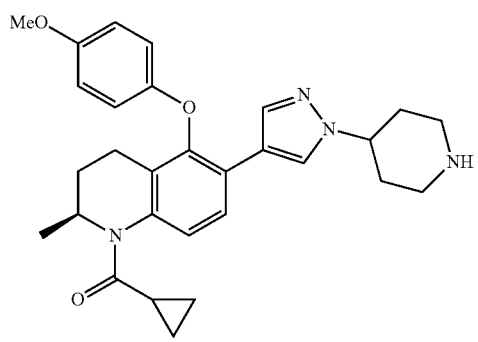 [SMILES: COc1ccc(Oc2c(-c3cnn(C4CCNCC4)c3)ccc3c2CC[C@H](C)N3C(=O)C2CC2)cc1]

$^1$H NMR (400 MHz, CD$_3$OD) δ ppm 0.63-0.71 (m, 1H), 0.83-0.91 (m, 2H), 0.96-1.11 (m, 4H), 1.25-1.31 (m, 1H), 1.66-1.78 (m, 2H), 1.85-1.95 (m, 3H), 2.10-2.21 (m, 2H), 2.57-2.69 (m, 3H), 3.02-3.08 (m, 2H), 3.61 (s, 3H), 4.09-4.19 (m, 1H), 4.63-4.69 (m, 1H), 6.57-6.61 (m, 2H), 6.70-6.73 (m, 2H), 7.24 (d, J=8.40 Hz, 1H), 7.51 (d, J=8.40 Hz, 1H), 7.69 (s, 1H), 7.81 (s, 1H). MS (ESI, pos. ion) m/z 487 [M+H]+.

(S)-methyl 5-(2-methoxyphenoxy)-2-methyl-6-(1-(piperidin-4-yl)-1H-pyrazol-4-yl)-3,4-dihydroquinoline-1(2H)-carboxylate (I-197)

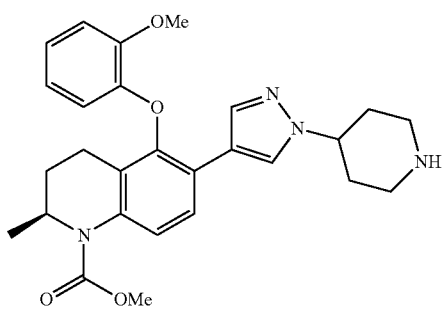 [SMILES: COC(=O)N1c2ccc(-c3cnn(C4CCNCC4)c3)c(Oc3ccccc3OC)c2CC[C@@H]1C]

$^1$H NMR (400 MHz, CD$_3$OD) δ ppm 1.04 (d, J=6.40 Hz, 3H), 1.42-1.49 (m, 1H), 1.69-1.78 (m, 2H), 1.90-1.99 (m, 3H), 2.31-2.39 (m, 1H), 2.52-2.59 (m, 1H), 2.61-2.68 (m, 2H), 3.05-3.11 (m, 2H), 3.70 (s, 3H), 3.89 (s, 3H), 4.05-4.15 (m, 1H), 4.46-4.58 (m, 1H), 6.15-6.17 (m, 1H), 6.52-6.58 (m, 1H), 6.75-6.81 (m, 1H), 6.96-9.99 (m, 1H), 7.44 (s, 1H), 7.71 (s, 1H), 7.90 (s, 1H). MS (ESI, pos. ion) m/z 477 [M+H]+.

(S)-methyl 5-(3-methoxyphenoxy)-2-methyl-6-(1-(piperidin-4-yl)-1H-pyrazol-4-yl)-3,4-dihydroquinoline-1(2H)-carboxylate (I-198)

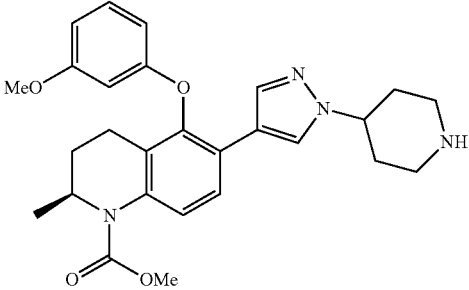 [SMILES: COC(=O)N1c2ccc(-c3cnn(C4CCNCC4)c3)c(Oc3cccc(OC)c3)c2CC[C@@H]1C]

$^1$H NMR (400 MHz, CD$_3$OD) δ ppm 1.15 (d, J=6.40 Hz, 3H), 1.42-1.49 (m, 1H), 1.78-1.91 (m, 2H), 2.01-2.13 (m, 3H), 2.41-2.48 (m, 1H), 7.26-2.78 (m, 3H), 3.12-3.20 (m, 2H), 3.72 (s, 3H), 3.82 (s, 3H), 4.18-4.28 (m, 1H), 4.63-4.72

(m, 1H), 6.29-6.36 (m, 1H), 6.53-6.58 (m, 1H), 7.10-7.17 (m, 1H), 7.55 (s, 1H), 7.77 (s, 1H), 7.91 (s, 1H). MS (ESI, pos. ion) m/z 477 [M+H]$^+$.

(S)-methyl 5-(4-methoxyphenoxy)-2-methyl-6-(1-(piperidin-4-yl)-1H-pyrazol-4-yl)-3,4-dihydroquinoline-1(2H)-carboxylate (I-199)

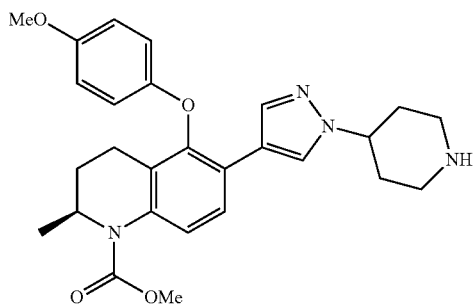 [SMILES: COC(=O)N1c2ccc(-c3cnn(C4CCNCC4)c3)c(Oc3ccc(OC)cc3)c2CC[C@@H]1C]

$^1$H NMR (400 MHz, CD$_3$OD) δ ppm 1.15 (d, J=6.40 Hz, 3H), 1.42-1.49 (m, 1H), 1.80-1.91 (m, 2H), 2.01-2.13 (m, 3H), 2.41-2.48 (m, 1H), 2.63-2.79 (m, 3H), 3.12-3.20 (m, 2H), 3.72 (s, 3H), 3.81 (s, 3H), 4.18-4.28 (m, 1H), 4.63-4.69 (m, 1H), 6.68-6.70 (m, 2H), 6.80-6.80 (m, 2H), 7.53 (s, 2H), 7.53 (s, 1H), 7.95 (s, 1H). MS (ESI, pos. ion) m/z 477 [M+H]$^+$.

(S)-methyl 2-methyl-5-phenoxy-6-(1-(piperidin-4-yl)-1H-pyrazol-4-yl)-3,4-dihydroquinoline-1(2H)-carboxylate (I-200)

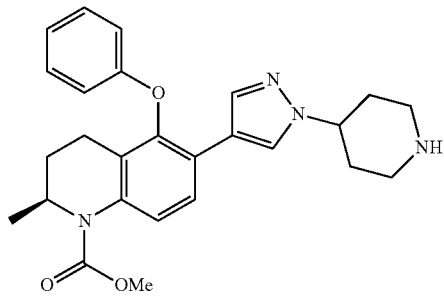 [SMILES: COC(=O)N1c2ccc(-c3cnn(C4CCNCC4)c3)c(Oc3ccccc3)c2CC[C@@H]1C]

$^1$H NMR (300 MHz, CDCl$_3$) δ ppm 1.10-1.15 (m, 3H), 1.48-1.59 (m, 1H), 1.75-1.95 (m, 2H), 1.96-2.12 (m, 3H), 2.40-2.50 (m, 1H), 2.56-2.81 (m, 3H), 3.16-3.37 (m, 2H), 3.81 (s, 3H), 4.08-4.20 (m, 1H), 4.61-4.72 (m, 1H), 6.71-6.79

(m, 2H), 6.89-6.95 (m, 1H), 7.21-7.26 (m, 2H), 7.45-7.48 (m, 1H), 7.63-7.68 (m, 2H), 7.72 (s, 1H). MS (ESI, pos. ion) m/z 447 [M+H]$^+$.

(S)-1-(2-methyl-5-phenoxy-6-(1-(piperidin-4-yl)-1H-pyrazol-4-yl)-3,4-dihydroquinolin-1(2H)-yl)ethanone (I-201)

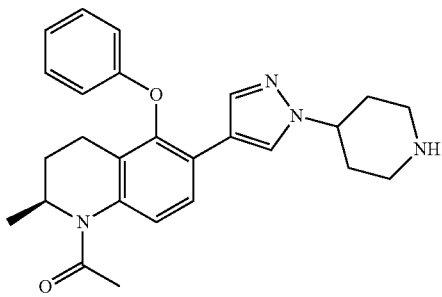 [SMILES: CC(=O)N1c2ccc(-c3cnn(C4CCNCC4)c3)c(Oc3ccccc3)c2CC[C@@H]1C]

$^1$H NMR (300 MHz, CD$_3$OD) δ ppm 1.14 (d, J=6.60 Hz, 3H), 1.30-1.43 (m, 1H), 1.76-1.90 (m, 2H), 1.97-2.11 (m, 2H), 2.21-2.32 ((m, 5H), 2.65-2.80 (m, 3H), 3.10-3.21 (m, 2H), 4.15-4.29 (m, 1H), 4.71-4.84 (m, 1H), 6.75-6.81 (m, 2H), 6.98 (d, J=7.20 Hz, 1H), 7.25-7.34 (m, 3H), 7.62 (d, J=6.60 Hz, 1H), 7.80 (s, 1H), 7.95 (s, 1H). MS (ESI, pos. ion) m/z 431 [M+H]$^+$.

(S)-3-(1-(cyclopropanecarbonyl)-2-methyl-6-(1-(piperidin-4-yl)-1H-pyrazol-4-yl)-1,2,3,4-tetrahydroquinolin-5-yloxy)benzonitrile (I-202)

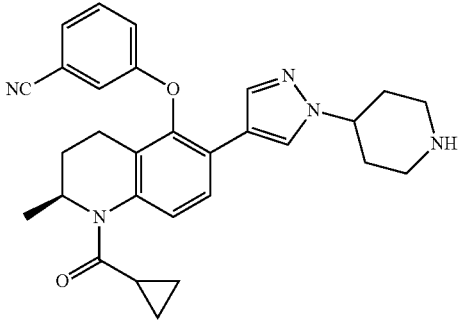 [SMILES: C[C@H]1CCc2c(ccc(-c3cnn(C4CCNCC4)c3)c2Oc2cccc(C#N)c2)N1C(=O)C1CC1]

$^1$H NMR (400 MHz, CD$_3$OD) δ ppm 0.76-0.8 3 (m, 1H), 1.13-1.22 (m, 4H), 1.29-1.38 (m, 1H), 1.81-1.94 (m, 2H), 1.96-2.10 (m, 3H), 2.22-2.38 (m, 2H), 2.36-2.78 (m, 3H), 3.15-3.21 (m, 2H), 4.24-4.31 (m, 1H), 4.80-4.85 (m, 1H), 7.78 (s, 1H), 7.89 (s, 1H). MS (ESI, pos. ion) m/z 482 [M+H]⁺.

(S)-1-(2-methyl-6-(1-(piperidin-4-yl)-1H-pyrazol-4-yl)-5-(pyridin-2-yloxy)-3,4-dihydroquinolin-1(2H)-yl)ethanone (I-203)

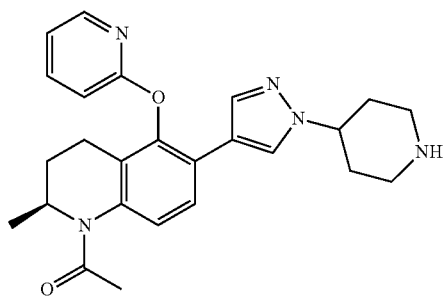 [SMILES: CC(=O)N1c2ccc(-c3cnn(C4CCNCC4)c3)c(Oc3ccccn3)c2CC[C@@H]1C]

¹H NMR (300 MHz, CD₃OD) δ ppm 1.11 (d, J=6.60 Hz, 3H), 1.29-1.49 (m, 1H), 1.75-1.90 (m, 2H), 1.92-2.01 (m, 2H), 2.18 (s, 5H), 2.59-2.69 (m, 1H), 2.70-2.80 (m, 2H), 4.15-4.26 (m, 1H), 4.68-4.81 (m, 1H), 6.85-6.91 (m, 1H), 6.95-7.04 (m, 1H), 7.21-7.33 (m, 1H), 7.55-7.58 (m, 1H), 7.71-7.79 (m, 2H), 7.89 (s, 1H), 7.97-8.04 (m, 1H). MS (ESI, pos. ion) m/z 432 [M+H]⁺.

(S)-cyclopropyl(8-fluoro-2-methyl-5-phenoxy-6-(1-(piperidin-4-yl)-1H-pyrazol-4-yl)-3,4-dihydroquinolin-1(2H)-yl)methanone (I-204)

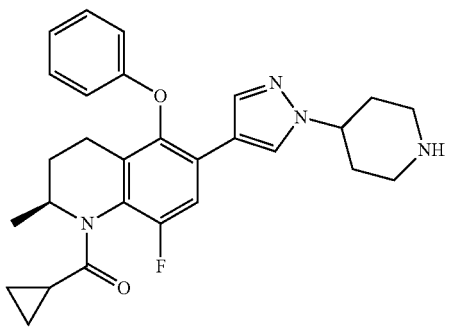 [SMILES: C[C@H]1CCc2c(Oc3ccccc3)c(-c3cnn(C4CCNCC4)c3)cc(F)c2N1C(=O)C1CC1]

¹H NMR (400 MHz, DMSO-d₆) δ ppm 0.63-0.95 (m, 4H), 1.04-1.31 (m, 4H), 1.60-1.71 (m, 3H), 1.82-1.91 (m, 2H), 2.11-2.23 (m, 2H), 2.54-2.57 (m, 2H), 2.95-3.05 (m, 1H), 3.27-3.40 (m, 1H), 4.60-4.71 (m, 1H), 6.81 (d, J=8.00 Hz, 2H), 6.95-7.01 (m, 1H), 7.25-7.32 (m, 2H), 7.64-7.70 (m, 1H), 7.80 (s, 1H), 8.10 (s, 1H). MS (ESI, pos. ion) m/z 475 [M+H]⁺.

(S)-methyl 8-fluoro-2-methyl-5-phenoxy-6-(1-(piperidin-4-yl)-1H-pyrazol-4-yl)-3,4-dihydroquinoline-1(2H)-carboxylate (I-205)

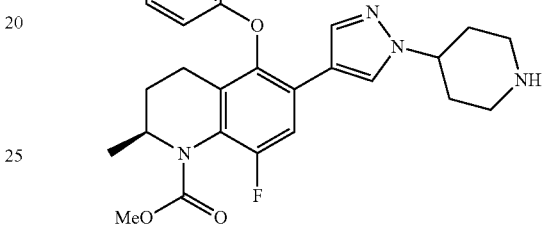

¹H NMR (400 MHz, CD₃OD) δ ppm 1.18 (d, J=6.40 Hz, 3H), 1.35-1.46 (m 1H), 1.76-1.84 (m, 2H), 1.96-2.05 (m, 2H), 2.20-2.32 (m, 2H), 2.68-2.73 (m, 3H), 3.15-3.20 (m, 2H), 3.79 (s, 3H), 4.17-4.22 (m, 1H), 4.43-4.53 (m, 1H), 6.75-6.78 (m, 2H), 6.95-7.00 (m, 1H), 7.25-7.31 (m, 2H), 7.45-7.52 (m, 1H), 7.79 (s, 1H), 7.97 (s, 1H). MS (ESI, pos. ion) m/z 465 [M+H]⁺.

(S)-1-(8-fluoro-2-methyl-5-phenoxy-6-(1-(piperidin-4-yl)-1H-pyrazol-4-yl)-3,4-dihydroquinolin-1(2H)-yl)ethanone (I-206)

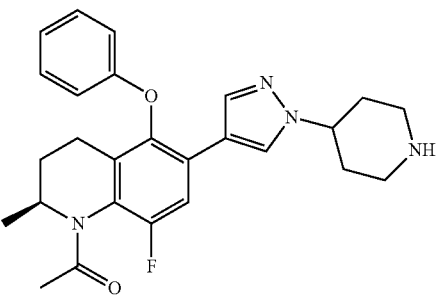 [SMILES: CC(=O)N1c2c(F)cc(-c3cnn(C4CCNCC4)c3)c(Oc3ccccc3)c2CC[C@@H]1C]

¹H NMR (400 MHz, CD₃OD) δ ppm 1.10-1.25 (m, 4H), 1.78-1.91 (m, 2H), 1.96-2.07 (m, 2H), 2.10-2.20 (m, 3H), 2.25-2.37 (m, 2H), 2.67-2.79 (m, 3H), 3.10-3.18 (m, 2H), 4.18-4.18 (m 1H), 4.77-4.83 (m, 1H), 6.79-6.82 (m, 2H), 6.95-7.03 (m, 1H), 7.25-7.30 (m, 2H), 7.55-7.59 (m, 1H), 7.83 (s, 1H), 8.05 (s, 1H). MS (ESI, pos. ion) m/z 449 [M+H]+.

(S)-cyclopropyl(8-fluoro-5-(3-methoxyphenoxy)-2-methyl-6-(1-(piperidin-4-yl)-1H-pyrazol-4-yl)-3,4-dihydroquinolin-1(2H)-yl)methanone (I-207)

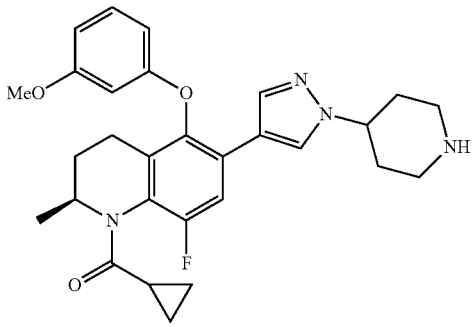 [SMILES: COc1cccc(Oc2c(-c3cnn(C4CCNCC4)c3)cc(F)c3c2CC[C@H](C)N3C(=O)C2CC2)c1]

$^1$H NMR (400 MHz, CD$_3$OD) δ ppm 0.61-0.85 (m, 4H), 1.02-1.11 (m, 4H), 1.60 (m, 1H), 2.04-2.20 (m, 6H), 2.62-2.66 (m, 1H), 3.03-3.10 (m, 2H), 3.39-3.42 (m, 2H), 3.63 (s, 3H), 4.37-4.42 (m, 1H), 4.60-4.67 (m, 1H), 6.23-6.28 (m, 2H), 6.46-6.48 (m, 1H), 7.03-7.08 (m, 1H), 7.40-7.42 (m, 1H), 7.78 (s, 1H), 7.90 (s, 1H). MS (ESI, pos. ion) m/z 505 [M+H]+.

(S)-methyl 6-(1-(azetidin-3-yl)-1H-pyrazol-4-yl)-5-(3-chloro-4-fluorophenoxy)-2-methyl-3,4-dihydroquinoline-1(2H)-carboxylate (I-208)

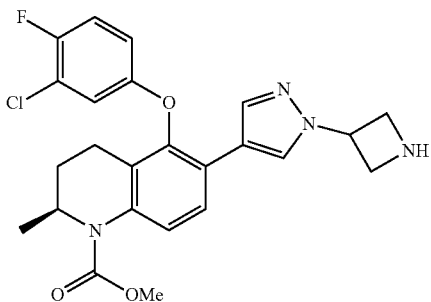 [SMILES: COC(=O)N1c2ccc(-c3cnn(C4CNC4)c3)c(Oc3ccc(F)c(Cl)c3)c2CC[C@@H]1C]

$^1$H NMR (300 MHz, DMSO-d$_6$) δ ppm 0.99 (d, J=6.45 Hz, 3H), 1.33-1.56 (m, 2H), 1.80-2.02 (m, 2H), 2.22-2.40 (m, 2H), 3.34-3.48 (m, 1H), 3.55-3.64 (m, 1H), 3.65 (s, 3H), 3.69-3.84 (m, 1H), 4.36-4.61 (m, 1H), 4.70-4.93 (m, 1H), 6.52-6.70 (m, 1H), 6.87-7.04 (m, 1H), 7.12-7.31 (m, 1H), 7.52 (s, 2H), 7.69-7.79 (m, 1H), 8.06 (br d, J=13.49 Hz, 1H). MS (ESI, pos. ion) m/z 471 [M+H]+.

Example 39

(S)-4-(1-acetyl-6-(1-cyclopropyl-1H-pyrazol-4-yl)-2-methyl-1,2,3,4-tetrahydroquinolin-5-yloxy)benzamide (I-209)

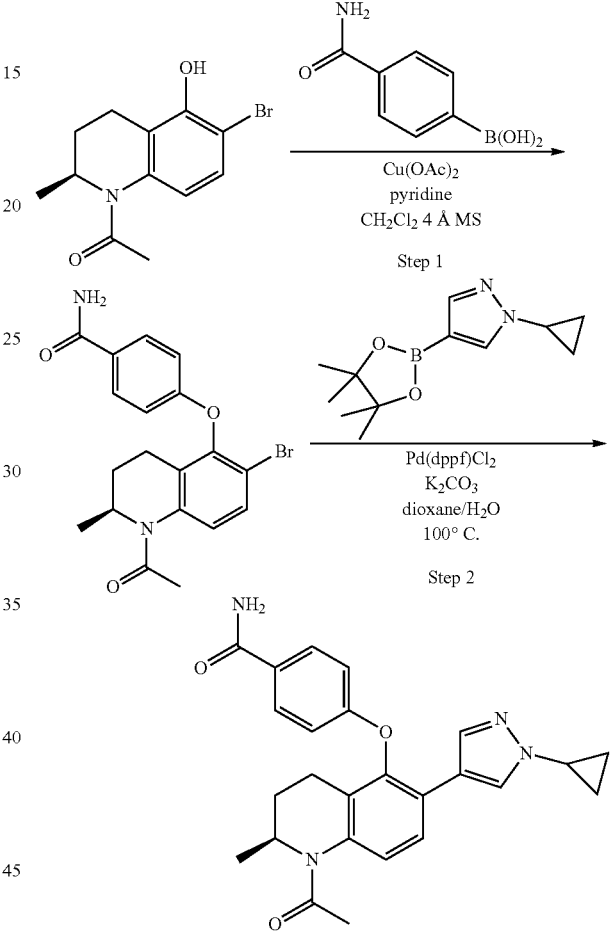

Step 1. (S)-4-(1-acetyl-6-bromo-2-methyl-1,2,3,4-tetrahydroquinolin-5-yloxy)benzamide A 100-mL, round-bottom flask equipped with a balloon filled with air was charged with (S)-1-(6-bromo-5-hydroxy-2-methyl-3,4-dihydroquinolin-1(2H)-yl)ethanone (0.300 g, 1.06 mmol), 4-carbamoylphenylboronic acid (0.437 g, 2.65 mmol), pyridine (1 mL), dichloromethane (40 mL), copper (II) acetate (0.580 g, 3.20 mmol) and 4 Å molecular sieves (4.0 g). The resulting mixture stirred for 3 days at room temperature. The reaction mixture was filtered, and the filtrate was concentrated under vacuum. The residue was purified by preparative thin layer chromatography (eluting with 3:1, ethyl acetate/petroleum ether) to afford (S)-4-(1-acetyl-6-bromo-2-methyl-1,2,3,4-tetrahydroquinolin-5-yloxy)benzamide (0.148 g, 35%) as yellow oil. MS (ESI, pos. ion) m/z 403, 405 [M+H]+.

Step 2. (S)-4-(1-acetyl-6-(1-cyclopropyl-1H-pyrazol-4-yl)-2-methyl-1,2,3,4-tetrahydroquinolin-5-yloxy)benzamide A 50-mL, round-bottom flask was charged with (S)-4-(1-acetyl-6-bromo-2-methyl-1,2,3,4-tetrahydroquinolin-5-yloxy)benzamide (0.068 g, 0.17 mmol), 1-cyclopropyl-4-(4,4,5,5-tetramethyl-1,3,2-dioxaborolan-2-yl)-1H-pyrazole (0.059 g, 0.25 mmol), [1,1'-bis(diphenylphosphino)ferrocene]dichloropalladium(II), complex with dichloromethane (0.014 g, 0.02 mmol), potassium carbonate (0.070 g, 0.50 mmol), 1,4-dioxane (20 mL) and water (2 mL). The resulting mixture stirred overnight at 100° C. After cooling to room temperature, the reaction mixture was passed through a short pad of celite, and the filtrate was concentrated under vacuum. The residue was purified by preparative thin layer chromatography (eluting with 1:1, ethyl acetate/petroleum ether). The product was further purified by preparative-HPLC with the following conditions (Waters I): Column, XBridge Prep C18 OBD Column, 19×150 mm 5 um 13 nm; mobile phase, water (0.05% ammonium bicarbonate) and acetonitrile (15.0% to 95% acetonitrile in 12 min; flow rate: 20 mL/min); Detector, UV 254/220 nm. This afforded (S)-4-(1-acetyl-6-(1-cyclopropyl-1H-pyrazol-4-yl)-2-methyl-1,2,3,4-tetrahydroquinolin-5-yloxy)benzamide (0.029 g, 40%) as an off-white solid. $^1$H NMR (300 MHz, CD$_3$OD) δ ppm 0.93-1.03 (m, 4H), 1.15 (d, J=6.60 Hz, 3H), 1.19-1.42 (m, 1H), 2.18-2.27 (m, 5H), 2.67-2.75 (m, 1H), 3.56-3.63 (m, 1H), 4.77-4.79 (m, 1H), 6.85-6.88 (m, 2H), 7.37 (m, 1H), 7.63 (d, J=8.40 Hz, 1H), 7.77 (s, 1H), 7.81-7.85 (m, 2H), 7.94 (s, 1H). MS (ESI, pos. ion) m/z 431 [M+H]$^+$.

The compounds below were synthesized according to the procedures outlined above for Example 39:

(S)-1-(6-(1-cyclopropyl-1H-pyrazol-4-yl)-5-(2-fluorophenoxy)-2-methyl-3,4-dihydroquinolin-1(2H)-yl)ethanone (I-210)

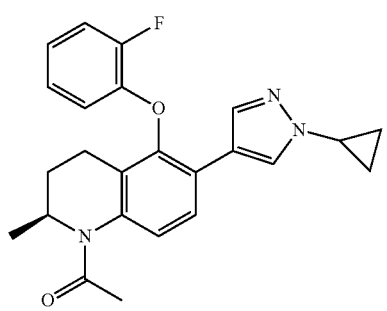

$^1$H NMR (300 MHz, CD$_3$OD) δ ppm 0.95-1.02 (m, 4H), 1.16 (d, J=6.60 Hz, 3H), 1.30-1.48 (m, 1H), 2.15-2.40 (m, 5H), 2.65-2.80 (m, 1H), 3.55-3.65 (m, 1H), 4.70-4.89 (m, 1H), 6.35-6.45 (m, 1H), 6.95-7.00 (m, 2H), 7.15-7.25 (m, 1H), 7.29-7.38 (m, 1H), 7.61 (d, J=8.40 Hz, 1H), 7.79 (s, 1H), 7.97 (s, 1H). MS (ESI, pos. ion) m/z 406 [M+H]$^+$.

(S)-1-(5-(2-chlorophenoxy)-6-(1-cyclopropyl-1H-pyrazol-4-yl)-2-methyl-3,4-dihydroquinolin-1(2H)-yl)ethanone (I-211)

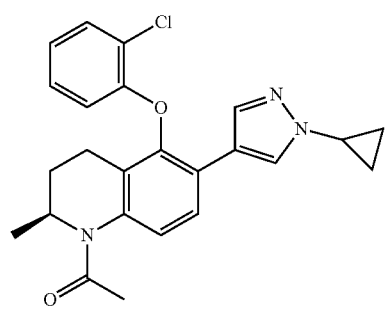 [SMILES: CC(=O)N1c2ccc(-c3cnn(C4CC4)c3)c(Oc3ccccc3Cl)c2CC[C@@H]1C]

$^1$H NMR (400 MHz, CD$_3$OD) δ ppm 0.89-1.01 (m, 4H), 1.15 (d, J=6.80 Hz, 3H), 1.30-1.45 (m, 1H), 2.05-2.34 (m, 5H), 2.55-2.78 (m, 1H), 3.55-3.65 (m, 1H), 4.68-4.88 (m, 1H), 6.31-6.38 (m, 1H), 6.97 (t, J=7.20 Hz, 1H), 7.07 (t, J=7.20 Hz, 1H), 7.25-7.40 (m, 1H), 7.45-7.50 (m, 1H), 7.58-7.65 (m, 1H), 7.81 (s, 1H), 7.98 (s, 1H). MS (ESI, pos. ion) m/z 422 [M+H]$^+$.

(S)-methyl 6-(1-cyclopropyl-1H-pyrazol-4-yl)-5-(4-fluorophenoxy)-2-methyl-3,4-dihydroquinoline-1(2H)-carboxylate (I-212)

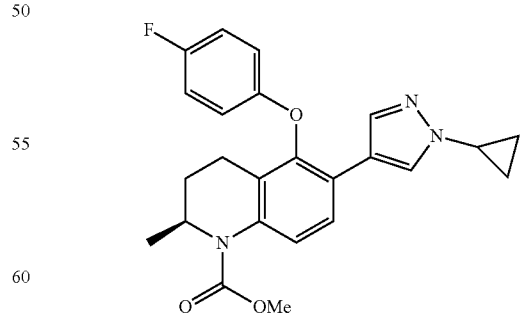

$^1$H NMR (400 MHz, CD$_3$OD) δ ppm 0.95-1.01 (m, 4H), 1.13 (d, J=6.80 Hz, 3H), 1.51-1.65 (m, 1H), 2.01-2.10 (m, 1H), 2.35-2.45 (m, 1H), 2.58-2.71 (m, 1H), 3.55-3.60 (m, 1H), 3.81 (s, 3H), 4.58-4.62 (m, 1H), 6.69-6.75 (m, 2H), 6.91-7.01 (m, 2H), 7.49-7.59 (m, 2H), 7.74 (s, 1H), 7.89 (s, 1H). MS (ESI, pos. ion) m/z 422 [M+H]⁺.

Example 13

5. (S)-methyl 5-(4-cyanophenoxy)-6-(1-cyclopropyl-1H-pyrazol-4-yl)-2-methyl-3,4-dihydroquinoline-1(2H)-carboxylate (I-213)

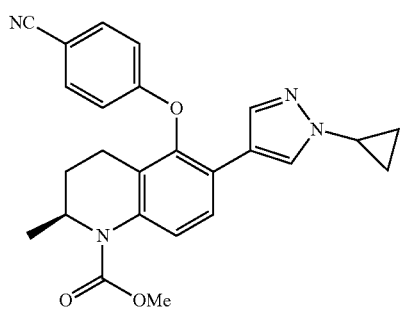 [SMILES: COC(=O)N1c2ccc(-c3cnn(C4CC4)c3)c(Oc3ccc(C#N)cc3)c2CC[C@@H]1C]

$^1$H NMR (300 MHz, CD$_3$OD) δ ppm 0.97-1.01 (m, 4H), 1.15 (d, J=6.60 Hz, 3H), 1.55-1.65 (m, 1H), 1.98-2.15 (m, 1H), 2.35-2.45 (m, 1H), 2.55-2.68 (m, 1H), 3.50-3.60 (m, 1H), 3.83 (s, 3H), 4.61-4.72 (m, 1H), 6.90-6.98 (m, 2H), 7.51-7.71 (m, 5H), 7.89 (s, 1H). MS (ESI, pos. ion) m/z 429 [M+H]⁺.

(S)-methyl 5-(4-chlorophenoxy)-6-(1-cyclopropyl-1H-pyrazol-4-yl)-2-methyl-3,4-dihydroquinoline-1(2H)-carboxylate (I-214)

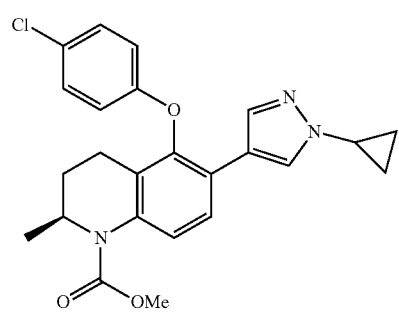 [SMILES: COC(=O)N1c2ccc(-c3cnn(C4CC4)c3)c(Oc3ccc(Cl)cc3)c2CC[C@@H]1C]

$^1$H NMR (300 MHz, CD$_3$OD) δ ppm 0.97-1.01 (m, 4H), 1.16 (d, J=6.60 Hz, 3H), 1.50-1.68 (m, 1H), 1.99-2.15 (m, 1H), 2.35-2.48 (m, 1H), 2.55-2.75 (m, 1H), 3.52-3.62 (m, 1H), 3.82 (s, 3H), 4.58-4.70 (m, 1H), 6.75-6.81 (m, 2H), 7.20-7.28 (m, 2H), 7.48-7.60 (m, 2H), 7.73 (s, 1H), 7.89 (s, 1H). MS (ESI, pos. ion) m/z 438 [M+H]⁺.

(S)-methyl 5-(2-chlorophenoxy)-6-(1-cyclopropyl-1H-pyrazol-4-yl)-2-methyl-3,4-dihydroquinoline-1(2H)-carboxylate (I-215)

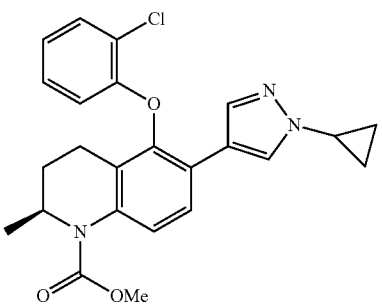 [SMILES: COC(=O)N1c2ccc(-c3cnn(C4CC4)c3)c(Oc3ccccc3Cl)c2CC[C@@H]1C]

$^1$H NMR (300 MHz, CD$_3$OD) δ ppm 0.90-1.01 (m, 4H), 1.15 (d, J=6.60 Hz, 3H), 1.52-1.65 (m, 1H), 1.99-2.10 (m, 1H), 2.10-2.90 (br m, 2H), 3.50-3.60 (m, 1H), 3.81 (s, 3H), 4.61-4.71 (m, 1H), 6.29-6.38 (m, 1H), 6.85-6.95 (m, 1H), 6.98-7.05 (m, 1H), 7.45-7.62 (m, 3H), 7.76 (s, 1H), 7.92 (s, 1H). MS (ESI, pos. ion) m/z 438 [M+H]⁺.

(S)-methyl 5-(4-carbamoylphenoxy)-6-(1-cyclopropyl-1H-pyrazol-4-yl)-2-methyl-3,4-dihydroquinoline-1(2H)-carboxylate (I-216)

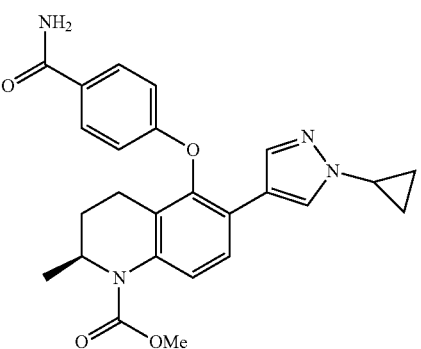 [SMILES: COC(=O)N1c2ccc(-c3cnn(C4CC4)c3)c(Oc3ccc(C(N)=O)cc3)c2CC[C@@H]1C]

$^1$H NMR (300 MHz, CD$_3$OD) δ ppm 0.89-1.05 (m, 4H), 1.16 (d, J=6.60 Hz, 3H), 1.55-1.65 (m, 1H), 1.98-2.15 (m, 1H), 2.38-2.48 (m, 1H), 2.55-2.75 (m, 1H), 3.50-3.60 (m, 1H), 3.83 (s, 3H), 4.60-4.75 (m, 1H), 6.85 (d, J=8.70 Hz, 2H), 7.50-7.62 (m, 2H), 7.70-7.92 (m, 4H). MS (ESI, pos. ion) m/z 447 [M+H]⁺.

(S)-4-(1-acetyl-6-(1-cyclopropyl-1H-pyrazol-4-yl)-2-methyl-1,2,3,4-tetrahydroquinolin-5-yloxy)benzonitrile (I-217)

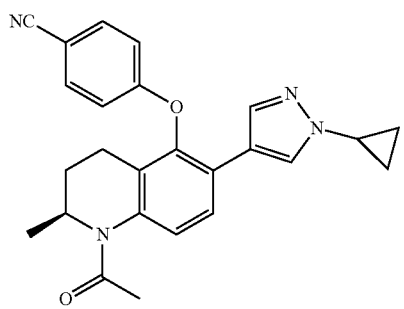 [SMILES: CC(=O)N1c2ccc(-c3cnn(C4CC4)c3)c(Oc3ccc(C#N)cc3)c2CC[C@@H]1C]

¹H NMR (300 MHz, CD₃OD) δ ppm 0.93-0.99 (m, 4H), 1.12 (d, J=6.60 Hz, 3H), 1.30-1.45 (m, 1H), 2.10-2.30 (m, 5H), 2.55-2.70 (m, 1H), 3.50-3.60 (m, 1H), 4.65-4.83 (m, 1H), 6.93 (d, J=9.00 Hz, 2H), 7.28-7.35 (m, 1H), 7.55-7.68 (m, 3H), 7.71 (s, 1H), 7.90 (s, 1H). MS (ESI, pos. ion) m/z 413 [M+H]⁺.

(S)-cyclopropyl(2-methyl-5-phenoxy-6-(1H-pyrazol-5-yl)-3,4-dihydroquinolin-1(2H)-yl)methanone (I-218)

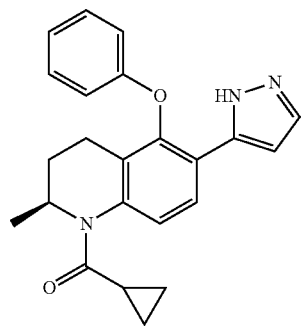 [SMILES: C[C@H]1CCc2c(ccc(-c3ccn[nH]3)c2Oc2ccccc2)N1C(=O)C1CC1]

¹H NMR (400 MHz, CD₃OD) δ ppm 0.72-0.87 (m, 1H), 0.95-1.08 (m, 2H), 1.11-1.22 (m, 4H), 1.35-1.51 (m, 1H), 1.95-2.08 (m, 1H), 2.18-2.28 (m, 1H), 2.29-2.39 (m, 1H), 2.69-2.79 (m, 1H), 4.72-4.84 (m, 1H), 6.51-6.69 (m, 2H), 6.71-6.82 (m, 2H), 6.89-7.02 (m, 1H), 7.12-7.37 (m, 2H), 7.39-8.00 (m, 3H). MS (ESI, pos. ion) m/z 374 [M+H]⁺.

(S)-cyclopropyl(2-methyl-6-(1-methyl-1H-1,2,3-triazol-4-yl)-5-phenoxy-3,4-dihydroquinolin-1(2H)-yl)methanone (I-219)

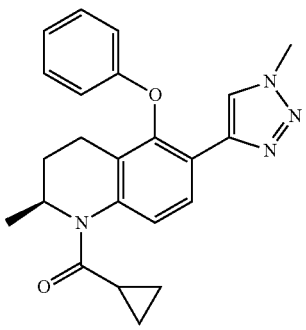 [SMILES: C[C@H]1CCc2c(ccc(-c3cn(C)nn3)c2Oc2ccccc2)N1C(=O)C1CC1]

¹H NMR (300 MHz, CD₃OD) δ ppm 0.63-99 (m, 3H), 1.03 (d, J=9.90 Hz, 4H), 1.30-1.50 (m, 1H), 1.88-2.01 (m, 1H), 2.01-2.18 (m, 1H), 2.20-2.39 (m, 1H), 2.53-2.62 (m, 1H), 4.00 (s, 3H), 4.58-4.79 (m, 1H), 6.74-6.89 (m, 2H), 6.90-7.09 (m, 1H), 7.19-7.37 (m, 2H), 7.42-7.54 (m, 1H), 8.03-8.15 (m, 2H). MS (ESI, pos. ion) m/z 389 [M+H]⁺.

(S)-cyclopropyl(2-methyl-6-(5-methyl-1,3,4-thiadiazol-2-yl)-5-phenoxy-3,4-dihydroquinolin-1(2H)-yl)methanone (I-220)

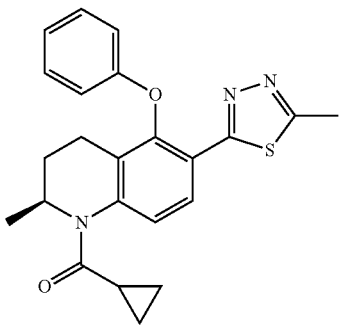

¹H NMR (300 MHz, CD₃OD) δ ppm 0.72-0.89 (m, 1H), 0.92-1.09 (m, 2H), 1.11-1.29 (m, 4H), 1.35-1.52 (m, 1H), 1.88-2.07 (m, 1H), 2.08-2.27 (m, 1H), 2.27-2.46 (m, 1H), 2.62-2.81 (m, 4H), 4.74-4.83 (m, 1H), 6.71-6.98 (m, 2H), 6.89-7.19 (m, 1H), 7.28-7.39 (m, 2H), 7.39-7.69 (m, 1H), 8.21-8.39 (m, 1H). MS (ESI, pos. ion) m/z 406 [M+H]+.

(S)-cyclopropyl(2-methyl-6-(1-methyl-1H-imidazol-4-yl)-5-phenoxy-3,4-dihydroquinolin-1(2H)-yl) methanone (I-221)

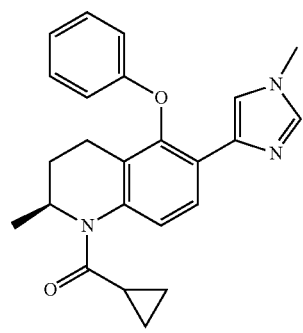 [SMILES: C[C@H]1CCc2c(ccc(-c3cn(C)cn3)c2Oc2ccccc2)N1C(=O)C1CC1]

¹H NMR (300 MHz, CD₃OD) δ ppm 0.72-0.84 (m, 1H), 0.91-1.03 (m, 2H), 1.08-1.19 (m, 4H), 1.29-1.44 (m, 1H), 1.88-2.07 (m, 1H), 2.13-2.33 (m, 2H), 2.62-2.76 (m, 1H), 3.64 (s, 3H), 4.76-4.83 (m, 1H), 6.74-6.79 (m, 2H), 6.86-7.06 (m, 1H), 7.20-7.37 (m, 3H), 7.38-7.47 (m, 1H), 7.61 (s, 1H), 7.76-8.02 (m, 1H). MS (ESI, pos. ion) m/z 388 [M+H]+.

Methyl (2S)-6-(1-(1,1-dioxidotetrahydro-2H-thiopyran-3-yl)-1H-pyrazol-4-yl)-5-(4-fluorophenoxy)-2-methyl-3,4-dihydroquinoline-1(2H)-carboxylate (I-222)

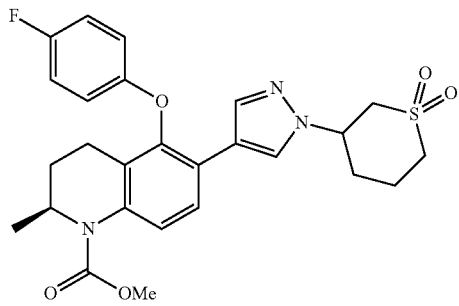 [SMILES: COC(=O)N1c2ccc(-c3cnn(C4CCCS(=O)(=O)C4)c3)c(Oc3ccc(F)cc3)c2CC[C@@H]1C]

MS (ESI, pos. ion) m/z 514 [M+H]+.

methyl (S)-6-(1-(1,1-dioxidothietan-3-yl)-1H-pyrazol-4-yl)-5-(4-fluorophenoxy)-2-methyl-3,4-dihydroquinoline-1(2H)-carboxylate (I-223)

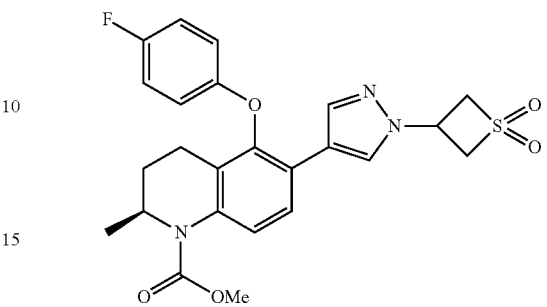

MS (ESI, pos. ion) m/z 486 [M+H]+.

(S)-cyclopropyl(2-methyl-6-(1-methyl-1H-pyrazol-4-yl)-5-phenoxy-3,4-dihydroquinolin-1(2H)-yl) methanone (I-224)

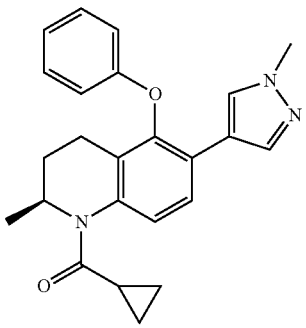 [SMILES: C[C@H]1CCc2c(ccc(-c3cnn(C)c3)c2Oc2ccccc2)N1C(=O)C1CC1]

¹H NMR (400 MHz, CDCl₃) δ ppm 0.75-0.88 (m, 1H), 0.93-1.04 (m, 2H), 1.11-1.23 (m, 4H), 1.38-1.52 (m, 1H), 1.95-2.08 (m, 1H), 2.17-2.29 (m, 1H), 2.29-2.38 (m, 1H), 2.66-2.81 (m, 1H), 4.72-4.86 (m, 1H), 6.69-6.89 (m, 2H), 6.96-7.12 (m, 1H), 7.22-7.37 (m, 2H), 7.45-7.54 (m, 1H), 8.03 (s, 1H), 8.00-8.14 (m, 1H). MS (ESI, pos. ion) m/z 388 [M+H]+.

(S)-1-(6-(1-cyclopropyl-1H-pyrazol-4-yl)-5-(4-fluorophenoxy)-2-methyl-3,4-dihydroquinolin-1(2H)-yl) ethanone (I-225)

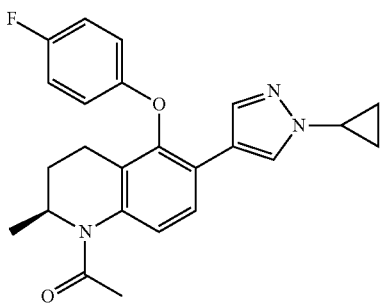 [SMILES: CC(=O)N1c2ccc(-c3cnn(C4CC4)c3)c(Oc3ccc(F)cc3)c2CC[C@@H]1C]

¹H NMR (300 MHz, CD₃OD) δ ppm 1.00-1.03 (m, 4H), 1.14 (d, J=6.30 Hz, 3H), 1.36-1.38 (m, 1H), 2.19-2.24 (m, 5H), 2.66-2.76 (m, 1H), 3.57-3.64 (m, 1H), 4.77 (m, 1H), 6.75-6.81 (m, 2H), 6.97-7.04 (m, 2H), 7.32 (m, 1H), 7.61 (d, J=8.40 Hz, 1H), 7.75 (s, 1H), 7.91 (s, 1H). MS (ESI, pos. ion) m/z 406 [M+H]⁺.

(S)-1-(5-(4-chlorophenoxy)-6-(1-cyclopropyl-1H-pyrazol-4-yl)-2-methyl-3,4-dihydroquinolin-1(2H)-yl)ethanone (I-226)

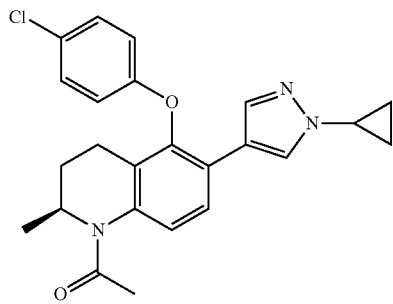 [SMILES: CC(=O)N1c2ccc(-c3cnn(C4CC4)c3)c(Oc3ccc(Cl)cc3)c2CC[C@@H]1C]

¹H NMR (300 MHz, CD₃OD) δ 0.89-0.94 (m, 4H), 1.15 (d, J=6.60 Hz, 3H), 1.34-1.44 (m, 1H), 2.26-2.34 (m, 5H), 2.60-2.65 (m, 1H), 4.70 (m, 1H), 6.75 (d, J=8.40 Hz, 2H), 7.35 (m, 1H), 7.60 (d, J=8.40 Hz, 1H), 7.75 (s, 1H), 7.91 (s, 1H). MS (ESI, pos. ion) m/z 422 [M+H]⁺.

(S)-methyl 6-(1-cyclopropyl-1H-pyrazol-4-yl)-5-(2-fluorophenoxy)-2-methyl-3,4-dihydroquinoline-1(2H)-carboxylate (I-227)

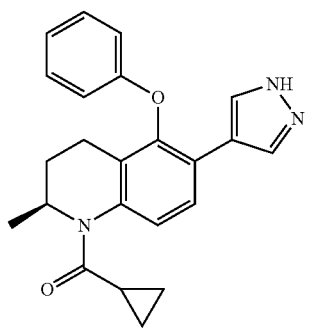 [SMILES: C[C@H]1CCc2c(ccc(-c3cn[nH]c3)c2Oc2ccccc2)N1C(=O)C1CC1]

¹H NMR (300 MHz, CD₃OD) δ ppm 0.73-0.82 (m, 1H), 0.90-1.01 (m, 2H), 1.11-1.21 (m, 4H), 1.25-1.31 (m, 1H), 1.31-1.44 (m, 1H), 1.93-2.09 (m, 2H), 2.13-2.45 (m, 2H), 2.68-2.77 (m, 1H), 4.73-4.81 (m, 1H), 6.79 (d, J=7.80 Hz, 2H), 6.95-7.02 (m, 1H), 7.28-7.33 (m, 2H), 7.39 (d, J=8.40 Hz, 1H), 7.66 (d, J=8.40 Hz, 1H), 7.91 (s, 2H). MS (ESI, pos. ion) m/z 374 [M+H]⁺.

3-[4-[(2S)-1-cyclopropanecarbonyl-5-(4-fluorophenoxy)-2-methyl-1,2,3,4-tetrahydroquinolin-6-yl]-1H-pyrazol-1-yl]-1λ⁶-thietane-1,1-dione (I-229)

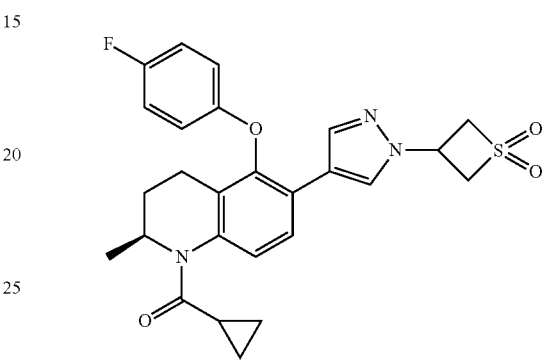

¹H NMR (400 MHz, CD₃OD) δ ppm 0.92-1.01 (m, 2H), 1.12-1.23 (m, 4H), 1.37-1.46 (m, 1H), 1.96-2.05 (m, 1H), 2.11-2.36 (m, 2H), 2.65-2.78 (m, 1H), 4.56-4.79 (m, 4H), 4.73-4.83 (m, 1H), 5.22-5.34 (m, 1H), 6.75-6.81 (m, 2H), 6.95-7.06 (m, 2H), 7.40 (d, J=8.40 Hz, 1H), 7.63 (d, J=8.80 Hz, 1H), 7.92 (s, 1H), 8.12 (s, 1H). MS (ESI, pos. ion) m/z 524 [M+H]⁺.

3-[4-[(2S)-1-cyclopropanecarbonyl-2-methyl-5-phenoxy-1,2,3,4-tetrahydroquinolin-6-yl]-1H-pyrazol-1-yl]-1λ⁶-thietane-1,1-dione (I-230)

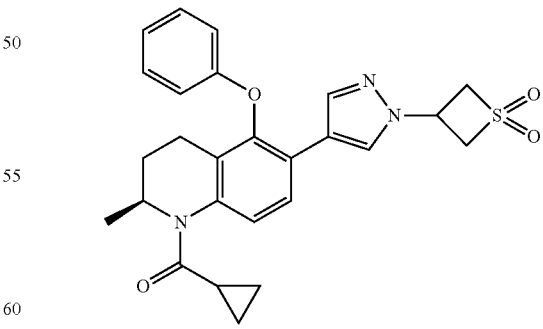

¹H NMR (300 MHz, CD₃OD) δ ppm 0.64-0.81 (m, 1H), 0.89-1.02 (m, 2H), 1.12-1.22 (m, 4H), 1.33-1.45 (m, 1H), 1.92-2.05 (m, 1H), 2.15-4.41 (m, 2H), 2.63-2.77 (m, 1H), 4.54-4.63 (m, 4H), 4.75-4.79 (m, 1H), 5.25-5.34 (m, 1H), 6.79 (d, J=7.80 Hz, 2H), 6.95-7.04 (m, 1H), 7.25-7.29 (m, (S)-cyclopropyl(6-(isoxazol-4-yl)-2-methyl-5-phenoxy-3,4-dihydroquinolin-1(2H)-yl)methanone (I-231)

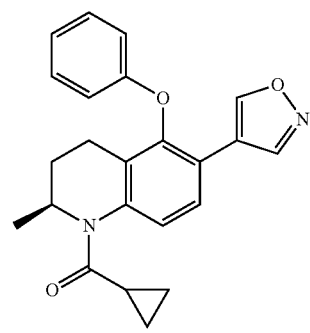 [SMILES: C[C@H]1CCc2c(ccc(-c3cnoc3)c2Oc2ccccc2)N1C(=O)C1CC1]

¹H NMR (400 MHz, CD₃OD) δ ppm 0.75-0.82 (m, 1H), 0.85-1.14 (m, 2H), 1.11-1.25 (m, 4H), 1.40-1.49 (m, 1H), 1.95-2.08 (m, 1H), 2.15-2.34 (m, 2H), 2.67-2.76 (m, 1H), 4.77-4.85 (m, 1H), 6.78-6.81 (m, 2H), 6.99-7.04 (m, 1H), 7.25-7.35 (m, 2H), 7.45-7.53 (m, 1H), 7.66-7.71 (m, 1H), 8.78 (s, 1H), 8.88 (s, 1H). MS (ESI, pos. ion) m/z 375 [M+H]⁺.

(S)-methyl 2-methyl-6-(1-methyl-1H-1,2,3-triazol-4-yl)-5-phenoxy-3,4-dihydroquinoline-1(2H)-carboxylate (I-232)

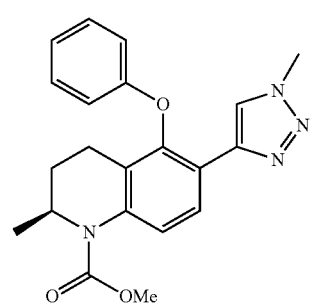 [SMILES: COC(=O)N1c2ccc(-c3cn(C)nn3)c(Oc3ccccc3)c2CC[C@@H]1C]

¹H NMR (400 MHz, CD₃OD) δ ppm 1.04 (d, J=6.40 Hz, 3H), 1.39-1.43 (m, 1H), 1.81-2.02 (m, 1H), 2.25-2.42 (m, 1H), 2.45-2.62 (m, 1H), 3.71 (s, 1H), 3.92 (s, 2H), 4.42-4.65 (m, 1H), 6.68 (d, J=8.00 Hz, 2H), 6.88 (t, J=7.20 Hz, 1H), 2H), 7.35-7.42 (m, 1H), 7.63 (d, J=8.40 Hz, 1H), 7.90 (s, 1H), 8.11 (s, 1H). MS (ESI, pos. ion) m/z 478 [M+H]⁺.

(S)-1-(2-methyl-6-(1-methyl-1H-1,2,3-triazol-4-yl)-5-phenoxy-3,4-dihydroquinolin-1(2H)-yl)ethanone (I-233)

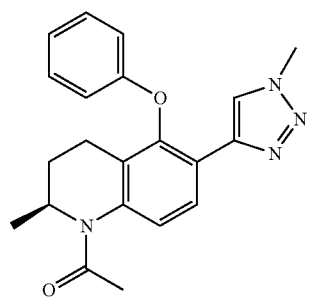 [SMILES: CC(=O)N1c2ccc(-c3cn(C)nn3)c(Oc3ccccc3)c2CC[C@@H]1C]

¹H NMR (300 MHz, CD₃OD) δ ppm 1.16 (d, J=6.60 Hz, 3H), 1.30-1.40 (m, 1H), 2.15-2.26 (m, 5H), 2.64-2.74 (m, 1H), 4.04 (s, 3H), 4.76-4.80 (m, 1H), 6.80-6.83 (m, 2H), 6.99-7.02 (m, 1H), 7.24-7.30 (m, 2H), 7.41-7.43 (m, 1H), 8.01 (s, 1H), 8.08 (d, J=8.40 Hz, 1H). MS (ESI, pos. ion) m/z 363 [M+H]⁺.

(S)-cyclopropyl(5-(3-methoxyphenoxy)-2-methyl-6-(1-methyl-1H-1,2,3-triazol-4-yl)-3,4-dihydroquinolin-1(2H)-yl)methanone (I-234)

¹H NMR (400 MHz, CD₃OD) δ ppm 0.70-0.80 (m, 1H), 0.89-1.02 (m, 2H), 1.13-1.20 (m, 4H), 1.30-1.45 (m, 1H), 1.98-2.05 (m, 1H), 2.15-2.35 (m, 2H), 2.70-2.75 (m, 1H), 3.75 (s, 3H), 4.06 (s, 3H), 4.79-4.83 (m, 1H), 6.33-6.37 (m, 1H), 6.41-6.43 (m, 1H), 6.57-6.61 (m, 1H), 7.14-7.19 (m, 1H), 7.48 (d, J=8.40 Hz, 1H), 8.00 (s, 1H), 8.07 (d, J=8.40 Hz, 1H). MS (ESI, pos. ion) m/z 419 [M+H]⁺.

(S)-cyclopropyl(5-(3-fluorophenoxy)-2-methyl-6-(1-methyl-1H-1,2,3-triazol-4-yl)-3,4-dihydroquinolin-1(2H)-yl)methanone (I-235)

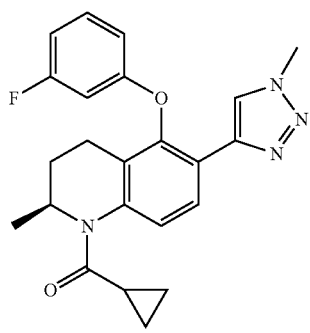 [SMILES: C[C@H]1CCc2c(ccc(-c3cn(C)nn3)c2Oc2cccc(F)c2)N1C(=O)C1CC1]

¹H NMR (400 MHz, CD₃OD) δ ppm 0.75-0.83 (m, 1H), 0.89-1.05 (m, 2H), 1.10-1.25 (m, 4H), 1.35-1.45 (m, 1H), 1.95-2.05 (m, 1H), 2.15-2.48 (m, 2H), 2.65-2.75 (m, 1H), 4.06 (s, 3H), 4.75-4.85 (m, 1H), 6.55-6.67 (m, 2H), 6.69-6.77 (m, 1H), 7.09-7.27 (m, 1H), 7.51 (d, J=8.70 Hz, 1H), 8.04 (s, 1H), 8.07 (d, J=8.40 Hz, 1H). MS (ESI, pos. ion) m/z 407 [M+H]⁺.

(S)-cyclopropyl(5-(4-fluorophenoxy)-2-methyl-6-(1-methyl-1H-1,2,3-triazol-4-yl)-3,4-dihydroquinolin-1(2H)-yl)methanone (I-236)

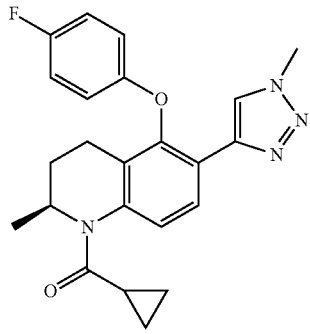 [SMILES: C[C@H]1CCc2c(ccc(-c3cn(C)nn3)c2Oc2ccc(F)cc2)N1C(=O)C1CC1]

¹H NMR (300 MHz, CD₃OD) δ ppm 0.72-0.82 (m, 1H), 0.87-1.02 (m, 2H), 1.08-1.21 (m, 4H), 1.37-1.48 (m, 1H), 1.95-2.05 (m, 1H), 2.15-2.36 (m, 2H), 2.65-2.78 (m, 1H), 4.71-4.85 (m, 1H), 6.75-6.83 (m, 2H), 6.95-7.05 (m, 2H), 7.48 (d, J=8.40 Hz, 1H), 8.03 (s, 1H), 8.07 (d, J=8.70 Hz, 1H). MS (ESI, pos. ion) m/z 407 [M+H]⁺.

(S)-cyclopropyl(6-(1-cyclopropyl-1H-pyrazol-4-yl)-8-fluoro-2-methyl-5-phenoxy-3,4-dihydroquinolin-1(2H)-yl)methanone (I-237)

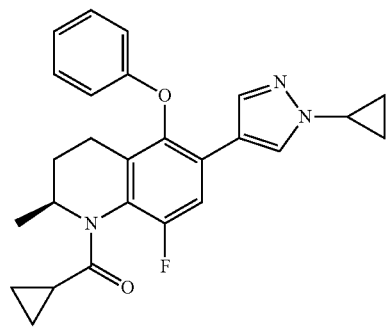 [SMILES: C[C@H]1CCc2c(Oc3ccccc3)c(-c3cnn(C4CC4)c3)cc(F)c2N1C(=O)C1CC1]

¹H NMR (300 MHz, DMSO-d₆) δ ppm 0.63-0.72 (m, 1H), 0.83-0.99 (m, 5H), 1.04-1.31 (m, 4H), 1.60-1.71 (m, 3H), 2.11-2.33 (m, 2H), 2.68-2.77 (m, 1H), 3.52-3.59 (m, 1H), 4.71-4.78 (m, 1H), 6.73-6.78 (m, 2H), 6.95-7.01 (m, 1H), 7.25-7.32 (m, 2H), 7.45-7.55 (m, 1H), 7.75 (s, 1H), 7.92 (s, 1H). MS (ESI, pos. ion) m/z 432 [M+H]⁺.

(S)-cyclopropyl(8-fluoro-2-methyl-5-phenoxy-6-(1H-pyrazol-4-yl)-3,4-dihydroquinolin-1(2H)-yl)methanone (I-238)

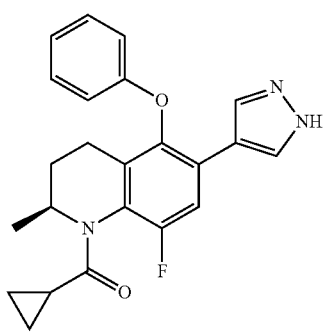 [SMILES: C[C@H]1CCc2c(Oc3ccccc3)c(-c3cn[nH]c3)cc(F)c2N1C(=O)C1CC1]

¹H NMR (300 MHz, DMSO-d₆) δ ppm 0.69-0.80 (m, 1H), 0.91-1.08 (m, 3H), 1.10-1.36 (m, 4H), 1.70-1.80 (m, 1H), 2.11-2.33 (m, 2H), 2.71-2.79 (m, 1H), 4.73-4.80 (m, 1H), 6.76-6.82 (m, 2H), 6.95-7.03 (m, 1H), 7.25-7.32 (m, 2H), 7.51-7.62 (m, 1H), 7.93 (s, 1H). MS (ESI, pos. ion) m/z 392 [M+H]⁺.

(S)-methyl 6-(1-cyclopropyl-1H-pyrazol-4-yl)-8-fluoro-2-methyl-5-phenoxy-3,4-dihydroquinoline-1(2H)-carboxylate (I-239)

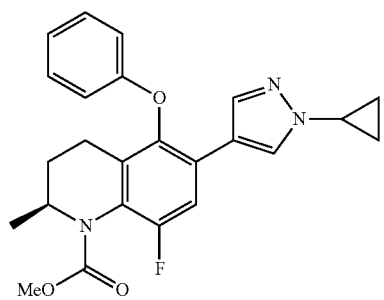 [SMILES: COC(=O)N1c2c(F)cc(-c3cnn(C4CC4)c3)c(Oc3ccccc3)c2CC[C@@H]1C]

$^1$H NMR (400 MHz, CD$_3$OD) δ ppm 0.95-1.01 (m, 4H), 1.18 (d, J=6.40 Hz, 3H), 1.35-1.46 (m 1H), 2.20-2.32 (m, 2H), 2.68-2.73 (m, 1H), 3.55-3.62 (m, 1H), 3.79 (s, 3H), 4.43-4.53 (m, 1H), 6.75-6.78 (m, 2H), 6.95-7.02 (m, 1H), 7.25-7.29 (m, 2H), 7.41-7.45 (m, 1H), 7.77 (s, 1H), 7.93 (s, 1H). MS (ESI, pos. ion) m/z 422 [M+H]⁺.

(S)-methyl 8-fluoro-2-methyl-5-phenoxy-6-(1H-pyrazol-4-yl)-3,4-dihydroquinoline-1(2H)-carboxylate (I-240)

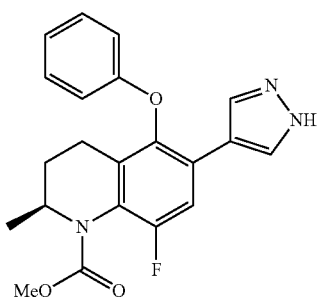 [SMILES: COC(=O)N1c2c(F)cc(-c3cn[nH]c3)c(Oc3ccccc3)c2CC[C@@H]1C]

$^1$H NMR (400 MHz, CD$_3$OD) δ ppm 1.19 (d, J=6.40 Hz, 3H), 1.35-1.46 (m 1H), 2.20-2.32 (m, 2H), 2.68-2.73 (m, 1H), 3.79 (s, 3H), 4.46-4.53 (m, 1H), 6.77-6.79 (m, 2H), 6.95-7.02

(m, 1H), 7.25-7.29 (m, 2H), 7.42-7.45 (m, 1H), 7.91 (br s, 2H). MS (ESI, pos. ion) m/z 382 [M+H]⁺.

(S)-1-(6-(1-cyclopropyl-1H-pyrazol-4-yl)-8-fluoro-2-methyl-5-phenoxy-3,4-dihydroquinolin-1(2H)-yl)ethanone (I-241)

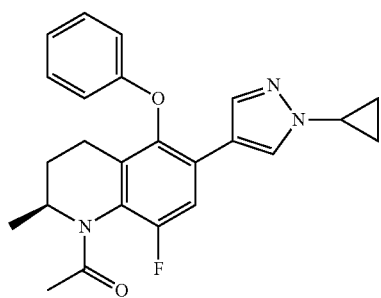 [SMILES: CC(=O)N1c2c(F)cc(-c3cnn(C4CC4)c3)c(Oc3ccccc3)c2CC[C@@H]1C]

$^1$H NMR (300 MHz, CD$_3$OD) δ ppm 0.95-1.02 (m, 4H), 1.10-1.23 (m, 4H), 2.16-2.15 (m, 3H), 2.24-2.37 (m, 2H), 2.68-2.80 (m, 1H), 3.55-3.64 (m, 1H), 4.76-4.85 (m, 1H), 6.77-6.82 (m, 2H), 6.95-7.03 (m, 1H), 7.25-7.33 (m, 2H), 7.49-7.54 (m, 1H), 7.81 (s, 1H), 7.98 (s, 1H). MS (ESI, pos. ion) m/z 406 [M+H]⁺.

(S)-1-(8-fluoro-2-methyl-5-phenoxy-6-(1H-pyrazol-4-yl)-3,4-dihydroquinolin-1(2H)-yl)ethanone (I-242)

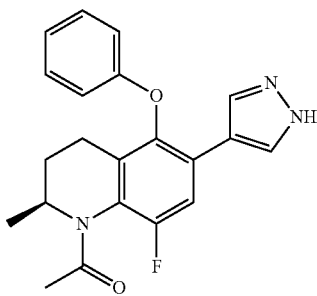 [SMILES: CC(=O)N1c2c(F)cc(-c3cn[nH]c3)c(Oc3ccccc3)c2CC[C@@H]1C]

$^1$H NMR (300 MHz, CD$_3$OD) δ ppm 1.09-1.30 (m, 4H), 2.11-2.37 (m, 5H), 2.71-2.81 (m, 1H), 4.75-4.85 (m, 1H), 6.81 (d, J=7.80 Hz, 2H), 7.00 (t, J=7.20 Hz, 1H), 7.29 (t, J=8.10 Hz, 2H), 7.57 (d, J=10.80 Hz, 2H), 7.95 (s, 2H). MS (ESI, pos. ion) m/z 366 [M+H]⁺.

(S)-cyclopropyl(6-cyclopropyl-2-methyl-5-phenoxy-3,4-dihydroquinolin-1(2H)-yl) methanone (I-243)

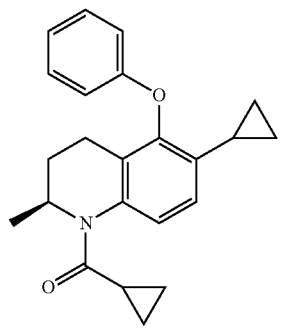 [SMILES: C[C@H]1CCc2c(ccc(C3CC3)c2Oc2ccccc2)N1C(=O)C1CC1]

$^1$H NMR (300 MHz, CDCl$_3$) δ ppm 0.57-0.72 (m, 3H), 0.79-0.91 (m, 3H), 1.91-2.03 (m, 1H), 1.09 (d, J=6.60 Hz, 3H), 1.25-1.31 (m, 1H), 1.32-1.34 (m, 1H), 1.84-1.91 (m, 2H), 2.13-2.21 (m, 1H), 2.25-2.37 (m, 1H), 2.66-2.75 (m, 1H), 4.78-4.65 (m, 1H), 6.73-6.81 (m, 3H), 6.95-7.04 (m, 1H), 7.19 (d, J=7.80 Hz, 1H), 7.26-7.33 (m, 2H). MS (ESI, pos. ion) m/z 348 [M+H]⁺.

(S)-methyl 6-cyclopropyl-2-methyl-5-phenoxy-3,4-dihydroquinoline-1(2H)-carboxylate (I-244)

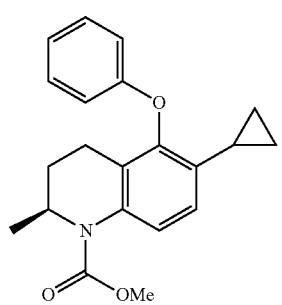 [SMILES: COC(=O)N1c2ccc(C3CC3)c(Oc3ccccc3)c2CC[C@@H]1C]

$^1$H NMR (400 MHz, CD$_3$OD) δ ppm 0.55-0.60 (m, 2H), 0.62-0.77 (m, 2H), 1.11 (d, J=6.60 Hz, 3H), 1.49-1.59 (m, 1H), 1.82-1.88 (m, 1H), 2.00-2.07 (m, 1H), 2.39-2.49 (m, 1H), 2.58-2.67 (m, 1H), 3.79 (s, 3H), 4.62-4.68 (m, 1H), 6.73-6.80 (m, 3H), 6.95-7.00 (m, 1H), 7.23-7.26 (m, 1H), 7.25-7.27 (m, 1H), 7.43 (d, J=8.70 Hz, 1H). MS (ESI, pos. ion) m/z 338 [M+H]⁺.

Example 40 methyl (S)-5-(4-chloro-2-cyanophenoxy)-2-methyl-6-(1-(1-methylpiperidin-4-yl)-1H-pyrazol-4-yl)-3,4-dihydroquinoline-1(2H)-carboxylate (I-245)

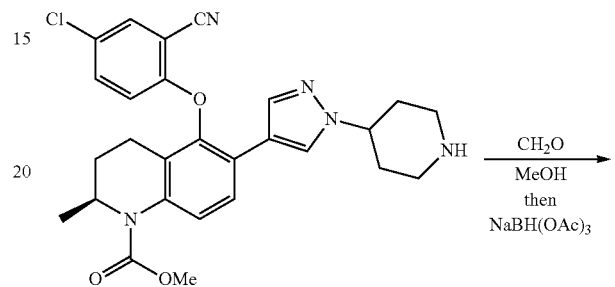

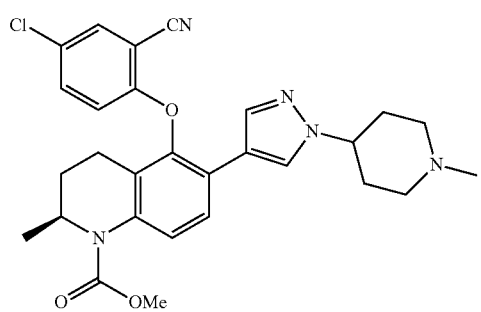

Formaldehyde (37% aqueous solution, 0.015 mL, 0.198 mmol) was added to a solution of (S)-methyl 5-(4-chloro-2-cyanophenoxy)-2-methyl-6-(1-(piperidin-4-yl)-1H-pyrazol-4-yl)-3,4-dihydroquinoline-1(2H)-carboxylate (0.010 g, 0.020 mmol) in methanol (1.0 mL), and the reaction mixture stirred for 2 h. The mixture was cooled to 0° C. and sodium triacetoxyborohydride (8.4 mg, 0.040 mmol) was added. The reaction mixture stirred at 0° C. and was allowed to warm to room temperature overnight. The reaction mixture was partitioned between ethyl acetate and water. The aqueous phase was extracted with ethyl acetate and the combined organic phases were washed with brine, dried over anhydrous sodium sulfate, filtered and concentrated to afford (S)-methyl 5-(4-chloro-2-cyanophenoxy)-2-methyl-6-(1-(1-methylpiperidin-4-yl)-1H-pyrazol-4-yl)-3,4-dihydroquinoline-1(2H)-carboxylate (0.0095 g, 92%) as a white solid. $^1$H NMR (300 MHz, DMSO-d$_6$) δ ppm 1.06 (br d, J=6.74 Hz, 3H), 1.47-1.69 (m, 4H), 1.71-2.13 (m, 4H), 2.19 (s, 3H), 2.71-2.90 (m, 2H), 3.72 (s, 3H), 3.93-4.13 (m, 1H), 4.32-4.45 (m, 1H), 4.50-4.65

(m, 1H), 6.35-6.54 (m, 1H), 7.45-7.65 (m, 4H), 7.65-7.72 (m, 1H), 7.97 (s, 1H), 8.11 (d, J=2.64 Hz, 1H). MS (ESI, pos. ion) m/z 521 [M+H]⁺.

Example 41

(S)-2-((1-acetyl-2-methyl-6-(1-(1-methylpiperidin-4-yl)-1H-pyrazol-4-yl)-1,2,3,4-tetrahydroquinolin-5-yl)oxy)benzonitrile (I-246)

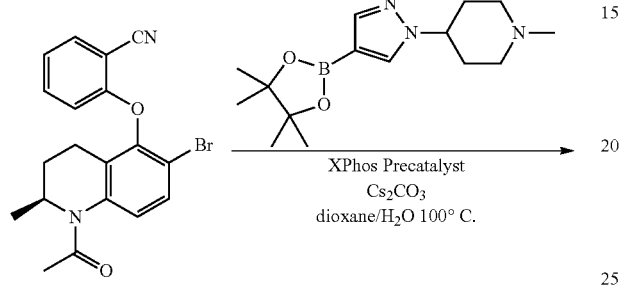

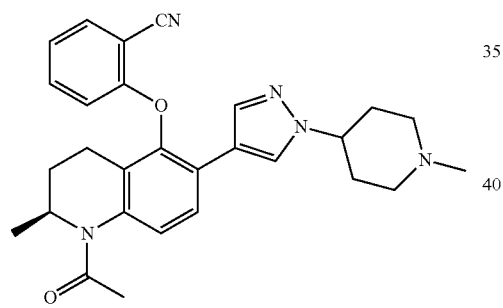

A mixture of (S)-2-((1-acetyl-6-bromo-2-methyl-1,2,3,4-tetrahydroquinolin-5-yl)oxy)benzonitrile (0.017 g, 0.044 mmol), 1-methyl-4-(4-(4,4,5,5-tetramethyl-1,3,2-dioxaborolan-2-yl)-1H-pyrazol-1-yl)piperidine (0.030 g, 0.101 mmol), XPhos Precatalyst 2nd Generation (3.47 mg, 4.41 µmol), and cesium carbonate (0.058 g, 0.177 mmol) in dioxane (2.0 mL) and water (0.400 mL) was heated at 100° C. for 16 h. The reaction mixture was filtered through Celite and concentrated to afford an orange oil. This material was purified via column chromatography on silica gel (Biotage 25 g column, gradient elution with 0-50% (90:10:1, dichloromethane/methanol/ammonium hydroxide)-dichloromethane) to afford (S)-2-(1-acetyl-2-methyl-6-(1-(1-methylpiperidin-4-yl)-1H-pyrazol-4-yl)-1,2,3,4-tetrahydroquinolin-5-yl)oxy)benzonitrile (0.017 g, 82%) as a white solid. ¹H NMR (300 MHz, DMSO-d₆) δ ppm 1.04 (d, J=7.04 Hz, 3H), 1.27-1.58 (m, 2H), 1.77-1.97 (m, 4H), 1.97-2.14 (m, 4H), 2.17 (s, 3H), 2.19 (s, 3H), 2.81 (br d, J=11.43 Hz, 2H), 3.90-4.17 (m, 1H), 4.62 (br s, 1H), 6.48 (br s, 1H), 7.14 (t, J=7.62 Hz, 1H), 7.39-7.56 (m, 2H), 7.61 (d, J=8.50 Hz, 1H), 7.72 (s, 1H), 7.89 (dd, J=7.77, 1.61 Hz, 1H), 8.01 (s, 1H). MS (ESI, pos. ion) m/z 470 [M+H]

Example 42

(2S)-methyl 5-cyclobutoxy-2-methyl-6-(1-(1-methylpyrrolidin-3-yl)-1H-pyrazol-4-yl)-3,4-dihydroquinoline-1(2H)-carboxylate (I-247)

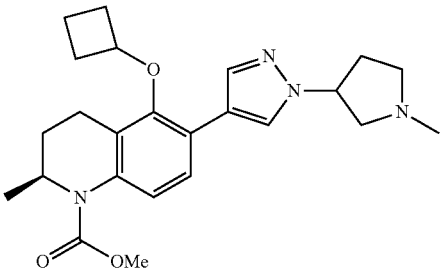

(2S)-Methyl 5-cyclobutoxy-2-methyl-6-(1-(1-methylpyrrolidin-3-yl)-1H-pyrazol-4-yl)-3,4-dihydroquinoline-1(2H)-carboxylate was synthesized from (2S)-methyl 5-cyclobutoxy-2-methyl-6-(1-(pyrrolidin-3-yl)-1H-pyrazol-4-yl)-3,4-dihydroquinoline-1(2H)-carboxylate according to the procedure outlined above for Example 40. ¹H NMR (400 MHz, CD₃OD) δ ppm 1.17 (d, J=6.40 Hz, 3H), 1.25-1.48 (m, 2H), 1.55-1.65 (m, 1H), 1.99-2.20 (m, 4H), 2.21-2.28 (m, 1H), 2.30-2.50 (m, 2H), 2.75-2.99 (m, 2H), 3.01-3.20 (m, 3H), 3.30-3.40 (m, 1H), 3.55-3.72 (m, 1H), 3.78 (s, 3H), 3.90-4.05 (m, 2H), 4.10-4.25 (m, 1H), 4.48-4.60 (m, 1H), 7.20-7.30 (m, 2H), 7.95 (s, 1H), 8.09 (s, 1H). MS (ESI, pos. ion) m/z 425 [M+H]⁺.

Example 43

(2S)-methyl 5-cyclobutoxy-2-methyl-6-(1-(2-methyl-octahydrocyclopenta[c]pyrrol-5-yl)-1H-pyrazol-4-yl)-3,4-dihydroquinoline-1(2H)-carboxylate (I-248)

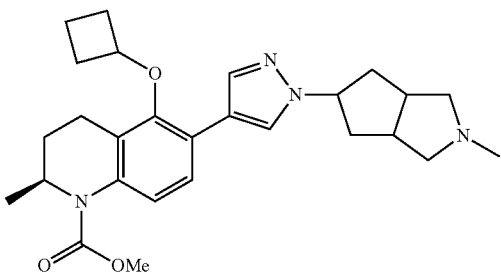

(2S)-Methyl 5-cyclobutoxy-2-methyl-6-(1-(2-methyl-octahydrocyclopenta[c]pyrrol-5-yl)-1H-pyrazol-4-yl)-3,4-dihydroquinoline-1(2H)-carboxylate was synthesized from (2S)-methyl 5-cyclobutoxy-2-methyl-6-(1-(octahydrocyclopenta[c]pyrrol-5-yl)-1H-pyrazol-4-yl)-3,4-dihydroquinoline-1(2H)-carboxylate according to the procedure outlined above for Example 40. ¹H NMR (400 MHz, CD₃OD) 1.17 (d, J=6.40 Hz, 3H), 1.28-1.48 (m, 2H), 1.55-1.70 (m, 1H), 1.99-2.20 (m, 6H), 2.21-2.50 (m, 9H), 2.79-2.98 (m, 5H), 3.78 (s, 3H), 4.05-4.15 (m, 1H), 4.45-4.55 (m, 1H), 4.85-4.95 (m, 1H), 7.20-7.30 (m, 2H), 7.83 (s, 1H), 8.01 (s, 1H). MS (ESI, pos. ion) m/z 465 [M+H]$^+$.

Example 44

(2S)-methyl 5-(4-fluorophenoxy)-2-methyl-6-(1-(1-methylpyrrolidin-3-yl)-1H-pyrazol-4-yl)-3,4-dihydroquinoline-1(2H)-carboxylate (I-249)

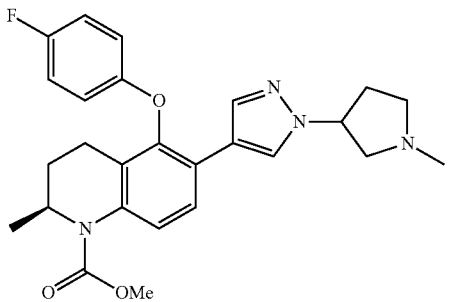

(2S)-Methyl 5-(4-fluorophenoxy)-2-methyl-6-(1-(1-methylpyrrolidin-3-yl)-1H-pyrazol-4-yl)-3,4-dihydroquinoline-1(2H)-carboxylate was synthesized from (2S)-methyl 5-(4-fluorophenoxy)-2-methyl-6-(1-(pyrrolidin-3-yl)-1H-pyrazol-4-yl)-3,4-dihydroquinoline-1(2H)-carboxylate according to the procedure outlined above for Example 40. $^1$H NMR (400 MHz, CD$_3$OD) δ ppm 1.15 (d, J=6.40 Hz, 3H), 1.48-1.65 (m, 1H), 2.01-2.10 (m, 1H), 2.12-2.23 (m, 1H), 2.38-2.45 (m, 1H), 2.55-2.85 (m, 2H), 2.92-3.05 (m, 3H), 3.20-3.30 (m, 1H), 3.40-4.60 (m, 1H), 3.82 (s, 3H), 3.89-3.95 (m, 2H), 4.58-4.65 (m, 1H), 5.15-5.25 (m, 1H), 6.68-6.74 (m, 2H), 6.95-7.02 (m, 2H), 7.48-6.60 (m, 2H), 7.89 (s, 1H), 7.99 (s, 1H). MS (ESI, pos. ion) m/z 465 [M+H]$^+$.

Example 45

(2S)-methyl 5-(4-fluorophenoxy)-2-methyl-6-(1-(2-methyl-octahydrocyclopenta[c]pyrrol-5-yl)-1H-pyrazol-4-yl)-3,4-dihydroquinoline-1(2H)-carboxylate (I-250)

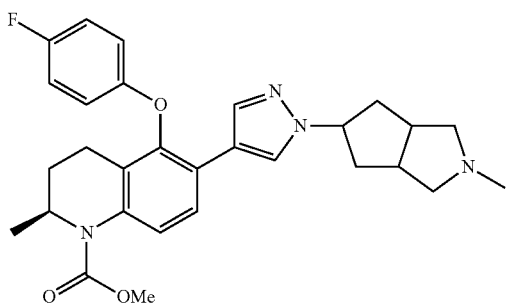

(2S)-Methyl 5-(4-fluorophenoxy)-2-methyl-6-(1-(2-methyl-octahydrocyclopenta[c]pyrrol-5-yl)-1H-pyrazol-4-yl)-3,4-dihydroquinoline-1(2H)-carboxylate was synthesized from (2S)-methyl 5-(4-fluorophenoxy)-2-methyl-6-(1-(octahydrocyclopenta[c]pyrrol-5-yl)-1H-pyrazol-4-yl)-3,4-dihydroquinoline-1(2H)-carboxylate according to the procedure outlined above for Example 40. $^1$H NMR (300 MHz, CD$_3$OD) δ ppm 1.14 (d, J=6.60 Hz, 3H), 1.50-1.62 (m, 1H), 1.85-1.99 (m, 2H), 2.01-2.20 (m, 3H), 2.25-2.45 (m, 6H), 2.55-2.75 (m, 5H), 4.55-4.70 (m, 1H), 4.70-4.82 (m, 1H), 6.65-6.75 (m, 2H), 6.90-7.02 (m, 2H), 7.48-7.52 (m, 2H), 7.75 (s, 1H), 7.89 (s, 1H). MS (ESI, pos. ion) m/z 505 [M+H]$^+$.

Example 46

(S)-methyl 6-(1-cyclopropyl-1H-pyrazol-4-yl)-5-(1-ethylazetidin-3-yloxy)-2-methyl-3,4-dihydroquinoline-1(2H)-carboxylate (I-251)

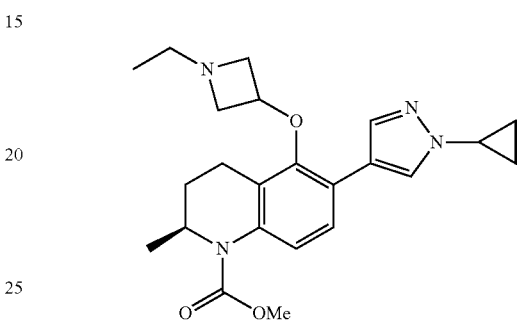

(S)-Methyl 6-(1-cyclopropyl-1H-pyrazol-4-yl)-5-(1-ethylazetidin-3-yloxy)-2-methyl-3,4-dihydroquinoline-1(2H)-carboxylate was synthesized from (S)-methyl 5-(azetidin-3-yloxy)-6-(1-cyclopropyl-1H-pyrazol-4-yl)-2-methyl-3,4-dihydroquinoline-1(2H)-carboxylate and acetaldehyde according to the procedure outlined above for Example 40. $^1$H NMR (400 MHz, CD$_3$OD) δ ppm 0.96 (t, J=7.20 Hz, 3H), 1.05-1.20 (m, 7H), 1.42-1.55 (m, 1H), 2.15-2.25 (m, 1H), 2.40-2.52 (m, 3H), 2.81-2.95 (m, 1H), 3.01-3.15 (m, 2H), 3.41-3.52 (m, 2H), 3.68-3.71 (m, 1H), 3.78 (s, 3H), 4.21-4.28 (m, 1H), 4.51-4.61 (m, 1H), 7.20-7.32 (m, 2H), 7.76 (s, 1H), 7.99 (s, 1H). MS (ESI, pos. ion) m/z 411 [M+H]$^+$.

Example 47

(S)-methyl 6-(1-cyclopropyl-1H-pyrazol-4-yl)-5-(1-isopropylazetidin-3-yloxy)-2-methyl-3,4-dihydroquinoline-1(2H)-carboxylate (I-252)

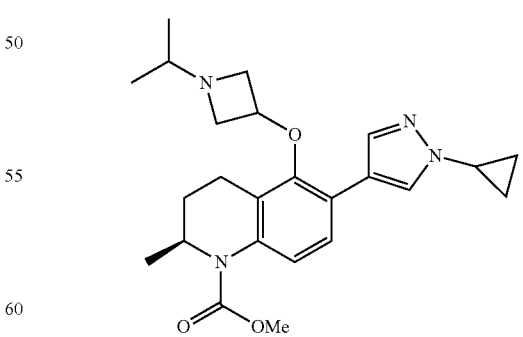

(S)-Methyl 6-(1-cyclopropyl-1H-pyrazol-4-yl)-5-(1-isopropylazetidin-3-yloxy)-2-methyl-3,4-dihydroquinoline-1 (2H)-carboxylate was synthesized from (S)-methyl 5-(azetidin-3-yloxy)-6-(1-cyclopropyl-1H-pyrazol-4-yl)-2-methyl-3,4-dihydroquinoline-1(2H)-carboxylate and acetone according to the procedure outlined above for Example 40. ¹H NMR (400 MHz, CD₃OD) δ ppm 0.85-0.95 (m, 6H), 1.05-1.15 (m, 7H), 1.45-1.55 (m, 1H), 2.15-2.52 (m, 3H), 2.80-2.90 (m, 1H), 3.01-3.11 (m, 2H), 3.40-3.50 (m, 2H), 3.67-3.71 (m, 1H), 3.78 (s, 3H), 4.15-4.25 (m, 1H), 4.51-4.62 (m, 1H), 7.20-7.35 (m, 2H), 7.76 (s, 1H), 7.97 (s, 1H). MS (ESI, pos. ion) m/z 425 [M+H]⁺.

Example 48

(S)-1-(6-(1-cyclopropyl-1H-pyrazol-4-yl)-5-(1-ethylazetidin-3-yloxy)-2-methyl-3,4-dihydroquinolin-1(2H)-yl)ethanone (I-253)

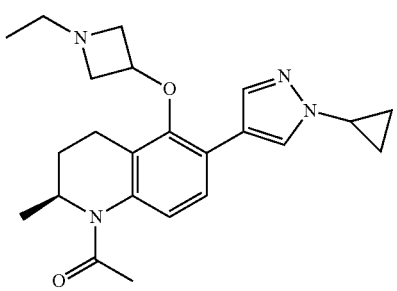 [SMILES: CCN1CC(Oc2c(-c3cnn(C4CC4)c3)ccc3c2CC[C@H](C)N3C(C)=O)C1]

(S)-1-(6-(1-Cyclopropyl-1H-pyrazol-4-yl)-5-(1-ethylazetidin-3-yloxy)-2-methyl-3,4-dihydroquinolin-1(2H)-yl)ethanone was synthesized from (S)-1-(5-(azetidin-3-yloxy)-6-(1-cyclopropyl-1H-pyrazol-4-yl)-2-methyl-3,4-dihydroquinolin-1(2H)-yl)ethanone and acetaldehyde according to the procedure outlined above for Example 40. ¹H NMR (400 MHz, CD₃OD) δ ppm 0.97 (t, J=7.20 Hz, 3H), 1.05-1.18 (m, 7H), 1.10-1.35 (m, 1H), 2.16 (s, 3H), 2.20-2.40 (m, 2H), 2.51 (q, J=7.20 Hz, 2H), 2.88-2.98 (m, 1H), 3.07 (t, J=7.20 Hz, 1H), 3.15 (t, J=7.20 Hz, 1H), 3.41-3.55 (m, 1H), 3.68-3.75 (m, 1H), 4.25-4.32 (m, 1H), 4.65-4.80 (m, 1H), 7.01-7.12 (m, 1H), 7.37 (d, J=8.00 Hz, 1H), 7.81 (s, 1H), 8.02 (s, 1H). MS (ESI, pos. ion) m/z 395 [M+H]⁺.

Example 49

(S)-1-(6-(1-cyclopropyl-1H-pyrazol-4-yl)-5-(1-isopropylazetidin-3-yloxy)-2-methyl-3,4-dihydroquinolin-1(2H)-yl)ethanone (I-254)

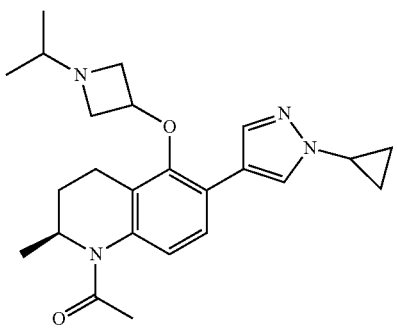 [SMILES: CC(=O)N1c2ccc(-c3cnn(C4CC4)c3)c(OC3CN(C(C)C)C3)c2CC[C@@H]1C]

(S)-1-(6-(1-cyclopropyl-1H-pyrazol-4-yl)-5-(1-isopropylazetidin-3-yloxy)-2-methyl-3,4-dihydroquinolin-1(2H)-yl)ethanone was synthesized from (S)-1-(5-(azetidin-3-yloxy)-6-(1-cyclopropyl-1H-pyrazol-4-yl)-2-methyl-3,4-dihydroquinolin-1(2H)-yl)ethanone and acetone according to the procedure outlined above for Example 40. ¹H NMR (400 MHz, CD₃OD) δ ppm 0.89-1.01 (m, 6H), 1.01-1.15 (m, 7H), 1.21-1.35 (m, 1H), 2.16 (s, 3H), 2.25-2.45 (m, 3H), 2.85-2.95 (m, 1H), 3.06 (t, J=7.20 Hz, 1H), 3.15 (t, J=7.20 Hz, 1H), 3.41-3.55 (m, 2H), 3.68-3.73 (m, 1H), 4.21-4.29 (m, 1H), 4.65-4.81 (m, 1H), 7.01-7.12 (m, 1H), 7.36 (d, J=8.00 Hz, 1H), 7.81 (s, 1H), 8.03 (s, 1H). MS (ESI, pos. ion) m/z 409 [M+H]⁺.

Example 50

1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one (I-255)

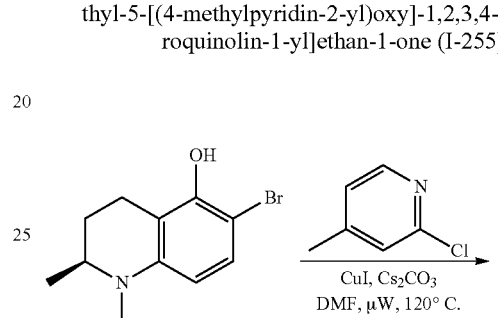

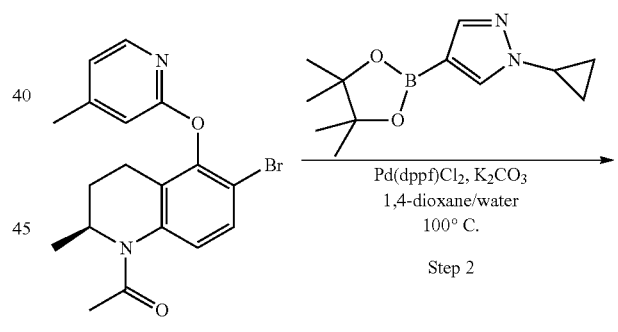

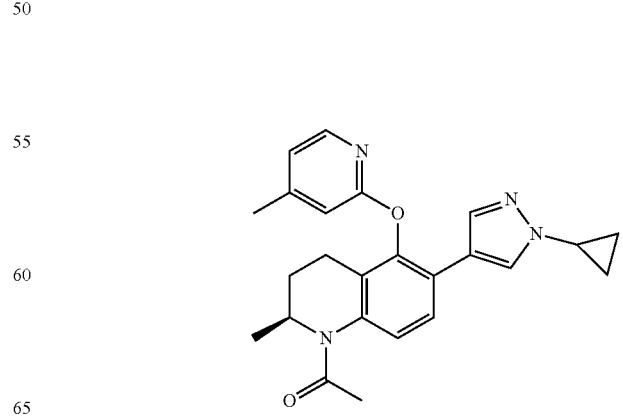

Step 1. 1-[(2S)-6-bromo-2-methyl-5-[(4-methylpyridin-2-yl)oxy]-1,2,3,4-tetrahydroquinolin-1-yl]ethan-1-one A 20-mL microwave tube was charged with 1-[(2S)-6-bromo-5-hydroxy-2-methyl-1,2,3,4-tetrahydroquinolin-1-yl]ethan-1-one (200 mg, 0.70 mmol), 2-chloro-4-methylpyridine (180 mg, 1.41 mmol), N,N-dimethylformamide (15 mL), copper (I) iodide (133 mg, 0.70 mmol), and cesium carbonate (700 mg, 2.10 mmol). The reaction mixture was heated with microwave radiation for 8 h at 120° C. After cooling to room temperature, the resulting mixture was diluted with ethyl acetate (50 mL), washed with water (3×15 mL) and brine (15 mL), dried over anhydrous sodium sulfate, filtered, and concentrated. The residue was purified via column chromatography on silica gel (eluting with 2:1, ethyl acetate/petroleum ether) to afford 1-[(2S)-6-bromo-2-methyl-5-[(4-methylpyridin-2-yl)oxy]-1,2,3,4-tetrahydroquinolin-1-yl]ethan-1-one (111 mg, 42%) as a light yellow solid. MS (ESI, pos. ion) m/z 375, 377 [M+H]+.

Step 2. 1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one A 50-mL round-bottom flask was purged and maintained with an inert atmosphere of nitrogen, and charged with 1-[(2S)-6-bromo-2-methyl-5-[(4-methylpyridin-2-yl)oxy]-1,2,3,4-tetrahydroquinolin-1-yl]ethan-1-one (111 mg, 0.30 mmol), 1,4-dioxane (15 mL), 1-cyclopropyl-4-(tetramethyl-1,3,2-dioxaborolan-2-yl)-1H-pyrazole (139 mg, 0.59 mmol), [1,1'-bis(diphenylphosphino)ferrocene]dichloropalladium (II) (30 mg, 0.04 mmol), potassium carbonate (124 mg, 0.90 mmol), and water (5 mL). The resulting mixture stirred overnight at 100° C. After cooling to room temperature, the solution was diluted with ethyl acetate (10 mL). The aqueous layer was separated and extracted with ethyl acetate (2×20 mL). The combined organic layers were washed with brine, dried over anhydrous sodium sulfate, filtered, and concentrated under vacuum. The residue was purified via column chromatography on silica gel (eluting with 1:1, ethyl acetate/petroleum ether). The collected fractions were combined and concentrated under vacuum. The crude product was further purified by Prep-HPLC with the following conditions (Waters I): Column, SunFire Prep C18, 5 um, 19×100 mm; mobile phase, water (0.05% ammonium bicarbonate) and acetonitrile (65% to 85% acetonitrile in 7 min, flow rate 20 mL/min); Detector, UV 220&254 nm. This afforded 1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one (63.6 mg, 53%) as an off-white solid. $^1$H NMR (300 MHz, CD$_3$OD) δ ppm 0.95-1.01 (m, 4H), 1.14 (d, J=6.30 Hz, 3H), 1.30-1.45 (m, 1H), 2.10-2.30 (m, 5H), 2.34 (s, 3H), 2.55-2.70 (m, 1H), 3.55-3.65 (m, 1H), 4.68-4.85 (m, 1H), 6.75 (s, 1H), 6.85-6.95 (m, 1H), 7.20-7.32 (m, 1H), 7.55-7.58 (m, 1H), 7.72 (s, 1H), 7.89-7.93 (m, 2H). MS (ESI, pos. ion) m/z 403 [M+H]+.

The following examples were made according to the procedure outlined for Example 50:

(S)-1-(6-(1-cyclopropyl-1H-pyrazol-4-yl)-2-methyl-5-(6-methylpyridin-2-yloxy)-3,4-dihydroquinolin-1(2H)-yl)ethanone (I-256)

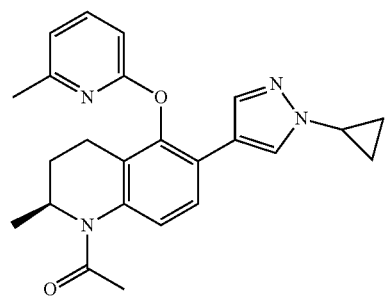 [SMILES: CC(=O)N1c2ccc(-c3cnn(C4CC4)c3)c(Oc3cccc(C)n3)c2CC[C@@H]1C]

$^1$H NMR (300 MHz, CD$_3$OD) δ ppm 0.91-0.99 (m, 4H), 1.12 (d, J=6.60 Hz, 3H), 1.25-1.45 (m, 1H), 2.10-2.30 (m, 5H), 2.37 (s, 3H), 2.55-2.68 (m, 1H), 3.55-3.62 (m, 1H), 4.65-4.83 (m, 1H), 6.45 (d, J=8.40 Hz, 1H), 6.89 (d, J=7.50 Hz, 1H), 7.20-7.35 (m, 1H), 7.50-7.62 (m, 2H), 7.73 (s, 1H), 7.93 (s, 1H). MS (ESI, pos. ion) m/z 403 [M+H]+.

(S)-1-(6-(1-cyclopropyl-1H-pyrazol-4-yl)-5-(isoquinolin-1-yloxy)-2-methyl-3,4-dihydroquinolin-1(2H)-yl)ethanone (I-257)

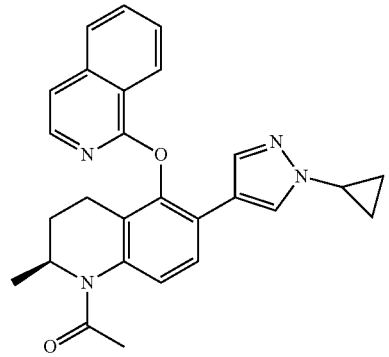 [SMILES: CC(=O)N1c2ccc(-c3cnn(C4CC4)c3)c(Oc3nccc4ccccc34)c2CC[C@@H]1C]

$^1$H NMR (300 MHz, CD$_3$OD) δ ppm 0.68-0.71 (m, 2H), 0.83-0.90 (m, 2H), 1.19 (d, J=6.60 Hz, 3H), 1.46 (m, 1H), 2.18-2.31 (m, 5H), 2.67 (m, 1H), 3.43-3.48 (m, 1H), 4.75-4.80 (m, 1H), 7.36-7.44 (m, 1H), 7.57 (d, J=4.80 Hz, 1H), 7.60-7.67 (m, 1H), 7.74 (s, 1H), 7.76-7.79 (m, 1H), 7.89 (m, 3H), 7.91-7.98 (m, 1H), 8.61 (d, J=8.10 Hz, 1H). MS (ESI, pos. ion) m/z 439 [M+H]+.

Example 51

(S)-1-(5-(2-fluorophenoxy)-2-methyl-6-(1-(piperidin-4-yl)-1H-pyrazol-4-yl)-3,4-dihydroquinolin-1(2H)-yl)ethanone (I-258)

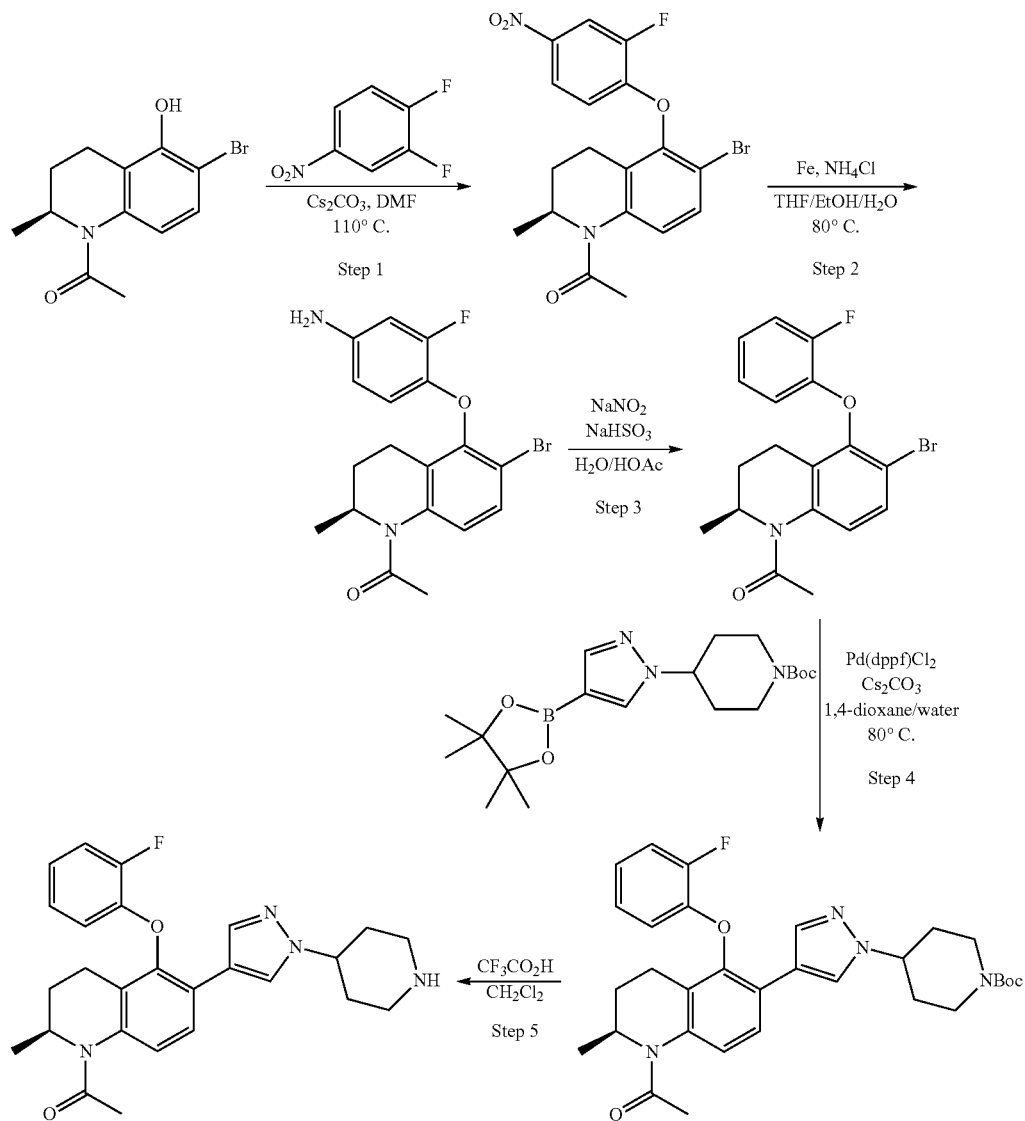

Step 1. 1-[(2S)-6-bromo-5-(2-fluoro-4-nitrophenoxy)-2-methyl-1,2,3,4-tetrahydroquinolin-1-yl]ethan-1-one A 50-mL round-bottom flask was purged and maintained with an inert atmosphere of nitrogen and charged with 1-[(2S)-6-bromo-5-hydroxy-2-methyl-1,2,3,4-tetrahydroquinolin-1-yl]ethan-1-one (350 mg, 1.23 mmol), N,N-dimethylformamide (10 mL), 1,2-difluoro-4-nitrobenzene (415 mg, 2.61 mmol) and cesium carbonate (1.3 g, 3.99 mmol). The resulting mixture stirred for 3 h at 110° C. After cooling to room temperature, the reaction mixture was poured into dichloromethane (50 mL), washed with water (10 mL) and brine (10 mL), dried over anhydrous sodium sulfate, filtered, and concentrated under vacuum. The residue was purified via column chromatography on silica gel (eluting with 5:1, ethyl acetate/petroleum ether) to afford 1-[(2S)-6-bromo-5-(2-fluoro-4-nitrophenoxy)-2-methyl-1,2,3,4-tetrahydroquinolin-1-yl]ethan-1-one (450 mg, 86%) of as yellow oil. MS (ESI, neg. ion) m/z 421, 423[M−H].

Step 2. 1-[(2S)-5-(4-amino-2-fluorophenoxy)-6-bromo-2-methyl-1,2,3,4-tetrahydroquinolin-1-yl]ethan-1-one A 100-mL round-bottom flask was purged and maintained with an inert atmosphere of nitrogen, and charged with 1-[(2S)-6-bromo-5-(2-fluoro-4-nitrophenoxy)-2-methyl-1, 2,3,4-tetrahydroquinolin-1-yl]ethan-1-one (500 mg, 1.18 mmol), iron powder (331 mg, 5.91 mmol), ammonium chloride (128 mg, 2.37 mmol), tetrahydrofuran (9 mL), ethanol (3 mL), and water (9 mL). The resulting mixture stirred for 12 h at 80° C. and was then filtered. The filtrate was concentrated, and the residue was diluted with ethyl acetate, washed with water, dried over anhydrous sodium sulfate, filtered, and concentrated to afford 1-[(2S)-5-(4-amino-2-fluorophenoxy)-6-bromo-2-methyl-1,2,3,4-tetrahydroquinolin-1-yl]ethan-1-one (370 mg, 80%) as a light brown solid. MS (ESI, pos. ion) m/z 393, 395 [M+H]⁺.

Step 3. 1-[(2S)-6-bromo-5-(2-fluorophenoxy)-2-methyl-1,2,3,4-tetrahydroquinolin-1-yl]ethan-1-one A 100-mL round-bottom flask was charged with 1-[(2S)-5-(4-amino-2-fluorophenoxy)-6-bromo-2-methyl-1,2,3,4-tetrahydroquinolin-1-yl]ethan-1-one (370 mg, 0.92 mmol) and acetic acid (5 mL). Sodium nitrite (1.3 g, 18.8 mmol) was added in portions, and the mixture stirred at room temperature for 30 minutes. Sodium bisulfite (2.0 g, 18.8 mmol) and ethanol (5 mL) were added, and the resulting mixture stirred for 12 h at room temperature. The reaction mixture was concentrated under vacuum, diluted with dichloromethane, washed with water and brine, dried over anhydrous sodium sulfate, filtered, and concentrated. The residue was purified via column chromatography on silica gel (eluting with 5:1, ethyl acetate/petroleum ether) to afford 1-[(2S)-6-bromo-5-(2-fluorophenoxy)-2-methyl-1,2,3,4-tetrahydroquinolin-1-yl]ethan-1-one (300 mg, 86%) of as yellow oil. MS (ESI, pos. ion) m/z 378, 380 [M+H]⁺.

Step 4. (S)-tert-butyl 4-(4-(1-acetyl-5-(2-fluorophenoxy)-2-methyl-1,2,3,4-tetrahydroquinolin-6-yl)-1H-pyrazol-1-yl)piperidine-1-carboxylate A 100-mL round-bottom flask was purged and maintained with an inert atmosphere of nitrogen, and charged with 1-[(2S)-6-bromo-5-(2-fluorophenoxy)-2-methyl-1,2,3,4-tetrahydroquinolin-1-yl]ethan-1-one (300 mg, 0.79 mmol), 1,4-dioxane (18 mL), water (3 mL), [1,1'-bis(diphenylphosphino)ferrocene]dichloropalladium(II) (65 mg, 0.08 mmol), cesium carbonate (776 mg, 2.37 mmol), and tert-butyl 4-(4-(4,4,5,5-tetramethyl-1,3,2-dioxaborolan-2-yl)-1H-pyrazol-1-yl)piperidine-1-carboxylate (378 mg, 1.00 mmol). The resulting mixture stirred for 12 h at 80° C. After cooling to room temperature, the reaction mixture was passed through a short pad of Celite and concentrated under vacuum. The residue was purified via column chromatography on silica gel (eluting with 5:1, ethyl acetate/petroleum ether) to afford (S)-tert-butyl 4-(4-(1-acetyl-5-(2-fluorophenoxy)-2-methyl-1,2,3,4-tetrahydroquinolin-6-yl)-1H-pyrazol-1-yl)piperidine-1-carboxylate (370 mg, 85%) as yellow oil. MS (ESI, pos. ion) m/z 549 [M+H]⁺.

Step 5. (S)-1-(5-(2-fluorophenoxy)-2-methyl-6-(1-(piperidin-4-yl)-1H-pyrazol-4-yl)-3,4-dihydroquinolin-1(2H)-yl)ethanone A 100-mL round-bottom flask was charged with (S)-tert-butyl 4-(4-(1-acetyl-5-(2-fluorophenoxy)-2-methyl-1,2,3,4-tetrahydroquinolin-6-yl)-1H-pyrazol-1-yl)piperidine-1-carboxylate (370 mg, 0.67 mmol), dichloromethane (10 mL) and trifluoroacetic acid (4 mL). The resulting solution stirred for 2 h at room temperature. The pH value of the solution was adjusted to 8 with saturated aqueous potassium carbonate solution. The resulting mixture was extracted with ethyl acetate. The organic layers were combined, dried over anhydrous sodium sulfate, filtered, and concentrated under vacuum. The residue was purified via column chromatography on silica gel (eluting with 5:1, ethyl acetate/petroleum ether) to afford (S)-1-(5-(2-fluorophenoxy)-2-methyl-6-(1-(piperidin-4-yl)-1H-pyrazol-4-yl)-3,4-dihydroquinolin-1 (2H)-yl)ethanone (141 mg, 47%) as a white solid. ¹H NMR (300 MHz, CD₃OD) δ ppm 1.15 (d, J=6.60 Hz, 3H), 1.25-1.45 (m, 1H), 1.75-1.95 (m, 2H), 1.97-2.08 (m, 2H), 2.15-2.35 (m, 5H), 2.65-2.89 (m, 3H), 3.09-3.20 (m, 2H), 4.15-4.29 (m, 1H), 4.65-4.85 (m, 1H), 6.35-6.48 (m, 1H), 6.85-6.98 (m, 2H), 7.13-7.22 (m, 1H), 7.27-7.42 (m, 1H), 7.61 (d, J=8.40 Hz, 1H), 7.81 (s, 1H), 7.99 (s, 1H). MS (ESI, pos. ion) m/z 449 [M+H]⁺.

The following examples were made according to the procedure outlined for Example 51:

(S)-methyl 5-(2-fluorophenoxy)-2-methyl-6-(1-(piperidin-4-yl)-1H-pyrazol-4-yl)-3,4-dihydroquinoline-1(2H)-carboxylate (I-259)

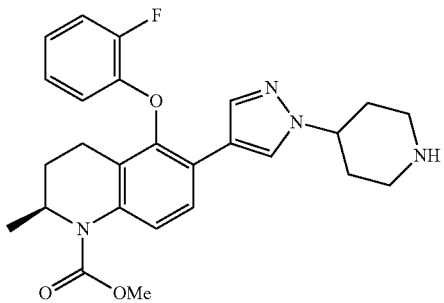 [SMILES: COC(=O)N1c2ccc(-c3cnn(C4CCNCC4)c3)c(Oc3ccccc3F)c2CC[C@@H]1C]

¹H NMR (400 MHz, CD₃OD) δ ppm 1.17 (d, J=6.80 Hz, 3H), 1.55-1.68 (m, 1H), 1.78-1.92 (m, 2H), 1.97-2.13 (m, 3H), 2.45-2.55 (m, 1H), 2.60-2.79 (m, 3H), 3.11-3.18 (m, 2H), 4.18-4.25 (m, 1H), 4.62-4.70 (m, 1H), 6.38-6.42 (m, 1H), 6.85-6.95 (m, 2H), 7.15-7.25 (m, 1H), 7.50-7.62 (m, 2H), 7.78 (s, 1H), 7.93 (s, 1H). MS (ESI, pos. ion) m/z 465 [M+H]⁺.

(S)-cyclopropyl(5-(2-fluorophenoxy)-2-methyl-6-(1-(piperidin-4-yl)-1H-pyrazol-4-yl)-3,4-dihydroquinolin-1(2H)-yl)methanone (I-260)

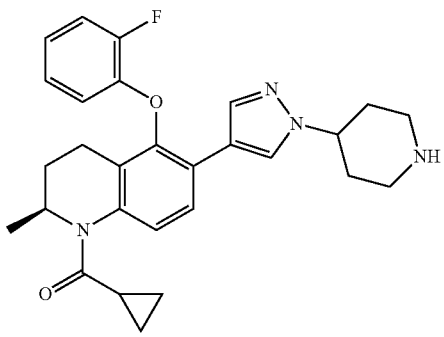 [SMILES: C[C@H]1CCc2c(ccc(-c3cnn(C4CCNCC4)c3)c2Oc2ccccc2F)N1C(=O)C1CC1]

¹H NMR (400 MHz, CD₃OD) δ ppm 0.75-0.85 (m, 1H), 8.87-1.01 (m, 2H), 1.10-1.20 (m, 4H), 1.39-1.50 (m, 1H), 1.78-1.90 (m, 2H), 1.95-2.09 (m, 3H), 2.15-2.38 (m, 2H), 2.65-2.80 (m, 3H), 3.11-3.19 (m, 2H), 4.18-4.28 (m, 1H), 4.75-4.85 (m, 1H), 6.41-6.48 (m, 1H), 6.85-6.99 (m, 2H), 7.18-7.28 (m, 1H), 7.42 (d, J=8.40 Hz, 1H), 7.63 (d, J=8.80 Hz, 1H), 7.81 (s, 1H), 8.01 (s, 1H). MS (ESI, pos. ion) m/z 475 [M+H]⁺.

(S)-methyl 6-(1-(azetidin-3-yl)-1H-pyrazol-4-yl)-5-(2-fluorophenoxy)-2-methyl-3,4-dihydroquinoline-1(2H)-carboxylate (I-261)

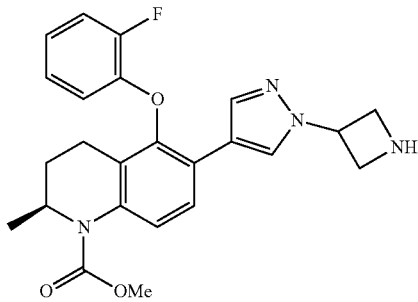 [SMILES: COC(=O)N1c2ccc(-c3cnn(C4CNC4)c3)c(Oc3ccccc3F)c2CC[C@@H]1C]

¹H NMR (400 MHz, CD₃OD) δ ppm 1.16 (d, J=6.40 Hz, 3H), 1.55-1.64 (m, 1H), 2.05-2.14 (m, 1H), 2.45-2.52 (m, 1H), 2.63-2.72 (m, 1H), 3.82 (s, 3H), 3.90-3.98 (m, 2H), 4.03-4.11 (m, 2H), 4.63-4.73 (m, 1H), 5.19-5.29 (m, 1H), 6.35-6.42 (m, 1H), 6.83-6.95 (m, 2H), 7.17-7.25 (m, 1H), 7.20-7.25 (m, 1H), 7.53-7.62 (m, 2H), 7.65-7.70 (m, 1H), 8.03 (s, 1H). MS (ESI, pos. ion) m/z 437 [M+H]⁺.

(S)-(6-(1-(azetidin-3-yl)-1H-pyrazol-4-yl)-5-(2-fluorophenoxy)-2-methyl-3,4-dihydroquinolin-1(2H)-yl)(cyclopropyl)methanone (I-262)

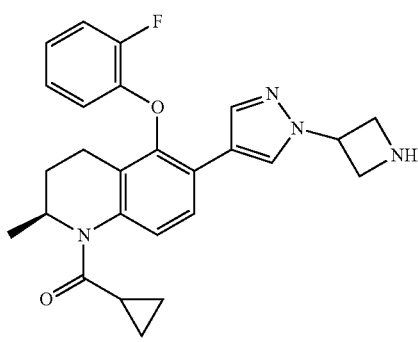 [SMILES: C[C@H]1CCc2c(ccc(-c3cnn(C4CNC4)c3)c2Oc2ccccc2F)N1C(=O)C1CC1]

¹H NMR (400 MHz, CD₃OD) δ ppm 0.60-0.70 (m, 1H), 0.75-0.90 (m, 2H), 1.00-1.10 (m, 4H), 1.20-1.30 (m, 1H), 1.80-1.92 (m, 1H), 2.05-2.25 (m, 2H), 2.55-2.65 (m, 1H), 3.72-3.80 (m, 2H), 3.85-3.95 (m, 2H), 4.65-4.75 (m, 1H), 5.05-5.15 (m, 1H), 6.25-6.35 (m, 1H), 6.70-6.90 (m, 2H), 7.05-7.15 (m, 1H), 7.30 (d, J=8.40 Hz, 1H), 7.51 (d, J=8.40 Hz, 1H), 7.78 (s, 1H), 7.95 (s, 1H). MS (ESI, pos. ion) m/z 447 [M+H]⁺.

The examples below were made according to the procedure outlined above for Example 51, with the following changes to Step 1: (1) 1,2,5-trifluoro-3-nitrobenzene was used in place of 1,2-difluoro-4-nitrobenzene; (2) potassium tert-butoxide was used instead of cesium carbonate; (3) tetrahydrofuran was used as the solvent in place of DMF; (4) the reaction was run at 0° C. for 1 hour as opposed to 3 h at 110° C.

(S)-methyl 5-(2,4-difluorophenoxy)-2-methyl-6-(1-(piperidin-4-yl)-1H-pyrazol-4-yl)-3,4-dihydroquinoline-1(2H)-carboxylate (I-263)

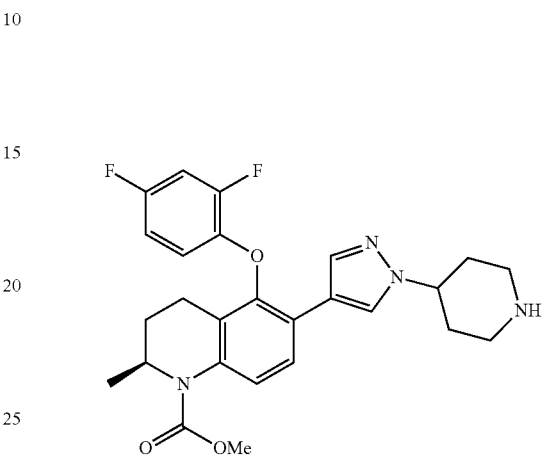

¹H NMR (400 MHz, CDCl₃) δ ppm 1.15 (d, J=6.80 Hz, 3H), 1.55-1.65 (m, 1H), 1.80-1.95 (m, 2H), 2.01-2.15 (m, 3H), 2.35-2.45 (m, 1H), 2.60-2.80 (m, 3H), 3.20-3.30 (m, 2H), 4.08-4.20 (m, 1H), 4.60-4.70 (m, 1H), 6.30-6.40 (m, 1H), 6.50-6.60 (m, 1H), 6.85-6.95 (m, 1H), 7.41 (d, J=8.80 Hz, 1H), 7.60 (d, J=8.40 Hz, 1H), 7.69-7.62 (m, 2H). MS (ESI, pos. ion) m/z 483 [M+H]⁺.

(S)-cyclopropyl (5-(2,4-difluorophenoxy)-2-methyl-6-(1-(piperidin-4-yl)-1H-pyrazol-4-yl)-3,4-dihydroquinolin-1(2H)-yl)methanone (I-264)

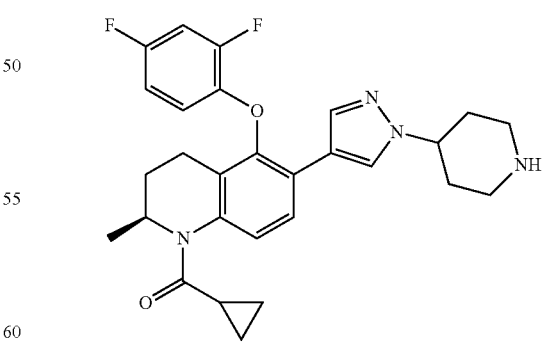

¹H NMR (400 MHz, CD₃OD) δ ppm 0.70-0.80 (m, 1H), 0.89-1.03 (m, 2H), 1.09-1.20 (m, 4H), 1.35-1.45 (m, 1H), 1.80-2.10 (m, 5H), 2.15-2.40 (m, 2H), 2.68-2.80 (m, 3H), 3.10-3.20 (m, 2H), 4.20-4.30 (m, 1H), 4.75-4.85 (m, 1H), 6.40-6.50 (m, 1H), 6.70-6.80 (m, 1H), 7.05-7.12 (m, 1H), 7.42 (d, J=8.40 Hz, 1H), 7.61 (d, J=8.80 Hz, 1H), 7.80 (s, 1H), 8.01 (s, 1H). MS (ESI, pos. ion) m/z 493 [M+H]⁺.

(S)-(6-(1-(azetidin-3-yl)-1H-pyrazol-4-yl)-5-(2,4-difluorophenoxy)-2-methyl-3,4-dihydroquinolin-1(2H)-yl)(cyclopropyl)methanone (I-265)

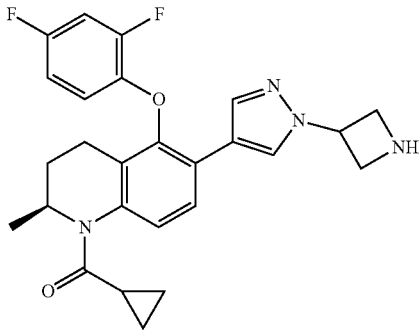 [SMILES: C[C@H]1CCc2c(ccc(-c3cnn(C4CNC4)c3)c2Oc2ccc(F)cc2F)N1C(=O)C1CC1]

¹H NMR (400 MHz, CD₃OD) δ ppm 0.70-0.82 (m, 1H), 0.89-1.02 (m, 2H), 1.10-1.22 (m, 3H), 1.40-1.52 (m, 1H), 1.95-2.05 (m, 1H), 2.15-2.42 (m, 2H), 2.68-2.80 (m, 1H), 3.65-3.85 (m, 2H), 4.10-4.30 (m, 2H), 4.75-4.85 (m, 1H), 4.90-5.05 (m, 1H), 6.40-6.50 (m, 1H), 6.65-6.75 (m, 1H), 7.05-7.15 (m, 1H), 7.43 (d, J=8.40 Hz, 1H), 7.55-7.65 (m, 1H), 7.80-8.10 (m, 2H). MS (ESI, pos. ion) m/z 465 [M+H]⁺.

(S)-methyl 6-(1-(azetidin-3-yl)-1H-pyrazol-4-yl)-5-(2,4-difluorophenoxy)-2-methyl-3,4-dihydroquinoline-1(2H)-carboxylate (I-266)

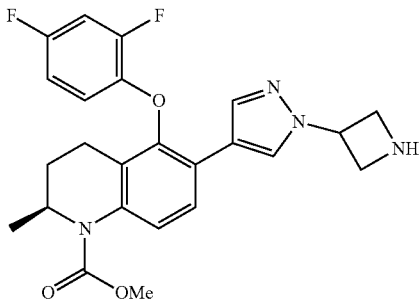 [SMILES: COC(=O)N1c2ccc(-c3cnn(C4CNC4)c3)c(Oc3ccc(F)cc3F)c2CC[C@@H]1C]

¹H NMR (400 MHz, CD₃OD) δ ppm 1.17 (d, J=6.40 Hz, 3H), 1.56-1.66 (m, 1H), 2.07-2.15 (m, 1H), 2.45-2.51 (m, 1H), 2.63-2.71 (m, 1H), 3.82 (s, 3H), 3.92-3.97 (m, 2H), 4.06-4.12 (m, 2H), 4.65-4.71 (m, 1H), 7.51-7.56 (m, 1H), 7.57-7.64 (m, 1H), 7.85 (m, 1H), 8.05 (s, 1H). MS (ESI, pos. ion) m/z 455 [M+H]⁺.

The examples below were made according to the procedure outlined above for Example 51, with the following changes to Step 1: (1) 1,2,3-trifluoro-4-nitrobenzene was used in place of 1,2-difluoro-4-nitrobenzene; (2) potassium tert-butoxide was used instead of cesium carbonate; (3) tetrahydrofuran was used as the solvent in place of DMF; (4) the reaction was run at 0° C. for 1 hour as opposed to 3 h at 110° C.

(S)-cyclopropyl(5-(2,3-difluorophenoxy)-2-methyl-6-(1-(piperidin-4-yl)-1H-pyrazol-4-yl)-3,4-dihydroquinolin-1(2H)-yl)methanone (I-267)

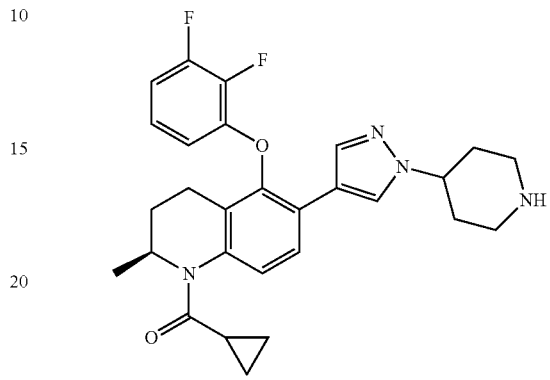

¹H NMR (400 MHz, CD₃OD) δ ppm 0.75-0.80 (m, 1H), 0.85-1.01 (m, 2H), 1.10-1.21 (m, 4H), 1.40-1.50 (m, 1H), 1.80-2.10 (m, 5H), 2.15-2.40 (m, 2H), 2.68-2.82 (m, 3H), 3.10-3.25 (m, 2H), 4.20-4.34 (m, 1H), 4.75-4.85 (m, 1H), 6.20-6.30 (m, 1H), 6.80-6.95 (m, 2H), 7.44 (d, J=8.40 Hz, 1H), 7.62 (d, J=8.40 Hz, 1H), 7.79 (s, 1H), 7.99 (s, 1H). MS (ESI, pos. ion) m/z 493 [M+H]⁺.

(S)-(6-(1-(azetidin-3-yl)-1H-pyrazol-4-yl)-5-(2,3-difluorophenoxy)-2-methyl-3,4-dihydroquinolin-1(2H)-yl)(cyclopropyl)methanone (I-268)

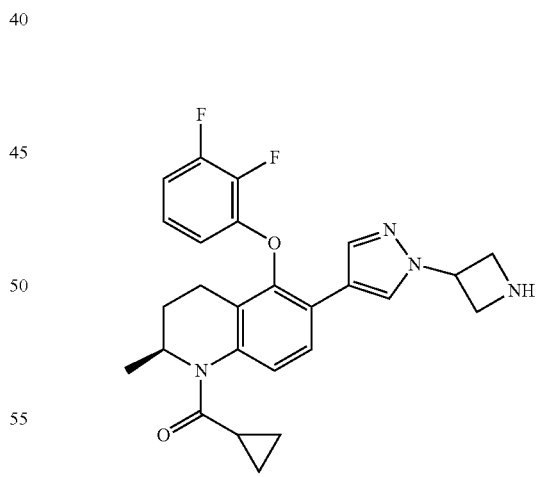

¹H NMR (400 MHz, CD₃OD) δ ppm 0.72-0.80 (m, 1H), 0.85-1.01 (m, 2H), 1.10-1.20 (m, 4H), 1.40-1.52 (m, 1H), 1.95-2.05 (m, 1H), 2.15-2.45 (m, 2H), 2.65-2.80 (m, 1H), 3.60-3.82 (m, 2H), 3.85-4.12 (m, 3H), 4.75-4.85 (m, 1H), 5.15-5.30 (m, 1H), 6.20-6.30 (m, 1H), 6.82-6.95 (m, 2H), 7.44 (d, J=8.80 Hz, 1H), 7.62 (d, J=8.40 Hz, 1H), 7.80-7.90 (m, 1H), 8.02-8.12 (m, 1H). MS (ESI, pos. ion) m/z 465 [M+H]+.

(S)-methyl 5-(2,3-difluorophenoxy)-2-methyl-6-(1-(piperidin-4-yl)-1H-pyrazol-4-yl)-3,4-dihydroquinoline-1(2H)-carboxylate (I-269)

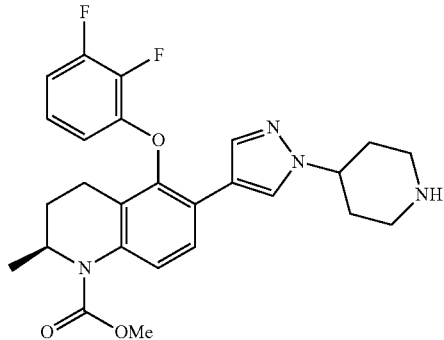

¹H NMR (400 MHz, CD₃OD) 1.05 (d, J=6.80 Hz, 3H), 1.55-1.65 (m, 1H), 1.65-1.80 (m, 2H), 1.85-2.05 (m, 3H), 2.30-2.42 (m, 1H), 2.50-2.65 (m, 3H), 3.01-3.10 (m, 2H), 3.71 (s, 1H), 4.05-4.15 (m, 1H), 4.52-4.62 (m, 1H), 6.05-6.15 (M, 1H), 6.68-6.78 (m, 2H), 7.41 (d, J=8.80 Hz, 1H), 7.51 (d, J=8.80 Hz, 1H), 7.64 (s, 1H), 7.83 (s, 1H). MS (ESI, pos. ion) m/z 483 [M+H]+.

(S)-methyl 6-(1-(azetidin-3-yl)-1H-pyrazol-4-yl)-5-(2,3-difluorophenoxy)-2-methyl-3,4-dihydroquinoline-1(2H)-carboxylate (I-270)

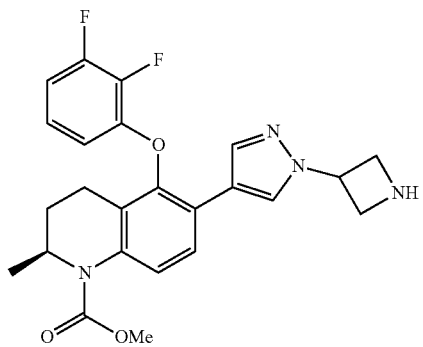 [SMILES: COC(=O)N1c2ccc(-c3cnn(C4CNC4)c3)c(Oc3cccc(F)c3F)c2CC[C@@H]1C]

¹H NMR (400 MHz, CD₃OD) δ ppm 1.09 (d, J=6.40 Hz, 3H), 1.60-1.66 (m, 1H), 2.08-2.13 (m, 1H), 2.46-2.52 (m, 1H), 2.63-2.71 (m, 1H), 3.82 (s, 3H), 3.92-3.98 (m, 2H), 4.06-4.13 (m, 2H), 4.64-4.71 (m, 1H), 5.21-5.28 (m, 1H), 6.21-6.28 (m, 1H), 6.84-6.91 (m, 2H), 7.54 (d, J=8.80 Hz, 1H), 7.63 (d, J=8.40 Hz, 1H), 7.85 (s, 1H), 8.02 (s, 1H). MS (ESI, pos. ion) m/z 455 [M+H]+.

The examples below were made according to the procedure outlined above for Example 51, with the following changes to Step 1: (1) 1,2,4-trifluoro-5-nitrobenzene was used in place of 1,2-difluoro-4-nitrobenzene; (2) potassium tert-butoxide was used instead of cesium carbonate; (3) tetrahydrofuran was used as the solvent in place of DMF; (4) the reaction was run at 0° C. for 1 hour as opposed to 3 h at 110° C.

(S)-methyl 6-(1-(azetidin-3-yl)-1H-pyrazol-4-yl)-5-(2,5-difluorophenoxy)-2-methyl-3,4-dihydroquinoline-1(2H)-carboxylate (I-271)

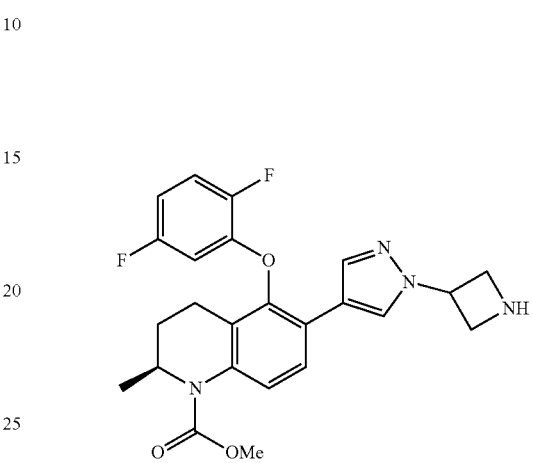

¹H NMR (300 MHz, DMSO-d6) δ ppm 0.98-1.16 (m, 3H), 1.49-1.55 (m, 1H), 1.95-2.06 (m, 1H), 2.36-2.44 (m, 2H), 3.61-3.68 (m, 2H), 3.69-3.75 (m 3H), 3.77-3.85 (m, 2H), 4.46 (m, 1H), 5.02-5.20 (m, 1H), 6.35-6.61 (m, 1H), 6.85-7.11 (m, 1H), 7.18-7.43 (m, 1H), 7.58 (s, 2H), 7.79 (s, 1H), 8.13 (s, 1H). MS (ESI, pos. ion) m/z 455 [M+H]+.

(S)-(6-(1-(azetidin-3-yl)-1H-pyrazol-4-yl)-5-(2,5-difluorophenoxy)-2-methyl-3,4-dihydroquinolin-1(2H)-yl)(cyclopropyl)methanone (I-272)

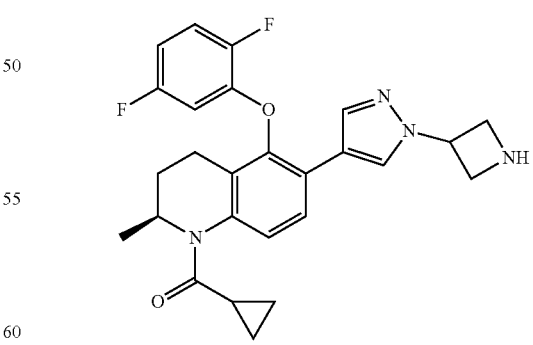

¹H NMR (400 MHz, CD₃OD) δ ppm 0.59-0.72 (m, 1H), 0.82-0.93 (m, 2H), 1.02-1.09 (m, 4H), 1.30-1.43 (m, 1H), 1.88-1.95 (m, 1H), 2.13-2.23 (m, 1H), 2.60-2.70 (m, 1H), 3.53-3.69 (m, 1H), 3.82-4.05 (m, 3H), 4.69-4.74 (m, 1H), 5.13-5.19 (m, 1H), 6.03-6.11 (m, 1H), 7.08-7.19 (m, 1H), 7.34-7.38 (m, 1H), 7.50-7.55 (m, 1H), 7.73-7.77 (m, 1H), 7.93-7.99 (m, 1H). MS (ESI, pos. ion) m/z 465 [M+H]+.

(S)-methyl 5-(2,5-difluorophenoxy)-2-methyl-6-(1-(piperidin-4-yl)-1H-pyrazol-4-yl)-3,4-dihydroquinoline-1(2H)-carboxylate (I-273)

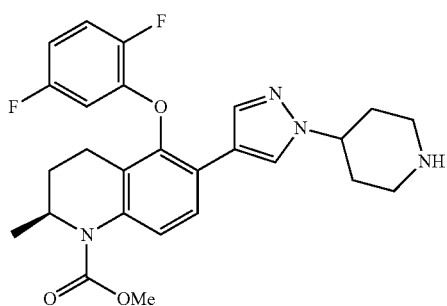

$^1$H NMR (400 MHz, CD$_3$OD) δ ppm 1.18 (d, J=6.80 Hz, 3H), 1.50-1.59 (m, 1H), 2.11-2.22 (m, 5H), 2.45-2.54 (m, 1H), 2.63-2.72 (m, 1H), 3.04-3.11 (m, 2H), 3.39-3.46 (m, 2H), 3.83 (m, 3H), 4.49-4.59 (m, 1H), 4.66-4.71 (m, 1H), 6.08-6.16 (m, 1H), 6.62-6.74 (m, 1H), 7.18-7.27 (m, 1H), 7.56 (d, J=8.40 Hz, 1H), 7.65 (d, J=8.40 Hz, 1H), 7.82 (s, 1H), 7.96 (s, 1H), 8.57 (br s, 1H). MS (ESI, pos. ion) m/z 483 [M+H]+.

(S)-cyclopropyl(5-(2,5-difluorophenoxy)-2-methyl-6-(1-(piperidin-4-yl)-1H-pyrazol-4-yl)-3,4-dihydroquinolin-1(2H)-yl)methanone (I-274)

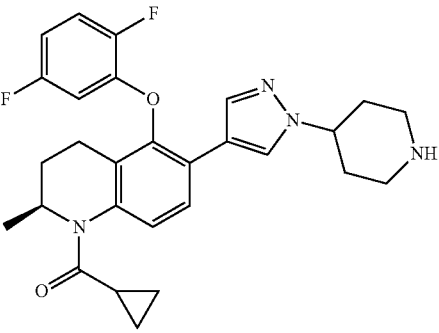 [SMILES: C[C@H]1CCc2c(ccc(-c3cnn(C4CCNCC4)c3)c2Oc2cc(F)ccc2F)N1C(=O)C1CC1]

$^1$H NMR (400 MHz, CD$_3$OD) δ ppm 0.75-0.82 (m, 1H), 0.91-1.02 (m, 2H), 1.11-1.22 (m, 4H), 1.41-1.52 (m, 1H), 1.80-1.91 (m, 2H), 1.98-2.07 (m, 3H), 2.21-2.32 (m, 1H), 2.33-2.41 (m, 1H), 2.64-2.79 (m, 3H), 3.11-3.15 (m, 2H), 4.18-4.29 (m, 1H), 4.71-4.83 (m, 1H), 6.12-6.21 (m, 1H), 6.63-6.74 (m, 1H), 7.22-7.29 (m, 1H), 7.45 (d, J=8.40 Hz, 1H), 7.63 (d, J=8.40 Hz, 1H), 7.80 (m, 1H). MS (ESI, pos. ion) m/z 493 [M+H]+.

Example 52

(S)-1-(5-(3,4-difluorophenoxy)-2-methyl-6-(1-(piperidin-4-yl)-1H-pyrazol-4-yl)-3,4-dihydroquinolin-1(2H)-yl)ethanone (I-275) and (S)-1-(5-(2,5-difluorophenoxy)-2-methyl-6-(1-(piperidin-4-yl)-1H-pyrazol-4-yl)-3,4-dihydroquinolin-1(2H)-yl)ethanone (I-276)

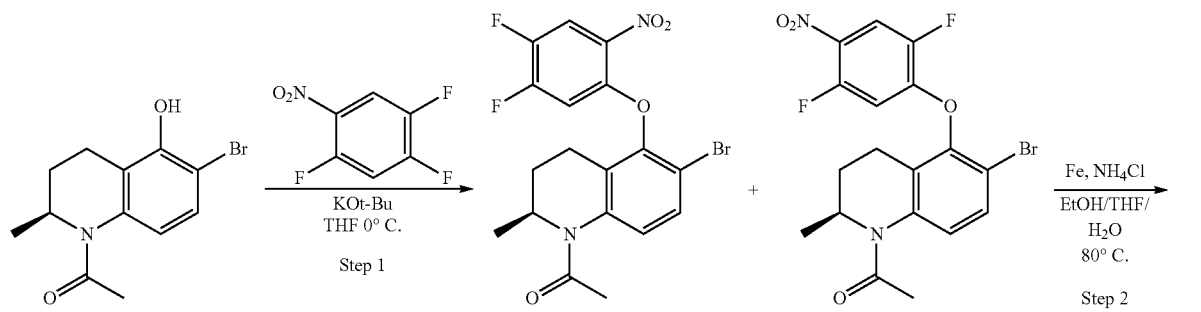

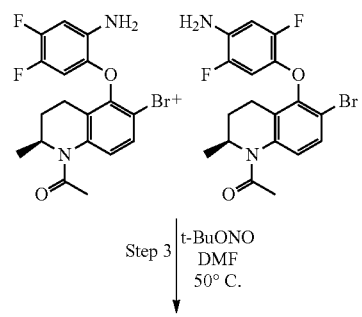

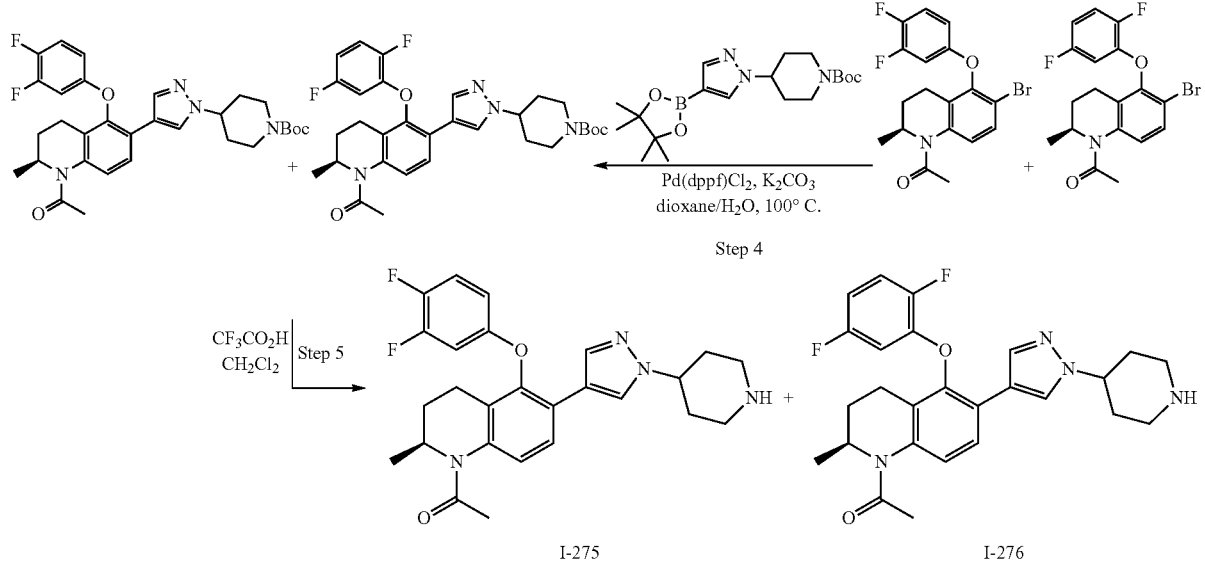

Step 4

Step 5 CF₃CO₂H / CH₂Cl₂

I-275          I-276

Step 1. (S)-(6-bromo-5-(2,5-difluoro-4-nitrophenoxy)-2-methyl-3,4-dihydroquinolin-1(2H)-yl)(cyclopropyl)methanone and (S)-(6-bromo-5-(4,5-difluoro-2-nitrophenoxy)-2-methyl-3,4-dihydroquinolin-1(2H)-yl)(cyclopropyl)methanone A 100-mL, 3-necked round-bottom flask was charged with a solution of (S)-(6-bromo-5-hydroxy-2-methyl-3,4-dihydroquinolin-1(2H)-yl)(cyclopropyl)methanone (2.00 g, 6.45 mmol) in tetrahydrofuran (20 mL). Potassium tert-butoxide (0.797 g, 7.10 mmol) was added in portions at 0° C. and the mixture stirred for 5 minutes. 1,2,4-Trifluoro-5-nitrobenzene (1.72 g, 9.71 mmol) was then added, and the resulting mixture stirred at 0° C. for 3 h. Hydrochloric acid (1 N aqueous, 10 mL) was added, and the aqueous phase was separated and extracted with ethyl acetate (2×15 mL). The combined organic layers were dried over anhydrous sodium sulfate, filtered, and concentrated under vacuum. The residue was purified via column chromatography on silica gel (eluting with 1:10, ethyl acetate/petroleum ether) to afford a mixture of (S)-(6-bromo-5-(2,5-difluoro-4-nitrophenoxy)-2-methyl-3,4-dihydroquinolin-1(2H)-yl)(cyclopropyl)methanone and (S)-(6-bromo-5-(4,5-difluoro-2-nitrophenoxy)-2-methyl-3,4-dihydroquinolin-1(2H)-yl)(cyclopropyl)methanone (2.1 g, 70%) as yellow oil. MS (ESI, pos. ion) m/z 467, 469 [M+H]⁺

Step 2. (S)-(5-(4-amino-2,5-difluorophenoxy)-6-bromo-2-methyl-3,4-dihydroquinolin-1(2H)-yl)(cyclopropyl)methanone and (S)-(5-(2-amino-4,5-difluorophenoxy)-6-bromo-2-methyl-3,4-dihydroquinolin-1(2H)-yl)(cyclopropyl)methanone A 100-mL, round-bottom flask was charged with a mixture of (S)-(6-bromo-5-(2,5-difluoro-4-nitrophenoxy)-2-methyl-3,4-dihydroquinolin-1(2H)-yl)(cyclopropyl)methanone and (S)-(6-bromo-5-(4,5-difluoro-2-nitrophenoxy)-2-methyl-3,4-dihydroquinolin-1(2H)-yl)(cyclopropyl)methanone (2.1 g, 4.49 mmol), iron powder (1.26 g, 22.5 mmol), ammonium chloride (0.476 g, 8.90 mmol), tetrahydrofuran (10 mL), ethanol (10 mL), and water (3 mL). The resulting mixture stirred overnight at 80° C. After cooling to room temperature, the reaction mixture was filtered, and the filtrate was extracted with ethyl acetate (2×15 mL). The combined organic layers were concentrated under vacuum to afford a mixture of (S)-(5-(4-amino-2,5-difluorophenoxy)-6-bromo-2-methyl-3,4-dihydroquinolin-1(2H)-yl)(cyclopropyl)methanone and (S)-(5-(2-amino-4,5-difluorophenoxy)-6-bromo-2-methyl-3,4-dihydroquinolin-1(2H)-yl)(cyclopropyl)methanone (1.8 g, 96%) as brown oil, which was directly used in next step without further purification. MS (ESI, pos. ion) m/z 437, 439 [M+H]⁺

Step 3. (S)-(6-bromo-5-(3,4-difluorophenoxy)-2-methyl-3,4-dihydroquinolin-1(2H)-yl)(cyclopropyl)methanone and (S)-(6-bromo-5-(2,5-difluorophenoxy)-2-methyl-3,4-dihydroquinolin-1(2H)-yl)(cyclopropyl)methanone A 100-mL, round-bottom flask was charged with a mixture of (S)-(5-(2-amino-4,5-difluorophenoxy)-6-bromo-2-methyl-3,4-dihydroquinolin-1(2H)-yl)(cyclopropyl)methanone and (S)-(5-(4-amino-2,5-difluorophenoxy)-6-bromo-2-methyl-3,4-dihydroquinolin-1(2H)-yl)(cyclopropyl)methanone (1.8 g, 4.12 mmol) and N,N-dimethylformamide (10 mL). A solution of tert-butyl nitrite (1.2 g, 11.64 mmol) in N,N-dimethylformamide (10 mL) was added dropwise, and the resulting solution stirred for 4 h at 50° C. After cooling to room temperature, the reaction mixture was diluted with ethyl acetate (100 mL). The organic layer was washed with water (3×20 mL) and brine (20 mL), dried over anhydrous sodium sulfate, filtered, and concentrated under vacuum. The residue was purified via column chromatography on silica gel (eluting with 1:10, ethyl acetate/petroleum ether) to afford a mixture of (S)-(6-bromo-5-(3,4-difluorophenoxy)-2-methyl-3,4-dihydroquinolin-1 (2H)-yl)(cyclopropyl)methanone and (S)-(6-bromo-5-(2,5-difluorophenoxy)-2-methyl-3,4-dihydroquinolin-1(2H)-yl)(cyclopropyl)methanone (0.600 g, 35%) as yellow oil. MS (ESI, pos. ion) m/z 422, 424 [M+H]⁺.

Step 4. tert-butyl 4-[4-[(2S)-1-acetyl-5-(3,4-difluorophenoxy)-2-methyl-1,2,3,4-tetrahydroquinolin-6-yl]-1H-pyrazol-1-yl]piperidine-1-carboxylate and tert-butyl 4-[4-[(2S)-1-acetyl-5-(2,5-difluorophenoxy)-2-methyl-1,2,3,4-tetrahydroquinolin-6-yl]-1H-pyrazol-1-yl]piperidine-1-carboxylate A 100-mL, round-bottom flask was charged with a mixture of (S)-1-(6-bromo-5-(3,4-difluorophenoxy)-2-methyl-3,4-dihydroquinolin-1(2H)-yl)ethanone and (S)-1-(6-bromo-5-(2,5-difluorophenoxy)-2-methyl-3,4-dihydroquinolin-1(2H)-yl)ethanone (0.130 g, 0.33 mmol), tert-butyl 4-[3-(tetramethyl-1,3,2-dioxaborolan-2-yl)-1H-pyrazol-1-yl]piperidine-1-carboxylate (0.149 mg, 0.39 mmol), [1,1'-bis(diphenylphosphino)ferrocene]dichloropalladium(II) dichlormethane adduct (0.027 g, 0.03 mmol), potassium carbonate (0.137 mg, 0.99 mmol), 1,4-dioxane (15 mL) and water (3 mL). The resulting mixture stirred overnight at 100° C. After cooling to room temperature, the reaction mixture was passed through a short pad of Celite, and the filtrate was concentrated under vacuum. The residue was purified via preparative thin layer chromatography (eluting with 1:1, ethyl acetate/petroleum ether) to afford a mixture of tert-butyl 4-[4-[(2S)-1-acetyl-5-(3,4-difluorophenoxy)-2-methyl-1,2,3,4-tetrahydroquinolin-6-yl]-1H-pyrazol-1-yl]piperidine-1-carboxylate and tert-butyl 4-[4-[(2S)-1-acetyl-5-(2,5-difluorophenoxy)-2-methyl-1,2,3,4-tetrahydroquinolin-6-yl]-1H-pyrazol-1-yl]piperidine-1-carboxylate (0.160 g, 86%) as yellow oil. MS (ESI, pos. ion) m/z 567 [M+H]+.

Step 5. (S)-1-(5-(3,4-difluorophenoxy)-2-methyl-6-(1-(piperidin-4-yl)-1H-pyrazol-4-yl)-3,4-dihydroquinolin-1(2H)-yl)ethanone and (S)-1-(5-(2,5-difluorophenoxy)-2-methyl-6-(1-(piperidin-4-yl)-1H-pyrazol-4-yl)-3,4-dihydroquinolin-1(2H)-yl)ethanone A 100-mL, round-bottom flask was charged with a mixture of (S)-tert-butyl 4-(4-(1-acetyl-5-(3,4-difluorophenoxy)-2-methyl-1,2,3,4-tetrahydroquinolin-6-yl)-1H-pyrazol-1-yl)piperidine-1-carboxylate and (S)-tert-butyl 4-(4-(1-acetyl-5-(2,5-difluorophenoxy)-2-methyl-1,2,3,4-tetrahydroquinolin-6-yl)-1H-pyrazol-1-yl)piperidine-1-carboxylate (0.160 g, 0.28 mmol), dichloromethane (9 mL), and trifluoroacetic acid (3 mL). The resulting solution stirred for 2 h at room temperature. The pH of the solution was adjusted to 7-8 with saturated aqueous potassium carbonate solution. The aqueous layer was separated and extracted with dichloromethane (3×10 mL). The combined organic layers were dried over anhydrous sodium sulfate, filtered, and concentrated under vacuum. The residue was purified by preparative-HPLC with the following conditions (Waters I): Column: XBridge RP C18, 19×150 mm, 5 um; Mobile Phase: water (0.05% ammonium bicarbonate) and acetonitrile; (5% to 60% acetonitrile in 7.0 min, flow rate: 20 mL/min); Detector, UV 254&220 nm. This afforded:

(S)-1-(5-(3,4-difluorophenoxy)-2-methyl-6-(1-(piperidin-4-yl)-1H-pyrazol-4-yl)-3,4-dihydroquinolin-1(2H)-yl)ethanone (0.031 g, 24%) as a light yellow solid. 1H NMR (300 MHz, CD3OD) δ ppm 1.10 (d, J=6.60 Hz, 3H), 1.18-1.41 (m, 1H), 1.72-1.89 (m, 2H), 1.92-2.01 (m, 2H), 2.10-2.31 (m, 2H), 2.16 (s, 3H), 2.58-2.74 (m, 3H), 3.3.08-3.12 (m, 2H), 4.10-4.23 (m, 1H), 4.63-4.83 (m, 1H), 6.45-6.52 (m, 1H), 6.60-6.73 (m, 1H), 7.11 (q, J=9.30 Hz, 1H), 7.20-7.33 (m, 1H), 7.57 (d, J=8.40 Hz, 1H), 7.74 (s, 1H), 7.92 (s, 1H). MS (ESI, pos. ion) m/z 467 [M+H]+.

and (S)-1-(5-(2,5-difluorophenoxy)-2-methyl-6-(1-(piperidin-4-yl)-1H-pyrazol-4-yl)-3,4-dihydroquinolin-1(2H)-yl)ethanone (0.006 g, 5%) as a light yellow solid. 1H NMR (300 MHz, CD3OD) δ ppm 1.11 (d, J=6.60 Hz, 3H), 1.25-1.49 (m, 1H), 1.71-1.87 (m, 2H), 1.92-2.05 (m, 2H), 2.19 (s, 3H), 2.15-2.38 (m, 2H), 2.59-2.73 (m, 3H), 3.11 (d, J=12.60 Hz, 2H), 4.10-4.22 (m, 1H), 4.65-4.85 (m, 1H), 6.05-6.15 (m, 1H), 6.57-6.71 (m, 1H), 7.13-7.21 (m, 1H), 7.22-7.39 (m, 1H), 7.58 (d, J=8.40 Hz, 1H), 7.75 (s, 1H), 7.93 (s, 1H). MS (ESI, pos. ion) m/z 467 [M+H]+.

Example 53

(S,E)-1-(5-(2-chlorovinyloxy)-6-(1-cyclopropyl-1H-pyrazol-4-yl)-2-methyl-3,4-dihydroquinolin-1(2H)-yl)ethanone (I-277)

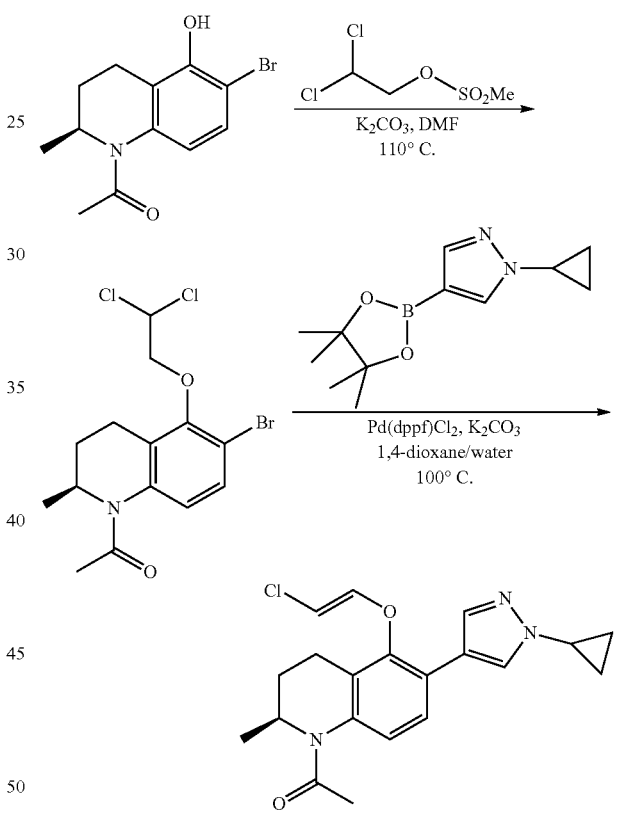

Step 1. 1-[(2S)-6-bromo-5-(2,2-dichloroethoxy)-2-methyl-1,2,3,4-tetrahydroquinolin-1-yl]ethan-1-one A 40-mL resealable tube was charged with 1-[(2S)-6-bromo-5-hydroxy-2-methyl-1,2,3,4-tetrahydroquinolin-1-yl]ethan-1-one (90 mg, 0.32 mmol), 2,2-dichloroethyl methanesulfonate (82 mg, 0.42 mmol), potassium carbonate (135 mg, 0.96 mmol), and N,N-dimethylformamide (10 mL). The resulting mixture stirred for 48 h at 110° C. After cooling to room temperature, the reaction mixture was filtered and concentrated under reduced pressure. The residue was purified by preparative thin layer chromatography (eluting with petroleum ether/ethyl acetate, 10:1 then 1:2) to afford 1-[(2S)-6-bromo-5-(2,2-dichloro ethoxy)-2-methyl-1,2,3,4-tetrahydroquinolin-1-yl]ethan-1-one (56 mg, 46%) as light yellow oil. MS (ESI, pos. ion) m/z 31, 383 [M+H]⁺.

Step 2. (S,E)-1-(5-(2-chlorovinyloxy)-6-(1-cyclopropyl-1H-pyrazol-4-yl)-2-methyl-3,4-dihydroquinolin-1(2H)-yl)ethanone A 50-mL round-bottom flask was purged and maintained with an inert atmosphere of nitrogen and charged with 1-[(2S)-6-bromo-5-(2,2-dichloroethoxy)-2-methyl-1,2,3,4-tetrahydroquinolin-1-yl]ethan-1-one (43 mg, 0.11 mmol), 1-cyclopropyl-4-(tetramethyl-1,3,2-dioxaborolan-2-yl)-1H-pyrazole (40 mg, 0.17 mmol), [1,1'-bis(diphenylphosphino)ferrocene]dichloropalladium(II) (8 mg, 0.01 mmol), potassium carbonate (31 mg, 0.22 mmol), 1,4-dioxane (24 mL), and water (4 mL). The resulting mixture stirred for 15 h at 100° C. in an oil bath. After cooling to room temperature, the reaction mixture was passed a short pad of celite and concentrated under vacuum. The residue was purified by preparative thin layer chromatography (eluting with dichloromethane/methanol, 50:1 then 20:1) to afford (S,E)-1-(5-(2-chlorovinyloxy)-6-(1-cyclopropyl-1H-pyrazol-4-yl)-2-methyl-3,4-dihydroquinolin-1(2H)-yl)ethanone (12 mg, 26%) as a white solid. ¹H NMR (300 MHz, CD₃OD) δ ppm 1.05-1.15 (m, 7H), 1.35-1.58 (m, 1H), 2.21 (s, 3H), 2.25-2.50 (m, 2H), 2.80-2.93 (m, 1H), 3.65-3.75 (m, 1H), 4.61 (s, 1H), 4.70-4.85 (m, 1H), 5.52 (d, J=4.20 Hz, 1H), 6.52 (d, J=4.20 Hz, 1H), 7.15-7.25 (m, 1H), 7.54 (d, J=8.40 Hz, 1H), 7.89 (s, 1H), 8.07 (s, 1H). MS (ESI, pos. ion) m/z 372 [M+H]⁺.

Example 54

(2S)-5-cyclobutoxy-6-(2,3-dihydro-1H-pyrazolo[1,5-a]imidazol-7-yl)-2-methyl-3,4-dihydroquinolin-1(2H)-yl)(cyclopropyl)methanone (I-278

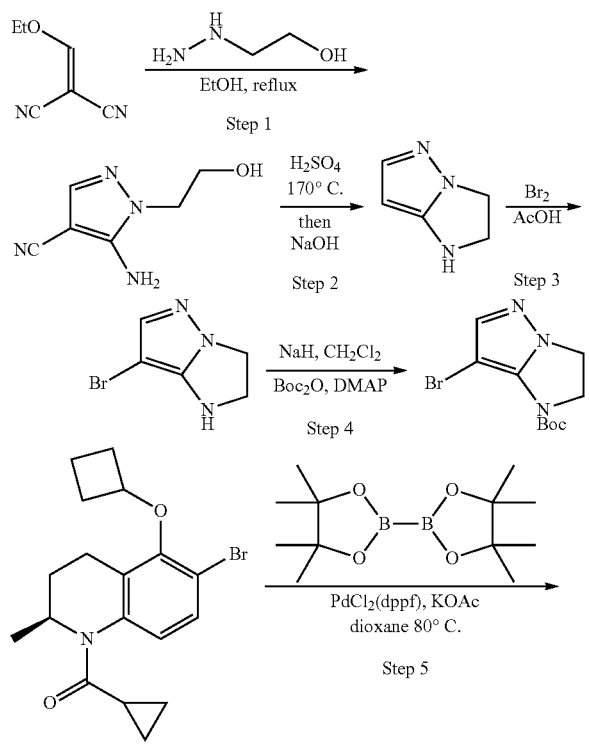

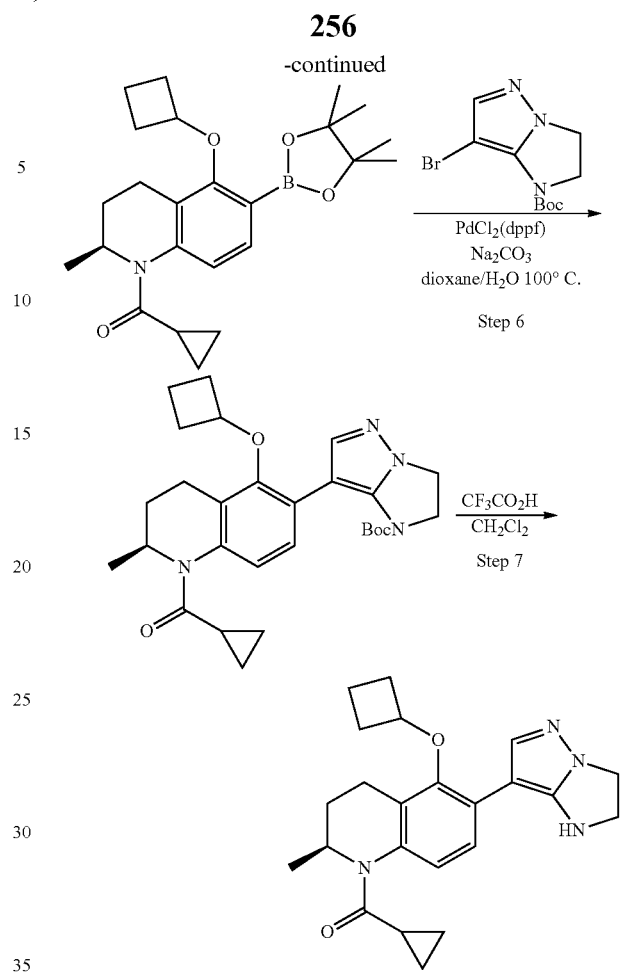

Step 1. 5-Amino-1-(2-hydroxyethyl)-1H-pyrazole-4-carbonitrile

A 100-mL round-bottom flask was charged with 2-(ethoxymethylene)malononitrile (4.88 g, 39.96 mmol), ethanol (50 mL) and 2-hydrazinylethan-1-ol (4.4 g, 57.82 mmol). The resulting solution stirred for 10 h at 95° C. After cooling to room temperature, the reaction mixture was concentrated under vacuum. The residue was purified via column chromatography on silica gel (eluting with 9:1, dichloromethane/methanol) to afford 5-amino-1-(2-hydroxyethyl)-1H-pyrazole-4-carbonitrile (3.9 g, 63%) as a yellow solid. MS (ESI, pos. ion) m/z 153 [M+H]⁺.

Step 2. 2,3-dihydro-1H-imidazo[1,2-b]pyrazole

A 250-mL 3-necked round-bottom flask was charged with 5-amino-1-(2-hydroxyethyl)-1H-pyrazole-4-carbonitrile (6.00 g, 39.4 mmol) and concentrated sulfuric acid (80 mL). The resulting solution stirred overnight at 170° C. After cooling to 0° C. with an ice/water bath, the pH of the solution was adjusted to 8 with sodium hydroxide. The resulting solution was extracted with chloroform (4×500 mL). The organic layers were combined, dried over anhydrous sodium sulfate, filtered, and concentrated under vacuum. The residue was purified via column chromatography on silica gel (eluting with 1:4, ethyl acetate/petroleum ether). The crude product was further purified by re-crystallization with diethyl ether to afford 2,3-dihydro-1H-imidazo[1,2-b]pyrazole (2.0 g, 46%) as a yellow solid. MS (ESI, pos. ion) m/z 110 [M+H]⁺.

Step 3.
7-bromo-2,3-dihydro-1H-imidazo[1,2-b]pyrazole hydrobromide

A 100-mL round-bottom flask was charged with 2,3-dihydro-1H-imidazo[1,2-b]pyrazole (1.7 g, 15.6 mmol) and acetic acid (5 mL). A solution of bromine (7.39 g, 46.2 mmol) in acetic acid (47 mL) was then added slowly. The resulting solution stirred for 3 h at room temperature. The reaction mixture was filtered and the filtrate was concentrated under vacuum to afford 7-bromo-2,3-dihydro-1H-imidazo[1,2-b]pyrazole hydrobromide (3.0 g, 72%) as a yellow solid. MS (ESI, pos. ion) m/z 188, 190 [M+H]⁺.

Step 4. tert-butyl 7-bromo-2,3-dihydro-1H-imidazo[1,2-b]pyrazole-1-carboxylate

A 50-mL round-bottom flask was charged with a solution of 7-bromo-2,3-dihydro-1H-imidazo[1,2-b]pyrazole hydrobromide (100 mg, 0.53 mmol) in dichloromethane (5 mL). Sodium hydride (30 mg, 1.20 mmol) was added, and the reaction mixture stirred at room temperature for 15 min. Di-tert-butyl dicarbonate (232 mg, 1.06 mmol) and 4-dimethylaminopyridine (6.5 mg, 0.05 mmol) were added, and the resulting mixture stirred for 3.5 h at room temperature. The reaction mixture was poured into 10 mL of water and the layers were separated. The aqueous layer was extracted with ethyl acetate (3×50 mL). The organic layers were combined, washed with brine (3×20 mL), dried over anhydrous sodium sulfate, filtered, and concentrated under vacuum. The residue was purified via column chromatography on silica gel (eluting with 35% ethyl acetate-petroleum ether) to afford tert-butyl 7-bromo-2,3-dihydro-1H-imidazo[1,2-b]pyrazole-1-carboxylate (100 mg, 65%) as a white solid. MS (ESI, pos. ion) m/z 288, 290 [M+H]⁺.

Step 5. (2S)-5-cyclobutoxy-1-cyclopropanecarbonyl-2-methyl-6-(tetramethyl-1,3,2-dioxaborolan-2-yl)-1,2,3,4-tetrahydroquinoline A 100-mL round-bottom flask was charged with (2S)-6-bromo-5-cyclobutoxy-1-cyclopropanecarbonyl-2-methyl-1,2,3,4-tetrahydroquinoline (1.54 g, 4.25 mmol), bis(pinacolato)diboron (3.22 g, 12.68 mmol), [1,1'-bis(diphenylphosphino)ferrocene]dichloropalladium(II) dichloromethane adduct (347 mg, 0.04 mmol), potassium acetate (1.04 g, 10.60 mmol), and 1,4-dioxane (15 mL). The resulting mixture stirred overnight at 80° C. After cooling to room temperature, the reaction mixture was poured into 50 mL of water and the layers were separated. The aqueous layer was extracted with ethyl acetate (3×100 mL). The organic layers were combined, dried over anhydrous sodium sulfate, filtered, and concentrated under vacuum. The residue was purified via column chromatography on silica gel (eluting with 9% ethyl acetate-petroleum ether) to afford (2S)-5-cyclobutoxy-1-cyclopropanecarbonyl-2-methyl-6-(tetramethyl-1,3,2-dioxaborolan-2-yl)-1,2,3,4-tetrahydroquinoline (0.9 g, 55%) as yellow oil. MS (ESI, pos. ion) m/z 386 [M+H]⁺.

Step 6. tert-butyl 7-((2S)-5-cyclobutoxy-1-(cyclopropanecarbonyl)-2-methyl-1,2,3,4-tetrahydroquinolin-6-yl)-2,3-dihydroimidazo[1,2-b]pyrazole-1-carboxylate An 8-mL resealable tube was charged with (2S)-5-cyclobutoxy-1-cyclopropanecarbonyl-2-methyl-6-(tetramethyl-1,3,2-dioxaborolan-2-yl)-1,2,3,4-tetrahydroquinoline (60 mg, 0.15 mmol), tert-butyl 7-bromo-2,3-dihydro-1H-imidazo[1,2-b]pyrazole-1-carboxylate (45 mg, 0.16 mmol), [1,1'-bis(diphenylphosphino)ferrocene]dichloropalladium (II) dichloromethane adduct (11 mg, 0.02 mmol), sodium carbonate (30 mg, 0.28 mmol), 1,4-dioxane (1.5 mL) and water (0.5 mL). The resulting mixture stirred overnight at 80° C. After cooling to room temperature, the reaction mixture was poured into 20 mL of ethyl acetate. The organic layer was separated and washed with water and brine, dried over anhydrous sodium sulfate, filtered and concentrated under vacuum. The residue was purified via column chromatography on silica gel (eluting with 40% ethyl acetate-petroleum ether) to afford tert-butyl 7-((2S)-5-cyclobutoxy-1-(cyclopropanecarbonyl)-2-methyl-1,2,3,4-tetrahydroquinolin-6-yl)-2,3-dihydroimidazo[1,2-b]pyrazole-1-carboxylate (50 mg, 69%) of as a black solid. MS (ESI, pos. ion) m/z 493 [M+H]⁺.

Step 7. 02S)-5-cyclobutoxy-6-(2,3-dihydro-1H-imidazo[1,2-b]pyrazol-7-yl)-2-methyl-3,4-dihydroquinolin-1(2H)-yl)(cyclopropyl)methanone An 8-mL vial was charged with tert-butyl 7-425)-5-cyclobutoxy-1-(cyclopropanecarbonyl)-2-methyl-1,2,3,4-tetrahydroquinolin-6-yl)-2,3-dihydroimidazo[1,2-b]pyrazole-1-carboxylate (50 mg, 0.10 mmol), dichloromethane (3 mL) and trifluoroacetic acid (1 mL). The resulting solution stirred for 4 h at room temperature. The reaction mixture was concentrated under vacuum. The residue was purified via preparative thin layer chromatography (eluting with 30% ethyl acetate-petroleum ether) to afford ((2S)-5-cyclobutoxy-6-(2,3-dihydro-1H-imidazo[1,2-b]pyrazol-7-yl)-2-methyl-3,4-dihydroquinolin-1(2H)-yl)(cyclopropyl)methanone (11.7 mg, 20%) as a white solid. ¹H NMR (400 MHz, CD₃OD) δ ppm 0.65-0.75 (m, 1H), 0.85-0.95 (m, 2H), 1.05-1.15 (m, 4H), 1.20-1.45 (m, 2H), 1.58-1.72 (m, 1H), 1.85-1.95 (m, 1H), 1.98-2.45 (m, 6H), 3.01-3.09 (m, 1H), 3.99-4.09 (m, 2H), 4.10-4.22 (m, 3H), 4.65-4.75 (m, 1H), 7.14 (d, J=8.00 Hz, 1H), 7.30 (d, J=8.00 Hz, 1H). 7.65 (s, 1H). MS (ESI, pos. ion) m/z 393 [M+H]⁺.

Example 55

(2S)-5-cyclobutoxy-2-methyl-6-(1-(methylsulfonyl)-2,3-dihydro-1H-pyrazolo[1,5-a]imidazol-7-yl)-3,4-dihydroquinolin-1(2H)-yl)(cyclopropyl)methanone (I-279)

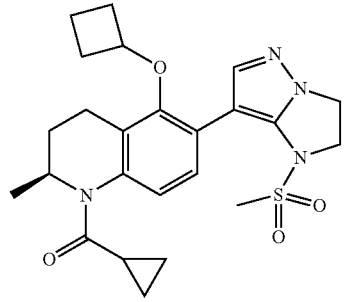 [SMILES: C[C@H]1CCc2c(ccc(-c3cnn4c3N(S(C)(=O)=O)CC4)c2OC2CCC2)N1C(=O)C1CC1]

((2S)-5-Cyclobutoxy-2-methyl-6-(1-(methylsulfonyl)-2,3-dihydro-1H-pyrazolo[1,5-a]imidazol-7-yl)-3,4-dihydroquinolin-1(2H)-yl)(cyclopropyl)methanone was prepared according to the procedure outlined above for (2S)-5-cyclobutoxy-1-cyclopropanecarbonyl-2-methyl-6-(tetramethyl-1,3,2-dioxaborolan-2-yl)-1,2,3,4-tetrahydroquinoline (Example 54) with the following changes: (1) in Step 4, triethylamine was used as the base instead of sodium hydride, methanesulfonyl chloride was substituted for di-tert-butyl dicarbonate, and DMAP was not added (2) Step 7 (Boc-deprotection) was eliminated. ¹H NMR (400 MHz, CD₃OD) δ ppm 0.72 (d, J=7.60 Hz, 1H), 0.85-0.96 (m, 2H), 1.14 (d, J=7.60 Hz, 4H), 1.28-1.46 (m, 2H), 1.55-1.60 (m, 1H), 1.88-2.21 (m, 5H), 2.21-2.33 (m, 2H), 2.95-3.05 (m, 1H), 3.08 (s, 3H), 4.05-4.18 (m, 1H), 4.26-4.51 (m, 2H), 4.51-4.69 (m, 2H), 4.70-4.80 (m, 1H), 7.13 (d, J=8.40 Hz, 1H), 7.24 (d, J=8.00 Hz, 1H), 7.59 (s, 1H). MS (ESI, pos. ion) m/z 471 [M+H]⁺.

Example 56 methyl (S)-5-cyclobutoxy-6-(2-(4-hydroxypiperidin-4-yl)thiazol-4-yl)-2-methyl-3,4-dihydroquinoline-1(2H)-carboxylate (I-280)

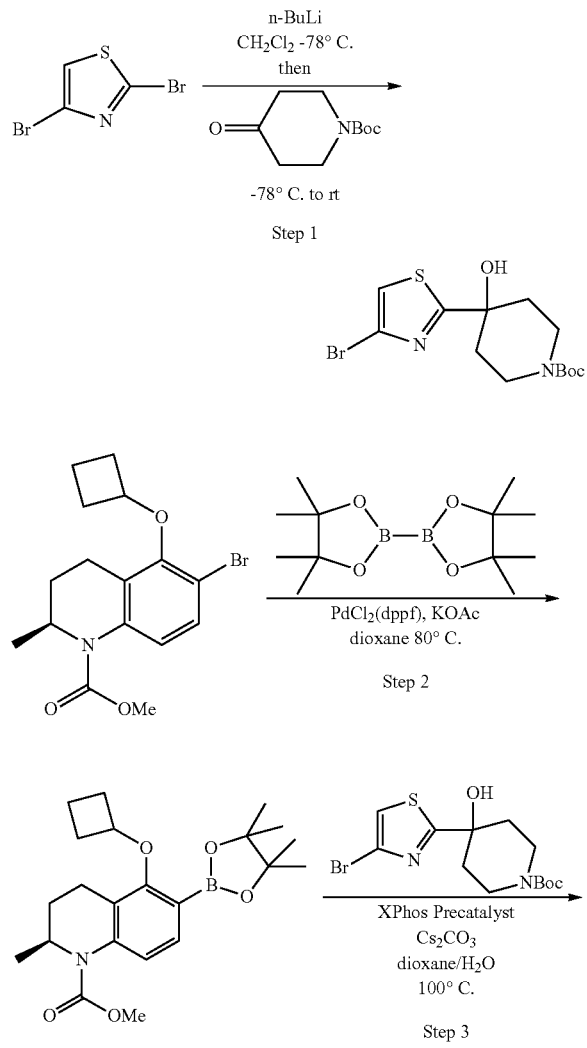

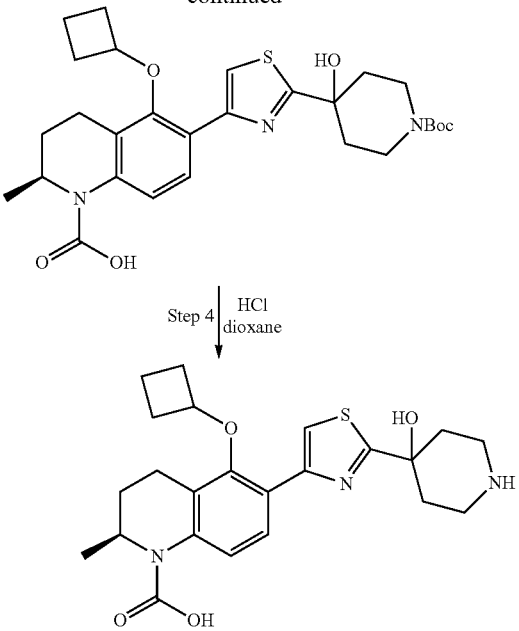

Step 1. tert-butyl 4-(4-bromothiazol-2-yl)-4-hydroxypiperidine-1-carboxylate n-Butyllithium (1.6 M in hexanes, 1.48 mL, 2.37 mmol) was added dropwise to a −78° C. solution of 2,4-dibromothiazole (0.524 g, 2.16 mmol) in dichloromethane (11 mL). The mixture stirred at −78° C. for 20 minutes, and then tert-butyl 4-oxopiperidine-1-carboxylate (0.516 g, 2.59 mmol) was added in 8 portions. The reaction mixture stirred at −78° C. for 10 minutes. The cooling bath was removed, and the reaction was allowed to warm to rt over 1 h. The reaction mixture was cooled to −30° C. and was then quenched by the addition of saturated aqueous ammonium chloride solution. The aqueous phase was separated and extracted with dichloromethane, and the combined organic phases were dried over anhydrous sodium sulfate, filtered, and concentrated. The residue was purified via column chromatography on silica gel (Biotage 50 g column, gradient elution with 5-60% ethyl acetate-hexane) to afford tert-butyl 4-(4-bromothiazol-2-yl)-4-hydroxypiperidine-1-carboxylate (0.744 g, 95%). MS (ESI, pos. ion) m/z 363, 365 [M+H]⁺.

Step 2. (S)-methyl 5-cyclobutoxy-2-methyl-6-(4,4,5,5-tetramethyl-1,3,2-dioxaborolan-2-yl)-3,4-dihydroquinoline-1(2H)-carboxylate A mixture of (S)-methyl 6-bromo-5-cyclobutoxy-2-methyl-3,4-dihydroquinoline-1(2H)-carboxylate (0.534 g, 1.51 mmol), bis(pinacolato)diboron (0.421 g, 1.66 mmol), potassium acetate (0.370 g, 3.77 mmol) and [1,1'-bis(diphenylphosphino)ferrocene]dichloropalladium(II) dichloromethane adduct (0.123 g, 0.151 mmol) in 1,4-dioxane (5.0 mL) was heated at 80° C. overnight. The reaction mixture was cooled to room temperature, filtered through a pad of Celite, and concentrated. The residue was purified via column chromatography on silica gel (Biotage 25 g column, gradient elution with 5-10% ethyl acetate-hexane) to afford (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.217 g, 36%) as a colorless oil. MS (ESI, pos. ion) m/z 402 [M+H]⁺.

Step 3. (S)-methyl 6-(2-(1-(tert-butoxycarbonyl)-4-hydroxypiperidin-4-yl)thiazol-4-yl)-5-cyclobutoxy-2-methyl-3,4-dihydroquinoline-1(2H)-carboxylate A mixture of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.109 g, 0.273 mmol), tert-butyl 4-(4-bromothiazol-2-yl)-4-hydroxypiperidine-1-carboxylate (0.090 g, 0.248 mmol), XPhos Precatalyst 2nd Generation (0.019 g, 0.025 mmol), and cesium carbonate (0.242 g, 0.743 mmol) in 1,4-dioxane (1.0 mL) and water (0.2 mL) was heated at 100° C. for 2.5 h. The reaction mixture was cooled to room temperature, filtered through a pad of Celite, and concentrated. The residue was purified via column chromatography on silica gel (Biotage 25 g column, gradient elution with 5-50% ethyl acetate-hexane) to afford (S)-methyl 6-(2-(1-(tert-butoxycarbonyl)-4-hydroxypiperidin-4-yl)thiazol-4-yl)-5-cyclobutoxy-2-methyl-3,4-dihydroquinoline-1(2H)-carboxylate (0.128 g, 93%). MS (ESI, pos. ion) m/z 558 [M+H]$^+$.

Step 4. methyl (S)-5-cyclobutoxy-6-(2-(4-hydroxypiperidin-4-yl)thiazol-4-yl)-2-methyl-3,4-dihydroquinoline-1(2H)-carboxylate HCl (4 M in 1,4-dioxane, 0.58 mL, 2.30 mmol) was added to a solution of (S)-methyl 6-(2-(1-(tert-butoxycarbonyl)-4-hydroxypiperidin-4-yl)thiazol-4-yl)-5-cyclobutoxy-2-methyl-3,4-dihydroquinoline-1(2H)-carboxylate (0.128 g, 0.230 mmol) in 1,4-dioxane (1.0 mL), and the reaction mixture stirred at rt for 1 h. The reaction mixture was concentrated and the residue was partitioned between ethyl acetate and saturated aqueous sodium bicarbonate solution. The aqueous phase was separated and extracted with ethyl acetate. The combined organic phases were dried over anhydrous sodium sulfate, filtered, and concentrated. The residue was dissolved in dichloromethane and then filtered through a plug of silica gel (eluting with 10% ethanol-ethyl acetate). The filtrate was concentrated to afford methyl (S)-5-cyclobutoxy-6-(2-(4-hydroxypiperidin-4-yl)thiazol-4-yl)-2-methyl-3,4-dihydroquinoline-1(2H)-carboxylate (62 mg, 59%). $^1$H NMR (300 MHz, DMSO-d6) δ ppm 1.11 (d, J=6.45 Hz, 3H), 1.22-1.72 (m, 6H), 1.93-2.24 (m, 7H), 2.39-2.49 (m, 2H), 2.71-2.96 (m, 4H), 3.69 (s, 3H), 4.05-4.20 (m, 1H), 4.47 (dq, J=13.05, 6.50 Hz, 1H), 5.88 (s, 1H), 7.33 (d, J=8.79 Hz, 1H), 7.69 (d, J=8.50 Hz, 1H), 7.77 (s, 1H). MS (ESI, pos. ion) m/z 458 [M+H]$^+$.

Example 57 methyl (S)-5-cyclobutoxy-6-(2-(4-fluoropiperidin-4-yl)thiazol-4-yl)-2-methyl-3,4-dihydroquinoline-1(2H)-carboxylate (I-281)

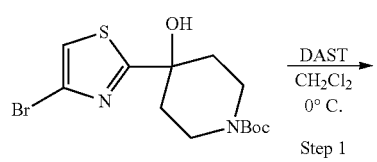

DAST
CH$_2$Cl$_2$
0° C.

Step 1

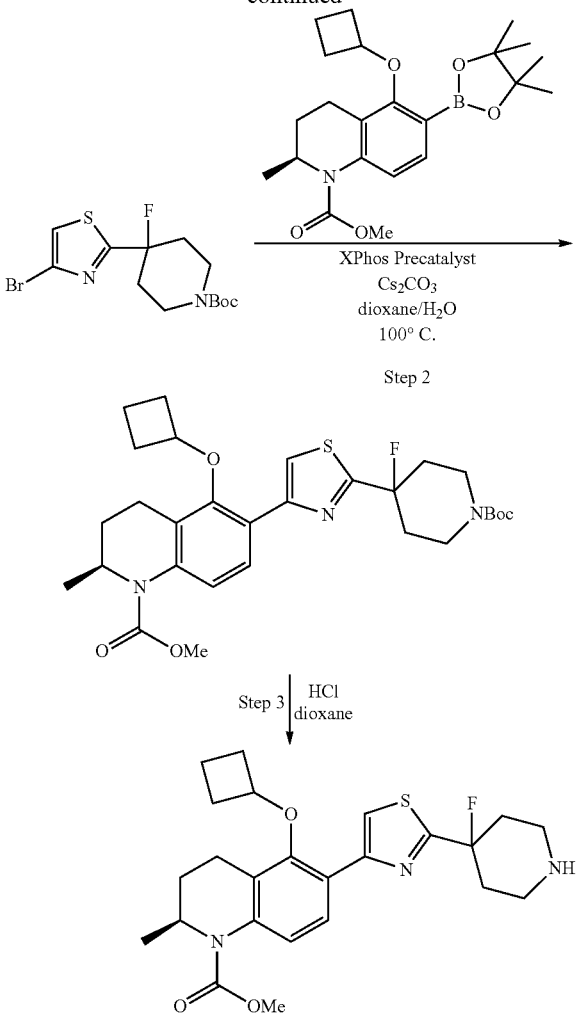

Step 1. tert-butyl 4-(4-bromothiazol-2-yl)-4-fluoropiperidine-1-carboxylate

Diethylaminosulfur trifluoride (DAST) (0.083 mL, 0.627 mmol) was added to a 0° C. of tert-butyl 4-(4-bromothiazol-2-yl)-4-hydroxypiperidine-1-carboxylate (0.207 g, 0.570 mmol) in dichloromethane (2.8 mL). After 5 minutes, the cooling bath was removed and the reaction mixture was allowed to stir at room temperature overnight. Saturated aqueous sodium bicarbonate solution was added, and the aqueous phase was separated and extracted with dichloromethane. The combined organic phases were dried over anhydrous sodium sulfate, filtered, and concentrated. The residue was purified via column chromatography on silica gel (Biotage 25 g column, gradient elution with 5-50% ethyl acetate-hexane) to afford tert-butyl 4-(4-bromothiazol-2-yl)-4-fluoropiperidine-1-carboxylate (0.163 g, 78%) as a colorless, waxy solid. MS (ESI, pos. ion) m/z 387, 389 [M+Na]$^+$.

Step 2. (S)-methyl 6-(2-(1-(tert-butoxycarbonyl)-4-fluoropiperidin-4-yl)thiazol-4-yl)-5-cyclobutoxy-2-methyl-3,4-dihydroquinoline-1(2H)-carboxylate A mixture of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.099 g, 0.247 mmol), tert-butyl 4-(4-bromothiazol-2-yl)-4-fluoropiperidine-1-carboxylate (0.082 g, 0.224 mmol), XPhos Precatalyst 2nd Generation (0.018 g, 0.022 mmol), and cesium carbonate (0.219 g, 0.673 mmol) in 1,4-dioxane (1.0 mL) and water (0.2 mL) was heated at 100° C. for 2 h. The reaction mixture was cooled to room temperature, filtered through a pad of Celite, and concentrated. The residue was purified via column chromatography on silica gel (Biotage 25 g column, gradient elution with 25-50% ethyl acetate-hexane) to afford (S)-methyl 6-(2-(1-(tert-butoxycarbonyl)-4-fluoropiperidin-4-yl)thiazol-4-yl)-5-cyclobutoxy-2-methyl-3,4-dihydroquinoline-1(2H)-carboxylate (0.072 g, 57%). MS (ESI, pos. ion) m/z 558 [M+H]$^+$.

Step 3. methyl (S)-5-cyclobutoxy-6-(2-(4-hydroxypiperidin-4-yl)thiazol-4-yl)-2-methyl-3,4-dihydroquinoline-1(2H)-carboxylate HCl (4 M in 1,4-dioxane, 0.32 mL, 1.28 mmol) was added to a solution of (S)-methyl 6-(2-(1-(tert-butoxycarbonyl)-4-fluoropiperidin-4-yl)thiazol-4-yl)-5-cyclobutoxy-2-methyl-3,4-dihydroquinoline-1(2H)-carboxylate (0.072 g, 0.128 mmol) in 1,4-dioxane (0.5 mL), and the reaction mixture stirred at rt for 1 h. The reaction mixture was concentrated and the residue was purified by mass triggered preparatory HPLC. The product-containing fractions were combined and concentrated in a Genevac to afford the methyl (S)-5-cyclobutoxy-6-(2-(4-hydroxypiperidin-4-yl)thiazol-4-yl)-2-methyl-3,4-dihydroquinoline-1(2H)-carboxylate. MS (ESI, pos. ion) m/z 460 [M+H]$^+$.

Example 58

Methyl (S)-5-(4-fluorophenoxy)-2-methyl-6-(1-(1-methylazetidin-3-yl)-1H-pyrazol-4-yl)-3,4-dihydroquinoline-1(2H)-carboxylate (I-282)

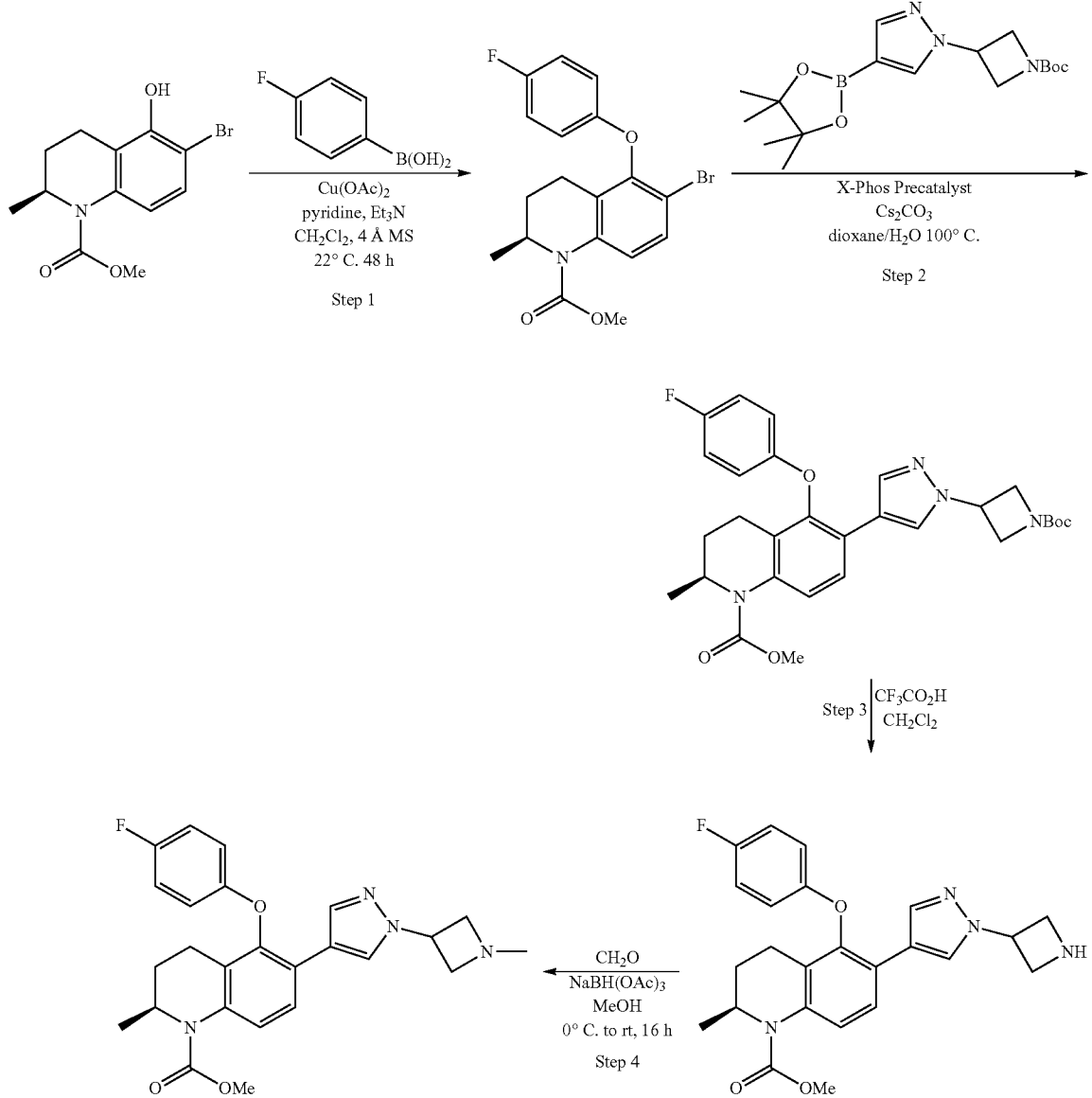

Step 1. Methyl (S)-6-bromo-5-(4-fluorophenoxy)-2-methyl-3,4-dihydroquinoline-1(2H)-carboxylate A mixture of (S)-methyl 6-bromo-5-hydroxy-2-methyl-3,4-dihydroquinoline-1(2H)-carboxylate (2.00 g, 6.66 mmol), (4-fluorophenyl)boronic acid (1.865 g, 13.33 mmol), copper (II) acetate (1.33 g, 7.33 mmol), 4 Å molecular sieves (1 g), triethylamine (0.93 mL, 6.66 mmol), and pyridine (1.08 mL, 13.33 mmol) in dichloromethane (30 mL) was stirred opened to air at rt for two days. The reaction mixture was filtered through Celite and the filtrate was concentrated to afford a brown oil. This material was purified via column chromatography on silica gel (Biotage 25 g column, gradient elution with 0-10% ethyl acetate-hexane) to afford methyl (S)-6-bromo-5-(4-fluorophenoxy)-2-methyl-3,4-dihydroquinoline-1(2H)-carboxylate (1.81 g, 69%) as a colorless film. MS (ESI, pos. ion) m/z 394, 396 [M+H]$^+$.

Step 2. Methyl-(S)-6-(1-(1-(tert-butoxycarbonyl)azetidin-3-yl)-1H-pyrazol-4-yl)-5-(4-fluorophenoxy)-2-methyl-3,4-dihydroquinoline-1(2H)-carboxylate A mixture of methyl (S)-6-bromo-5-(4-fluorophenoxy)-2-methyl-3,4-dihydroquinoline-1(2H)-carboxylate (0.100 g, 0.254 mmol), tert-butyl 3-(4-(4,4,5,5-tetramethyl-1,3,2-dioxaborolan-2-yl)-1H-pyrazol-1-yl)azetidine-1-carboxylate (0.106 g, 0.304 mmol), XPhos Precatalyst 2nd Generation (0.004 g, 0.005 mmol), and cesium carbonate (0.246 g, 0.761 mmol) in 1,4-dioxane (2.0 mL) and water (0.40 mL) was heated at 100° C. for 16 h. The reaction mixture was filtered through Celite and concentrated to afford a green oil. This material was purified via column chromatography on silica gel (Biotage 10 g column, gradient elution with 25-50% ethyl acetate-hexane) to afford methyl (S)-6-(1-(1-(tert-butoxycarbonyl)azetidin-3-yl)-1H-pyrazol-4-yl)-5-(4-fluorophenoxy)-2-methyl-3,4-dihydroquinoline-1(2H)-carboxylate (0.098 g, 72%) as a colorless oil. MS (ESI, pos. ion) m/z 537 [M+H]$^+$.

Step 3. Methyl (S)-6-(1-(azetidin-3-yl)-1H-pyrazol-4-yl)-5-(4-fluorophenoxy)-2-methyl-3,4-dihydroquinoline-1(2H)-carboxylate Trifluoroacetic acid (1.0 mL, 6.49 mmol) was added to a solution of (S)-methyl 6-(1-(1-(tert-butoxycarbonyl)azetidin-3-yl)-1H-pyrazol-4-yl)-5-(3-chloro-4-fluorophenoxy)-2-methyl-3,4-dihydroquinoline-1(2H)-carboxylate (0.098 g, 0.033 mmol) in dichloromethane (1.0 mL) and the reaction mixture stirred at rt for 2 h. The mixture was then concentrated and the residue was partitioned between dichloromethane and saturated aqueous sodium bicarbonate solution. The organic phase was separated, dried over anhydrous sodium sulfate, filtered, and concentrated to afford methyl (S)-6-(1-(1-(tert-butoxycarbonyl)azetidin-3-yl)-1H-pyrazol-4-yl)-5-(4-fluorophenoxy)-2-methyl-3,4-dihydroquinoline-1(2H)-carboxylate (0.105 g, 100%) as an off-white solid. MS (ESI, pos. ion) m/z 437 [M+H]$^+$.

Step 4. Methyl (S)-5-(4-fluorophenoxy)-2-methyl-6-(1-(1-methylazetidin-3-yl)-1H-pyrazol-4-yl)-3,4-dihydroquinoline-1(2H)-carboxylate Methyl (S)-6-(1-(azetidin-3-yl)-1H-pyrazol-4-yl)-5-(4-fluorophenoxy)-2-methyl-3,4-dihydroquinoline-1(2H)-carboxylate (105 mg, 0.241 mmol) was dissolved in methanol and formaldehyde (179 μL, 2.41 mmol) was added. The reaction was stirred for 4 h at ambient temperature and then cooled to 0° C. Sodium triacetoxyborohydride (0.102 g, 0.481 mmol) was added and the reaction was slowly warmed to ambient temperature. After 16 h the reaction was complete, and the reaction mixture was partitioned between ethyl acetate and water. The aqueous phase was separated and extracted with ethyl acetate, and the combined organic layers were washed with brine, dried over anhydrous sodium sulfate, filtered, and concentrated to afford methyl (S)-5-(4-fluorophenoxy)-2-methyl-6-(1-(1-methylazetidin-3-yl)-1H-pyrazol-4-yl)-3,4-dihydroquinoline-1(2H)-carboxylate (0.086 g, 79%) as a pale orange oil. $^1$H NMR (300 MHz, CDCl$_3$) δ ppm 1.13 (d, J=6.45 Hz, 3H) 1.18-1.20 (m, 1H) 1.20-1.33 (m, 1H) 1.55 (br dd, J=13.34, 5.42 Hz, 1H) 1.94-2.18 (m, 4H) 2.22-2.49 (m, 1H) 2.49-2.69 (m, 1H) 3.81 (s, 3H) 4.26 (br s, 1H) 4.61-4.89 (m, 2H) 5.13-5.32 (m, 1H) 6.63-6.82 (m, 2H) 6.83-7.01 (m, 2H) 7.40 (d, J=8.79 Hz, 1H) 7.54-7.67 (m, 2H) 7.79-8.02 (m, 1H). MS (ESI, pos. ion) m/z 451 [M+H]$^+$.

Example 59

Methyl (S)-5-(4-fluorophenoxy)-2-methyl-6-(1-(1-methylpiperidin-4-yl)-1H-pyrazol-4-yl)-3,4-dihydroquinoline-1(2H)-carboxylate (I-283)

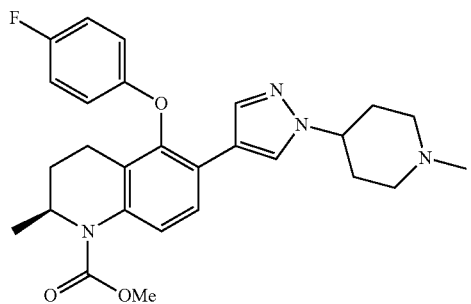

Methyl (S)-5-(4-fluorophenoxy)-2-methyl-6-(1-(1-methylpiperidin-4-yl)-1H-pyrazol-4-yl)-3,4-dihydroquinoline-1(2H)-carboxylate was synthesized from methyl (S)-6-bromo-5-(4-fluorophenoxy)-2-methyl-3,4-dihydroquinoline-1(2H)-carboxylate, and tert-butyl 4-(4-(4,4,5,5-tetramethyl-1,3,2-dioxaborolan-2-yl)-1H-pyrazol-1-yl)piperidine-1-carboxylate according to the procedure outlined above for Example 58. $^1$H NMR (300 MHz, CDCl$_3$) δ ppm 0.74-1.01 (m, 1H), 1.14 (d, J=6.74 Hz, 3H), 1.47-1.82 (m, 2H), 1.99-2.07 (m, 1H), 2.31 (br s, 1H), 2.44 (dt, J=17.00, 5.72 Hz, 1H), 2.52-2.72 (m, 1H), 2.77 (s, 3H), 3.16 (br s, 1H), 3.27-3.62 (m, 2H), 3.82 (s, 3H), 4.43 (br s, 1H), 4.57-4.84 (m, 2H), 4.85-

5.10 (m, 1H), 6.68-6.75 (m, 2H), 6.86-6.98 (m, 2H), 7.27 (s, 1H), 7.41 (d, J=8.50 Hz, 1H), 7.57-7.78 (m, 2H). MS (ESI, pos. ion) m/z 479 [M+H]+.

Example 60

Methyl (S)-5-cyclobutoxy-2-methyl-6-(1-(1-methylazetidin-3-yl)-1H-pyrazol-4-yl)-3,4-dihydroquinoline-1(2H)-carboxylate (I-284)

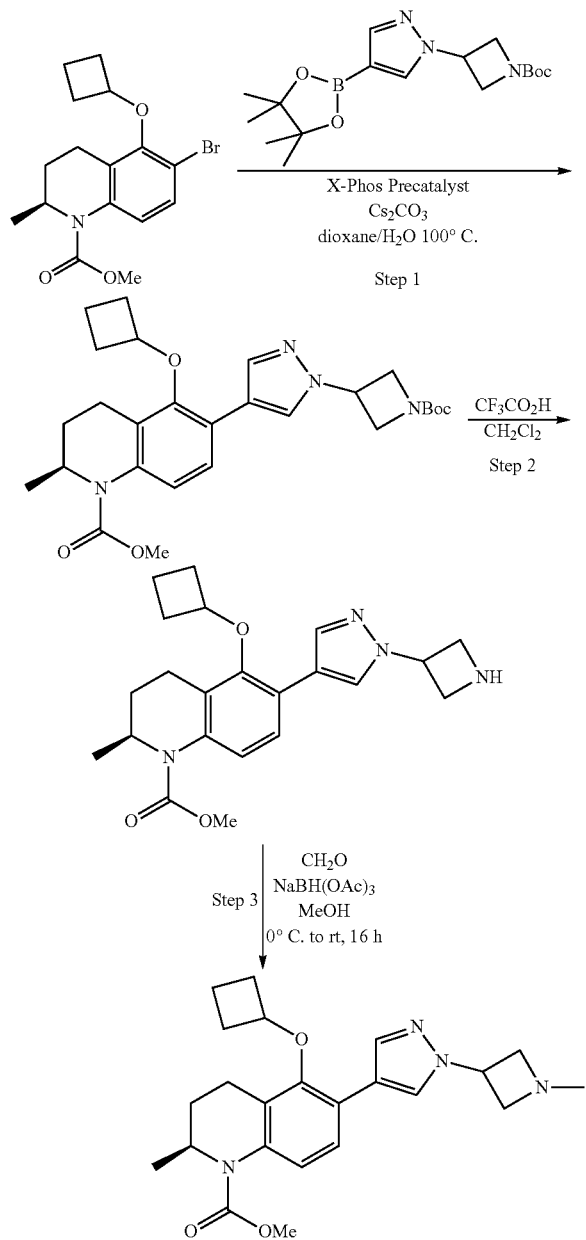

Step 1. Methyl (S)-6-(1-(1-(tert-butoxycarbonyl)azetidin-3-yl)-1H-pyrazol-4-yl)-5-cyclobutoxy-2-methyl-3,4-dihydroquinoline-1(2H)-carboxylate A mixture of methyl (S)-6-bromo-5-cyclobutoxy-2-methyl-3,4-dihydroquinoline-1(2H)-carboxylate (0.096 g, 0.254 mmol), tert-butyl 3-(4-(4,4,5,5-tetramethyl-1,3,2-dioxaborolan-2-yl)-1H-pyrazol-1-yl)azetidine-1-carboxylate (0.113 g, 0.325 mmol), and cesium carbonate (0.264 g, 0.811 mmol) in dioxane (2.0 mL) and water (0.40 mL) was purged with nitrogen to remove any oxygen. XPhos Precatalyst 2nd Generation (0.020 g, 0.027 mmol) was added and the reaction was purged with nitrogen and then heated at 100° C. for 16 h. The reaction mixture was concentrated and the residue was partitioned between ethyl acetate and saturated aqueous sodium bicarbonate solution. The aqueous phase was separated and extracted with ethyl acetate, and the combined organic phases were concentrated to afford an oil. This material was purified via column chromatography on silica gel (Biotage 10 g column, gradient elution with 25-50% ethyl acetate-hexane) to afford methyl (S)-6-(1-(1-(tert-butoxycarbonyl)azetidin-3-yl)-1H-pyrazol-4-yl)-5-cyclobutoxy-2-methyl-3,4-dihydroquinoline-1(2H)-carboxylate (0.132 g, 98%) as a colorless oil. MS (ESI, pos. ion) m/z 497 [M+H]+.

Step 2. Methyl (S)-6-(1-(azetidin-3-yl)-1H-pyrazol-4-yl)-5-(4-fluorophenoxy)-2-methyl-3,4-dihydroquinoline-1(2H)-carboxylate Trifluoroacetic acid (1.0 mL, 6.49 mmol) was added to a solution of (S)-methyl 6-(1-(1-(tert-butoxycarbonyl)azetidin-3-yl)-1H-pyrazol-4-yl)-5-(3-chloro-4-fluorophenoxy)-2-methyl-3,4-dihydroquinoline-1(2H)-carboxylate (0.132 g, 0.265 mmol) in dichloromethane (1.0 mL) and the reaction mixture stirred at rt for 2 h. The reaction mixture was concentrated and the residue was partitioned between dichloromethane and saturated aqueous sodium bicarbonate solution. The organic phase was separated, dried over anhydrous sodium sulfate, filtered, and concentrated to afford methyl (S)-6-(1-(azetidin-3-yl)-1H-pyrazol-4-yl)-5-cyclobutoxy-2-methyl-3,4-dihydroquinoline-1(2H)-carboxylate (0.115 g, 88%) as an off-white solid. MS (ESI, pos. ion) m/z 396 [M+H]+.

Step 3. Methyl (S)-5-cyclobutoxy-2-methyl-6-(1-(1-methylazetidin-3-yl)-1H-pyrazol-4-yl)-3,4-dihydroquinoline-1(2H)-carboxylate (S)-6-(1-(Azetidin-3-yl)-1H-pyrazol-4-yl)-5-cyclobutoxy-2-methyl-3,4-dihydroquinoline-1(2H)-carboxylate (0.115 g, 0.290 mmol) was dissolved in methanol (3.6 mL), and formaldehyde (216 µL, 2.90 mmol) was added. The reaction was stirred for 4 h at ambient temperature and was cooled to 0° C. Sodium triacetoxyborohydride (0.123 g, 0.58 mmol) was added, and the reaction was slowly warmed to ambient temperature. After 16 h the reaction was partitioned between ethyl acetate and water. The aqueous phase was separated and extracted with ethyl acetate, and the combined organic phases were washed with brine, and dried over anhydrous sodium sulfate, filtered, and concentrated to afford methyl (S)-5-cyclobutoxy-2-methyl-6-(1-(1-methylazetidin-3-yl)-1H-pyrazol-4-yl)-3,4-dihydroquinoline-1(2H)-carboxylate (0.115 g, 97%) as a pale orange oil. $^1$H NMR (300 MHz, CDCl3) δ ppm 1.16-1.33 (m, 4H), 1.33-1.41 (m, 1H), 1.41-1.54 (m, 1H), 1.55-1.68 (m, 1H), 1.95-2.30 (m, 4H), 2.34-2.67 (m, 1H), 2.92 (dt, J=15.68, 6.08 Hz, 1H), 3.06 (s, 2H), 3.22 (br d, J=15.54 Hz, 1H), 3.33-3.64 (m, 2H), 3.69-3.89 (m, 3H), 4.33 (br s, 2H), 4.54 (dq, J=13.34, 6.69 Hz, 1H), 4.78-

4.97 (m, 1H), 5.32 (quin, J=7.40 Hz, 1H), 7.08-7.43 (m, 2H), 7.68-7.87 (m, 1H), 7.96 (s, 1H). MS (ESI, pos. ion) m/z 411 [M+H]+.

Example 61

Methyl (S)-5-cyclobutoxy-2-methyl-6-(1-(1-methylpiperidin-4-yl)-1H-pyrazol-4-yl)-3,4-dihydroquinoline-1(2H)-carboxylate (I-285)

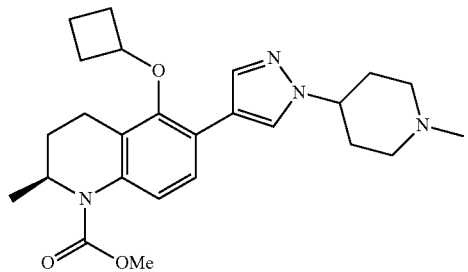

Methyl (S)-5-cyclobutoxy-2-methyl-6-(1-(1-methylpiperidin-4-yl)-1H-pyrazol-4-yl)-3,4-dihydroquinoline-1(2H)-carboxylate was synthesized from methyl (S)-6-bromo-5-cyclobutoxy-2-methyl-3,4-dihydroquinoline-1(2H)-carboxylate and tert-butyl 4-(4-(4,4,5,5-tetramethyl-1,3,2-dioxaborolan-2-yl)-1H-pyrazol-1-yl)piperidine-1-carboxylate according to the procedure outlined above for Example 60. $^1$H NMR (300 MHz, CDCl$_3$) δ ppm 0.64-0.99 (m, 1H), 1.12-1.26 (m, 4H), 1.39-1.52 (m, 1H), 1.55-1.67 (m, 1H), 1.97-2.14 (m, 5H), 2.14-2.27 (m, 1H), 2.30-2.58 (m, 2H), 2.63 (br s, 1H), 2.73-2.78 (m, 1H), 2.79 (s, 3H), 2.84-3.09 (m, 1H), 3.15 (br s, 1H), 3.37-3.63 (m, 4H), 3.64-3.92 (m, 3H), 4.54 (s, 1H), 7.14-7.39 (m, 2H), 7.81 (d, J=8.21 Hz, 2H). MS (ESI, pos. ion) m/z 439 [M+H]$^+$.

Example 62

(S)-1-(6-(1-cyclopropyl-1H-pyrazol-4-yl)-2-methyl-5-(3-methylpyridin-2-yloxy)-3,4-dihydroquinolin-1(2H)-yl)ethanone (I-286)

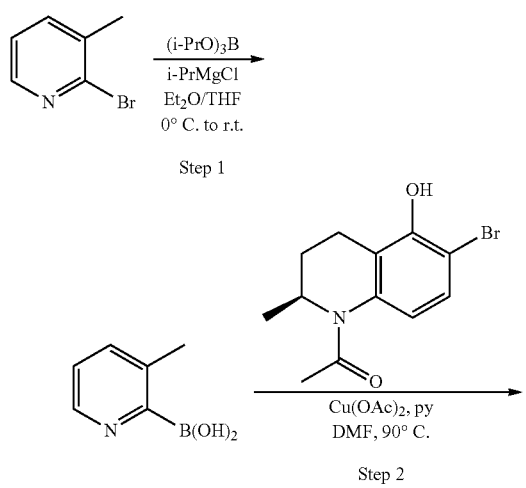

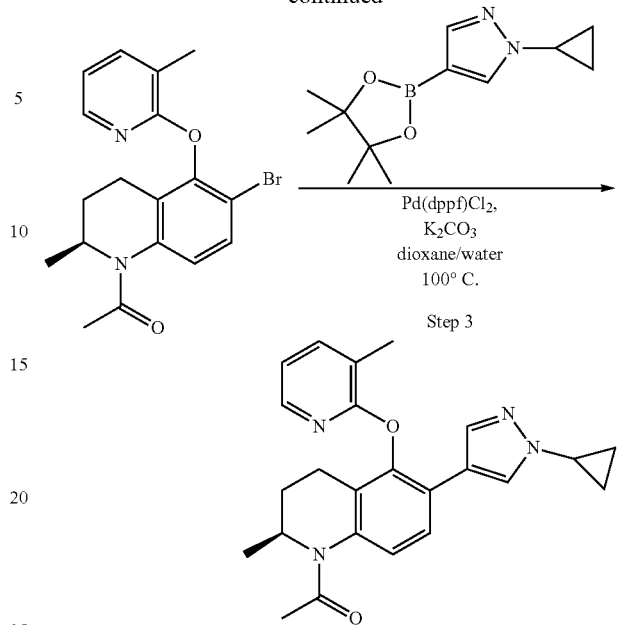

Step 1. 3-methylpyridin-2-ylboronic acid

A 100-mL, 3-necked round-bottom flask was charged with 2-bromo-3-methylpyridine (1.00 g, 5.81 mmol) and diethyl ether (30 mL). A solution of isopropylmagnesium chloride (2 M in THF, 8.0 mL, 16.0 mmol) was added dropwise with stirring at 0° C., and the resulting solution stirred for 3 h at 0° C. Triisopropyl borate (2.6 g, 13.8 mmol) was added, and the solution stirred for 1 h at room temperature. The reaction was then quenched by the addition of saturated aqueous ammonium chloride solution (10 mL). The aqueous layer was separated and extracted with ethyl acetate (2×10 mL). The combined organic layers were dried over anhydrous sodium sulfate, filtered, and concentrated under vacuum to afford 3-methylpyridin-2-ylboronic acid (0.730 g, 92%) as light yellow oil. MS (ESI, pos. ion) m/z 138 [M+H]$^+$.

Step 2. (S)-1-(6-bromo-2-methyl-5-(3-methylpyridin-2-yloxy)-3,4-dihydroquinolin-1(2H)-yl)ethanone A 100-mL, round-bottom flask equipped with a balloon filled with air was charged with (S)-1-(6-bromo-5-hydroxy-2-methyl-3,4-dihydroquinolin-1(2H)-yl)ethanone (0.200 g, 0.70 mmol), pyridine (1 mL), copper (II) acetate (0.382 g, 2.10 mmol), 3-methylpyridin-2-ylboronic acid 0.190 g, 1.39 mmol) and N,N-dimethylformamide (8 mL). The resulting mixture stirred at 90° C. overnight. After cooling to room temperature, the reaction mixture was filtered, and the filtrate was concentrated under vacuum. The residue was purified by column chromatography on silica gel (eluting with 1:8, ethyl acetate/petroleum ether) to afford (S)-1-(6-bromo-2-methyl-5-(3-methylpyridin-2-yloxy)-3,4-dihydroquinolin-1(2H)-yl) ethanone (0.129 g, 49%) as yellow oil. MS (ESI, pos. ion) m/z 375, 377 [M+H]$^+$.

Step 3. (S)-1-(6-(1-cyclopropyl-1H-pyrazol-4-yl)-2-methyl-5-(3-methylpyridin-2-yloxy)-3,4-dihydroquinolin-1(2H)-yl)ethanone A 100-mL, round-bottom flask was charged with (S)-1-(6-bromo-2-methyl-5-(3-methylpyridin-2-yloxy)-3,4-dihydroquinolin-1(2H)-yl)ethanone (0.129 g, 0.34 mmol), [1,1'-bis(diphenylphosphino)ferrocene]dichloropalladium(II) (0.025 g, 0.03 mmol), potassium carbonate (0.142 g, 1.03 mmol), 1-cyclopropyl-4-(4,4,5,5-tetramethyl-1,3,2-dioxaborolan-2-yl)-1H-pyrazole (0.243 g, 1.04 mmol), 1.4-dioxane (10 mL) and water (2 mL). The resulting mixture stirred overnight at 100° C. After cooling to room temperature, the reaction mixture was passed through a short pad of Celite, and the filtrate was concentrated under vacuum. The residue was purified by preparative thin layer chromatography (eluting with 50% ethyl acetate-petroleum ether). The product was further purified by preparative-HPLC with the following conditions (Waters I): Column, SunFire Prep C18, 19×150 mm; mobile phase, water (0.05% ammonium bicarbonate) and acetonitrile (54% to 80% acetonitrile in 10 min, flow rate: 20 mL/min); Detector, UV 220&254 nm. This afforded (S)-1-(6-(1-cyclopropyl-1H-pyrazol-4-yl)-2-methyl-5-(3-methylpyridin-2-yloxy)-3,4-dihydroquinolin-1(2H)-yl)ethanone (0.0285 g, 21%) as an off-white solid. $^1$H NMR (300 MHz, CD$_3$OD) δ ppm 1.00-1.03 (m, 4H), 1.16 (d, J=6.60 Hz, 3H), 1.32-1.42 (m, 1H), 2.20-2.28 (m, 5H), 2.48 (s, 3H), 2.54-2.59 (m, 1H), 3.57-3.64 (m, 1H), 4.75-4.80 (m, 1H), 6.95-7.00 (m, 1H), 7.22-7.27 (m, 1H), 7.54 (d, J=8.40 Hz, 1H), 7.63 (s, 1H), 7.72-7.77 (m, 2H), 7.80 (s, 1H). MS (ESI, pos. ion) m/z 403 [M+H]$^+$.

The following examples were made according to the procedure outlined for Example 62:

(S)-1-(6-(1-cyclopropyl-1H-pyrazol-4-yl)-2-methyl-5-(5-methylpyridin-2-yloxy)-3,4-dihydroquinolin-1(2H)-yl)ethanone (I-287)

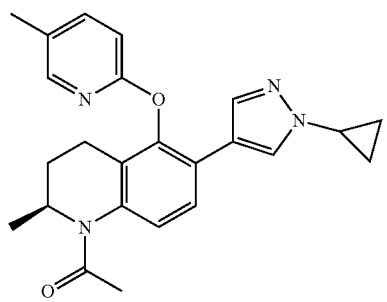 [SMILES: CC(=O)N1c2ccc(-c3cnn(C4CC4)c3)c(Oc3ccc(C)cn3)c2CC[C@@H]1C]

$^1$H NMR (300 MHz, CD$_3$OD) δ ppm 1.01-1.04 (m, 4H), 1.16 (d, J=6.60 Hz, 3H), 1.30-1.40 (m, 1H), 2.06-2.27 (m, 8H), 2.63-2.68 (m, 1H), 3.57-3.62 (m, 1H), 4.80 (m, 1H), 6.80 (d, J=8.40 Hz, 1H), 7.31-7.32 (m, 1H), 7.56-7.66 (m, 2H), 7.74 (s, 1H), 7.88-7.92 (m, 2H). MS (ESI, pos. ion) m/z 403 [M+H]$^+$.

(S)-1-(5-(5-chloropyridin-2-yloxy)-6-(1-cyclopropyl-1H-pyrazol-4-yl)-2-methyl-3,4-dihydroquinolin-1(2H)-yl)ethanone (I-288)

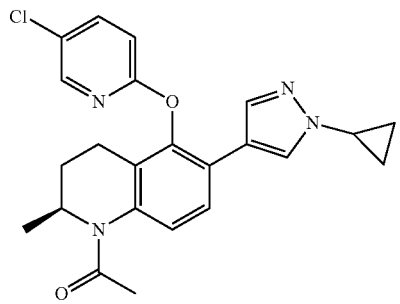 [SMILES: CC(=O)N1c2ccc(-c3cnn(C4CC4)c3)c(Oc3ccc(Cl)cn3)c2CC[C@@H]1C]

$^1$H NMR (300 MHz, CD$_3$OD) 0.90-1.02 (m, 4H), 1.14 (d, J=6.30 Hz, 3H), 1.42 (br s, 1H), 2.10-2.32 (m, 5H), 2.55-2.69 (m, 1H), 3.52-3.69 (m, 1H), 4.65-4.90 (m, 1H), 7.00 (d, J=8.70 Hz, 1H), 7.30 (br s, 1H), 7.53 (d, J=8.70 Hz, 1H), 7.70 (s, 1H), 7.75-7.85 (m, 1H), 7.90 (s, 1H), 8.00 (d, J=2.70 Hz, 1H). MS (ESI, pos. ion) m/z 423 [M+H]$^+$.

Example 63

(S)-1-(5-(7H-purin-2-yloxy)-6-(1-cyclopropyl-1H-pyrazol-4-yl)-2-methyl-3,4-dihydroquinolin-1(2H)-yl)ethanone (I-289)

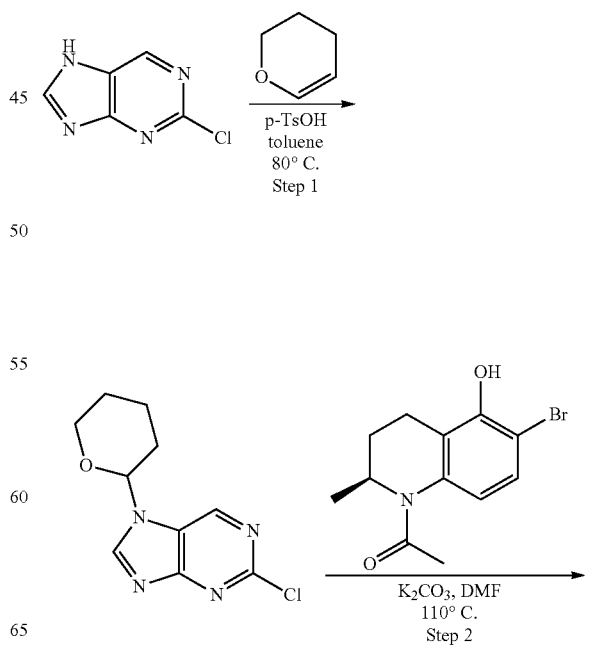

-continued

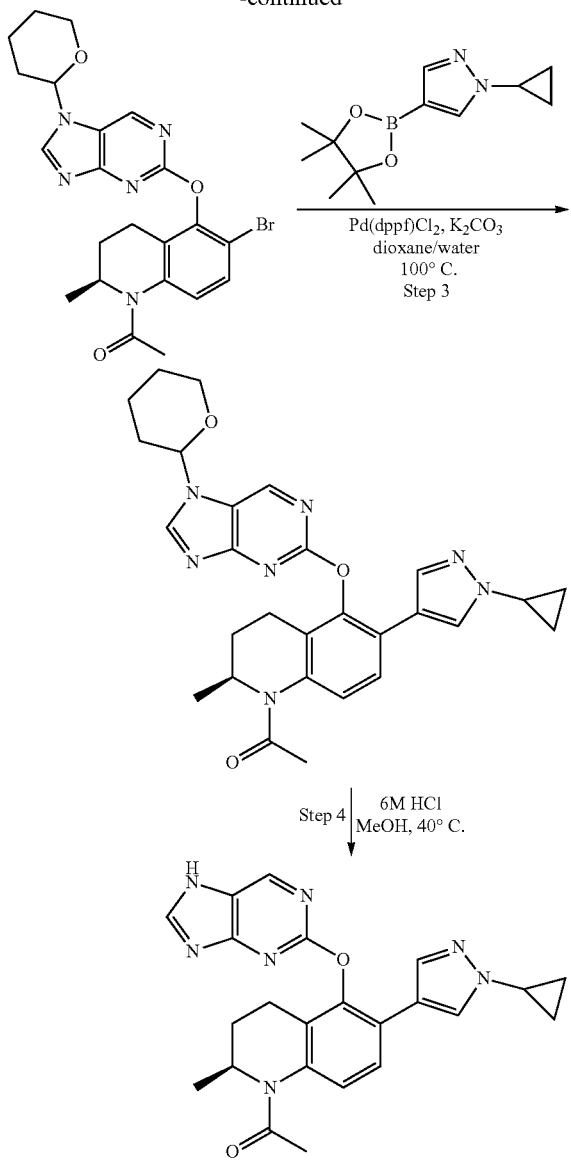

Step 1. 2-chloro-7-(tetrahydro-2H-pyran-2-yl)-7H-purine

A 100-mL, round-bottom flask was charged with 2-chloro-7H-purine (0.200 g, 1.29 mmol), toluene (20 mL), p-toluene sulfonic acid (0.011 g, 0.06 mmol), 3,4-dihydro-2H-pyran (0.328 g, 3.90 mmol), and the resulting solution stirred for 2 h at 80° C. After cooling to room temperature, the reaction mixture was concentrated under vacuum. The residue was purified by column chromatography on silica gel (eluting 1:5, with ethyl acetate/petroleum ether) to afford 2-chloro-7-(tetrahydro-2H-pyran-2-yl)-7H-purine (0.245 g, 79%) as brown oil. MS (ESI, pos. ion) m/z 239 [M+H]$^+$.

Step 2. 1-((S)-6-bromo-2-methyl-5-(7-(tetrahydro-2H-pyran-2-yl)-7H-purin-2-yloxy)-3,4-dihydroquinolin-1(2H)-yl)ethanone A 100-mL, round-bottom flask was charged with (S)-1-(6-bromo-5-hydroxy-2-methyl-3,4-dihydroquinolin-1(2H)-yl) ethanone (0.170 g, 0.60 mmol), 2-chloro-7-(tetrahydro-2H-pyran-2-yl)-7H-purine (0.200 g, 0.84 mmol), potassium carbonate (0.247 g, 1.79 mmol) and N,N-dimethylformamide (6 mL). The resulting mixture stirred overnight at 110° C. After cooling to room temperature, the reaction mixture was filtered, and the filtrate was concentrated under vacuum. The residue was purified by preparative thin layer chromatography (eluting with 1:1, ethyl acetate/petroleum ether) to afford 1-((S)-6-bromo-2-methyl-5-(7-(tetrahydro-2H-pyran-2-yl)-7H-purin-2-yloxy)-3,4-dihydroquinolin-1(2H)-yl)ethanone (0.200 g, 69%) as yellow oil. MS (ESI, pos. ion) m/z 486, 488 [M+H]$^+$.

Step 3. 1-((S)-6-(1-cyclopropyl-1H-pyrazol-4-yl)-2-methyl-5-(7-(tetrahydro-2H-pyran-2-yl)-7H-purin-2-yloxy)-3,4-dihydroquinolin-1(2H)-yl)ethanone A 100-mL, round-bottom flask was charged with 1-((S)-6-bromo-2-methyl-5-(7-(tetrahydro-2H-pyran-2-yl)-7H-purin-2-yloxy)-3,4-dihydroquinolin-1(2H)-yl)ethanone (0.200 g, 0.41 mmol), [1,1'-bis(diphenylphosphino)ferrocene] dichloropalladium(II) (0.030 g, 0.04 mmol), potassium carbonate (0.170 g, 1.23 mmol), 1-cyclopropyl-4-(4,4,5,5-tetramethyl-1,3,2-dioxaborolan-2-yl)-1H-pyrazole (0.288 g, 1.23 mmol), 1,4-dioxane (20 mL), and water (2 mL). The resulting mixture stirred overnight at 100° C. After cooling to room temperature, the reaction mixture was passed through a short pad of Celite, and the filtrate was concentrated under vacuum. The residue was purified by preparative thin layer chromatography (eluting with 1:2, ethyl acetate/petroleum ether) to afford 1-((S)-6-(1-cyclopropyl-1H-pyrazol-4-yl)-2-methyl-5-(7-(tetrahydro-2H-pyran-2-yl)-7H-purin-2-yloxy)-3,4-dihydroquinolin-1(2H)-yl)ethanone (0.150 g, 71%) as light yellow oil. MS (ESI, pos. ion) m/z 514 [M+H]$^+$.

Step 4. (S)-1-(5-(7H-purin-2-yloxy)-6-(1-cyclopropyl-1H-pyrazol-4-yl)-2-methyl-3,4-dihydroquinolin-1(2H)-yl)ethanone A 100-mL, round-bottom flask was charged with 1-((S)-6-(1-cyclopropyl-1H-pyrazol-4-yl)-2-methyl-5-(7-(tetrahydro-2H-pyran-2-yl)-7H-purin-2-yloxy)-3,4-dihydroquinolin-1(2H)-yl)ethanone (0.150 g, 0.29 mmol), HCl (6 M aqueous solution, 3 mL) and methanol (20 mL). The resulting solution stirred overnight at 40° C. After cooling to room temperature, the pH of the reaction mixture was adjusted to 7-8 with saturated aqueous sodium carbonate solution. The resulting mixture was concentrated to remove the methanol and ethyl acetate was added. The aqueous layer was separated and extracted with ethyl acetate (3×20 mL). The combined organic layers were dried over anhydrous sodium sulfate, filtered, and concentrated. The residue was purified by preparative-HPLC with the following conditions (Waters I): Column, SunFire Prep C18, 19×150 mm; mobile phase, water (0.05% ammonium bicarbonate) and acetonitrile (37% acetonitrile up to 58% in 10 min, flow rate: 20 mL/min); Detector, UV 220&254 nm. This afforded (S)-1-(5-(7H-purin-2-yloxy)-6-(1-cyclopropyl-1H-pyrazol-4-yl)-2-methyl-3,4-dihydroquinolin-1(2H)-yl)ethanone (0.030 g, 24%) as a yellow solid. $^1$H NMR (300 MHz, CD$_3$OD) δ ppm 0.86-1.00 (m, 4H), 1.16 (d, J=6.30 Hz, 3H), 1.21-1.49 (m, 1H), 2.18-2.47 (m, 5H), 2.63-2.72 (m, 1H), 3.52-3.59 (m, 1H), 4.72-4.80 (m, 1H), 7.19-7.30 (m, 1H), 7.56 (d, J=8.40 Hz, 1H), 7.60 (s, 1H), 7.99 (s, 1H), 8.41 (s, 1H), 8.79 (s, 1H). MS (ESI, pos. ion) m/z 430 [M+H]$^+$.

Example 64

(2S)-methyl 5-cyclobutoxy-6-(1-(3-methoxypiperidin-4-yl)-1H-pyrazol-4-yl)-2-methyl-3,4-dihydroquinoline-1(2H)-carboxylate (I-290)

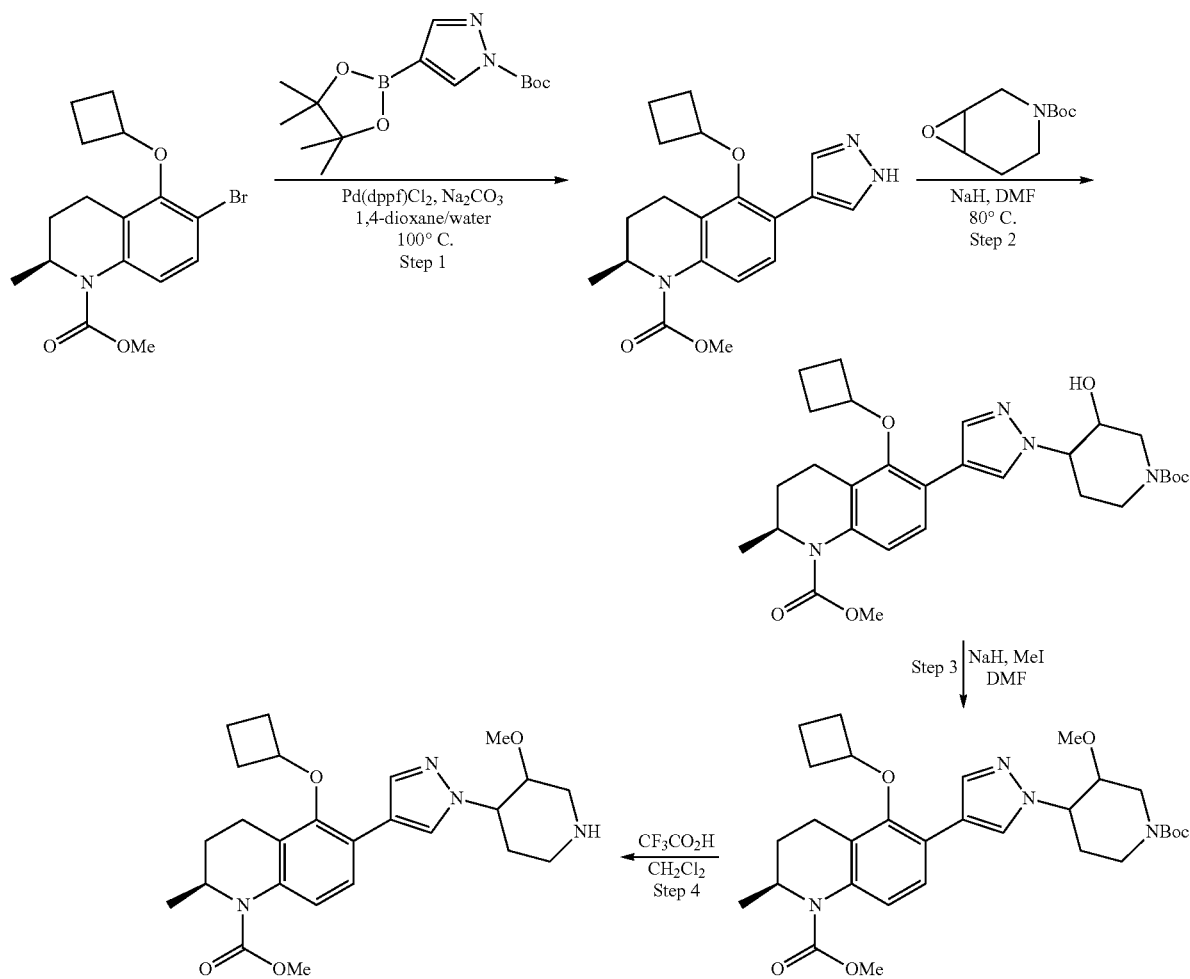

Step 1. (S)-methyl 5-cyclobutoxy-2-methyl-6-(1H-pyrazol-4-yl)-3,4-dihydroquinoline-1(2H)-carboxylate A 100-mL round-bottom flask was charged with tert-butyl 4-(tetramethyl-1,3,2-dioxaborolan-2-yl)-1H-pyrazole-1-carboxylate (250 mg, 0.85 mmol), (S)-methyl 6-bromo-5-cyclobutoxy-2-methyl-3,4-dihydroquinoline-1(2H)-carboxylate (317 mg, 0.89 mmol), sodium carbonate (150 mg, 1.42 mmol), [1,1'-bis(diphenylphosphino)ferrocene]dichloropalladium(II) (58 mg, 0.18 mmol), 1,4-dioxane (10 mL), and water (2 mL). The resulting mixture stirred overnight at 100° C. in an oil bath. After cooling to room temperature, the reaction mixture was poured into 10 mL of water and the layers were separated. The aqueous layer was extracted with ethyl acetate (3×10 mL). The organic layers were combined, dried over anhydrous sodium sulfate, filtered, and concentrated under vacuum. The residue was purified via column chromatography on silica gel (eluting with 5:1, ethyl acetate/petroleum ether) to afford (S)-methyl 5-cyclobutoxy-2-methyl-6-(1H-pyrazol-4-yl)-3,4-dihydroquinoline-1(2H)-carboxylate (200 mg, 52%) as yellow oil. MS (ESI, pos. ion) m/z 342 [M+H]$^+$.

Step 2. Methyl (2S)-6-(1-[1-[(tert-butoxy)carbonyl]-3-hydroxypiperidin-4-yl]-1H-pyrazol-4-yl)-5-cyclobutoxy-2-methyl-1,2,3,4-tetrahydroquinoline-1-carboxylate A 100-mL round-bottom flask was charged with (S)-methyl 5-cyclobutoxy-2-methyl-6-(1H-pyrazol-4-yl)-3,4-dihydroquinoline-1(2H)-carboxylate (200 mg, 0.59 mmol) and N,N-dimethylformamide (10 mL). Sodium hydride (47 mg, 1.96 mmol) was added and the mixture stirred at room temperature for 30 minutes. tert-Butyl 7-oxa-3-azabicyclo[4.1.0]heptane-3-carboxylate (995 mg, 4.99 mmol) was added, and the resulting solution stirred overnight at 80° C. in an oil bath. After cooling to room temperature, the reaction mixture was poured into ethyl acetate (50 mL), washed with water (3×10 mL) and brine (10 mL), dried over anhydrous sodium sulfate, filtered, and concentrated under vacuum. The residue was purified via column chromatography on silica gel (eluting with 10:1, dichloromethane/methanol) to afford methyl (2S)-6-(1-[1-[(tert-butoxy)carbonyl]-3-hydroxypiperidin-4-yl]-

1H-pyrazol-4-yl)-5-cyclobutoxy-2-methyl-1,2,3,4-tetrahydroquinoline-1-carboxylate (250 mg, 78%) as yellow oil. MS (ESI, pos. ion) m/z 541 [M+H]+.

Step 3. (2S)-methyl 6-(1-(1-(tert-butoxycarbonyl)-3-methoxypiperidin-4-yl)-1H-pyrazol-4-yl)-5-cyclobutoxy-2-methyl-3,4-dihydroquinoline-1(2H)-carboxylate A 50-mL round-bottom flask was charged with methyl (2S)-6-(1-[1-[(tert-butoxy)carbonyl]-3-hydroxypiperidin-4-yl]-1H-pyrazol-4-yl)-5-cyclobutoxy-2-methyl-1,2,3,4-tetrahydroquinoline-1-carboxylate (250 mg, 0.46 mmol,) and N,N-dimethylformamide (5 mL). Sodium hydride (78 mg, 3.25 mmol,) was added, and the mixture stirred at room temperature for 30 minutes. Methyl iodide (0.079 mL, 1.28 mmol) was added, and the resulting solution stirred for 4 h at room temperature. The reaction mixture was then poured into 20 mL of water and extracted with ethyl acetate (3×20 mL). The organic layers were combined, dried over anhydrous sodium sulfate, filtered, and concentrated under vacuum. The residue was purified via column chromatography on silica gel (eluting with 1:5, ethyl acetate/petroleum ether) to afford (2S)-methyl 6-(1-(1-(tert-butoxycarbonyl)-3-methoxypiperidin-4-yl)-1H-pyrazol-4-yl)-5-cyclobutoxy-2-methyl-3,4-dihydroquinoline-1(2H)-carboxylate (80 mg, 31%) as colorless oil. MS (ESI, pos. ion) m/z 555 [M+H]+.

Step 4. (2S)-methyl 5-cyclobutoxy-6-(1-(3-methoxypiperidin-4-yl)-1H-pyrazol-4-yl)-2-methyl-3,4-dihydroquinoline-1(2H)-carboxylate A 25-mL round-bottom flask was charged with (2S)-methyl 6-(1-(1-(tert-butoxycarbonyl)-3-methoxypiperidin-4-yl)-1H-pyrazol-4-yl)-5-cyclobutoxy-2-methyl-3,4-dihydroquinoline-1(2H)-carboxylate (40 mg, 0.07 mmol), dichloromethane (3 mL), and trifluoroacetic acid (1 mL). The resulting solution stirred for 1 h at room temperature. The reaction mixture was concentrated under vacuum. The residue was purified by Prep-HPLC with the following conditions: Column: Xbridge RP C18, 19×150 mm, 5 um; Mobile Phase water (0.05% trifluoroacetic acid), acetonitrile (15% to 43% acetonitrile in 9 min, flow rate: 20 mL/min); Detector, 254/220 nm. The fractions were combined and concentrated under vacuum and the residue was further purified via reverse phase chromatography (acetonitrile/water (0.05% ammonium bicarbonate)=5/95-95/5). The fractions were combined, concentrated and lyophilized to afford methyl (2S)-5-cyclobutoxy-6-[1-(3-methoxypiperidin-4-yl)-1H-pyrazol-4-yl]-2-methyl-1,2,3,4-tetrahydroquinoline-1-carboxylate (14 mg, 43%) as an off-white solid. 1H NMR (300 MHz, CD3OD) δ ppm 1.10-1.20 (m, 3H), 1.25-1.50 (m, 2H), 1.50-1.70 (m, 1H), 1.95-2.52 (m, 8H), 2.80-3.10 (m, 2H), 3.10-3.35 (m, 4H), 3.55-3.90 (m, 6H), 4.05-3.15 (m, 1H), 4.40-4.65 (m, 2H), 7.18-7.35 (m, 2H), 7.93 (s, 1H), 8.01-8.12 (m, 2H). MS (ESI, pos. ion) m/z 455 [M+H]+.

Example 65

(2S)-methyl 5-(4-fluorophenoxy)-6-(1-(3-methoxypiperidin-4-yl)-1H-pyrazol-4-yl)-2-methyl-3,4-dihydroquinoline-1(2H)-carboxylate (I-291)

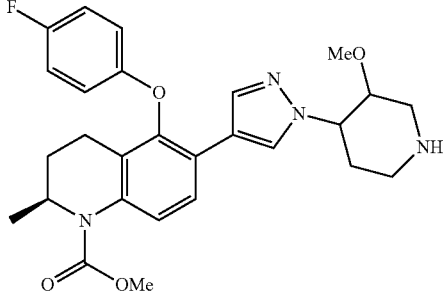 [SMILES: COC(=O)N1c2ccc(-c3cnn(C4CCNCC4OC)c3)c(Oc3ccc(F)cc3)c2CC[C@@H]1C]

(2S)-methyl 5-(4-fluorophenoxy)-6-(1-(3-methoxypiperidin-4-yl)-1H-pyrazol-4-yl)-2-methyl-3,4-dihydroquinoline-1(2H)-carboxylate was synthesized from methyl (S)-6-bromo-5-(4-fluorophenoxy)-2-methyl-3,4-dihydroquinoline-1(2H)-carboxylate according to the procedure outlined for Example 52. 1H NMR (400 MHz, CD3OD) δ ppm 1.16 (d, J=6.40 Hz, 3H), 1.55-1.65 (m, 1H), 2.01-2.12 (m, 1H), 2.20-2.50 (m, 3H), 2.60-2.72 (m, 1H), 2.90-3.01 (m, 3H), 3.08-3.15 (m, 2H), 3.45-3.75 (m, 3H), 3.82 (s, 3H), 4.25-4.35 (m, 1H), 4.60-4.70 (m, 1H), 6.65-4.75 (m, 2H), 6.90-7.00 (m, 2H), 7.50-7.60 (m, 2H), 7.82-8.01 (m, 2H). MS (ESI, pos. ion) m/z 495 [M+H]+.

Example 69

(2S)-methyl 5-cyclobutoxy-6-(1-(3-methoxy-1-methylpiperidin-4-yl)-1H-pyrazol-4-yl)-2-methyl-3,4-dihydroquinoline-1(2H)-carboxylate (I-292)

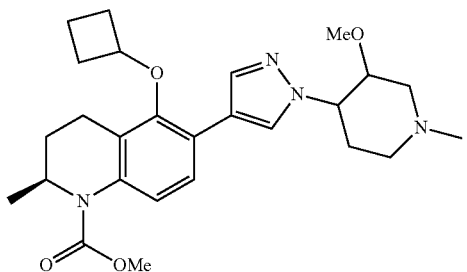

(2S)-Methyl 5-cyclobutoxy-6-(1-(3-methoxy-1-methylpiperidin-4-yl)-1H-pyrazol-4-yl)-2-methyl-3,4-dihydroquinoline-1(2H)-carboxylate was synthesized from (2S)-methyl 6-(1-(1-(tert-butoxycarbonyl)-3-methoxypiperidin-4-yl)-1H-pyrazol-4-yl)-5-cyclobutoxy-2-methyl-3,4-dihydroquinoline-1(2H)-carboxylate and formaldehyde according to the procedure outlined above for Example 40. 1H NMR (300 MHz, CD3OD) δ ppm 1.19 (d, J=6.00 Hz, 3H), 1.20-1.50 (m, 2H), 1.55-1.85 (m, 1H), 2.01-2.22 (m, 4H), 2.22-2.68 (m, 4H), 2.88-3.08 (m, 5H), 3.10-3.22 (m, 2H), 3.50-3.60 (m, 1H), 3.80 (s, 3H), 3.81-4.01 (m, 1H), 4.05-4.25 (m, 1H), 4.30-4.45 (m, 1H), 4.48-4.70 (m, 1H), 7.20-7.40 (m, 2H), 7.85-8.10 (m, 2H). MS (ESI, pos. ion) m/z 469 [M+H]⁺.

Example 70

(2S)-methyl 5-(4-fluorophenoxy)-6-(1-(3-methoxy-1-methylpiperidin-4-yl)-1H-pyrazol-4-yl)-2-methyl-3,4-dihydroquinoline-1(2H)-carboxylate (I-293)

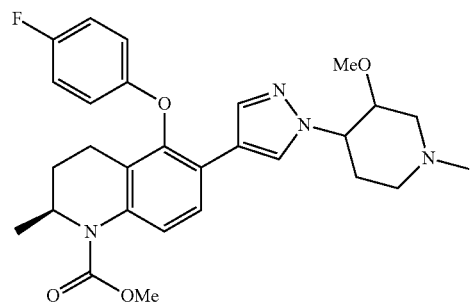

(2S)-Methyl 5-(4-fluorophenoxy)-6-(1-(3-methoxy-1-methylpiperidin-4-yl)-1H-pyrazol-4-yl)-2-methyl-3,4-dihydroquinoline-1(2H)-carboxylate was synthesized from (2S)-methyl 5-(4-fluorophenoxy)-6-(1-(3-methoxypiperidin-4-yl)-1H-pyrazol-4-yl)-2-methyl-3,4-dihydroquinoline-1(2H)-carboxylate and formaldehyde according to the procedure outlined above for Example 40. ¹H NMR (400 MHz, CD₃OD) δ ppm 1.16 (d, J=6.80 Hz, 3H), 1.50-1.65 (m, 1H), 1.98-2.11 (m, 1H), 2.15-2.22 (m, 1H), 2.40-2.70 (m, 3H), 2.78-3.01 (m, 5H), 3.02-3.18 (m, 1H), 3.42-3.85 (m, 8H), 4.15-4.25 (m, 1H), 4.55-4.72 (m, 1H), 6.72-6.80 (m, 2H), 6.90-7.01 (m, 2H), 7.50-7.62 (m, 2H), 7.80-8.10 (m, 2H). MS (ESI, pos. ion) m/z 509 [M+H]⁺.

Example 71

3-{4-[(2S)-1-cyclopropanecarbonyl-2-methyl-5-phenoxy-1,2,3,4-tetrahydroquinolin-6-yl]-1H-pyrazol-1-yl}-1λ⁶-thiane-1,1-dione (I-294)

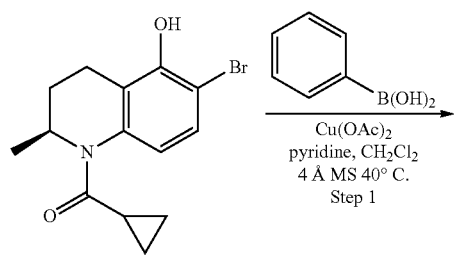

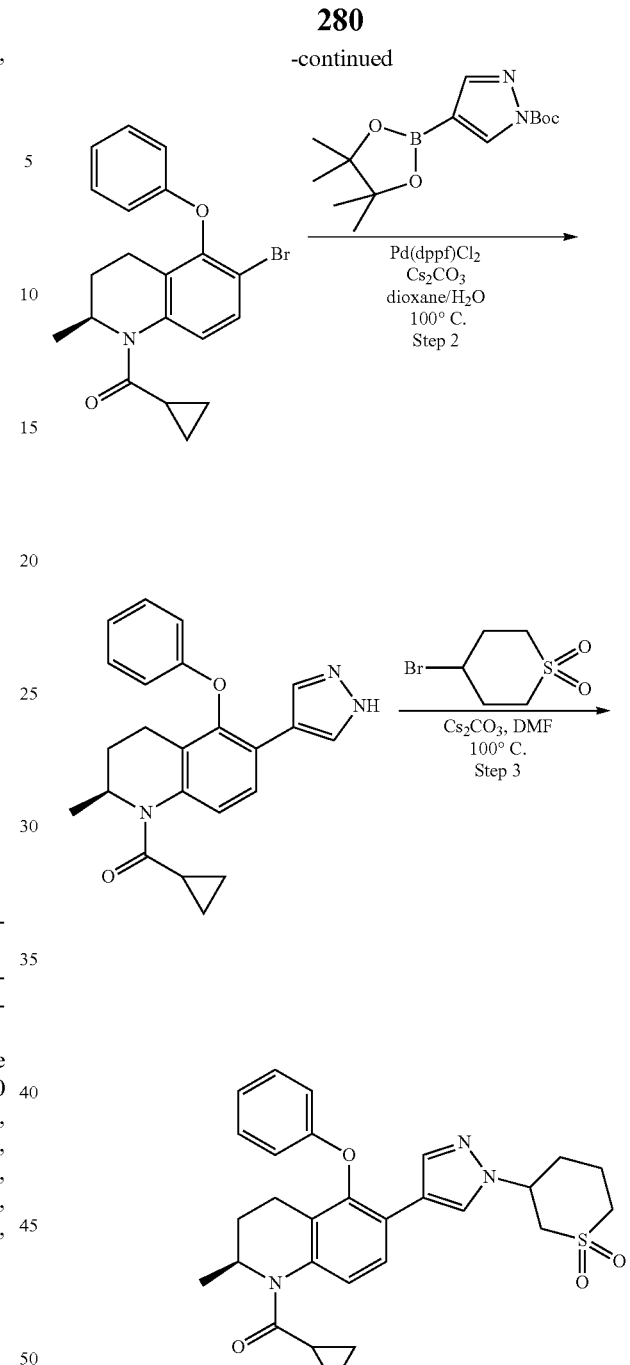

Step 1. (S)-(6-bromo-2-methyl-5-phenoxy-3,4-dihydroquinolin-1(2H)-yl)(cyclopropyl)methanone A 100-mL round-bottom flask equipped with a balloon filled with air was charged with (S)-(6-bromo-5-hydroxy-2-methyl-3,4-dihydroquinolin-1(2H)-yl)(cyclopropyl)methanone (0.800 g, 2.58 mmol), phenylboronic acid (0.937 g, 7.68 mmol), pyridine (0.83 mL, 10.30 mmol), dichloromethane (50 mL), and copper (II) acetate (0.934 g, 5.14 mmol). The resulting mixture stirred at 40° C. for 1 day. The mixture was cooled to room temperature and filtered. The filtrate was concentrated under vacuum, and the residue was purified via column chromatography on silica gel (gradient elution with 5-10% ethyl acetate/petroleum ether) to afford (S)-(6-bromo- 2-methyl-5-phenoxy-3,4-dihydroquinolin-1(2H)-yl)(cyclopropyl)methanone (0.700 g, 70%) as a white solid. MS (ESI, pos. ion) m/z 386, 388 [M+H]+.

Step 2. (S)-cyclopropyl(2-methyl-5-phenoxy-6-(1H-pyrazol-4-yl)-3,4-dihydroquinolin-1(2H)-yl)methanone A 100-mL round-bottom flask was charged with (S)-(6-bromo-2-methyl-5-phenoxy-3,4-dihydroquinolin-1(2H)-yl)(cyclopropyl)methanone (0.400 g, 1.04 mmol), [1,1'-bis(diphenylphosphino)ferrocene]dichloropalladium(II) dichloromethane adduct (0.083 g, 0.10 mmol), cesium carbonate (0.985 g, 3.02 mmol), tert-butyl 4-(4,4,5,5-tetramethyl-1,3,2-dioxaborolan-2-yl)-1H-pyrazole-1-carboxylate (0.343 g, 1.17 mmol), 1,4-dioxane (10 mL) and water (3 mL). The resulting mixture stirred at 100° C. overnight and was cooled to room temperature. The reaction mixture was passed through a short pad of Celite, and the filtrate was concentrated under vacuum. The residue was purified via column chromatography on silica gel (gradient elution with 10-25% ethyl acetate/petroleum ether) to afford (S)-cyclopropyl(2-methyl-5-phenoxy-6-(1H-pyrazol-4-yl)-3,4-dihydroquinolin-1(2H)-yl)methanone (0.200 g, 52%) as a light yellow solid. MS (ESI, pos. ion) m/z 374 [M+H]+.

Step 3. 3-{4-[(2S)-1-cyclopropanecarbonyl-2-methyl-5-phenoxy-1,2,3,4-tetrahydroquinolin-6-yl]-1H-pyrazol-1-yl}-1λ6-thiane-1,1-dione A 100-mL, round-bottom flask was charged with (S)-cyclopropyl(2-methyl-5-phenoxy-6-(1H-pyrazol-4-yl)-3,4-dihydroquinolin-1(2H)-yl)methanone (0.200 g, 0.56 mmol), cesium carbonate (0.114 g, 0.35 mmol), N,N-dimethylformamide (5 mL), and 4-bromo-1λ6-thiane-1,1-dione (0.114 g, 0.53 mmol). The resulting mixture stirred at 100° C. for 4 h and was then cooled to room temperature. The reaction mixture was diluted with ethyl acetate (50 mL) and washed with water (3×10 mL). The organic phase was dried over anhydrous sodium sulfate, filtered, and concentrated under vacuum. The residue was purified via column chromatography on silica gel (gradient elution with 25-50% ethyl acetate/petroleum). The product was further purified by preparative-HPLC with the following conditions (Waters I): Column, SunFire Prep C18, 5 um, 19×100 mm; mobile phase, Water and acetonitrile (55% to 75% acetonitrile in 7 min, flow rate: 20 mL/min); Detector, UV 220&254 nm. This afforded 3-{4-[(2S)-1-cyclopropanecarbonyl-2-methyl-5-phenoxy-1,2,3,4-tetrahydroquinolin-6-yl]-1H-pyrazol-1-yl}-1λ6-thiane-1,1-dione (0.122 g, 43%) as a white solid. 1H NMR (400 MHz, CD3OD) δ ppm 0.76-0.82 (m, 1H), 0.92-1.02 (m, 2H), 1.13-1.22 (m, 4H), 1.42-1.50 (m, 1H), 1.95-2.08 (m, 3H), 2.08-2.13 (m, 1H), 2.14-2.37 (m, 3H), 2.68-2.77 (m, 1H), 3.11-3.19 (m, 2H), 3.37 (s, 1H), 3.53-3.60 (m, 1H), 4.66-4.72 (m, 1H), 4.74-4.81 (m, 1H), 6.79 (d, J=8.00 Hz, 2H), 6.98 (t, J=7.60 Hz, 1H), 7.23 (t, J=7.60 Hz, 2H), 7.62 (d, J=8.40 Hz, 1H), 7.83 (s, 1H), 8.05 (s, 1H). MS (ESI, pos. ion) m/z 506 [M+H]+.

The following example was made according to the procedure outlined for Example 71:

3-{4-[(2S)-1-cyclopropanecarbonyl-5-(4-fluorophenoxy)-2-methyl-1,2,3,4-tetrahydroquinolin-6-yl]-1H-pyrazol-1-yl}-1λ6-thiane-1,1-dione (I-295)

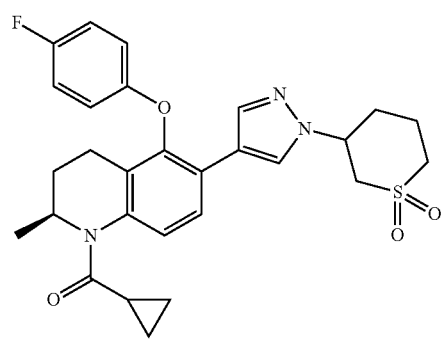 [SMILES: C[C@H]1CCc2c(ccc(-c3cnn(C4CCCS(=O)(=O)C4)c3)c2Oc2ccc(F)cc2)N1C(=O)C1CC1]

1H NMR (300 MHz, CD3OD) δ ppm 0.73-0.81 (m, 1H), 0.91-1.01 (m, 2H), 1.13 (d, J=6.30 Hz, 4H), 1.32-147 (m, 1H), 1.94-2.15 (m, 5H), 2.16-2.34 (m, 3H), 2.78-2.87 (m, 1H), 3.13-3.19 (m, 2H), 3.53-3.62 (m, 1H), 4.65-4.79 (m, 2H), 6.74-6.79 (m, 2H), 6.93-7.02 (m, 2H), 7.38 (d, J=8.70 Hz, 1H), 7.60 (d, J=8.40 Hz, 1H), 8.02 (s, 1H). MS (ESI, pos. ion) m/z 524 [M+H]+.

Example 72

(2S)-methyl 5-cyclobutoxy-2-methyl-6-(1-(2-oxopiperidin-4-yl)-1H-pyrazol-4-yl)-3,4-dihydroquinoline-1(2H)-carboxylate (I-296)

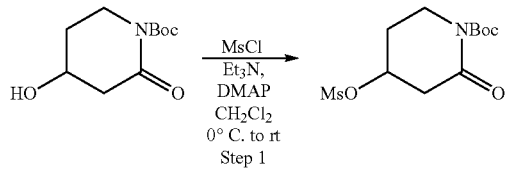

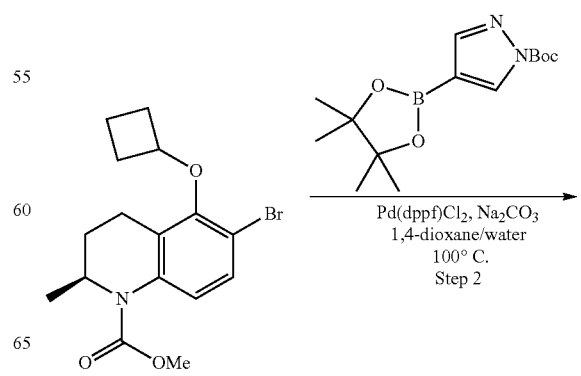

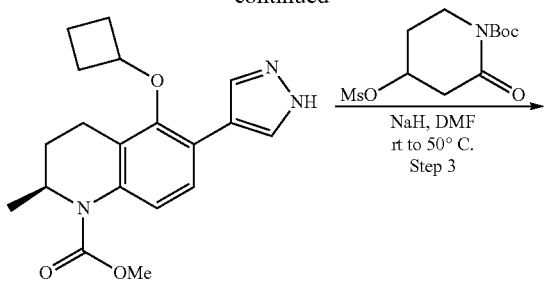

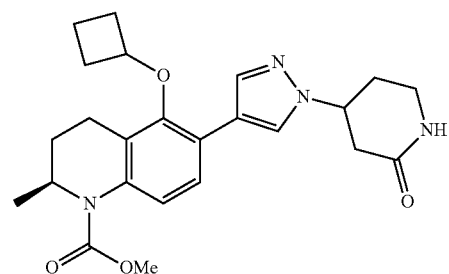

Step 1. tert-butyl 4-(methylsulfonyloxy)-2-oxopiperidine-1-carboxylate

A 100-mL round-bottom flask was charged with a solution of tert-butyl 4-hydroxy-2-oxopiperidine-1-carboxylate (1.00 g, 4.65 mmol) in dichloromethane (30 mL). Triethylamine (1.03 mL, 7.42 mmol) and 4-dimethylaminopyridine (0.057 g, 0.47 mmol) were added, and the mixture was cooled to 0° C. Methanesulfonyl chloride (0.47 mL, 6.05 mmol) was added dropwise and the resulting solution stirred for 1 h at room temperature. The reaction mixture was washed with water (2×10 mL) and 0.1 M aqueous HCl solution (2×10 mL), dried over anhydrous sodium sulfate, filtered, and concentrated under vacuum to afford tert-butyl 4-(methylsulfonyloxy)-2-oxopiperidine-1-carboxylate (0. 900 g, 66%) as a brown solid. MS (ESI, pos. ion) m/z 294 [M+H]⁺.

Step 2. (S)-methyl 5-cyclobutoxy-2-methyl-6-(1H-pyrazol-4-yl)-3,4-dihydroquinoline-1(2H)-carboxylate A 100-mL round-bottom flask was charged with tert-butyl 4-(tetramethyl-1,3,2-dioxaborolan-2-yl)-1H-pyrazole-1-carboxylate (0.250 g, 0.85 mmol), (S)-methyl 6-bromo-5-cyclobutoxy-2-methyl-3,4-dihydroquinoline-1(2H)-carboxylate (0.317 g, 0.89 mmol), sodium carbonate (0.150 g, 1.42 mmol), [1,1'-bis(diphenylphosphino)ferrocene]dichloropalladium(II) dichloromethane adduct (0.070 g, 0.085 mmol), 1,4-dioxane (10 mL), and water (2 mL). The resulting mixture stirred overnight at 100° C., was cooled to room temperature, and water (10 mL) was added. The aqueous layer was separated and extracted with ethyl acetate (3×10 mL). The combined organic layers were dried over anhydrous sodium sulfate, filtered, and concentrated under vacuum. The residue was purified via column chromatography on silica gel (eluting with 5:1, ethyl acetate/petroleum ether) to afford (S)-methyl 5-cyclobutoxy-2-methyl-6-(1H-pyrazol-4-yl)-3,4-dihydroquinoline-1(2H)-carboxylate (0.200 g, 52%) as yellow oil. MS (ESI, pos. ion) m/z 342 [M+H]⁺.

Step 3. (2S)-methyl 5-cyclobutoxy-2-methyl-6-(1-(2-oxopiperidin-4-yl)-1H-pyrazol-4-yl)-3,4-dihydroquinoline-1(2H)-carboxylate An 8-mL resealable tube was charged with (S)-methyl 5-cyclobutoxy-2-methyl-6-(1H-pyrazol-4-yl)-3,4-dihydroquinoline-1(2H)-carboxylate (0.050 g, 0.15 mmol) and N,N-dimethylformamide (2 mL). Sodium hydride (60% dispersion in mineral oil, 0.012 g, 0.50 mmol) was added, and the resulting mixture stirred for 15 min at room temperature. tert-Butyl 4-(methylsulfonyloxy)-2-oxopiperidine-1-carboxylate (0.141 g, 0.48 mmol) was added, and the resulting mixture stirred overnight at 50° C. The reaction mixture was cooled to room temperature and water (10 mL) was added. The aqueous phase was separated and extracted with ethyl acetate (3×10 mL). The combined organic layers were dried over anhydrous sodium sulfate, filtered, and concentrated under vacuum. The residue was purified by preparative-HPLC with the following conditions (Waters I): Column, Xbridge RPC18, 19×150 mm, 5 um; mobile phase, water (0.05% ammonium bicarbonate) and acetonitrile (13% to 60% acetonitrile in 8 min; flow rate: 20 mL/min); Detector, UV254&220. This afforded (2S)-methyl 5-cyclobutoxy-2-methyl-6-(1-(2-oxopiperidin-4-yl)-1H-pyrazol-4-yl)-3,4-dihydroquinoline-1(2H)-carboxylate (0.0091 mg, 14%) as a white solid. ¹H NMR (400 MHz, CD₃OD) δ ppm 1.17-1.20 (m, 3H), 1.29-1.40 (m, 1H), 1.40-1.51 (m, 1H), 1.58-1.68 (m, 1H), 2.03-2.19 (m, 4H) m 2.22-2.35 (m, 3H), 2.41-2.49 (m, 1H), 2.92-2.99 (m, 1H), 3.32-3.48 (m, 2H), 3.78 (s, 3H), 4.12-4.22 (m, 1H), 4.50-4.60 (m, 1H), 4.78-4.88 (m, 1H), 7.25-7.33 (m, 2H), 7.87 (s, 1H), 8.05 (s, 1H). MS (ESI, pos. ion) m/z 439 [M+H]⁺.

The following example was made according to the procedure outlined for Example 72:

(2S)-methyl 5-(4-fluorophenoxy)-2-methyl-6-(1-(2-oxopiperidin-4-yl)-1H-pyrazol-4-yl)-3,4-dihydroquinoline-1(2H)-carboxylate (I-297)

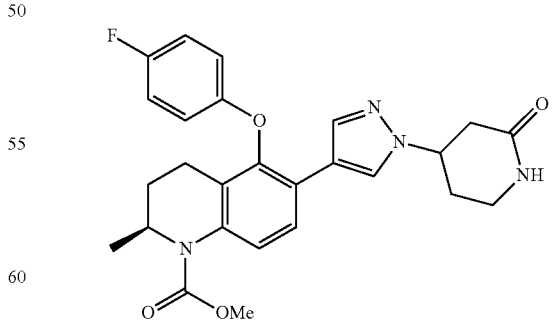

¹H NMR (400 MHz, CD₃OD) δ ppm 1.17-1.20 (m, 3H), 1.54-1.62 (m, 1H), 2.13-2.20 (m, 3H), 2.41-2.50 (m, 1H), 2.60-2.71 (m, 1H), 2.75-2.81 (m, 2H), 6.72-6.79 (m, 2H), 2.92-2.99 (m, 1H), 3.32-3.48 (m, 2H), 3.78 (s, 3H), 4.62-4.75

(m, 1H), 6.72-6.79 (m, 2H), 6.95-7.02 (m, 2H), 7.52-7.61 (m, 2H), 7.81 (s, 1H), 7.94 (s, 1H). MS (ESI, pos. ion) m/z 479 [M+H]+.

Example 73 methyl (2S)-5-(4-fluorophenoxy)-2-methyl-6-(1-(2-methylazetidin-3-yl)-1H-pyrazol-4-yl)-3,4-dihydroquinoline-1(2H)-carboxylate (I-298)

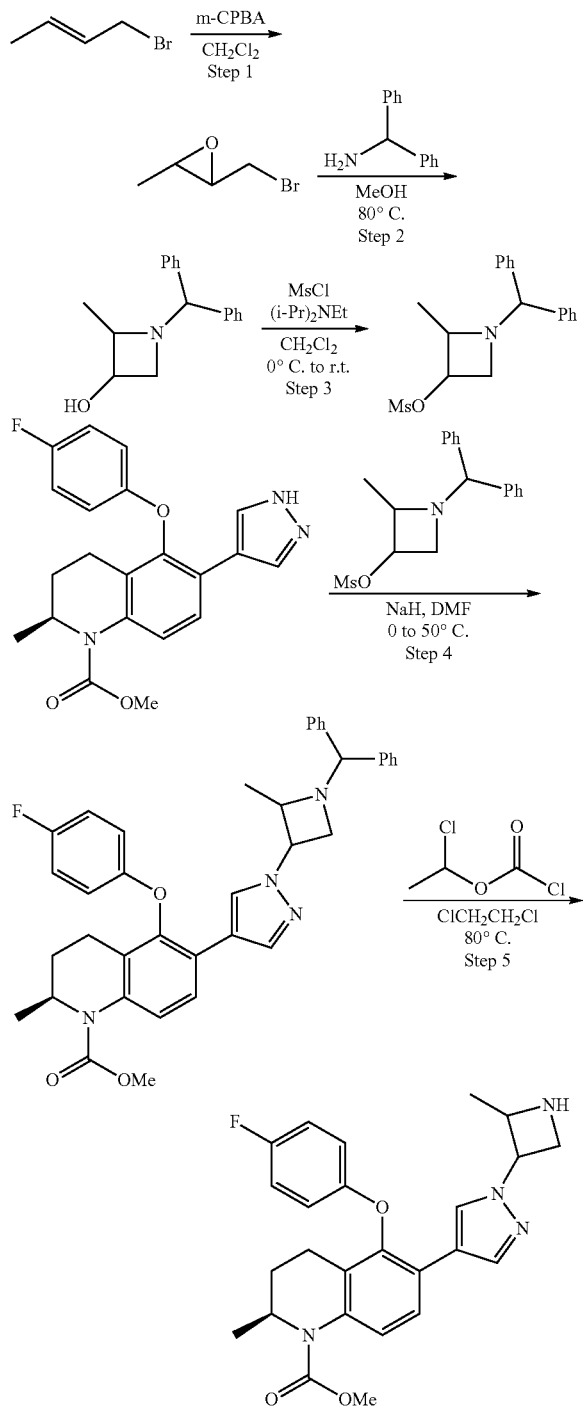

Step 1. 2-(bromomethyl)-3-methyloxirane

A 2000-mL round-bottom flask was charged with (E)-1-bromobut-2-ene (50.0 g, 370.4 mmol) and dichloromethane (1000 mL). 3-Chlorobenzoperoxoic acid (75 wt %, 94 g, 407 mmol) was added in portions over 1.5 h, and the resulting mixture stirred overnight at room temperature. The reaction mixture was washed with saturated aqueous sodium bicarbonate solution (3×200 mL) and brine (2×200 mL), dried over anhydrous sodium sulfate, filtered, and concentrated to afford 2-(bromomethyl)-3-methyloxirane (42.4 g, 84%) as light yellow oil. MS (ESI, pos. ion) m/z 192, 194 [M+H+MeCN]+.

Step 2. 1-benzhydryl-2-methylazetidin-3-ol

A 500-mL round-bottom flask was charged with 2-(bromomethyl)-3-methyloxirane (42.4 g, 280 mmol), methanol (120 mL), and diphenylmethanamine (44 mL, 260 mmol), and the resulting solution stirred overnight at 80° C. The reaction mixture was cooled to room temperature and concentrated. The residue was purified via column chromatography on silica gel (eluting with 50:1, dichloromethane/methanol) to afford 1-benzhydryl-2-methylazetidin-3-ol (25 g, 35%) as a white solid. MS (ESI, pos. ion) m/z 254 [M+H]+.

Step 3. 1-benzhydryl-2-methylazetidin-3-yl methanesulfonate

A 500-mL round-bottom flask was charged with 1-benzhydryl-2-methylazetidin-3-ol (15.0 g, 59.2 mmol), dichloromethane (30 mL), and N,N-diisopropylamine (21 mL, 160 mmol), and the solution was cooled to 0° C. A solution of methanesulfonyl chloride (6.2 mL, 77 mmol) in dichloromethane (10 mL) was added, and the resulting solution stirred overnight at room temperature. The reaction mixture was poured into 200 mL of water, and the aqueous phase was separated and extracted with dichloromethane (2×100 mL). The combined organic layers were washed with brine (2×100 mL), dried over anhydrous sodium sulfate, filtered, and concentrated under vacuum. The residue was purified via column chromatography on silica gel (eluting with 20:1, dichloromethane-ethyl acetate). The product was further purified by re-crystallization from hexane to afford 1-benzhydryl-2-methylazetidin-3-yl methanesulfonate (5.6 g, 29%) as a white solid. MS (ESI, pos. ion) m/z 332 [M+H]+.

Step 4. (2S)-methyl 6-(1-(1-benzhydryl-2-methylazetidin-3-yl)-1H-pyrazol-4-yl)-5-(4-fluorophenoxy)-2-methyl-3,4-dihydroquinoline-1(2H)-carboxylate A 100-mL round-bottom flask was charged with (S)-methyl 5-(4-fluorophenoxy)-2-methyl-6-(1H-pyrazol-4-yl)-3,4-dihydroquinoline-1(2H)-carboxylate (0.300 g, 0.79 mmol) and N,N-dimethylformamide (10 mL), and the solution was cooled to 0° C. Sodium hydride (60% dispersion in mineral oil, 0.047 g, 1.17 mmol) was added, and the resulting mixture stirred for 30 min at room temperature. 1-Benzhydryl-2-methylazetidin-3-yl methanesulfonate (0.286 g, 0.86 mmol) was added, and the resulting mixture stirred overnight at 50° C. The reaction mixture was cooled to room temperature and poured into water (30 mL). The aqueous phase was separated and extracted with ethyl acetate (3×20 mL). The combined organic layers were dried over anhydrous sodium sulfate, filtered, and concentrated under vacuum. The residue was purified via column chromatography on silica gel (eluting with 25% ethyl acetate-petroleum ether) to afford (2S)-methyl 6-(1-(1-benzhydryl-2-methylazetidin-3-yl)-1H-pyrazol-4-yl)-5-(4-fluorophenoxy)-2-methyl-3,4-dihydroquinoline-1(2H)-carboxylate (0.100 g, 21%) as yellow oil. MS (ESI, pos. ion) m/z 617 [M+H]$^+$.

Step 5. methyl (2S)-5-(4-fluorophenoxy)-2-methyl-6-(1-(2-methylazetidin-3-yl)-1H-pyrazol-4-yl)-3,4-dihydroquinoline-1(2H)-carboxylate A 50-mL round-bottom flask was charged with (2S)-methyl 6-(1-(1-benzhydryl-2-methylazetidin-3-yl)-1H-pyrazol-4-yl)-5-(4-fluorophenoxy)-2-methyl-3,4-dihydroquinoline-1(2H)-carboxylate (0.020 g, 0.03 mmol), 1,2-dichloroethane (5 mL) and 1-chloroethyl chloroformate (1 mL), and the resulting solution stirred for 3 h at 80° C. The reaction mixture was cooled to room temperature and then diluted with ethyl acetate (20 mL). The organic phase was separated and washed with water (10 mL), dried over anhydrous sodium sulfate, filtered, and concentrated under vacuum. The residue was purified via column chromatography on silica gel (eluting 25% ethyl acetate-petroleum ether). The product was further purified by preparative-HPLC with the following conditions (Waters I): Column, Xbridge RP C18, 19×150 mm, 5 um; mobile phase, water (0.05% ammonium bicarbonate) and acetonitrile (20% to 80% acetonitrile in 10 min; flow rate: 20 mL/min); Detector, UV254&220. This afforded methyl (2S)-5-(4-fluorophenoxy)-2-methyl-6-(1-(2-methylazetidin-3-yl)-1H-pyrazol-4-yl)-3,4-dihydroquinoline-1(2H)-carboxylate (0.0021 g, 14%) as a white solid. $^1$H NMR (300 MHz, CD$_3$OD) δ ppm 0.75 (d, J=6.40 Hz, 3H), 0.85-0.97 (m, 1H), 1.10-1.18 (m, 3H), 1.29-1.39 (m, 3H), 1.52-1.65 (m, 1H), 1.99-2.25 (m, 2H), 2.41-2.75 (m, 2H), 3.82 (s, 3H), 4.05-4.17 (m, 2H), 4.26-4.35 (m, 1H), 4.62-4.73 (m, 1H), 5.16-5.23 (m, 1H), 6.73-6.81 (m, 2H), 6.93-6.99 (m, 2H), 7.51-7.62 (m, 2H), 7.85 (s, 1H), 8.05 (s, 1H). MS (ESI, pos. ion) m/z 451 [M+H]$^+$.

The following example was made according to the procedure outlined for Example 73:

methyl (2S)-5-cyclobutoxy-2-methyl-6-(1-(2-methylazetidin-3-yl)-1H-pyrazol-4-yl)-3,4-dihydroquinoline-1(2H)-carboxylate (I-299)

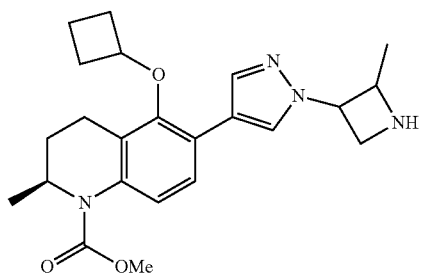 [SMILES: COC(=O)N1c2ccc(-c3cnn(C4CNC4C)c3)c(OC3CCC3)c2CC[C@@H]1C]

$^1$H NMR (300 MHz, CD$_3$OD) δ ppm 0.85-0.92 (m, 1H), 1.17-1.19 (m, 6H), 1.25-1.51 (m, 11H), 1.52-1.70 (m, 2H), 1.99-2.32 (m, 7H), 2.38-2.48 (m, 1H), 2.90-3.01 (m, 1H), 3.77 (s, 1H), 4.14-4.19 (m, 1H), 4.49-4.68 (m, 2H), 4.72-4.82 (m, 1H), 4.92-5.10 (m, 1H), 5.31-5.45 (m, 1H), 7.26-7.33 (m, 2H), 8.03 (s, 2H). MS (ESI, pos. ion) m/z 411 [M+H]$^+$.

Example 74

N-(4-((2S)-5-cyclobutoxy-1-(cyclopropanecarbonyl)-2-methyl-1,2,3,4-tetrahydroquinolin-6-yl)-1-cyclopropyl-1H-pyrazol-5-yl)methanesulfonamide (I-300)

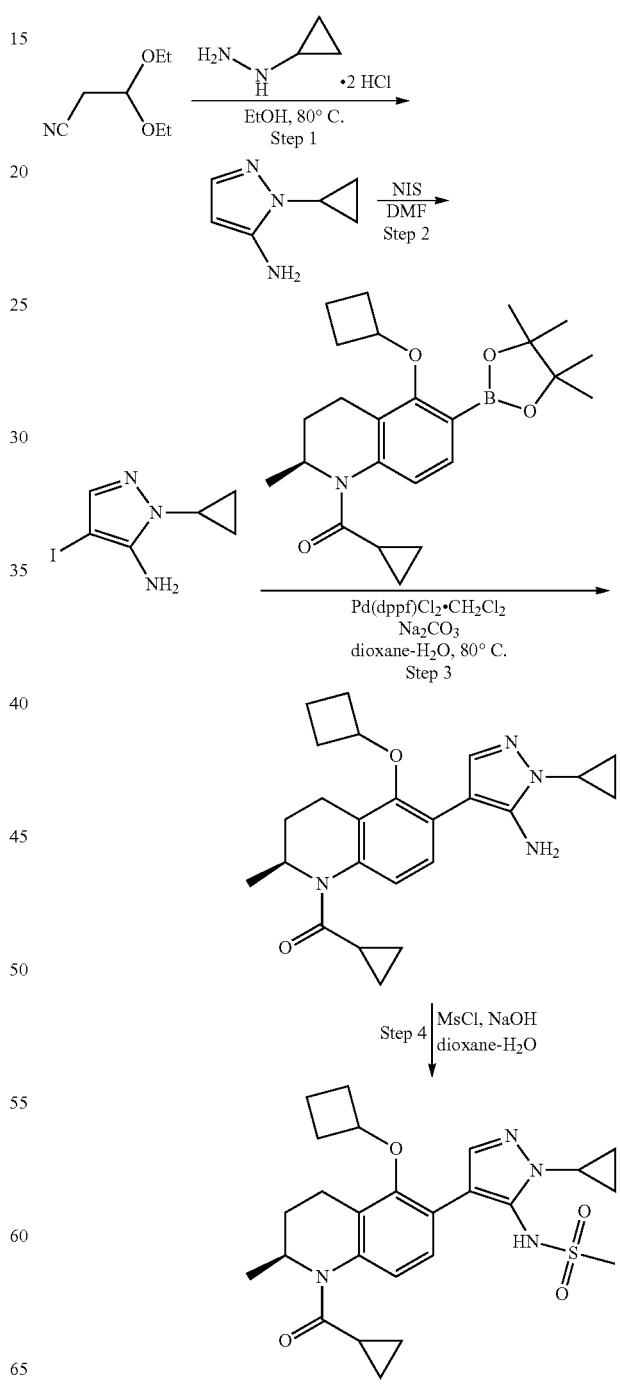

Step 1. 1-cyclopropyl-1H-pyrazol-5-amine

A 100-mL round-bottom flask was charged with 3,3-diethoxypropanenitrile (0.600 g, 4.19 mmol), cyclopropylhydrazine di-hydrochloride (0.610 g, 4.21 mmol) and ethanol (20 mL), and the resulting solution stirred for 18 h at 80° C. The reaction mixture was cooled to room temperature and concentrated under vacuum. The residue was purified via column chromatography on silica gel (eluting with 10:1, dichloromethane/methanol) to afford 1-cyclopropyl-1H-pyrazol-5-amine (0.206 g, 36%) as light yellow oil. MS (ESI, pos. ion) m/z 124 [M+H]+.

Step 2. 1-cyclopropyl-4-iodo-1H-pyrazol-5-amine

A 100-mL round-bottom flask was charged with 1-cyclopropyl-1H-pyrazol-5-amine (0.410 g, 3.33 mmol) and N,N-dimethylformamide (10 mL). N-Iodosuccinimide (0.820 g, 3.64 mmol) was added, and the resulting solution stirred for 18 h at room temperature. The reaction mixture was poured into saturated aqueous sodium bisulfite solution (50 mL) and extracted with ethyl acetate (3×20 mL). The combined organic layers were washed with brine (10 mL), dried over anhydrous sodium sulfate, filtered, and concentrated under vacuum. The residue was purified via column chromatography on silica gel (eluting with 1:1, ethyl acetate/petroleum ether) to afford 1-cyclopropyl-4-iodo-1H-pyrazol-5-amine (0.440 g, 48%) as light yellow oil. MS (ESI, pos. ion) m/z 250 [M+H]+.

Step 3. 02S)-6-(5-amino-1-cyclopropyl-1H-pyrazol-4-yl)-5-cyclobutoxy-2-methyl-3,4-dihydroquinolin-1(2H)-yl)(cyclopropyl)methanone A 50-mL round-bottom flask was charged with (S)-(5-cyclobutoxy-2-methyl-6-(4,4,5,5-tetramethyl-1,3,2-dioxaborolan-2-yl)-3,4-dihydroquinolin-1(2H)-yl)(cyclopropyl)methanone (0.140 g, 0.34 mmol), 1-cyclopropyl-4-iodo-1H-pyrazol-5-amine (0.071 g, 0.29 mmol), [1,1'-bis(diphenylphosphino)ferrocene]dichloropalladium(II) dichloromethane adduct (23.2 mg, 0.03 mmol, 0.10 equiv), sodium carbonate (0.061 g, 0.58 mmol), 1,4-dioxane (10 mL) and water (3 mL). The resulting mixture stirred for 18 h at 80° C. and was then cooled to room temperature. The reaction mixture was filtered through a short pad of Celite, and the filtrate was concentrated under vacuum. The residue was purified via column chromatography on silica gel (eluting with 1:5, ethyl acetate/petroleum ether) to afford ((2S)-6-(5-amino-1-cyclopropyl-1H-pyrazol-4-yl)-5-cyclobutoxy-2-methyl-3,4-dihydroquinolin-1(2H)-yl)(cyclopropyl)methanone (0.025 g (20%) as light yellow oil. MS (ESI, pos. ion) m/z 407 [M+H]+.

Step 4. N-(4-((2S)-5-cyclobutoxy-1-(cyclopropanecarbonyl)-2-methyl-1,2,3,4-tetrahydroquinolin-6-yl)-1-cyclopropyl-1H-pyrazol-5-yl)methanesulfonamide An 8-mL round-bottom flask was charged with ((2S)-6-(5-amino-1-cyclopropyl-1H-pyrazol-4-yl)-5-cyclobutoxy-2-methyl-3,4-dihydroquinolin-1(2H)-yl)(cyclopropyl)methanone (0.020 g, 0.05 mmol), 1,4-dioxane (1 mL) and 4 M aqueous sodium hydroxide solution (1 mL). Methanesulfonyl chloride (0.028 g, 0.019 mL, 0.24 mmol) was added, and the resulting solution stirred overnight at room temperature. The pH of the reaction mixture was adjusted to 7 with 1 N aqueous HCl solution, and the mixture was extracted with ethyl acetate (3×5 mL). The combined organic layers were dried over anhydrous sodium sulfate, filtered, and concentrated under vacuum. The residue was purified by preparative-HPLC with the following conditions (Waters I): Column, SunFire Prep C18, 5 um, 19×100 mm; mobile phase, Water (0.05% ammonium bicarbonate) and acetonitrile (20% to 80% acetonitrile in 10 min, flow rate: 20 mL/min); Detector, UV 220&254 nm. This afforded N-(4-((2S)-5-cyclobutoxy-1-(cyclopropanecarbonyl)-2-methyl-1,2,3,4-tetrahydroquinolin-6-yl)-1-cyclopropyl-1H-pyrazol-5-yl)methanesulfonamide (0.010 g, 42%) as yellow oil. ¹H NMR (300 MHz, CD₃OD) δ ppm 0.63-0.75 (m, 1H), 0.80-1.00 (m, 2H), 1.00-1.18 (m, 8H), 1.25-1.34 (m, 2H), 1.51-1.68 (m, 1H), 1.85-2.11 (m, 5H), 2.25-2.42 (m, 2H), 2.99-3.08 (m, 1H), 3.13 (s, 3H), 3.65-3.75 (m, 1H), 3.96-4.17 (m, 1H), 4.66-4.74 (m, 1H), 7.15 (d, J=8.10 Hz, 1H), 7.38 (d, J=8.40 Hz, 1H), 7.82 (s, 1H). MS (ESI, pos. ion) m/z 485 [M+H]+.

Example 75

N-(4-((2S)-5-cyclobutoxy-1-(cyclopropanecarbonyl)-2-methyl-1,2,3,4-tetrahydroquinolin-6-yl)-1-cyclopropyl-1H-pyrazol-5-yl)acetamide (I-301)

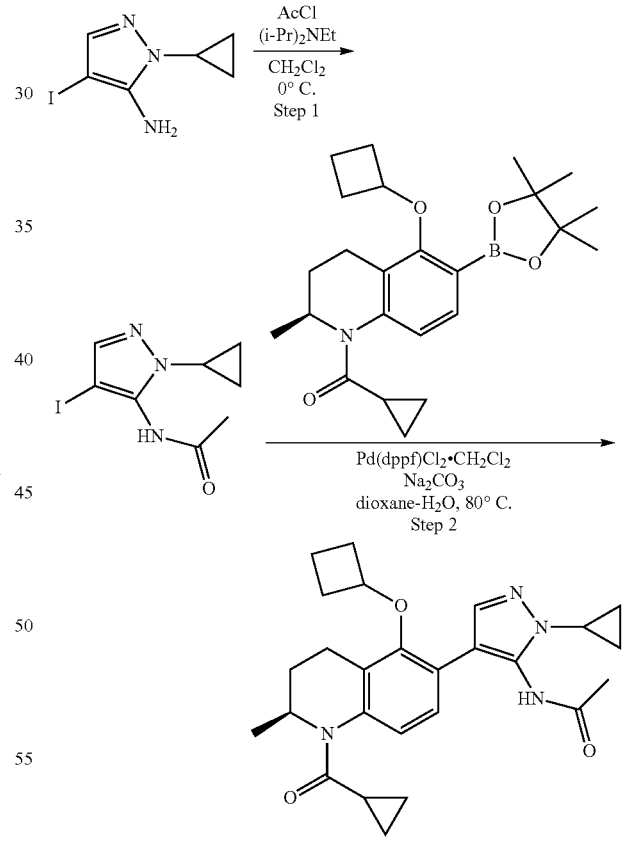

Step 1. N-(1-cyclopropyl-4-iodo-1H-pyrazol-5-yl)acetamide

A 100-mL round-bottom flask was charged with 1-cyclopropyl-4-iodo-1H-pyrazol-5-amine (0.250 g, 1.00 mmol), N,N-diisopropylamine (0.52 mL, 2.99 mmol) and dichloromethane (8 mL), and the solution was cooled to 0° C. A solution of acetyl chloride (0.085 mL, 1.19 mmol) in dichloromethane (2 mL) was added dropwise, and the resulting solution stirred for 1 h at 0° C. The reaction mixture was concentrated under vacuum, and the residue was purified via column chromatography on silica gel (gradient elution with 0.5-50% ethyl acetate/petroleum ether) to afford N-(1-cyclopropyl-4-iodo-1H-pyrazol-5-yl)acetamide (0.300 g, 92%) as yellow oil. MS (ESI, pos. ion) m/z 292 [M+H]+.

Step 2. N-(4-((2S)-5-cyclobutoxy-1-(cyclopropanecarbonyl)-2-methyl-1,2,3,4-tetrahydroquinolin-6-yl)-1-cyclopropyl-1H-pyrazol-5-yl)acetamide A 25-mL round-bottom flask was charged with N-(1-cyclopropyl-4-iodo-1H-pyrazol-5-yl)acetamide (0.067 g, 0.23 mmol), (S)-(5-cyclobutoxy-2-methyl-6-(4,4,5,5-tetramethyl-1,3,2-dioxaborolan-2-yl)-3,4-dihydroquinolin-1(2H)-yl)(cyclopropyl)methanone (0.103 g, 0.25 mmol), [1,1'-bis(diphenylphosphino)ferrocene]dichloropalladium(II) dichloromethane adduct (0.019 mg, 0.02 mmol), sodium carbonate (0.048 g, 0.45 mmol), 1,4-dioxane (10 mL) and water (3 mL). The resulting mixture stirred for 18 h at 80° C. and was cooled to room temperature. The reaction mixture was filtered through a short pad of Celite, and the filtrate was concentrated under vacuum. The residue was purified via column chromatography on silica gel (gradient elution with 0.5-50% ethyl acetate/petroleum ether). The product was further purified by preparative-HPLC with the following conditions (Waters I): Column, XBridge RP C18 OBD Column, 5 um, 19×150 mm; mobile phase, water (0.03% aqueous ammonia) and acetonitrile (16% to 34% acetonitrile in 10 min, flow rate: 20 mL/min); Detector, UV254&220 nm. This resulted in 23 mg (22%) of N-(4425)-5-cyclobutoxy-1-(cyclopropanecarbonyl)-2-methyl-1,2,3,4-tetrahydroquinolin-6-yl)-1-cyclopropyl-1H-pyrazol-5-yl)acetamide as a white solid. 1H NMR (400 MHz, CD3OD) δ ppm 0.68-0.80 (m, 1H), 0.91-0.99 (m, 2H), 1.06-1.19 (m, 8H), 1.28-1.45 (m, 3H), 1.55-1.68 (m, 1H), 1.90-2.11 (m, 8H), 2.29-2.48 (m, 2H), 2.94-3.15 (m, 1H), 3.62-3.78 (m, 1H), 4.00-4.20 (m, 1H), 4.67-4.83 (m, 1H), 7.14 (d, J=8.00 Hz, 1H), 7.21 (d, J=8.40 Hz, 1H), 7.83 (s, 1H). MS (ESI, pos. ion) m/z 449 [M+H]+.

Example 76

(S)-methyl 5-cyclobutoxy-6-(1-(3-hydroxycyclobutyl)-1H-pyrazol-4-yl)-2-methyl-3,4-dihydroquinoline-1(2H)-carboxylate (I-302)

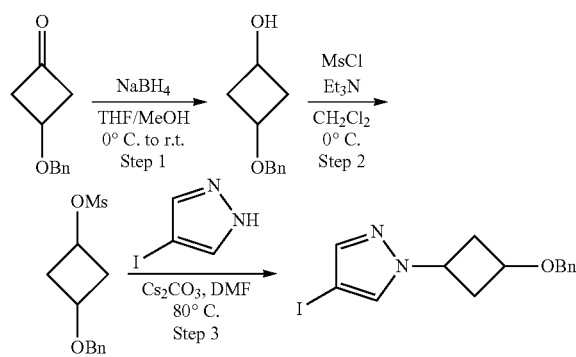

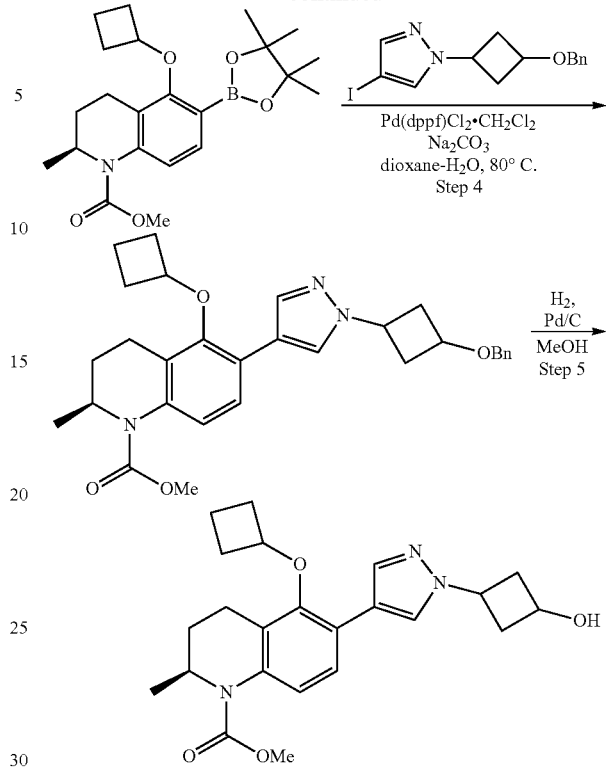

Step 1. 3-(benzyloxy)cyclobutanol

A 100-mL round-bottom flask was charged with 3-(benzyloxy)cyclobutanone (2.00 g, 11.4 mmol), tetrahydrofuran (20 mL), and methanol (1 mL), and the solution was cooled to 0° C. Sodium borohydride (0.475 g, 12.5 mmol) was added portionwise, and the resulting mixture stirred for 30 min at room temperature. The reaction mixture was poured into water (30 mL), and extracted with ethyl acetate (2×30 mL). The combined organic layers were dried over anhydrous sodium sulfate, filtered, and concentrated to afford 3-(benzyloxy)cyclobutanol (1.83 g, 90%) as yellow oil. MS (ESI, pos. ion) m/z 179 [M+H]+.

Step 2. 3-(benzyloxy)cyclobutyl methanesulfonate

A 100-mL round-bottom flask was charged with 3-(benzyloxy)cyclobutanol (1.83 g, 10.3 mmol), dichloromethane (20 mL) and triethylamine (2.15 mL, 15.4 mmol), and the solution was cooled to 0° C. Methanesulfonyl chloride (1.20 mL, 1.77 g, 15.4 mmol) was added dropwise, and the resulting solution stirred for 30 min at 0° C. The reaction mixture was poured into water (30 mL) and extracted with dichloromethane (2×30 mL). The combined organic layers were dried over anhydrous sodium sulfate, filtered, and concentrated to afford 3-(benzyloxy)cyclobutyl methanesulfonate (2.60 g, 99%) as a light yellow solid. MS (ESI, pos. ion) m/z 257 [M+H]+.

Step 3. 1-(3-(benzyloxy)cyclobutyl)-4-iodo-1H-pyrazole

A 250-mL round-bottom flask was charged with 4-iodo-1H-pyrazole (1.97 g, 10.2 mmol), N,N-dimethylformamide (20 mL), 3-(benzyloxy)cyclobutyl methanesulfonate (2.60 g, 10.2 mmol) and cesium carbonate (9.75 g, 29.9 mmol), and the resulting mixture stirred overnight at 80° C. The reaction mixture was cooled to room temperature, poured into water (50 mL), and extracted with ethyl acetate (3×50 mL). The combined organic layers were washed with brine (50 mL), dried over anhydrous sodium sulfate, filtered, and concentrated to afford 1-(3-(benzyloxy)cyclobutyl)-4-iodo-1H-pyrazole (3.00 g, 83%) as yellow oil. MS (ESI, pos. ion) m/z 355 [M+H]⁺.

Step 4. (S)-methyl 6-(1-(3-(benzyloxy)cyclobutyl)-1H-pyrazol-4-yl)-5-cyclobutoxy-2-methyl-3,4-dihydroquinoline-1(2H)-carboxylate A 25-mL round-bottom flask was charged with (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.100 g, 0.25 mmol), 1-(3-(benzyloxy)cyclobutyl)-4-iodo-1H-pyrazole (0.106 g, 0.30 mmol), [1,1'-bis(diphenylphosphino)ferrocene]dichloropalladium(II) dichloromethane adduct (0.020 g, 0.02 mmol), sodium carbonate (0.053 g, 0.50 mmol), 1,4-dioxane (10 mL) and water (3 mL). The resulting mixture was stirred overnight at 80° C., and then cooled to room temperature. The reaction mixture was diluted with ethyl acetate (20 mL), washed with water (10 mL) and brine (10 mL), dried over anhydrous sodium sulfate, filtered, and concentrated under vacuum. The residue was purified via column chromatography on silica gel (gradient elution with 1-10% ethyl acetate/petroleum ether) to afford (S)-methyl 6-(1-(3-(benzyloxy)cyclobutyl)-1H-pyrazol-4-yl)-5-cyclobutoxy-2-methyl-3,4-dihydroquinoline-1(2H)-carboxylate (0.060 g, 48%) as a yellow solid. MS (ESI, pos. ion) m/z 502 [M+H]⁺.

Step 5. (S)-methyl 5-cyclobutoxy-6-(1-(3-hydroxycyclobutyl)-1H-pyrazol-4-yl)-2-methyl-3,4-dihydroquinoline-1(2H)-carboxylate Palladium on carbon (10 wt %, 0.060 g) was added to a solution of (S)-methyl 6-(1-(3-(benzyloxy)cyclobutyl)-1H-pyrazol-4-yl)-5-cyclobutoxy-2-methyl-3,4-dihydroquinoline-1(2H)-carboxylate (0.060 g, 0.12 mmol) in methanol (10 mL), and the resulting mixture stirred at room temperature under an atmosphere of hydrogen for 16 h. The reaction mixture was filtered, and the filtrate was concentrated under vacuum. The residue was purified by preparative-HPLC with the following conditions (Waters I): Column, XBridge Prep Shield RP18 OBD Column, 19×150 mm, 5 um; mobile phase, Water (0.05% ammonium bicarbonate) and acetonitrile (30% to 50% acetonitrile in 10 min, flow rate: 20 mL/min); Detector, UV254&220 nm. This afforded (S)-methyl 5-cyclobutoxy-6-(1-(3-hydroxycyclobutyl)-1H-pyrazol-4-yl)-2-methyl-3,4-dihydroquinoline-1(2H)-carboxylate (0.031 g, 63%) as a white solid. ¹H NMR (300 MHz, CD₃OD) δ ppm 1.16 (d, J=6.30 Hz, 3H), 1.32-1.51 (m, 2H), 1.55-1.68 (m, 1H), 2.00-2.33 (m, 5H), 2.33-2.58 (m, 3H), 2.76-2.84 (m, 2H), 2.93-3.01 (m, 1H), 3.77 (s, 3H), 4.12-4.19 (m, 1H), 4.51-4.64 (m, 2H), 4.99-5.08 (m, 1H), 7.24-7.35 (m, 2H), 7.86 (s, 1H), 8.04 (s, 1H). MS (ESI, pos. ion) m/z 412 [M+H]⁺.

Example 77 methyl (S)-5-cyclobutoxy-2-methyl-6-(2-(piperidin-4-yl)-1H-imidazol-4-yl)-3,4-dihydroquinoline-1(2H)-carboxylate (I-303)

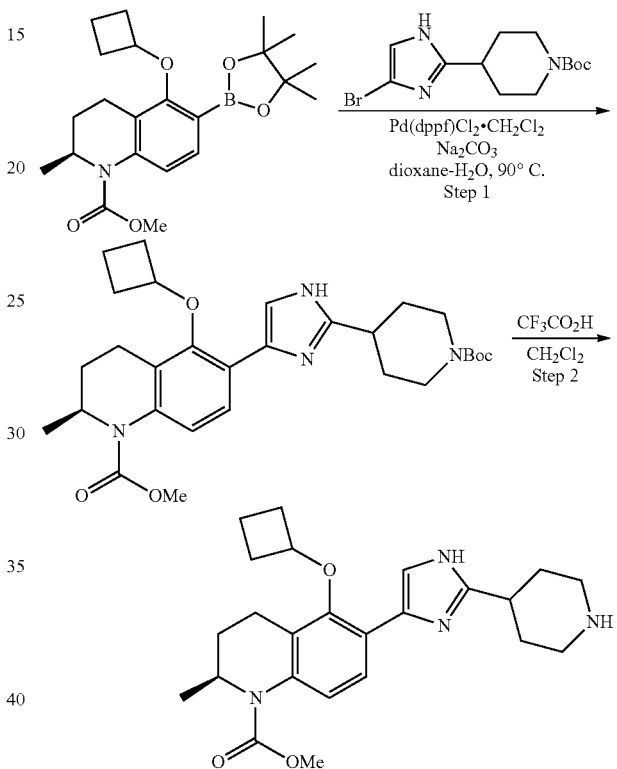

Step 1. (S)-methyl 6-(2-(1-(tert-butoxycarbonyl)piperidin-4-yl)-1H-imidazol-4-yl)-5-cyclobutoxy-2-methyl-3,4-dihydroquinoline-1(2H)-carboxylate A mixture of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.080 g, 0.20 mmol), tert-butyl 4-(4-bromo-1H-imidazol-2-yl)piperidine-1-carboxylate (0.200 g, 0.61 mmol), sodium carbonate (0.45 g, 0.42 mmol), and [1,1'-bis(diphenylphosphino)ferrocene]dichloropalladium (II) dichloromethane adduct (0.010 g, 0.01 mmol) in 1,4-dioxane (10 mL) and water (3 mL) was stirred at 90° C. overnight. The reaction mixture was cooled to room temperature, filtered through a short pad of Celite, and concentrated under vacuum. The residue was purified via preparative thin layer chromatography (eluting with 1:1, ethyl acetate/petroleum ether) to afford (S)-methyl 6-(2-(1-(tert-butoxycarbonyl)piperidin-4-yl)-1H-imidazol-4-yl)-5-cyclobutoxy-2-methyl-3,4-dihydroquinoline-1(2H)-carboxylate (0.050 g, 48%) as a light yellow solid. MS (ESI, pos. ion) m/z 525 [M+H]⁺.

Step 2. methyl (S)-5-cyclobutoxy-2-methyl-6-(2-(piperidin-4-yl)-1H-imidazol-4-yl)-3,4-dihydro-quinoline-1(2H)-carboxylate Trifluoroacetic acid (3 mL) was added to a solution of (S)-methyl 6-(2-(1-(tert-butoxycarbonyl)piperidin-4-yl)-1H-imidazol-4-yl)-5-cyclobutoxy-2-methyl-3,4-dihydroquinoline-1(2H)-carboxylate (0.050 g, 0.09 mmol) in dichloromethane (6 mL), and the reaction mixture stirred at room temperature for 3 h. The reaction mixture was concentrated under vacuum, and the residue was purified via preparative-HPLC (Waters I): Column: Waters HSS C18, 2.1×50 mm, 1.8 um; Mobile Phase water (0.05% ammonium bicarbonate) and acetonitrile (5% to 95% acetonitrile in 10 min, flow rate: 20 mL/min); Detector: UV254&220 nm. This afforded methyl (S)-5-cyclobutoxy-2-methyl-6-(2-(piperidin-4-yl)-1H-imidazol-4-yl)-3,4-dihydroquinoline-1(2H)-carboxylate (0.0039 g, 10%) as an off-white solid. $^1$H NMR (300 MHz, CD$_3$OD) δ ppm 1.15-1.26 (m, 2H), 1.32-1.68 (m, 3H), 1.95-2.55 (m, 8H), 2.97-3.19 (m, 3H), 3.40-3.47 (m, 2H), 3.77-3.82 (m, 2H), 4.13-4.25 (m, 1H), 4.51-4.71 (m, 3H), 7.28-7.47 (m, 2H), 8.55-8.61 (m, 1H). MS (ESI, pos. ion) m/z 425 [M+H]$^+$.

The following example was made according to the procedure described above for Example 77:

methyl (S)-5-cyclobutoxy-2-methyl-6-(1-methyl-2-(piperidin-4-yl)-1H-imidazol-4-yl)-3,4-dihydro-quinoline-1(2H)-carboxylate (I-304)

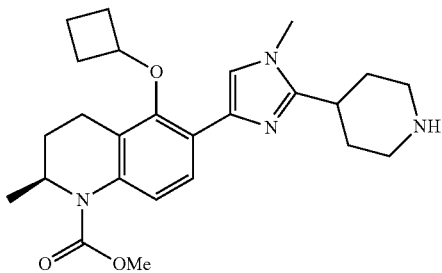 [SMILES: COC(=O)N1c2ccc(-c3cn(C)c(C4CCNCC4)n3)c(OC3CCC3)c2CC[C@@H]1C]

$^1$H NMR (300 MHz, CD$_3$OD) δ ppm 1.17 (d, J=6.30 Hz, 3H), 1.25-1.33 (m, 1H), 1.85-1.99 (m, 8H), 2.18-2.27 (m, 1H), 2.50-2.61 (m, 1H), 2.81-2.95 (m, 3H), 3.01-3.15 (m, 1H), 3.21-3.26 (m, 2H), 3.47 (s, 3H), 3.79 (s, 3H), 3.93-3.99 (m, 1H), 6.86 (s, 1H), 7.08 (d, J=8.70 Hz, 1H), 7.37 (d, J=8.70 Hz, 1H). MS (ESI, pos. ion) m/z 439 [M+H]$^+$.

(S)-(5-cyclobutoxy-2-methyl-6-(1-(piperidin-4-yl)-1H-pyrazol-3-yl)-3,4-dihydroquinolin-1(2H)-yl)(cyclopropyl)methanone (I-305)

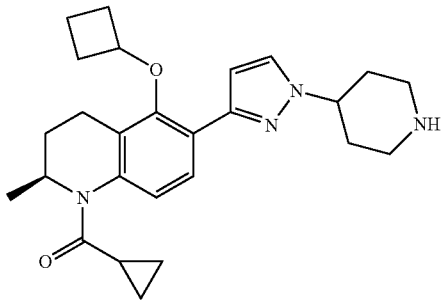 [SMILES: C[C@H]1CCc2c(ccc(-c3ccn(C4CCNCC4)n3)c2OC2CCC2)N1C(=O)C1CC1]

$^1$H NMR (400 MHz, DMSO-d$_6$) δ ppm 0.63-0.68 (m, 1H), 0.75-0.80 (m, 1H), 0.80-0.85 (m, 1H), 0.95-1.01 (m, 1H), 1.05 (d, J=6.40 Hz, 3H), 1.22-1.35 (m, 2H), 1.52-1.61 (m, 1H), 1.75-1.87 (m, 3H), 1.93-2.12 (m, 5H), 2.27-2.33 (m, 2H), 2.55-2.61 (m, 2H), 2.89-2.95 (m, 1H), 3.01-3.07 (m, 2H), 4.15-4.28 (m, 2H), 4.59-4.68 (m, 1H), 6.64 (s, 1H), 7.13 (d, J=8.40 Hz, 1H), 7.64 (d, J=8.40 Hz, 1H), 7.79 (s, 1H). MS (ESI, pos. ion) m/z 435 [M+H]$^+$.

(2S)-5-cyclobutoxy-2-methyl-6-(1-(piperidin-4-yl)-1H-pyrazol-5-yl)-3,4-dihydroquinolin-1(2H)-yl)(cyclopropyl)methanone (I-306)

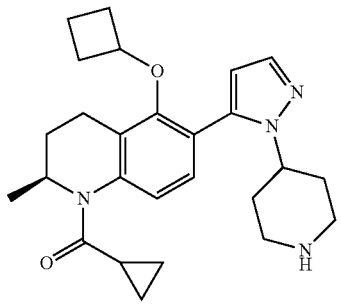 [SMILES: C[C@H]1CCc2c(ccc(-c3ccnn3C3CCNCC3)c2OC2CCC2)N1C(=O)C1CC1]

$^1$H NMR (400 MHz, DMSO-d$_6$) δ ppm 0.67-0.75 (m, 1H), 0.75-0.85 (m, 1H), 0.85-0.89 (m, 1H), 0.99-1.05 (m, 1H), 1.07 (d, J=6.40 Hz, 3H), 1.17-1.23 (m, 1H), 1.41-1.51 (m, 2H), 1.67-1.78 (m, 3H), 1.78-1.99 (m, 6H), 2.22-2.29 (m, 1H), 2.31-2.49 (m, 3H), 2.83-2.91 (m, 1H), 2.92-3.01 (m, 2H), 3.85-3.96 (m, 2H), 4.86-4.78 (m, 1H), 6.24 (s, 1H), 7.11

(d, J=8.40 Hz, 1H), 7.23 (d, J=8.40 Hz, 1H), 7.53 (s, 1H). MS (ESI, pos. ion) m/z 435 [M+H]+.

(S)-cyclopropyl(2-methyl-5-phenoxy-6-(1-(piperidin-4-yl)-1H-pyrazol-3-yl)-3,4-dihydroquinolin-1(2H)-yl)methanone (I-307)

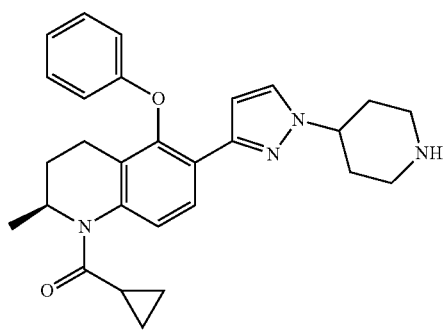 [SMILES: C[C@H]1CCc2c(ccc(-c3ccn(C4CCNCC4)n3)c2Oc2ccccc2)N1C(=O)C1CC1]

¹H NMR (400 MHz, DMSO-d₆) δ ppm 0.68-0.75 (m, 1H), 0.81-0.89 (m, 1H), 0.90-0.97 (m, 1H), 1.01-1.08 (m, 4H), 1.31-1.42 (m, 1H), 1.69-1.79 (m, 2H), 1.81-1.98 (m, 3H), 2.05-2.15 (m, 1H), 2.21-2.32 (m, 1H), 2.51-2.60 (m, 3H), 2.99-3.05 (m, 2H), 4.11-4.19 (m, 1H), 4.65-4.77 (m, 1H), 6.42 (s, 1H), 6.76-6.82 (m, 2H), 6.96-7.01 (m, 1H), 7.28-7.33 (m, 2H), 7.36-7.41 (m, 1H), 7.66 (s, 1H), 7.93 (m, 1H). MS (ESI, pos. ion) m/z 457 [M+H]+.

cyclopropyl((2S)-2-methyl-5-phenoxy-6-(1-(piperidin-4-yl)-1H-pyrazol-5-yl)-3,4-dihydroquinolin-1(2H)-yl)methanone (I-308)

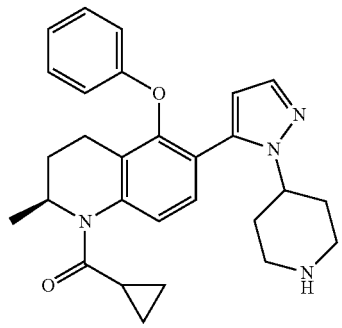 [SMILES: C[C@H]1CCc2c(ccc(-c3ccnn3C3CCNCC3)c2Oc2ccccc2)N1C(=O)C1CC1]

¹H NMR (400 MHz, DMSO-d₆) δ ppm 0.72-0.88 (m, 2H), 0.90-0.97 (m, 1H), 1.01-1.08 (m, 4H), 1.45-1.51 (m, 2H), 1.55-1.62 (m, 1H), 1.77-1.95 (m, 2H), 1.97-2.03 (m, 1H), 2.05-2.14 (m, 1H), 2.32-2.41 (m, 3H), 2.53-2.59 (m, 1H), 2.91-2.99 (m, 2H), 3.89-3.95 (m, 1H), 4.73-4.81 (m, 1H), 6.08 (s, 1H), 6.62-6.67 (m, 2H), 6.91-6.96 (m, 1H), 7.20-7.40 (m, 3H), 7.36 (s, 1H), 7.47 (m, 1H). MS (ESI, pos. ion) m/z 457 [M+H]+.

(S)-(5-cyclobutoxy-2-methyl-6-(2-(piperidin-4-yl)-2H-1,2,3-triazol-4-yl)-3,4-dihydroquinolin-1(2H)-yl)(cyclopropyl)methanone (3929975) (I-309)

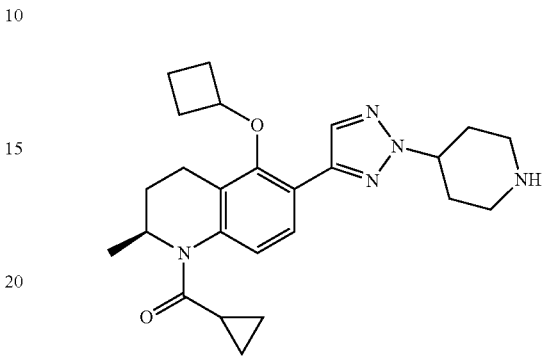

¹H NMR (300 MHz, CD₃OD) δ ppm 0.68-0.77 (m, 1H), 0.89-0.99 (m, 2H), 1.13 (d, J=6.60 Hz, 4H), 1.25-1.42 (m, 2H), 1.61-1.72 (m, 1H), 1.85-1.96 (m, 1H), 2.05-2.26 (m, 9H), 2.29-2.56 (m, 2H), 2.75-2.88 (m, 2H), 3.02-3.11 (m, 1H), 3.19-3.28 (m, 2H), 4.17-4.19 (m, 1H), 4.63-4.74 (m, 2H), 7.22 (d, J=8.40 Hz, 1H), 7.72 (d, J=8.40 Hz, 1H), 8.05 (s, 1H). MS (ESI, pos. ion) m/z 436 [M+H]+. Triazole regiochemistry tentatively assigned.

(S)-(5-cyclobutoxy-2-methyl-6-(1-(piperidin-4-yl)-1H-1,2,3-triazol-4-yl)-3,4-dihydroquinolin-1(2H)-yl)(cyclopropyl)methanone (I-310)

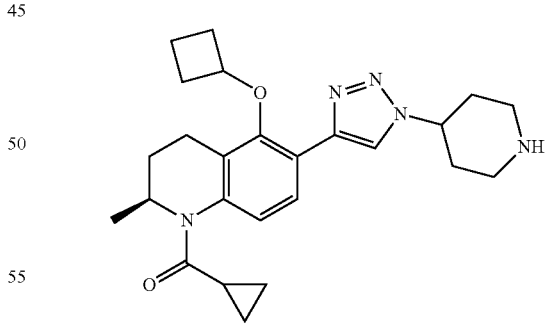

¹H NMR (300 MHz, CD₃OD) δ ppm 0.68-0.77 (m, 1H), 0.89-0.99 (m, 2H), 1.13 (d, J=6.60 Hz, 4H), 1.25-1.47 (m, 2H), 1.61-1.69 (m, 1H), 1.85-1.96 (m, 1H), 2.05-2.48 (m, 10H), 2.82-3.11 (m, 3H), 3.23-3.28 (m, 2H), 4.17-4.26 (m, 1H), 4.70-4.81 (m, 2H), 7.25 (d, J=8.40 Hz, 1H), 7.82 (d, J=8.40 Hz, 1H), 8.35 (s, 1H). MS (ESI, pos. ion) m/z 436 [M+H]⁺. Triazole regiochemistry tentatively assigned.

(S)-cyclopropyl(2-methyl-5-phenoxy-6-(2-(piperidin-4-yl)-2H-1,2,3-triazol-4-yl)-3,4-dihydroquinolin-1(2H)-yl)methanone (I-311)

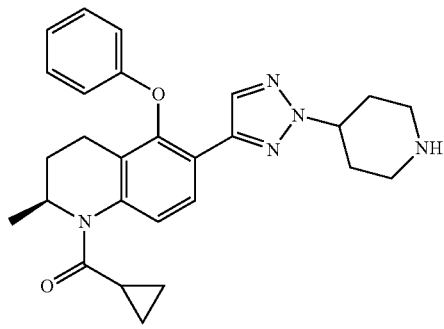 [SMILES: C[C@H]1CCc2c(ccc(-c3cnn(C4CCNCC4)n3)c2Oc2ccccc2)N1C(=O)C1CC1]

¹H NMR (300 MHz, CD₃OD) δ ppm 0.75-0.87 (m, 1H), 0.90-1.07 (m, 2H), 1.12-1.23 (m, 4H), 1.31-1.49 (m, 1H), 1.95-2.40 (m, 7H), 2.69-2.83 (m, 3H), 3.11-3.19 (m, 2H), 3.34 (s, 1H), 4.53-4.66 (m, 1H), 4.80-4.85 (m, 1H), 6.78-6.83 (m, 2H), 6.95-7.03 (m, 1H), 7.24-7.30 (m, 2H), 7.43-7.59 (m, 1H), 7.78 (s, 1H), 7.98 (d, J=8.40 Hz, 1H). MS (ESI, pos. ion) m/z 458 [M+H]⁺. Triazole regiochemistry tentatively assigned.

(S)-cyclopropyl(2-methyl-5-phenoxy-6-(1-(piperidin-4-yl)-1H-1,2,3-triazol-4-yl)-3,4-dihydroquinolin-1(2H)-yl)methanone (I-312)

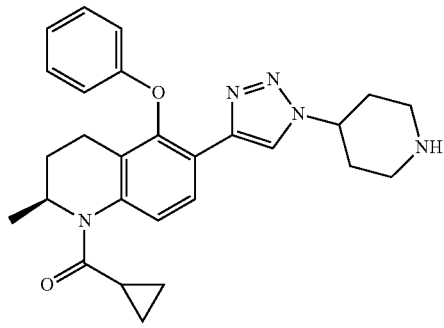 [SMILES: C[C@H]1CCc2c(ccc(-c3cn(C4CCNCC4)nn3)c2Oc2ccccc2)N1C(=O)C1CC1]

¹H NMR (300 MHz, CD₃OD) δ ppm 0.73-0.83 (m, 1H), 0.90-1.05 (m, 2H), 1.11-1.22 (m, 4H), 1.35-1.47 (m, 1H), 1.83-2.10 (m, 5H), 2.17-2.41 (m, 2H), 2.69-2.80 (m, 3H), 3.10-3.20 (m, 2H), 4.51-4.62 (m, 1H), 4.75-4.83 (m, 1H), 6.78-6.82 (m, 2H), 6.93-7.01 (m, 1H), 7.23-7.30 (m, 2H), 7.45-7.51 (m, 1H), 8.04-8.09 (m, 2H). MS (ESI, pos. ion) m/z 458 [M+H]⁺. Triazole regiochemistry tentatively assigned.

(S)-methyl 6-(2-(azetidin-3-yl)thiazol-4-yl)-5-cyclobutoxy-2-methyl-3,4-dihydroquinoline-1(2H)-carboxylate (I-313)

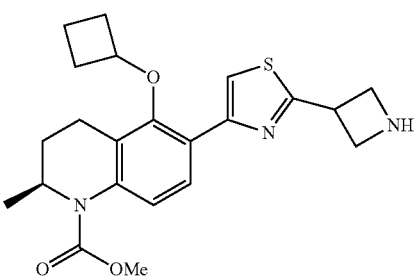 [SMILES: COC(=O)N1c2ccc(-c3csc(C4CNC4)n3)c(OC3CCC3)c2CC[C@@H]1C]

¹H NMR (300 MHz, CD₃OD) δ ppm 1.13-1.21 (m, 3H), 1.23-1.41 (m, 1H), 1.45-1.64 (m, 2H), 1.95-2.14 (m, 4H), 2.18-2.31 (m, 1H), 2.45-4.53 (m, 1H), 2.91-3.02 (m, 1H), 3.78 (s, 3H), 4.01-4.19 (m, 5H), 4.33-4.48 (m, 1H), 4.51-4.65 (m, 1H), 7.34 (d, J=8.70 Hz, 1H), 7.69 (d, J=8.40 Hz, 1H), 7.76 (s, 1H). MS (ESI, pos. ion) m/z 414 [M+H]⁺.

(S)-methyl-5-cyclobutoxy-6-(2-(3-hydroxyazetidin-3-yl)thiazol-4-yl)-2-methyl-3,4-dihydroquinoline-1(2H)-carboxylate (I-314)

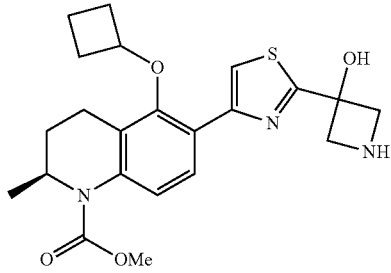 [SMILES: COC(=O)N1c2ccc(-c3csc(C4(O)CNC4)n3)c(OC3CCC3)c2CC[C@@H]1C]

¹H NMR (400 MHz, CD₃OD) δ ppm 1.08 (d, J=6.40 Hz, 3H), 1.16-1.25 (m, 1H), 1.33-1.45 (m, 1H), 1.46-1.52 (m, 1H), 1.90-2.09 (m, 4H), 2.12-2.21 (m, 1H), 2.35-2.42 (m, 1H), 2.83-2.92 (m, 1H), 3.68 (s, 3H), 3.76-3.78 (m, 2H), 3.80-3.86 (m, 1H), 4.03-4.12 (m, 3H), 4.45-4.51 (m, 1H), 7.24-7.27 (m, 1H), 7.67-7.73 (m, 2H). MS (ESI, pos. ion) m/z 430 [M+H]⁺.

Example 78

(S)-methyl 5-cyclobutoxy-2-methyl-6-(1-methyl-2-(piperazin-1-yl)-1H-imidazol-4-yl)-3,4-dihydroquinoline-1(2H)-carboxylate (I-315)

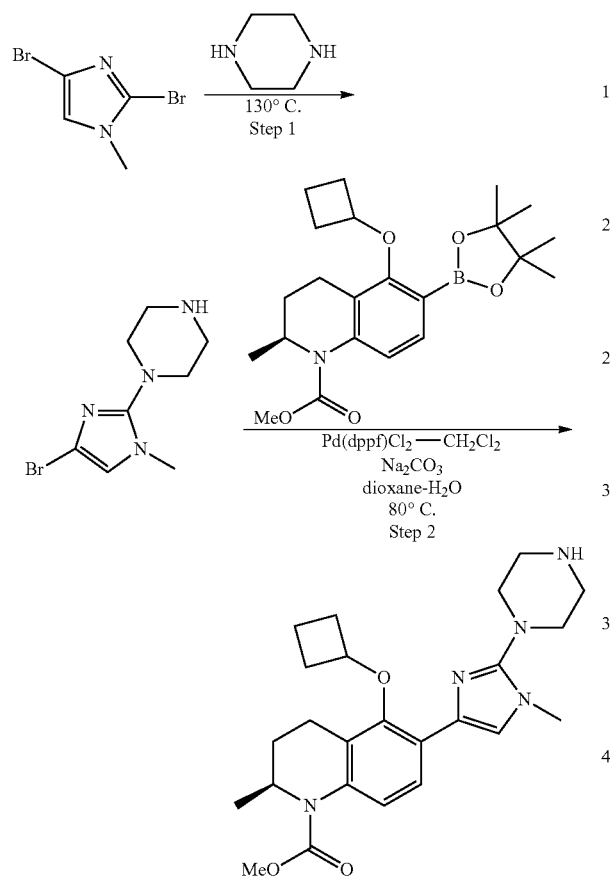

Step 1.
1-(4-bromo-1-methyl-1H-imidazol-2-yl)piperazine

A 20-mL resealable tube was charged with 2,4-dibromo-1-methyl-1H-imidazole (0.480 g, 2.00 mmol) and piperazine (3.4 g, 39.5 mmol), and the resulting mixture was stirred for 3 h at 130° C. The reaction mixture was cooled to room temperature, diluted with dichloromethane (20 mL), washed with water (2×10 mL), dried over anhydrous sodium sulfate, filtered, and concentrated under vacuum. The residue was purified via column chromatography on silica gel (eluting with 10:1, dichloromethane/methanol) to afford 1-(4-bromo-1-methyl-1H-imidazol-2-yl)piperazine (0.300 g, 61%) as a light yellow solid. MS (ESI, pos. ion) m/z 245, 247 [M+H]⁺.

Step 2. (S)-methyl 5-cyclobutoxy-2-methyl-6-(4,4,5,5-tetramethyl-1,3,2-dioxaborolan-2-yl)-3,4-dihydroquinoline-1(2H)-carboxylate A 100-mL round-bottom flask was charged with (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.580 g, 1.47 mmol), 1-(4-bromo-1-methyl-1H-imidazol-2-yl)piperazine (0.300 g, 1.22 mmol), [1,1'-bis(diphenylphosphino)ferrocene]dichloropalladium(II) dichloromethane adduct (0.100 g, 0.12 mmol), sodium carbonate (0.260 g, 2.45 mmol), 1,4-dioxane (9 mL) and water (3 mL). The resulting mixture stirred for 18 h at 80° C. The reaction mixture was cooled to room temperature, filtered through a short pad of Celite, and the filtrate was concentrated under vacuum. The residue was purified via column chromatography on silica gel (eluting with 10:1, dichloromethane/methanol). The product was further purified by Prep-HPLC with the following conditions (Waters I): Column, XBridge Prep C18 OBD Column, 5 um, 19×150 mm; mobile phase, water (0.03% aqueous ammonia) and acetonitrile (16.0% to 34.0% acetonitrile in 10 min, flow rate: 20 mL/min); Detector, UV 220&254 nm. This afforded (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.015 g, 6%) as a light yellow solid. ¹H NMR (400 MHz, CD₃OD) δ ppm 1.17 (d, J=4.80 Hz, 3H), 1.25-1.33 (m, 1H), 1.34-1.49 (m, 2H), 1.57-1.68 (m, 1H), 2.03-2.28 (m, 5H), 2.39-2.49 (m, 1H), 2.93-2.99 (m, 1H), 2.99-3.02 (m, 4H), 3.09-3.13 (m, 4H), 3.59 (s, 3H), 3.77 (s, 3H), 4.18-4.23 (m, 1H), 4.51-4.53 (m, 1H), 7.18-7.29 (m, 2H), 7.53-7.57 (m, 1H). MS (ESI, pos. ion) m/z 440 [M+H]⁺.

Example 79

(S)-methyl 5-cyclobutoxy-2-methyl-6-(2-(piperazin-1-yl)thiazol-4-yl)-3,4-dihydroquinoline-1(2H)-carboxylate (I-316)

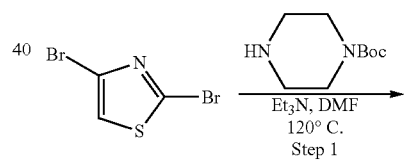

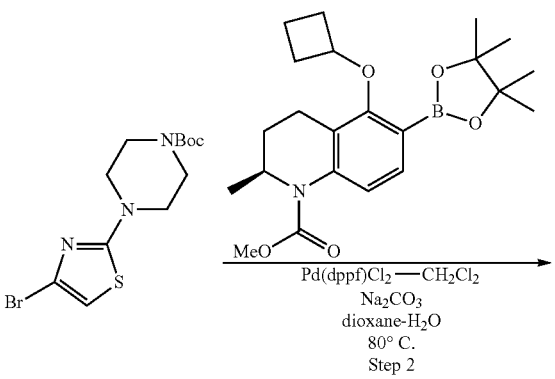

-continued

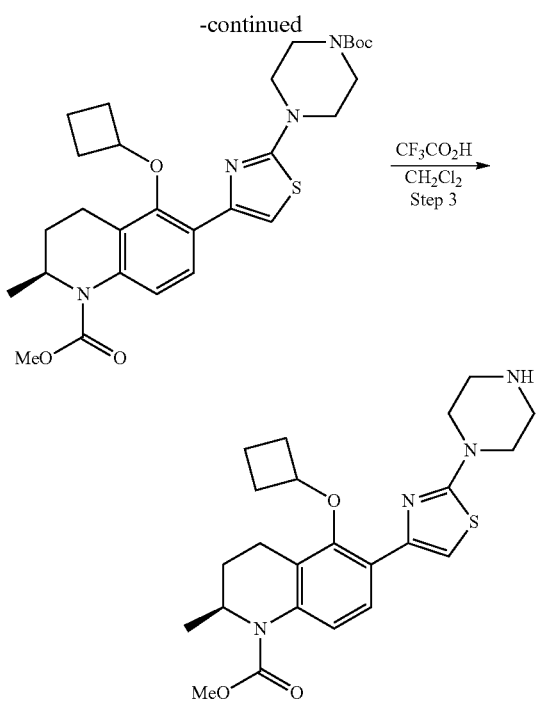

Step 1. tert-butyl 4-(4-bromothiazol-2-yl)piperazine-1-carboxylate

A 100-mL round-bottom flask was charged with 2,4-dibromothiazole (1.00 g, 4.12 mmol), tert-butyl piperazine-1-carboxylate (0.918 g, 4.93 mmol), triethylamine (1.72 mL, 12.35 mmol) and N,N-dimethylformamide (20 mL). The resulting solution stirred for 18 h at 120° C. The reaction mixture was cooled to room temperature, poured into water (50 mL), and extracted with ethyl acetate (3×20 mL). The combined organic layers were dried over anhydrous sodium sulfate, filtered, and concentrated under vacuum. The residue was purified via column chromatography on silica gel (eluting with 10:1, dichloromethane/methanol) to afford tert-butyl 4-(4-bromothiazol-2-yl)piperazine-1-carboxylate (0.350 g, 23%) as brown oil. MS (ESI, pos. ion) m/z 348, 350 [M+H]$^+$.

Step 2. (S)-methyl 6-(2-(4-(tert-butoxycarbonyl)piperazin-1-yl)thiazol-4-yl)-5-cyclobutoxy-2-methyl-3,4-dihydroquinoline-1(2H)-carboxylate A 50-mL round-bottom flask was charged with (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.080 g, 0.20 mmol), tert-butyl 4-(4-bromothiazol-2-yl)piperazine-1-carboxylate (0.083 g, 0.24 mmol), sodium carbonate (0.042 g, 0.40 mmol), [1,1'-bis(diphenylphosphino)ferrocene]dichloropalladium(II) dichloromethane adduct (0.081 g, 0.10 mmol), 1,4-dioxane (10 mL) and water (3 mL). The resulting mixture stirred for 4 h at 80° C. The reaction mixture was cooled to room temperature, filtered through a short pad of Celite, and the filtrate was concentrated under vacuum. The residue was purified via preparative thin layer chromatography (eluting with 10:1, dichloromethane/methanol) to afford (S)-methyl 6-(2-(4-(tert-butoxycarbonyl)piperazin-1-yl)thiazol-4-yl)-5-cyclobutoxy-2-methyl-3,4-dihydroquinoline-1(2H)-carboxylate (0.070 g, 64%) as a light yellow solid. MS (ESI, pos. ion) m/z 543 [M+H]$^+$.

Step 3. (S)-methyl 5-cyclobutoxy-2-methyl-6-(2-(piperazin-1-yl)thiazol-4-yl)-3,4-dihydroquinoline-1(2H)-carboxylate Trifluoroacetic acid (1 mL) was added to a solution of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.070 g, 0.13 mmol) in dichloromethane (3 mL) and the resulting solution stirred for 2 h at room temperature. The reaction solution was concentrated under vacuum, and the residue was purified by preparative-HPLC with the following conditions (Waters 1): Column, SunFire Prep C18, 5 um, 19×100 mm; Mobile phase, water (0.05% ammonium bicarbonate) and acetonitrile (55% to 75% acetonitrile in 7 min, flow rate: 20 mL/min); Detector, UV 220&254 nm. This afforded (S)-methyl 5-cyclobutoxy-2-methyl-6-(2-(piperazin-1-yl)thiazol-4-yl)-3,4-dihydroquinoline-1(2H)-carboxylate (0.010 mg, 9%) as a white solid. $^1$H NMR (300 MHz, DMSO-d$_6$) δ ppm 1.19 (d, J=6.30 Hz, 3H), 1.20-1.45 (m, 3H), 1.45-1.52 (m, 1H), 2.03-2.21 (m, 5H), 2.80-2.86 (m, 4H), 3.33-3.42 (m, 5H), 3.68 (s, 3H), 4.15-4.22 (m, 1H), 4.40-4.50 (m, 1H), 7.15 (s, 1H), 7.27 (d, J=8.70 Hz, 1H), 7.67 (d, J=8.70 Hz, 1H). MS (ESI, pos. ion) m/z 443 [M+H]$^+$.

Example 80

(S)-methyl 5-cyclobutoxy-6-(2-(3-hydroxyazetidin-1-yl)thiazol-4-yl)-2-methyl-3,4-dihydroquinoline-1(2H)-carboxylate (I-317)

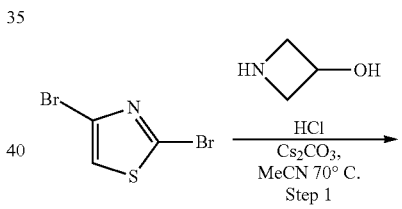

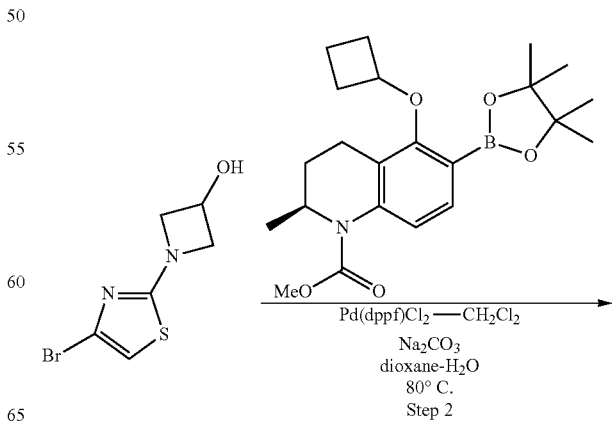

-continued

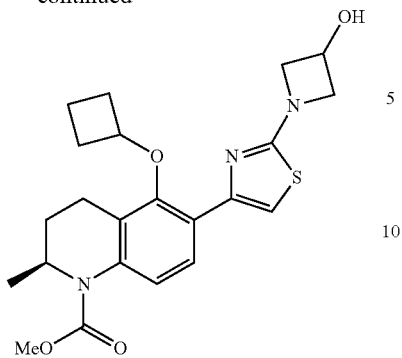

Step 1. 1-(4-bromothiazol-2-yl)azetidin-3-ol

A mixture of 2,4-dibromothiazole (1.00 g, 4.12 mmol), azetidin-3-ol hydrochloride (0.543 g, 4.96 mmol), and cesium carbonate (4.03 g, 12.37 mmol) in acetonitrile (30 mL) was stirred for 18 h at 70° C. The reaction mixture was cooled to room temperature and filtered. The filtrate was concentrated under vacuum, and the residue was purified via column chromatography on silica gel (eluting with 10:1, dichloromethane/methanol) to afford 1-(4-bromothiazol-2-yl)azetidin-3-ol (0.535 g, 53%) as a light yellow solid. MS (ESI, pos. ion) m/z 235, 237 [M+H]$^+$.

Step 2. (S)-methyl 5-cyclobutoxy-6-(2-(3-hydroxyazetidin-1-yl)thiazol-4-yl)-2-methyl-3,4-dihydroquinoline-1(2H)-carboxylate A mixture of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.080 g, 0.20 mmol), 1-(4-bromothiazol-2-yl)azetidin-3-ol (0.056 g, 0.24 mmol), sodium carbonate (0.042 g, 0.40 mmol), and [1,1'-bis(diphenylphosphino)ferrocene]dichloropalladium(II) dichloromethane adduct (0.081 g, 0.10 mmol) in 1,4-dioxane (10 mL) and water (3 mL) was stirred for 4 h at 80° C. The reaction mixture was cooled to room temperature and filtered through a short pad of Celite. The filtrate was concentrated under vacuum, and the residue was purified via column chromatography on silica gel (eluting with 2:1, ethyl acetate/petroleum ether). The product was further purified by preparative-HPLC with the following conditions (Waters I): Column, XBridge Prep C18 OBD Column, 5 um, 19×150 mm; mobile phase, water (0.03% aqueous ammonia) and acetonitrile (16.0 to 34.0% acetonitrile in 10 min, flow rate: 20 mL/min); Detector: UV 254&220 nm. This afforded (S)-methyl 5-cyclobutoxy-6-(2-(3-hydroxyazetidin-1-yl)thiazol-4-yl)-2-methyl-3,4-dihydroquinoline-1(2H)-carboxylate (0.030 g, 34%) as a white solid. $^1$H NMR (400 MHz, CD$_3$OD) δ ppm 1.17 (d, J=6.40 Hz, 3H), 1.32-1.41 (m, 1H), 1.42-1.54 (m, 1H), 1.55-1.67 (m, 1H), 2.04-2.18 (m, 4H), 2.21-2.29 (m, 1H), 2.45-2.55 (m, 1H), 2.91-3.00 (m, 1H), 3.78 (s, 3H), 3.90-3.96 (m, 2H), 4.15-4.21 (m, 1H), 4.32-4.39 (m, 2H), 4.53-4.59 (m, 1H), 4.73-4.80 (m, 1H), 6.99 (s, 1H), 7.28-7.30 (m, 1H), 7.53-7.55 (m, 1H). MS (ESI, pos. ion) m/z 430 [M+H]$^+$.

Example 81

(S)-cyclopropyl(5-(2,5-difluorophenoxy)-2-methyl-6-(1-methyl-1H-1,2,3-triazol-4-yl)-3,4-dihydroquinolin-1(2H)-yl)methanone (I-318) and (S)-cyclopropyl(5-(3,4-difluorophenoxy)-2-methyl-6-(1-methyl-1H-1,2,3-triazol-4-yl)-3,4-dihydroquinolin-1(2H)-yl)methanone (I-319)

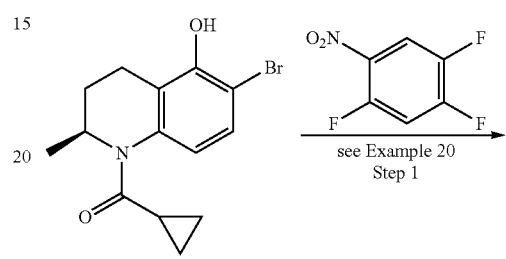

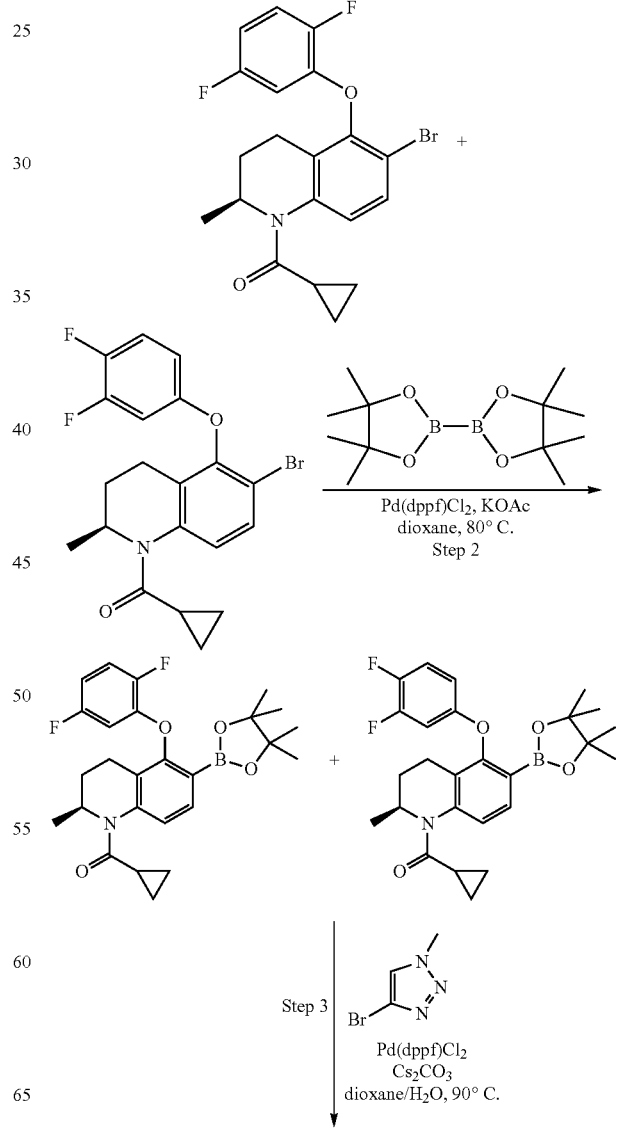

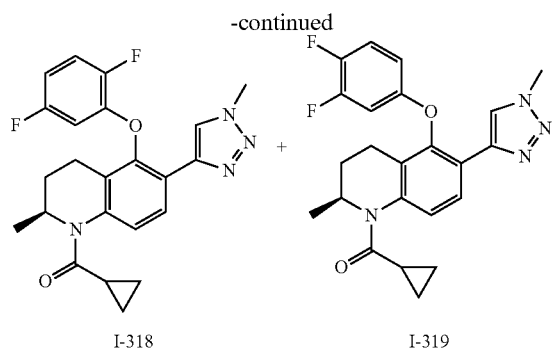

I-318            I-319

Step 1. (S)-(6-Bromo-5-(3,4-difluorophenoxy)-2-methyl-3,4-dihydroquinolin-1(2H)-yl)(cyclopropyl)methanone and (S)-(6-bromo-5-(2,5-difluorophenoxy)-2-methyl-3,4-dihydroquinolin-1(2H)-yl)(cyclopropyl)methanone (S)-(6-Bromo-5-(3,4-difluorophenoxy)-2-methyl-3,4-dihydroquinolin-1(2H)-yl)(cyclopropyl)methanone and (S)-(6-bromo-5-(2,5-difluorophenoxy)-2-methyl-3,4-dihydroquinolin-1(2H)-yl)(cyclopropyl)methanone were prepared from (S)-(6-bromo-5-hydroxy-2-methyl-3,4-dihydroquinolin-1(2H)-yl)(cyclopropyl)methanone and 1,2,4-trifluoro-5-nitrobenzene according to the procedure described above for (S)-(6-bromo-5-(3,4-difluorophenoxy)-2-methyl-3,4-dihydroquinolin-1(2H)-yl)(cyclopropyl)methanone and (S)-(6-bromo-5-(2,5-difluorophenoxy)-2-methyl-3,4-dihydroquinolin-1(2H)-yl)(cyclopropyl)methanone (Example 52, Steps 1-3). MS (ESI, pos. ion) m/z 422, 424 [M+H]$^+$.

Step 2. (S)-cyclopropyl(5-(3,4-difluorophenoxy)-2-methyl-6-(4,4,5,5-tetramethyl-1,3,2-dioxaborolan-2-yl)-3,4-dihydroquinolin-1(2H)-yl)methanone and (S)-cyclopropyl(5-(2,5-difluorophenoxy)-2-methyl-6-(4,4,5,5-tetramethyl-1,3,2-dioxaborolan-2-yl)-3,4-dihydroquinolin-1(2H)-yl)methanone A mixture of (S)-(6-bromo-5-(3,4-difluorophenoxy)-2-methyl-3,4-dihydroquinolin-1(2H)-yl)(cyclopropyl)methanone and (S)-(6-bromo-5-(2,5-difluorophenoxy)-2-methyl-3,4-dihydroquinolin-1(2H)-yl)(cyclopropyl)methanone (0.100 g, 0.24 mmol), bis(pinacolato)diboron (0.600 g, 2.37 mmol), [1,1'-bis(diphenylphosphino)ferrocene]dichloropalladium(II) dichloromethane adduct (0.019 g, 0.02 mmol), and potassium acetate (0.046 mg, 0.47 mmol) in 1,4-dioxane (10 mL) was stirred overnight at 80° C. The reaction mixture was cooled to room temperature, diluted with ethyl acetate (50 mL), washed with water (20 mL) and brine (20 mL), dried over anhydrous sodium sulfate, filtered, and concentrated under vacuum. The residue was purified by preparative thin layer chromatography (eluting with 1:5, ethyl acetate/petroleum ether) to afford a mixture of (S)-cyclopropyl(5-(3,4-difluorophenoxy)-2-methyl-6-(4,4,5,5-tetramethyl-1,3,2-dioxaborolan-2-yl)-3,4-dihydroquinolin-1(2H)-yl)methanone and (S)-cyclopropyl(5-(2,5-difluorophenoxy)-2-methyl-6-(4,4,5,5-tetramethyl-1,3,2-dioxaborolan-2-yl)-3,4-dihydroquinolin-1(2H)-yl)methanone (0.080 g, 72%) as yellow oil. MS (ESI, pos. ion) m/z 470 [M+H]$^+$.

Step 3. (S)-cyclopropyl(5-(2,5-difluorophenoxy)-2-methyl-6-(1-methyl-1H-1,2,3-triazol-4-yl)-3,4-dihydroquinolin-1(2H)-yl)methanone and (S)-cyclopropyl(5-(3,4-difluorophenoxy)-2-methyl-6-(1-methyl-1H-1,2,3-triazol-4-yl)-3,4-dihydroquinolin-1(2H)-yl)methanone A mixture of (S)-cyclopropyl(5-(3,4-difluorophenoxy)-2-methyl-6-(4,4,5,5-tetramethyl-1,3,2-dioxaborolan-2-yl)-3,4-dihydroquinolin-1(2H)-yl)methanone and (S)-cyclopropyl(5-(2,5-difluorophenoxy)-2-methyl-6-(4,4,5,5-tetramethyl-1,3,2-dioxaborolan-2-yl)-3,4-dihydroquinolin-1(2H)-yl)methanone (0.080 g, 0.09 mmol), 4-bromo-1-methyl-1H-1,2,3-triazole (0.062 g, 0.38 mmol), [1,1'-bis(diphenylphosphino)ferrocene]dichloropalladium(II) dichloromethane adduct (0.021 g, 0.03 mmol), and cesium carbonate (0.167 g, 0.51 mmol) in 1,4-dioxane (10 mL) and water (3 mL) was stirred overnight at 90° C. The reaction mixture was cooled to room temperature, diluted with ethyl acetate (50 mL), washed with water (20 mL) and brine (20 mL), dried over anhydrous sodium sulfate, filtered, and concentrated under vacuum. The residue was purified via column chromatography on silica gel (eluting with 1:5, ethyl acetate/petroleum ether). The product was further purified by preparative-HPLC with the following conditions (Waters I): Column, Xbridge Prep C18 OBD column, 5 um, 19×150 mm; mobile phase, Water (0.03% ammonium hydroxide) and acetonitrile (16% to 34% acetonitrile in 10 min, flow rate: 20 mL/min); Detector, UV 220&254 nm.

This afforded:

(S)-cyclopropyl(5-(2,5-difluorophenoxy)-2-methyl-6-(1-methyl-1H-1,2,3-triazol-4-yl)-3,4-dihydroquinolin-1(2H)-yl)methanone (0.0083 g, 23%) (I-318) as a white solid. $^1$H NMR (300 MHz, CD$_3$OD) δ ppm 0.75-0.82 (m, 1H), 0.85-1.05 (m, 2H), 1.10-1.23 (m, 4H), 1.38-1.52 (m, 1H), 1.95-2.05 (m, 1H), 2.17-2.42 (m, 2H), 2.65-2.79 (m, 1H), 4.08 (s, 3H), 4.75-4.88 (m, 1H), 6.18-6.28 (m, 1H), 6.67-6.78 (m, 1H), 7.23-7.31 (m, 1H), 7.54 (d, J=8.40 Hz, 1H), 8.01-8.10 (m, 2H). MS (ESI, pos. ion) m/z 425 [M+H]$^+$.

and (S)-cyclopropyl(5-(3,4-difluorophenoxy)-2-methyl-6-(1-methyl-1H-1,2,3-triazol-4-yl)-3,4-dihydroquinolin-1(2H)-yl)methanone (0.0053 g, 15%) (I-319) as a white solid. $^1$H NMR (300 MHz, CD$_3$OD) δ ppm 0.72-0.83 (m, 1H), 0.89-1.02 (m, 2H), 1.11-1.22 (m, 4H), 1.35-1.49 (m, 1H), 1.96-2.05 (m, 1H), 2.18-2.39 (m, 2H), 2.67-2.75 (m, 1H), 4.07 (s, 3H), 4.75-4.88 (m, 1H), 6.51-6.62 (m, 1H), 6.78-6.89 (m, 1H), 7.13 (d, J=9.00 Hz, 1H), 7.20 (d, J=9.00 Hz, 1H), 7.51 (d, J=8.40 Hz, 1H), 8.03-8.09 (m, 2H). MS (ESI, pos. ion) m/z 425 [M+H]⁺.

Example 82

(S)-cyclopropyl(5-(2-fluorophenoxy)-2-methyl-6-(1-methyl-1H-1,2,3-triazol-4-yl)-3,4-dihydroquinolin-1(2H)-yl)methanone (I-320)

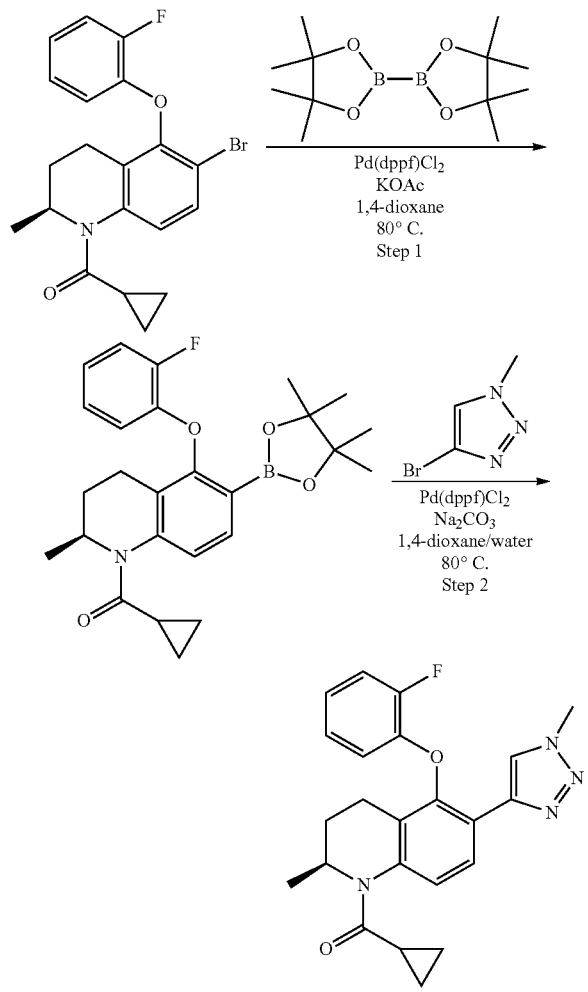

Step 1. (S)-cyclopropyl(5-(2-fluorophenoxy)-2-methyl-6-(4,4,5,5-tetramethyl-1,3,2-dioxaborolan-2-yl)-3,4-dihydroquinolin-1(2H)-yl)methanone A mixture of (S)-(6-bromo-5-(2-fluorophenoxy)-2-methyl-3,4-dihydroquinolin-1(2H)-yl)(cyclopropyl)methanone (prepared according to the procedures described for 1-[(2S)-6-bromo-5-(2-fluorophenoxy)-2-methyl-1,2,3,4-tetrahydroquinolin-1-yl]ethan-1-one (Example 51, Steps 1-3), 0.270 g, 0.67 mmol), bis(pinacolato)diboron (3.30 g, 13.00 mmol), [1,1'-bis(diphenylphosphino)ferrocene]dichloropalladium (II) dichloromethane adduct (50 mg, 0.07 mmol), and potassium acetate (0.170 g, 1.73 mmol) in 1,4-dioxane (10 mL) was stirred overnight at 80° C. The reaction mixture was cooled to room temperature, diluted with ethyl acetate 920 mL), washed with water (2×10 mL) and brine (10 mL), dried over anhydrous sodium sulfate, filtered, and concentrated under vacuum. The residue was purified via column chromatography on silica gel (eluting with 5-10% ethyl acetate-petroleum ether) to afford (S)-cyclopropyl(5-(2-fluorophenoxy)-2-methyl-6-(4,4,5,5-tetramethyl-1,3,2-dioxaborolan-2-yl)-3,4-dihydroquinolin-1(2H)-yl)methanone (0.140 g, 46%) as a light yellow solid. MS (ESI, pos. ion) m/z 452 [M+H]⁺.

Step 2. (S)-cyclopropyl(5-(2-fluorophenoxy)-2-methyl-6-(1-methyl-1H-1,2,3-triazol-4-yl)-3,4-dihydroquinolin-1(2H)-yl)methanone A mixture of (S)-cyclopropyl(5-(2-fluorophenoxy)-2-methyl-6-(4,4,5,5-tetramethyl-1,3,2-dioxaborolan-2-yl)-3,4-dihydroquinolin-1(2H)-yl)methanone (0.140 g, 0.31 mmol), 4-bromo-1-methyl-1H-1,2,3-triazole (0.050 g, 0.31 mmol), sodium carbonate (0.090 g, 0.85 mmol), and [1,1'-bis(diphenylphosphino)ferrocene]dichloropalladium(II) dichloromethane adduct (0.010 g, 0.01 mmol) in 1,4-dioxane (10 mL) and water (3 mL) was stirred overnight at 80° C. The reaction mixture was cooled to room temperature, filtered through a short pad of Celite, and concentrated under vacuum. The residue was purified via preparative thin layer chromatography (eluting with 2:1, petroleum ether-ethyl acetate). The product was further purified by preparative-HPLC with the following conditions (Waters I): Column, XBridge C18, 19×150 mm, 5 um; Mobile Phase water (0.05% ammonium bicarbonate) and acetonitrile (35% to 65% acetonitrile in 10 min, flow rate: 20 mL/min); Detector: UV254&220 nm. This afforded (S)-cyclopropyl(5-(2-fluorophenoxy)-2-methyl-6-(1-methyl-1H-1,2,3-triazol-4-yl)-3,4-dihydroquinolin-1(2H)-yl)methanone (0.033 g, 26%) as a white solid. ¹H NMR (400 MHz, CD₃OD) δ ppm 0.74-0.81 (m, 1H), 0.89-1.03 (m, 2H), 1.11-1.21 (m, 4H), 1.35-1.47 (m, 1H), 1.95-2.05 (m, 1H), 2.17-2.40 (m, 2H), 2.65-2.78 (m, 1H), 4.07 (s, 3H), 4.75-4.81 (m, 1H), 6.40-6.49 (m, 1H), 6.89-6.97 (m, 2H), 7.21-7.27 (m, 1H), 7.51 (d, J=8.40 Hz, 1H), 8.03 (s, 1H), 8.08 (d, J=8.40 Hz, 1H). MS (ESI, pos. ion) m/z 407 [M+H]⁺.

The following example was made according to the procedure described above for Example 82:

(S)-cyclopropyl(8-fluoro-2-methyl-6-(1-methyl-1H-1,2,3-triazol-4-yl)-5-phenoxy-3,4-dihydroquinolin-1(2H)-yl)methanone (I-321)

¹H NMR (400 MHz, CD₃OD) δ ppm 0.64-0.87 (m, 1H), 0.92-1.10 (m, 3H), 1.10-1.35 (m, 4H), 1.65-1.80 (m, 1H), 2.10-2.41 (m, 2H), 2.68-2.79 (m, 1H), 4.05 (s, 3H), 4.70-4.89

(m, 1H), 6.85 (d, J=8.00 Hz, 2H), 7.03 (t, J=7.60 Hz, 1H), 7.31 (t, J=8.00 Hz, 2H), 7.93-7.97 (m, 1H), 8.06 (s, 1H). MS (ESI, pos. ion) m/z 407 [M+H]$^+$.

(S)-methyl 8-fluoro-2-methyl-6-(1-methyl-1H-1,2,3-triazol-4-yl)-5-phenoxy-3,4-dihydroquinoline-1(2H)-carboxylate (I-322)

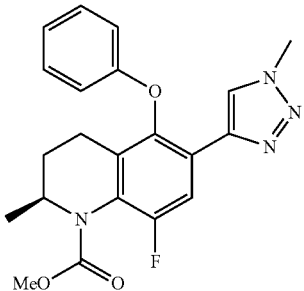 [SMILES: COC(=O)N1c2c(F)cc(-c3cn(C)nn3)c(Oc3ccccc3)c2CC[C@@H]1C]

$^1$H NMR (300 MHz, DMSO-d$_6$) δ ppm 1.11 (d, J=6.60, 3H), 1.21-1.36 (m, 2H), 2.05-2.15 (m, 1H), 2.17-2.30 (m, 1H), 3.70 (s, 3H), 4.40 (d, J=6.60 Hz, 3H), 4.35-4.45 (m, 1H), 6.81 (d, J=7.80 Hz, 2H), 7.01 (t, J=7.50 Hz, 1H), 7.28-7.34 (m, 2H), 7.84 (d, J=11.4 Hz, 1H), 8.11 (s, 1H). MS (ESI, pos. ion) m/z 397 [M+H]$^+$.

(S)-1-(8-fluoro-2-methyl-6-(1-methyl-1H-1,2,3-triazol-4-yl)-5-phenoxy-3,4-dihydroquinolin-1(2H)-yl)ethanone (I-323)

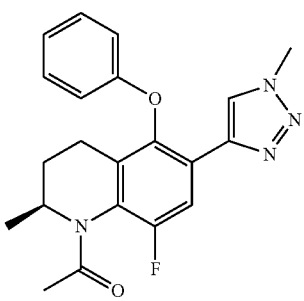 [SMILES: CC(=O)N1c2c(F)cc(-c3cn(C)nn3)c(Oc3ccccc3)c2CC[C@@H]1C]

$^1$H NMR (300 MHz, CD$_3$OD) δ ppm 1.05-1.31 (m, 4H), 2.10-2.44 (m, 5H), 2.61-2.80 (m, 1H), 4.05 (s, 3H), 4.70-4.90 (m, 1H), 6.78-6.90 (m, 2H), 6.95-7.10 (m, 1H), 7.25-7.40 (m, 2H), 7.90-8.10 (m, 2H). MS (ESI, pos. ion) m/z 381 [M+H]$^+$.

Example 83

(S)-(5-cyclobutoxy-2-methyl-6-(1H-pyrazol-1-yl)-3,4-dihydroquinolin-1(2H)-yl)(cyclopropyl)methanone (I-324)

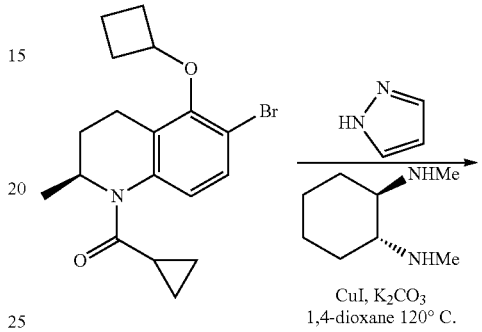

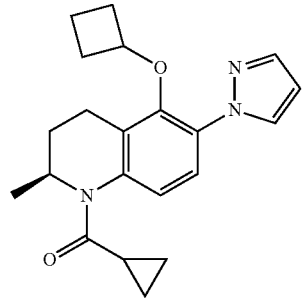

A mixture of (S)-(6-bromo-5-cyclobutoxy-2-methyl-3,4-dihydroquinolin-1(2H)-yl)(cyclopropyl)methanone (0.182 g, 0.50 mmol,), 1H-pyrazole (0.340 g, 5.00 mmol), copper (I) iodide (0.038 g, 0.20 mmol), (1R,2R)—N$^1$,N$^2$-dimethylcyclohexane-1,2-diamine (0.57 g, 0.40 mmol), and potassium carbonate (0.276 g, 2.00 mmol) in 1,4-dioxane (10 mL) stirred for 18 h at 120° C. The reaction mixture was cooled to room temperature and poured into ethyl acetate (50 mL). The mixture was washed with water (3×10 mL), dried over anhydrous sodium sulfate, filtered, and concentrated under vacuum. The residue was purified by preparative thin layer chromatography (eluting with 1:2, ethyl acetate/petroleum ether) to afford (S)-(5-cyclobutoxy-2-methyl-6-(1H-pyrazol-1-yl)-3,4-dihydroquinolin-1(2H)-yl)(cyclopropyl)methanone (0.023 g, 13%) as a white solid. $^1$H NMR (300 MHz, DMSO-d$_6$) δ ppm 0.63-0.72 (m, 1H), 0.77-0.91 (m, 2H), 0.99-1.10 (m, 4H), 1.15-1.19 (m, 1H), 1.30-1.53 (m, 2H), 1.72-1.95 (m, 5H), 2.22-2.43 (m, 2H), 2.95-2.96 (m, 1H), 3.88-3.95 (m, 1H), 4.63-4.71 (m, 1H), 6.51 (s, 1H), 7.24 (d, J=8.70 Hz, 1H), 7.41 (d, J=8.70 Hz, 1H), 7.73 (s, 1H), 8.08 (s, 1H). MS (ESI, pos. ion) m/z 352 [M+H]$^+$.

The following example was prepared according to the procedures described above for Example 83:

(S)-cyclopropyl(2-methyl-5-phenoxy-6-(1H-pyrazol-1-yl)-3,4-dihydroquinolin-1(2H)-yl)methanone (I-325)

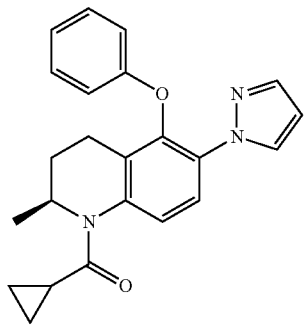 [SMILES: C[C@H]1CCc2c(ccc(-n3cccn3)c2Oc2ccccc2)N1C(=O)C1CC1]

$^1$H NMR (300 MHz, DMSO-d$_6$) δ ppm 0.65-0.99 (m, 3H), 0.95-1.11 (m, 4H), 1.35-1.50 (m, 1H), 1.85-2.00 (m, 1H), 2.02-2.15 (m, 1H), 2.23-2.42 (m, 1H), 2.50-2.65 (m, 1H), 4.65-4.75 (m, 1H), 6.31-6.35 (m, 1H), 6.71-6.78 (m, 2H), 6.90-7.01 (m, 1H), 7.18-7.30 (m, 2H), 7.45-7.50 (m, 1H), 7.58-7.68 (m, 2H), 8.02 (s, 1H). MS (ESI, pos. ion) m/z 374 [M+H]$^+$.

Example 84

(S)-(5-cyclobutoxy-2-methyl-6-(2H-1,2,3-triazol-2-yl)-3,4-dihydroquinolin-1(2H)-yl)(cyclopropyl)methanone (I-326)

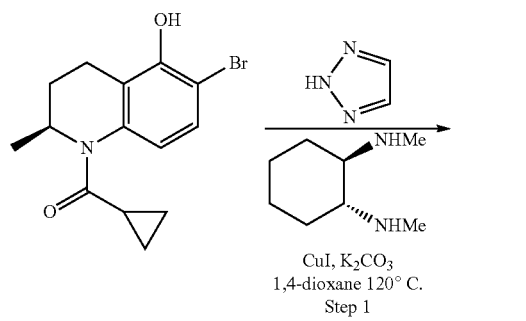

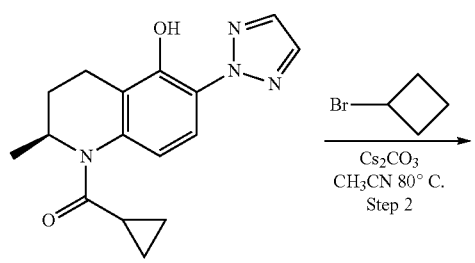

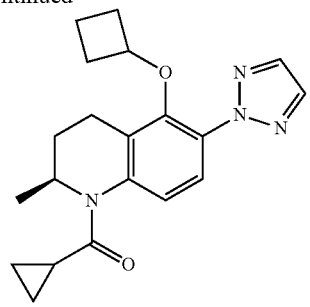

Step 1. (S)-cyclopropyl(5-hydroxy-2-methyl-6-(2H-1,2,3-triazol-2-yl)-3,4-dihydroquinolin-1(2H)-yl)methanone A mixture of (S)-(6-bromo-5-hydroxy-2-methyl-3,4-dihydroquinolin-1(2H)-yl)(cyclopropyl)methanone (1.20 g, 3.87 mmol), 2H-1,2,3-triazole (0.258 g, 3.74 mmol), copper (I) iodide (0.030 g, 0.16 mmol), (1R,2R)—N$^1$,N$^2$-dimethylcyclohexane-1,2-diamine (0.044 g, 0.31 mmol), and potassium carbonate (1.60 g, 11.61 mmol) in N,N-dimethylformamide (20 mL) stirred for 24 h at 120° C. The reaction mixture was cooled to room temperature and poured into ethyl acetate (100 mL). The mixture was washed with water (3×20 mL), dried over anhydrous sodium sulfate, filtered, and concentrated under vacuum. The residue was purified by column chromatography on silica gel (eluting with 1:3, ethyl acetate/petroleum ether) to afford (S)-cyclopropyl(5-hydroxy-2-methyl-6-(2H-1,2,3-triazol-2-yl)-3,4-dihydroquinolin-1(2H)-yl)methanone (0.150 g, 13%) as light yellow oil. MS (ESI, pos. ion) m/z 299 [M+H]$^+$.

Step 2. (S)-(5-cyclobutoxy-2-methyl-6-(2H-1,2,3-triazol-2-yl)-3,4-dihydroquinolin-1(2H)-yl)(cyclopropyl)methanone A mixture of (S)-cyclopropyl(5-hydroxy-2-methyl-6-(2H-1,2,3-triazol-2-yl)-3,4-dihydroquinolin-1(2H)-yl)methanone (0.055 g, 0.18 mmol), bromocyclobutane (0.050 g, 0.37 mmol), and cesium carbonate (0.150 g, 0.46 mmol) in acetonitrile (5 mL) stirred for 18 h at 80° C. The reaction mixture was cooled to room temperature and filtered, and the filtrate was concentrated under vacuum. The residue was purified by preparative-HPLC with the following conditions (Waters 1): Column, XBridge Prep C18 OBD Column, 5 um, 19×150 mm; mobile phase, water (0.03% aqueous ammonia) and acetonitrile (16% to 34% acetonitrile in 10 min, flow rate: 20 mL/min); Detector: UV 220&254 nm. This afforded (S)-(5-cyclobutoxy-2-methyl-6-(2H-1,2,3-triazol-2-yl)-3,4-dihydroquinolin-1(2H)-yl)(cyclopropyl)methanone (0.030 g, 45%) as a white solid. $^1$H NMR (300 MHz, CD$_3$OD) δ ppm 0.67-0.75 (m, 1H), 0.85-0.95 (m, 2H), 1.11-1.17 (m, 4H), 1.22-1.55 (m, 3H), 1.74-2.01 (m, 5H), 2.31-2.46 (m, 2H), 2.95-3.07 (m, 1H), 3.88-3.94 (m, 1H), 4.72-4.82 (m, 1H), 7.28 (d, J=8.40 Hz, 1H), 7.37 (d, J=8.40 Hz, 1H), 7.99 (s, 2H). MS (ESI, pos. ion) m/z 353 [M+H]+.

Example 85

(S)-cyclopropyl(2-methyl-5-phenoxy-6-(2H-1,2,3-triazol-2-yl)-3,4-dihydroquinolin-1(2H)-yl)methanone (I-327)

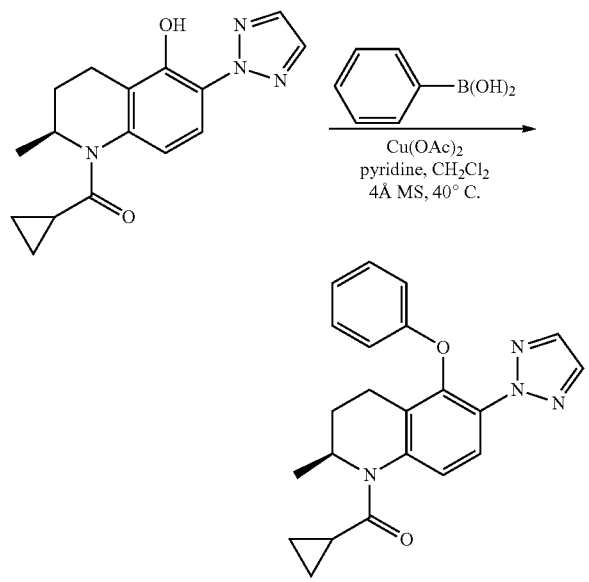

A 50-mL round-bottom flask equipped with balloon of air was charged with (S)-cyclopropyl(5-hydroxy-2-methyl-6-(2H-1,2,3-triazol-2-yl)-3,4-dihydroquinolin-1(2H)-yl)methanone (0.150 g, 0.50 mmol), phenylboronic acid (0.185 g, 1.52 mmol), copper (II) acetate (0.228 g, 1.26 mmol), pyridine (0.12 mL, 1.49 mmol), triethyl amine (0.10 mL, 0.75 mmol), and dichloromethane (4 mL), and the resulting mixture stirred for 18 h at 40° C. The reaction mixture was cooled to room temperature and filtered, and the filtrate was concentrated under vacuum. The residue was purified via column chromatography on silica gel (eluting with 5% dichloromethane/methanol). The product was further purified by preparative-HPLC with the following conditions (Waters I): Column, SunFire Prep C18, 5 um, 19×100 mm; Mobile phase, water (0.05% ammonium bicarbonate) and acetonitrile (55% to 75% acetonitrile in 7 min, flow rate: 20 mL/min); Detector, UV 220&254 nm. This afforded (S)-cyclopropyl(2-methyl-5-phenoxy-6-(2H-1,2,3-triazol-2-yl)-3,4-dihydroquinolin-1(2H)-yl)methanone (0.025 g, 14%) as a white solid. $^1$H NMR (300 MHz, CD$_3$OD) δ ppm 0.76-0.84 (m, 1H), 0.91-1.06 (m, 2H), 1.15-1.23 (m, 4H), 1.43-1.52 (m, 1H), 1.94-2.04 (m, 1H), 2.21-2.49 (m, 2H), 2.75-2.88 (m, 1H), 4.75-4.83 (m, 1H), 6.65-6.74 (m, 2H), 6.92 (d, J=7.20 Hz, 1H), 7.17 (t, J=7.50 Hz, 2H), 7.52 (d, J=8.70 Hz, 1H), 7.62 (d, J=8.70 Hz, 1H), 7.75 (s, 2H). MS (ESI, pos. ion) m/z 375 [M+H]+.

Example 86

(S)-(5-cyclobutoxy-2-methyl-6-(5-(piperidin-4-yl)-1H-imidazol-2-yl)-3,4-dihydroquinolin-1(2H)-yl)(cyclopropyl)methanone (I-328)

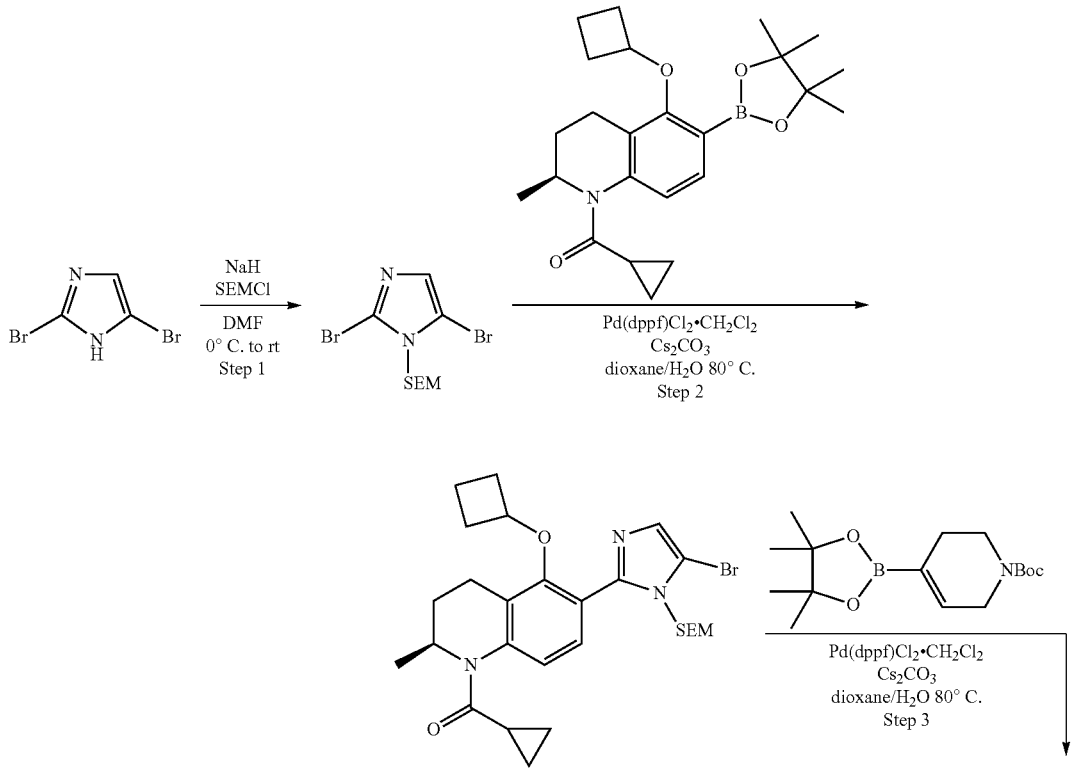

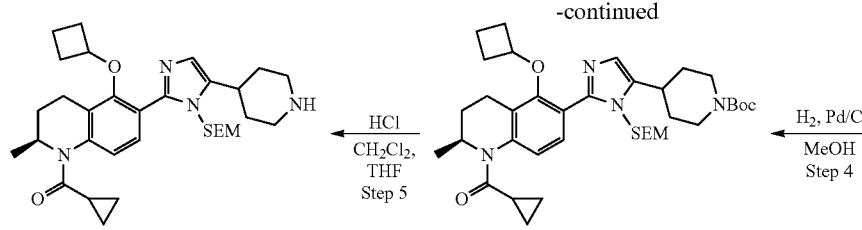
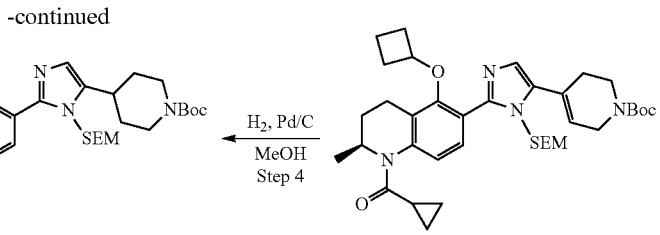

Step 1. 2,5-dibromo-1-((2-(trimethylsilyl)ethoxy)methyl)-1H-imidazole

Sodium hydride (60% dispersion in mineral oil, 0.212 g, 5.30 mmol) was added in portions to a 0° C. solution of 2,5-dibromo-1H-imidazole (0.600 g, 2.67 mmol) in N,N-dimethylformamide (4 mL), and the resulting mixture stirred for 30 min at 0° C. A solution of 2-(trimethylsilyl)ethoxymethyl chloride (0.665 g, 4.01 mmol) in N,N-dimethylformamide (0.5 mL) was added at 0° C., and the resulting solution stirred for an additional 2.5 h at room temperature. The reaction mixture was poured into ethyl acetate (20 mL), washed with brine (3×5 mL), dried over anhydrous sodium sulfate, filtered, and concentrated under vacuum. The residue was purified via column chromatography on silica gel (eluting with 10:1, ethyl acetate/petroleum ether) to afford 2,5-dibromo-1-((2-(trimethylsilyl)ethoxy)methyl)-1H-imidazole (0.390 g, 41%) as light yellow oil. MS (ESI, pos. ion) m/z 357, 355, 359 [M+H]$^+$.

Step 2. 08)-6-(5-bromo-1-((2-(trimethylsilyl)ethoxy)methyl)-1H-imidazol-2-yl)-5-cyclobutoxy-2-methyl-3,4-dihydroquinolin-1(2H)-yl)(cyclopropyl)methanone A mixture of (S)-(5-cyclobutoxy-2-methyl-6-(4,4,5,5-tetramethyl-1,3,2-dioxaborolan-2-yl)-3,4-dihydroquinolin-1(2H)-yl)(cyclopropyl)methanone (0.200 g, 0.49 mmol), 2,5-dibromo-1-[[2-(trimethylsilyl)ethyl]methyl]-1H-imidazole (0.178 g, 0.50 mmol), [1,1'-bis(diphenylphosphino)ferrocene]dichloropalladium(II) dichloromethane adduct (0.046 g, 0.06 mmol), and cesium carbonate (0.549 g, 1.68 mmol) in water (3 mL) and 1,4-dioxane (10 mL) stirred overnight at 80° C. The reaction mixture was cooled to room temperature and filtered through a short pad of celite, and the filtrate was concentrated under vacuum. The residue was purified by preparative thin layer chromatography (eluting with 50% ethyl acetate/petroleum ether) to afford ((S)-6-(5-bromo-1-((2-(trimethylsilyl)ethoxy)methyl)-1H-imidazol-2-yl)-5-cyclobutoxy-2-methyl-3,4-dihydroquinolin-1(2H)-yl)(cyclopropyl)methanone (0.091 g, 32%) as a white solid. MS (ESI, pos. ion) m/z 560, 562 [M+H]$^+$.

Step 3. tert-butyl 4-(2-((S)-5-cyclobutoxy-1-(cyclopropanecarbonyl)-2-methyl-1,2,3,4-tetrahydroquinolin-6-yl)-1-((2-(trimethylsilyl)ethoxy)methyl)-1H-imidazol-5-yl)-5,6-dihydropyridine-1(2H)-carboxylate A mixture of ((S)-6-(5-bromo-1-((2-(trimethylsilyl)ethoxy)methyl)-1H-imidazol-2-yl)-5-cyclobutoxy-2-methyl-3,4-dihydroquinolin-1 (2H)-yl)(cyclopropyl)methanone (0.0.091 g, 0.16 mmol), tert-butyl 4-(4,4,5,5-tetramethyl-1,3,2-dioxaborolan-2-yl)-5,6-dihydropyridine-1(2H)-carboxylate (0.050 g, 0.16 mmol), [1,1'-bis(diphenylphosphino)ferrocene]dichloropalladium(II) dichloromethane adduct (0.013 g, 0.02 mmol), and cesium carbonate (0.159 g, 0.49 mmol) in water (3 mL) and 1,4-dioxane (10 mL) stirred overnight at 80° C. The reaction mixture was cooled to room temperature and filtered through a short pad of celite, and the filtrate was concentrated under vacuum. The residue was purified by preparative thin layer chromatography (eluting with 1:2, ethyl acetate/petroleum ether) to afford tert-butyl 4-(2-((S)-5-cyclobutoxy-1-(cyclopropanecarbonyl)-2-methyl-1,2,3,4-tetrahydroquinolin-6-yl)-1-((2-(trimethylsilyl)ethoxy)methyl)-1H-imidazol-5-yl)-5,6-dihydropyridine-1(2H)-carboxylate (0.094 g, 87%) as a light yellow solid. MS (ESI, pos. ion) m/z 663 [M+H]$^+$.

Step 4. tert-butyl 4-(2-((S)-5-cyclobutoxy-1-(cyclopropanecarbonyl)-2-methyl-1,2,3,4-tetrahydroquinolin-6-yl)-1-((2-(trimethylsilyl)ethoxy)methyl)-1H-imidazol-5-yl)piperidine-1-carboxylate A mixture of tert-butyl 4-[2-[(2S)-5-cyclobutoxy-1-cyclopropanecarbonyl-2-methyl-1,2,3,4-tetrahydroquinolin-6-yl]-1-[[2-(trimethylsilyl)ethoxy]methyl]-1H-imidazol-5-yl]-1,2,3,6-tetrahydropyridine-1-carboxylate (0.094 g, 0.14 mmol) and palladium on carbon (10 wt %, 0.047 g) in methanol (4 mL) stirred under a hydrogen atmosphere at room temperature for 30 minutes. The reaction mixture was filtered, and the filtrate was concentrated under vacuum to afford tert-butyl 4-(2-((S)-5-cyclobutoxy-1-(cyclopropanecarbonyl)-2-methyl-1,2,3,4-tetrahydroquinolin-6-yl)-1-((2-(trimethylsilyl)ethoxy)methyl)-1H-imidazol-5-yl)piperidine-1-carboxylate (0.094 g, 100%) as a light yellow solid. MS (ESI, pos. ion) m/z 665 [M+H]$^+$.

Step 5. (S)-(5-cyclobutoxy-2-methyl-6-(5-(piperidin-4-yl)-1H-imidazol-2-yl)-3,4-dihydroquinolin-1(2H)-yl)(cyclopropyl)methanone Hydrogen chloride (gas) was bubbled into a solution of tert-butyl 4-(2-((S)-5-cyclobutoxy-1-(cyclopropanecarbonyl)-2-methyl-1,2,3,4-tetrahydroquinolin-6-yl)-1-((2-(trimethylsilyl)ethoxy)methyl)-1H-imidazol-5-yl)piperidine-1-carboxylate (0.094 g, 0.14 mmol) in dichloromethane (4 mL) and tetrahydrofuran (1 mL), and the resulting solution stirred for 1.5 h at room temperature. The reaction mixture was concentrated under vacuum, and the residue was dissolved in methanol (5 mL). The pH of the solution was adjusted to 8 with saturated aqueous sodium carbonate solution, and the resulting solution was extracted with ethyl acetate (3×10 mL). The combined organic layers were dried over anhydrous sodium sulfate, filtered, and concentrated under vacuum. The residue was purified by preparative-HPLC with the following conditions (Waters I): Column, SunFire Prep C18, 5 um, 19×100 mm; mobile phase, water (0.05% ammonium bicarbonate) and acetonitrile (55% to 75% acetonitrile in 7 min, flow rate: 20 mL/min); Detector, UV 220&254 nm. This afforded (S)-(5-cyclobutoxy-2-methyl-6-(5-(piperidin-4-yl)-1H-imidazol-2-yl)-3,4-dihydroquinolin-1(2H)-yl)(cyclopropyl)methanone (0.0018 g, 3%) as a white solid. $^1$H NMR (400 MHz, CD$_3$OD) δ ppm 0.71-0.78 (m, 1H), 0.82-0.99 (m, 2H), 1.13-1.18 (m, 4H), 1.21-1.41 (m, 5H), 1.55-1.65 (m, 1H), 1.75-2.21 (m, 9H), 2.32-2.48 (m, 2H), 2.89-3.11 (m, 4H), 3.31-3.34 (m, 1H), 4.16-4.21 (m, 1H), 4.70-4.81 (m, 1H), 6.97 (s, 1H), 7.26 (d, J=8.40 Hz, 1H), 7.65 (d, J=8.40 Hz, 1H). MS (ESI, pos. ion) m/z 435 [M+H]$^+$.

The following example was prepared according to the procedures described above for Example 86:

(S)-cyclopropyl(2-methyl-5-phenoxy-6-(5-(piperidin-4-yl)-1H-imidazol-2-yl)-3,4-dihydroquinolin-1(2H)-yl)methanone (I-329)

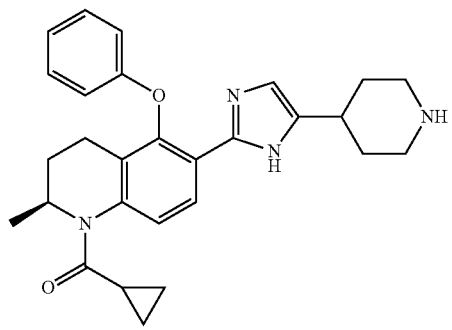 [SMILES: C[C@H]1CCc2c(ccc(-c3ncc(C4CCNCC4)[nH]3)c2Oc2ccccc2)N1C(=O)C1CC1]

$^1$H NMR (400 MHz, CD$_3$OD) δ ppm 0.75-0.83 (m, 1H), 0.85-1.01 (m, 4H), 1.14-1.18 (m, 3H), 1.18-1.21 (m, 1H), 1.25-1.40 (m, 2H), 1.42-1.51 (m, 1H), 1.52-1.77 (m, 3H), 1.93-2.14 (m, 4H), 2.18-2.22 (m, 2H), 2.31-2.42 (m, 2H), 2.72-2.89 (m, 2H), 2.89-2.99 (m, 2H), 3.20-3.31 (m, 2H), 4.75 (s, 1H), 4.81-4.86 (m, 1H), 6.72-6.82 (m, 3H), 6.92-6.99 (m, 1H), 7.20-7.25 (m, 2H), 7.48 (d, J=8.40 Hz, 1H), 7.83 (d, J=8.40 Hz, 1H). MS (ESI, pos. ion) m/z 457 [M+H]$^+$.

Example 87

(S)-cyclopropyl(5-(2,6-dimethylpyridin-4-yloxy)-2-methyl-6-(1-(piperidin-4-yl)-1H-pyrazol-4-yl)-3,4-dihydroquinolin-1(2H)-yl)methanone (I-330)

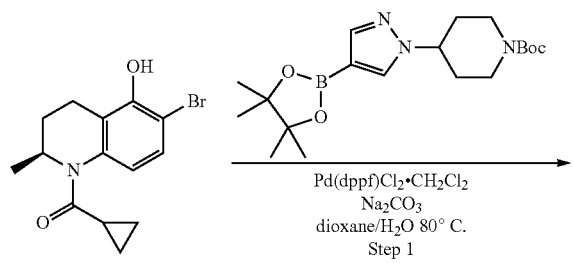

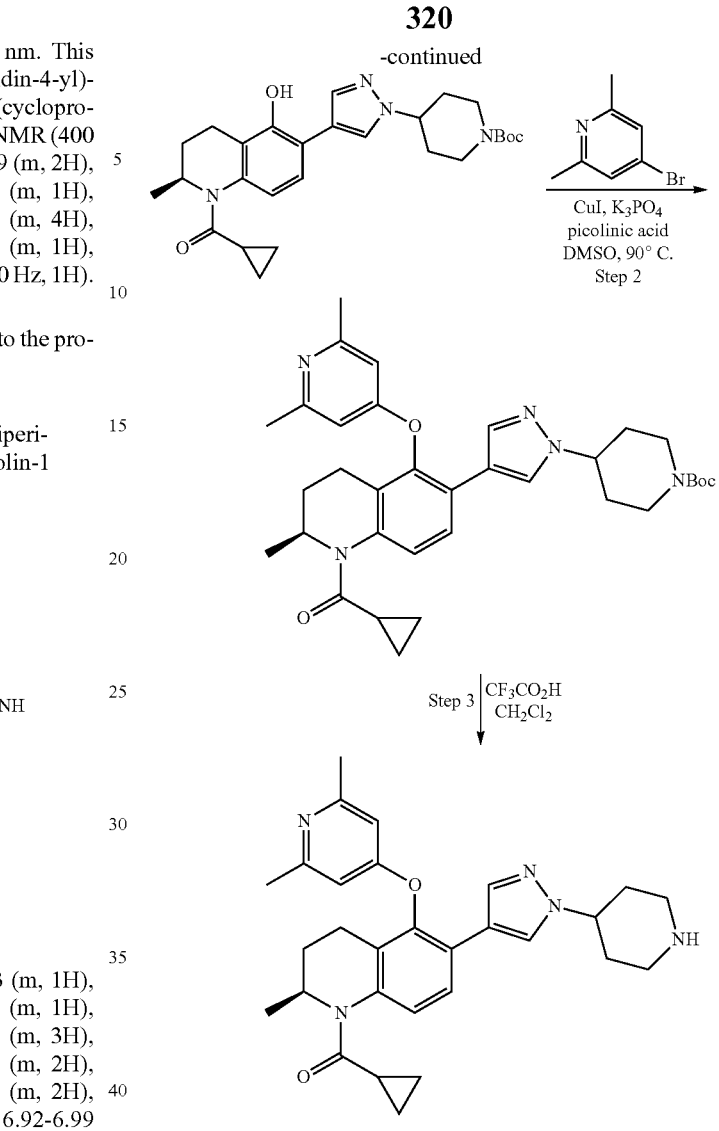

Step 1. (S)-tert-butyl 4-(4-(1-(cyclopropanecarbonyl)-5-hydroxy-2-methyl-1,2,3,4-tetrahydroquinolin-6-yl)-1H-pyrazol-1-yl)piperidine-1-carboxylate A mixture of (S)-(6-bromo-5-hydroxy-2-methyl-3,4-dihydroquinolin-1(2H)-yl)(cyclopropyl)methanone (1.00 g, 3.24 mmol), tert-butyl 4-(4-(4,4,5,5-tetramethyl-1,3,2-dioxaborolan-2-yl)-1H-pyrazol-1-yl)piperidine-1-carboxylate (2.40 g, 6.37 mmol), sodium carbonate (0.686 g, 6.47 mmol), [1,1'-bis(diphenylphosphino)ferrocene]dichloropalladium(II) dichloromethane adduct (0.263 g, 0.32 mmol), 1,4-dioxane (15 mL), and water (5 mL) stirred overnight at 80° C. The reaction mixture was cooled to room temperature, poured into water (20 mL), and extracted with ethyl acetate (3×20 mL). The combined organic layers were dried over anhydrous sodium sulfate, filtered, and concentrated under vacuum. The residue was purified via column chromatography on silica gel (eluting with 70% ethyl acetate/petroleum ether) to afford (S)-tert-butyl 4-(4-(1-(cyclopropanecarbonyl)-5-hydroxy-2-methyl-1,2,3,4-tetrahydroquinolin-6-yl)-1H-pyrazol-1-yl)piperidine-1-carboxylate (0.400 g, 26%) as a dark red solid. MS (ESI, pos. ion) m/z 481 [M+H]$^+$.

Step 2. (S)-tert-butyl 4-(4-(1-(cyclopropanecarbonyl)-5-(2,6-dimethylpyridin-4-yloxy)-2-methyl-1,2,3,4-tetrahydroquinolin-6-yl)-1H-pyrazol-1-yl)piperidine-1-carboxylate A mixture of (S)-tert-butyl 4-(4-(1-(cyclopropanecarbonyl)-5-hydroxy-2-methyl-1,2,3,4-tetrahydroquinolin-6-yl)-1H-pyrazol-1-yl)piperidine-1-carboxylate (0.100 g, 0.21 mmol), 4-bromo-2,6-dimethylpyridine (0.077 g, 0.42 mmol), copper (I) iodide (0.004 g, 0.02 mmol), picolinic acid (0.013 g, 0.10 mmol), and potassium phosphate (0.133 g, 0.63 mmol) in DMSO (2 mL) stirred overnight at 90° C. The reaction mixture was cooled to room temperature, poured into water (5 mL), and extracted with ethyl acetate (3×5 mL). The combined organic layers were dried over anhydrous sodium sulfate, filtered, and concentrated under vacuum. The residue was purified via column chromatography on silica gel (eluting with 1; 2, ethyl acetate/petroleum ether) to afford (S)-tert-butyl 4-(4-(1-(cyclopropanecarbonyl)-5-(2,6-dimethylpyridin-4-yloxy)-2-methyl-1,2,3,4-tetrahydroquinolin-6-yl)-1H-pyrazol-1-yl)piperidine-1-carboxylate (0.030 g, 25%) as yellow oil. MS (ESI, pos. ion) m/z 586 $[M+H]^+$.

Step 3. (S)-cyclopropyl(5-(2,6-dimethylpyridin-4-yloxy)-2-methyl-6-(1-(piperidin-4-yl)-1H-pyrazol-4-yl)-3,4-dihydroquinolin-1(2H)-yl)methanone Trifluoroacetic acid (1 mL) was added to a solution of (S)-tert-butyl 4-(4-(1-(cyclopropanecarbonyl)-5-(2,6-dimethylpyridin-4-yloxy)-2-methyl-1,2,3,4-tetrahydroquinolin-6-yl)-1H-pyrazol-1-yl)piperidine-1-carboxylate (0.030 g, 0.05 mmol) in dichloromethane (3 mL), and the resulting solution stirred for 1 h at room temperature. The reaction mixture was concentrated under vacuum, and the residue was purified via column chromatography on silica gel (eluting with 1:2, ethyl acetate/petroleum ether). The crude product was further purified by preparative-HPLC with the following conditions (Waters I): Column, SunFire Prep C18, 5 um, 19×100 mm; mobile phase, water (0.05% ammonium bicarbonate) and acetonitrile (65% to 85% acetonitrile in 7 min, flow rate: 20 mL/min); Detector, UV 220254 nm. This afforded (S)-cyclopropyl(5-(2,6-dimethylpyridin-4-yloxy)-2-methyl-6-(1-(piperidin-4-yl)-1H-pyrazol-4-yl)-3,4-dihydroquinolin-1(2H)-yl)methanone (0.003 g, 12%) as a white powder. $^1$H NMR (400 MHz, CD$_3$OD) δ ppm 0.73-0.84 (m, 1H), 0.92-1.03 (m, 2H), 1.12-1.21 (m, 4H), 1.42-1.51 (m, 1H), 1.99-2.20 (m, 5H), 2.20-2.29 (m, 2H), 2.29-2.41 (m, 6H), 2.63-2.72 (m, 1H), 2.95-3.04 (m, 2H), 3.31-3.41 (m, 2H), 4.35-4.45 (m, 1H), 4.79-4.90 (m, 1H), 6.53 (s, 2H), 7.45 (d, J=8.40 Hz, 1H), 7.63 (d, J=8.80 Hz, 1H), 7.79 (s, 1H), 7.96 (s, 1H). MS (ESI, pos. ion) m/z 486 $[M+H]^+$.

The following examples were made according to the procedure described above for Example 87:

(S)-cyclopropyl(2-methyl-5-(6-methylpyridin-2-yloxy)-6-(1-(piperidin-4-yl)-1H-pyrazol-4-yl)-3,4-dihydroquinolin-1(2H)-yl)methanone (I-331)

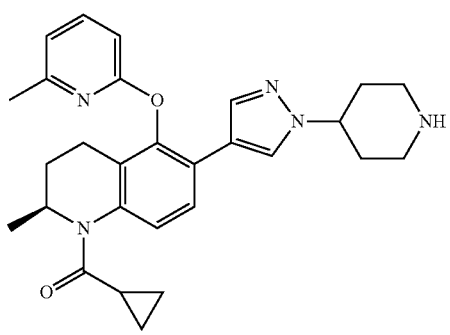 [SMILES: Cc1cccc(Oc2c(-c3cnn(C4CCNCC4)c3)ccc3c2CC[C@H](C)N3C(=O)C2CC2)n1]

$^1$H NMR (400 MHz, CD$_3$OD) δ ppm 0.62-0.71 (m, 1H), 0.80-0.90 (m, 2H), 1.03-1.10 (m, 4H), 1.31-1.38 (m, 1H), 1.70-1.81 (m, 2H), 1.89-1.97 (m, 3H), 2.11-2.27 (m, 2H), 2.26 (s, 3H), 2.55-2.69 (m, 3H), 3.03-3.09 (m, 2H), 4.05-4.16 (m, 1H), 4.68-4.73 (m, 1H), 6.39 (d, J=8.40 Hz, 1H), 6.80 (d, J=8.40 Hz, 1H), 7.28 (d, J=8.40 Hz, 1H), 7.46-7.51 (m, 2H), 7.67 (s, 1H), 7.86 (s, 1H). MS (ESI, pos. ion) m/z 472 $[M+H]^+$.

(S)-cyclopropyl(5-(2,6-dimethylpyridin-3-yloxy)-2-methyl-6-(1-(piperidin-4-yl)-1H-pyrazol-4-yl)-3,4-dihydroquinolin-1(2H)-yl)methanone (I-332)

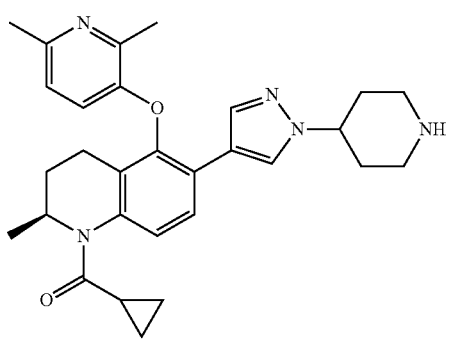 [SMILES: Cc1ccc(Oc2c(-c3cnn(C4CCNCC4)c3)ccc3c2CC[C@H](C)N3C(=O)C2CC2)c(C)n1]

$^1$H NMR (300 MHz, CD$_3$OD) δ ppm 0.73-0.84 (m, 1H), 0.88-1.01 (m, 2H), 1.11-1.23 (m, 4H), 1.25-1.33 (m, 1H), 1.36-1.43 (m, 1H), 1.91-2.11 (m, 5H), 2.19-2.37 (m, 2H), 2.40 (s, 3H), 2.53-2.71 ((m, 4H), 2.80-2.92 (m, 2H), 3.22-3.27 (m, 1H), 4.28-4.37 (m, 1H), 4.76-4.85 (m, 1H), 6.58 (d, J=8.40 Hz, 1H), 6.88 (d, J=8.40 Hz, 1H), 7.38-7.41 (m, 1H), 7.55-7.61 (m, 1H), 7.71 (s, 1H), 7.86 (s, 1H). MS (ESI, pos. ion) m/z 486 [M+H]⁺.

(S)-methyl 2-methyl-5-(6-methylpyridin-2-yloxy)-6-(1-(piperidin-4-yl)-1H-pyrazol-4-yl)-3,4-dihydro-quinoline-1(2H)-carboxylate (I-333)

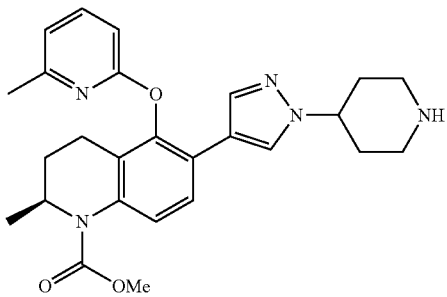 [SMILES: COC(=O)N1c2ccc(-c3cnn(C4CCNCC4)c3)c(Oc3cccc(C)n3)c2CC[C@@H]1C]

¹H NMR (300 MHz, CD₃OD) δ ppm 1.13-1.19 (m, 3H), 1.54-1.64 (m, 1H), 1.88-1.99 (m, 2H), 2.00-2.14 (m, 3H), 2.41 (s, 4H), 2.54-2.67 (m, 1H), 2.69-2.79 (m, 2H), 3.14-3.22 (m, 2H), 3.82 (s, 3H), 4.18-4.41 (m, 1H), 4.65-4.73 (m, 1H), 6.41 (d, J=8.10 Hz, 1H), 6.91 (d, J=7.50 Hz, 1H), 7.50-7.62 (m, 3H), 7.76 (s, 1H), 7.94 (s, 1H). MS (ESI, pos. ion) m/z 462 [M+H]⁺.

(S)-1-(2-methyl-5-(6-methylpyridin-2-yloxy)-6-(1-(piperidin-4-yl)-1H-pyrazol-4-yl)-3,4-dihydroquino-lin-1(2H)-yl)ethanone (I-334)

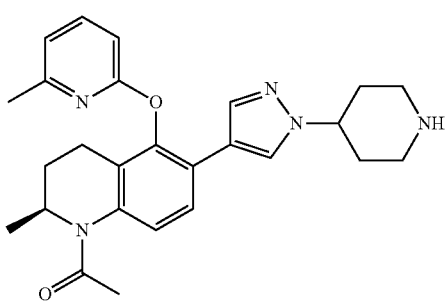 [SMILES: CC(=O)N1c2ccc(-c3cnn(C4CCNCC4)c3)c(Oc3cccc(C)n3)c2CC[C@@H]1C]

¹H NMR (300 MHz, CD₃OD) δ ppm 1.09-1.21 (m, 3H), 1.35-1.51 (m, 1H), 1.81-1.95 (m, 2H), 1.96-2.10 (m, 2H), 2.16-2.31 (m, 5H), 2.38 (s, 3H), 2.61-2.81 (m, 3H), 3.13-3.21 (m, 2H), 4.19-4.29 (m, 1H), 4.72-4.83 (m, 1H), 6.49 (d, J=8.70 Hz, 1H), 6.90 (d, J=7.20 Hz, 1H), 7.32 (br s, 1H), 7.55-7.63 (m, 2H), 7.78 (s, 1H), 7.96 (s, 1H). MS (ESI, pos. ion) m/z 446 [M+H]⁺.

(S)-methyl 5-(6-methoxypyridin-2-yloxy)-2-methyl-6-(1-(piperidin-4-yl)-1H-pyrazol-4-yl)-3,4-dihydro-quinoline-1(2H)-carboxylate (I-335)

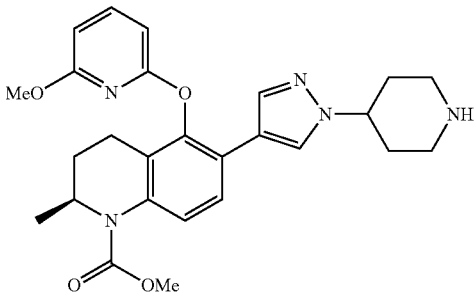 [SMILES: COC(=O)N1c2ccc(-c3cnn(C4CCNCC4)c3)c(Oc3cccc(OC)n3)c2CC[C@@H]1C]

¹H NMR (300 MHz, CD₃OD) δ ppm 1.15 (d, J=6.60 Hz, 3H), 1.55-1.69 (m, 1H), 1.75-1.91 (m, 2H), 1.95-2.15 (m, 3H), 2.40-2.79 (m, 4H), 3.07-3.18 (m, 2H), 3.66 (s, 3H), 3.80 (s, 3H), 4.15-4.22 (m, 1H), 4.60-4.75 (m, 1H), 6.30 (d, J=7.80 Hz, 1H), 6.38 (d, J=7.80 Hz, 1H), 7.48-7.61 (m, 3H), 7.74 (s, 1H). 7.92 (s, 1H). MS (ESI, pos. ion) m/z 478 [M+H]⁺.

(S)-1-(5-(6-methoxypyridin-2-yloxy)-2-methyl-6-(1-(piperidin-4-yl)-1H-pyrazol-4-yl)-3,4-dihydroquino-lin-1(2H)-yl)ethanone (I-336)

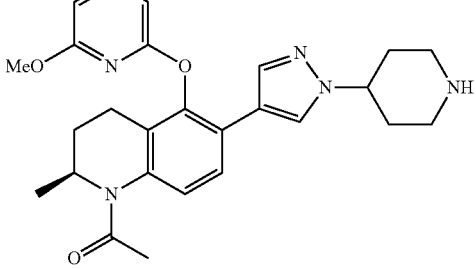

¹H NMR (300 MHz, CD₃OD) δ ppm 1.11 (d, J=6.60 Hz, 3H), 1.31-1.48 (m, 1H), 1.78-1.94 (m, 2H), 1.95-2.08 (m, 2H), 2.18-2.39 (m, 2H), 2.22 (s, 3H), 2.60-2.82 (m, 3H), 3.09-3.18 (m, 2H), 3.60 (s, 3H), 4.15-4.28 (m, 1H), 4.70-4.88

(m, 1H), 6.36-6.42 (m, 2H), 7.18-7.34 (m, 1H), 7.55-7.65 (m, 2H), 7.77 (s, 1H), 7.20 (s, 1H). MS (ESI, pos. ion) m/z 462 [M+H]⁺.

Example 88

(S)-cyclopropyl(2-methyl-5-phenoxy-6-(4-(piperazin-1-yl)-1H-pyrazol-1-yl)-3,4-dihydroquinolin-1(2H)-yl)methanone (I-337)

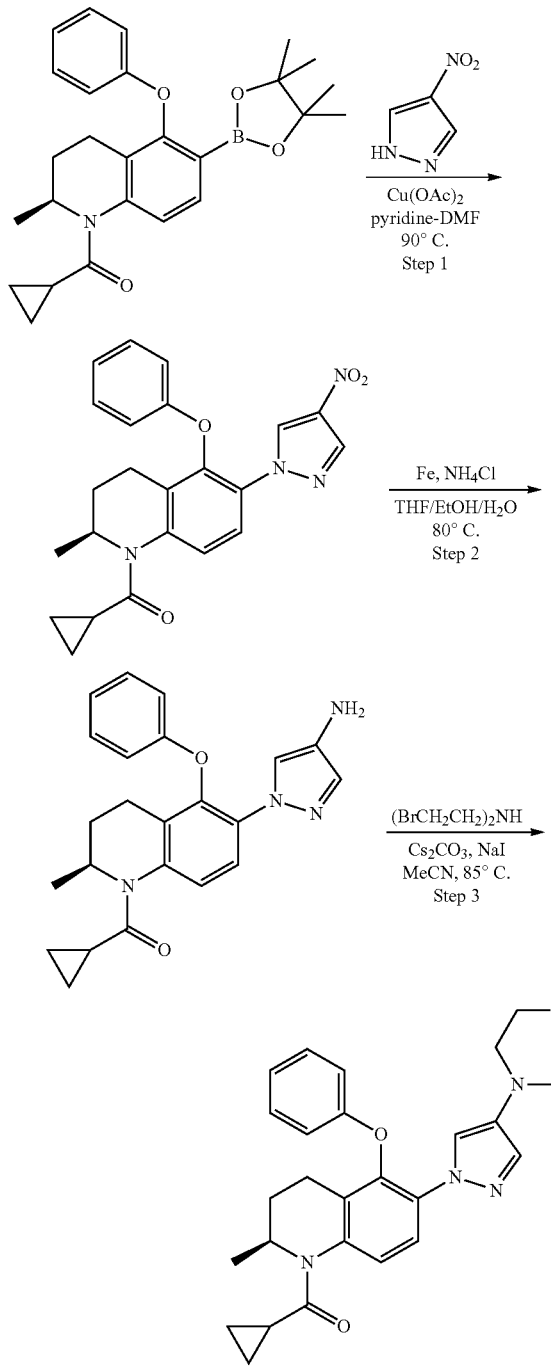

Step 1. (S)-cyclopropyl(2-methyl-6-(4-nitro-1H-pyrazol-1-yl)-5-phenoxy-3,4-dihydroquinolin-1(2H)-yl)methanone A 100-mL round-bottom flask equipped with a balloon filled with air was charged with (S)-cyclopropyl(2-methyl-5-phenoxy-6-(4,4,5,5-tetramethyl-1,3,2-dioxaborolan-2-yl)-3,4-dihydroquinolin-1(2H)-yl)methanone (0.240 g, 0.55 mmol), 4-nitro-1H-pyrazole (0.188 g, 1.66 mmol), copper (II) acetate (0.301 g, 1.66 mmol), pyridine (0.2 mL), and N,N-dimethylformamide (5 mL), and the resulting mixture stirred overnight at 90° C. The reaction mixture was cooled to room temperature and filtered through a pad of Celite. The filtrate was concentrated, and the residue was purified by preparative thin layer chromatography (eluting with 1:3, ethyl acetate/petroleum ether) to afford (S)-cyclopropyl(2-methyl-6-(4-nitro-1H-pyrazol-1-yl)-5-phenoxy-3,4-dihydroquinolin-1(2H)-yl)methanone (0.060 g, 26%) as yellow oil. MS (ESI, pos. ion) m/z 419 [M+H]⁺.

Step 2. (S)-(6-(4-amino-1H-pyrazol-1-yl)-2-methyl-5-phenoxy-3,4-dihydroquinolin-1(2H)-yl)(cyclopropyl)methanone A mixture of (S)-cyclopropyl(2-methyl-6-(4-nitro-1H-pyrazol-1-yl)-5-phenoxy-3,4-dihydroquinolin-1(2H)-yl) methanone (0.060 g, 0.15 mmol), iron powder (0.040 g, 0.72 mmol), ammonium chloride (0.023 g, 0.43 mmol), tetrahydrofuran (4 mL), ethanol (4 mL), and water (1 mL) stirred overnight at 80° C. The reaction mixture was cooled to room temperature and filtered. The filtrate was concentrated under vacuum, and the residue was purified by preparative thin layer chromatography (eluting with 1:1, ethyl acetate/petroleum ether) to afford (S)-(6-(4-amino-1H-pyrazol-1-yl)-2-methyl-5-phenoxy-3,4-dihydroquinolin-1(2H)-yl)(cyclopropyl)methanone (0.045 g, 81%) as a brown solid. MS (ESI, pos. ion) m/z 389 [M+H]⁺.

Step 3. (S)-cyclopropyl(2-methyl-5-phenoxy-6-(4-(piperazin-1-yl)-1H-pyrazol-1-yl)-3,4-dihydroquinolin-1(2H)-yl)methanone A mixture of (S)-(6-(4-amino-1H-pyrazol-1-yl)-2-methyl-5-phenoxy-3,4-dihydroquinolin-1(2H)-yl)(cyclopropyl) methanone (0.020 g, 0.05 mmol), bis(2-bromoethyl)amine (0.020 g, 0.09 mmol), sodium iodide (0.003 g, 0.02 mmol), and cesium carbonate (0.084 g, 0.26 mmol) in acetonitrile (2 mL) stirred overnight at 85° C. The reaction mixture was cooled to room temperature and filtered. The filtrate was concentrated under vacuum, and the residue was purified by preparative thin layer chromatography (eluting with 10% methanol/dichloromethane). The product was further purified by preparative-HPLC with the following conditions: Column: XBridge RP C18, 19×150 mm, 5 um; Mobile Phase: water (0.05% ammonium bicarbonate) and acetonitrile (5% to 60% acetonitrile in 7.0 min, flow rate: 20 mL/min); Detector: UV220&254 nm. This afforded (5)-cyclopropyl(2-methyl-5-phenoxy-6-(4-(piperazin-1-yl)-1H-pyrazol-1-yl)-3,4-dihydroquinolin-1(2H)-yl)methanone (0.0011 g, 5%) as a light yellow solid. ¹H NMR (300 MHz, CD₃OD) δ ppm 0.96-0.82 (m, 1H), 0.91-1.06 (m, 2H), 1.15-1.22 (m, 3H), 1.31-1.38 (m, 2H), 1.42-1.51 (m, 1H), 1.95-2.07 (m, 1H), 2.21-2.32 (m, 1H), 2.33-2.45 (m, 1H), 2.73-2.92 (m, 9H), 4.55-4.65 (m, 1H), 6.71-6.79 (m, 2H), 6.93-7.01 (m, 1H), 7.19-7.26 (m, 2H), 7.40 (s, 1H), 7.45-7.50 (m, 1H), 7.54-7.63 (m, 2H). MS (ESI, pos. ion) m/z 458 [M+H]⁺.

The following examples were made according to the procedure described above for Example 88:

(S)-cyclopropyl(2-methyl-6-(4-morpholino-1H-pyrazol-1-yl)-5-phenoxy-3,4-dihydroquinolin-1(2H)-yl)methanone (I-338)

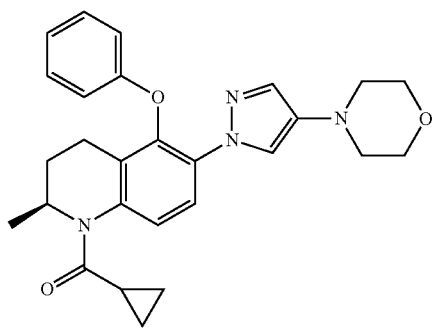 [SMILES: C[C@H]1CCc2c(ccc(-n3cc(N4CCOCC4)cn3)c2Oc2ccccc2)N1C(=O)C1CC1]

$^1$H NMR (300 MHz, CD$_3$OD) δ ppm 0.74-0.86 (m, 1H), 0.89-1.03 (m, 2H), 1.13-1.24 (m, 4H), 1.42-1.51 (m, 1H), 1.93-2.07 (m, 1H), 2.21-2.33 (m, 1H), 2.33-2.47 (m, 1H), 2.78-2.88 (m, 5H), 3.70-3.80 (m, 4H), 4.78-4.81 (m, 1H), 6.74-6.78 (m, 2H), 6.93-7.01 (m, 1H), 7.18-7.24 (m, 2H), 7.40-7.51 (m, 2H), 7.55-7.63 (m, 2H). MS (ESI, pos. ion) m/z 459 [M+H]$^+$.

(S)-methyl 2-methyl-6-(4-morpholino-1H-pyrazol-1-yl)-5-phenoxy-3,4-dihydroquinoline-1(2H)-carboxylate (I-339)

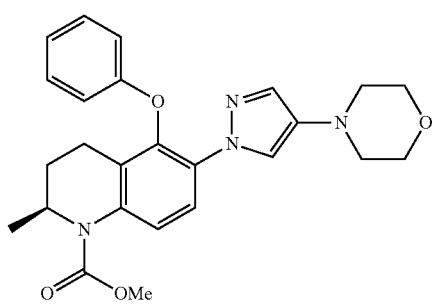 [SMILES: COC(=O)N1c2ccc(-n3cc(N4CCOCC4)cn3)c(Oc3ccccc3)c2CC[C@@H]1C]

$^1$H NMR (300 MHz, CD$_3$OD) δ ppm 1.17 (d, J=6.60 Hz, 3H), 1.55-1.64 (m, 1H), 2.05-2.18 (m, 1H), 2.49-2.58 (m, 1H), 2.67-2.80 (m, 1H), 2.80-2.86 (m, 4H), 3.72-3.80 (m, 4H), 3.84 (s, 3H), 4.65-4.74 (m, 1H), 6.68-6.73 (m, 2H), 6.93-7.01 (m, 1H), 7.16-7.23 (m, 2H), 7.37 (s, 1H), 7.49-7.55 (m, 2H), 7.65-7.71 (m, 1H). MS (ESI, pos. ion) m/z 449 [M+H]$^+$.

(S)-methyl 2-methyl-5-phenoxy-6-(4-(piperazin-1-yl)-1H-pyrazol-1-yl)-3,4-dihydroquinoline-1(2H)-carboxylate (I-340)

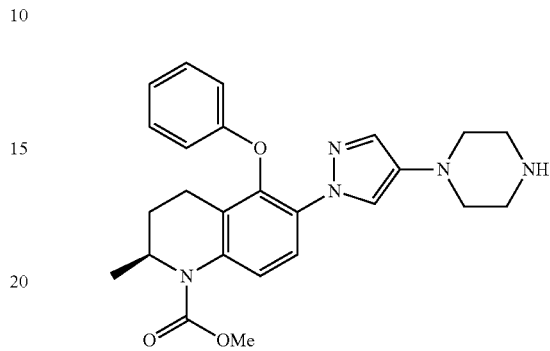

$^1$H NMR (300 MHz, CD$_3$OD) δ ppm 1.17 (d, J=6.30 Hz, 3H), 1.29-1.34 (m, 1H), 1.56-1.65 (m, 1H), 2.05-2.13 (m, 1H), 2.50-2.59 (m, 1H), 2.65-2.78 (m, 1H), 2.82-2.91 (m, 4H), 2.92-2.97 (m, 4H), 3.82 (s, 3H), 4.64-4.72 (m, 1H), 6.68-6.74 (m, 2H), 6.91-6.99 (m, 1H), 7.15-7.24 (m, 2H), 7.39 (s, 1H), 7.50-7.54 (m, 2H), 7.64-7.70 (m, 1H). MS (ESI, pos. ion) m/z 448 [M+H]$^+$.

Example 89 methyl (2S)-5-cyclobutoxy-6-[1-(1,1-dioxo-1λ$^6$-thian-4-yl)-1H-pyrazol-4-yl]-2-methyl-1,2,3,4-tetrahydroquinoline-1-carboxylate (I-341)

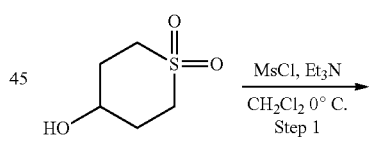

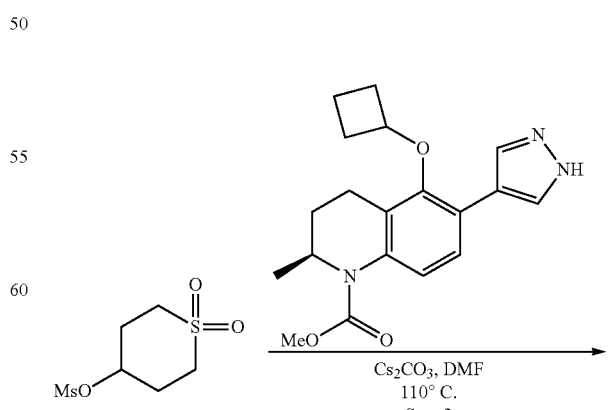

-continued

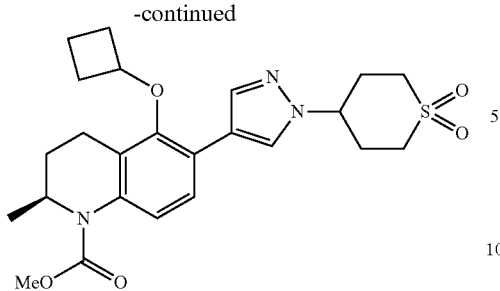

Step 1. 1,1-dioxidotetrahydro-2H-thiopyran-4-yl methanesulfonate

Triethylamine (7.80 mL, 55.9 mmol) was added to a solution of 4-hydroxytetrahydro-2H-thiopyran 1,1-dioxide (3.5 g, 23.3 mmol) in dichloromethane (35.0 mL). The reaction solution was cooled to 0° C. and methanesulfonyl chloride (3.25 ml, 41.9 mmol) was added. After 10 minutes, the reaction solution was warmed to room temperature and stirred for 3 h. The reaction was quenched via the addition of saturated aqueous ammonium chloride solution (15 mL). The organic layer was separated and washed with saturated aqueous sodium bicarbonate solution (15 mL) and brine (15 mL), dried over anhydrous sodium sulfate, filtered and concentrated in vacuo to afford an off-white solid. The solid residue was suspended in ethyl acetate (20 mL) and filtered. The filtered solid was then collected and dried in vacuo affording 1,1-dioxidotetrahydro-2H-thiopyran-4-yl methanesulfonate (5.1 g, 95%) as a white solid. $^1$H NMR (400 MHz, CDCl$_3$) δ ppm 2.38-2.56 (m, 4H) 2.94-3.06 (m, 2H) 3.10 (s, 3H) 3.23-3.39 (m, 2H) 5.03 (tt, J=4.74, 2.49 Hz, 1H)

Step 2. methyl (2S)-5-cyclobutoxy-6-[1-(1,1-dioxo-1λ$^6$-thian-4-yl)-1H-pyrazol-4-yl]-2-methyl-1,2,3,4-tetrahydroquinoline-1-carboxylate A mixture of (S)-methyl 5-cyclobutoxy-2-methyl-6-(1H-pyrazol-4-yl)-3,4-dihydroquinoline-1(2H)-carboxylate (0.160 g, 0.47 mmol), 1,1-dioxidotetrahydro-2H-thiopyran-4-yl methanesulfonate (0.320 g, 1.40 mmol) and cesium carbonate (0.457 g, 1.40 mmol) in N,N-dimethylformamide (5 mL) stirred overnight at 110° C. The reaction mixture was cooled to room temperature, diluted with water (20 mL), and extracted with ethyl acetate (3×10 mL). The combined organic layers were dried over anhydrous sodium sulfate, filtered, and concentrated under vacuum. The residue was purified by preparative thin layer chromatography (eluting with 50% ethyl acetate/petroleum ether). The product was further purified by preparative-HPLC with the following conditions (Waters I): Column, Xbridge RP18 5 um, 19×150 mm; Mobile phase, water (0.05% ammonium bicarbonate) and acetonitrile (40% to 80% acetonitrile in 10 min; flow rate: 20 mL/min); Detector, UV 220&254 nm. This afforded of methyl (2S)-5-cyclobutoxy-6-[1-(1,1-dioxo-1λ$^6$-thian-4-yl)-1H-pyrazol-4-yl]-2-methyl-1,2,3,4-tetrahydroquinoline-1-carboxylate (0.040 g, 18%) as a white solid. $^1$H NMR (400 MHz, CD$_3$OD) δ ppm 1.18 (d, J=6.40 Hz, 3H), 1.29-1.31 (m, 1H), 1.47-1.49 (m, 1H), 1.60-1.62 (m, 1H), 2.01-2.08 (m, 4H), 2.11-2.24 (m, 1H), 2.45-2.47 (m, 1H), 2.63-2.68 (m, 4H), 2.90-2.94 (m, 1H), 3.10-3.17 (m, 2H), 3.45-3.47 (m, 2H), 3.78 (s, 3H), 4.06-1.10 (m, 1H), 4.45-4.58 (m, 2H), 7.22 (d, J=8.40 Hz, 1H), 7.31 (d, J=8.40 Hz, 1H), 7.81 (s, 2H). MS (ESI, pos. ion) m/z 474 [M+H]$^+$.

The following examples were made according to the procedure described above for Example 89:

4-[4-[(2S)-5-cyclobutoxy-1-cyclopropanecarbonyl-2-methyl-1,2,3,4-tetrahydroquinolin-6-yl]-1H-pyrazol-1-yl]-1λ$^6$-thiane-1,1-dione (I-342)

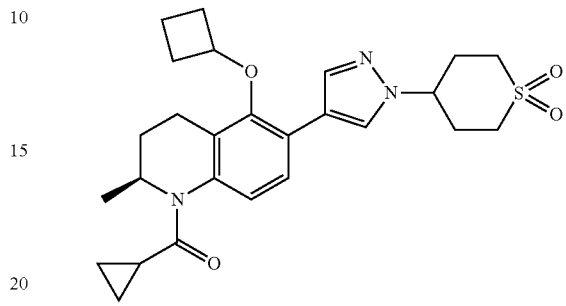

$^1$H NMR (400 MHz, CD$_3$OD) δ ppm 0.64-0.66 (m, 1H), 0.83-0.85 (m, 1H), 0.98-0.99 (m, 1H), 1.13 (d, J=6.40 Hz, 3H), 1.24-1.37 (m, 3H), 1.58-1.65 (m, 1H), 1.82-1.85 (m, 1H), 2.05-2.17 (m, 4H), 2.32-2.36 (m, 2H), 2.65-2.68 (m, 4H), 2.92-2.99 (m, 1H), 3.01-3.17 (m, 2H), 3.45-3.46 (m, 2H), 4.11-4.15 (m, 1H), 4.50-4.58 (m, 1H), 4.75-4.77 (m, 1H), 7.14 (d, J=8.00 Hz, 1H), 7.26 (d, J=8.00 Hz, 1H), 7.85 (s, 1H), 7.96 (s, 1H). MS (ESI, pos. ion) m/z 484 [M+H]$^+$.

Example 90

(S)-1-(cyclopropanecarbonyl)-2-methyl-5-phenoxy-1,2,3,4-tetrahydroquinoline-6-carbonitrile (I-343)

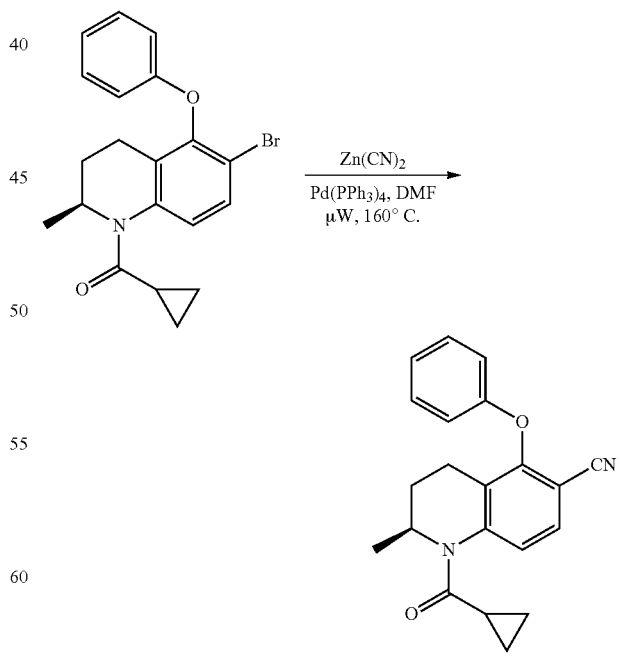

A mixture of (S)-(6-bromo-2-methyl-5-phenoxy-3,4-dihydroquinolin-1(2H)-yl)(cyclopropyl)methanone (0.100 g, 0.26 mmol), tetrakis(triphenylphosphine)palladium (O)

(0.30 g, 0.03 mmol), and zinc cyanide (0.036 g, 0.31 mmol) in N,N-dimethylformamide (2 mL) was heated with microwave irradiation for 30 min at 160° C. The reaction mixture was cooled to room temperature, poured into ethyl acetate (10 mL), washed with water (3×2 mL), dried over anhydrous sodium sulfate, filtered, and concentrated under vacuum. The residue was purified via column chromatography on silica gel (eluting with 1:8, ethyl acetate/petroleum ether) to afford (S)-1-(cyclopropanecarbonyl)-2-methyl-5-phenoxy-1,2,3,4-tetrahydroquinoline-6-carbonitrile (0.27 g, 32%) as a colorless oil. ¹H NMR (300 MHz, CDCl₃) δ ppm 0.74-0.82 (m, 1H), 0.90-1.10 (m, 2H), 1.10-1.18 (m, 3H), 1.28-1.39 (m, 1H), 1.49-1.61 (m, 1H), 1.80-1.91 (m, 1H), 2.10-2.22 (m, 1H), 2.39-2.51 (m, 1H), 2.67-2.80 (m, 1H), 4.71-4.89 (m, 1H), 6.85 (d, J=8.10 Hz, 2H), 7.08 (t, J=7.50 Hz, 1H), 7.28-7.38 (m, 2H), 7.40-7.47 (m, 1H), 7.49-7.55 (m, 1H). MS (ESI, pos. ion) m/z 333 [M+H]⁺.

(S)-methyl 6-cyano-2-methyl-5-phenoxy-3,4-dihydroquinoline-1(2H)-carboxylate (I-344)

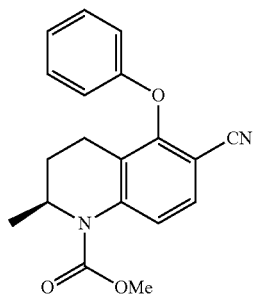 [SMILES: COC(=O)N1c2ccc(C#N)c(Oc3ccccc3)c2CC[C@@H]1C]

(S)-Methyl 6-cyano-2-methyl-5-phenoxy-3,4-dihydroquinoline-1(2H)-carboxylate was synthesized according to the procedure outlined above for (S)-1-(cyclopropanecarbonyl)-2-methyl-5-phenoxy-1,2,3,4-tetrahydroquinoline-6-carbonitrile (Example 90). ¹H NMR (300 MHz, CD₃Cl) δ ppm 1.12 (d, J=6.60 Hz, 3H), 1.52-1.70 (m, 1H), 1.88-2.10 (m, 1H), 2.42-2.72 (m, 2H), 3.84 (s, 3H), 4.62-4.80 (m, 1H), 6.82 (d, J=8.10 Hz, 2H), 7.06 (t, J=7.50 Hz, 1H), 7.20-7.35 (m, 2H), 7.48 (d, J=8.70 Hz, 1H), 7.75 (d, J=8.70 Hz, 1H). MS (ESI, pos. ion) m/z 323 [M+H]⁺.

Example 91

(S)-cyclopropyl(6-ethynyl-2-methyl-5-phenoxy-3,4-dihydroquinolin-1(2H)-yl)methanone (I-345)

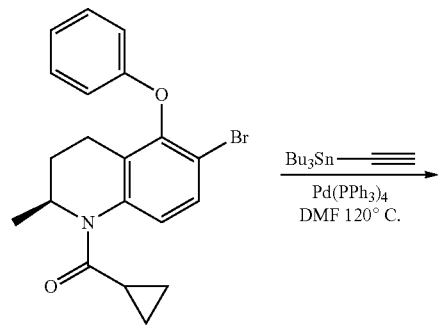

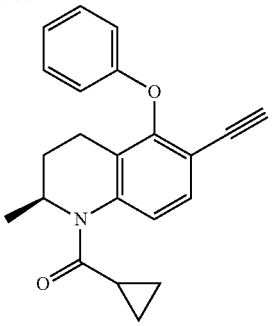

A mixture of (S)-(6-bromo-2-methyl-5-phenoxy-3,4-dihydroquinolin-1(2H)-yl)(cyclopropyl)methanone (0.030 g, 0.08 mmol), tributyl(ethynyl)stannane (0.030 g, 0.09 mmol), and tetrakis(triphenylphosphine)palladium (O) (0.037 g, 0.03 mmol) in N,N-dimethylformamide (1.5 mL) stirred overnight at 120° C. The reaction mixture was cooled to room temperature, poured into ethyl acetate (15 mL), washed with water (2×5 mL) and brine (5 mL), dried over anhydrous sodium sulfate, filtered, and concentrated under vacuum. The residue was purified via preparative thin layer chromatography (eluting with 1:5, ethyl acetate/petroleum ether). The product was further purified by preparative-HPLC with the following conditions (Waters III): Column, Xbridge RP C18, 19×150 mm, 5 um; mobile phase, water (0.05% ammonium bicarbonate) and acetonitrile (50% to 100% acetonitrile in 10 min, flow rate: 20 mL/min); Detector, UV 220&254 nm. This afforded (S)-cyclopropyl(6-ethynyl-2-methyl-5-phenoxy-3,4-dihydroquinolin-1(2H)-yl)methanone (0.004 g, 16%) as a brown semi-solid. ¹H NMR (300 MHz, CD₃OD) δ ppm 0.65-0.85 (m, 1H), 0.87-1.04 (m, 2H), 1.05-1.25 (m, 4H), 1.38-1.52 (m, 1H), 1.85-2.02 (m, 1H), 2.11-2.47 (m, 2H), 2.62-2.85 (m, 1H), 3.47 (m, 1H), 4.75-4.82 (m, 1H), 6.79 (d, J=8.10 Hz, 2H), 6.95-7.05 (m, 1H), 7.19-7.39 (m, 3H), 7.45 (d, J=8.40 Hz, 1H). MS (ESI, pos. ion) m/z 332 [M+H]⁺.

Example 92

(S)-methyl 6-ethynyl-2-methyl-5-phenoxy-3,4-dihydroquinoline-1(2H)-carboxylate (I-346)

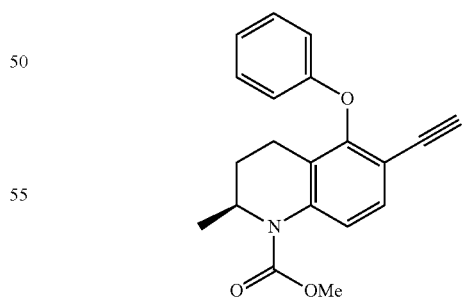

(S)-Methyl 6-ethynyl-2-methyl-5-phenoxy-3,4-dihydroquinoline-1(2H)-carboxylate was synthesized according to the procedure outlined above for (S)-cyclopropyl(6-ethynyl-2-methyl-5-phenoxy-3,4-dihydroquinolin-1(2H)-yl)methanone (Example 91). ¹H NMR (300 MHz, CD₃OD) δ ppm 1.06 (d, J=6.60 Hz, 3H), 1.49-1.71 (m, 1H), 1.85-2.06 (m, 1H), 2.33-2.49 (m, 2H), 3.73 (s, 3H), 4.07 (s, 1H), 4.54-4.60

(m, 1H), 6.76 (d, J=7.80 Hz, 2H), 7.01 (t, J=7.50 Hz, 1H), 7.45-7.21 (m, 3H), 7.57 (d, J=8.70 Hz, 1H). MS (ESI, pos. ion) m/z 322 [M+H]⁺.

Example 93

(S)-cyclopropyl(2-methyl-5-phenoxy-6-(prop-1-ynyl)-3,4-dihydroquinolin-1(2H)-yl)methanone (I-347)

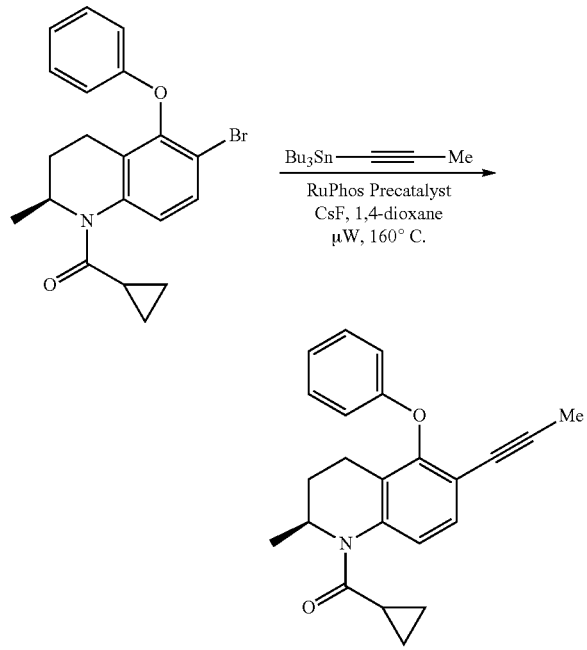

A mixture of (S)-(6-bromo-2-methyl-5-phenoxy-3,4-dihydroquinolin-1(2H)-yl)(cyclopropyl)methanone (0.050 g, 0.13 mmol), RuPhos Precatalyst 3$^{rd}$ generation ((2-dicyclohexylphosphino-2',6'-diisopropoxy-1,1'-biphenyl)[2-(2'-amino-1,1'-biphenyl)]palladium(II) methanesulfonate) (0.011 g, 0.01 mmol), cesium fluoride (0.099 g, 0.65 mmol), and tributyl(prop-1-ynyl)stannane (0.107 g, 0.32 mmol) in 1,4-dioxane (4 mL) was heated with microwave irradiation for 1 h at 160° C. The reaction mixture was cooled to room temperature, passed through a short pad of Celite and concentrated under vacuum. The residue was purified via preparative thin layer chromatography (eluting with 1:5, ethyl acetate/petroleum ether). The product was further purified by preparative-HPLC with the following conditions (Waters I): Column, SunFire Prep C18, 5 um, 19×100 mm; mobile phase, water (0.05% ammonium bicarbonate) and acetonitrile (50% to 100% acetonitrile in 10 min, flow rate: 20 mL/min); Detector: UV 220&254 nm. This afforded (S)-cyclopropyl(2-methyl-5-phenoxy-6-(prop-1-ynyl)-3,4-dihydroquinolin-1(2H)-yl)methanone (0.011 g, 26%) as a light brown semi-solid. ¹H NMR (400 MHz, CD₃OD) δ ppm 0.65-0.85 (m, 1H), 1.02-0.87 (m, 2H), 1.03-1.22 (m, 4H), 1.37-1.51 (m, 1H), 1.82 (s, 3H), 1.88-2.03 (m, 1H), 2.07-2.42 (m, 2H), 2.58-2.82 (m, 1H), 4.85-4.72 (m, 1H), 6.78 (d, J=7.80 Hz, 2H) 7.00 (t, J=7.50 Hz, 1H), 7.25-7.31 (m, 4H). MS (ESI, pos. ion) m/z 346 [M+H]⁺.

Example 94

(S)-cyclopropyl(2-methyl-5-phenoxy-6-(4-(piperidin-4-yl)-1H-pyrazol-1-yl)-3,4-dihydroquinolin-1(2H)-yl)methanone (I-348)

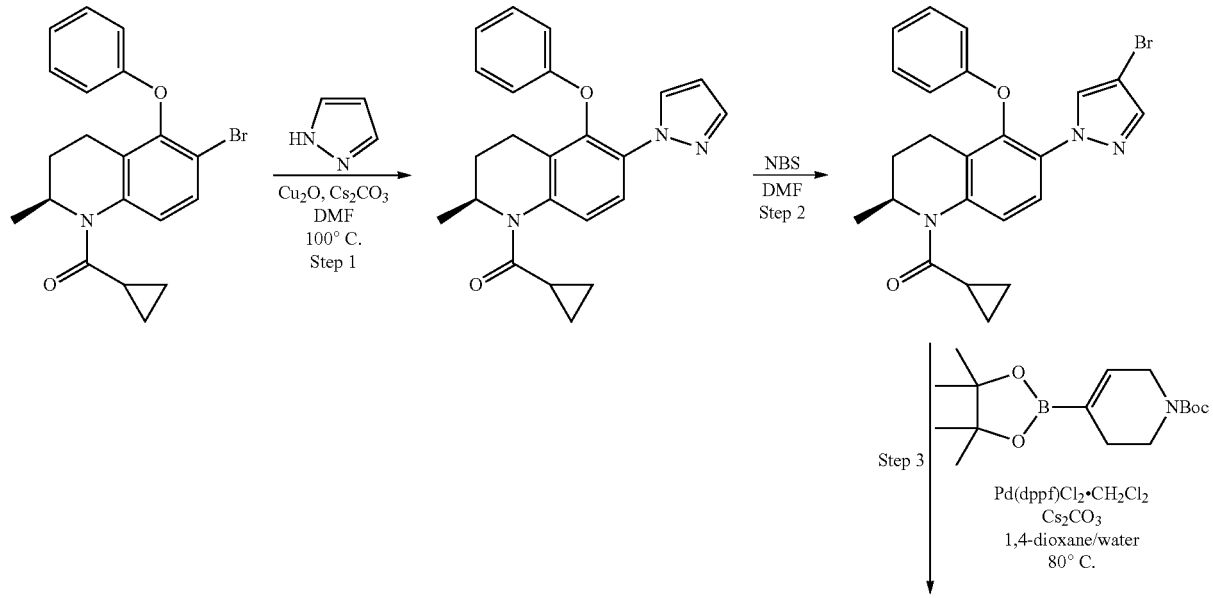

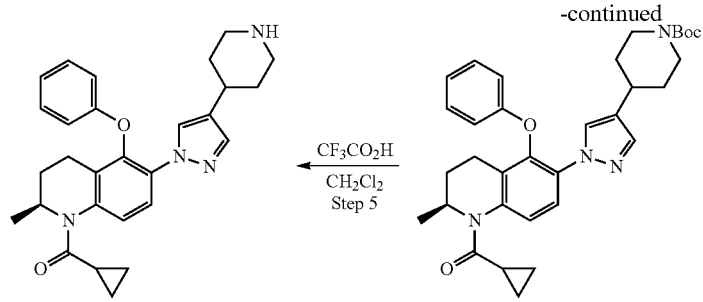
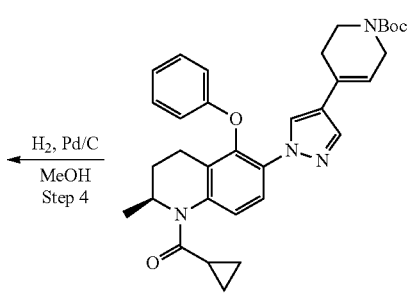

Step 1. (S)-cyclopropyl(2-methyl-5-phenoxy-6-(1H-pyrazol-1-yl)-3,4-dihydroquinolin-1(2H)-yl)methanone A mixture of (S)-(6-bromo-2-methyl-5-phenoxy-3,4-dihydroquinolin-1 (2H)-yl)(cyclopropyl)methanone (0.300 g, 0.78 mmol), 1H-pyrazole (0.053 g, 0.78 mmol), copper (I) oxide (0.056 g, 0.39 mmol), cesium carbonate (0.508 g, 1.56 mmol) in N,N-dimethylformamide (5 mL) stirred for 18 h at 100° C. The resulting mixture was cooled to room temperature, diluted with water (20 mL) and extracted with ethyl acetate (3×20 mL). The combined organic layers were dried over anhydrous sodium sulfate, filtered, and concentrated under vacuum. The residue was purified via preparative thin layer chromatography (eluting with 1:10, ethyl acetate/petroleum ether) to afford (S)-cyclopropyl(2-methyl-5-phenoxy-6-(1H-pyrazol-1-yl)-3,4-dihydroquinolin-1 (2H)-yl)methanone (0.050 g, 17%) as a yellow solid. MS (ESI, pos. ion) m/z 374 [M+H]$^+$.

Step 2. (S)-(6-(4-bromo-1H-pyrazol-1-yl)-2-methyl-5-phenoxy-3,4-dihydroquinolin-1(2H)-yl)(cyclopropyl)methanone N-Bromosuccinimide (0.025 g, 0.15 mmol) was added to a solution of (S)-cyclopropyl(2-methyl-5-phenoxy-6-(1H-pyrazol-1-yl)-3,4-dihydroquinolin-1 (2H)-yl)methanone (0.050 g, 0.13 mmol) in N,N-dimethylformamide (2 mL), and the resulting solution stirred overnight at room temperature. The reaction mixture was diluted with water (5 mL) and extracted with ethyl acetate (3×10 mL). The combined organic layers were dried over anhydrous sodium sulfate, filtered, and concentrated under vacuum. The residue was purified via preparative thin layer chromatography (eluting with 1:10, ethyl acetate/petroleum ether) to afford (S)-(6-(4-bromo-1H-pyrazol-1-yl)-2-methyl-5-phenoxy-3,4-dihydroquinolin-1(2H)-yl)(cyclopropyl)methanone (0.055 g, 91%) as yellow oil. MS (ESI, pos. ion) m/z 452, 454 [M+H]$^+$.

Step 3. (S)-tert-butyl 4-(1-(1-(cyclopropanecarbonyl)-2-methyl-5-phenoxy-1,2,3,4-tetrahydroquinolin-6-yl)-1H-pyrazol-4-yl)-5,6-dihydropyridine-1(2H)-carboxylate A mixture of (S)-(6-(4-bromo-1H-pyrazol-1-yl)-2-methyl-5-phenoxy-3,4-dihydroquinolin-1(2H)-yl)(cyclopropyl)methanone (0.060 g, 0.14 mmol), tert-butyl 4-(tetramethyl-1,3,2-dioxaborolan-2-yl)-1,2,3,6-tetrahydropyridine-1-carboxylate (0.049 g, 0.16 mmol), [1,1'-bis(diphenylphosphino)ferrocene]dichloropalladium(II) dichloromethane adduct (0.011 g, 0.01 mmol), and cesium carbonate (0.085 g, 0.26 mmol) in 1,4-dioxane (8 mL) and water (2 mL) stirred overnight at 80° C. The reaction mixture was cooled to room temperature, passed through a short pad of Celite, and concentrated under vacuum. The residue was purified via preparative thin layer chromatography (eluting with 50% ethyl acetate/petroleum ether) afforded (S)-tert-butyl 4-(1-(1-(cyclopropanecarbonyl)-2-methyl-5-phenoxy-1,2,3,4-tetrahydroquinolin-6-yl)-1H-pyrazol-4-yl)-5,6-dihydropyridine-1(2H)-carboxylate (0.050 g, 68%) as a white solid. MS (ESI, pos. ion) m/z 555 [M+H]$^+$.

Step 4. (S)-tert-butyl 4-(1-(1-(cyclopropanecarbonyl)-2-methyl-5-phenoxy-1,2,3,4-tetrahydroquinolin-6-yl)-1H-pyrazol-4-yl)piperidine-1-carboxylate A mixture of (5)-tert-butyl 4-(1-(1-(cyclopropanecarbonyl)-2-methyl-5-phenoxy-1,2,3,4-tetrahydroquinolin-6-yl)-1H-pyrazol-4-yl)-5,6-dihydropyridine-1(2H)-carboxylate (0.050 g, 0.09 mmol) and palladium on charcoal (10% wt %, 0.040 g) in methanol (15 mL) stirred under an atmosphere of hydrogen for 20 min at room temperature. The reaction mixture was filtered and concentrated under vacuum to afford (S)-tert-butyl 4-(1-(1-(cyclopropanecarbonyl)-2-methyl-5-phenoxy-1,2,3,4-tetrahydroquinolin-6-yl)-1H-pyrazol-4-yl)piperidine-1-carboxylate (0.048 g, 99%) as a white solid. MS (ESI, pos. ion) m/z 557 [M+H]$^+$.

Step 5. (S)-cyclopropyl(2-methyl-5-phenoxy-6-(4-(piperidin-4-yl)-1H-pyrazol-1-yl)-3,4-dihydroquinolin-1(2H)-yl)methanone Trifluoroacetic acid (3 mL) was added to a solution of tert-butyl (S)-tert-butyl 4-(1-(1-(cyclopropanecarbonyl)-2-methyl-5-phenoxy-1,2,3,4-tetrahydroquinolin-6-yl)-1H-pyrazol-4-yl)piperidine-1-carboxylate (0.048 g, 0.09 mmol) in dichloromethane (10 mL), and the resulting solution stirred for 20 min at room temperature. The pH of the solution was adjusted to 8 with saturated aqueous potassium carbonate solution, and the resulting solution was extracted with dichloromethane (2×10 mL). The combined organic layers were dried over anhydrous sodium sulfate, filtered, and concentrated under vacuum. The residue was purified by preparative-HPLC with the following conditions (Waters I): Column, SunFire Prep C18, 5 um, 19×100 mm; mobile phase, water (0.05% ammonium bicarbonate) and acetonitrile (20% to 50% acetonitrile in 10 min, flow rate: 20 mL/min); Detector, UV 220&254 nm. This afforded (S)-cyclopropyl(2-methyl-5-phenoxy-6-(4-(piperidin-4-yl)-1H-pyrazol-1-yl)-3,4-dihydroquinolin-1(2H)-yl)methanone (0.0095 g, 24%) as a light yellow solid. $^1$H NMR (400 MHz, CDCl$_3$) δ ppm 0.65-0.78 (m, 1H), 0.89-0.99 (m, 2H), 1.03-1.16 (m, 4H), 1.28-1.45 (m, 3H), 1.61-1.82 (m, 2H), 1.83-2.02 (m, 1H), 2.18-2.22 (m, 1H), 2.24-2.38 (m, 1H), 2.45-2.62 (m, 3H), 2.68-2.82 (m, 1H), 2.88-3.01 (m, 2H), 4.69-4.78 (m, 1H), 6.64 (d, J=8.80

Hz, 2H), 6.84 (t, J=7.60 Hz, 1H), 7.08-7.11 (m, 2H), 7.42-7.28 (m, 2H), 7.38 (d, J=8.80 Hz, 1H), 7.48 (s, 1H). MS (ESI, pos. ion) m/z 457 [M+H]

Example 95

(S)-methyl 5-cyclobutoxy-6-(2-(3-fluoroazetidin-3-yl)thiazol-4-yl)-2-methyl-3,4-dihydroquinoline-1(2H)-carboxylate (I-349)

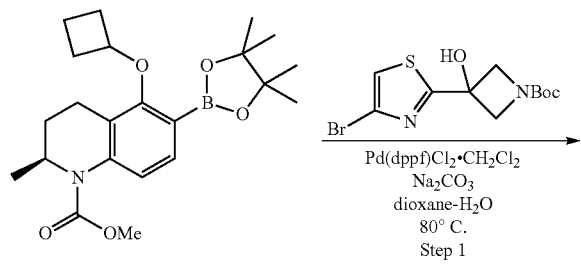

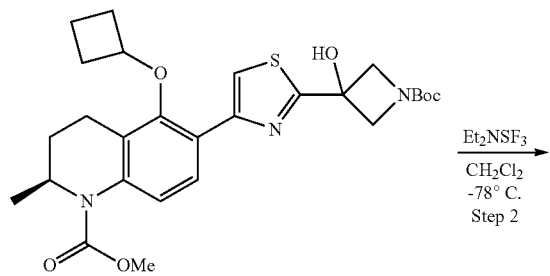

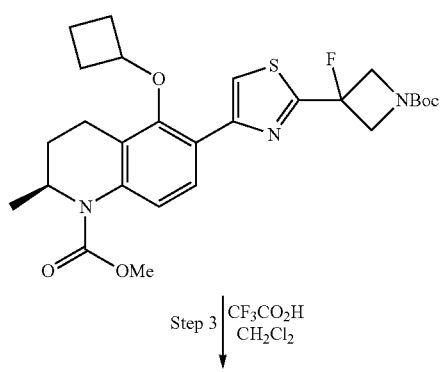

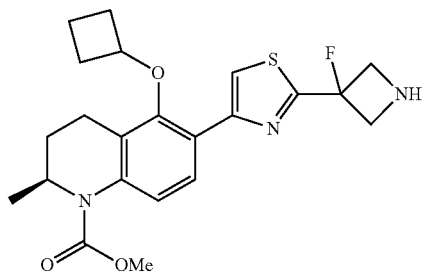

Step 1. (S)-methyl 6-(2-(1-(tert-butoxycarbonyl)-3-hydroxyazetidin-3-yl)thiazol-4-yl)-5-cyclobutoxy-2-methyl-3,4-dihydroquinoline-1(2H)-carboxylate A solution of (S)-methyl 5-cyclobutoxy-2-methyl-6-(4,4,5,5-tetramethyl-1,3,2-dioxaborolan-2-yl)-3,4-dihydroquinoline-1(2H)-carboxylate (0.400 g, 1.00 mmol), tert-butyl 3-(4-bromothiazol-2-yl)-3-hydroxyazetidine-1-carboxylate (0.367 g, 1.10 mmol), sodium carbonate (0.212 g, 2.00 mmol), and [1,1'-bis(diphenylphosphino)ferrocene]dichloropalladium(II) dichloromethane adduct (0.082 g, 0.10 mmol) in 1,4-dioxane (10 mL) and water (3 mL) stirred overnight at 80° C. The reaction mixture was cooled to room temperature, filtered through a pad of Celite, and concentrated under vacuum. The residue was purified via column chromatography on silica gel (eluting with 30% ethyl acetate/petroleum ether) to afford (S)-methyl 6-(2-(1-(tert-butoxycarbonyl)-3-hydroxyazetidin-3-yl)thiazol-4-yl)-5-cyclobutoxy-2-methyl-3,4-dihydroquinoline-1(2H)-carboxylate (0.366 g, 69%) as a yellow solid. MS (ESI, pos. ion) m/z 530 [M+H]$^+$.

Step 2. (S)-methyl 6-(2-(1-(tert-butoxycarbonyl)-3-fluoroazetidin-3-yl)thiazol-4-yl)-5-cyclobutoxy-2-methyl-3,4-dihydroquinoline-1(2H)-carboxylate (Diethylamino)sulfur trifluoride (DAST) (0.152 g, 0.94 mmol) was added to a −78° C. solution of (S)-methyl 6-(2-(1-(tert-butoxycarbonyl)-3-hydroxyazetidin-3-yl)thiazol-4-yl)-5-cyclobutoxy-2-methyl-3,4-dihydroquinoline-1(2H)-carboxylate (0.100 g, 0.19 mmol) in dichloromethane (4 mL), and the resulting solution stirred for 2 h at −78° C. The reaction mixture was poured into saturated aqueous sodium bicarbonate solution (20 mL) and extracted with dichloromethane (3×20 mL). The combined organic layers were dried over anhydrous sodium sulfate, filtered, and concentrated under vacuum. The residue was purified via preparative thin layer chromatography (eluting with 30% ethyl acetate/petroleum ether) to afford (S)-methyl 6-(2-(1-(tert-butoxycarbonyl)-3-fluoro azetidin-3-yl)thiazol-4-yl)-5-cyclobutoxy-2-methyl-3,4-dihydroquinoline-1(2H)-carboxylate (0.059 g, 59%) as a yellow solid. MS (ESI, pos. ion) m/z 532 [M+H]$^+$.

Step 3. (S)-methyl 5-cyclobutoxy-6-(2-(3-fluoroazetidin-3-yl)thiazol-4-yl)-2-methyl-3,4-dihydroquinoline-1(2H)-carboxylate Trifluoroacetic acid (1 mL) was added to a solution of (S)-methyl 6-(2-(1-(tert-butoxycarbonyl)-3-fluoro azetidin-3-yl)thiazol-4-yl)-5-cyclobutoxy-2-methyl-3,4-dihydroquinoline-1(2H)-carboxylate (0.059 g, 0.11 mmol) in dichloromethane (3 mL), and the resulting solution stirred for 2 h at room temperature and was then concentrated under vacuum. The residue was purified by preparative-HPLC with the following conditions (Waters I): Column, XBridge C18, 19×150 mm, 5 um; Mobile phase: water (0.05% ammonium bicarbonate) and acetonitrile (5% to 95% acetonitrile in 8 min; flow rate: 20 mL/min); Detector, UV 220&254 nm. This afforded (S)-methyl 5-cyclobutoxy-6-(2-(3-fluoro azetidin-3-yl)thiazol-4-yl)-2-methyl-3,4-dihydroquinoline-1(2H)-carboxylate (0.025 g, 53%) as a white solid. $^1$H NMR (400 MHz, CD$_3$OD) δ ppm 1.20 (d, J=6.40 Hz, 3H), 1.31-1.40 (m, 1H), 1.45-1.55 (m, 1H), 1.55-1.66 (m, 1H), 2.02-2.18 (m, 4H), 2.22-2.31 (m, 1H), 2.49-2.55 (m, 1H), 2.95-3.06 (m, 1H), 3.80 (s, 3H), 4.08-4.20 (m, 3H), 4.28-4.36 (m, 2H), 4.56-4.64 (m, 1H), 7.24-7.27 (m, 1H), 7.67-7.73 (m, 2H). MS (ESI, pos. ion) m/z 432 [M+H]⁺.

Example 96

(S)-methyl 5-cyclobutoxy-6-(2-(3-methoxyazetidin-3-yl)thiazol-4-yl)-2-methyl-3,4-dihydroquinoline-1(2H)-carboxylate (I-350)

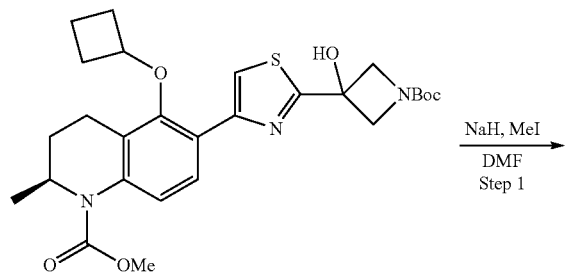

Step 1. (S)-methyl 6-(2-(1-(tert-butoxycarbonyl)-3-methoxyazetidin-3-yl)thiazol-4-yl)-5-cyclobutoxy-2-methyl-3,4-dihydroquinoline-1(2H)-carboxylate Sodium hydride (60% dispersion in mineral oil, 0.012 g, 0.30 mmol) was added to a solution of (S)-methyl 6-(2-(1-(tert-butoxycarbonyl)-3-hydroxyazetidin-3-yl)thiazol-4-yl)-5-cyclobutoxy-2-methyl-3,4-dihydroquinoline-1(2H)-carboxylate (0.100 g, 0.19 mmol) in N,N-dimethylformamide (2 mL), and the resulting mixture was stirred for 30 min at room temperature. Methyl iodide (0.014 mL, 0.23 mmol) was added, and the resulting mixture s stirred overnight at room temperature. The reaction mixture was poured into 10 mL of water, extracted with 3×10 mL of ethyl acetate. The organic layers were combined, dried over anhydrous sodium sulfate and concentrated under vacuum. The residue was purified by Prep-TLC with ethyl acetate/petroleum ether (13). This resulted in 70 mg (68%) of (S)-methyl 6-(2-(1-(tert-butoxycarbonyl)-3-methoxyazetidin-3-yl)thiazol-4-yl)-5-cyclobutoxy-2-methyl-3,4-dihydroquinoline-1(2H)-carboxylate as colorless oil. MS (ESI, pos. ion) m/z 544 [M+H]⁺.

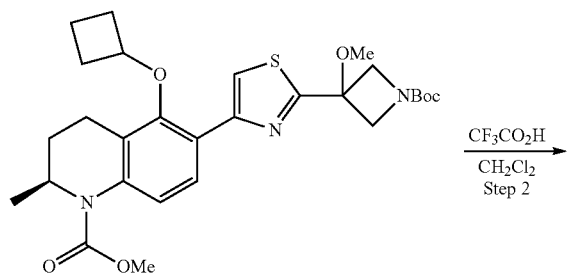

Step 2. (S)-methyl 5-cyclobutoxy-6-(2-(3-methoxyazetidin-3-yl)thiazol-4-yl)-2-methyl-3,4-dihydroquinoline-1(2H)-carboxylate Trifluoroacetic acid (1 mL) was added to a solution of (S)-methyl 6-(2-(1-(tert-butoxycarbonyl)-3-methoxyazetidin-3-yl)thiazol-4-yl)-5-cyclobutoxy-2-methyl-3,4-dihydroquinoline-1(2H)-carboxylate (0.070 g, 0.13 mmol) in dichloromethane (3 mL), and the resulting solution stirred for 2 h at room temperature. The reaction mixture was concentrated under vacuum, and the residue was purified by preparative-HPLC with the following conditions (Waters I): Column, Xbridge C18, 5 um, 19×150 nm; Mobile phase water (0.05% ammonium bicarbonate) and acetonitrile (25% to 65% acetonitrile in 10 min; flow rate: 20 mL/min); Detector, 220&254 nm. This afforded (S)-methyl 5-cyclobutoxy-6-(2-(3-methoxyazetidin-3-yl)thiazol-4-yl)-2-methyl-3,4-dihydroquinoline-1(2H)-carboxylate (0.037 g, 65%) as an off-white solid. ¹H NMR (400 MHz, CD3OD) 1.20 (d, J=6.80 Hz, 3H), 1.25-65 (m, 3H), 1.95-2.20 (m, 4H), 2.20-2.31 (m, 1H), 2.45-2.55 (m, 1H), 2.90-3.01 (m, 1H), 3.30 (s, 3H), 3.80 (s, 3H), 3.92-3.98 (m, 2H), 4.10-4.22 (m, 3H), 4.55-4.62 (m, 1H), 7.36 (d, J=8.40 Hz, 1H), 7.82 (d, J=8.40 Hz, 1H), 7.95 (s, 1H). MS (ESI, pos. ion) m/z 444 [M+H]⁺.

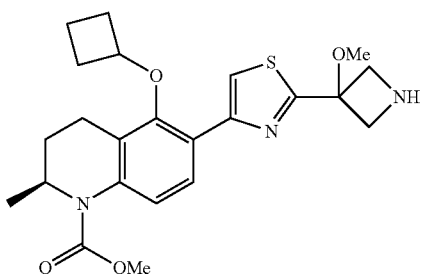

Example 97

(S,E)-1-(6-(1-cyclopropyl-1H-pyrazol-4-yl)-2-methyl-5-(1-(prop-1-enyl)-1H-benzo[d]imidazol-2-yloxy)-3,4-dihydroquinolin-1(2H)-yl)ethanone (I-351) and (S,Z)-1-(6-(1-cyclopropyl-1H-pyrazol-4-yl)-2-methyl-5-(1-(prop-1-enyl)-1H-benzo[d]imidazol-2-yloxy)-3,4-dihydroquinolin-1(2H)-yl)ethanone (I-352)

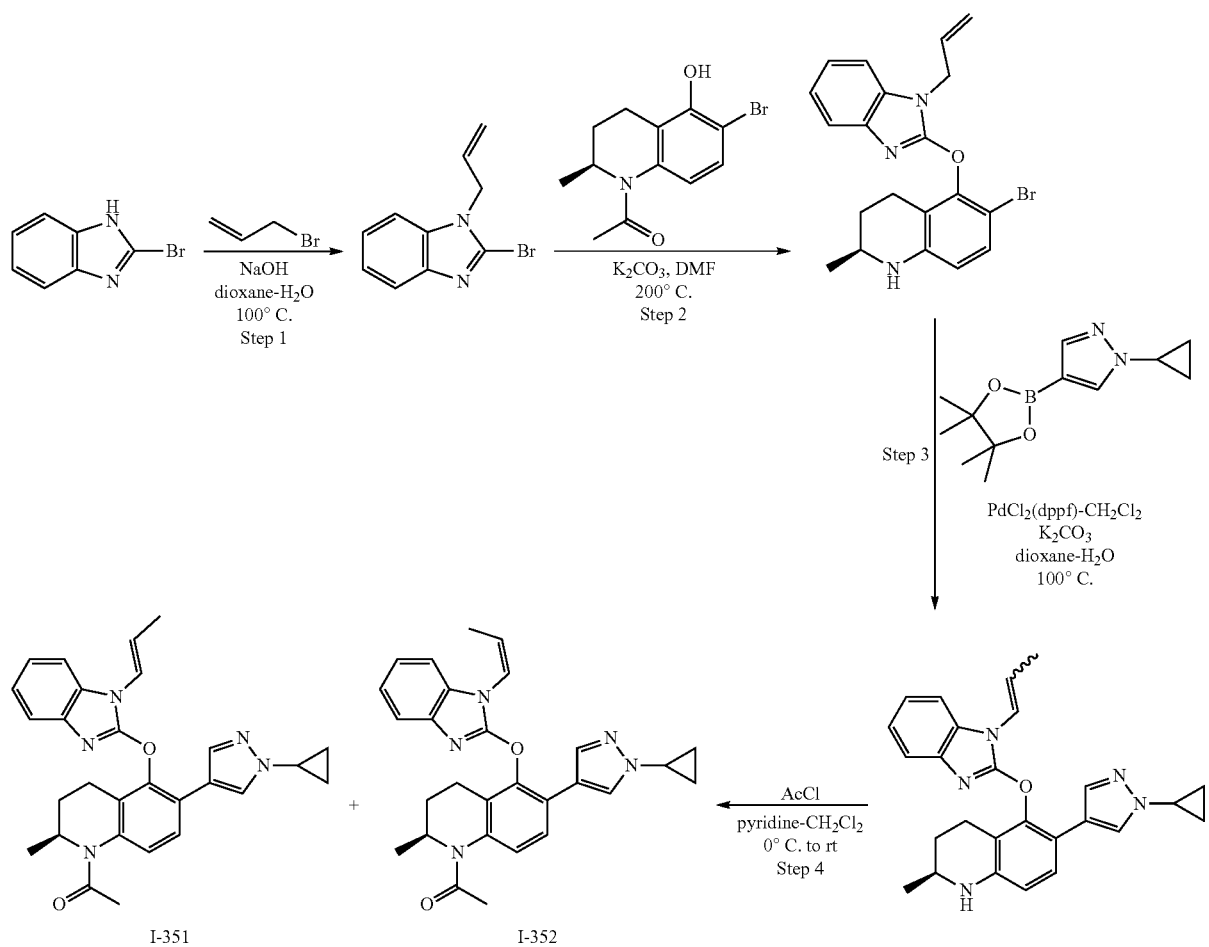

Step 1. 1-allyl-2-bromo-1H-benzo[d]imidazole

A mixture of 2-bromo-1H-benzo[d]imidazole (0.400 g, 2.04 mmol), allyl bromide (0.35 mL, 4.08 mmol), 1,4-dioxane (15 mL), and 2 M aqueous sodium hydroxide solution (15 mL, 3.00 mmol) stirred for 2 h at 100° C. The reaction mixture was cooled to room temperature and diluted with ethyl acetate (50 mL). The organic phase was separated and washed with brine (30 mL), dried over anhydrous sodium sulfate, filtered, and concentrated under vacuum. The residue was purified via preparative thin layer chromatography (eluting with 20% ethyl acetate/petroleum ether) to afford 1-allyl-2-bromo-1H-benzo[d]imidazole (0.251 g, 52%) as a yellow oil. MS (ESI, pos. ion) m/z 237, 239 [M+H]+.

Step 2. (S)-5-(1-allyl-1H-benzo[d]imidazol-2-yloxy)-6-bromo-2-methyl-1,2,3,4-tetrahydroquinoline A mixture of (S)-1-(6-bromo-5-hydroxy-2-methyl-3,4-dihydroquinolin-1(2H)-yl)ethanone (0.200 g, 0.71 mmol), 1-allyl-2-bromo-1H-benzo[d]imidazole (0.340 g, 1.44 mmol), and potassium carbonate (0.293 g, 2.12 mmol) in N,N-dimethylacetamide (10 mL) was heated in the microwave for 2 h at 200° C. The reaction mixture was cooled to room temperature, filtered, and concentrated under vacuum. The residue was purified via preparative thin layer chromatography (eluting with 20% ethyl acetate/petroleum ether) to afford (S)-5-(1-allyl-1H-benzo[d]imidazol-2-yloxy)-6-bromo-2-methyl-1,2,3,4-tetrahydroquinoline (0.115 g, 41%) of as a light yellow solid. MS (ESI, pos. ion) m/z 398, 400 [M+H]+.

Step 3. (E/Z)—(S)-6-(1-cyclopropyl-1H-pyrazol-4-yl)-2-methyl-5-((1-(prop-1-en-1-yl)-1H-benzo[d]imidazol-2-yl)oxy)-1,2,3,4-tetrahydroquinoline A mixture of (S)-5-(1-allyl-1H-benzo[d]imidazol-2-yloxy)-6-bromo-2-methyl-1,2,3,4-tetrahydroquinoline (0.115 g, 0.29 mmol), 1-cyclopropyl-4-(4,4,5,5-tetramethyl-1,3,2-dioxaborolan-2-yl)-1H-pyrazole (0.269 g, 1.15 mmol), potassium carbonate (0.118 g, 0.85 mmol), and [1,1'-bis(diphenylphosphino)ferrocene]dichloropalladium(II) dichloromethane adduct (0.023 g, 0.03 mmol) in 1,4-dioxane (10 mL) and water (3 mL) stirred for 3 h at 100° C. The reaction mixture was cooled to room temperature, filtered through a short pad of Celite and concentrated under vacuum. The residue was purified via preparative thin layer chromatography (eluting with 1:2, ethyl acetate/petroleum ether) to afford (S)-6-(1-cyclopropyl-1H-pyrazol-4-yl)-2-methyl-5-((1-(prop-1-en-1-yl)-1H-benzo[d]imidazol-2-yl)oxy)-1,2,3,4-tetrahydroquinoline (0.106 g, 86%) as a red oil which is mixture of E and Z isomers. MS (ESI, pos. ion) m/z 426 [M+H]$^+$.

Step 4. E- and Z—(S)-1-(6-(1-cyclopropyl-1H-pyrazol-4-yl)-2-methyl-5-(1-(prop-1-enyl)-1H-benzo[d]imidazol-2-yloxy)-3,4-dihydroquinolin-1(2H)-yl)ethanone Acetyl chloride (0.035 mL, 0.49 mmol) was added dropwise to a 0° C. solution of E- and Z—(S)-6-(1-cyclopropyl-1H-pyrazol-4-yl)-2-methyl-5-(1-(prop-1-enyl)-1H-benzo[d]imidazol-2-yloxy)-1,2,3,4-tetrahydroquinoline (0.070 g, 0.16 mmol) and pyridine (0.029 mL, 0.36 mmol) in dichloromethane (20 mL). The resulting solution was for 2 h at room temperature and was then concentrated under vacuum. The residue was purified by preparative-HPLC with the following conditions (Waters I): Column, Xbridge Prep C18, 19×150 mm; mobile phase, water (0.05% ammonium bicarbonate) and acetonitrile (37% to 56% acetonitrile in 10 min, flow rate: 20 mL/min); Detector, UV220&254 nm. This afforded (S,E)-1-(6-(1-cyclopropyl-1H-pyrazol-4-yl)-2-methyl-5-(1-(prop-1-enyl)-1H-benzo[d]imidazol-2-yloxy)-3,4-dihydroquinolin-1(2H)-yl)ethanone (2.6 mg, 3%) as a light yellow solid. (I-351) $^1$H NMR (300 MHz, CD$_3$OD) δ ppm 0.92-1.00 (m, 4H), 1.19 (d, J=6.60 Hz, 3H), 1.51 (br s, 1H), 1.71-1.80 (m, 3H), 2.15-2.30 (m, 4H), 2.31-2.45 (m, 1H), 2.67-2.81 (m, 1H), 3.51-3.65 (m, 1H), 4.70-4.92 (m, 1H), 6.11-6.25 (m, 1H), 6.70-6.79 (m, 1H), 7.10-7.25 (m, 3H), 7.29-7.45 (m, 2H), 7.54 (d, J=8.40 Hz, 1H), 7.66 (s, 1H), 7.86 (s, 1H). MS (ESI, pos. ion) m/z 468 [M+H]$^+$. E-Propene stereochemistry tentatively assigned.

(S,Z)-1-(6-(1-cyclopropyl-1H-pyrazol-4-yl)-2-methyl-5-(1-(prop-1-enyl)-1H-benzo[d]imidazol-2-yloxy)-3,4-dihydroquinolin-1(2H)-yl)ethanone (2.4 mg, 3%) was also obtained as a light yellow solid. (I-352). $^1$H NMR (300 MHz, CD$_3$OD) δ ppm 0.88-1.00 (m, 4H), 1.18 (d, J=6.60 Hz, 3H), 1.50 (br s, 1H), 2.01-2.05 (m, 3H), 2.15-2.30 (m, 4H), 2.31-2.45 (m, 1H), 2.65-2.82 (m, 1H), 3.48-3.62 (m, 1H), 4.72-4.92 (m, 1H), 6.25-6.42 (m, 1H), 7.05-7.35 (m, 4H), 7.36-7.45 (m, 1H), 7.48-7.58 (m, 2H), 7.65 (s, 1H), 7.84 (s, 1H). MS (ESI, pos. ion) m/z 468 [M+H]$^+$. Z-Propene stereochemistry tentatively assigned.

Example 98

(S)-1-(2-methyl-6-(piperidin-4-yl)-5-propoxy-3,4-dihydroquinolin-1(2H)-yl)ethan-1-one (I-353)

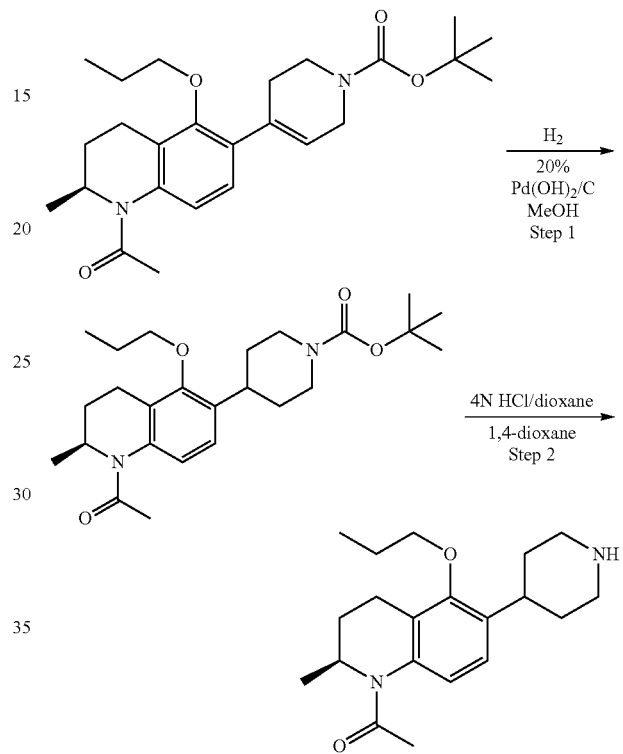

Step 1. tert-butyl (S)-4-(1-acetyl-2-methyl-5-propoxy-1,2,3,4-tetrahydroquinolin-6-yl)piperidine-1-carboxylate Balloon pressured hydrogen gas was charged into a round bottom flask containing a suspension of (S)-tert-butyl 4-(1-acetyl-2-methyl-5-propoxy-1,2,3,4-tetrahydroquinolin-6-yl)-5,6-dihydropyridine-1(2H)-carboxylate (500 mg, 1.17 mmol) and 20% palladium hydroxide on carbon (30 mg, 0.21 mmol) in methanol (10 mL). The reaction was stirred under balloon pressure for 2 hours. The reaction was vented to nitrogen and filtered through a pad of Celite. The filtered solution was concentrated in vacuo and purified via column chromatography on silica gel (Biotage 25 g column, gradient elution with 20-40% ethyl acetate-hexane) to afford tert-butyl (S)-4-(1-acetyl-2-methyl-5-propoxy-1,2,3,4-tetrahydroquinolin-6-yl)piperidine-1-carboxylate (500 mg, 100%) as a colorless oil. MS (ESI, pos. ion) m/z 432 [M+H]$^+$.

Step 2. (S)-1-(2-methyl-6-(piperidin-4-yl)-5-propoxy-3,4-dihydroquinolin-1(2H)-yl)ethan-1-one A solution of hydrogen chloride (4.0 N in 1,4-dioxane, 1.4 mL, 5.6 mmol) was added to a solution of (S)-tert-butyl 4-(1-acetyl-2-methyl-5-propoxy-1,2,3,4-tetrahydroquinolin-6-yl)piperidine-1-carboxylate (480 mg, 1.1 mmol) in 1,4-dioxane (3 mL). The reaction was stirred for 3 hours resulting in a white precipitate. The reaction solution was diluted with diethyl ether (10 mL) and the precipitate was collected by filtration. The filtrate was further washed with diethyl ether (10 mL), collected and dried in vacuo affording the hydrochloride salt of the title compound as a white powder. The salt was free based via neutralization in ethyl acetate with saturated aqueous sodium carbonate solution until a pH=7.5 was achieved. The organic layer was dried over anhydrous sodium sulfate, filtered and concentrated in vacuo affording (S)-1-(2-methyl-6-(piperidin-4-yl)-5-propoxy-3,4-dihydroquinolin-1(2H)-yl)ethan-1-one (356 mg, 97%) as a colorless solid. $^1$H NMR (300 MHz, DMSO-d$_6$) δ ppm 0.96-1.06 (m, 6H), 1.11-1.26 (m, 1H), 1.38-1.61 (m, 4H), 1.66-1.89 (m, 2H), 2.20 (s, 3H), 2.16-2.28 (m, 2H), 2.52 (m, 2H), 2.67-2.80 (m, 2H), 2.83-2.94 (m, 1H), 2.99 (br d, J=12.02 Hz, 2H), 3.58-3.72 (m, 2H), 4.40-4.63 (br d, J=6.75 Hz, 1H), 7.03 (br s, 2H). MS (ESI, pos. ion) m/z 331 [M+H]$^+$.

Example 99

(S)-1-(4-(1-acetyl-2-methyl-5-propoxy-1,2,3,4-tetrahydroquinolin-6-yl)piperidin-1-yl)ethan-1-one (I-354)

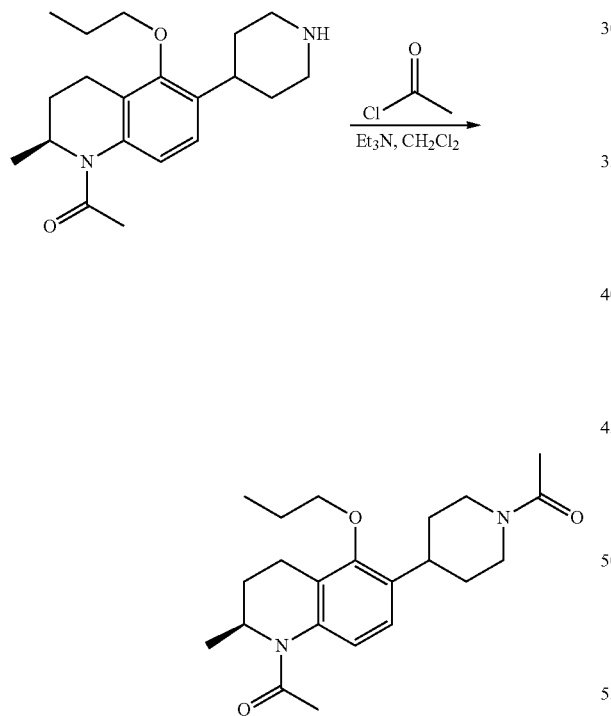

Acetyl chloride (6 µL, 0.08 mmol) was added to a solution of (S)-1-(2-methyl-6-(piperidin-4-yl)-5-propoxy-3,4-dihydroquinolin-1(2H)-yl)ethanone (26.1 mg, 0.07 mmol) and triethylamine (0.03 mL, 0.21 mmol) in dichloromethane (1.0 mL), and the reaction stirred at room temperature overnight. The reaction solution was purified directly via column chromatography on silica gel (Biotage 10 g column, gradient elution with 10-20% methanol in ethyl acetate) to afford (S)-1-(4-(1-acetyl-2-methyl-5-propoxy-1,2,3,4-tetrahydroquinolin-6-yl)piperidin-1-yl)ethan-1-one (19 mg, 71%) as an off-white solid. $^1$H NMR (300 MHz, DMSO-d$_6$) δ ppm 0.98-1.05 (m, 6H), 1.17-1.29 (m, 1H), 1.38-1.47 (m, 1H), 1.54-1.59 (m, 1H), 1.65-1.81 (m, 5H), 2.01 (s, 6H), 2.16-2.35 (m, 2H), 2.48-2.59 (m, 1H), 2.71-2.78 (m, 1H), 3.01-3.03 (m, 2H), 3.55-3.76 (m, 2H), 3.90 (br d, J=14.66 Hz, 1H), 4.52 (br d, J=13.20 Hz, 1H), 7.04 (br s, 2H). MS (ESI, pos. ion) m/z 373 [M+H]$^+$.

Example 100

(S)-1-(2-methyl-6-(1-(methylsulfonyl)piperidin-4-yl)-5-propoxy-3,4-dihydroquinolin-1(2H)-yl)ethan-1-one (I-355)

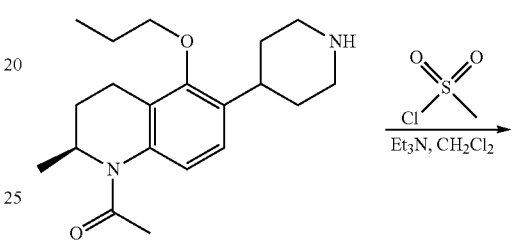

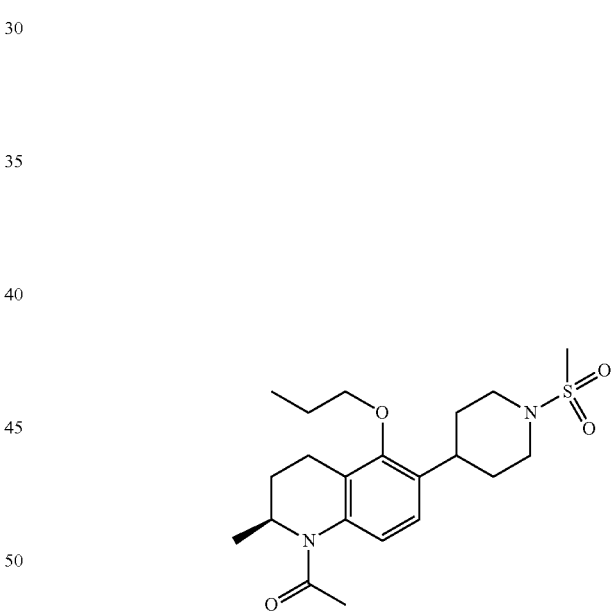

Methanesulfonyl chloride (4 µL, 0.05 mmol) was added to a solution of (S)-1-(2-methyl-6-(piperidin-4-yl)-5-propoxy-3,4-dihydroquinolin-1(2H)-yl)ethanone (17.0 mg, 0.05 mmol) and triethylamine (0.02 mL, 0.14 mmol) in dichloromethane (1.0 mL), and the reaction stirred at room temperature overnight. The reaction solution was purified directly via column chromatography on silica gel (Biotage 10 g column, gradient elution with 10-0% hexanes in ethyl acetate) to afford (S)-1-(2-methyl-6-(1-(methylsulfonyl)piperidin-4-yl)-5-propoxy-3,4-dihydroquinolin-1(2H)-yl)ethan-1-one (14 mg, 72%) as a white solid. $^1$H NMR (300 MHz, DMSO-d$_6$) δ ppm 0.98-1.04 (m, 6H), 1.19-1.26 (m, 1H), 1.58-1.81 (m, 6H), 2.02 (s, 3H), 2.17-2.30 (m, 2H), 2.68-2.85 (m, 3H), 2.89 (s, 3H), 2.89-2.99 (m, 1H), 3.60-3.76 (m, 4H), 4.57 (br d, J=6.45 Hz, 1H), 7.09 (br s, 2H). MS (ESI, pos. ion) m/z 409 [M+H]⁺.

Example 101

(S)-4-(1-acetyl-2-methyl-5-propoxy-1,2,3,4-tetrahydroquinolin-6-yl)-N-ethylpiperidine-1-carboxamide
(I-356)

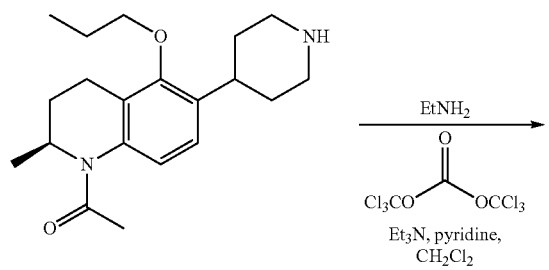

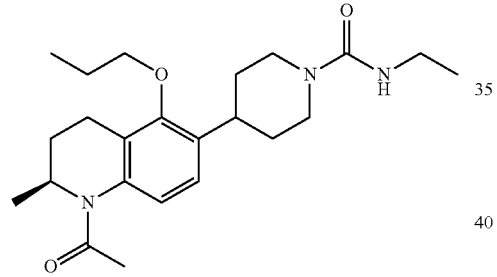

Triethylamine (0.05 mL, 0.35 mmol) was added to a solution of (S)-1-(2-methyl-6-(piperidin-4-yl)-5-propoxy-3,4-dihydroquinolin-1(2H)-yl)ethanone (20.0 mg, 0.06 mmol) in dichloromethane (5 mL). The reaction was cooled to 0° C. and triphosgene (6.3 mg, 0.02 mmol) dissolved in dichloromethane (3 mL) was added. The reaction mixture was warmed to room temperature and stirred for 3 hours. Pyridine (3 µL, 0.03 mmol) and ethylamine (2.7 mg, 0.06 mmol) were then added in sequence and the solution was stirred overnight. The reaction was quenched via the addition of water (5 mL) and 1 M citric acid (1 mL). The organic layer was collected and further washed with water (5 mL) and brine (5 mL). The organic layer was dried over anhydrous sodium sulfate, filtered and concentrated in vacuo. The residue was purified via column chromatography on silica gel (Biotage 10 g column, gradient elution with 0-5% methanol in ethyl acetate) to afford (S)-4-(1-acetyl-2-methyl-5-propoxy-1,2,3,4-tetrahydroquinolin-6-yl)-N-ethylpiperidine-1-carboxamide (15 mg, 61%) as a colorless oil. ¹H NMR (300 MHz, DMSO-d₆) δ ppm 0.97-1.05 (m, 6H), 1.15 (t, J=7.04 Hz, 3H), 1.18-1.27 (m, 1H), 1.37-1.53 (m, 2H), 1.63 (br d, J=11.73 Hz, 2H), 1.69-1.78 (m, 2H), 2.02 (s, 3H), 2.15-2.30 (m, 2H), 2.63-2.79 (m, 3H), 2.90-3.07 (m, 3H), 3.60-3.75 (m, 2H), 4.07 (br d, J=16.12 Hz, 2H), 4.50-4.62 (m, 1H), 6.45 (br t, J=5.42 Hz, 1H), 7.03 (br s, 2H). MS (ESI, pos. ion) m/z 402 [M+H]⁺.

Example 102 methyl (S)-4-(1-acetyl-2-methyl-5-propoxy-1,2,3,4-tetrahydroquinolin-6-yl)piperidine-1-carboxylate
(I-357)

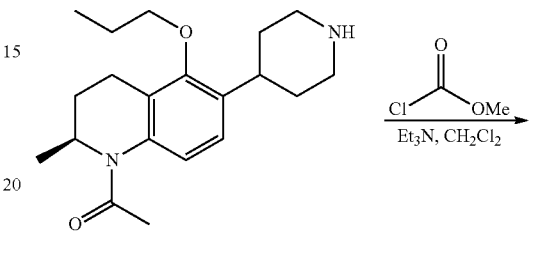

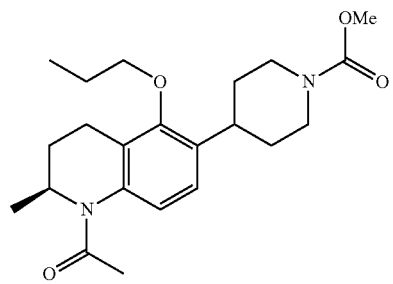

Methyl chloroformate (5 µL, 0.06 mmol) was added to a solution of (S)-1-(2-methyl-6-(piperidin-4-yl)-5-propoxy-3,4-dihydroquinolin-1(2H)-yl)ethanone (20 mg, 0.05 mmol) and triethylamine (0.04 mL, 0.27 mmol) in dichloromethane (0.5 mL), and the reaction stirred at room temperature overnight. The reaction was quenched via the addition of water (5 mL). The organic layer was collected and further washed with water (5 mL) and brine (5 mL). The organic layer was dried over anhydrous sodium sulfate, filtered and concentrated in vacuo. The residue was purified via column chromatography on silica gel (Biotage 10 g column, gradient elution with 10-20% methanol in ethyl acetate) to afford methyl (S)-4-(1-acetyl-2-methyl-5-propoxy-1,2,3,4-tetrahydroquinolin-6-yl)piperidine-1-carboxylate (19 mg, 89%) as a colorless oil. ¹H NMR (300 MHz, DMSO-d₆) δ ppm 0.94-1.07 (m, 6H), 1.17-1.26 (m, 1H), 1.43-1.57 (m, 2H), 1.60-1.79 (m, 4H), 2.01 (s, 3H), 2.16-2.31 (m, 2H), 2.68-2.91 (m, 3H), 2.95-3.03 (m, 1H), 3.58 (s, 3H), 3.61-3.73 (m, 2H), 4.04-4.15 (m, 2H), 4.56 (br d, J=6.45 Hz, 1H), 7.05 (br s, 2H). MS (ESI, pos. ion) m/z 389 [M+H]$^+$.

Example 103

(S)-1-(6-(1-ethylpiperidin-4-yl)-2-methyl-5-propoxy-3,4-dihydroquinolin-1(2H)-yl)ethan-1-one (I-358)

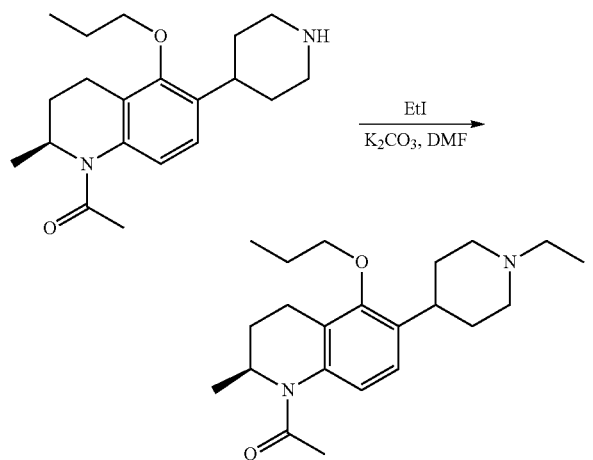

Iodoethane (5 μl, 0.06 mmol) was added to a solution of (S)-1-(2-methyl-6-(piperidin-4-yl)-5-propoxy-3,4-dihydroquinolin-1(2H)-yl)ethanone (20 mg, 0.06 mmol) and potassium carbonate (38 mg, 0.27 mmol) in DMF (1.0 mL), and the reaction was stirred at room temperature overnight. The reaction was quenched via the addition of water (5 mL) and extracted with ethyl acetate (2×10 mL). The organic layer was collected and further washed with water (5 mL) and brine (5 mL), dried over anhydrous sodium sulfate, filtered, and concentrated in vacuo. The residue was purified via column chromatography on silica gel (Biotage 10 g column, gradient elution with 50-80% methanol in ethyl acetate) to afford (S)-1-(6-(1-ethylpiperidin-4-yl)-2-methyl-5-propoxy-3,4-dihydroquinolin-1(2H)-yl)ethan-1-one (10 mg, 51%) as a light yellow oil. $^1$H NMR (300 MHz, DMSO-d$_6$) δ ppm 0.96-1.06 (m, 6H), 1.15 (t, J=7.04 Hz, 3H), 1.15-1.26 (m, 1H), 1.38-1.61 (m, 4H), 1.66-1.89 (m, 2H), 2.20 (s, 3H), 2.16-2.28 (m, 2H), 2.52 (m, 2H), 2.67-2.80 (m, 2H), 2.83-2.94 (m, 1H), 2.92-3.07 (m, 3H), 3.58-3.72 (m, 2H), 4.40-4.63 (br d, J=6.75 Hz, 1H), 7.03 (br s, 2H). MS (ESI, pos. ion) m/z 359 [M+H]$^+$.

Example 104

(S)-1-(2-methyl-5-(phenylamino)-6-(1-(piperidin-4-yl)-1H-pyrazol-4-yl)-3,4-dihydroquinolin-1(2H)-yl)ethan-1-one (I-359)

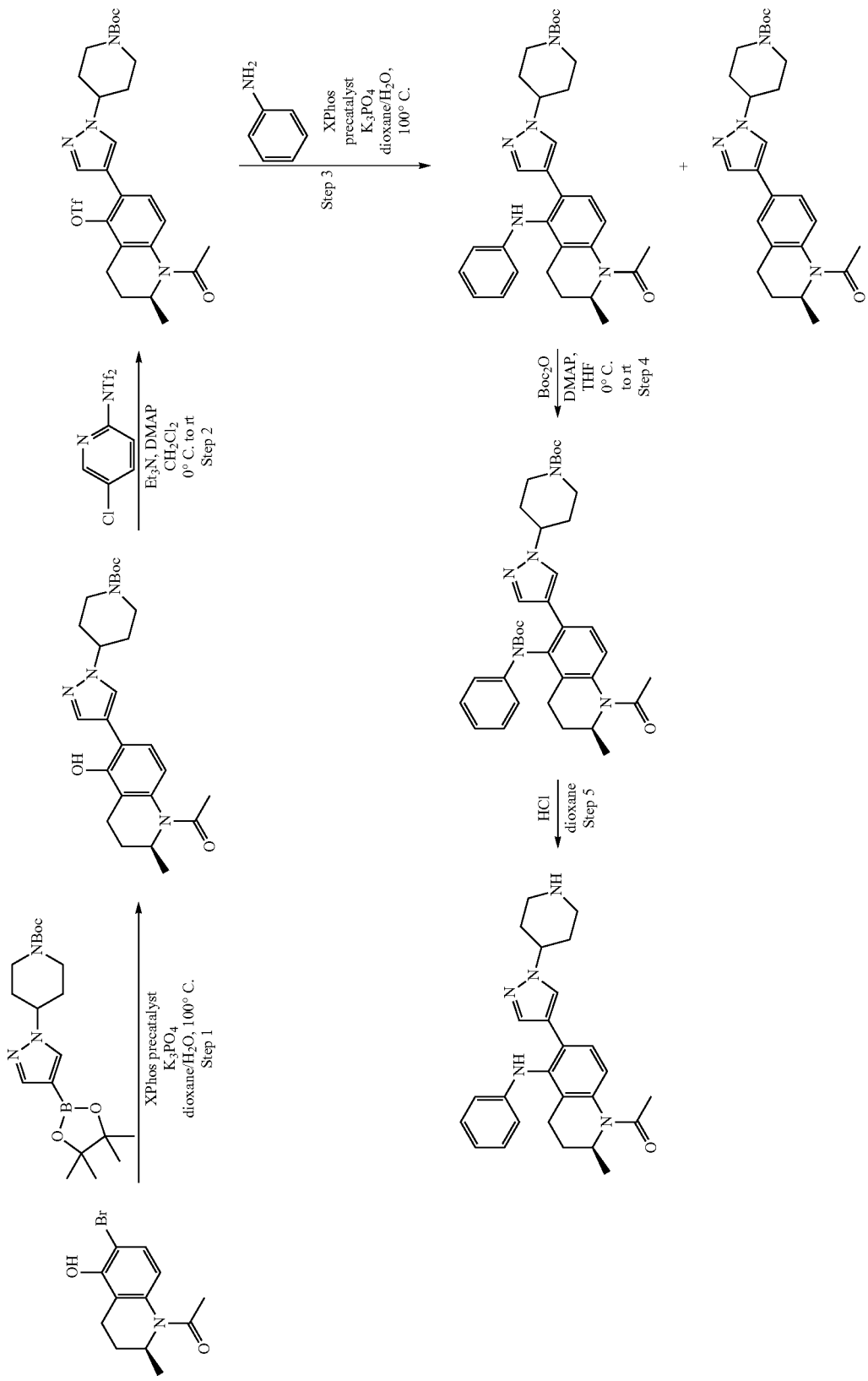

Step 1. tert-butyl (S)-4-(4-(1-acetyl-5-hydroxy-2-methyl-1,2,3,4-tetrahydroquinolin-6-yl)-1H-pyrazol-1-yl)piperidine-1-carboxylate XPhos Precatalyst 2nd Generation (0.186 g, 0.24 mmol) was added to a nitrogen purged solution of (S)-1-(6-bromo-5-hydroxy-2-methyl-3,4-dihydroquinolin-1(2H)-yl)ethanone (0.672 g, 2.36 mmol), tert-butyl 4-(4-(4,4,5,5-tetramethyl-1,3,2-dioxaborolan-2-yl)-1H-pyrazol-1-yl)piperidine-1-carboxylate (0.892 g, 2.36 mmol), and potassium phosphate (2.51 g, 11.8 mmol) in 1,4-dioxane (4.0 mL) and water (0.8 mL), and the reaction mixture was heated at 100° C. overnight. The crude reaction mixture was purified directly via column chromatography on silica gel (Biotage 25 g column, gradient elution with 30-10% hexanes in ethyl acetate) to afford tert-butyl (S)-4-(4-(1-acetyl-5-hydroxy-2-methyl-1,2,3,4-tetrahydroquinolin-6-yl)-1H-pyrazol-1-yl)piperidine-1-carboxylate (225 mg, 21%) as a white fluffy powder. MS (ESI, pos. ion) m/z 455 [M+H]$^+$.

Step 2. tert-butyl (S)-4-(4-(1-acetyl-2-methyl-5-0 (trifluoromethyl)sulfonyl)oxy)-1,2,3,4-tetrahydroquinolin-6-yl)-1H-pyrazol-1-yl)piperidine-1-carboxylate Triethylamine (0.07 mL, 0.54 mmol) and N,N-dimethylpyridin-4-amine (6.1 mg, 0.049 mmol) were added to a solution of (S)-tert-butyl 4-(4-(1-acetyl-5-hydroxy-2-methyl-1,2,3,4-tetrahydroquinolin-6-yl)-1H-pyrazol-1-yl)piperidine-1-carboxylate (225 mg, 0.495 mmol) in dichloromethane (4.5 mL). The reaction solution was cooled to 0° C. and N-(5-chloropyridin-2-yl)-1,1,1-trifluoro-N-((trifluoromethyl)sulfonyl)methanesulfonamide (214 mg, 0.544 mmol) was added dropwise (clear solution turns a light yellow orange color). The reaction mixture was then slowly warmed back up to room temperature and allowed to stir for 2 hours. The reaction solution was purified directly via column chromatography on silica gel (Biotage 25 g column, gradient elution with 0-4% MeOH in dichloromethane) to afford tert-butyl (S)-4-(4-(1-acetyl-2-methyl-5-(((trifluoromethyl)sulfonyl)oxy)-1,2,3,4-tetrahydroquinolin-6-yl)-1H-pyrazol-1-yl)piperidine-1-carboxylate (290 mg, 100%) as a white solid. MS (ESI, pos. ion) m/z 587 [M+H]$^+$.

Step 3. tert-butyl (S)-4-(4-(1-acetyl-2-methyl-5-(phenylamino)-1,2,3,4-tetrahydroquinolin-6-yl)-1H-pyrazol-1-yl)piperidine-1-carboxylate XPhos Precatalyst 2nd Generation (10.7 mg, 0.014 mmol) was added to a nitrogen purged solution of (S)-tert-butyl 4-(4-(1-acetyl-2-methyl-5-(((trifluoromethyl)sulfonyl)oxy)-1,2,3,4-tetrahydroquinolin-6-yl)-1H-pyrazol-1-yl)piperidine-1-carboxylate (40 mg, 0.068 mmol), aniline (7 μL, 0.075 mmol) and potassium phosphate (43.4 mg, 0.20 mmol) in 1,4-dioxane (0.5 mL), and the reaction mixture was heated at 100° C. overnight. The crude reaction mixture was purified directly via column chromatography on silica gel (Biotage 25 g column, gradient elution with 25-40% ethyl acetate in hexanes) to afford a mixture of tert-butyl (S)-4-(4-(1-acetyl-2-methyl-5-(phenylamino)-1,2,3,4-tetrahydroquinolin-6-yl)-1H-pyrazol-1-yl)piperidine-1-carboxylate and tert-butyl (S)-4-(4-(1-acetyl-2-methyl-1,2,3,4-tetrahydroquinolin-6-yl)-1H-pyrazol-1-yl)piperidine-1-carboxylate (31 mg) as a light yellow oil. MS (ESI, pos. ion) m/z 530 [M+H]$^+$ and 438 [M+H]$^+$.

Step 4. tert-butyl (S)-4-(4-(1-acetyl-5-((tert-butoxycarbonyl)(phenyl)amino)-2-methyl-1,2,3,4-tetrahydroquinolin-6-yl)-1H-pyrazol-1-yl)piperidine-1-carboxylate Di-tert-butyl dicarbonate (0.02 mL, 0.088 mmol) was added to a 0° C. solution containing a mixture of (S)-tert-butyl 4-(4-(1-acetyl-2-methyl-5-(phenylamino)-1,2,3,4-tetrahydroquinolin-6-yl)-1H-pyrazol-1-yl)piperidine-1-carboxylate and tert-butyl (S)-4-(4-(1-acetyl-2-methyl-1,2,3,4-tetrahydroquinolin-6-yl)-1H-pyrazol-1-yl)piperidine-1-carboxylate (31 mg, 0.059 mmol) and DMAP (7.2 mg, 0.059 mmol) in THF (1.0 mL). The reaction mixture was warmed to room temperature and stirred for 3 hours. The reaction solution was concentrated in vacuo and the crude product was purified directly via column chromatography on silica gel (Biotage 25 g column, gradient elution with 40-50% ethyl acetate in hexanes) to afford tert-butyl (S)-4-(4-(1-acetyl-5-((tert-butoxycarbonyl)(phenyl)amino)-2-methyl-1,2,3,4-tetrahydroquinolin-6-yl)-1H-pyrazol-1-yl)piperidine-1-carboxylate (29.5 mg, 80%) as a white solid. MS (ESI, pos. ion) m/z 630 [M+H]$^+$.

Step 5. (S)-1-(6-(1-ethylpiperidin-4-yl)-2-methyl-5-propoxy-3,4-dihydroquinolin-1(2H)-yl)ethan-1-one Hydrogen chloride (4 N in 1,4-dioxane, 0.024 mL, 0.095 mmol) was added to a solution of (S)-tert-butyl 4-(4-(1-acetyl-5-((tert-butoxycarbonyl)(phenyl)amino)-2-methyl-1,2,3,4-tetrahydroquinolin-6-yl)-1H-pyrazol-1-yl)piperidine-1-carboxylate (12 mg, 0.019 mmol) in dioxane (1.0 mL). The reaction solution stirred at room temperature for 1 hour resulting in a white precipitate. The reaction solution was concentrated under a stream of nitrogen, diethyl ether (1 mL) was added and the product was neutralized via the addition of saturated aqueous sodium bicarbonate (1 mL). The organic layer was collected, dried over anhydrous sodium sulfate, filtered, and concentrated in vacuo to afford (S)-1-(6-(1-ethylpiperidin-4-yl)-2-methyl-5-propoxy-3,4-dihydroquinolin-1(2H)-yl)ethan-1-one (5.1 mg, 62%) as a light yellow waxy solid. $^1$H NMR (300 MHz, DMSO-d$_6$) δ ppm 1.03 (d, J=6.74 Hz, 3H), 1.11-1.25 (m, 2H), 1.35-1.52 (m, 1H), 1.61-1.69 (m, 1H), 1.76-1.90 (m, 2H), 1.97-2.10 (m, 2H), 2.15 (s, 3H), 2.19-2.30 (m, 1H), 2.36-2.44 (m, 1H), 2.91-3.01 (m, 2H), 3.98-4.16 (m, 1H), 4.53-4.68 (m, 1H), 6.84-7.04 (m, 2H), 7.04-7.11 (m, 1H), 7.12-7.19 (m, 1H), 7.29-7.37 (m, 3H), 7.83 (s, 1H), 8.11 (s, 1H), 10.02 (br s, 1H). MS (ESI, pos. ion) m/z 430 [M+H]$^+$.

Example 105 methyl (S)-5-cyclobutoxy-6-(5-fluoro-1-(piperidin-4-yl)-1H-pyrazol-4-yl)-2-methyl-3,4-dihydroquinoline-1(2H)-carboxylate (I-360)

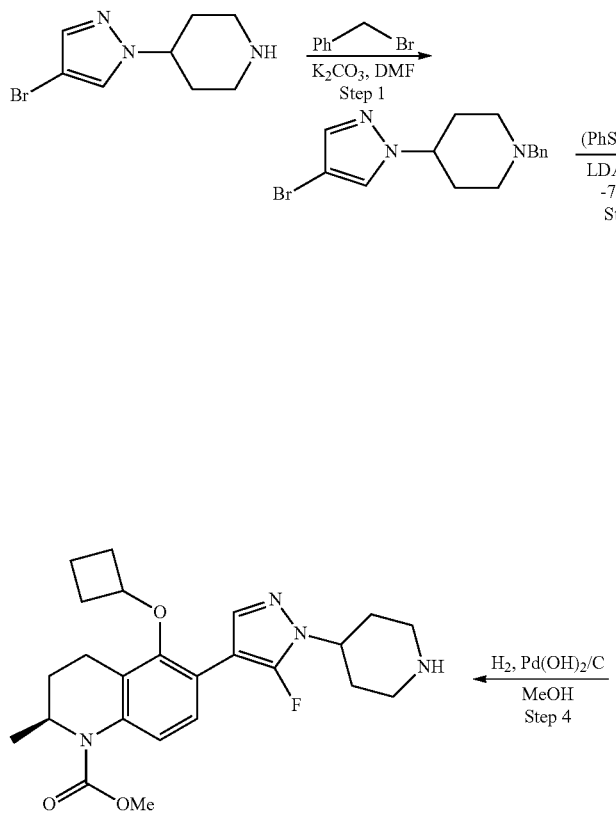

Step 1. 1-benzyl-4-(4-bromo-1H-pyrazol-1-yl)piperidine

Benzyl bromide (0.42 mL, 3.56 mmol) and potassium carbonate (670 mg, 4.85 mmol) were added to a solution of 4-(4-bromo-1H-pyrazol-1-yl)piperidine (743.7 mg, 3.23 mmol) in DMF (10 mL), and the reaction stirred at room temperature overnight. The reaction was quenched with the addition of water (50 mL) and extracted with ethyl acetate (3×50 mL). The organic extracts were combined and washed with water (2×50 mL) and brine (30 mL), dried over anhydrous sodium sulfate, filtered and concentrated in vacuo. The crude product was purified directly via column chromatography on silica gel (Biotage 25 g column, gradient elution with 20-30% ethyl acetate in hexanes) to afford 1-benzyl-4-(4-bromo-1H-pyrazol-1-yl)piperidine (673 mg, 65%) as a light yellow oil. MS (ESI, pos. ion) m/z 321 [M+H]+.

Step 2. 1-benzyl-4-(4-bromo-5-fluoro-1H-pyrazol-1-yl)piperidine

A solution of lithium diisopropylamide (1.0 M in THF/hexanes) (1.25 mL, 1.25 mmol) was slowly added to a −78° C. solution of 1-benzyl-4-(4-bromo-1H-pyrazol-1-yl)piperidine (200 mg, 0.625 mmol) in THF (2.0 mL), and the reaction was allowed to stir at −78° C. for 1 hour. N-fluoro-N-(phenylsulfonyl)benzenesulfonamide (295 mg, 0.937 mmol) was added, and the reaction stirred for an additional 1 hour at −78° C. The reaction was quenched via the addition of saturated aqueous ammonium chloride (5 mL). The reaction was warmed to room temperature and concentrated in vacuo. Ethyl acetate (25 mL) was added, and the organic solution was washed with water (2×10 mL) and brine (10 mL). The organic layer was dried over anhydrous sodium sulfate, filtered, and concentrated in vacuo. The crude product was purified directly via column chromatography on silica gel (Biotage 25 g column, gradient elution with 20-30% ethyl acetate in hexanes) to afford 1-benzyl-4-(4-bromo-5-fluoro-1H-pyrazol-1-yl)piperidine (53 mg, 25%) as a light yellow oil. MS (ESI, pos. ion) m/z 339 [M+H]+.

Step 3. methyl (S)-6-(1-(1-benzylpiperidin-4-yl)-5-fluoro-1H-pyrazol-4-yl)-5-cyclobutoxy-2-methyl-3,4-dihydroquinoline-1(2H)-carboxylate XPhos Precatalyst 2nd Generation (6.0 mg, 0.008 mmol) was added to a nitrogen purged solution of (S)-methyl 5-cyclobutoxy-2-methyl-6-(4,4,5,5-tetramethyl-1,3,2-dioxaborolan-2-yl)-3,4-dihydroquinoline-1(2H)-carboxylate (30.8 mg, 0.077 mmol), 1-benzyl-4-(4-bromo-5-fluoro-1H-pyrazol-1-yl)piperidine (26.0 mg, 0.077 mmol), and potassium phosphate (81 mg, 0.384 mmol) in 1,4-dioxane (1.00 mL) and water (0.20 mL), and the reaction mixture was heated at 100° C. overnight. The crude reaction mixture was purified directly via column chromatography on silica gel (Biotage 25 g column, gradient elution with 10-20% ethyl acetate in hexanes) to afford methyl (S)-6-(1-(1-benzylpiperidin-4-yl)-5-fluoro-1H-pyrazol-4-yl)-5-cyclobutoxy-2- methyl-3,4-dihydroquinoline-1(2H)-carboxylate (16 mg, 39%) as a white solid. MS (ESI, pos. ion) m/z 533 [M+H]+.

Step 4. methyl (S)-5-cyclobutoxy-6-(5-fluoro-1-(piperidin-4-yl)-1H-pyrazol-4-yl)-2-methyl-3,4-dihydroquinoline-1(2H)-carboxylate Balloon filled hydrogen was charged into a nitrogen purged suspension of (S)-methyl 6-(1-(1-benzylpiperidin-4-yl)-5-fluoro-1H-pyrazol-4-yl)-5-cyclobutoxy-2-methyl-3,4-dihydroquinoline-1(2H)-carboxylate (15.0 mg, 0.028 mmol) and 20% palladium hydroxide on carbon (40 mg, 0.285 mmol) in methanol (10 mL). The reaction flask was backfilled with hydrogen 3 times. The reaction solution was then stirred under a hydrogen atmosphere for 2 hours. The flask was purged with nitrogen, and the reaction mixture was filtered through of Celite and the bed of Celite was washed with ethyl acetate (10 mL). The filtered solvent was then concentrated in vacuo. The crude product was added directly to a plug of silica gel and eluted with 30% ethyl acetate in methanol to afford methyl (S)-5-cyclobutoxy-6-(5-fluoro-1-(piperidin-4-yl)-1H-pyrazol-4-yl)-2-methyl-3,4-dihydroquinoline-1 (2H)-carboxylate (7.2 mg, 58%) as an off-white solid. $^1$H NMR (300 MHz, DMSO-$d_6$) δ ppm 1.09 (d, J=6.45 Hz, 3H), 1.21-1.30 (m, 2H), 1.42-1.57 (m, 1H), 1.76-1.88 (m, 3H), 1.89-2.01 (m, 5H), 2.34-2.43 (m, 2H), 2.53-2.61 (m, 1H), 2.71-2.85 (m, 2H), 3.03 (br d, J=12.31 Hz, 1H), 3.13-3.21 (m, 1H), 3.68 (s, 3H), 3.95-4.05 (m, 1H), 4.15-4.30 (m, 1H), 4.41-4.52 (m, 1H), 7.14 (d, J=8.15 Hz, 1H), 7.29 (d, J=8.79 Hz, 1H), 7.61 (s, 1H). MS (ESI, pos. ion) m/z 443 [M+H]+.

Example 106 methyl (S)-5-cyclobutoxy-6-(1-((3S,4R)-3-fluoropiperidin-4-yl)-1H-pyrazol-4-yl)-2-methyl-3,4-dihydroquinoline-1(2H)-carboxylate (I-361)

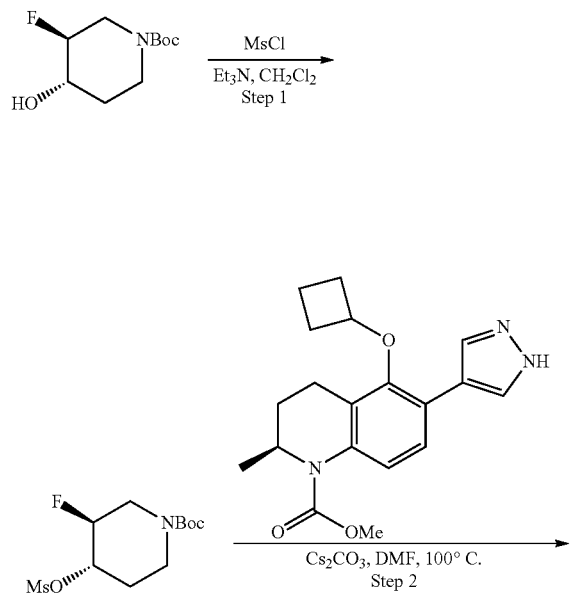

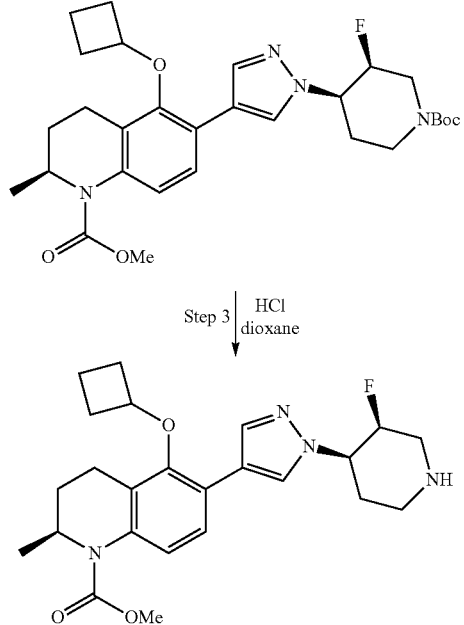

Step 1. tert-butyl (3S,4S)-3-fluoro-4-((methylsulfonyl)oxy)piperidine-1-carboxylate Triethylamine (0.95 mL, 6.8 mmol) was added to a 0° C. solution of (3S,4S)-tert-butyl 3-fluoro-4-hydroxypiperidine-1-carboxylate (500.0 mg, 2.28 mmol) and methanesulfonyl chloride (0.27 mL, 3.4 mmol) in dichloromethane (9 mL), and the resulting mixture was warmed to room temperature and stirred overnight. The reaction was quenched with saturated aqueous sodium bicarbonate (10 mL). Additional dichloromethane (10 mL) was added, and the layers were separated. The organic layer was washed with 1M aqueous citric acid (10 mL) and brine (10 mL), dried over anhydrous sodium sulfate, filtered and concentrated in vacuo. The crude product was purified directly via column chromatography on silica gel (Biotage 50 g column, gradient elution with 20-30% ethyl acetate in hexanes) to afford tert-butyl (3S,4S)-3-fluoro-4-((methylsulfonyl)oxy)piperidine-1-carboxylate (629 mg, 93%) as a colorless oil that solidified to a white solid upon standing. $^1$H NMR (300 MHz, CDCl$_3$) δ ppm 1.46 (s, 9H), 1.73-1.87 (m, 1H), 2.15-2.25 (m, 1H), 2.97-3.12 (m, 2H), 3.08 (s, 3H), 3.85-3.95 (m, 1H), 4.39-4.46 (m, 1H), 4.55-4.62 (m, 1H), 4.65-4.78 (m, 1H).

Step 2. methyl (S)-6-(1-((3S,4R)-1-(tert-butoxycarbonyl)-3-fluoropiperidin-4-yl)-1H-pyrazol-4-yl)-5-cyclobutoxy-2-methyl-3,4-dihydroquinoline-1(2H)-carboxylate (3S,4S)-tert-Butyl 3-fluoro-4-((methylsulfonyl)oxy)piperidine-1-carboxylate (96 mg, 0.322 mmol) was added to a solution of (S)-methyl 5-cyclobutoxy-2-methyl-6-(1H-pyrazol-4-yl)-3,4-dihydroquinoline-1(2H)-carboxylate (100 mg, 0.293 mmol) and cesium carbonate (153 mg, 0.469 mmol) in DMF (1.0 mL), and the reaction mixture was heated at 100° C. for 1 hour. The reaction solution was cooled to room temperature, diluted with water and extracted with ethyl acetate (3×50 mL). The combined organic layers were washed with water (2×25 mL) and brine (25 mL), dried over anhydrous sodium sulfate, filtered, and concentrated in vacuo. The crude product was purified via column chromatography on silica gel (Biotage 25 g column, gradient elution with 20-30% ethyl acetate in hexanes) to afford methyl (S)-6-(1-((3S,4R)-1-(tert-butoxycarbonyl)-3-fluoropiperidin-4-yl)-1H-pyrazol-4-yl)-5-cyclobutoxy-2-methyl-3,4-dihydroquinoline-1(2H)-carboxylate (89 mg, 56%) as a colorless oil. MS (ESI, pos. ion) m/z 543 [M+H]$^+$.

Step 3. methyl (S)-5-cyclobutoxy-6-(1-((3S,4R)-3-fluoropiperidin-4-yl)-1H-pyrazol-4-yl)-2-methyl-3,4-dihydroquinoline-1(2H)-carboxylate Hydrogen chloride (4.0 N in 1,4-dioxane, 0.23 mL, 0.931 mmol) was added to a solution of (S)-methyl 6-(1-((3S,4R)-1-(tert-butoxycarbonyl)-3-fluoropiperidin-4-yl)-1H-pyrazol-4-yl)-5-cyclobutoxy-2-methyl-3,4-dihydroquinoline-1(2H)-carboxylate (101 mg, 0.186 mmol) in 1,4-dioxane (1.0 mL), and the reaction mixture stirred at room temperature for 3 h. The reaction solution was concentrated under a stream of nitrogen, diluted with saturated aqueous sodium bicarbonate (1 mL) and extracted with ethyl acetate (3×1 mL). The combined organic layers were added directly to a plug of silica gel and eluted with 30% ethyl acetate in methanol to afford methyl (S)-5-cyclobutoxy-6-(1-((3S,4R)-3-fluoropiperidin-4-yl)-1H-pyrazol-4-yl)-2-methyl-3,4-dihydroquinoline-1(2H)-carboxylate (38 mg, 47%) as a white solid. $^1$H NMR (300 MHz, DMSO-d$_6$) δ ppm 1.07 (d, J=6.45 Hz, 3H), 1.19-1.39 (m, 2H), 1.47-1.58 (m, 1H), 1.96-2.18 (m, 8H), 2.34-2.43 (m, 2H), 2.55-2.72 (m, 1H), 2.77-2.89 (m, 2H), 3.00-3.13 (m, 1H), 3.14 (br d, J=4.98 Hz, 1H), 3.65 (s, 3H), 4.02-4.12 (m, 1H), 4.37-4.49 (m, 1H), 4.78-4.94 (m, 1H), 7.21 (d, J=8.50 Hz, 1H), 7.32 (d, J=8.79 Hz, 1H), 7.83 (s, 1H), 8.02 (s, 1H). MS (ESI, pos. ion) m/z 443 [M+H]$^+$.

The following example was made according to the procedure described above for Example 106:

methyl (2S)-5-cyclobutoxy-6-{1-[(3R,4S)-3-fluoropiperidin-4-yl]-1H-pyrazol-4-yl}-2-methyl-1,2,3,4-tetrahydroquinoline-1-carboxylate (I-362)

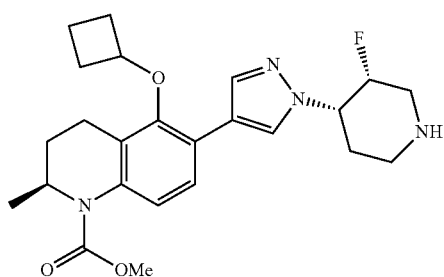 [SMILES: COC(=O)N1c2ccc(-c3cnn([C@H]4CCNC[C@H]4F)c3)c(OC3CCC3)c2CC[C@@H]1C]

$^1$H NMR (300 MHz, DMSO-d$_6$) δ ppm 1.07 (d, J=6.45 Hz, 3H), 1.19-1.39 (m, 2H), 1.47-1.58 (m, 1H), 1.96-2.18 (m, 8H), 2.34-2.43 (m, 2H), 2.55-2.72 (m, 1H), 2.77-2.89 (m, 2H), 3.00-3.13 (m, 1H), 3.14 (br d, J=4.98 Hz, 1H), 3.65 (s, 3H), 4.02-4.12 (m, 1H), 4.31-4.49 (m, 1H), 4.72-4.94 (m, 1H), 7.21 (d, J=8.50 Hz, 1H), 7.32 (d, J=8.79 Hz, 1H), 7.83 (s, 1H), 8.00 (s, 1H). MS (ESI, pos. ion) m/z 443 [M+H]$^+$.

methyl (2S)-5-cyclobutoxy-6-{1-[(3S,4S)-3-fluoropiperidin-4-yl]-1H-pyrazol-4-yl}-2-methyl-1,2,3,4-tetrahydroquinoline-1-carboxylate (I-363)

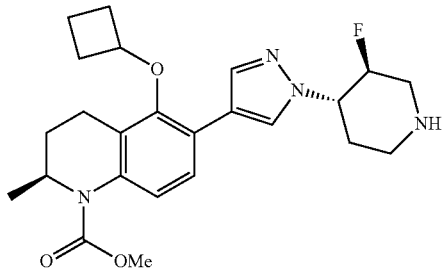 [SMILES: COC(=O)N1c2ccc(-c3cnn([C@H]4CCNC[C@@H]4F)c3)c(OC3CCC3)c2CC[C@@H]1C]

$^1$H NMR (300 MHz, DMSO-d$_6$) δ ppm 1.06 (d, J=6.45 Hz, 3H), 1.19-1.39 (m, 2H), 1.47-1.58 (m, 1H), 1.89-2.18 (m, 8H), 2.34-2.43 (m, 2H), 2.55-2.72 (m, 1H), 2.77-2.87 (m, 2H), 2.88-2.95 (m, 1H), 3.65 (s, 3H), 4.01-4.11 (m, 1H), 4.31-4.45 (m, 1H), 4.60-4.84 (m, 1H), 7.21 (d, J=8.50 Hz, 1H), 7.28 (d, J=8.79 Hz, 1H), 7.82 (s, 1H), 8.08 (s, 1H). MS (ESI, pos. ion) m/z 443 [M+H]$^+$.

methyl (2S)-5-(4-fluorophenoxy)-6-{1-[(3S,4S)-3-fluoropiperidin-4-yl]-1H-pyrazol-4-yl}-2-methyl-1,2,3,4-tetrahydroquinoline-1-carboxylate (I-364)

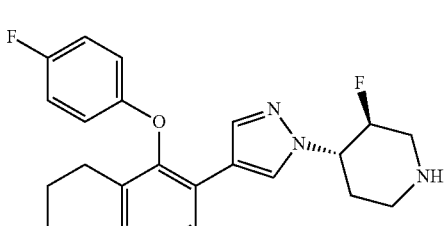

$^1$H NMR (300 MHz, DMSO-d$_6$) δ ppm 1.04 (d, J=6.74 Hz, 3H), 1.51 (dd, J=13.34, 5.72 Hz, 1H), 1.79-1.98 (m, 4H), 2.34-2.46 (m, 4H), 2.87 (br d, J=9.09 Hz, 1H), 3.19-3.29 (m, 1H), 3.70 (s, 3H), 4.17-4.35 (m, 1H), 4.50-4.77 (m, 2H), 6.73-6.77

(m, 2H), 7.06-7.12 (m, 2H), 7.54 (d, J=2.93 Hz, 2H), 7.76 (s, 1H), 8.02 (s, 1H). MS (ESI, pos. ion) m/z 483 [M+H]+.

methyl (2S)-5-(4-fluorophenoxy)-6-{1-[(3S,4R)-3-fluoropiperidin-4-yl]-1H-pyrazol-4-yl}-2-methyl-1,2,3,4-tetrahydroquinoline-1-carboxylate (I-365)

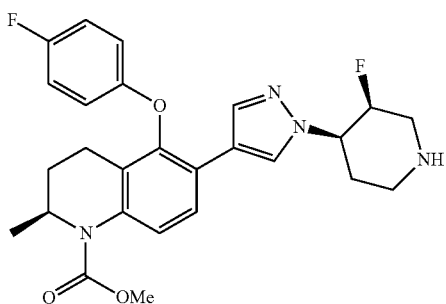 [SMILES: COC(=O)N1c2ccc(-c3cnn([C@@H]4CCNC[C@@H]4F)c3)c(Oc3ccc(F)cc3)c2CC[C@@H]1C]

$^1$H NMR (300 MHz, DMSO-d$_6$) δ ppm 1.04 (d, J=6.74 Hz, 3H), 1.51 (dd, J=13.92, 4.84 Hz, 1H), 1.71-1.80 (m, 1H), 1.90-2.04 (m, 3H), 2.34-2.46 (m, 4H), 2.93-3.10 (m, 1H), 3.11-3.19 (m, 1H), 3.70 (s, 3H), 4.27-4.42 (m, 1H), 4.48-4.57 (m, 1H), 4.65-4.84 (m, 1H), 6.72-6.76 (m, 2H), 7.06-7.12 (m, 2H), 7.51-7.61 (m, 2H), 7.76 (s, 1H), 7.94 (s, 1H). MS (ESI, pos. ion) m/z 483 [M+H]+.

methyl (2S)-5-(4-fluorophenoxy)-6-{1-[(3R,4S)-3-fluoropiperidin-4-yl]-1H-pyrazol-4-yl}-2-methyl-1,2,3,4-tetrahydroquinoline-1-carboxylate (I-366)

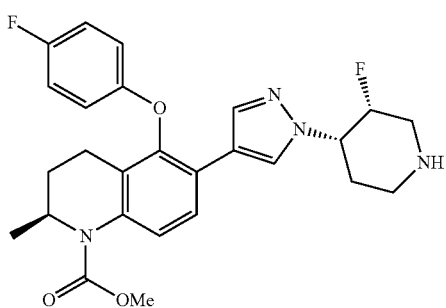 [SMILES: COC(=O)N1c2ccc(-c3cnn([C@H]4CCNC[C@H]4F)c3)c(Oc3ccc(F)cc3)c2CC[C@@H]1C]

$^1$H NMR (300 MHz, DMSO-d$_6$) δ ppm 1.04 (d, J=6.74 Hz, 3H), 1.51 (dd, J=13.92, 4.84 Hz, 1H), 1.71-1.80 (m, 1H), 1.90-2.04 (m, 3H), 2.34-2.46 (m, 4H), 2.93-3.10 (m, 1H), 3.11-3.19 (m, 1H), 3.70 (s, 3H), 4.27-4.42 (m, 1H), 4.48-4.57 (m, 1H), 4.63-4.85 (m, 1H), 6.72-6.76 (m, 2H), 7.06-7.12 (m, 2H), 7.51-7.61 (m, 2H), 7.76 (s, 1H), 7.94 (s, 1H). MS (ESI, pos. ion) m/z 483 [M+H]+.

methyl (2S)-5-cyclobutoxy-6-{1-[(3R,4R)-3-fluoropiperidin-4-yl]-1H-pyrazol-4-yl}-2-methyl-1,2,3,4-tetrahydroquinoline-1-carboxylate (I-367)

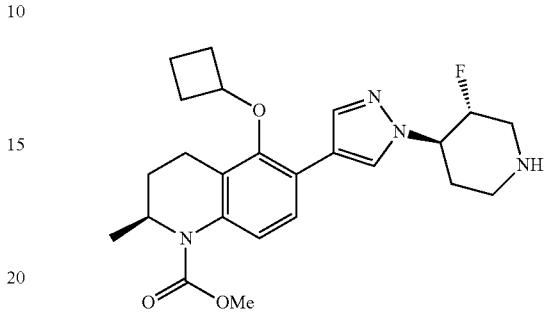

$^1$H NMR (300 MHz, DMSO-d$_6$) δ ppm 1.06 (d, J=6.45 Hz, 3H), 1.17-1.28 (m, 1H), 1.29-1.42 (m, 1H), 1.47-1.56 (m, 1H), 1.86-2.17 (m, 8H), 2.34-2.43 (m, 2H), 2.55-2.72 (m, 1H), 2.77-2.87 (m, 2H), 2.88-2.95 (m, 1H), 3.65 (s, 3H), 4.01-4.11 (m, 1H), 4.31-4.45 (m, 1H), 4.60-4.84 (m, 1H), 7.21 (d, J=8.50 Hz, 1H), 7.28 (d, J=8.79 Hz, 1H), 7.82 (s, 1H), 8.08 (s, 1H). MS (ESI, pos. ion) m/z 443 [M+H]+.

methyl (2S)-5-(4-fluorophenoxy)-6-{1-[(3R,4R)-3-fluoropiperidin-4-yl]-1H-pyrazol-4-yl}-2-methyl-1,2,3,4-tetrahydroquinoline-1-carboxylate (I-368)

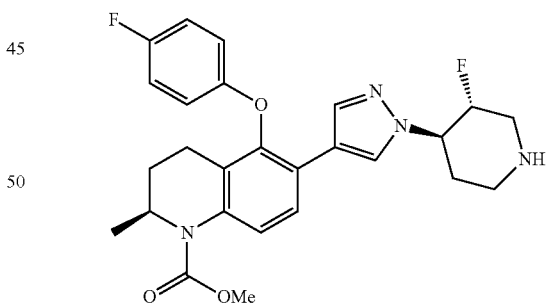

$^1$H NMR (300 MHz, DMSO-d$_6$) δ ppm 1.04 (d, J=6.74 Hz, 3H), 1.51 (dd, J=13.92, 4.84 Hz, 1H), 1.71-1.84 (m, 2H), 1.90-2.04 (m, 3H), 2.67-2.73 (m, 1H), 2.81-2.93 (m, 2H), 3.11-3.19 (m, 1H), 3.70 (s, 3H), 4.23-4.36 (m, 1H), 4.50-4.60 (m, 1H), 4.63-4.83 (m, 1H), 6.72-6.76 (m, 2H), 7.06-7.12 (m, 2H), 7.54 (d, J=2.93 Hz, 2H), 7.76 (s, 1H), 8.02 (s, 1H). MS (ESI, pos. ion) m/z 483 [M+H]⁺.

(2S)-5-cyclobutoxy-1-cyclopropanecarbonyl-6-{1-[(3S,4R)-3-fluoropiperidin-4-yl]-1H-pyrazol-4-yl}-2-methyl-1,2,3,4-tetrahydroquinoline (I-369)

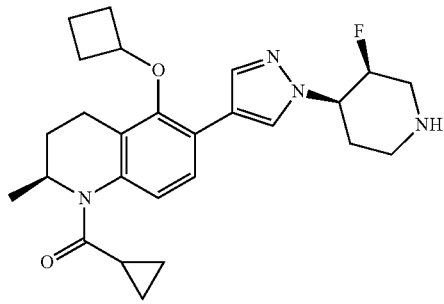

$^1$H NMR (300 MHz, DMSO-d$_6$) δ ppm 0.59-0.68 (m, 1H), 0.73-0.87 (m, 2H), 0.91-0.98 (m, 1H), 1.01 (d, J=6.45 Hz, 3H), 1.17-1.31 (m, 2H), 1.49-1.59 (m, 1H), 1.73-1.93 (m, 2H), 1.96-2.17 (m, 6H), 2.23-2.33 (m, 2H), 2.60-2.77 (m, 1H), 2.86-2.95 (m, 2H), 4.05-4.18 (m, 1H), 4.29-4.39 (m, 1H), 4.43-4.62 (m, 2H), 4.74-4.97 (m, 1H), 7.08 (d, J=8.50 Hz, 1H), 7.42 (d, J=8.50 Hz, 1H), 7.87 (s, 1H), 8.07 (s, 1H). MS (ESI, pos. ion) m/z 453 [M+H]⁺.

methyl (2S)-5-cyclobutoxy-6-{1-[(3R,4S)-4-fluoropyrrolidin-3-yl]-1H-pyrazol-4-yl}-2-methyl-1,2,3,4-tetrahydroquinoline-1-carboxylate (I-370) and methyl (2S)-5-cyclobutoxy-6-{1-[(3S,4R)-4-fluoropyrrolidin-3-yl]-1H-pyrazol-4-yl}-2-methyl-1,2,3,4-tetrahydroquinoline-1-carboxylate (I-371)

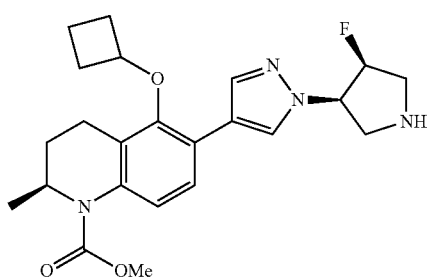

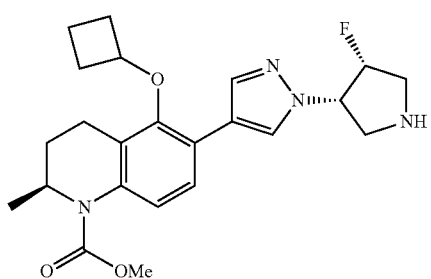

2:1 Mixture of isomers. Major isomer: $^1$H NMR (300 MHz, DMSO-d$_6$) δ ppm 1.09 (d, J=6.45 Hz, 3H), 1.19-1.43 (m, 2H), 1.49-1.60 (m, 1H), 1.99-2.22 (m, 4H), 2.35-2.43 (m, 1H), 2.79-3.11 (m, 4H), 3.68 (s, 3H), 4.07-4.15 (m, 1H), 4.40-4.47 (m, 1H), 4.69-4.85 (m, 1H), 5.01-5.18 (m, 2H), 5.26-5.37 (m, 1H), 7.23 (d, J=8.50 Hz, 1H), 7.33 (d, J=8.79 Hz, 1H), 7.84 (s, 1H), 8.10 (s, 1H). MS (ESI, pos. ion) m/z 429 [M+H]⁺.

(2S)-5-cyclobutoxy-1-cyclopropanecarbonyl-6-{1-[(3R,4S)-4-fluoropiperidin-3-yl]-1H-pyrazol-4-yl}-2-methyl-1,2,3,4-tetrahydroquinoline (I-372) and (2S)-5-cyclobutoxy-1-cyclopropanecarbonyl-6-{1-[(3S,4R)-4-fluoropiperidin-3-yl]-1H-pyrazol-4-yl}-2-methyl-1,2,3,4-tetrahydroquinoline (I-373)

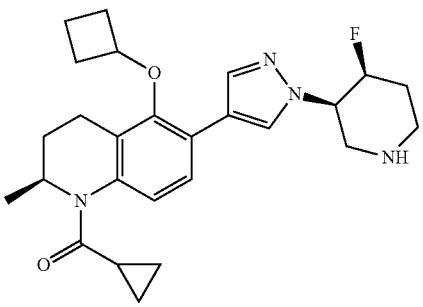

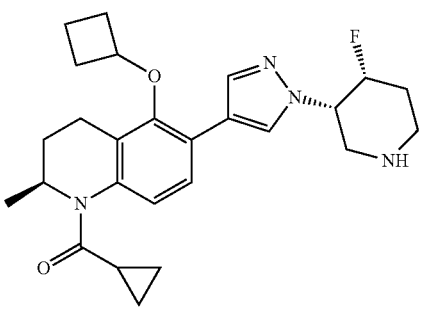

1:1 mixture of isomers. $^1$H NMR (300 MHz, CDCl$_3$) δ ppm 0.51-0.62 (m, 1H), 0.73-0.83 (m, 2H), 0.87-0.95 (m, 1H), 1.06 (d, J=6.45 Hz, 3H), 1.12-1.30 (m, 4H), 1.50-1.63 (m, 1H), 1.73-1.82 (m, 1H), 1.90-2.15 (m, 7H), 2.23-2.33 (m, 2H), 2.88-2.98 (m, 1H), 3.05-3.32 (m, 1H), 3.41-3.62 (m, 1H), 4.00-4.11 (m, 1H), 4.60-4.73 (m, 1H), 4.96-5.29 (m, 1H), 7.06 (d, J=8.21 Hz, 1H), 7.19 (m, 1H), 7.78 (s, 1H), 7.89 (s, 1H). MS (ESI, pos. ion) m/z 453 [M+H]⁺.

Example 107 methyl (S)-5-cyclobutoxy-2-methyl-6-(1-((2S,4R)-2-methylpiperidin-4-yl)-1H-pyrazol-4-yl)-3,4-dihydroquinoline-1(2H)-carboxylate (I-374) and methyl (S)-5-cyclobutoxy-2-methyl-6-(1-((2R,4S)-2-methylpiperidin-4-yl)-1H-pyrazol-4-yl)-3,4-dihydroquinoline-1(2H)-carboxylate (I-375)

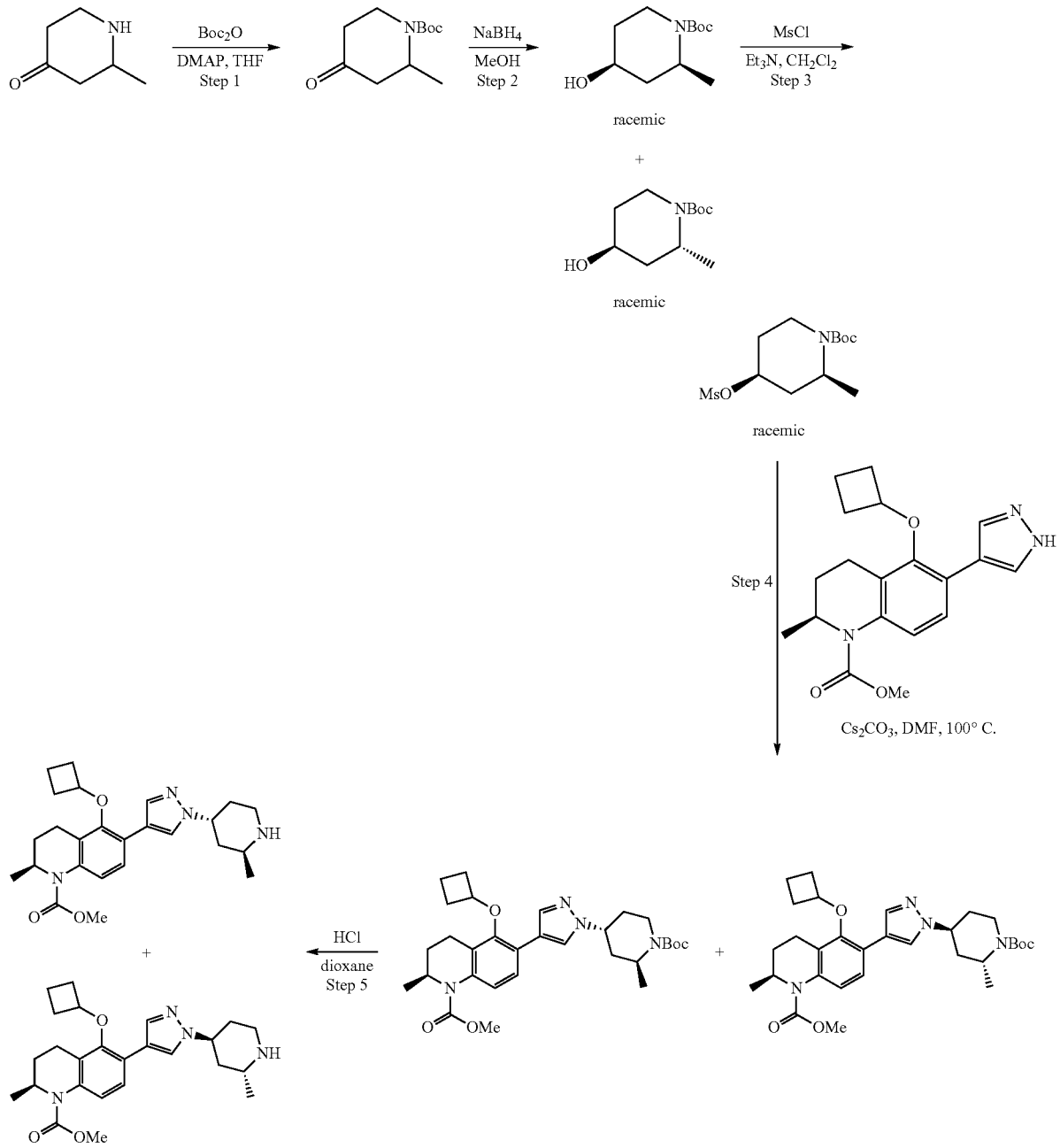

Step 1. tert-butyl 2-methyl-4-oxopiperidine-1-carboxylate

Di-tert-butyl dicarbonate (1.09 g, 5.01 mmol) was added to a 0° C. solution of 2-methylpiperidin-4-one hydrochloride (1:1 mixture of isomers, 0.500 g, 3.34 mmol) and DMAP (0.817 g, 6.68 mmol) in dry THF (10 mL), and the resulting mixture was stirred at 0° C. for 2 h. The reaction was quenched by the addition of saturated aqueous ammonium chloride solution (50 mL) and ethyl acetate (70 mL) was added. The aqueous phase was separated and extracted with ethyl acetate (2×50 mL). The combined organic layers were washed with brine (50 mL), dried over anhydrous sodium sulfate, filtered, and concentrated in vacuo. The residue was purified via column chromatography on silica gel (Biotage 50 g column, gradient elution with 25-35% ethyl acetate in hexanes) to afford tert-butyl 2-methyl-4-oxopiperidine-1-carboxylate (0.660 g, 93%) as a white solid. $^1$H NMR (300 MHz, DMSO-$d_6$) δ ppm 1.06 (d, J=6.74 Hz, 3H), 1.40 (s, 9H), 2.11-2.25 (m, 2H), 2.36-2.45 (m, 1H), 2.68 (dd, J=14.51, 6.6 Hz, 1H), 3.25-3.36 (m, 1H), 3.93-4.06 (m, 1H), 4.42-4.48 (m, 1H).

Step 2. (rac)-tert-butyl (cis)-4-hydroxy-2-methylpiperidine-1-carboxylate and (rac)-tert-butyl (trans)-4-hydroxy-2-methylpiperidine-1-carboxylate Following the procedure found in Plettenburg, Oliver et. Al (PCT Int. Appl., 2007012421), sodium borohydride (213 mg, 5.6 mmol) was added portion-wise to a solution of tert-butyl 2-methyl-4-oxopiperidine-1-carboxylate (1.0 g, 4.7 mmol) in ethanol (10 mL). The mixture was stirred at room temperature for 2 h. The solution was concentrated in vacuo and then partitioned between water (40 mL) and ethyl acetate (40 mL). The aqueous layer was extracted twice with ethyl acetate (40 mL). The combined organic layers were washed with brine (20 mL), dried over anhydrous sodium sulfate, filtered, and concentrated in vacuo. The residue was purified via column chromatography on silica gel (Biotage 50 g column, gradient elution with 40-50% ethyl acetate in hexanes) to afford (rac)-tert-butyl (cis)-4-hydroxy-2-methylpiperidine-1-carboxylate (367 mg, 36%) and (rac)-tert-butyl (trans)-4-hydroxy-2-methylpiperidine-1-carboxylate (205 mg, 20%) as white solids.

Step 3. (rac)-tert-butyl (cis)-2-methyl-4-((methylsulfonyl)oxy)piperidine-1-carboxylate Triethylamine (0.49 mL, 3.49 mmol) was added to a 0° C. solution of (rac)-tert-butyl (cis)-4-hydroxy-2-methylpiperidine-1-carboxylate (250 mg, 1.16 mmol) and methanesulfonyl chloride (0.14 mL, 1.74 mmol) in dichloromethane (4.5 mL). The resulting mixture was warmed to room temperature and stirred overnight. The reaction was quenched by the addition of saturated aqueous sodium bicarbonate (10 mL) and dichloromethane (10 mL) was added. The organic layer was separated and washed with 1M aqueous citric acid (10 mL) and brine (10 mL), dried over anhydrous sodium sulfate, filtered, and concentrated in vacuo. The residue was purified via column chromatography on silica gel (Biotage 50 g column, gradient elution with 20-30% ethyl acetate in hexanes) to afford (rac)-tert-butyl (cis)-2-methyl-4-((methylsulfonyl)oxy)piperidine-1-carboxylate (315 mg, 92%) as a colorless oil that slowly solidified to a white solid upon standing. $^1$H NMR (300 MHz, DMSO-$d_6$) δ ppm 1.17 (d, J=7.04 Hz, 3H), 1.38 (s, 9H), 1.63-1.76 (m, 1H), 1.85-1.90 (m, 3H), 2.96-3.06 (m, 1H), 3.18 (s, 3H), 3.72-3.78 (m, 1H), 4.16-4.24 (m, 1H), 4.93-4.98 (m, 1H).

Step 4. methyl (S)-6-(1-((2S,4R)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate and methyl (S)-6-(1-((2R,4S)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate (rac)-tert-Butyl (cis)-4-hydroxy-2-methylpiperidine-1-carboxylate (55.9 mg, 0.190 mmol) was added to a solution of (S)-methyl 5-cyclobutoxy-2-methyl-6-(1H-pyrazol-4-yl)-3,4-dihydroquinoline-1(2H)-carboxylate (50.0 mg, 0.146 mmol) and cesium carbonate (76 mg, 0.234 mmol) in DMF (1.0 mL), and the reaction mixture was heated to 100° C. and allowed to stir overnight. The mixture was cooled to room temperature, diluted with water, and extracted with ethyl acetate (3×50 mL). The combined organic layers were washed with water (2×25 mL) and brine (25 mL), dried over anhydrous sodium sulfate, filtered, and concentrated in vacuo. The residue was purified via column chromatography on silica gel (Biotage 25 g column, gradient elution with 20-30% ethyl acetate in hexanes) to afford a 1:1 mixture of methyl (S)-6-(1-((2S,4R)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate and methyl (S)-6-(1-((2R,4S)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate (54.2 mg, 69%) as a colorless oil. MS (ESI, pos. ion) m/z 539 [M+H]$^+$.

Step 5. methyl (S)-5-cyclobutoxy-2-methyl-6-(1-((2S,4R)-2-methylpiperidin-4-yl)-1H-pyrazol-4-yl)-3,4-dihydroquinoline-1(2H)-carboxylate and methyl (S)-5-cyclobutoxy-2-methyl-6-(1-((2R,4S)-2-methylpiperidin-4-yl)-1H-pyrazol-4-yl)-3,4-dihydroquinoline-1(2H)-carboxylate Hydrogen chloride (4.0 N in 1,4-dioxane, 0.126 mL, 0.503 mmol) was added to a solution containing a 1:1 mixture of methyl (S)-6-(1-((2S,4R)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate and methyl (S)-6-(1-((2R,4S)-1-(tert-butoxycarbonyl)-2-methylpiperidin-4-yl)-1H-pyrazol-4-yl)-5-cyclobutoxy-2-methyl-3,4-dihydroquinoline-1(2H)-carboxylate (54.2 mg, 0.101 mmol) in 1,4-dioxane (1.0 mL), and the reaction mixture stirred at room temperature for 3 h. The solution was concentrated under a stream of nitrogen, diluted with saturated aqueous sodium bicarbonate solution (1.0 mL) and extracted with ethyl acetate (3×1.0 mL). The combined organic layers were added directly to a plug of silica gel, and the product was eluted with 30% ethyl acetate in methanol to afford a 1:1 mixture of methyl (S)-5-cyclobutoxy-2-methyl-6-(1-((2S,4R)-2-methylpiperidin-4-yl)-1H-pyrazol-4-yl)-3,4-dihydroquinoline-1(2H)-carboxylate and methyl (S)-5-cyclobutoxy-2-methyl-6-(1-((2R,4S)-2-methylpiperidin-4-yl)-1H-pyrazol-4-yl)-3,4-dihydroquinoline-1(2H)-carboxylate (18.1 mg, 41%) as a white solid. $^1$H NMR (300 MHz, DMSO-$d_6$) δ ppm 0.81 (d, J=6.74 Hz, 3H), 1.05 (d, J=6.74 Hz, 3H), 1.22-1.43 (m, 3H), 1.48-1.65 (m, 2H), 1.81-2.22 (m, 8H), 2.34-2.43 (m, 1H), 2.72-2.87 (m, 2H), 2.90-3.00 (m, 1H), 3.10-3.17 (m, 1H), 3.66 (s, 3H), 4.05-4.12 (m, 1H), 4.40-4.52 (m, 1H), 7.21 (d, J=8.79 Hz, 1H), 7.30 (d, J=9.38 Hz, 1H), 7.78 (s, 1H), 8.08 (s, 1H). MS (ESI, pos. ion) m/z 439 [M+H]$^+$.

The following example was made according to the procedure described above for Example 107:

methyl (S)-5-cyclobutoxy-2-methyl-6-(1-((2S,4S)-2-methylpiperidin-4-yl)-1H-pyrazol-4-yl)-3,4-dihydroquinoline-1(2H)-carboxylate (I-376) and methyl (S)-5-cyclobutoxy-2-methyl-6-(1-((2R,4R)-2-methylpiperidin-4-yl)-1H-pyrazol-4-yl)-3,4-dihydroquinoline-1(2H)-carboxylate (I-377)

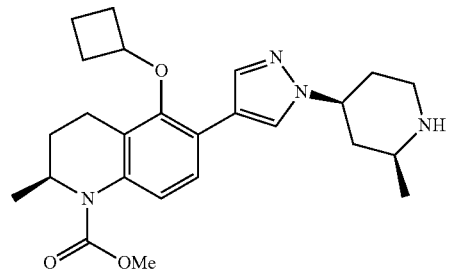 [SMILES: COC(=O)N1c2ccc(-c3cnn([C@@H]4CCNC[C@H]4F)c3)c(OC3CCC3)c2CC[C@@H]1C]

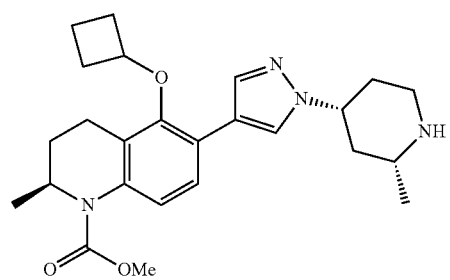

¹H NMR (300 MHz, DMSO-d6) δ ppm 0.80 (d, J=6.45 Hz, 3H), 1.05 (d, J=6.74 Hz, 3H), 1.22-1.43 (m, 3H), 1.48-1.75 (m, 2H), 1.90-2.13 (m, 8H), 2.34-2.45 (m, 1H), 2.58-2.70 (m, 2H), 2.76-2.86 (m, 1H), 2.99-3.05 (m, 1H), 3.66 (s, 3H), 4.02-4.12 (m, 1H), 4.15-4.26 4.36-4.48 (m, 1H), 7.20 (d, J=8.79 Hz, 1H), 7.29 (d, J=9.38 Hz, 1H), 7.76 (s, 1H), 8.01 (s, 1H). MS (ESI, pos. ion) m/z 439 [M+1-1]+.

Example 108

Library Protocol A

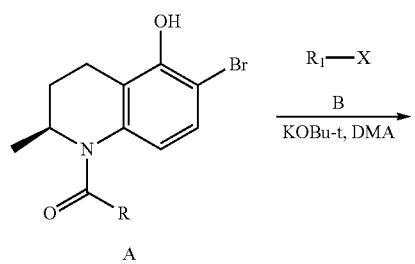

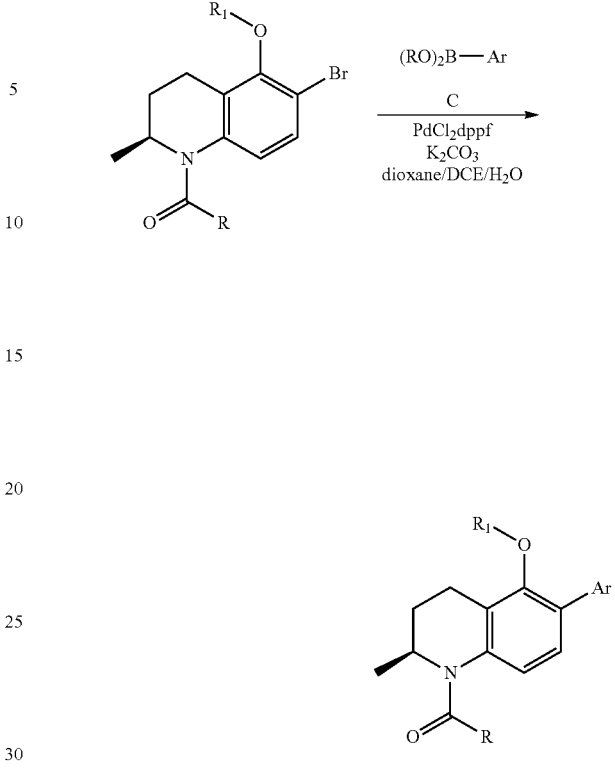

A half-dram vial was charged with (S)-6-bromo-2-methyl-1,2,3,4-tetrahydroquinolin-5-ol A (0.2 M in N,N-dimethylacetamide, 150 μL, 30 μmol) and potassium tert-butoxide (1 M in THF, 36 μL, 36 μmol), and the mixture was shaken for 5 seconds. Alkyl halide B (0.2 M in N,N-dimethylacetamide, 180 μL, 36 μmol) was added, and the system was sealed and shaken at 80° C. for 14 h. Ethyl acetate (0.7 mL) and 1 N sodium hydroxide in brine (0.5 mL) were added and the mixture was shaken. The organic layer was separated and the aqueous phase was extracted with ethyl acetate (1.0 mL). The combined organic phases were concentrated and the residue was dissolved in anhydrous 1,4-dioxane (100 μL). Aryl boronic ester C (0.2 M in 1,4-dioxane, 270 μL, 54 μmol), potassium carbonate (1 M aqueous solution, 90 μL, 90 μmol), and [1,1'-bis(diphenylphosphino)ferrocene]dichloropalladium(II) dichloromethane adduct (0.02 M in 1,2-dichloroethane, 150 μL, 3 μmol) were added, and the mixture was sealed and shaken at 80° C. for 14 h. Ethyl acetate (0.5 mL) and 1 N sodium hydroxide in brine (0.4 mL) were added and the mixture was shaken. The organic layer was separated and the aqueous phase was extracted with ethyl acetate (1.0 mL). The combined organic phases were concentrated to afford the crude product. This material was purified by mass triggered preparatory HPLC. The product-containing fractions were combined and concentrated in a Genevac to afford the desired product.

The following compounds in Table 1 were synthesized according to the above protocol:

TABLE 1

| Compounds | Structure | MW | LC-MS [M + 1]+ | HPLC RT (min) |
|---|---|---|---|---|
| I-378 | 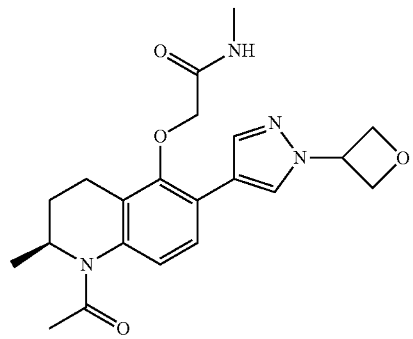 [SMILES: CNC(=O)COc1c(-c2cnn(C3COC3)c2)ccc2c1CC[C@H](C)N2C(C)=O] | 398.46 | 399 | 0.82 |
| I-379 | 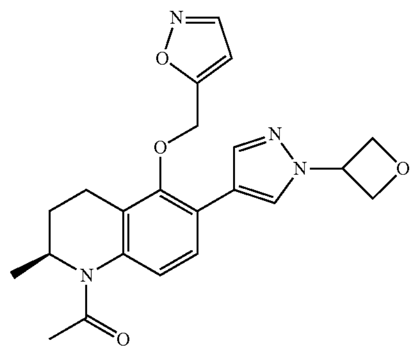 [SMILES: CC(=O)N1c2ccc(-c3cnn(C4COC4)c3)c(OCc3ccno3)c2CC[C@@H]1C] | 408.46 | 409 | 1.05 |
| I-380 | 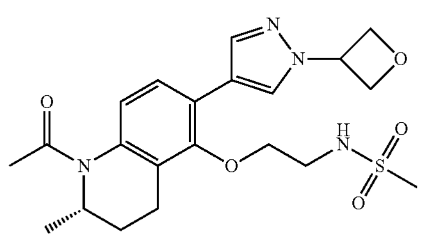 [SMILES: CC(=O)N1c2ccc(-c3cnn(C4COC4)c3)c(OCCNS(C)(=O)=O)c2CC[C@@H]1C] | 448.54 | 449 | 0.91 |
| I-381 | 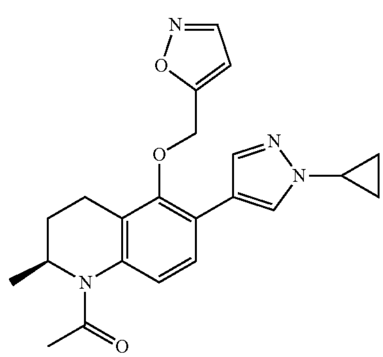 [SMILES: CC(=O)N1c2ccc(-c3cnn(C4CC4)c3)c(OCc3ccno3)c2CC[C@@H]1C] | 392.46 | 393 | 1.21 |

TABLE 1-continued

| Compounds | Structure | MW | LC-MS [M + 1]+ | HPLC RT (min) |
|---|---|---|---|---|
| I-382 | 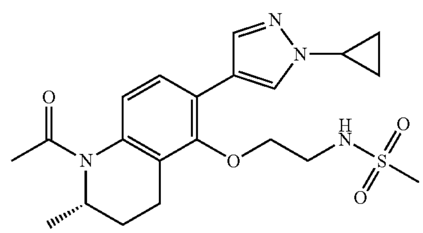 [SMILES: CC(=O)N1c2ccc(-c3cnn(C4CC4)c3)c(OCCNS(C)(=O)=O)c2CC[C@@H]1C] | 432.54 | 433 | 1.04 |
| I-383 | 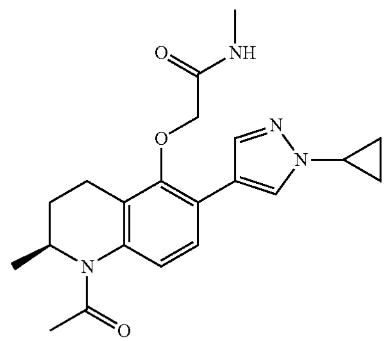 [SMILES: CNC(=O)COc1c(-c2cnn(C3CC3)c2)ccc2c1CC[C@H](C)N2C(C)=O] | 382.46 | 383 | 0.95 |
| I-384 | 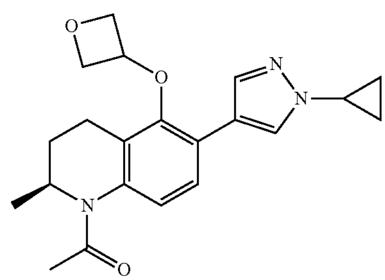 [SMILES: CC(=O)N1c2ccc(-c3cnn(C4CC4)c3)c(OC3COC3)c2CC[C@@H]1C] | 367.45 | 368 | 1.12 |
| I-385 | 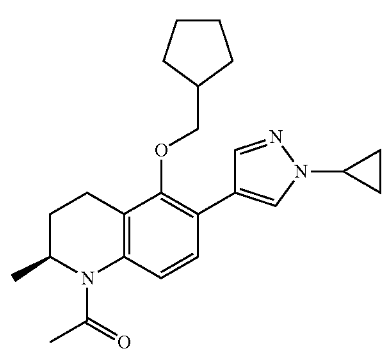 [SMILES: CC(=O)N1c2ccc(-c3cnn(C4CC4)c3)c(OCC3CCCC3)c2CC[C@@H]1C] | 393.53 | 394 | 1.75 |

TABLE 1-continued

| Compounds | Structure | MW | LC-MS [M + 1]+ | HPLC RT (min) |
|---|---|---|---|---|
| I-386 | 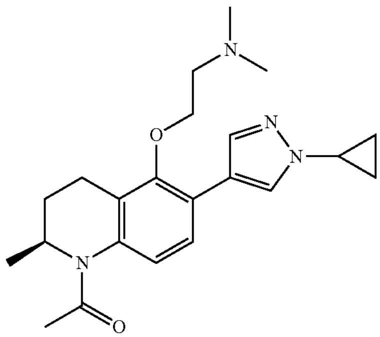 [SMILES: CC(=O)N1c2ccc(-c3cnn(C4CC4)c3)c(OCCN(C)C)c2CC[C@@H]1C] | 382.51 | 383 | 0.78 |
| I-387 | 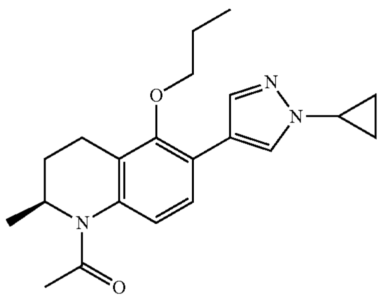 [SMILES: CCCOc1c(-c2cnn(C3CC3)c2)ccc2c1CC[C@H](C)N2C(C)=O] | 353.47 | 354 | 1.47 |
| I-388 | 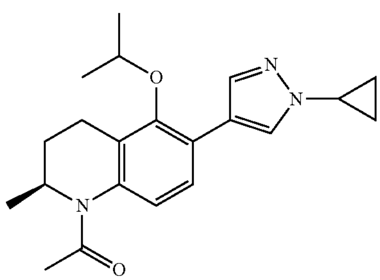 [SMILES: CC(=O)N1c2ccc(-c3cnn(C4CC4)c3)c(OC(C)C)c2CC[C@@H]1C] | 353.47 | 354 | 1.41 |
| I-389 | 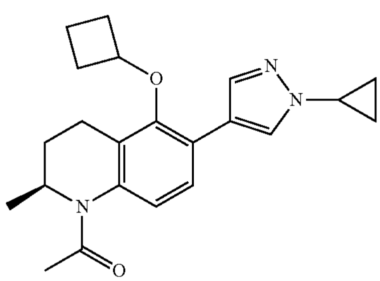 [SMILES: CC(=O)N1c2ccc(-c3cnn(C4CC4)c3)c(OC3CCC3)c2CC[C@@H]1C] | 365.48 | 366 | 1.50 |
| I-390 | 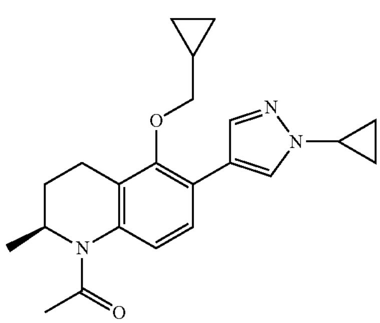 [SMILES: CC(=O)N1c2ccc(-c3cnn(C4CC4)c3)c(OCC3CC3)c2CC[C@@H]1C] | 365.48 | 366 | 1.49 |

TABLE 1-continued

| Compounds | Structure | MW | LC-MS [M + 1]+ | HPLC RT (min) |
|---|---|---|---|---|
| I-391 | 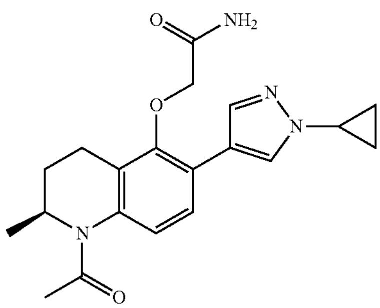 [SMILES: CC(=O)N1c2ccc(-c3cnn(C4CC4)c3)c(OCC(N)=O)c2CC[C@@H]1C] | 368.44 | 369 | 0.89 |
| I-392 | 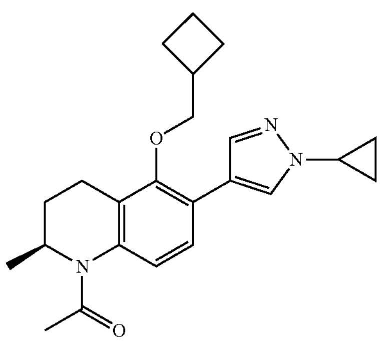 [SMILES: CC(=O)N1c2ccc(-c3cnn(C4CC4)c3)c(OCC3CCC3)c2CC[C@@H]1C] | 379.50 | 380 | 1.63 |
| I-393 | 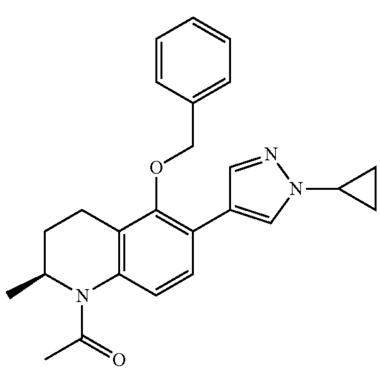 [SMILES: CC(=O)N1c2ccc(-c3cnn(C4CC4)c3)c(OCc3ccccc3)c2CC[C@@H]1C] | 401.51 | 402 | 1.57 |
| I-394 | 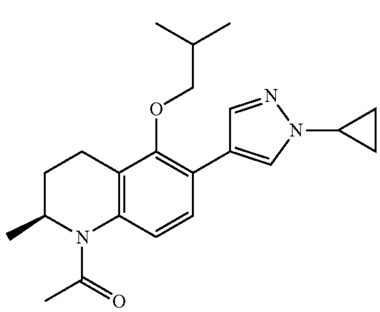 [SMILES: CC(=O)N1c2ccc(-c3cnn(C4CC4)c3)c(OCC(C)C)c2CC[C@@H]1C] | 367.49 | 368 | 1.60 |

TABLE 1-continued
| Compounds | Structure | MW | LC-MS [M + 1]+ | HPLC RT (min) |
|---|---|---|---|---|
| I-395 | 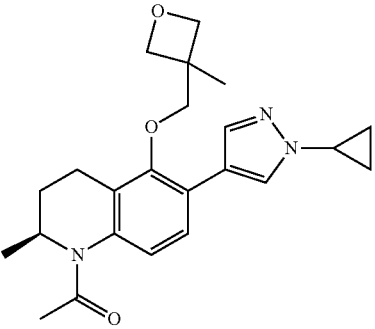 [SMILES: CC(=O)N1c2ccc(-c3cnn(C4CC4)c3)c(OCC3(C)COC3)c2CC[C@@H]1C] | 395.50 | 396 | 1.23 |
| I-396 | 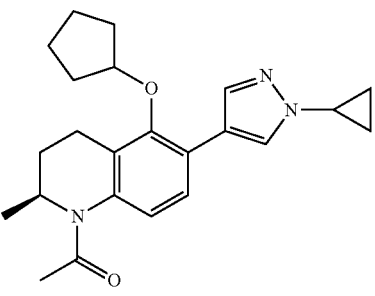 [SMILES: CC(=O)N1c2ccc(-c3cnn(C4CC4)c3)c(OC3CCCC3)c2CC[C@@H]1C] | 379.50 | 380 | 1.57 |
| I-397 | 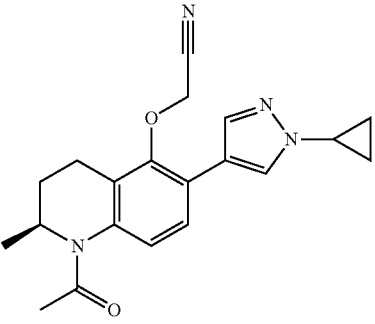 [SMILES: CC(=O)N1c2ccc(-c3cnn(C4CC4)c3)c(OCC#N)c2CC[C@@H]1C] | 350.42 | 351 | 1.19 |
| I-398 | 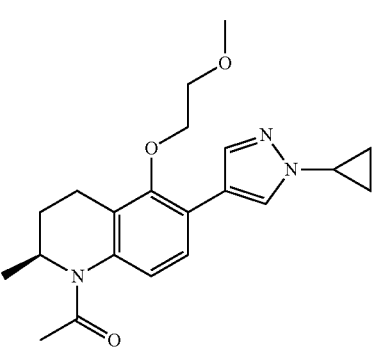 [SMILES: COCCOc1c(-c2cnn(C3CC3)c2)ccc2c1CC[C@H](C)N2C(C)=O] | 369.47 | 370 | 1.23 |

TABLE 1-continued

| Compounds | Structure | MW | LC-MS [M + 1]+ | HPLC RT (min) |
|---|---|---|---|---|
| I-399 | 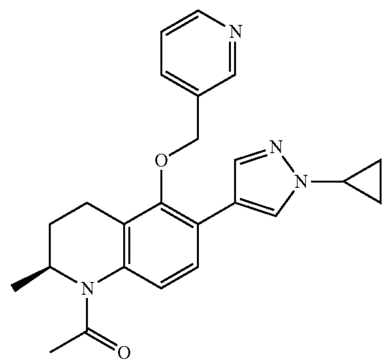 [SMILES: CC(=O)N1c2ccc(-c3cnn(C4CC4)c3)c(OCc3cccnc3)c2CC[C@@H]1C] | 402.50 | 403 | 1.05 |
| I-400 | 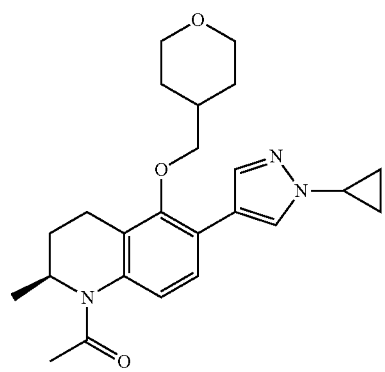 [SMILES: CC(=O)N1c2ccc(-c3cnn(C4CC4)c3)c(OCC3CCOCC3)c2CC[C@@H]1C] | 409.53 | 410 | 1.30 |
| I-401 | 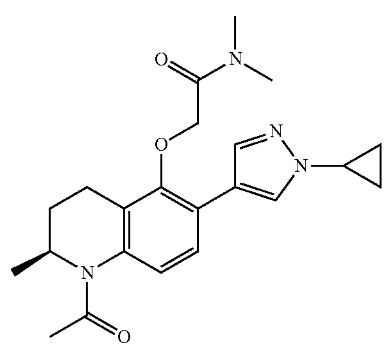 [SMILES: CC(=O)N1c2ccc(-c3cnn(C4CC4)c3)c(OCC(=O)N(C)C)c2CC[C@@H]1C] | 396.49 | 397 | 0.97 |
| I-402 | 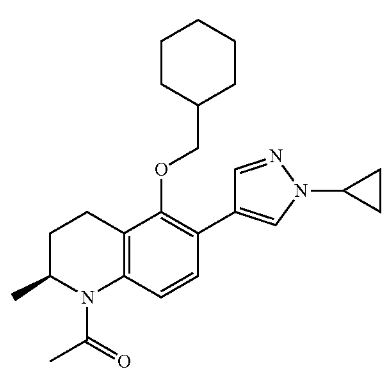 [SMILES: CC(=O)N1c2ccc(-c3cnn(C4CC4)c3)c(OCC3CCCCC3)c2CC[C@@H]1C] | 407.56 | 408 | 1.89 |

TABLE 1-continued
| Compounds | Structure | MW | LC-MS [M + 1]+ | HPLC RT (min) |
|---|---|---|---|---|
| I-403 | 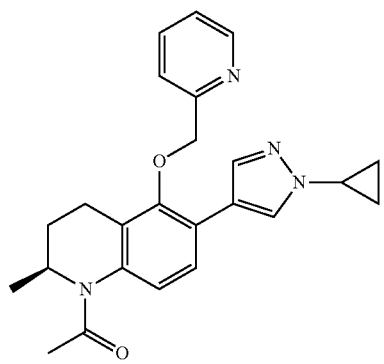 [SMILES: CC(=O)N1c2ccc(-c3cnn(C4CC4)c3)c(OCc3ccccn3)c2CC[C@@H]1C] | 402.50 | 403 | 1.19 |
| I-404 | 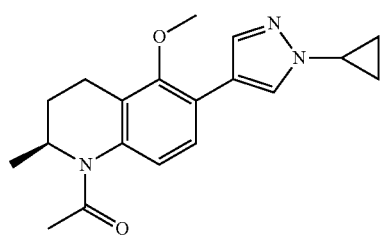 [SMILES: COc1c(-c2cnn(C3CC3)c2)ccc2c1CC[C@H](C)N2C(C)=O] | 325.41 | 326 | 1.22 |
| I-405 | 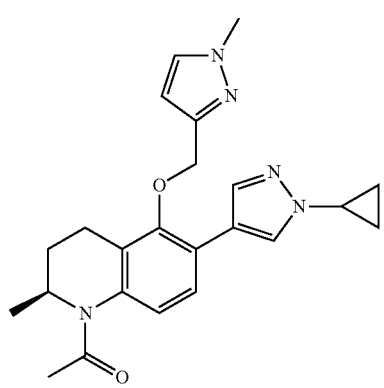 [SMILES: CC(=O)N1c2ccc(-c3cnn(C4CC4)c3)c(OCc3ccn(C)n3)c2CC[C@@H]1C] | 405.50 | 406 | 1.16 |
| I-406 | 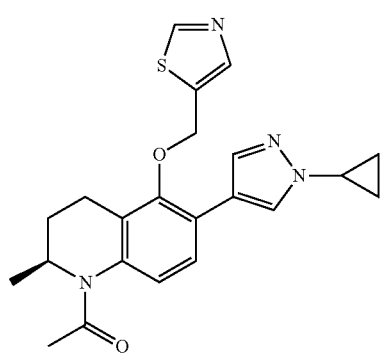 [SMILES: CC(=O)N1c2ccc(-c3cnn(C4CC4)c3)c(OCc3cncs3)c2CC[C@@H]1C] | 408.52 | 409 | 1.17 |

TABLE 1-continued
| Compounds | Structure | MW | LC-MS [M + 1]+ | HPLC RT (min) |
|---|---|---|---|---|
| I-407 | 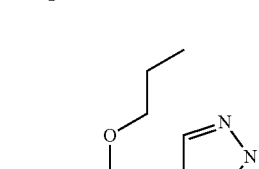 | 419.54 | 420 | 1.18 |
| I-408 | 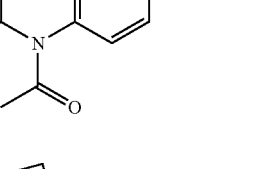 | 385.51 | 386 | 1.26 |
| I-409 | 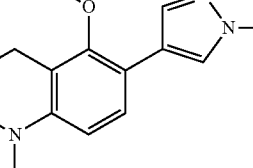 | 431.55 | 432 | 1.20 |
| I-410 | 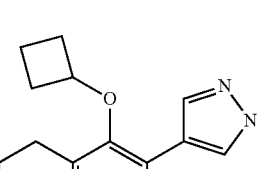 | 397.52 | 398 | 1.28 |
| I-411 | 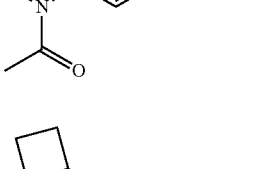 | 369.47 | 370 | 1.11 |

TABLE 1-continued

| Compounds | Structure | MW | LC-MS [M + 1]+ | HPLC RT (min) |
|---|---|---|---|---|
| I-412 | 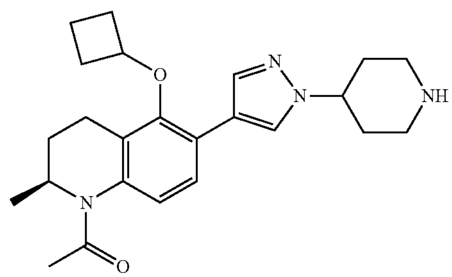 [SMILES: CC(=O)N1c2ccc(-c3cnn(C4CCNCC4)c3)c(OC3CCC3)c2CC[C@@H]1C] | 408.55 | 409 | 0.91 |
| I-413 | 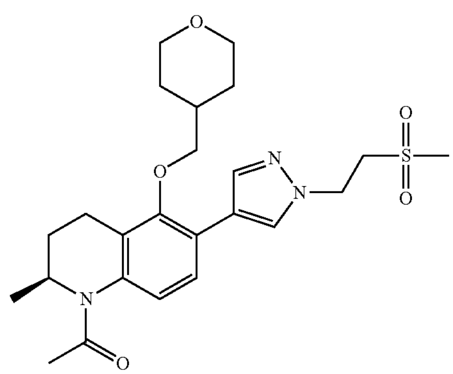 | 475.60 | 476 | 1.07 |
| I-414 | 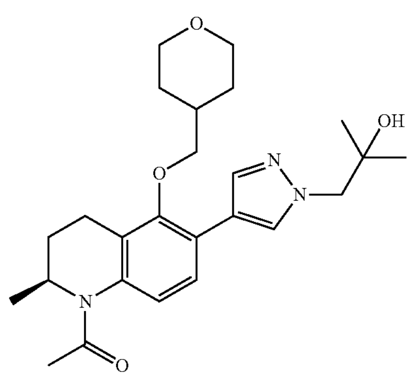 [SMILES: CC(=O)N1c2ccc(-c3cnn(CC(C)(C)O)c3)c(OCC3CCOCC3)c2CC[C@@H]1C] | 441.57 | 442 | 1.13 |
| I-415 | 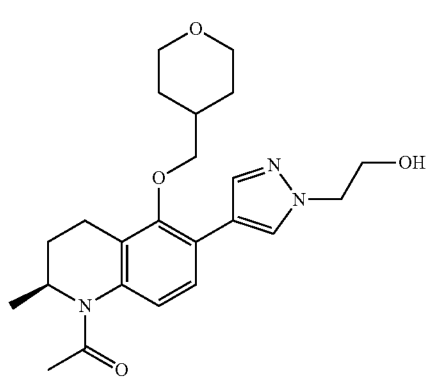 [SMILES: CC(=O)N1c2ccc(-c3cnn(CCO)c3)c(OCC3CCOCC3)c2CC[C@@H]1C] | 413.52 | 414 | 0.98 |

TABLE 1-continued

| Compounds | Structure | MW | LC-MS [M + 1]+ | HPLC RT (min) |
|---|---|---|---|---|
| I-416 | 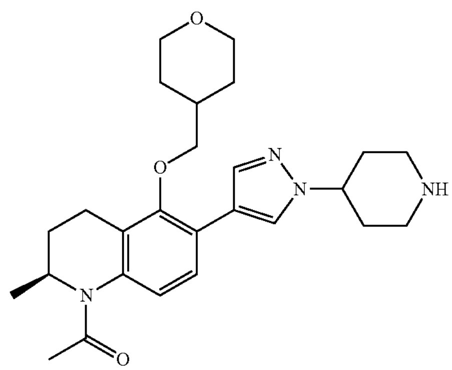 [SMILES: CC(=O)N1c2ccc(-c3cnn(C4CCNCC4)c3)c(OCC3CCOCC3)c2CC[C@@H]1C] | 452.60 | 453 | 0.84 |
| I-417 | 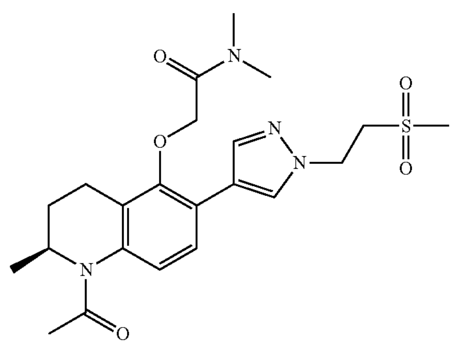 | 462.57 | 463 | 0.82 |
| I-418 | 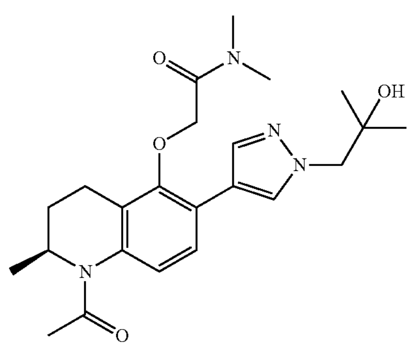 [SMILES: CC(=O)N1c2ccc(-c3cnn(CC(C)(C)O)c3)c(OCC(=O)N(C)C)c2CC[C@@H]1C] | 428.53 | 429 | 0.86 |
| I-419 | 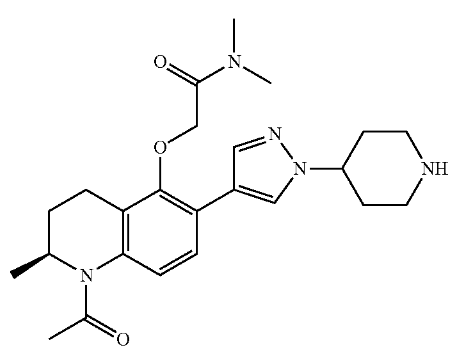 [SMILES: CC(=O)N1c2ccc(-c3cnn(C4CCNCC4)c3)c(OCC(=O)N(C)C)c2CC[C@@H]1C] | 439.56 | 440 | 0.67 |

TABLE 1-continued
| Compounds | Structure | MW | LC-MS [M + 1]+ | HPLC RT (min) |
|---|---|---|---|---|
| I-420 | 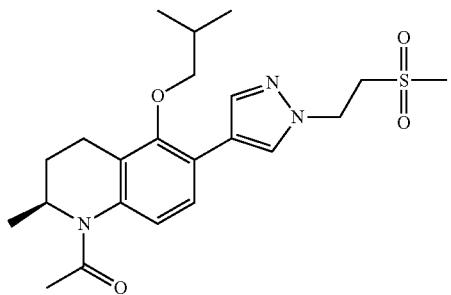 | 433.57 | 434 | 1.29 |
| I-421 | 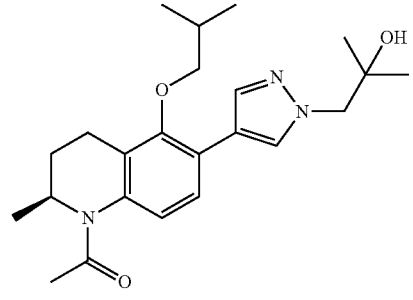 [SMILES: CC(=O)N1c2ccc(-c3cnn(CC(C)(C)O)c3)c(OCC(C)C)c2CC[C@@H]1C] | 399.54 | 400 | 1.39 |
| I-422 | 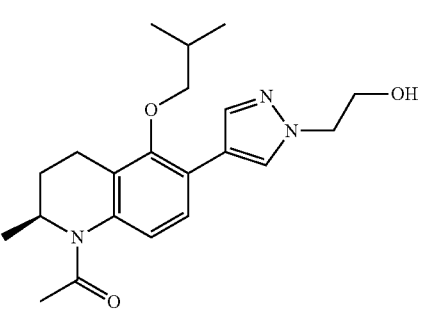 [SMILES: CC(=O)N1c2ccc(-c3cnn(CCO)c3)c(OCC(C)C)c2CC[C@@H]1C] | 371.48 | 372 | 1.20 |
| I-423 | 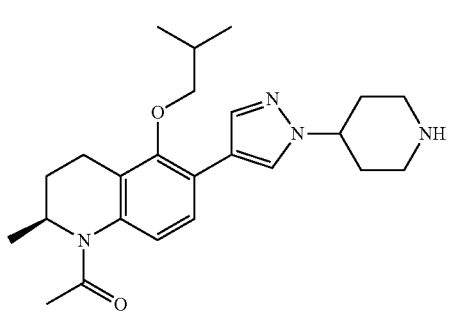 [SMILES: CC(=O)N1c2ccc(-c3cnn(C4CCNCC4)c3)c(OCC(C)C)c2CC[C@@H]1C] | 410.56 | 411 | 0.98 |

TABLE 1-continued

| Compounds | Structure | MW | LC-MS [M + 1]+ | HPLC RT (min) |
|---|---|---|---|---|
| I-424 | 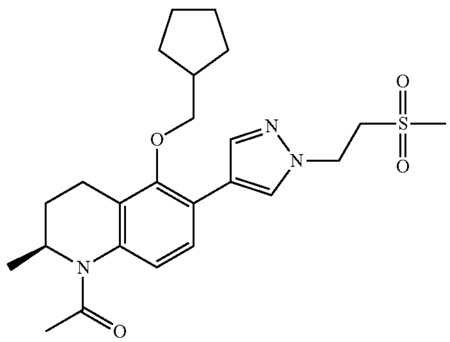 | 459.61 | 460 | 1.42 |
| I-425 | 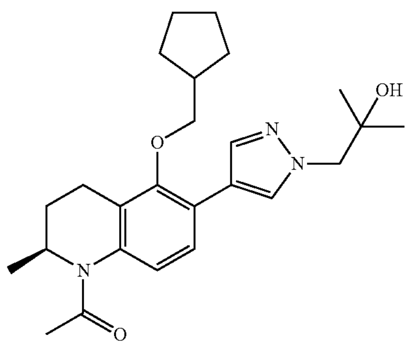 [SMILES: CC(=O)N1c2ccc(-c3cnn(CC(C)(C)O)c3)c(OCC3CCCC3)c2CC[C@@H]1C] | 425.57 | 426 | 1.52 |
| I-426 | 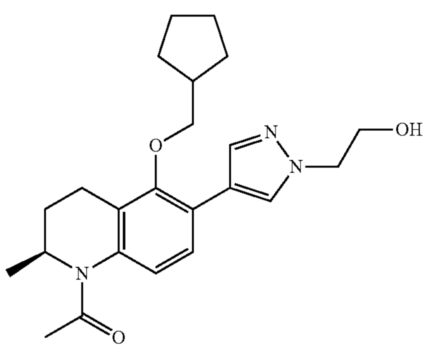 [SMILES: CC(=O)N1c2ccc(-c3cnn(CCO)c3)c(OCC3CCCC3)c2CC[C@@H]1C] | 397.52 | 398 | 1.33 |
| I-427 | 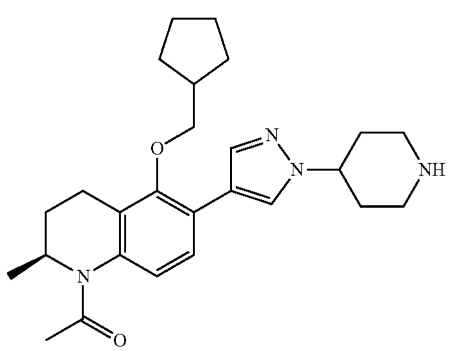 [SMILES: CC(=O)N1c2ccc(-c3cnn(C4CCNCC4)c3)c(OCC3CCCC3)c2CC[C@@H]1C] | 436.60 | 437 | 1.08 |

TABLE 1-continued

| Compounds | Structure | MW | LC-MS [M + 1]+ | HPLC RT (min) |
|---|---|---|---|---|
| I-428 | 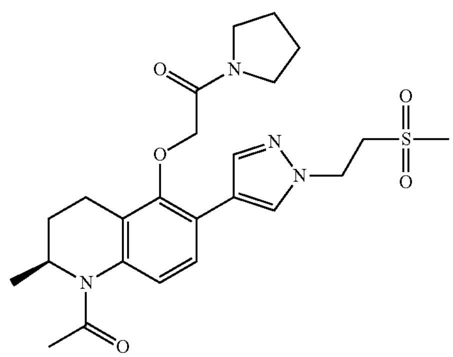 | 488.60 | 489 | 0.90 |
| I-429 | 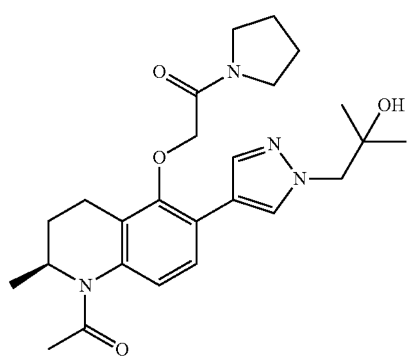 [SMILES: CC(=O)N1c2ccc(-c3cnn(CC(C)(C)O)c3)c(OCC(=O)N3CCCC3)c2CC[C@@H]1C] | 454.57 | 455 | 0.95 |
| I-430 | 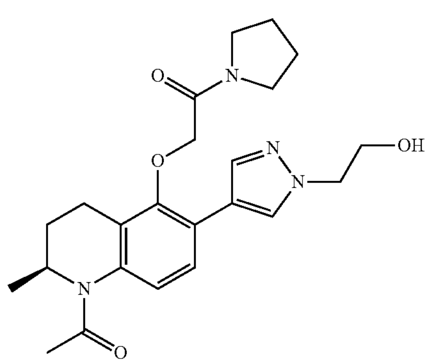 [SMILES: CC(=O)N1c2ccc(-c3cnn(CCO)c3)c(OCC(=O)N3CCCC3)c2CC[C@@H]1C] | 426.52 | 427 | 0.84 |
| I-431 | 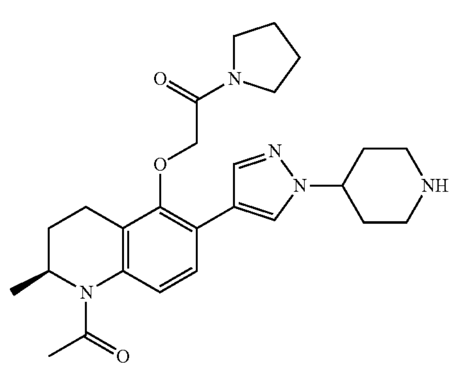 [SMILES: CC(=O)N1c2ccc(-c3cnn(C4CCNCC4)c3)c(OCC(=O)N3CCCC3)c2CC[C@@H]1C] | 465.60 | 466 | 0.75 |

TABLE 1-continued

| Compounds | Structure | MW | LC-MS [M + 1]+ | HPLC RT (min) |
|---|---|---|---|---|
| I-432 | 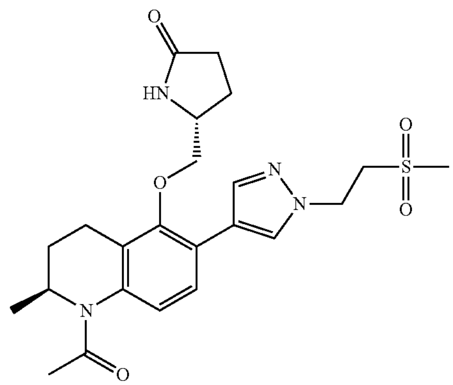 | 474.58 | 475 | 0.84 |
| I-433 | 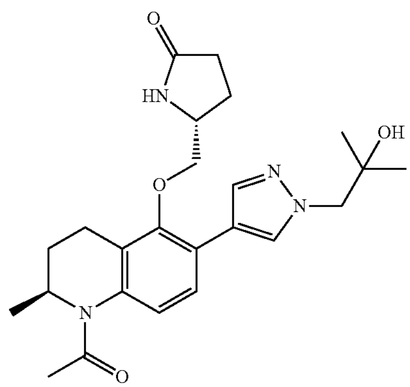 [SMILES: CC(=O)N1c2ccc(-c3cnn(CC(C)(C)O)c3)c(OC[C@H]3CCC(=O)N3)c2CC[C@@H]1C] | 440.54 | 441 | 0.88 |
| I-434 | 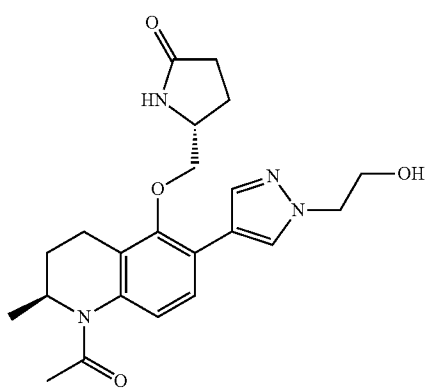 [SMILES: CC(=O)N1c2ccc(-c3cnn(CCO)c3)c(OC[C@H]3CCC(=O)N3)c2CC[C@@H]1C] | 412.49 | 413 | 0.79 |
| I-435 | 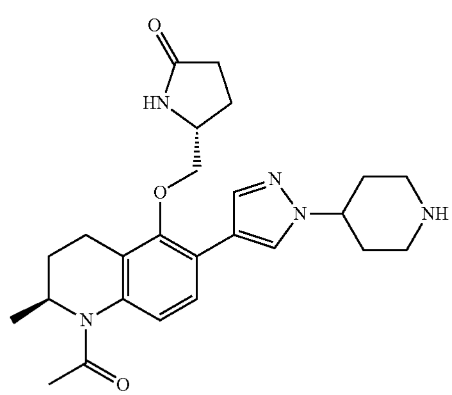 [SMILES: CC(=O)N1c2ccc(-c3cnn(C4CCNCC4)c3)c(OC[C@H]3CCC(=O)N3)c2CC[C@@H]1C] | 451.57 | 452 | 0.70 |

TABLE 1-continued

| Compounds | Structure | MW | LC-MS [M + 1]+ | HPLC RT (min) |
|---|---|---|---|---|
| I-436 | 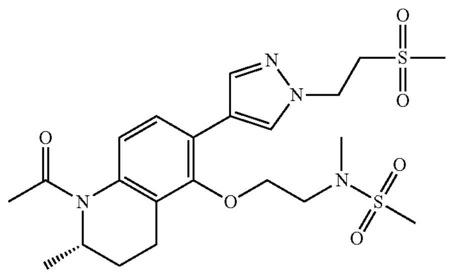 [SMILES: CC(=O)N1c2ccc(-c3cnn(CCS(C)(=O)=O)c3)c(OCCN(C)S(C)(=O)=O)c2CC[C@@H]1C] | 512.64 | 513 | 0.97 |
| I-437 | 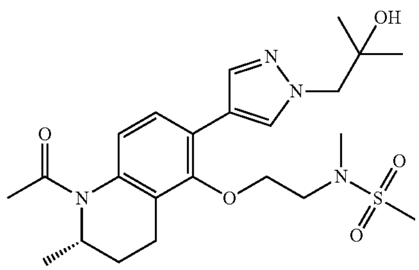 [SMILES: CC(=O)N1c2ccc(-c3cnn(CC(C)(C)O)c3)c(OCCN(C)S(C)(=O)=O)c2CC[C@@H]1C] | 478.61 | 479 | 1.01 |
| I-438 | 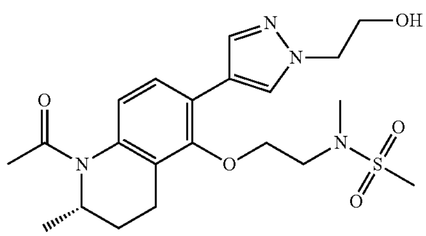 [SMILES: CC(=O)N1c2ccc(-c3cnn(CCO)c3)c(OCCN(C)S(C)(=O)=O)c2CC[C@@H]1C] | 450.55 | 451 | 0.89 |
| I-439 | 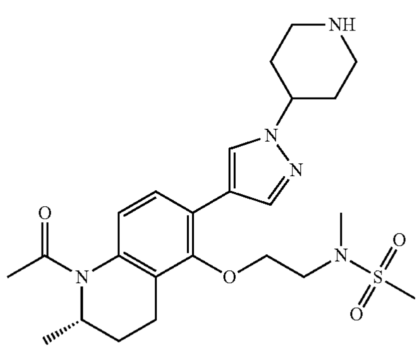 [SMILES: CC(=O)N1c2ccc(-c3cnn(C4CCNCC4)c3)c(OCCN(C)S(C)(=O)=O)c2CC[C@@H]1C] | 489.64 | 490 | 0.77 |
| I-440 | 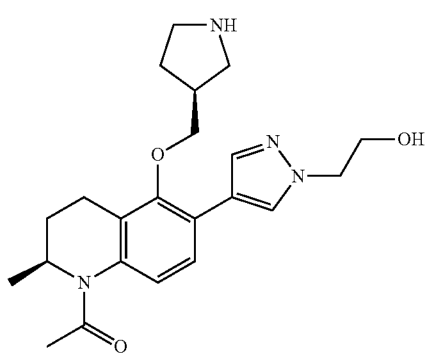 [SMILES: CC(=O)N1c2ccc(-c3cnn(CCO)c3)c(OC[C@H]3CCNC3)c2CC[C@@H]1C] | 398.51 | 399 | 0.66 |

TABLE 1-continued

| Compounds | Structure | MW | LC-MS [M + 1]+ | HPLC RT (min) |
|---|---|---|---|---|
| I-441 | 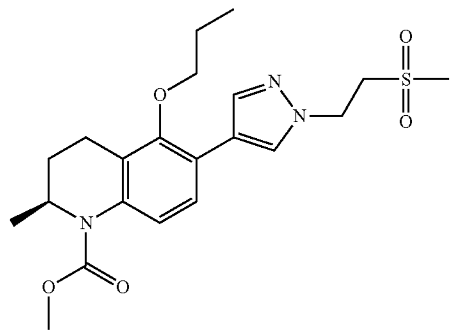 | 435.54 | 436 | 1.43 |
| I-442 | 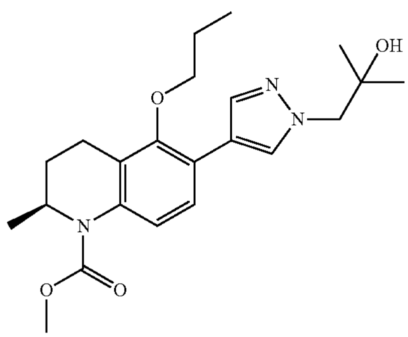 [SMILES: CCCOc1c(-c2cnn(CC(C)(C)O)c2)ccc2c1CC[C@H](C)N2C(=O)OC] | 401.51 | 402 | 1.51 |
| I-443 | 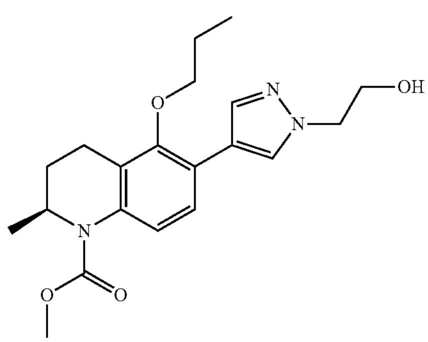 [SMILES: CCCOc1c(-c2cnn(CCO)c2)ccc2c1CC[C@H](C)N2C(=O)OC] | 373.45 | 374 | 1.33 |
| I-444 | 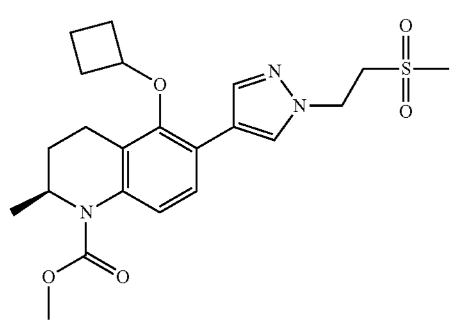 | 447.55 | 448 | 1.46 |

TABLE 1-continued

| Compounds | Structure | MW | LC-MS [M + 1]+ | HPLC RT (min) |
|---|---|---|---|---|
| I-445 | 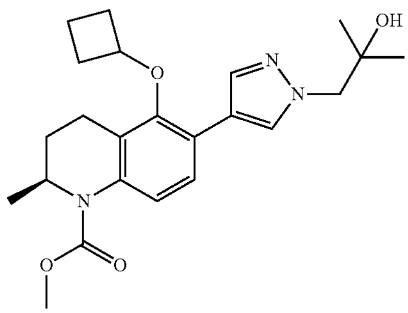 [SMILES: COC(=O)N1c2ccc(-c3cnn(CC(C)(C)O)c3)c(OC3CCC3)c2CC[C@@H]1C] | 413.52 | 414 | 1.52 |
| I-446 | 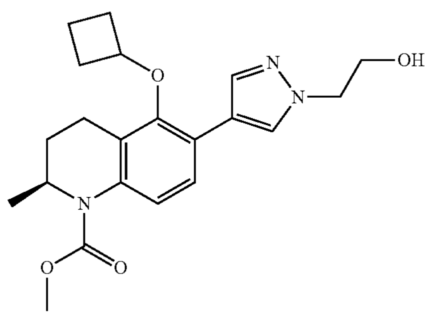 [SMILES: COC(=O)N1c2ccc(-c3cnn(CCO)c3)c(OC3CCC3)c2CC[C@@H]1C] | 385.46 | 386 | 1.33 |
| I-447 | 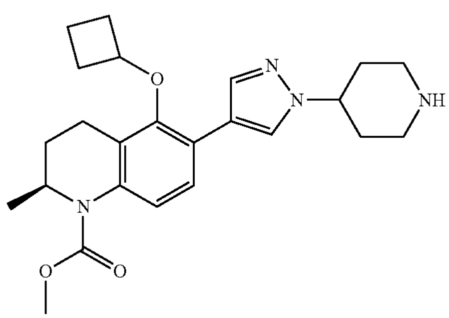 [SMILES: COC(=O)N1c2ccc(-c3cnn(C4CCNCC4)c3)c(OC3CCC3)c2CC[C@@H]1C] | 424.55 | 425 | 1.10 |
| I-448 | 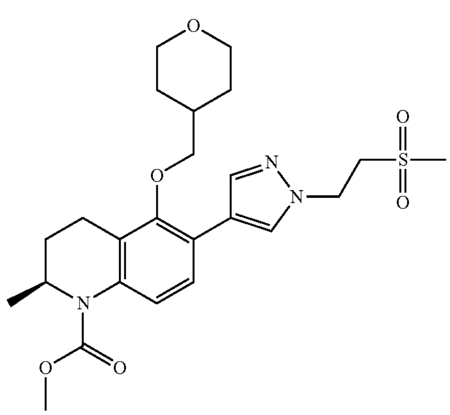 | 491.60 | 492 | 1.30 |

TABLE 1-continued

| Compounds | Structure | MW | LC-MS [M + 1]+ | HPLC RT (min) |
|---|---|---|---|---|
| I-449 | 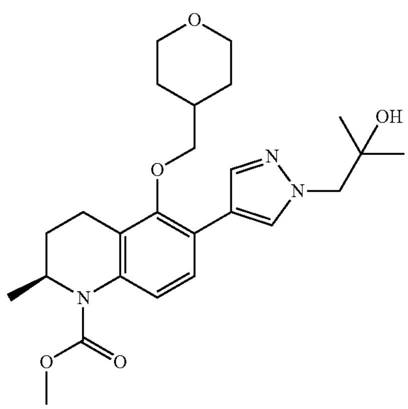 [SMILES: COC(=O)N1c2ccc(-c3cnn(CC(C)(C)O)c3)c(OCC3CCOCC3)c2CC[C@@H]1C] | 457.57 | 458 | 1.36 |
| I-450 | 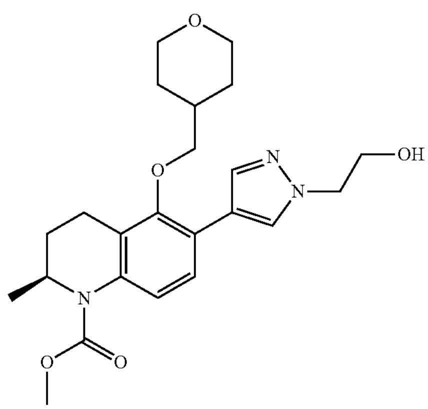 [SMILES: COC(=O)N1c2ccc(-c3cnn(CCO)c3)c(OCC3CCOCC3)c2CC[C@@H]1C] | 429.52 | 430 | 1.21 |
| I-451 | 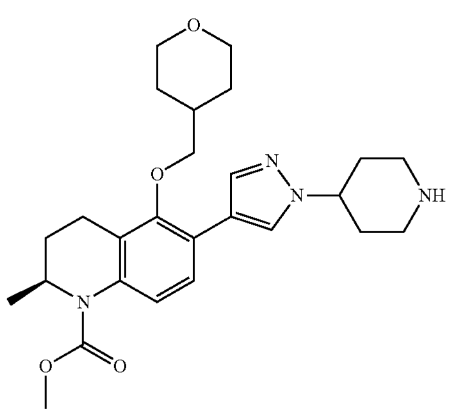 [SMILES: COC(=O)N1c2ccc(-c3cnn(C4CCNCC4)c3)c(OCC3CCOCC3)c2CC[C@@H]1C] | 468.60 | 469 | 1.04 |

TABLE 1-continued

| Compounds | Structure | MW | LC-MS [M + 1]+ | HPLC RT (min) |
|---|---|---|---|---|
| I-452 | 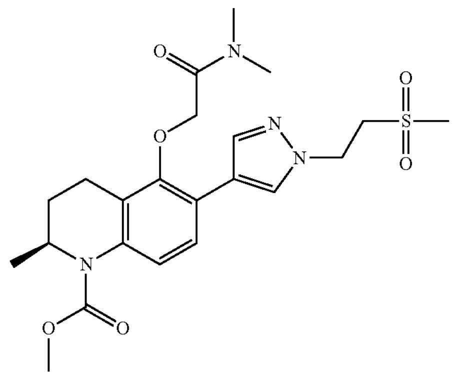 | 478.56 | 479 | 1.02 |
| I-453 | 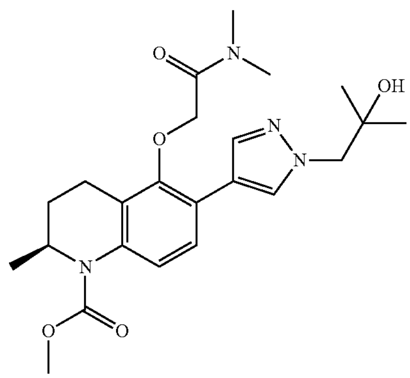 [SMILES: COC(=O)N1c2ccc(-c3cnn(CC(C)(C)O)c3)c(OCC(=O)N(C)C)c2CC[C@@H]1C] | 444.53 | 445 | 1.06 |
| I-454 | 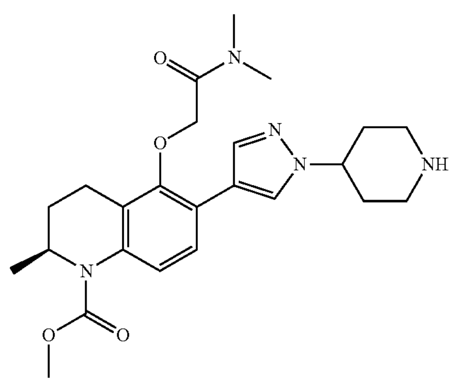 [SMILES: COC(=O)N1c2ccc(-c3cnn(C4CCNCC4)c3)c(OCC(=O)N(C)C)c2CC[C@@H]1C] | 455.56 | 456 | 0.86 |
| I-455 | 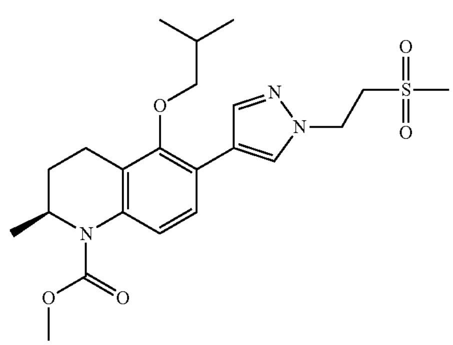 | 449.57 | 450 | 1.54 |

TABLE 1-continued

| Compounds | Structure | MW | LC-MS [M + 1]+ | HPLC RT (min) |
|---|---|---|---|---|
| I-456 | 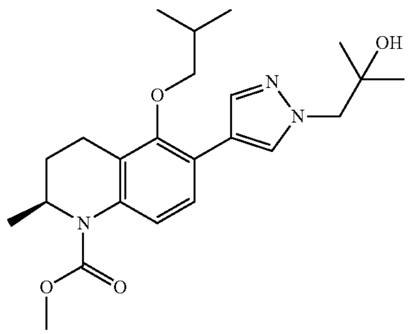 [SMILES: COC(=O)N1c2ccc(-c3cnn(CC(C)(C)O)c3)c(OCC(C)C)c2CC[C@@H]1C] | 415.53 | 416 | 1.64 |
| I-457 | 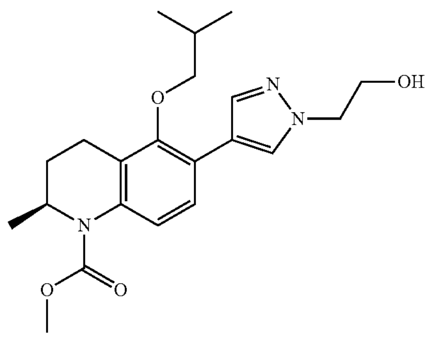 [SMILES: COC(=O)N1c2ccc(-c3cnn(CCO)c3)c(OCC(C)C)c2CC[C@@H]1C] | 387.48 | 388 | 1.45 |
| I-458 | 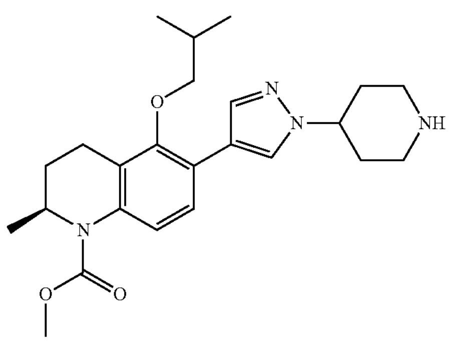 [SMILES: COC(=O)N1c2ccc(-c3cnn(C4CCNCC4)c3)c(OCC(C)C)c2CC[C@@H]1C] | 426.56 | 427 | 1.18 |
| I-459 | 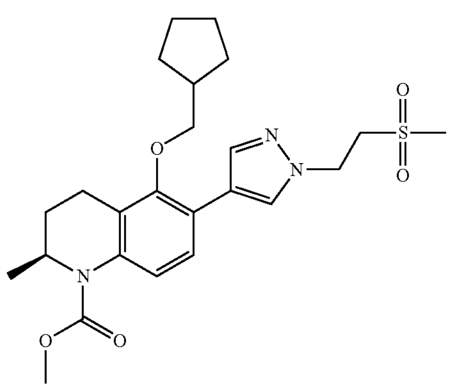 | 475.60 | 476 | 1.67 |

TABLE 1-continued

| Compounds | Structure | MW | LC-MS [M + 1]+ | HPLC RT (min) |
|---|---|---|---|---|
| I-460 | 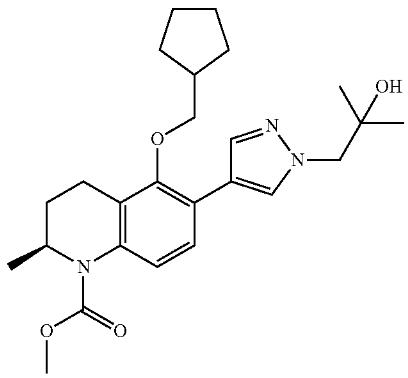 [SMILES: COC(=O)N1c2ccc(-c3cnn(CC(C)(C)O)c3)c(OCC3CCCC3)c2CC[C@@H]1C] | 441.57 | 442 | 1.78 |
| I-461 | 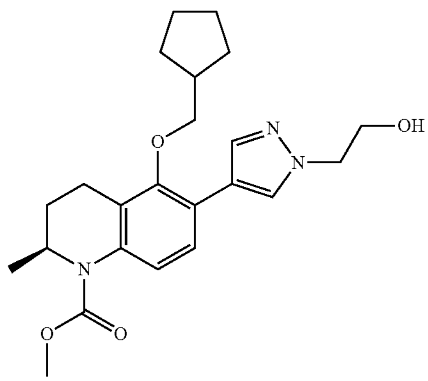 [SMILES: COC(=O)N1c2ccc(-c3cnn(CCO)c3)c(OCC3CCCC3)c2CC[C@@H]1C] | 413.52 | 414 | 1.58 |
| I-462 | 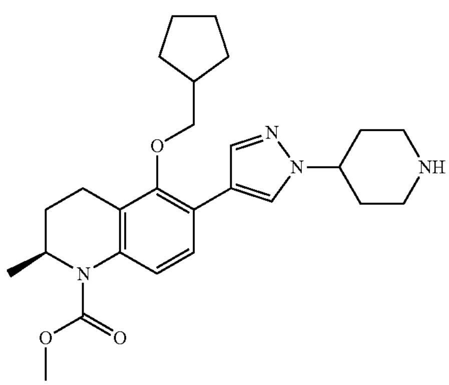 [SMILES: COC(=O)N1c2ccc(-c3cnn(C4CCNCC4)c3)c(OCC3CCCC3)c2CC[C@@H]1C] | 452.60 | 453 | 1.28 |
| I-463 | 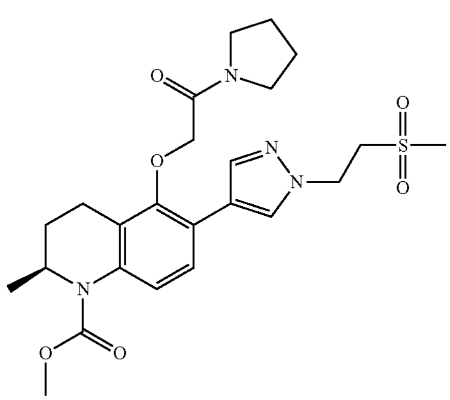 | 504.60 | 505 | 1.11 |

TABLE 1-continued
| Compounds | Structure | MW | LC-MS [M + 1]+ | HPLC RT (min) |
|---|---|---|---|---|
| I-464 | 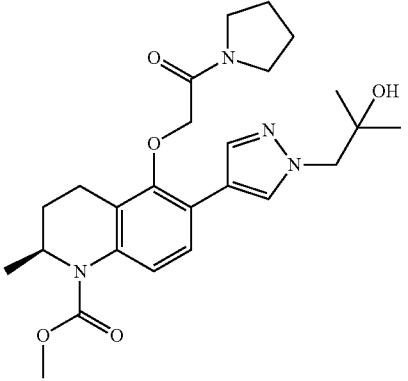 [SMILES: COC(=O)N1c2ccc(-c3cnn(CC(C)(C)O)c3)c(OCC(=O)N3CCCC3)c2CC[C@@H]1C] | 470.57 | 471 | 1.16 |
| I-465 | 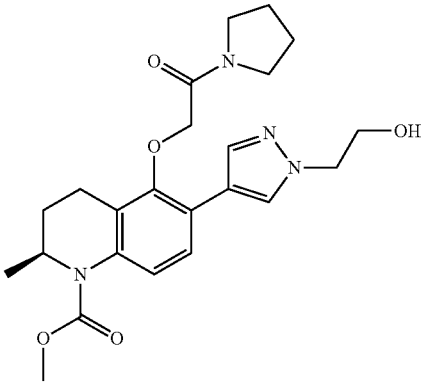 [SMILES: COC(=O)N1c2ccc(-c3cnn(CCO)c3)c(OCC(=O)N3CCCC3)c2CC[C@@H]1C] | 442.52 | 443 | 1.03 |
| I-466 | 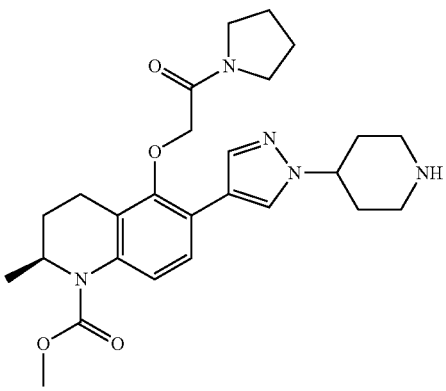 [SMILES: COC(=O)N1c2ccc(-c3cnn(C4CCNCC4)c3)c(OCC(=O)N3CCCC3)c2CC[C@@H]1C] | 481.60 | 482 | 0.93 |

TABLE 1-continued

| Compounds | Structure | MW | LC-MS [M + 1]+ | HPLC RT (min) |
|---|---|---|---|---|
| I-467 | 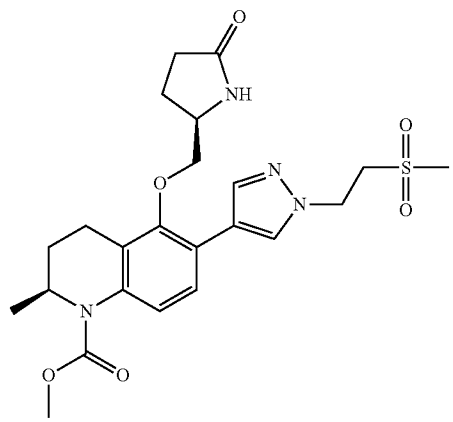 | 490.58 | 491 | 1.03 |
| I-468 | 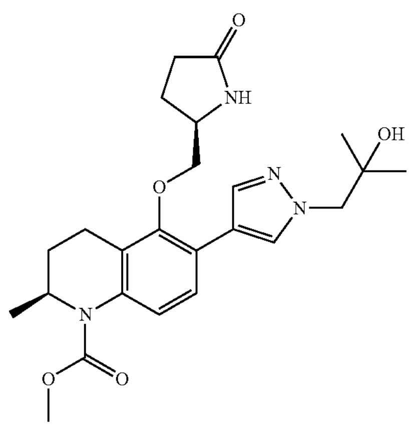 [SMILES: COC(=O)N1c2ccc(-c3cnn(CC(C)(C)O)c3)c(OC[C@H]3CCC(=O)N3)c2CC[C@@H]1C] | 456.54 | 457 | 1.07 |
| I-469 | 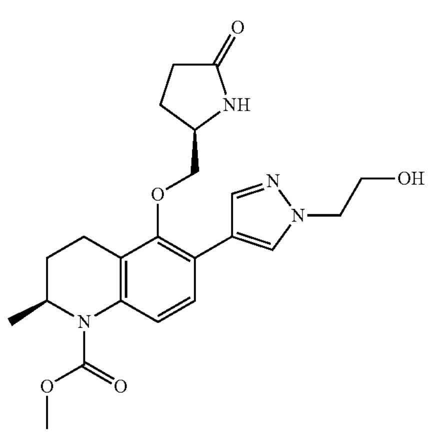 [SMILES: COC(=O)N1c2ccc(-c3cnn(CCO)c3)c(OC[C@H]3CCC(=O)N3)c2CC[C@@H]1C] | 428.49 | 429 | 0.98 |

TABLE 1-continued

| Compounds | Structure | MW | LC-MS [M + 1]+ | HPLC RT (min) |
|---|---|---|---|---|
| I-470 | 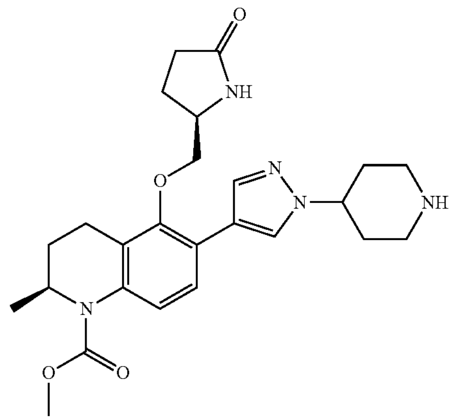 [SMILES: COC(=O)N1c2ccc(-c3cnn(C4CCNCC4)c3)c(OC[C@H]3CCC(=O)N3)c2CC[C@@H]1C] | 467.57 | 468 | 0.88 |
| I-471 | 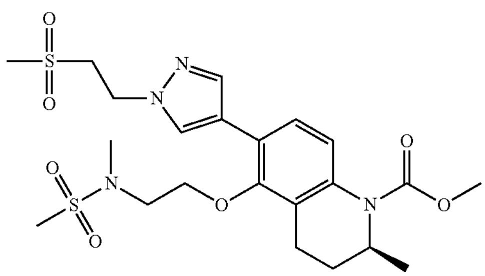 | 528.64 | 529 | 1.18 |
| I-472 | 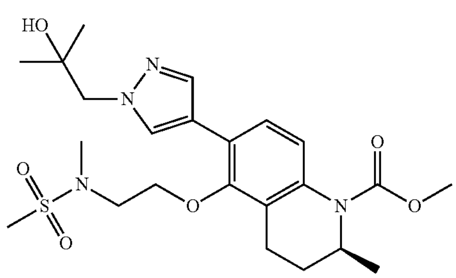 | 494.61 | 495 | 1.22 |
| I-473 | 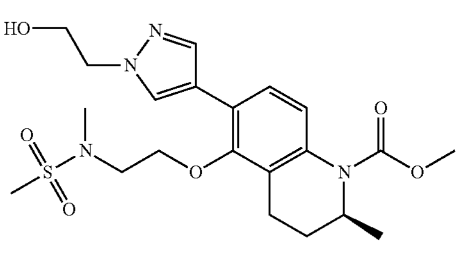 | 466.55 | 467 | 1.10 |

TABLE 1-continued

| Compounds | Structure | MW | LC-MS [M + 1]+ | HPLC RT (min) |
|---|---|---|---|---|
| I-474 | 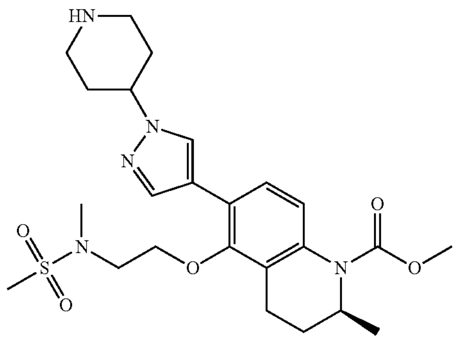 | 505.63 | 506 | 0.96 |
| I-475 | 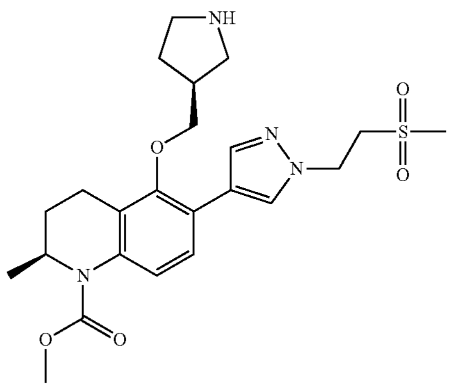 | 476.59 | 477 | 0.87 |
| I-476 | | 442.56 | 443 | 0.89 |
| I-476 | | 414.51 | 415 | 0.82 |

TABLE 1-continued
| Compounds | Structure | MW | LC-MS [M + 1]+ | HPLC RT (min) |
|---|---|---|---|---|
| I-477 | 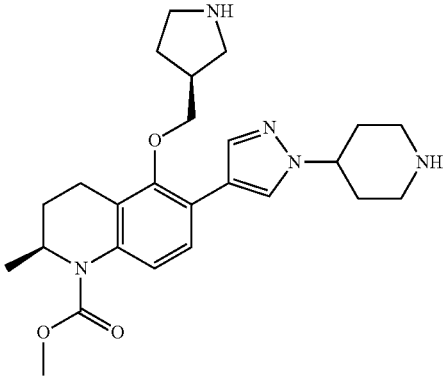 [SMILES: COC(=O)N1c2ccc(-c3cnn(C4CCNCC4)c3)c(OC[C@H]3CCNC3)c2CC[C@@H]1C] | 453.59 | 454 | 0.70 |
| I-478 | 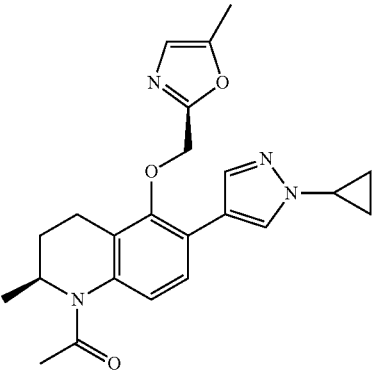 | 406.49 | 407.19 | 1.21 |
| I-479 | 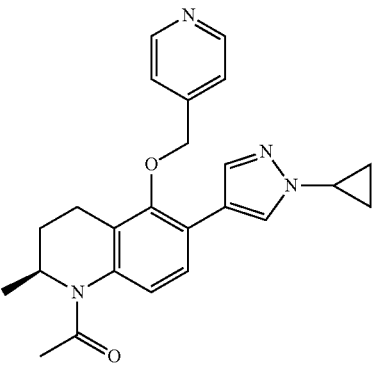 [SMILES: CC(=O)N1c2ccc(-c3cnn(C4CC4)c3)c(OCc3ccncc3)c2CC[C@@H]1C] | 402.50 | 403.19 | 0.98 |

TABLE 1-continued

| Compounds | Structure | MW | LC-MS [M + 1]+ | HPLC RT (min) |
|---|---|---|---|---|
| I-481 | 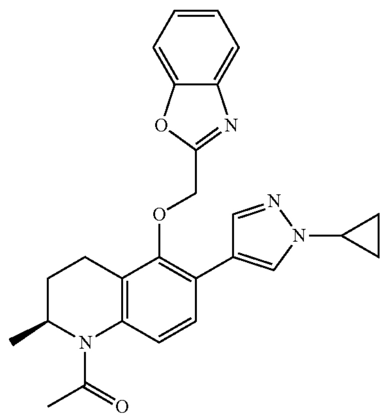 [SMILES: CC(=O)N1c2ccc(-c3cnn(C4CC4)c3)c(OCc3nc4ccccc4o3)c2CC[C@@H]1C] | 442.52 | 443.20 | 1.41 |
| I-482 | 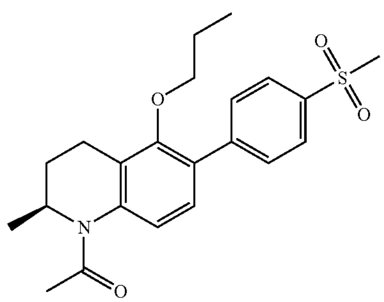 | 401.52 | 402.23 | 1.47 |
| I-483 | 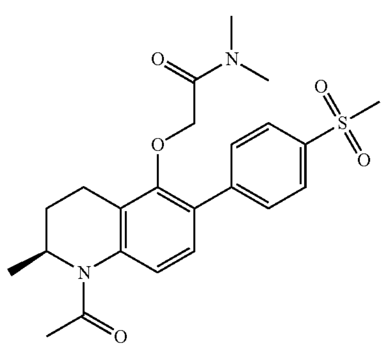 | 444.55 | 445.24 | 1.02 |
| I-484 | 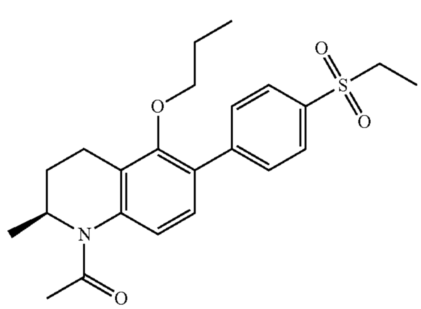 [SMILES: CCCOc1c(-c2ccc(S(=O)(=O)CC)cc2)ccc2c1CC[C@H](C)N2C(C)=O] | 415.55 | 416.26 | 1.57 |

TABLE 1-continued

| Compounds | Structure | MW | LC-MS [M + 1]+ | HPLC RT (min) |
|---|---|---|---|---|
| I-485 | 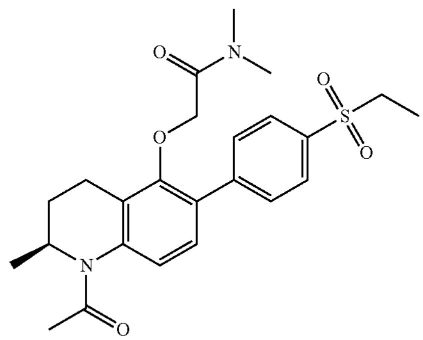 [SMILES: CCS(=O)(=O)c1ccc(-c2ccc3c(c2OCC(=O)N(C)C)CC[C@H](C)N3C(C)=O)cc1] | 458.57 | 459.25 | 1.10 |
| I-486 | 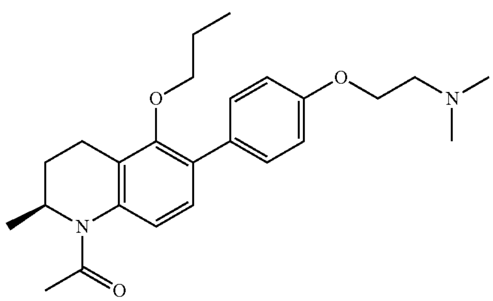 | 410.56 | 411.30 | 1.09 |
| I-487 | 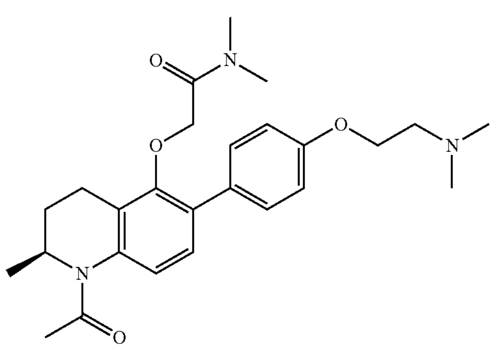 | 453.58 | 454.32 | 0.79 |
| I-488 | 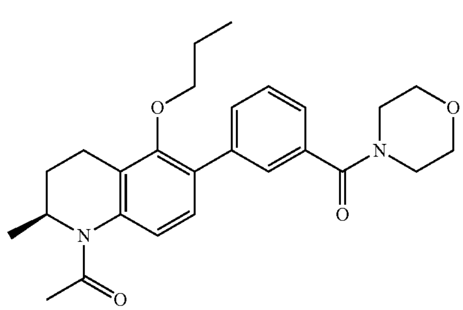 [SMILES: CCCOc1c(-c2cccc(C(=O)N3CCOCC3)c2)ccc2c1CC[C@H](C)N2C(C)=O] | 436.55 | 437.30 | 1.42 |

TABLE 1-continued

| Compounds | Structure | MW | LC-MS [M + 1]+ | HPLC RT (min) |
|---|---|---|---|---|
| I-489 | 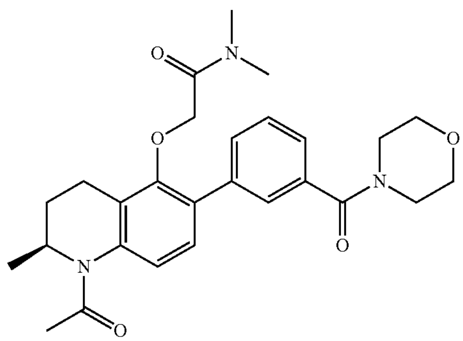 [SMILES: CC(=O)N1c2ccc(-c3cccc(C(=O)N4CCOCC4)c3)c(OCC(=O)N(C)C)c2CC[C@@H]1C] | 479.58 | 480.35 | 0.99 |
| I-490 | 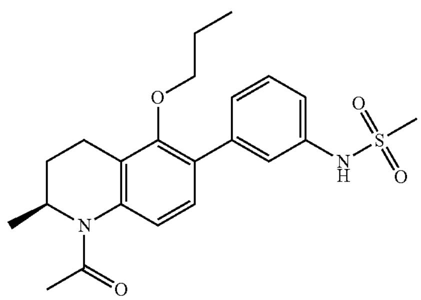 | 416.54 | 417.25 | 1.48 |
| I-491 | 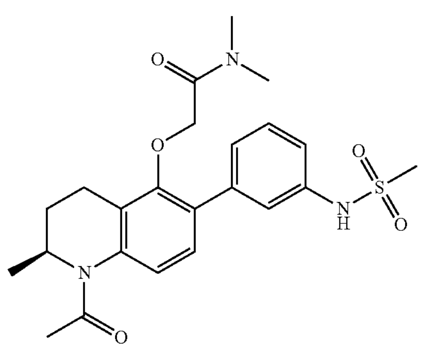 | 459.56 | 460.21 | 1.06 |
| I-492 | 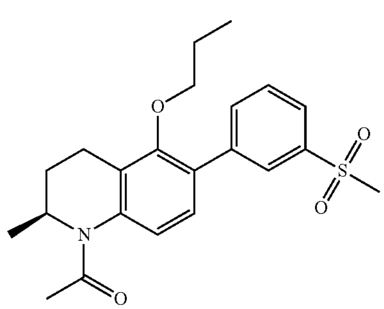 | 401.52 | 402.23 | 1.49 |

TABLE 1-continued

| Compounds | Structure | MW | LC-MS [M + 1]+ | HPLC RT (min) |
|---|---|---|---|---|
| I-493 | 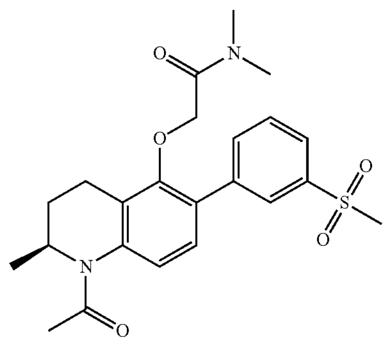 | 444.55 | 445.23 | 1.04 |
| I-494 | 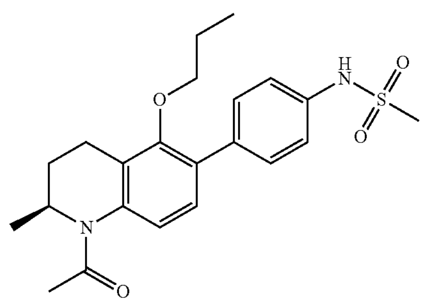 | 416.54 | 417.27 | 1.43 |
| I-495 | 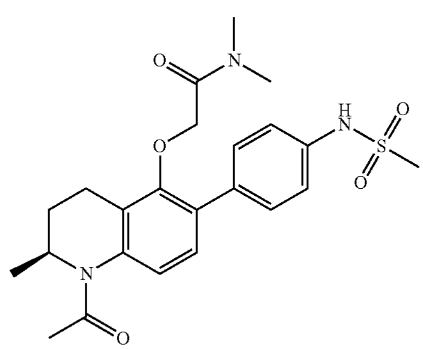 | 459.56 | 460.27 | 1.02 |
| I-496 | 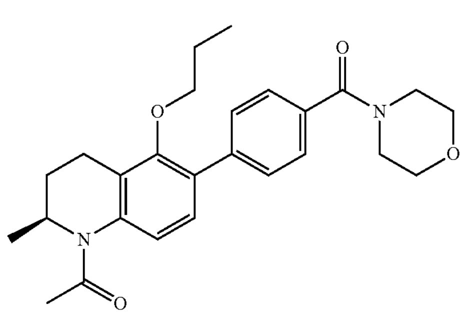 [SMILES: CCCOc1c(-c2ccc(C(=O)N3CCOCC3)cc2)ccc2c1CC[C@H](C)N2C(C)=O] | 436.55 | 437.30 | 1.40 |

TABLE 1-continued

| Compounds | Structure | MW | LC-MS [M + 1]+ | HPLC RT (min) |
|---|---|---|---|---|
| I-497 | 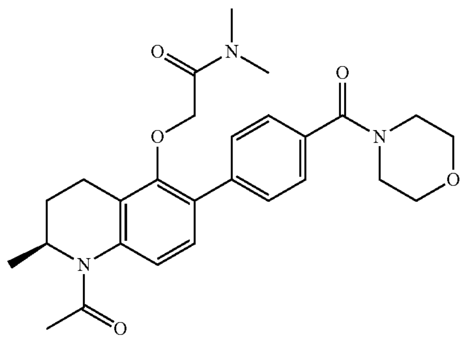 [SMILES: CC(=O)N1c2ccc(-c3ccc(C(=O)N4CCOCC4)cc3)c(OCC(=O)N(C)C)c2CC[C@@H]1C] | 479.58 | 480.33 | 0.98 |
| I-498 | 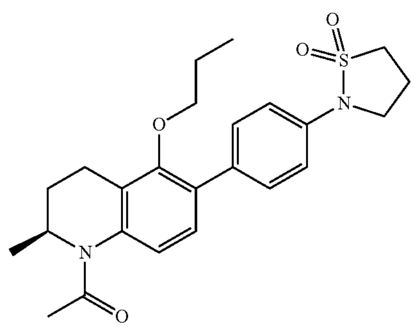 [SMILES: CCCOc1c(-c2ccc(N3CCCS3(=O)=O)cc2)ccc2c1CC[C@H](C)N2C(C)=O] | 442.57 | 443.26 | 1.53 |
| I-499 | 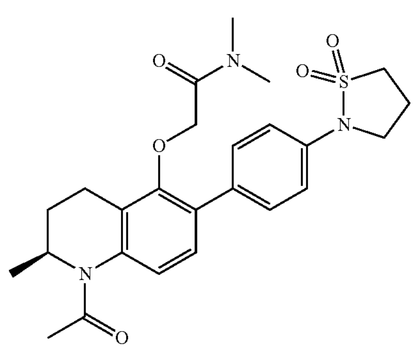 [SMILES: CC(=O)N1c2ccc(-c3ccc(N4CCCS4(=O)=O)cc3)c(OCC(=O)N(C)C)c2CC[C@@H]1C] | 485.60 | 486.30 | 1.09 |
| I-500 | 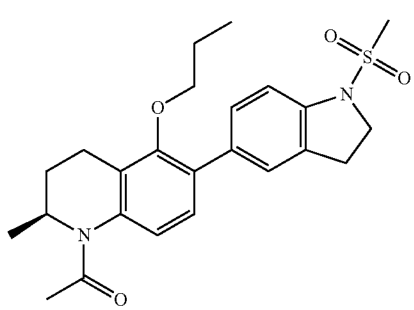 [SMILES: CCCOc1c(-c2ccc3c(c2)CCN3S(C)(=O)=O)ccc2c1CC[C@H](C)N2C(C)=O] | 442.57 | 443.25 | 1.64 |

TABLE 1-continued
| Compounds | Structure | MW | LC-MS [M + 1]+ | HPLC RT (min) |
|---|---|---|---|---|
| I-501 | 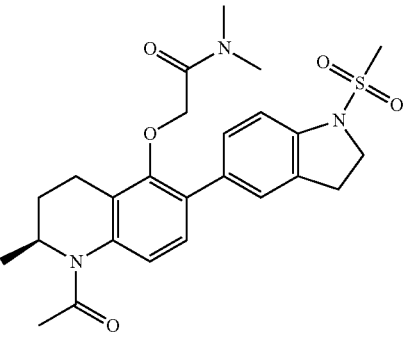 [SMILES: CC(=O)N1c2ccc(-c3ccc4c(c3)CCN4S(C)(=O)=O)c(OCC(=O)N(C)C)c2CC[C@@H]1C] | 485.60 | 486.32 | 1.17 |
| I-502 | 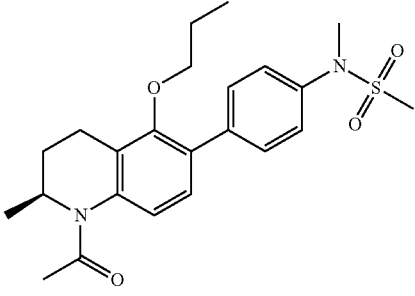 | 430.56 | 431.26 | 1.57 |
| I-503 | 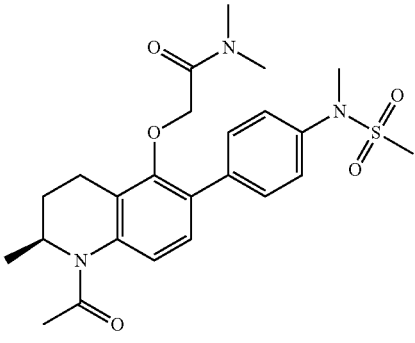 | 473.59 | 474.29 | 1.12 |
| I-504 | 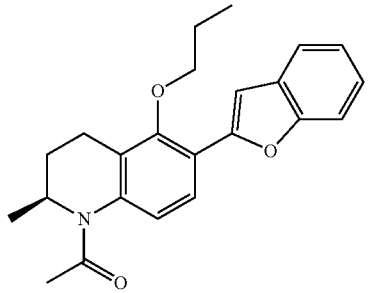 [SMILES: CCCOc1c(-c2cc3ccccc3o2)ccc2c1CC[C@H](C)N2C(C)=O] | 363.46 | 364.16 | 2.19 |

TABLE 1-continued

| Compounds | Structure | MW | LC-MS [M + 1]+ | HPLC RT (min) |
|---|---|---|---|---|
| I-505 | 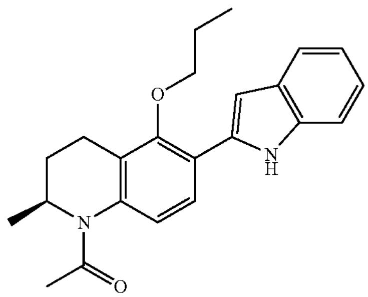 [SMILES: CCCOc1c(-c2cc3ccccc3[nH]2)ccc2c1CC[C@H](C)N2C(C)=O] | 362.47 | 363.20 | 1.97 |
| I-506 | | 396.49 | 397.13 | 1.10 |
| I-506 | | 384.48 | 385.16 | 1.10 |
| I-507 | 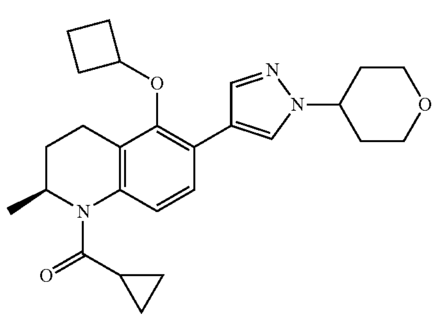 [SMILES: C[C@H]1CCc2c(ccc(-c3cnn(C4CCOCC4)c3)c2OC2CCC2)N1C(=O)C1CC1] | 435.57 | 436.25 | 1.60 |

TABLE 1-continued

| Compounds | Structure | MW | LC-MS [M + 1]+ | HPLC RT (min) |
|---|---|---|---|---|
| I-508 | 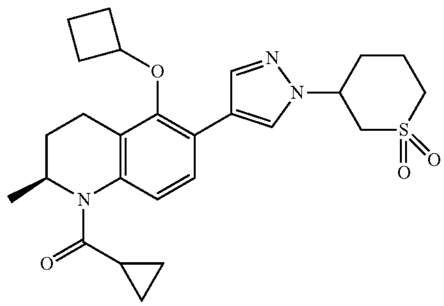 [SMILES: C[C@H]1CCc2c(ccc(-c3cnn(C4CCCS(=O)(=O)C4)c3)c2OC2CCC2)N1C(=O)C1CC1] | 483.63 | 484.21 | 1.51 |
| I-509 | 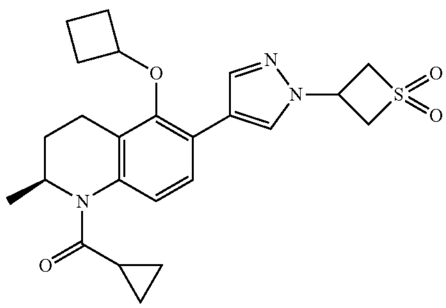 [SMILES: C[C@H]1CCc2c(ccc(-c3cnn(C4CS(=O)(=O)C4)c3)c2OC2CCC2)N1C(=O)C1CC1] | 455.57 | 456.22 | 1.51 |

Example 109

Library Protocol B

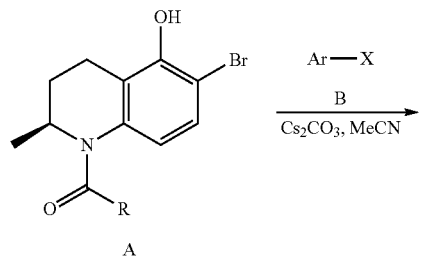

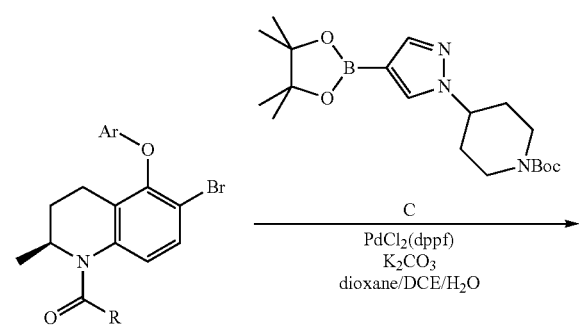

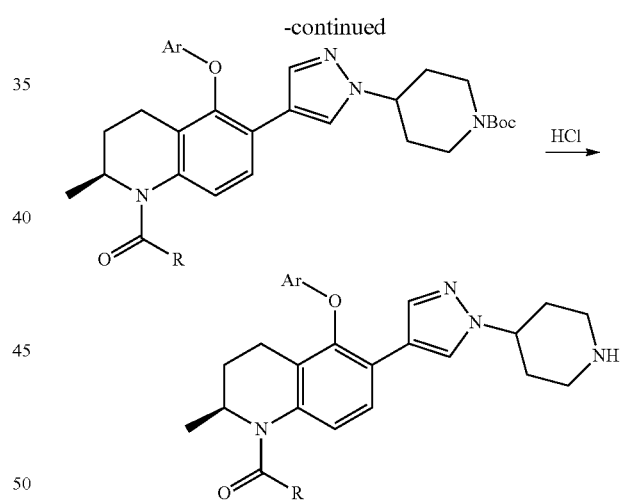

A half-dram vial was charged with (S)-6-bromo-2-methyl-1,2,3,4-tetrahydroquinolin-5-ol A (0.2 M in acetonitrile, 200 μL, 40 μmol) and aryl halide B (0.4 M in acetonitrile, 200 μL, 80 μmol). Cesium carbonate (66 mg, 200 μmol) was added, and the system was sealed and shaken at 80° C. for 14 h. Ethyl acetate (0.7 mL) and 1 N sodium hydroxide in brine (0.5 mL) were added and the mixture was shaken. The organic layer was separated and the aqueous phase was extracted with ethyl acetate (1.0 mL). The combined organic phases were concentrated and the residue was dissolved in anhydrous 1,4-dioxane (100 μL). Pyrazole boronic ester C (0.2 M in 1,4-dioxane, 360 μL, 72 μmol) and potassium carbonate (1 M aqueous solution, 120 μL, 120 μmol) were added, and the reaction was moved to a glove box. [1,1'-Bis(diphenylphosphino)ferrocene]dichloropalladium(II) dichloromethane adduct (0.02

M in 1,2-dichloroethane, 200 µL, 4 µmol) was added under a nitrogen atmosphere, and the mixture was sealed and shaken at 80° C. for 14 h. Ethyl acetate (0.5 mL) and 1 N sodium hydroxide in brine (0.4 mL) were added and the mixture was shaken. The organic layer was separated and the aqueous phase was extracted with ethyl acetate (1.0 mL). The combined organic phases were concentrated and the residue was dissolved in anhydrous 1,4-dioxane (200 µL). HCl (4 M in 1,4-dioxane, 100 µL) was added, and the system was sealed and shaken at 50° C. for 2 h. The mixture was concentrated and dissolved in ethyl acetate (500 µL). The solution was transferred to a silica-based, cation exchange column (SCX 0.5 g) and washed with ethyl acetate/methanol (3:1, 3 mL) (to elute waste) followed by ammonia (2 M in methanol, 3 mL) (to elute product). The ammonia solution was concentrated to afford the crude product. This material was purified by mass triggered preparatory HPLC. The product-containing fractions were combined and concentrated in a Genevac to afford the desired product.

The following compounds in Table 2 were synthesized according to the above protocol:

TABLE 2

| Compounds | Structure | MW | LC-MS [M + 1]+ | HPLC RT (min) |
|---|---|---|---|---|
| I-511 | 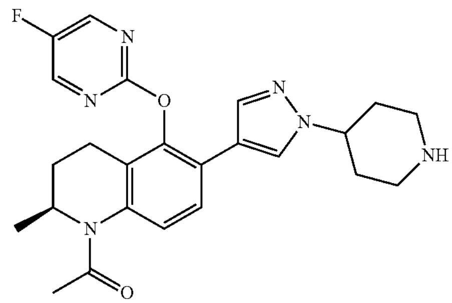 [SMILES: CC(=O)N1c2ccc(-c3cnn(C4CCNCC4)c3)c(Oc3ncc(F)cn3)c2CC[C@@H]1C] | 450.52 | 451.25 | 0.78 |
| I-512 | 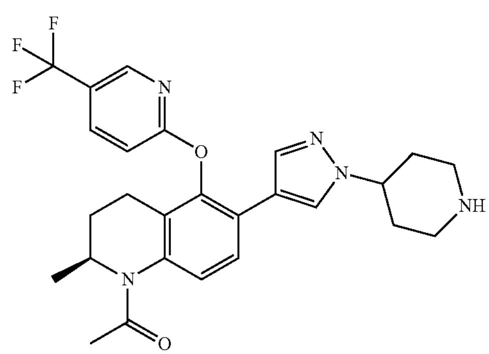 | 499.54 | 500.27 | 1.08 |
| I-513 | 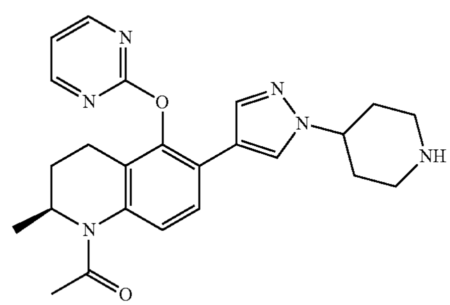 [SMILES: CC(=O)N1c2ccc(-c3cnn(C4CCNCC4)c3)c(Oc3ncccn3)c2CC[C@@H]1C] | 432.53 | 433.27 | 0.74 |

TABLE 2-continued

| Compounds | Structure | MW | LC-MS [M + 1]+ | HPLC RT (min) |
|---|---|---|---|---|
| I-514 | 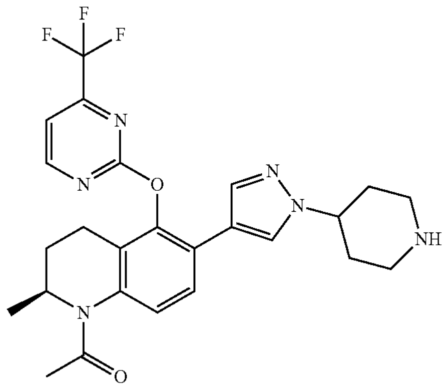 [SMILES: CC(=O)N1c2ccc(-c3cnn(C4CCNCC4)c3)c(Oc3nccc(C(F)(F)F)n3)c2CC[C@@H]1C] | 500.53 | 501.27 | 0.99 |
| I-515 | 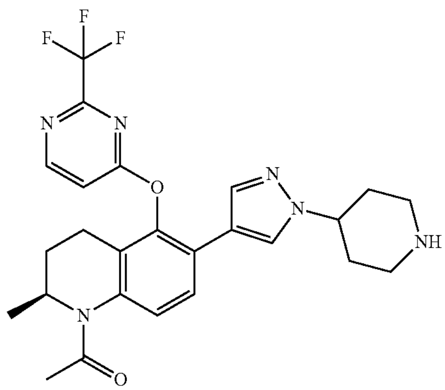 [SMILES: CC(=O)N1c2ccc(-c3cnn(C4CCNCC4)c3)c(Oc3ccnc(C(F)(F)F)n3)c2CC[C@@H]1C] | 500.53 | 501.29 | 1.00 |
| I-516 | 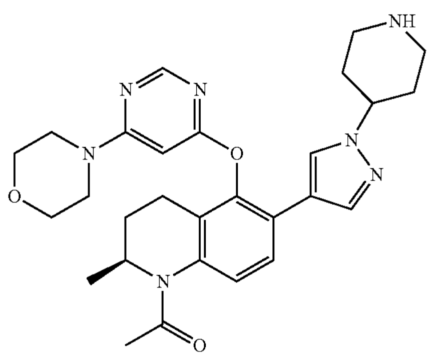 [SMILES: CC(=O)N1c2ccc(-c3cnn(C4CCNCC4)c3)c(Oc3cc(N4CCOCC4)ncn3)c2CC[C@@H]1C] | 517.63 | 518.28 | 0.82 |
| I-517 | 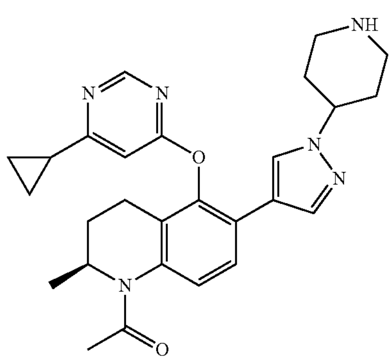 [SMILES: CC(=O)N1c2ccc(-c3cnn(C4CCNCC4)c3)c(Oc3cc(C4CC4)ncn3)c2CC[C@@H]1C] | 472.59 | 473.32 | 0.91 |

TABLE 2-continued

| Compounds | Structure | MW | LC-MS [M + 1]+ | HPLC RT (min) |
|---|---|---|---|---|
| I-518 | 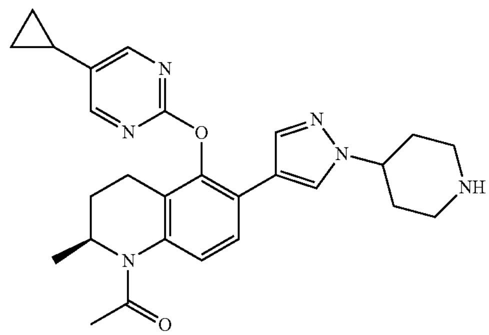 [SMILES: CC(=O)N1c2ccc(-c3cnn(C4CCNCC4)c3)c(Oc3ncc(C4CC4)cn3)c2CC[C@@H]1C] | 472.59 | 473.33 | 0.92 |
| I-519 | 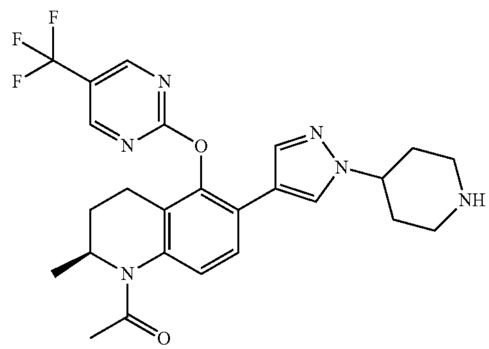 [SMILES: CC(=O)N1c2ccc(-c3cnn(C4CCNCC4)c3)c(Oc3ncc(C(F)(F)F)cn3)c2CC[C@@H]1C] | 500.53 | 501.29 | 0.98 |
| I-520 | 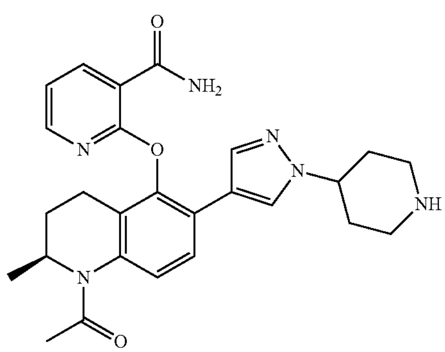 [SMILES: CC(=O)N1c2ccc(-c3cnn(C4CCNCC4)c3)c(Oc3ncccc3C(N)=O)c2CC[C@@H]1C] | 474.57 | 475.31 | 0.73 |
| I-521 | 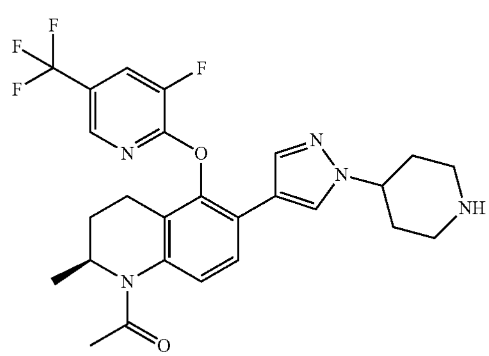 [SMILES: CC(=O)N1c2ccc(-c3cnn(C4CCNCC4)c3)c(Oc3ncc(C(F)(F)F)cc3F)c2CC[C@@H]1C] | 517.53 | 518.31 | 1.12 |

TABLE 2-continued

| Compounds | Structure | MW | LC-MS [M + 1]+ | HPLC RT (min) |
|---|---|---|---|---|
| I-522 | 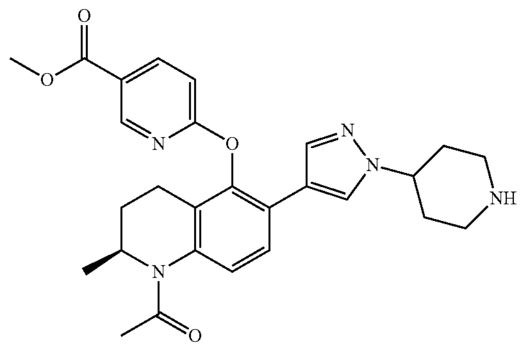 [SMILES: COC(=O)c1ccc(Oc2c(-c3cnn(C4CCNCC4)c3)ccc3c2CC[C@H](C)N3C(C)=O)nc1] | 489.58 | 490.29 | 0.94 |
| I-523 | 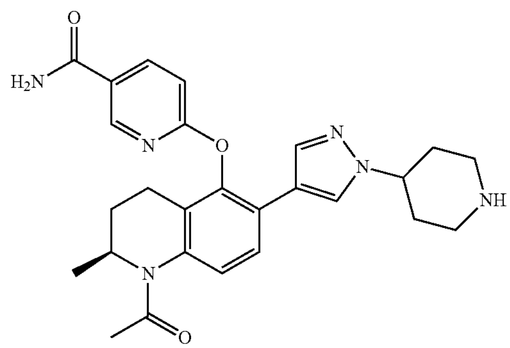 [SMILES: CC(=O)N1c2ccc(-c3cnn(C4CCNCC4)c3)c(Oc3ccc(C(N)=O)cn3)c2CC[C@@H]1C] | 474.57 | 475.29 | 0.74 |
| I-524 | 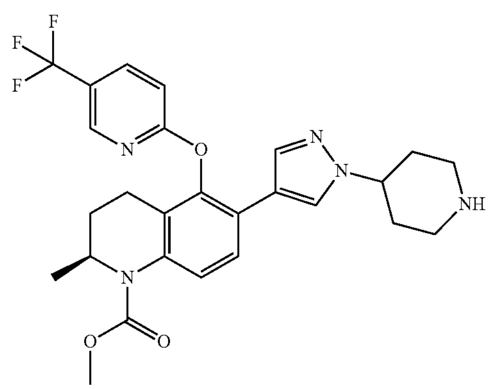 [SMILES: COC(=O)N1c2ccc(-c3cnn(C4CCNCC4)c3)c(Oc3ccc(C(F)(F)F)cn3)c2CC[C@@H]1C] | 515.54 | 516.28 | 1.24 |
| I-525 | 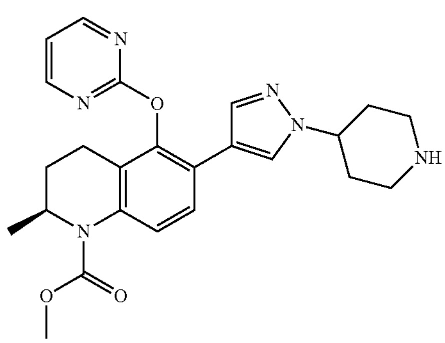 [SMILES: COC(=O)N1c2ccc(-c3cnn(C4CCNCC4)c3)c(Oc3ncccn3)c2CC[C@@H]1C] | 448.53 | 449.22 | 0.92 |

TABLE 2-continued

| Compounds | Structure | MW | LC-MS [M + 1]+ | HPLC RT (min) |
|---|---|---|---|---|
| I-526 | 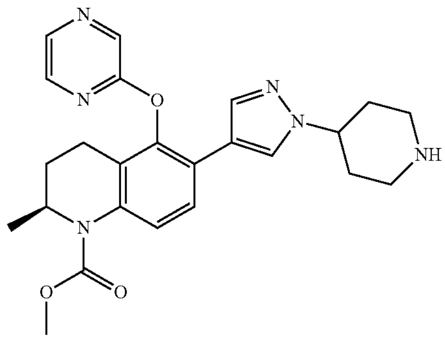 [SMILES: COC(=O)N1c2ccc(-c3cnn(C4CCNCC4)c3)c(Oc3cnccn3)c2CC[C@@H]1C] | 448.53 | 449.25 | 0.96 |
| I-527 | 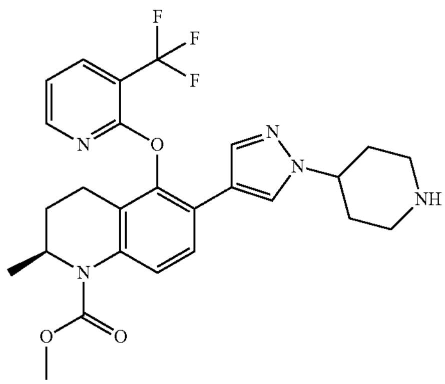 [SMILES: COC(=O)N1c2ccc(-c3cnn(C4CCNCC4)c3)c(Oc3ncccc3C(F)(F)F)c2CC[C@@H]1C] | 515.54 | 516.27 | 1.20 |
| I-528 | 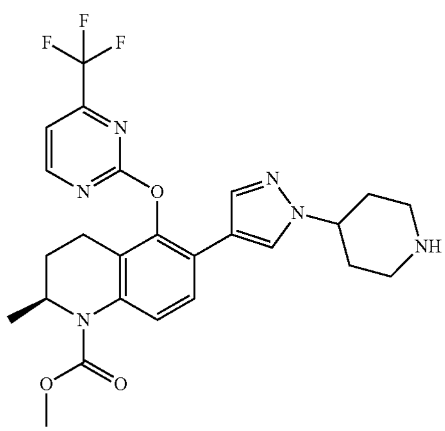 [SMILES: COC(=O)N1c2ccc(-c3cnn(C4CCNCC4)c3)c(Oc3nccc(C(F)(F)F)n3)c2CC[C@@H]1C] | 516.53 | 517.29 | 1.14 |
| I-529 | 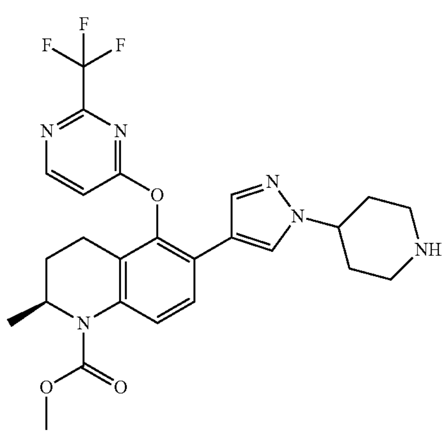 [SMILES: COC(=O)N1c2ccc(-c3cnn(C4CCNCC4)c3)c(Oc3ccnc(C(F)(F)F)n3)c2CC[C@@H]1C] | 516.53 | 517.29 | 1.16 |

TABLE 2-continued

| Compounds | Structure | MW | LC-MS [M + 1]+ | HPLC RT (min) |
|---|---|---|---|---|
| I-530 | 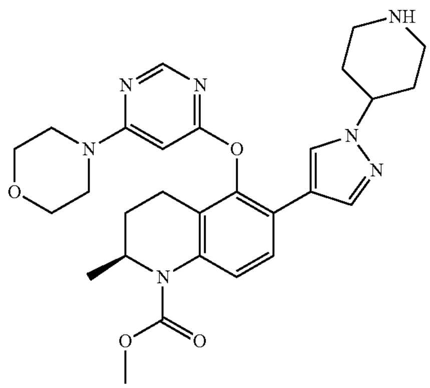 [SMILES: COC(=O)N1c2ccc(-c3cnn(C4CCNCC4)c3)c(Oc3cc(N4CCOCC4)ncn3)c2CC[C@@H]1C] | 533.63 | 534.34 | 1.00 |
| I-531 | 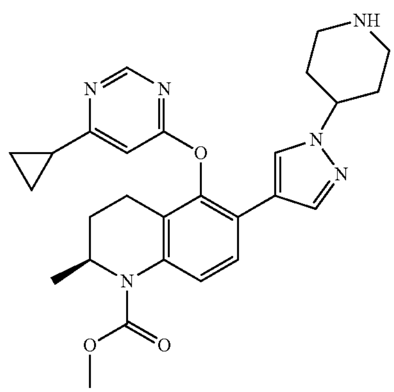 [SMILES: COC(=O)N1c2ccc(-c3cnn(C4CCNCC4)c3)c(Oc3cc(C4CC4)ncn3)c2CC[C@@H]1C] | 488.59 | 489.29 | 1.08 |
| I-532 | 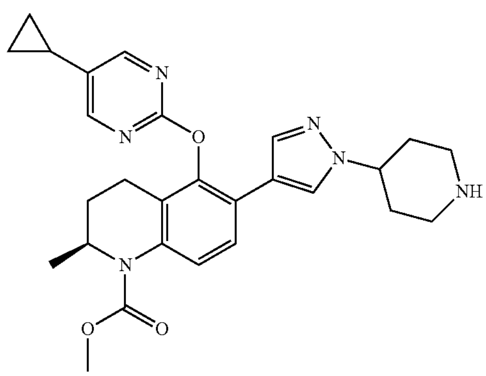 [SMILES: COC(=O)N1c2ccc(-c3cnn(C4CCNCC4)c3)c(Oc3ncc(C4CC4)cn3)c2CC[C@@H]1C] | 488.59 | 489.31 | 1.08 |
| I-533 | 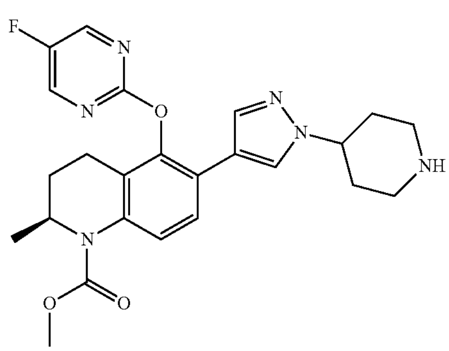 [SMILES: COC(=O)N1c2ccc(-c3cnn(C4CCNCC4)c3)c(Oc3ncc(F)cn3)c2CC[C@@H]1C] | 466.52 | 467.25 | 1.00 |

TABLE 2-continued

| Compounds | Structure | MW | LC-MS [M + 1]+ | HPLC RT (min) |
|---|---|---|---|---|
| I-534 | 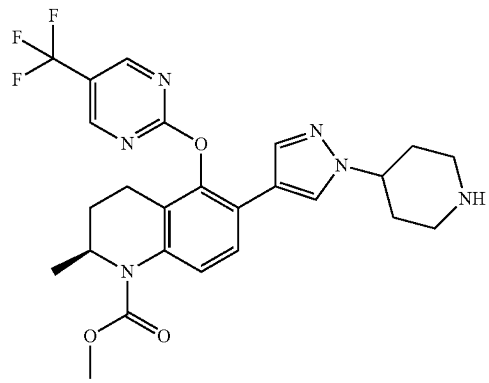 [SMILES: COC(=O)N1c2ccc(-c3cnn(C4CCNCC4)c3)c(Oc3ncc(C(F)(F)F)cn3)c2CC[C@@H]1C] | 516.53 | 517.27 | 1.15 |
| I-535 | 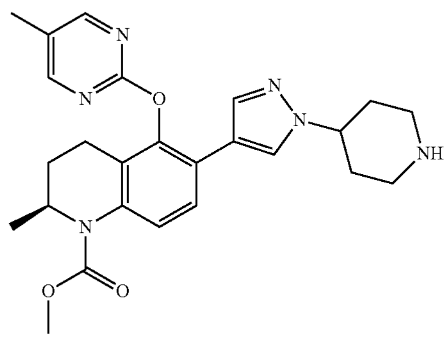 [SMILES: COC(=O)N1c2ccc(-c3cnn(C4CCNCC4)c3)c(Oc3ncc(C)cn3)c2CC[C@@H]1C] | 462.55 | 463.28 | 0.98 |
| I-536 | 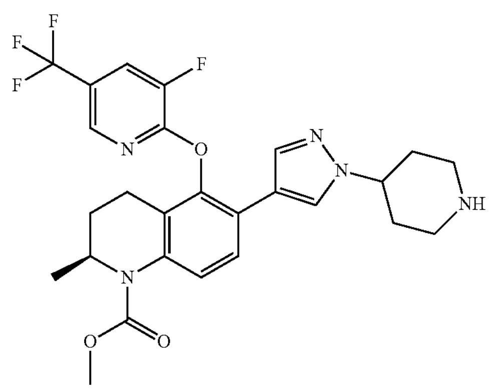 [SMILES: COC(=O)N1c2ccc(-c3cnn(C4CCNCC4)c3)c(Oc3ncc(C(F)(F)F)cc3F)c2CC[C@@H]1C] | 533.53 | 534.31 | 1.28 |
| I-537 | 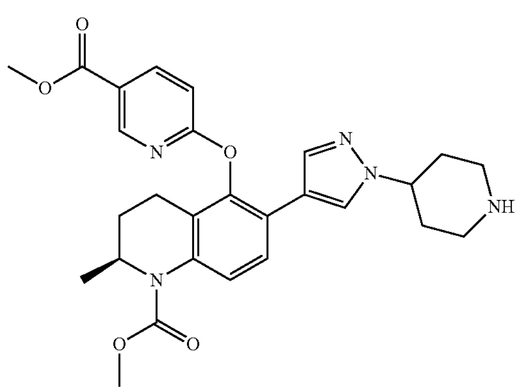 [SMILES: COC(=O)c1ccc(Oc2c(-c3cnn(C4CCNCC4)c3)ccc3c2CC[C@H](C)N3C(=O)OC)nc1] | 505.58 | 506.26 | 1.10 |

TABLE 2-continued

| Compounds | Structure | MW | LC-MS [M + 1]+ | HPLC RT (min) |
|---|---|---|---|---|
| I-538 | 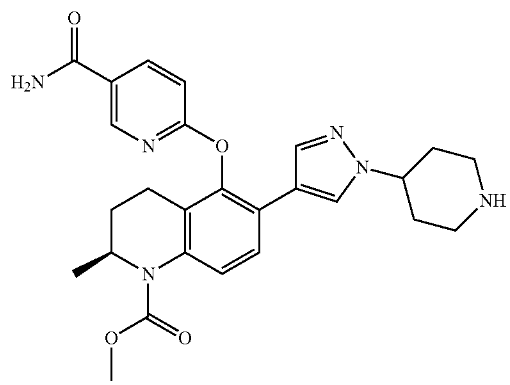 [SMILES: COC(=O)N1c2ccc(-c3cnn(C4CCNCC4)c3)c(Oc3ccc(C(N)=O)cn3)c2CC[C@@H]1C] | 490.56 | 491.28 | 0.89 |
| I-539 | 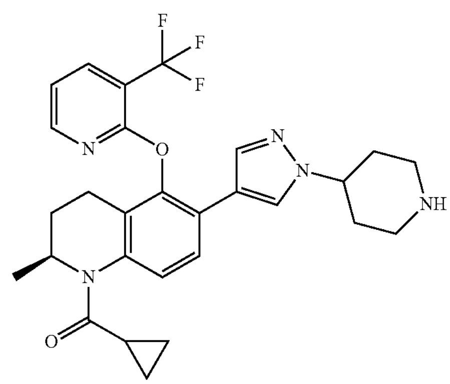 [SMILES: C[C@H]1CCc2c(ccc(-c3cnn(C4CCNCC4)c3)c2Oc2ncccc2C(F)(F)F)N1C(=O)C1CC1] | 525.58 | 526.17 | 1.15 |
| I-540 | 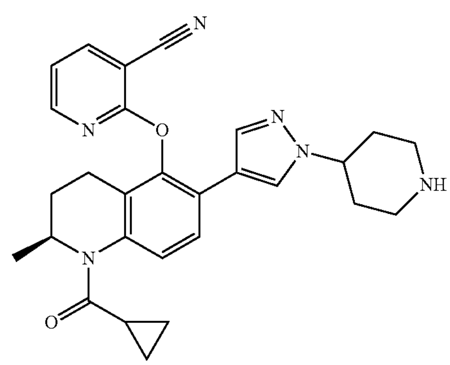 [SMILES: C[C@H]1CCc2c(ccc(-c3cnn(C4CCNCC4)c3)c2Oc2ncccc2C#N)N1C(=O)C1CC1] | 482.59 | 483.15 | 1.00 |
| I-541 | 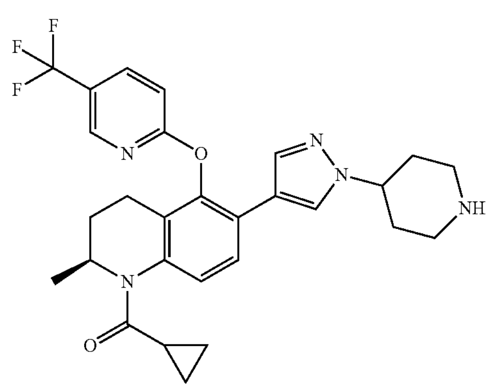 [SMILES: C[C@H]1CCc2c(ccc(-c3cnn(C4CCNCC4)c3)c2Oc2ccc(C(F)(F)F)cn2)N1C(=O)C1CC1] | 525.58 | 526.16 | 1.18 |

Example 110

Library Protocol C

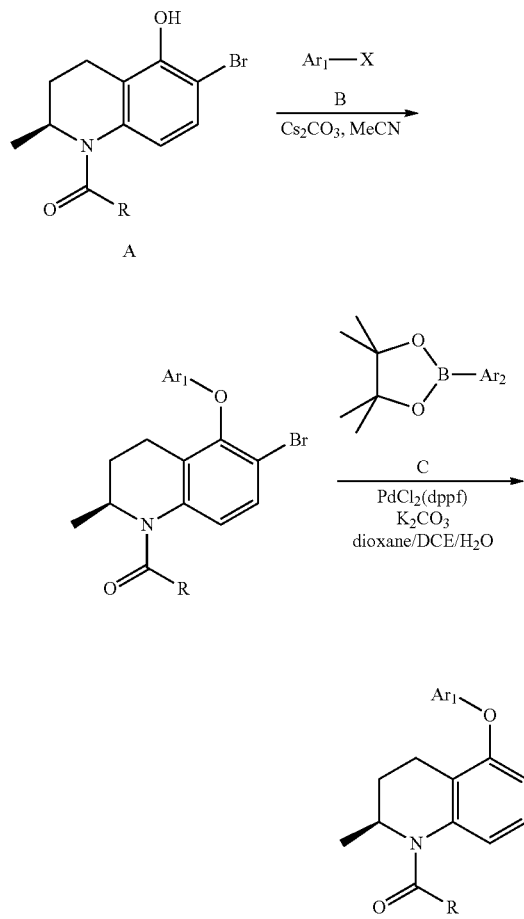

A half-dram vial was charged with (S)-6-bromo-2-methyl-1,2,3,4-tetrahydroquinolin-5-ol A (0.2 M in acetonitrile, 150 μL, 30 μmol) and aryl halide B (0.4 M in acetonitrile, 150 μL, 60 μmol). Cesium carbonate (50 mg, 150 μmol) was added, and the system was sealed and shaken at 80° C. for 14 h. Ethyl acetate (0.7 mL) and 1 N sodium hydroxide in brine (0.5 mL) were added and the mixture was shaken. The organic layer was separated and the aqueous phase was extracted with ethyl acetate (1.0 mL). The combined organic phases were concentrated and the residue was dissolved in anhydrous 1,4-dioxane (100 μL). Aryl boronic ester C (0.2 M in 1,4-dioxane, 270 μL, 54 μmol) and potassium carbonate (1 M aqueous solution, 90 μL, 90 μmol) were added, and the reaction was transferred to a glove box. [1,1'-Bis(diphenylphosphino)ferrocene]dichloropalladium(II) dichloromethane adduct (0.02 M in 1,2-dichloroethane, 150 μL, 3 μmol) was then added under a nitrogen atmosphere, and the mixture was sealed and shaken at 80° C. for 14 h. Ethyl acetate (0.5 mL) and brine (0.5 mL) were added and the mixture was shaken. The organic layer was separated and the aqueous phase was extracted with ethyl acetate (1.0 mL). The combined organic phases were concentrated and the residue was purified by mass triggered preparatory HPLC. The product-containing fractions were combined and concentrated in a Genevac to afford the desired product.

The following compounds in Table 3 were synthesized according to the above protocol:

TABLE 3

| Compounds | IUPAC Structure | MW | LC-MS [M + 1]+ | HPLC RT (min) |
|---|---|---|---|---|
| I-542 | | 461.45 | 462.26 | 1.11 |

TABLE 3-continued

| Compounds | IUPAC Structure | MW | LC-MS [M + 1]+ | HPLC RT (min) |
|---|---|---|---|---|
| I-543 | | 411.44 | 412.21 | 0.91 |
| I-544 | | 421.50 | 422.26 | 0.94 |
| I-545 | | 435.53 | 436.27 | 1.07 |
| I-546 | | 423.47 | 424.24 | 0.89 |

TABLE 3-continued

| Compounds | IUPAC Structure | MW | LC-MS [M + 1]+ | HPLC RT (min) |
|---|---|---|---|---|
| I-547 | | 433.51 | 434.28 | 1.02 |
| I-548 | | 496.56 | 497.20 | 1.33 |
| I-549 | | 455.50 | 456.17 | 1.18 |
| I-550 | | 473.52 | 474.18 | 0.98 |
| I-551 | | 439.49 | 440.20 | 1.03 |

TABLE 3-continued

| Compounds | IUPAC Structure | MW | LC-MS [M + 1]+ | HPLC RT (min) |
|---|---|---|---|---|
| I-552 | | 439.49 | 440.19 | 1.08 |
| I-553 | | 496.56 | 497.21 | 1.24 |
| I-554 | | 538.54 | 539.27 | 1.53 |
| I-555 | | 504.51 | 505.26 | 1.59 |

TABLE 3-continued

| Compounds | IUPAC Structure | MW | LC-MS [M + 1]+ | HPLC RT (min) |
|---|---|---|---|---|
| I-556 | | 476.46 | 477.21 | 1.46 |
| I-557 | | 472.47 | 473.22 | 1.75 |
| I-558 | | 471.53 | 472.22 | 1.18 |
| I-559 | | 437.50 | 438.26 | 1.22 |

TABLE 3-continued

| Compounds | IUPAC Structure | MW | LC-MS [M + 1]+ | HPLC RT (min) |
|---|---|---|---|---|
| I-560 | | 409.45 | 410.19 | 1.09 |
| I-561 | | 405.46 | 406.20 | 1.38 |
| I-562 | | 538.54 | 539.24 | 1.52 |
| I-563 | | 504.51 | 505.26 | 1.58 |

TABLE 3-continued

| Compounds | IUPAC Structure | MW | LC-MS [M + 1]+ | HPLC RT (min) |
|---|---|---|---|---|
| I-564 | | 476.46 | 477.23 | 1.43 |
| I-565 | | 472.47 | 473.21 | 1.76 |
| I-566 | | 495.55 | 496.22 | 1.31 |
| I-567 | | 461.52 | 462.24 | 1.34 |

TABLE 3-continued
| Compounds | IUPAC Structure | MW | LC-MS [M + 1]+ | HPLC RT (min) |
|---|---|---|---|---|
| I-568 | 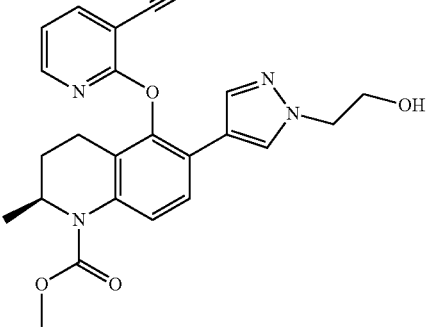 [SMILES: COC(=O)N1c2ccc(-c3cnn(CCO)c3)c(Oc3cnccn3)c2CC[C@@H]1C] | 433.47 | 434.21 | 1.22 |
| I-569 | 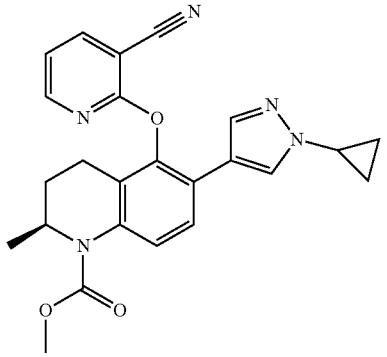 [SMILES: COC(=O)N1c2ccc(-c3cnn(C4CC4)c3)c(Oc3ncccc3C#N)c2CC[C@@H]1C] | 429.48 | 430.19 | 1.50 |
| I-570 | 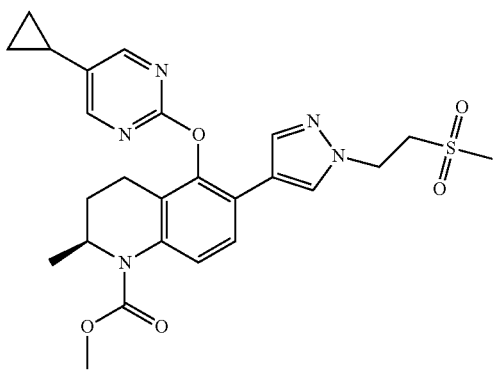 [SMILES: COC(=O)N1c2ccc(-c3cnn(CCS(C)(=O)=O)c3)c(Oc3ncc(C4CC4)cn3)c2CC[C@@H]1C] | 511.60 | 512.26 | 1.32 |
| I-571 | 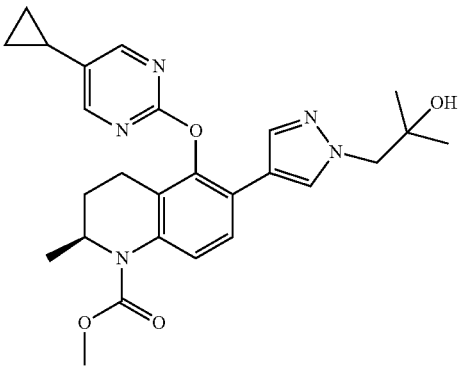 [SMILES: COC(=O)N1c2ccc(-c3cnn(CC(C)(C)O)c3)c(Oc3ncc(C4CC4)cn3)c2CC[C@@H]1C] | 477.57 | 478.26 | 1.36 |

TABLE 3-continued

| Compounds | IUPAC Structure | MW | LC-MS [M + 1]+ | HPLC RT (min) |
|---|---|---|---|---|
| I-572 | | 449.51 | 450.22 | 1.24 |
| I-573 | | 445.52 | 446.26 | 1.53 |
| I-574 | | 489.52 | 490.20 | 1.23 |
| I-575 | | 455.49 | 456.24 | 1.27 |

TABLE 3-continued

| Compounds | IUPAC Structure | MW | LC-MS [M + 1]+ | HPLC RT (min) |
|---|---|---|---|---|
| I-576 | | 427.44 | 428.21 | 1.14 |
| I-577 | | 423.45 | 424.18 | 1.43 |
| I-578 | | 539.53 | 540.24 | 1.41 |
| I-579 | | 505.50 | 506.26 | 1.46 |

TABLE 3-continued

| Compounds | IUPAC Structure | MW | LC-MS [M + 1]+ | HPLC RT (min) |
|---|---|---|---|---|
| I-580 | | 477.44 | 478.21 | 1.33 |
| I-581 | | 473.46 | 474.22 | 1.63 |
| I-582 | | 485.56 | 486.25 | 1.20 |
| I-583 | | 451.53 | 452.27 | 1.23 |

TABLE 3-continued

| Compounds | IUPAC Structure | MW | LC-MS [M + 1]+ | HPLC RT (min) |
|---|---|---|---|---|
| I-584 | | 423.47 | 424.21 | 1.11 |
| I-585 | | 419.49 | 420.21 | 1.40 |
| I-586 | | 513.57 | 514.26 | 1.04 |
| I-587 | | 447.50 | 448.22 | 1.18 |

TABLE 3-continued
| Compounds | IUPAC Structure | MW | LC-MS [M + 1]+ | HPLC RT (min) |
|---|---|---|---|---|
| I-588 | 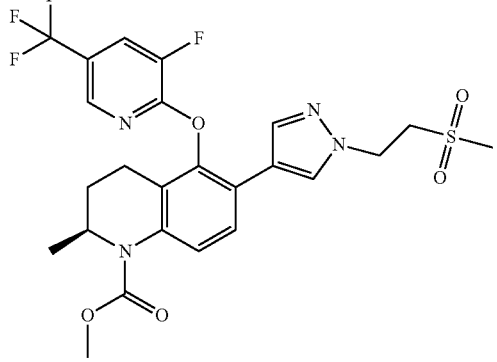 | 556.53 | 557.25 | 1.59 |
| I-589 | 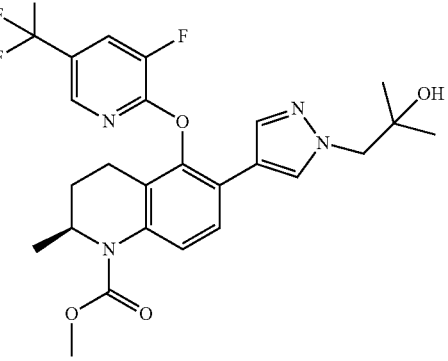 | 522.50 | 523.31 | 1.66 |
| I-590 | 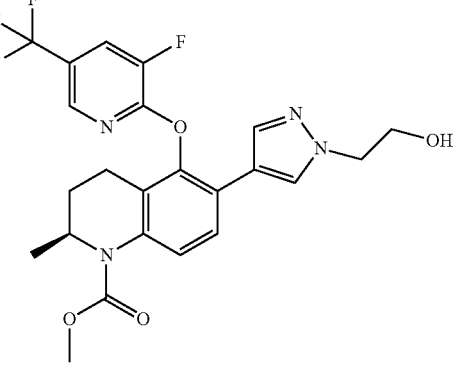 | 494.45 | 495.23 | 1.52 |
| I-591 | 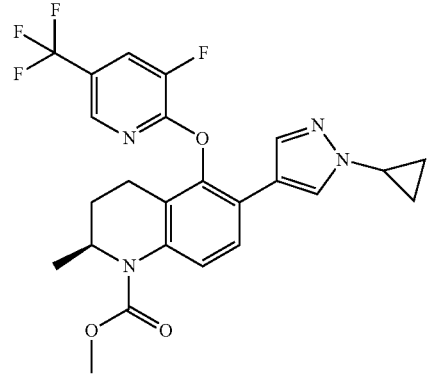 [SMILES: COC(=O)N1c2ccc(-c3cnn(C4CC4)c3)c(Oc3ncc(C(F)(F)F)cc3F)c2CC[C@@H]1C] | 490.46 | 491.25 | 1.82 |

TABLE 3-continued

| Compounds | IUPAC Structure | MW | LC-MS [M + 1]+ | HPLC RT (min) |
|---|---|---|---|---|
| I-592 | 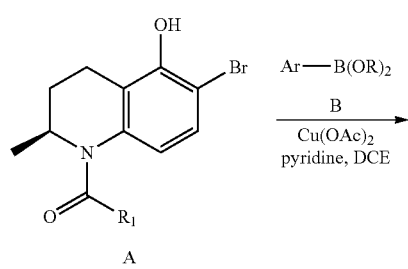 | 465.53 | 466.15 | 1.69 |
| I-593 | | 436.49 | 437.10 | 1.21 |

Example 111

Library Protocol D

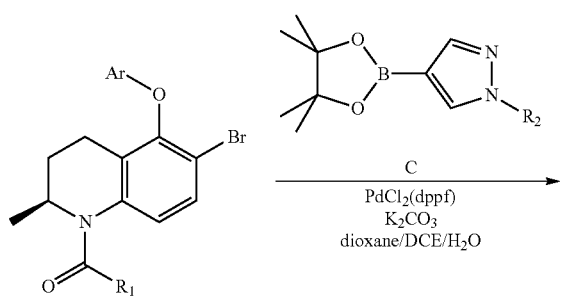

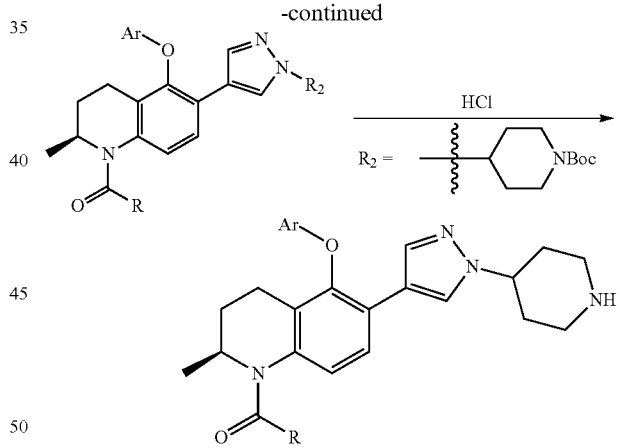

A half-dram vial was charged with aryl boronic acid B (0.2 M in 1,4-dioxane, 500 µL, 100 µmol) and copper (II) acetate (0.2 M in water, 260 µL, 52 µmol). The mixture was concentrated and molecular sieves (50 mg) were added. (S)-6-Bromo-2-methyl-1,2,3,4-tetrahydroquinolin-5-ol A (0.2 M in 1,2-dichloroethane, 200 µL, 40 µmol) and pyridine (0.5 M in 1,2-dichloroethane, 400 µL, 200 µmol) were added, and the system was sealed and shaken at 80° C. for 14 h. Ethyl acetate (0.7 mL) and saturated aqueous ammonium chloride solution (0.5 mL) were added and the mixture was shaken. The organic layer was separated and the aqueous phase was extracted with ethyl acetate (1.0 mL). The combined organic phases were concentrated and the residue was dissolved in anhydrous 1,4-dioxane (100 µL). Pyrazole boronic ester C (0.2 M in 1,4-dioxane, 400 µL, 80 µmol) and potassium carbonate (1 M aqueous solution, 120 µL, 120 µmol) were added, and the reaction was transferred to a glove box. [1,1-Bis(diphenylphosphino)ferrocene]dichloropalladium(II) dichloromethane adduct (0.02 M in 1,2-dichloroethane, 200 µL, 4 µmol) was then added under a nitrogen atmosphere, and the mixture was sealed and shaken at 80° C. for 14 h. Ethyl acetate (0.5 mL) and 1 N sodium hydroxide in brine (0.4 mL) were added and the mixture was shaken. The organic layer was separated and the aqueous phase was extracted with ethyl acetate (1.0 mL). The combined organic phases were concentrated and the residue was dissolved in anhydrous 1,4-dioxane (200 µL). (NOTE: For examples lacking a Boc-protected intermediate, the following acid hydrolysis step and SCX purification were omitted). HCl (4 M in 1,4-dioxane, 100 µL) was added, and the system was sealed and shaken at 50° C. for 2 h. The mixture was concentrated and dissolved in ethyl acetate (500 µL). The solution was transferred to a silica-based, cation exchange column (SCX 0.5 g) and washed with ethyl acetate/methanol (3:1, 3 mL) (to elute waste) followed by ammonia (2 M in methanol, 3 mL) (to elute product). The ammonia solution was concentrated to afford the crude product. This material was purified by mass triggered preparatory HPLC. The product-containing fractions were combined and concentrated in a Genevac to afford the desired product.

The following compounds in Table 4 were synthesized according to the above protocol:

TABLE 4

| Compounds | IUPAC Structure | MW | LC-MS [M + 1]+ | HPLC RT (min) |
|---|---|---|---|---|
| I-594 | | 387.48 | 388.14 | 1.55 |
| I-595 | | 458.56 | 459.17 | 1.23 |
| I-596 | | 471.56 | 472.11 | 1.16 |

Example 112

Library Protocol E

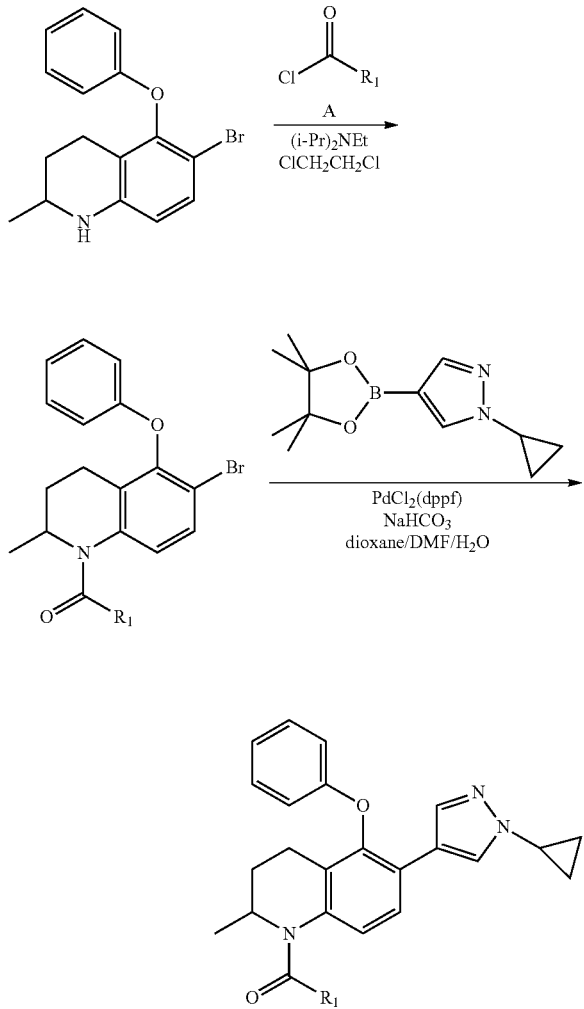

A reaction vial was charged with 6-bromo-2-methyl-5-phenoxy-1,2,3,4-tetrahydroquinoline (0.2 M in 1,2-dichloroethane, 0.10 mL, 0.02 mmol), N,N-diisopropylethyl amine (10.5 μL, 0.06 mmol), and an acid chloride or chloroformate (A) (0.5 M in 1,2-dichloroethane, 0.05 mL, 0.025 mmol), and the mixture was shaken at 50° C. for 2 h. Ethyl acetate and water were added and the mixture was shaken. The organic layer was separated and the aqueous phase was extracted with ethyl acetate. The combined organic phases were concentrated and the residue was dissolved in anhydrous 1,4-dioxane (100 μL). 1-Cyclopropyl-4-(4,4,5,5-tetramethyl-1,3,2-dioxaborolan-2-yl)-1H-pyrazole (0.2 M in 1,4-dioxane, 0.10 mL, 0.02 mmol) and sodium bicarbonate (1 M aqueous solution, 0.06 mL, 0.06 mmol) were added, and the reaction was transferred to a glove box. [1,1'-Bis(diphenylphosphino)ferrocene]dichloropalladium(II) dichloromethane adduct (0.02 M in 1,2-dichloroethane, 0.05 mL, 0.001 mmol) was then added under a nitrogen atmosphere, and the mixture was sealed and shaken at 80° C. for 18 h. Ethyl acetate and water were added and the mixture was shaken. The organic layer was separated and the aqueous phase was extracted with ethyl acetate. The combined organic phases were concentrated to afford the crude product. This material was purified by mass triggered preparatory HPLC. The product-containing fractions were combined and concentrated in a Genevac to afford the desired product.

The following compounds in Table 5 were synthesized according to the above protocol:

TABLE 5

| Compounds | IUPAC Structure | MW | LC-MS [M + 1]+ | HPLC RT (min) |
|---|---|---|---|---|
| I-597 | | 387.48 | 388 | 1.55 |

TABLE 5-continued
| Compounds | IUPAC Structure | MW | LC-MS [M + 1]+ | HPLC RT (min) |
|---|---|---|---|---|
| I-598 | | 413.52 | 414 | 1.76 |
| I-599 | | 403.48 | 404 | 1.81 |
Example 113
Library Protocol F
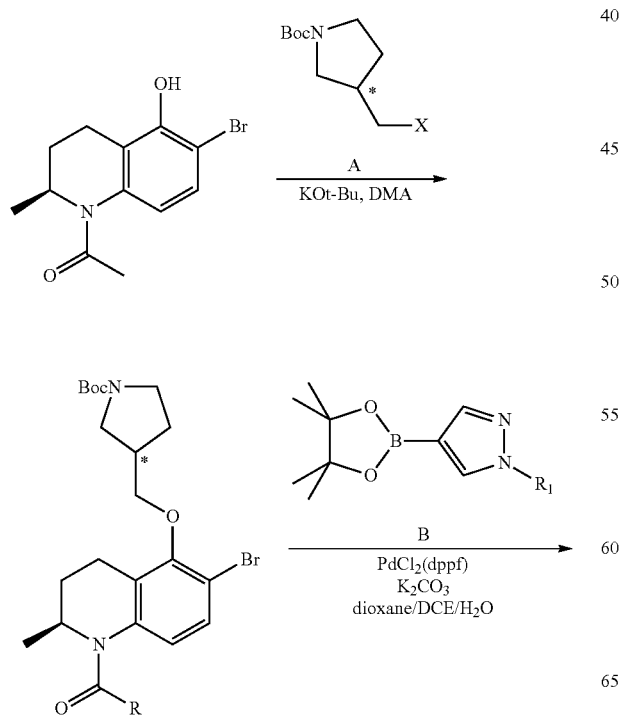
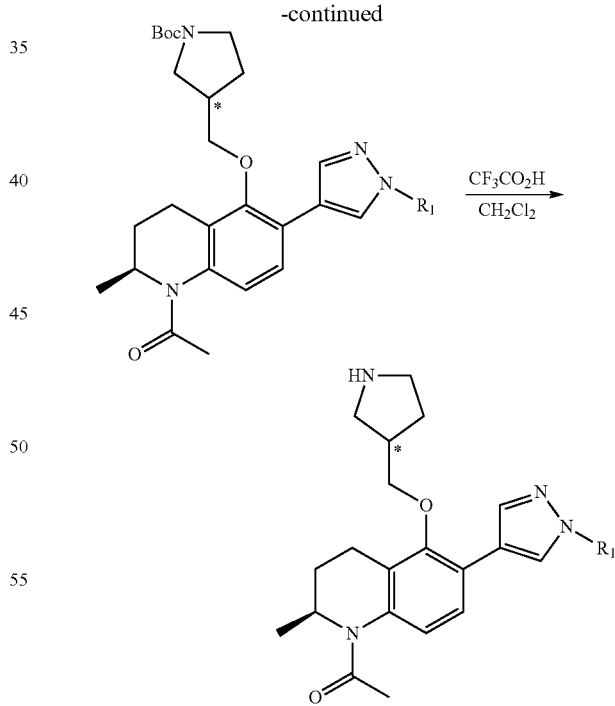
A reaction vial was charged with (S)-1-(6-bromo-5-hydroxy-2-methyl-3,4-dihydroquinolin-1(2H)-yl)ethanone (0.2 M in N,N-dimethylacetamide, 0.100 mL, 0.02 mmol) and (R)- or (S)-tert-butyl 3-(bromomethyl)pyrrolidine-1-carboxylate A (0.2 M in N,N-dimethylacetamide, 0.12 mL, 0.024 mmol). Potassium tert-butoxide (1 M in THF, 0.024 mL, 0.024 mmol) was added, and the system was sealed and shaken at 80° C. overnight. Ethyl acetate and 1 N sodium hydroxide in brine were added and the mixture was shaken. The organic layer was separated and the aqueous phase was extracted with ethyl acetate. The combined organic phases were concentrated and the residue was dissolved in anhydrous 1,4-dioxane (100 μL). Pyrazole boronic ester B (0.2 M in 1,4-dioxane, 0.15 mL, 0.030 mmol) and potassium carbonate (1 M aqueous solution, 0.060 mL, 0.060 mmol) were added, and the reaction was transferred to a glove box. [1,1'-Bis(diphenylphosphino)ferrocene]dichloropalladium(II) dichloromethane adduct (0.02 M in 1,2-dichloroethane, 0.10 mL, 2.0 μmol) was then added under a nitrogen atmosphere, and the mixture was sealed and shaken at 80° C. for 4 h. Ethyl acetate and 1 N sodium hydroxide in brine were added and the mixture was shaken. The organic layer was separated and the aqueous phase was extracted with ethyl acetate (1.0 mL). The combined organic phases were concentrated to afford the crude product. The residue was dissolved in 1,2-dichloroethane (0.1 mL), trifluoroacetic acid (0.1 mL, 1.3 mmol) was added, and the mixture stirred at rt for 2 h. The reaction mixture was concentrated and the residue was partitioned between ethyl acetate and saturated aqueous sodium bicarbonate solution. The aqueous layer was separated and extracted with ethyl acetate, and the combined organic layers were concentrated under a stream of nitrogen and vacuum. The crude product was purified by mass-triggered preparatory HPLC. The product-containing fractions were combined and concentrated in a Genevac to afford the desired product.

The following compounds in Table 6 were synthesized according to the above protocol:

TABLE 6

| Compounds | IUPAC Structure | MW | LC-MS [M + 1]+ | HPLC RT (min) |
|---|---|---|---|---|
| I-600 | | 410.52 | 411 | 0.73 |
| I-601 | | 410.52 | 411 | 0.73 |
| I-602 | | 394.52 | 395 | 0.83 |

TABLE 6-continued

| Compounds | IUPAC Structure | MW | LC-MS [M + 1]+ | HPLC RT (min) |
|---|---|---|---|---|
| I-603 | 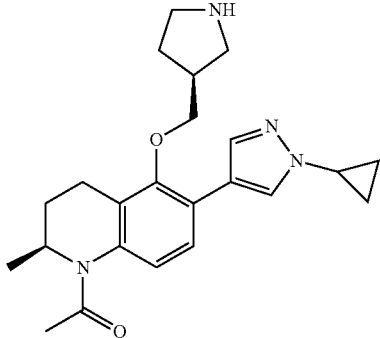 [SMILES: CC(=O)N1c2ccc(-c3cnn(C4CC4)c3)c(OC[C@H]3CCNC3)c2CC[C@@H]1C] | 394.52 | 395 | 0.83 |
| I-604 | 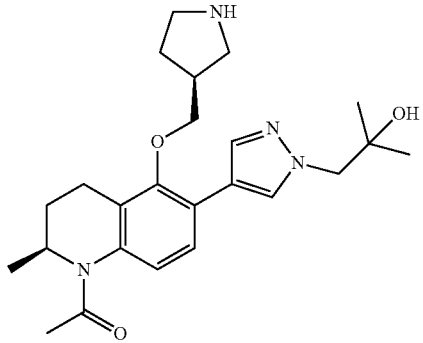 [SMILES: CC(=O)N1c2ccc(-c3cnn(CC(C)(C)O)c3)c(OC[C@H]3CCNC3)c2CC[C@@H]1C] | 426.56 | 427 | 0.75 |

Example 114

Library Protocol G

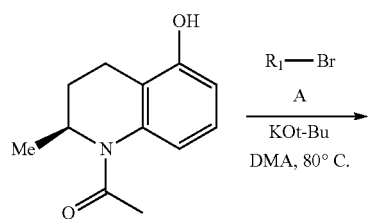

A 1.5-mL reaction vial was charged with (S)-1-(5-hydroxy-2-methyl-3,4-dihydroquinolin-1(2H)-yl)ethanone (0.2 M solution in N,N-dimethylacetamide, 0.1 mL g, 0.02 mmol) and potassium tert-butoxide (1 M in THF, 0.024 mL, 0.024 mmol). The aryl halide (A) (0.2 M solution in N,N-dimethylacetamide, 0.12 mL, 0.024 mmol) was then added, and the reaction was heated to 80° C. on a heater shaker overnight. The reaction was diluted with ethyl acetate and washed with 1 N aqueous sodium hydroxide solution. The aqueous layer was separated and washed with ethyl acetate and the combined organic layers were concentrated under a stream of nitrogen and vacuum. The crude product was purified by mass triggered preparatory HPLC. The product-containing fractions were combined and concentrated in a Genevac to afford the desired product.

The following examples in Table 7 were made according to the above protocol:

TABLE 7

| Compounds | IUPAC Structure | MW | LC-MS [M + 1]+ | HPLC RT (min) |
|---|---|---|---|---|
| I-605 | 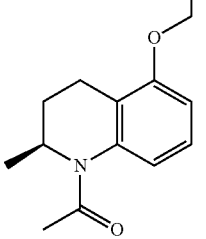 | 247.34 | 248 | 1.60 |

TABLE 7-continued

| Compounds | IUPAC Structure | MW | LC-MS [M + 1]+ | HPLC RT (min) |
|---|---|---|---|---|
| I-606 | | 290.36 | 291 | 0.90 |
| I-607 | | 287.40 | 288 | 1.95 |

Example 119

AlphaScreen Binding Assay

The binding of Example compounds to BRD4 Bromodomain 1 and BRD4 Bromodomain 2 was assessed using 384-well AlphaScreen assay technology. His-epitope tagged BRD4 BD1$_{44-168}$ and BRD4 BD2$_{333-460}$ were cloned, expressed, and purified to homogeneity. BRD4 BD1 and BRD4 BD2 binding and inhibition was assessed by monitoring the engagement of biotinylated Histone H4 (1-21) K5/8/12/16 tetra-acetylated peptide with the targets using the AlphaScreen technology (PerkinElmer). Specifically, in a 384-well black or white flat bottom plate, BRD4 BD1 (50 nM final) or BRD4 BD2 (100 nM final) was combined with peptide (50 nM final for BD1 or 100 nM final for BD2) in 50 mM HEPES (pH 7.3), 100 mM NaCl, 0.1% (w/v) BSA, and 0.01% (w/v) Triton X-100 either in the presence of DMSO (final 1.25% DMSO) or compound dilution series in DMSO. Alpha streptavidin donor beads and Nickel-chelate acceptor beads were added to a final concentration of 10 μg/ml each. After a minimum of 1 hour equilibration, plates were read on a BMG PHERAstar FS multi-label reader (BMG LabTech). The half maximal inhibitory concentration (IC$_{50}$) values were calculated using IDBS Activity Base software with a four parameter logistic curve fit by the equation $y=A+((B-A)/(1+((C/x)^D)))$, wherein A denotes the bottom plateau of the curve, B denotes the top plateau of the curve, C denotes the x value at the middle of the curve, D denotes the slope factor, x denotes the original known x values, and y denotes the original known y values. Data was fitted using the Levenburg Marquardt algorithm.

Table 8 below provides activity of representative compounds according to Inhibition of BRD4 BD1. The compounds are grouped in four categories; inhibition at a concentration <0.1 μM; inhibition at a concentration between 0.1 μM and 1 μM; inhibition at a concentration between 1 μM and 10 μM; inhibition at a concentration >10 μM.

TABLE 8

Exemplary compounds arranged according to inhibition of BRD4 BD1.

Compounds with BRD4 BD1 IC$_{50}$ < 0.1 μM

I-48
I-104
I-311
I-312
I-361
I-385
I-415
I-416
I-423
I-426
I-427
I-447

Compounds with BRD4 BD1 0.1 ≥ IC 50 ≤ 1 μM

I-1
I-7
I-8
I-17
I-22
I-23
I-24
I-31
I-39
I-42
I-43
I-44
I-49
I-50
I-51
I-53
I-54
I-55
I-57
I-61
I-62
I-67
I-68
I-71
I-72
I-73
I-77
I-78
I-79
I-80
I-81
I-84
I-86
I-88
I-89
I-91
I-92
I-93
I-96
I-97
I-98
I-99
I-100
I-101
I-102
I-103
I-105
I-107
I-108

TABLE 8-continued

Exemplary compounds arranged according to inhibition of BRD4 BD1.

I-109
I-110
I-113
I-124
I-124
I-127
I-128
I-129
I-130
I-132
I-133
I-134
I-135
I-136
I-137
I-138
I-139
I-140
I-141
I-142
I-143
I-144
I-145
I-146
I-148
I-149
I-150
I-151
I-152
I-153
I-155
I-156
I-157
I-158
I-159
I-160
I-161
I-162
I-163
I-164
I-165
I-166
I-167
I-168
I-169
I-170
I-171
I-172
I-173
I-174
I-175
I-176
I-177
I-178
I-179
I-180
I-181
I-182
I-183
I-184
I-185
I-186
I-187
I-188
I-189
I-190
I-191
I-192
I-193
I-194
I-195
I-196
I-197
I-198
I-199
I-200
I-201

TABLE 8-continued

Exemplary compounds arranged according to inhibition of BRD4 BD1.

I-202
I-203
I-204
I-205
I-206
I-207
I-209
I-210
I-211
I-213
I-216
I-217
I-219
I-221
I-222
I-223
I-224
I-225
I-226
I-228
I-229
I-230
I-232
I-233
I-236
I-240
I-241
I-242
I-243
I-245
I-246
I-247
I-248
I-249
I-250
I-255
I-256
I-258
I-259
I-260
I-261
I-263
I-263
I-264
I-265
I-266
I-267
I-268
I-269
I-270
I-271
I-272
I-273
I-274
I-275
I-276
I-278
I-281
I-282
I-283
I-285
I-287
I-288
I-290
I-291
I-292
I-293
I-294
I-295
I-296
I-297
I-298
I-302
I-303
I-307
I-310
I-313

TABLE 8-continued

Exemplary compounds arranged according to inhibition of BRD4 BD1.

| |
|---|
| I-315 |
| I-316 |
| I-317 |
| I-318 |
| I-320 |
| I-321 |
| I-322 |
| I-329 |
| I-330 |
| I-331 |
| I-332 |
| I-333 |
| I-335 |
| I-336 |
| I-341 |
| I-343 |
| I-360 |
| I-362 |
| I-363 |
| I-364 |
| I-365 |
| I-366 |
| I-367 |
| I-368 |
| I-369 |
| (I-370 + I-371)* |
| (I-374 + I-375)* |
| (I-376 + I-377)* |
| I-382 |
| I-387 |
| I-388 |
| I-389 |
| I-390 |
| I-392 |
| I-394 |
| I-395 |
| I-396 |
| I-398 |
| I-400 |
| I-401 |
| I-402 |
| I-407 |
| I-408 |
| I-409 |
| I-411 |
| I-412 |
| I-413 |
| I-420 |
| I-422 |
| I-424 |
| I-425 |
| I-431 |
| I-444 |
| I-446 |
| I-449 |
| I-458 |
| I-459 |
| I-461 |
| I-462 |
| I-466 |
| I-506 |
| I-506 |
| I-507 |
| I-508 |
| I-509 |
| I-511 |
| I-512 |
| I-518 |
| I-519 |
| I-521 |
| I-540 |
| I-542 |
| I-543 |
| I-545 |
| I-546 |
| I-547 |
| I-550 |

TABLE 8-continued

Exemplary compounds arranged according to inhibition of BRD4 BD1.

| |
|---|
| I-551 |
| I-552 |
| I-553 |
| I-585 |
| I-592 |
| I-593 |
| I-594 |
| I-595 |
| I-598 |
| I-600 |
| I-602 |
| I-603 |

Compounds with BRD4 BD1 $1 \geq IC_{50} \leq 10\ \mu M$

| |
|---|
| I-2 |
| I-3 |
| I-4 |
| I-5 |
| I-6 |
| I-10 |
| I-11 |
| I-13 |
| I-14 |
| I-15 |
| I-16 |
| I-18 |
| I-19 |
| I-25 |
| I-26 |
| I-27 |
| I-28 |
| I-29 |
| I-30 |
| I-32 |
| I-33 |
| I-35 |
| I-36 |
| I-37 |
| I-38 |
| I-40 |
| I-41 |
| I-46 |
| I-47 |
| I-56 |
| I-59 |
| I-63 |
| I-65 |
| I-69 |
| I-70 |
| I-74 |
| I-82 |
| I-83 |
| I-85 |
| I-87 |
| I-90 |
| I-94 |
| I-95 |
| I-106 |
| I-111 |
| I-114 |
| I-115 |
| I-117 |
| I-118 |
| I-119 |
| I-120 |
| I-121 |
| I-123 |
| I-125 |
| I-126 |
| I-131 |
| I-147 |
| I-154 |
| I-212 |
| I-214 |
| I-215 |

TABLE 8-continued

Exemplary compounds arranged according to inhibition of BRD4 BD1.

| |
|---|
| I-218 |
| I-220 |
| I-227 |
| I-231 |
| I-234 |
| I-235 |
| I-238 |
| I-239 |
| I-251 |
| I-252 |
| I-254 |
| I-257 |
| I-277 |
| I-279 |
| I-280 |
| I-284 |
| I-286 |
| I-289 |
| I-299 |
| I-301 |
| I-305 |
| I-309 |
| I-314 |
| I-319 |
| I-323 |
| I-328 |
| I-334 |
| I-337 |
| I-338 |
| I-339 |
| I-340 |
| I-348 |
| I-349 |
| I-350 |
| I-351 |
| I-352 |
| I-359 |
| (I-372 + I-373)* |
| I-378 |
| I-379 |
| I-380 |
| I-381 |
| I-383 |
| I-384 |
| I-386 |
| I-391 |
| I-393 |
| I-397 |
| I-399 |
| I-403 |
| I-404 |
| I-405 |
| I-406 |
| I-410 |
| I-414 |
| I-417 |
| I-418 |
| I-419 |
| I-421 |
| I-428 |
| I-429 |
| I-430 |
| I-432 |
| I-433 |
| I-434 |
| I-435 |
| I-436 |
| I-437 |
| I-438 |
| I-439 |
| I-440 |
| I-441 |
| I-442 |
| I-443 |
| I-445 |
| I-448 |
| I-450 |
| I-451 |
| I-452 |
| I-453 |
| I-454 |
| I-455 |
| I-456 |
| I-457 |
| I-460 |
| I-463 |
| I-464 |
| I-465 |
| I-467 |
| I-468 |
| I-469 |
| I-470 |
| I-471 |
| I-472 |
| I-473 |
| I-474 |
| I-475 |
| I-476 |
| I-476 |
| I-477 |
| I-478 |
| I-479 |
| I-482 |
| I-483 |
| I-484 |
| I-485 |
| I-486 |
| I-487 |
| I-488 |
| I-490 |
| I-491 |
| I-492 |
| I-493 |
| I-494 |
| I-495 |
| I-496 |
| I-497 |
| I-498 |
| I-499 |
| I-500 |
| I-501 |
| I-502 |
| I-503 |
| I-504 |
| I-505 |
| I-513 |
| I-514 |
| I-515 |
| I-516 |
| I-517 |
| I-520 |
| I-522 |
| I-523 |
| I-524 |
| I-525 |
| I-526 |
| I-527 |
| I-528 |
| I-529 |
| I-531 |
| I-532 |
| I-533 |
| I-534 |
| I-535 |
| I-536 |
| I-537 |
| I-538 |
| I-539 |
| I-541 |
| I-544 |
| I-548 |
| I-549 |
| I-554 |
| I-555 |

TABLE 8-continued

Exemplary compounds arranged according to inhibition of BRD4 BD1.

I-556
I-557
I-558
I-559
I-560
I-561
I-562
I-563
I-564
I-565
I-566
I-567
I-568
I-569
I-570
I-571
I-572
I-573
I-574
I-575
I-576
I-577
I-578
I-579
I-580
I-581
I-582
I-583
I-584
I-586
I-587
I-588
I-589
I-590
I-591
I-596
I-597
I-599
I-601
I-604

Compounds with BRD4 BD 1 IC$_{50}$ ≥ 10 µM

I-9
I-12
I-20
I-21
I-34
I-45
I-52
I-58
I-60
I-64
I-75
I-112
I-116
I-244
I-245
I-253
I-300
I-304
I-306
I-308
I-324
I-325
I-326
I-327
I-343
I-344
I-345
I-346
I-347
I-353
I-354
I-355
I-356

TABLE 8-continued

Exemplary compounds arranged according to inhibition of BRD4 BD1.

I-357
I-358
I-481
I-489
I-530
I-605
I-606
I-607

*refers to racemic mixtures of enantiomers

Table 9 provides the compounds arranged according to Inhibition of BRD4 BD2.

The compounds are grouped in three groups; IC$_{50}$<0.05 µM; 0.05≥IC$_{50}$≤0.5 µM; and IC$_{50}$>0.5 µM.

TABLE 9

Exemplary compounds arranged according to inhibition of BRD4 BD2

Compounds with BRD4 BD2 IC$_{50}$ < 0.05 µM

I-11
I-22
I-24
I-27
I-31
I-36
I-39
I-44
I-48
I-49
I-50
I-51
I-53
I-62
I-67
I-68
I-77
I-80
I-83
I-84
I-86
I-88
I-92
I-99
I-100
I-101
I-102
I-104
I-108
I-111
I-132
I-133
I-134
I-135
I-136
I-137
I-138
I-139
I-140
I-141
I-144
I-145
I-148
I-149
I-150
I-151
I-152
I-153
I-157
I-158
I-159

TABLE 9-continued

Exemplary compounds arranged according to inhibition of BRD4 BD2

| |
|---|
| I-160 |
| I-161 |
| I-162 |
| I-163 |
| I-164 |
| I-166 |
| I-167 |
| I-168 |
| I-169 |
| I-170 |
| I-185 |
| I-188 |
| I-189 |
| I-191 |
| I-200 |
| I-201 |
| I-210 |
| I-211 |
| I-214 |
| I-216 |
| I-217 |
| I-218 |
| I-224 |
| I-225 |
| I-227 |
| I-245 |
| I-246 |
| I-249 |
| I-255 |
| I-256 |
| I-257 |
| I-258 |
| I-259 |
| I-263 |
| I-263 |
| I-268 |
| I-270 |
| I-282 |
| I-283 |
| I-285 |
| I-287 |
| I-288 |
| I-351 |
| I-361 |
| I-362 |
| I-363 |
| I-364 |
| I-365 |
| I-366 |
| I-385 |
| I-387 |
| I-389 |
| I-390 |
| I-393 |
| I-396 |
| I-401 |
| I-407 |
| I-408 |
| I-409 |
| I-410 |
| I-411 |
| I-412 |
| I-415 |
| I-416 |
| I-420 |
| I-422 |
| I-423 |
| I-424 |
| I-426 |
| I-427 |
| I-442 |
| I-443 |
| I-444 |
| I-445 |
| I-447 |
| I-458 |
| I-461 |

TABLE 9-continued

Exemplary compounds arranged according to inhibition of BRD4 BD2

| |
|---|
| I-462 |
| I-479 |
| I-506 |
| I-511 |
| I-521 |
| I-545 |
| I-546 |
| I-547 |
| I-550 |
| I-551 |
| I-552 |
| I-553 |
| I-563 |
| I-592 |
| I-593 |
| I-594 |

Compounds with BRD4 BD2 $0.05 \geq IC_{50} \leq 0.5\ \mu M$

| |
|---|
| I-1 |
| I-2 |
| I-3 |
| I-4 |
| I-5 |
| I-7 |
| I-8 |
| I-10 |
| I-13 |
| I-14 |
| I-15 |
| I-16 |
| I-17 |
| I-18 |
| I-19 |
| I-21 |
| I-23 |
| I-25 |
| I-26 |
| I-29 |
| I-30 |
| I-32 |
| I-34 |
| I-35 |
| I-37 |
| I-38 |
| I-40 |
| I-41 |
| I-42 |
| I-43 |
| I-46 |
| I-47 |
| I-61 |
| I-63 |
| I-65 |
| I-78 |
| I-79 |
| I-81 |
| I-82 |
| I-85 |
| I-87 |
| I-89 |
| I-90 |
| I-91 |
| I-93 |
| I-107 |
| I-112 |
| I-113 |
| I-114 |
| I-115 |
| I-116 |
| I-117 |
| I-119 |
| I-121 |
| I-142 |
| I-143 |
| I-146 |

TABLE 9-continued

Exemplary compounds arranged according to inhibition of BRD4 BD2

I-147
I-155
I-190
I-209
I-212
I-213
I-215
I-226
I-247
I-251
I-254
I-277
I-284
I-286
I-289
I-352
I-356
I-359
I-378
I-379
I-380
I-381
I-382
I-383
I-384
I-388
I-392
I-395
I-397
I-398
I-399
I-400
I-402
I-403
I-404
I-405
I-406
I-413
I-414
I-417
I-418
I-419
I-421
I-425
I-428
I-429
I-430
I-431
I-432
I-433
I-434
I-435
I-436
I-437
I-438
I-439
I-440
I-441
I-446
I-448
I-449
I-450
I-451
I-452
I-453
I-454
I-455
I-456
I-457
I-459
I-460
I-463
I-464
I-465
I-466
I-467
I-468

TABLE 9-continued

Exemplary compounds arranged according to inhibition of BRD4 BD2

I-469
I-470
I-471
I-472
I-473
I-474
I-475
I-476
I-476
I-477
I-478
I-484
I-486
I-488
I-490
I-491
I-492
I-494
I-496
I-497
I-498
I-499
I-500
I-501
I-502
I-503
I-505
I-506
I-512
I-513
I-514
I-515
I-516
I-517
I-518
I-519
I-520
I-522
I-523
I-524
I-525
I-526
I-527
I-528
I-529
I-531
I-532
I-533
I-534
I-535
I-536
I-537
I-538
I-539
I-540
I-541
I-542
I-543
I-544
I-548
I-549
I-554
I-555
I-556
I-557
I-558
I-559
I-560
I-561
I-562
I-564
I-565
I-566
I-567
I-568
I-569
I-570

TABLE 9-continued

Exemplary compounds arranged according to inhibition of BRD4 BD2

I-571
I-572
I-573
I-574
I-575
I-577
I-578
I-579
I-580
I-581
I-582
I-583
I-584
I-585
I-586
I-587
I-588
I-589
I-590
I-591
I-595
I-596
I-597
I-598
I-599
I-600
I-601
I-602
I-603

Compounds with BRD4
BD2 IC$_{50}$ ≥ 0.5 μM

I-6
I-9
I-12
I-20
I-28
I-33
I-45
I-52
I-58
I-59
I-60
I-64
I-118
I-120
I-252
I-253
I-353
I-354
I-355
I-357
I-358
I-386
I-391
I-481
I-482
I-483
I-485
I-487
I-489
I-493
I-495
I-504
I-530
I-576
I-604
I-605
I-606
I-607

Example 120

Oncology Cell Growth Assay

The impact of Example compounds on cancer cell proliferation was determined using the acute myelocytic leukemia (AML) cell line MV4-11 (ATCC) in a 3-day proliferation assay. MV4-11 cells were maintained in RPMI 1640 media supplemented with 10% FBS at 37° C. and an atmosphere of 5% $CO_2$. For compound testing, compound dilutions series were prepared in DMSO via a 3-fold serial dilution from 2 mM to 0.001 mM in 384-well white flat bottom plates. The final compound concentrations in the wells were 10, 3.3, 1.1, 0.37, 0.12, 0.041, 0.013 and 0.0045 μM. MV4-11 cells were plated at a density of 3000 cells/well in final volume of 50 μl culture media and incubated for 72 hours. The amounts of viable cells were determined using the CellTiter-Glo Luminescent Cell Viability Assay kit (Promega) according to the manufacturer suggested protocol. Luminescent signal from the CellTiter-Glo assay was read on an EnVision multilabel plate reader (PerkinElmer). Values for the concentration that inhibited cell growth by 50% (gIC$_{50}$) between the DMSO control and background control (no cells) were determined using IDBS Activity Base software with a four parameter logistic curve fit by the equation $y=A+((B-A)/(1+((C/x)^D)))$, wherein A denotes the bottom plateau of the curve, B denotes the top plateau of the curve, C denotes the x value at the middle of the curve, D denotes the slope factor, x denotes the original known x values, and y denotes the original known y values. Data was fitted using the Levenburg Marquardt algorithm.

Table 10 provides the compounds arranged according to inhibition of proliferation of MV411 cell line. The compounds are grouped in three groups; IC$_{50}$<0.5 μM; 0.5 μM≥IC$_{50}$≤1.0 μM; and IC$_{50}$>1.0 μM.

TABLE 10

Exemplary compounds arranged according to inhibition of MV411

Compounds with MV 411
IC$_{50}$ < 0.5 μM

I-1
I-7
I-8
I-22
I-30
I-48
I-51
I-53
I-54
I-55
I-57
I-61
I-62
I-67
I-68
I-72
I-77
I-78
I-80
I-81
I-83
I-84
I-86
I-88
I-89
I-91
I-92
I-93
I-94

TABLE 10-continued

Exemplary compounds arranged according to inhibition of MV411

I-95
I-96
I-97
I-98
I-99
I-100
I-101
I-102
I-103
I-104
I-105
I-107
I-108
I-109
I-110
I-113
I-127
I-129
I-130
I-132
I-133
I-134
I-135
I-136
I-137
I-138
I-139
I-140
I-141
I-142
I-143
I-144
I-145
I-146
I-147
I-148
I-149
I-150
I-151
I-152
I-153
I-154
I-156
I-157
I-158
I-159
I-160
I-162
I-163
I-164
I-165
I-166
I-167
I-168
I-169
I-170
I-171
I-172
I-173
I-174
I-175
I-176
I-177
I-178
I-179
I-180
I-181
I-182
I-183
I-184
I-185
I-186
I-187
I-188
I-189
I-190
I-191

TABLE 10-continued

Exemplary compounds arranged according to inhibition of MV411

I-192
I-193
I-194
I-195
I-196
I-197
I-198
I-199
I-200
I-201
I-202
I-203
I-204
I-205
I-206
I-207
I-209
I-210
I-211
I-212
I-213
I-214
I-216
I-217
I-218
I-219
I-220
I-221
I-222
I-223
I-224
I-225
I-226
I-227
I-228
I-229
I-230
I-231
I-232
I-233
I-234
I-235
I-236
I-238
I-239
I-240
I-241
I-242
I-243
I-245
I-246
I-247
I-248
I-249
I-250
I-255
I-256
I-257
I-258
I-259
I-260
I-261
I-263
I-264
I-265
I-266
I-267
I-268
I-269
I-270
I-271
I-272
I-273
I-274
I-275
I-276
I-278

TABLE 10-continued

Exemplary compounds arranged according to inhibition of MV411

I-280
I-282
I-283
I-285
I-286
I-287
I-288
I-290
I-291
I-292
I-293
I-294
I-295
I-296
I-297
I-298
I-302
I-303
I-305
I-307
I-309
I-310
I-311
I-312
I-315
I-316
I-318
I-319
I-320
I-321
I-322
I-323
I-328
I-329
I-330
I-331
I-332
I-333
I-334
I-335
I-336
I-343
I-348
I-351
I-359
I-360
I-361
I-362
I-363
I-364
I-365
I-366
I-367
I-368
I-369
(I-374 + I-375)*
(I-376 + I-377)*
I-385
I-387
I-389
I-390
I-392
I-394
I-396
I-400
I-401
I-407
I-408
I-409
I-410
I-411
I-412
I-413
I-415
I-416
I-420
I-422
I-423
I-424
I-425
I-426
I-427
I-442
I-443
I-444
I-445
I-446
I-447
I-449
I-458
I-486
I-506
I-508
I-509
I-511
I-512
I-513
I-514
I-517
I-518
I-519
I-521
I-524
I-525
I-526
I-527
I-528
I-529
I-531
I-533
I-535
I-539
I-540
I-541
I-542
I-543
I-545
I-547
I-548
I-550
I-551
I-552
I-553
I-568
I-569
I-572
I-577
I-583
I-585
I-592
I-593
I-594
I-595
I-596
I-597
I-598
I-599

Compounds with MV411
$0.5\ \mu M \geq IC_{50} \leq 1.0\ \mu M$

I-564
I-546
I-215
I-584
I-352
I-39
I-506
I-82
I-71
I-128
I-590
I-46
I-121

TABLE 10-continued

Exemplary compounds arranged according to inhibition of MV411

I-431
I-402
I-119
I-284
I-124
I-56
I-131
I-591
I-50
I-516
I-549
I-36
I-561
I-124
I-567
I-556
I-522
I-589
I-573
I-536
I-515
I-574
I-388
I-560
I-31
I-462
I-341
I-398
I-70
I-289
I-537
I-281
I-562
I-575
I-73
I-580
I-317
I-565
I-382
(I-370 + I-371)*
I-587
I-44
I-69
I-17
I-74
I-263
I-532
I-534
I-507
I-35
I-338
I-13
I-571
I-461
I-23
I-395
I-299
I-559
I-602

Compounds with MV411 IC$_{50}$ > 1.0 µM

I-11
I-14
I-19
I-20
I-24
I-29
I-34
I-42
I-43
I-49
I-60
I-63
I-64
I-75

TABLE 10-continued

Exemplary compounds arranged according to inhibition of MV411

I-106
I-114
I-115
I-116
I-117
I-118
I-120
I-123
I-125
I-126
I-155
I-161
I-244
I-245
I-251
I-252
I-253
I-254
I-279
I-300
I-301
I-304
I-306
I-308
I-313
I-314
I-324
I-325
I-326
I-327
I-337
I-339
I-340
I-343
I-344
I-345
I-346
I-347
I-349
I-350
I-353
I-354
I-355
I-356
I-357
I-358
(I-372 + I-373)*
I-459
I-466
I-479
I-487
I-491
I-501
I-504
I-505
I-520
I-523
I-530
I-538
I-554
I-555
I-557
I-558
I-563
I-566
I-570
I-576
I-578
I-579
I-581
I-582
I-586
I-588
I-600
I-603

*refers to racemic mixtures of enantiomers

EQUIVALENTS

It is expected and indicated in the literature, that all BET family inhibitors have some activity for all BET bromodomains.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:
1. A compound of Formula I:

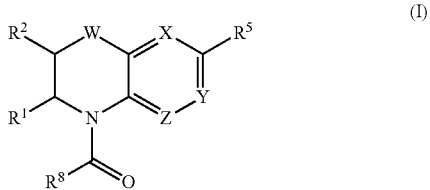

(I)

or a pharmaceutically acceptable salt, enantiomer, hydrate, solvate, isomer, or tautomer thereof,
wherein:
W is O, S, C(O), or $CHR^3$;
X is N or $CR^4$;
Y is N or $CR^6$;
Z is N or $CR^7$;
$R^1$ is $C_1$-$C_6$ alkyl, or $C_1$-$C_6$ haloalkyl;
$R^2$ is hydrogen or $NR^aR^b$;
$R^3$ is hydrogen, halogen, hydroxyl, $C_1$-$C_6$ alkyl, or $C_1$-$C_6$ haloalkyl;
$R^4$ is hydrogen, —$(CH_2)_nR^d$, —$O(CH_2)_nR^d$, —$N(CH_2)_nR^d$, —$O(CH_2)C(O)R^d$, or —$O(CH_2)_nS(O)_2R^d$;
$R^5$ is halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, heterocycloalkyl, cycloalkenyl, heterocycloalkenyl, aryl, heteroaryl, —$(C_1$-$C_6)$-alkylene-aryl, —$(C_1$-$C_6)$-alkylene-heteroaryl, —$(C_1$-$C_6)$-alkylene-heterocycloalkyl, —$(CR^aR^b)_nOR^c$, —$(CR^aR^b)_nR^c$, —$O(CR^aR^b)_nNR^aR^b$, —$NR^aR^b$, —$NR^aC(O)R^b$, —$NR^aS(O)_2R^b$, or $R^c$, wherein said alkyl, alkenyl, alkynyl, cycloalkyl, heterocycloalkyl, cycloalkenyl, heterocycloalkenyl, aryl, and heteroaryl are optionally substituted with one or more substituents independently selected from $R^a$, $R^b$, and $R^c$;
$R^6$ is hydrogen, halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, heterocycloalkyl, cycloalkenyl, heterocycloalkenyl, aryl, heteroaryl, —$(C_1$-$C_6)$-alkylene-aryl, —$(C_1$-$C_6)$-alkylene-heteroaryl, —$(C_1$-$C_6)$-alkylene-heterocycloalkyl, —$(CR^aR^b)_nOR^c$, —$(CR^aR^b)_nR^c$, —$O(CR^aR^b)_n NR^aR^b$, —$NR^aR^b$, —$NR^aC(O)R^b$, —$NR^aS(O)_2R^b$, or $R^c$, wherein said alkyl, alkenyl, alkynyl, cycloalkyl, heterocycloalkyl, cycloalkenyl, heterocycloalkenyl, aryl, and heteroaryl are optionally substituted with one or more substituents independently selected from $R^a$, $R^b$, and $R^c$;
$R^7$ is hydrogen or halogen;
$R^8$ is $R^a$, —OR, —$NR^a$, or heterocycloalkyl;
$R^a$ and $R^b$ are each independently hydrogen, halogen, $C_1$-$C_6$ alkyl, cycloalkyl, or heterocycloalkyl, wherein $C_1$-$C_6$ alkyl, cycloalkyl, or heterocycloalkyl is optionally substituted with one or more $R^e$;

$R^c$ is —$NH_2$, OH, —$NH(C_1$-$C_6$ alkyl), —$O(CH_2)_nNR^aR^b$, —$NH(C_1$-$C_6$ alkoxy), —$(CH_2)_nR$, —$(CH_2)_nOR^a$, —$C(O)R^a$, —$C(O)OR^a$, —$C(O)NR^aR^b$, —$(CH_2)_nS(O)_2CH_3$, —$S(O)_2R^a$, —$S(O)_2NR^aR^b$, —$NR^a$—$S(O)_2R^b$, —$NHC(O)R^a$, $C_1$-$C_6$ alkyl, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, aryl, heteroaryl, cycloalkyl, heterocycloalkyl, halo, cyano, or oxo, wherein $C_1$-$C_6$ alkyl, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, aryl, heteroaryl, cycloalkyl, and heterocycloalkyl are optionally susbtitued with one or more $R^e$;

or two adjacent $R^c$ can combine with the carbons to which they are attached to form a carbocycle or heterocycle;

$R^d$ is hydrogen, $NH(C_1$-$C_6$ alkyl), $N(C_1$-$C_6$ alkyl)$_2$, $C_1$-$C_6$ haloalkyl, $C_1$-$C_6$ haloalkoxy, $C_1$-$C_6$ alkoxy, $C_2$-$C_6$ alkenyl, $C_2$-$C_6$ alkynyl, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^c$;

$R^e$ is hydrogen, halogen, OH, $C_1$-$C_6$ alkyl, cycloalkyl, heterocycloalkyl, oxo, $C_1$-$C_6$ haloalkyl, $C_1$-$C_6$ haloalkoxy, $C_1$-$C_6$ alkoxy, or $S(O)_2(C_1$-$C_6$ alkyl); and n is 0, 1, or 2.

2. The compound of claim 1, wherein X is $CR^4$ and Y and Z are CH.

3. The compound of claim 2, wherein W is $CHR^3$.

4. The compound of claim 1, having the Formula II

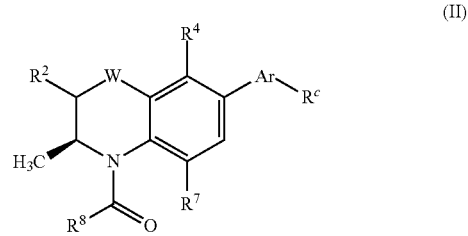

(II)

or a pharmaceutically acceptable salt, enantiomer, hydrate, solvate, isomer, or tautomer thereof,
wherein:
W is O, C(O), or $CHR^3$;
Ar is aryl or heteroaryl;
$R^2$ is hydrogen or $NR^aR^b$;
$R^3$ is hydrogen, hydroxy, or halo;
$R^4$ hydrogen, —$O(CH_2)_nR^d$, —$O(CH_2)_nC(O)R^d$, or —$O(CH_2)_nS(O)_2R^d$; $R^7$ is hydrogen or halo;
$R^8$ is $R^a$, —$OR^a$, or heterocycloalkyl;
$R^a$ and $R^b$ are independently hydrogen, $C_1$-$C_6$ alkyl, heterocycloalkyl, or cycloalkyl;
$R^c$ is $R^a$, —$(CH_2)_nOR^a$, —$C(O)R^a$, —$C(O)OR^a$, —$C(O)NR^aR^b$—$S(O)_2R^a$, halo, or oxo; and
n is 0, 1, or 2.

5. The compound of claim 4, wherein W is $CHR^3$.

6. The compound of claim 4, wherein Ar is pyrazole or phenyl.

7. The compound of claim 1, having the Formula III

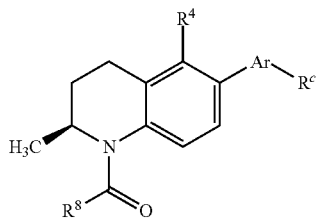

(III)

or a pharmaceutically acceptable salt, enantiomer, hydrate, solvate, isomer, or tautomer thereof,
wherein:
Ar is pyrazolyl or phenyl;
$R^4$ is hydrogen, —O(CH$_2$)$_n$R$^d$, —O(CH$_2$)$_n$C(O)R$^d$, or —O(CH$_2$)$_n$S(O)$_2$R$^d$;
$R^8$ is methyl, methoxy, or cyclopropyl;
$R^a$ and $R^b$ are independently hydrogen or $C_1$-$C_6$ alkyl;
$R^c$ is —(CH$_2$)$_n$R$^a$, —(CH$_2$)$_n$OR$^a$, —C(O)R$^a$, —C(O)OR$^a$, —C(O)NR$^a$R$^b$, —(CH$_2$)$_n$S(O)$_2$CH$_3$, —S(O)$_2$R$^a$, —S(O)$_2$NR$^a$R$^b$, $C_1$-$C_6$ haloalkyl, $C_1$-$C_6$ haloalkoxy, cycloalkyl, heterocycloalkyl, halo, cyano, or oxo;
$R^d$ is hydrogen, NH($C_1$-$C_6$ alkyl), N($C_1$-$C_6$ alkyl)$_2$, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^c$; and
n is 0, 1, or 2.

8. The compound of claim 7, wherein Ar is pyrazole and $R^c$ is cycloalkyl or heterocycloalkyl.

9. The compound of claim 8, wherein $R^c$ is cyclopropyl.

10. The compound of claim 7, wherein Ar is phenyl, $R^c$ is —(CH$_2$)$_n$S(O)$_2$CH$_3$.

11. The compound of claim 1, having the Formula IV

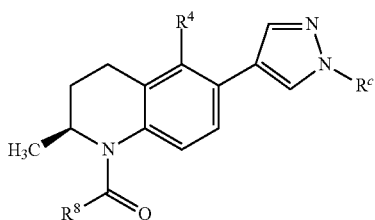

(IV)

or a pharmaceutically acceptable salt, enantiomer, hydrate, solvate, isomer, or tautomer thereof,
wherein:
$R^4$ is —O(CH$_2$)$_n$R$^d$, —O(CH$_2$)$_n$C(O)R$_d$, or —O(CH$_2$)$_n$S(O)$_2$R$^d$;
$R^8$ is alkyl, cycloalkyl, O-alkyl, or O-cycloalkyl
$R^a$ and $R^b$ are independently hydrogen or $C_1$-$C_6$ alkyl;
$R^c$ is —(CH$_2$)$_n$R$^a$, —(CH$_2$)$_n$OR$^a$, —C(O)R$^a$, —C(O)OR$^a$, —C(O)NR$^a$R$^b$—S(O)$_2$R$^a$, —S(O)$_2$NR$^a$R$^b$, $C_1$-$C_6$ haloalkyl, $C_1$-$C_6$ haloalkoxy, aryl, heteroaryl, cycloalkyl, heterocycloalkyl, halo, cyano, or oxo;
$R^d$ is hydrogen, NH($C_1$-$C_6$ alkyl), N($C_1$-$C_6$ alkyl)$_2$, $C_1$-$C_6$ alkyl, cycloalkyl, heterocycloalkyl, aryl, or heteroaryl, wherein said alkyl, cycloalkyl, heterocycloalkyl, aryl, and heteroaryl are optionally substituted with one or more substituents independently selected from $R^a$, $R^b$, and $R^c$; and
n is 0, 1, or 2.

12. The compound of claim 11, wherein $R^c$ is cycloalkyl, or heterocycloalkyl.

13. The compound of claim 12, wherein $R^4$ is —O(CH$_2$)$_n$R$^d$.

14. The compound of claim 13, wherein $R^d$ is aryl, heteroaryl, or cycloalkyl.

15. The compound of claim 1 selected from the group consisting of:
methyl (2S)-6-(1-cyclopropyl-1H-pyrazol-4-yl)-5-{[3-(hydroxymethyl)oxetan-3-yl]methoxy}-2-methyl-1,2,3,4-tetrahydroquinoline-1-carboxylate;
methyl (2S)-5-(4-fluorophenoxy)-2-methyl-6-(1-{octahydrocyclopenta[c]pyrrol-5-yl}-1H-pyrazol-4-yl)-1,2,3,4-tetrahydroquinoline-1-carboxylate;
methyl (2S)-6-(1-cyclopropyl-1H-pyrazol-4-yl)-5-(3,3-difluorocyclobutoxy)-2-methyl-1,2,3,4-tetrahydroquinoline-1-carboxylate;
(2S)-1-cyclopropanecarbonyl-2-methyl-5-phenoxy-6-(1H-1,2,3-triazol-4-yl)-1,2,3,4-tetrahydroquinoline;
methyl (2S)-5-(azetidin-3-ylmethoxy)-6-(1-cyclopropyl-1H-pyrazol-4-yl)-2-methyl-1,2,3,4-tetrahydroquinoline-1-carboxylate;
methyl (2S)-5-(3-fluorophenoxy)-2-methyl-6-[1-(piperidin-4-yl)-1H-pyrazol-4-yl]-1,2,3,4-tetrahydroquinoline-1-carboxylate;
1-[(2S)-6-(1-cyclopropyl-1H-pyrazol-4-yl)-2-methyl-5-(2,2,2-trifluoroethoxy)-1,2,3,4-tetrahydroquinolin-1-yl]ethan-1-one;
methyl (2S)-5-(3-chlorophenoxy)-2-methyl-6-[1-(piperidin-4-yl)-1H-pyrazol-4-yl]-1,2,3,4-tetrahydroquinoline-1-carboxylate;
1-[(2S)-6-(1-cyclopropyl-1H-pyrazol-4-yl)-5-(2,2-difluoroethoxy)-2-methyl-1,2,3,4-tetrahydroquinolin-1-yl]ethan-1-one;
1-[(2S)-5-(4-fluorophenoxy)-2-methyl-6-[1-(piperidin-4-yl)-1H-pyrazol-4-yl]-1,2,3,4-tetrahydroquinolin-1-yl]ethan-1-one;
1-[(2S)-6-(1-cyclopropyl-1H-pyrazol-4-yl)-5-(2,2-difluoropropoxy)-2-methyl-1,2,3,4-tetrahydroquinolin-1-yl]ethan-1-one;
1-[(2S)-5-(4-chlorophenoxy)-2-methyl-6-[1-(piperidin-4-yl)-1H-pyrazol-4-yl]-1,2,3,4-tetrahydroquinolin-1-yl]ethan-1-one;
1-[(2S)-6-(1-cyclopropyl-1H-pyrazol-4-yl)-5-[(1,3-difluoropropan-2-yl)oxy]-2-methyl-1,2,3,4-tetrahydroquinolin-1-yl]ethan-1-one;
methyl (2S)-6-[1-(azetidin-3-yl)-1H-pyrazol-4-yl]-5-(3,4-difluorophenoxy)-2-methyl-1,2,3,4-tetrahydroquinoline-1-carboxylate;
1-[(2S)-6-(1-cyclopropyl-1H-pyrazol-4-yl)-5-(3-hydroxy-2,2-dimethylpropoxy)-2-methyl-1,2,3,4-tetrahydroquinolin-1-yl]ethan-1-one;
methyl (2S)-6-[1-(azetidin-3-yl)-1H-pyrazol-4-yl]-2-methyl-5-phenoxy-1,2,3,4-tetrahydroquinoline-1-carboxylate;
2-{[(2S)-1-acetyl-6-(1-cyclopropyl-1H-pyrazol-4-yl)-2-methyl-1,2,3,4-tetrahydroquinolin-5-yl]oxy}-2-methylpropanamide;
(2S)-1-cyclopropanecarbonyl-5-(2-methoxyphenoxy)-2-methyl-6-[1-(piperidin-4-yl)-1H-pyrazol-4-yl]-1,2,3,4-tetrahydroquinoline;
1-[(2S)-6-(1-cyclopropyl-1H-pyrazol-4-yl)-2-methyl-5-(3,3,3-trifluoropropoxy)-1,2,3,4-tetrahydroquinolin-1-yl]ethan-1-one;

(2S)-1-cyclopropanecarbonyl-5-(3-methoxyphenoxy)-2-methyl-6-[1-(piperidin-4-yl)-1H-pyrazol-4-yl]-1,2,3,4-tetrahydroquinoline;

1-(2-{[(2S)-1-acetyl-6-(1-cyclopropyl-1H-pyrazol-4-yl)-2-methyl-1,2,3,4-tetrahydroquinolin-5-yl]oxy}ethyl)pyrrolidin-2-one;

(2S)-1-cyclopropanecarbonyl-5-(4-methoxyphenoxy)-2-methyl-6-[1-(piperidin-4-yl)-1H-pyrazol-4-yl]-1,2,3,4-tetrahydroquinoline;

2-{[(2S)-1-acetyl-6-(1-cyclopropyl-1H-pyrazol-4-yl)-2-methyl-1,2,3,4-tetrahydroquinolin-5-yl]oxy}-1-(morpholin-4-yl)ethan-1-one;

methyl (2S)-5-(2-methoxyphenoxy)-2-methyl-6-[1-(piperidin-4-yl)-1H-pyrazol-4-yl]-1,2,3,4-tetrahydroquinoline-1-carboxylate;

2-(2-{[(2S)-1-acetyl-6-(1-cyclopropyl-1H-pyrazol-4-yl)-2-methyl-1,2,3,4-tetrahydroquinolin-5-yl]oxy}ethyl)-1$\lambda^6$,2-thiazolidine-1,1-dione;

methyl (2S)-5-(3-methoxyphenoxy)-2-methyl-6-[1-(piperidin-4-yl)-1H-pyrazol-4-yl]-1,2,3,4-tetrahydroquinoline-1-carboxylate;

{[(2S)-1-acetyl-6-(1-cyclopropyl-1H-pyrazol-4-yl)-2-methyl-1,2,3,4-tetrahydroquinolin-5-yl]oxy}methanesulfonamide;

methyl (2S)-5-(4-methoxyphenoxy)-2-methyl-6-[1-(piperidin-4-yl)-1H-pyrazol-4-yl]-1,2,3,4-tetrahydroquinoline-1-carboxylate;

1-{[(2S)-1-acetyl-6-(1-cyclopropyl-1H-pyrazol-4-yl)-2-methyl-1,2,3,4-tetrahydroquinolin-5-yl]oxy}-N,N-dimethylmethanesulfonamide;

methyl (2S)-2-methyl-5-phenoxy-6-[1-(piperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-[2-(oxetan-3-yl)ethoxy]-1,2,3,4-tetrahydroquinolin-1-yl]ethan-1-one;

1-[(2S)-2-methyl-5-phenoxy-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-[(2,2-difluorocyclopropyl)methoxy]-2-methyl-1,2,3,4-tetrahydroquinolin-1-yl]ethan-1-one;

3-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;

1-[(2S)-6-(1-cyclopropyl-1H-pyrazol-4-yl)-5-{[3-(hydroxymethyl)oxetan-3-yl]methoxy}-2-methyl-1,2,3,4-tetrahydroquinolin-1-yl]ethan-1-one;

1-[(2S)-2-methyl-6-[1-(piperidin-4-yl)-1H-pyrazol-4-yl]-5-(pyridin-2-yloxy)-1,2,3,4-tetrahydroquinolin-1-yl]ethan-1-one;

1-[(2S)-6-(1-cyclopropyl-1H-pyrazol-4-yl)-5-[(3-fluorooxetan-3-yl)methoxy]-2-methyl-1,2,3,4-tetrahydroquinolin-1-yl]ethan-1-one;

1-[(2S)-5-(3-methoxyphenoxy)-2-methyl-6-[1-(piperidin-4-yl)-1H-pyrazol-4-yl]-1,2,3,4-tetrahydroquinolin-1-yl]ethan-1-one;

1-[(2S)-6-(1-cyclopropyl-1H-pyrazol-4-yl)-5-(3,3-difluorocyclobutoxy)-2-methyl-1,2,3,4-tetrahydroquinolin-1-yl]ethan-1-one;

1-[(2S)-5-(azetidin-3-ylmethoxy)-6-(1-cyclopropyl-1H-pyrazol-4-yl)-2-methyl-1,2,3,4-tetrahydroquinolin-1-yl]ethan-1-one;

(2S)-5-cyclobutoxy-1-cyclopropanecarbonyl-2-methyl-6-(1-methyl-1H-1,2,3-triazol-4-yl)-1,2,3,4-tetrahydroquinoline;

(2S)-5-cyclobutoxy-1-cyclopropanecarbonyl-2-methyl-6-(1H-pyrazol-4-yl)-1,2,3,4-tetrahydroquinoline;

(2S)-5-cyclobutoxy-1-cyclopropanecarbonyl-2-methyl-6-(1-methyl-1H-pyrazol-4-yl)-1,2,3,4-tetrahydroquinoline;

(2S)-5-cyclobutoxy-1-cyclopropanecarbonyl-2-methyl-6-(1H-pyrazol-5-yl)-1,2,3,4-tetrahydroquinoline;

(2S)-5-cyclobutoxy-1-cyclopropanecarbonyl-2-methyl-6-(1-methyl-1H-imidazol-4-yl)-1,2,3,4-tetrahydroquinoline;

methyl (2S)-5-({1-[(tert-butoxy)carbonyl]azetidin-3-yl}oxy)-6-(1-cyclopropyl-1H-pyrazol-4-yl)-2-methyl-1,2,3,4-tetrahydroquinoline-1-carboxylate;

methyl (2S)-5-(azetidin-3-yloxy)-6-(1-cyclopropyl-1H-pyrazol-4-yl)-2-methyl-1,2,3,4-tetrahydroquinoline-1-carboxylate;

1-[(2S)-5-(azetidin-3-yloxy)-6-(1-cyclopropyl-1H-pyrazol-4-yl)-2-methyl-1,2,3,4-tetrahydroquinolin-1-yl]ethan-1-one;

methyl (2S)-5-cyclobutoxy-6-[1-(1,1-dioxo-1$\lambda^6$-thietan-3-yl)-1H-pyrazol-4-yl]-2-methyl-1,2,3,4-tetrahydroquinoline-1-carboxylate;

methyl (2S)-5-cyclobutoxy-6-[1-(1,1-dioxo-1$\lambda^6$-thian-3-yl)-1H-pyrazol-4-yl]-2-methyl-1,2,3,4-tetrahydroquinoline-1-carboxylate;

(2R)-2-{[(2S)-1-acetyl-6-(1-cyclopropyl-1H-pyrazol-4-yl)-2-methyl-1,2,3,4-tetrahydroquinolin-5-yl]oxy}-2-fluoroacetamide;

(2S)-2-{[(2S)-1-acetyl-6-(1-cyclopropyl-1H-pyrazol-4-yl)-2-methyl-1,2,3,4-tetrahydroquinolin-5-yl]oxy}-2-fluoroacetamide;

methyl (2S)-6-(1-cyclopropyl-1H-pyrazol-4-yl)-5-[(3-fluorooxetan-3-yl)methoxy]-2-methyl-1,2,3,4-tetrahydroquinoline-1-carboxylate;

2-{(([(2S)-1-acetyl-6-(1-cyclopropyl-1H-pyrazol-4-yl)-2-methyl-1,2,3,4-tetrahydroquinolin-5-yl]oxy}-2,2-difluoroacetamide;

1-[(2S)-6-(1-cyclopropyl-1H-pyrazol-4-yl)-5-(2-fluoro-2-methylpropoxy)-2-methyl-1,2,3,4-tetrahydroquinolin-1-yl]ethan-1-one;

methyl (2S)-5-cyclobutoxy-2-methyl-6-[1-(oxan-4-yl)-1H-pyrazol-4-yl]-1,2,3,4-tetrahydroquinoline-1-carboxylate;

1-[(2S)-6-[1-(2-hydroxyethyl)-1H-pyrazol-4-yl]-2-methyl-5-propoxy-1,2,3,4-tetrahydroquinolin-1-yl]ethan-1-one;

2-{[(2S)-1-acetyl-6-[1-(2-hydroxyethyl)-1H-pyrazol-4-yl]-2-methyl-1,2,3,4-tetrahydroquinolin-5-yl]oxy}-N,N-dimethylacetamide;

methyl (2S)-5-[(dimethylcarbamoyl)methoxy]-6-[1-(2-hydroxyethyl)-1H-pyrazol-4-yl]-2-methyl-1,2,3,4-tetrahydroquinoline-1-carboxylate;

2-{[(2S)-1-acetyl-6-(1-cyclopropyl-1H-pyrazol-4-yl)-2-methyl-1,2,3,4-tetrahydroquinolin-5-yl]oxy}-N-ethylacetamide;

1-[(2S)-6-(1-cyclopropyl-1H-pyrazol-4-yl)-5-(2-fluoroethoxy)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}-N-cyclopropyl-N-methylacetamide;

2-{[(2S)-1-acetyl-6-(1-cyclopropyl-1H-pyrazol-4-yl)-2-methyl-1,2,3,4-tetrahydroquinolin-5-yl]oxy}-1-(azetidin-1-yl)ethan-1-one;

2-{[(2S)-1-acetyl-6-(1-cyclopropyl-1H-pyrazol-4-yl)-2-methyl-1,2,3,4-tetrahydroquinolin-5-yl]oxy}-1-(piperidin-1-yl)ethan-1-one;

methyl (2S)-6-(1-cyclopropyl-1H-pyrazol-4-yl)-2-methyl-5-(2,2,2-trifluoroethoxy)-1,2,3,4-tetrahydroquinoline-1-carboxylate;
methyl (2S)-6-(1-cyclopropyl-1H-pyrazol-4-yl)-5-(2,2-difluoroethoxy)-2-methyl-1,2,3,4-tetrahydroquinoline-1-carboxylate;
methyl (2S)-6-(1-cyclopropyl-1H-pyrazol-4-yl)-5-(2-fluoroethoxy)-2-methyl-1,2,3,4-tetrahydroquinoline-1-carboxylate;
methyl (2S)-6-(1-cyclopropyl-1H-pyrazol-4-yl)-5-(2,2-difluoropropoxy)-2-methyl-1,2,3,4-tetrahydroquinoline-1-carboxylate;
methyl (2S)-6-(1-cyclopropyl-1H-pyrazol-4-yl)-2-methyl-5-(3,3,3-trifluoropropoxy)-1,2,3,4-tetrahydroquinoline-1-carboxylate;
methyl (2S)-5-(carbamoyldifluoromethoxy)-6-(1-cyclopropyl-1H-pyrazol-4-yl)-2-methyl-1,2,3,4-tetrahydroquinoline-1-carboxylate;
methyl (2S)-6-(1-cyclopropyl-1H-pyrazol-4-yl)-5-[(1,3-difluoropropan-2-yl)oxy]-2-methyl-1,2,3,4-tetrahydroquinoline-1-carboxylate;
methyl (2S)-6-(1-cyclopropyl-1H-pyrazol-4-yl)-5-(2-fluoro-2-methylpropoxy)-2-methyl-1,2,3,4-tetrahydroquinoline-1-carboxylate;
methyl (2S)-6-(1-cyclopropyl-1H-pyrazol-4-yl)-5-(3-hydroxy-2,2-dimethylpropoxy)-2-methyl-1,2,3,4-tetrahydroquinoline-1-carboxylate;
methyl (2S)-5-(1-carbamoyl-1-methylethoxy)-6-(1-cyclopropyl-1H-pyrazol-4-yl)-2-methyl-1,2,3,4-tetrahydroquinoline-1-carboxylate;
methyl (2S)-5-[(R)-carbamoyl(fluoro)methoxy]-6-(1-cyclopropyl-1H-pyrazol-4-yl)-2-methyl-1,2,3,4-tetrahydroquinoline-1-carboxylate;
methyl (2S)-5-[(S)-carbamoyl(fluoro)methoxy]-6-(1-cyclopropyl-1H-pyrazol-4-yl)-2-methyl-1,2,3,4-tetrahydroquinoline-1-carboxylate;
methyl (2S)-6-(1-cyclopropyl-1H-pyrazol-4-yl)-5-[(ethylcarbamoyl)methoxy]-2-methyl-1,2,3,4-tetrahydroquinoline-1-carboxylate;
methyl (2S)-5-{[cyclopropyl(methyl)carbamoyl]methoxy}-6-(1-cyclopropyl-1H-pyrazol-4-yl)-2-methyl-1,2,3,4-tetrahydroquinoline-1-carboxylate;
methyl (2S)-5-[2-(azetidin-1-yl)-2-oxoethoxy]-6-(1-cyclopropyl-1H-pyrazol-4-yl)-2-methyl-1,2,3,4-tetrahydroquinoline-1-carboxylate;
methyl (2S)-6-(1-cyclopropyl-1H-pyrazol-4-yl)-2-methyl-5-[2-oxo-2-(piperidin-1-yl)ethoxy]-1,2,3,4-tetrahydroquinoline-1-carboxylate;
methyl (2S)-6-(1-cyclopropyl-1H-pyrazol-4-yl)-2-methyl-5-[2-(2-oxopyrrolidin-1-yl)ethoxy]-1,2,3,4-tetrahydroquinoline-1-carboxylate;
methyl (2S)-6-(1-cyclopropyl-1H-pyrazol-4-yl)-2-methyl-5-[2-(morpholin-4-yl)-2-oxoethoxy]-1,2,3,4-tetrahydroquinoline-1-carboxylate;
methyl (2S)-6-(1-cyclopropyl-1H-pyrazol-4-yl)-5-[2-(1,1-dioxo-1$\lambda^6$,2-thiazolidin-2-yl)ethoxy]-2-methyl-1,2,3,4-tetrahydroquinoline-1-carboxylate;
methyl (2S)-6-(1-cyclopropyl-1H-pyrazol-4-yl)-2-methyl-5-(sulfamoylmethoxy)-1,2,3,4-tetrahydroquinoline-1-carboxylate;
methyl (2S)-6-(1-cyclopropyl-1H-pyrazol-4-yl)-5-[(dimethylsulfamoyl)methoxy]-2-methyl-1,2,3,4-tetrahydroquinoline-1-carboxylate;
methyl (2S)-6-(1-cyclopropyl-1H-pyrazol-4-yl)-2-methyl-5-[2-(oxetan-3-yl)ethoxy]-1,2,3,4-tetrahydroquinoline-1-carboxylate;
methyl (2S)-6-(1-cyclopropyl-1H-pyrazol-4-yl)-5-[(2,2-difluorocyclopropyl)methoxy]-2-methyl-1,2,3,4-tetrahydroquinoline-1-carboxylate;
1-[(2S)-6-(1-cyclopropyl-1H-pyrazol-4-yl)-2-methyl-5-(quinazolin-2-yloxy)-1,2,3,4-tetrahydroquinolin-1-yl]ethan-1-one;
1-[(2S)-5-(1,3-benzoxazol-2-yloxy)-6-(1-cyclopropyl-1H-pyrazol-4-yl)-2-methyl-1,2,3,4-tetrahydroquinolin-1-yl]ethan-1-one;
1-[(2S)-5-(1,3-benzoxazol-2-yloxy)-2-methyl-6-[1-(oxetan-3-yl)-1H-pyrazol-4-yl]-1,2,3,4-tetrahydroquinolin-1-yl]ethan-1-one;
1-[(2S)-6-[1-(2-hydroxyethyl)-1H-pyrazol-4-yl]-2-methyl-5-(pyrimidin-2-yloxy)-1,2,3,4-tetrahydroquinolin-1-yl]ethan-1-one;
2-{[(2S)-1-acetyl-6-(1-cyclopropyl-1H-pyrazol-4-yl)-2-methyl-1,2,3,4-tetrahydroquinolin-5-yl]oxy}pyridine-3-carboxamide;
1-[(2S)-6-(1-cyclopropyl-1H-pyrazol-4-yl)-2-methyl-5-1H-pyrazolo[3,4-d]pyrimidin-6-yloxy)-1,2,3,4-tetrahydroquinolin-1-yl]ethan-1-one;
1-[(2S)-6-(1-cyclopropyl-1H-pyrazol-4-yl)-2-methyl-5-(1,3-thiazol-2-yloxy)-1,2,3,4-tetrahydroquinolin-1-yl]ethan-1-one;
2-{[(2S)-1-acetyl-6-(1-cyclopropyl-1H-pyrazol-4-yl)-2-methyl-1,2,3,4-tetrahydroquinolin-5-yl]oxy}pyridine-3-carbonitrile;
1-[(2S)-6-(1-cyclopropyl-1H-pyrazol-4-yl)-2-methyl-5-{[4-(trifluoromethyl)pyrimidin-2-yl]oxy}-1,2,3,4-tetrahydroquinolin-1-yl]ethan-1-one;
1-[(2S)-6-(1-cyclopropyl-1H-pyrazol-4-yl)-2-methyl-5-{[3-(trifluoromethyl)pyridin-2-yl]oxy}-1,2,3,4-tetrahydroquinolin-1-yl]ethan-1-one;
1-[(2S)-5-[(3-chloropyridin-2-yl)oxy]-6-(1-cyclopropyl-1H-pyrazol-4-yl)-2-methyl-1,2,3,4-tetrahydroquinolin-1-yl]ethan-1-one;
1-[(2S)-6-(1-cyclopropyl-1H-pyrazol-4-yl)-2-methyl-5-(pyrazin-2-yloxy)-1,2,3,4-tetrahydroquinolin-1-yl]ethan-1-one;
1-[(2S)-6-(1-cyclopropyl-1H-pyrazol-4-yl)-2-methyl-5-(pyridin-2-yloxy)-1,2,3,4-tetrahydroquinolin-1-yl]ethan-1-one;
1-[(2S)-6-(1-cyclopropyl-1H-pyrazol-4-yl)-5-[(4,6-dimethylpyrimidin-2-yl)oxy]-2-methyl-1,2,3,4-tetrahydroquinolin-1-yl]ethan-1-one;
6-{[(2S)-1-acetyl-6-(1-cyclopropyl-1H-pyrazol-4-yl)-2-methyl-1,2,3,4-tetrahydroquinolin-5-yl]oxy}pyridazine-3-carbonitrile;
1-[(2S)-6-(1-cyclopropyl-1H-pyrazol-4-yl)-2-methyl-5-[(5-methylpyrimidin-2-yl)oxy]-1,2,3,4-tetrahydroquinolin-1-yl]ethan-1-one;
1-[(2S)-6-(1-cyclopropyl-1H-pyrazol-4-yl)-2-methyl-5-{[2-(trifluoromethyl)pyrimidin-4-yl]oxy}-1,2,3,4-tetrahydroquinolin-1-yl]ethan-1-one;
(2S)-5-cyclobutoxy-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-2-methyl-6-[1-(piperidin-4-yl)-1H-pyrazol-4-yl]-5-propoxy-1,2,3,4-tetrahydroquinoline;
(2S)-6-[1-(azetidin-3-yl)-1H-pyrazol-4-yl]-5-cyclobutoxy-1-cyclopropanecarbonyl-2-methyl-1,2,3,4-tetrahydroquinoline;
(2S)-6-[1-(azetidin-3-yl)-1H-pyrazol-4-yl]-1-cyclopropanecarbonyl-2-methyl-5-propoxy-1,2,3,4-tetrahydroquinoline;

1-[(2S)-2-methyl-6-[1-(piperidin-4-yl)-1H-pyrazol-4-yl]-5-propoxy-1,2,3,4-tetrahydroquinolin-1-yl]ethan-1-one;

methyl (2S)-2-methyl-6-[1-(piperidin-4-yl)-1H-pyrazol-4-yl]-5-propoxy-1,2,3,4-tetrahydroquinoline-1-carboxylate;

methyl (2S)-5-cyclobutoxy-2-methyl-6-[1-(pyrrolidin-3-yl)-1H-pyrazol-4-yl]-1,2,3,4-tetrahydroquinoline-1-carboxylate;

methyl (2S)-5-cyclobutoxy-2-methyl-6-(1-{octahydrocyclopenta[c]pyrrol-5-yl}-1H-pyrazol-4-yl)-1,2,3,4-tetrahydroquinoline-1-carboxylate;

1-[6-(4-methanesulfonylphenyl)-2-methyl-5-phenoxy-1,2,3,4-tetrahydroquinolin-1-yl]ethan-1-one;

1-(2-methyl-5-phenoxy-1,2,3,4-tetrahydroquinolin-1-yl)ethan-1-one;

1-[(2S)-5-cyclopropoxy-6-(1-cyclopropyl-1H-pyrazol-4-yl)-2-methyl-1,2,3,4-tetrahydroquinolin-1-yl]ethan-1-one;

1-[(2S)-6-(5-methanesulfonylpyridin-2-yl)-2-methyl-5-propoxy-1,2,3,4-tetrahydroquinolin-1-yl]ethan-1-one;

N-{6-[(2S)-1-acetyl-2-methyl-5-propoxy-1,2,3,4-tetrahydroquinolin-6-yl]pyridin-3-yl}methanesulfonamide;

2-{[(2S)-1-acetyl-6-(5-methanesulfonylpyridin-2-yl)-2-methyl-1,2,3,4-tetrahydroquinolin-5-yl]oxy}-N,N-dimethylacetamide;

1-[(2S)-6-(1,3-benzoxazol-2-yl)-2-methyl-5-propoxy-1,2,3,4-tetrahydroquinolin-1-yl]ethan-1-one;

1-[(2S)-2-methyl-5-propoxy-6-(pyrazolo[1,5-a]pyridin-2-yl)-1,2,3,4-tetrahydroquinolin-1-yl]ethan-1-one;

1-[(2S)-6-{imidazo[1,2-a]pyridin-2-yl}-2-methyl-5-propoxy-1,2,3,4-tetrahydroquinolin-1-yl]ethan-1-one;

1-[(2S)-6-(1,3-benzothiazol-2-yl)-2-methyl-5-propoxy-1,2,3,4-tetrahydroquinolin-1-yl]ethan-1-one;

1-[(2S)-6-(1H-1,3-benzodiazol-2-yl)-2-methyl-5-propoxy-1,2,3,4-tetrahydroquinolin-1-yl]ethan-1-one;

(2S)-5-cyclobutoxy-1-cyclopropanecarbonyl-2-methyl-6-(5-methyl-1,3,4-thiadiazol-2-yl)-1,2,3,4-tetrahydroquinoline;

5-[(2S)-5-cyclobutoxy-1-cyclopropanecarbonyl-2-methyl-1,2,3,4-tetrahydroquinolin-6-yl]-1,3,4-thiadiazol-2-amine;

(2S)-5-cyclobutoxy-1-cyclopropanecarbonyl-2-methyl-6-(1H-1,2,3-triazol-4-yl)-1,2,3,4-tetrahydroquinoline;

methyl (2S)-5-(4-chloro-2-cyanophenoxy)-2-methyl-6-[1-(piperidin-4-yl)-1H-pyrazol-4-yl]-1,2,3,4-tetrahydroquinoline-1-carboxylate;

methyl (2S)-5-(2-cyano-4-fluorophenoxy)-2-methyl-6-[1-(piperidin-4-yl)-1H-pyrazol-4-yl]-1,2,3,4-tetrahydroquinoline-1-carboxylate;

methyl (2S)-5-(2-chloro-4-cyanophenoxy)-2-methyl-6-[1-(piperidin-4-yl)-1H-pyrazol-4-yl]-1,2,3,4-tetrahydroquinoline-1-carboxylate;

methyl (2S)-5-(4-cyano-2-fluorophenoxy)-2-methyl-6-[1-(piperidin-4-yl)-1H-pyrazol-4-yl]-1,2,3,4-tetrahydroquinoline-1-carboxylate 2-{[(2S)-1-acetyl-2-methyl-6-[1-(piperidin-4-yl)-1H-pyrazol-4-yl]-1,2,3,4-tetrahydroquinolin-5-yl]oxy}benzonitrile;

methyl (2S)-5-(2-cyanophenoxy)-2-methyl-6-[1-(piperidin-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(2-cyanophenoxy)-2-methyl-1,2,3,4-tetrahydroquinoline-1-carboxylate;

methyl (2S)-6-[1-(azetidin-3-yl)-1H-pyrazol-4-yl]-5-(2-cyano-3-fluorophenoxy)-2-methyl-1,2,3,4-tetrahydroquinoline-1-carboxylate;

4-{[(2S)-1-acetyl-2-methyl-6-[1-(piperidin-4-yl)-1H-pyrazol-4-yl]-1,2,3,4-tetrahydroquinolin-5-yl]oxy}benzonitrile;

1-[(2S)-2-methyl-6-[1-(piperidin-4-yl)-1H-pyrazol-4-yl]-5-{[3-(trifluoromethyl)pyridin-2-yl]oxy}-1,2,3,4-tetrahydroquinolin-1-yl]ethan-1-one;

1-[(2S)-5-[(3-chloropyridin-2-yl)oxy]-2-methyl-6-[1-(piperidin-4-yl)-1H-pyrazol-4-yl]-1,2,3,4-tetrahydroquinolin-1-yl]ethan-1-one;

2-{[(2S)-1-acetyl-2-methyl-6-[1-(piperidin-4-yl)-1H-pyrazol-4-yl]-1,2,3,4-tetrahydroquinolin-5-yl]oxy}pyridine-3-carbonitrile;

1-[(2S)-2-methyl-5-[(5-methylpyrimidin-2-yl)oxy]-6-[1-(piperidin-4-yl)-1H-pyrazol-4-yl]-1,2,3,4-tetrahydroquinolin-1-yl]ethan-1-one;

1-[(2S)-2-methyl-6-[1-(piperidin-4-yl)-1H-pyrazol-4-yl]-5-(pyrazin-2-yloxy)-1,2,3,4-tetrahydroquinolin-1-yl]ethan-1-one;

methyl (2S)-5-(4-cyanophenoxy)-2-methyl-6-[1-(piperidin-4-yl)-1H-pyrazol-4-yl]-1,2,3,4-tetrahydroquinoline-1-carboxylate;

methyl (2S)-5-[(3-cyanopyridin-2-yl)oxy]-2-methyl-6-[1-(piperidin-4-yl)-1H-pyrazol-4-yl]-1,2,3,4-tetrahydroquinoline-1-carboxylate;

methyl (2S)-5-(2-cyano-3-fluorophenoxy)-2-methyl-6-[1-(piperidin-4-yl)-1H-pyrazol-4-yl]-1,2,3,4-tetrahydroquinoline-1-carboxylate;

methyl (2S)-5-(3-chloro-2-cyanophenoxy)-2-methyl-6-[1-(piperidin-4-yl)-1H-pryazol-4-yl]-1,2,3,4-tetrahydroquinoline-1-carboxylate;

2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;

2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}-6-fluorobenzonitrile;

4-{[(2S)-1-cyclopropanecarbonyl-2-methyl-6-[1-(piperidin-4-yl)-1H-pyrazol-4-yl]-1,2,3,4-tetrahydroquinolin-5-yl]oxy)}-3-fluorobenzonitrile;

2-{[(2S)-1-acetyl-6-(1-cyclopropyl-1H-pyrazol-4-yl)-2-methyl-1,2,3,4-tetrahydroquinolin-5-yl]oxy}benzonitrile;

methyl (2S)-6-[1-(azetidin-3-yl)-1H-pyrazol-4-yl]-5-(3-chloro-4-fluorophenoxy)-2-methyl-1,2,3,4-tetrahydroquinoline-1-carboxylate;

4-{[(2S)-1-acetyl-2-methyl-6-[1-(piperidin-4-yl)-1H-pyrazol-4-yl]-1,2,3,4-tetrahydroquinolin-5-yl]oxy}benzamide;

1-[(2S)-5-(2-chlorophenoxy)-2-methyl-6-[1-(piperidin-4-yl)-1H-pyrazol-4-yl]-1,2,3,4-tetrahydroquinolin-1-yl]ethan-1-one;

methyl (2S)-5-(4-fluorophenoxy)-2-methyl-6-[1-(piperidin-4-yl)-1H-pyrazol-4-yl]-1,2,3,4-tetrahydroquinoline-1-carboxylate;

methyl (2S)-5-(4-chlorophenoxy)-2-methyl-6-[1-(piperidin-4-yl)-1H-pyrazol-4-yl]-1,2,3,4-tetrahydroquinoline-1-carboxylate;

methyl (2S)-5-(2-chlorophenoxy)-2-methyl-6-[1-(piperidin-4-yl)-1H-pyrazol-4-yl]-1,2,3,4-tetrahydroquinoline-1-carboxylate;

methyl (2S)-5-(4-carbamoylphenoxy)-2-methyl-6-[1-(piperidin-4-yl)-1H-pyrazol-4-yl]-1,2,3,4-tetrahydroquinoline-1-carboxylate;

methyl (2S)-5-(3-cyano-4-fluorophenoxy)-2-methyl-6-[1-(piperidin-4-yl)-1H-pyrazol-4-yl]-1,2,3,4-tetrahydroquinoline-1-carboxylate;
methyl (2S)-5-(3-chloro-4-fluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(4-fluorophenoxy)-2-methyl-6-[1-(piperidin-4-yl)-1H-pyrazol-4-yl]-1,2,3,4-tetrahydroquinoline;
(2S)-5-(2-chlorophenoxy)-1-cyclopropanecarbonyl-2-methyl-6-[1-(piperidin-4-yl)-1H-pyrazol-4-yl]-1,2,3,4-tetrahydroquinoline;
(2S)-5-(4-chlorophenoxy)-1-cyclopropanecarbonyl-2-methyl-6-[1-(piperidin-4-yl)-1H-pyrazol-4-yl]-1,2,3,4-tetrahydroquinoline;
4-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;
(2S)-1-cyclopropanecarbonyl-2-methyl-5-phenoxy-6-[1-(piperidin-4-yl)-1H-pyrazol-4-yl]-1,2,3,4-tetrahydroquinoline;
(2S)-5-(3-chloro-4-fluorophenoxy)-1-cyclopropanecarbonyl-2-methyl-6-[1-(piperidin-4-yl)-1H-pyrazol-4-yl]-1,2,3,4-tetrahydroquinoline;
(2S)-6-[1-(azetidin-3-yl)-1H-pyrazol-4-yl]-1-cyclopropanecarbonyl-5-(4-fluorophenoxy)-2-methyl-1,2,3,4-tetrahydroquinoline;
(2S)-1-cyclopropanecarbonyl-5-(3-fluorophenoxy)-2-methyl-6-[1-(piperidin-4-yl)-1H-pyrazol-4-yl]-1,2,3,4-tetrahydroquinoline;
(2S)-1-cyclopropanecarbonyl-5-(3,4-di fluorophenoxy)-2-methyl-6-[1-(piperidin-4-yl)-1H-pyrazol-4-yl]-1,2,3,4-tetrahydroquinoline;
(2S)-6-[1-(azetidin-3-yl)-1H-pyrazol-4-yl]-1-cyclopropanecarbonyl-5-(3-fluorophenoxy)-2-methyl-1,2,3,4-tetrahydroquinoline;
(2S)-6-[1-(azetidin-3-yl)-1H-pyrazol-4-yl]-1-cyclopropanecarbonyl-5-(3,4-di fluorophenoxy)-2-methyl-1,2,3,4-tetrahydroquinoline;
(2S)-6-[1-(azetidin-3-yl)-1H-pyrazol-4-yl]-1-cyclopropanecarbonyl-2-methyl-5-phenoxy-1,2,3,4-tetrahydroquinoline;
methyl (2S)-5-(3,4-difluorophenoxy)-2-methyl-6-[1-(piperidin-4-yl)-1H-pyrazol-4-yl]-1,2,3,4-tetrahydroquinoline-1-carboxylate;
methyl (2S)-6-[1-(azetidin-3-yl)-1H-pyrazol-4-yl]-5-(3-chlorophenoxy)-2-methyl-1,2,3,4-tetrahydroquinoline-1-carboxylate;
(2S)-6-[1-(azetidin-3-yl)-1H-pyrazol-4-yl]-5-(3-chlorophenoxy)-1-cyclopropanecarbonyl-2-methyl-1,2,3,4-tetrahydroquinoline;
(2S)-5-(3-chlorophenoxy)-1-cyclopropanecarbonyl-2-methyl-6-[1-(piperidin-4-yl)-1H-pyrazol-4-yl]-1,2,3,4-tetrahydroquinoline;
methyl (2S)-6-[1-(azetidin-3-yl)-1H-pyrazol-4-yl]-5-(3,5-difluorophenoxy)-2-methyl-1,2,3,4-tetrahydroquinoline-1-carboxylate;
(2S)-6-[1-(azetidin-3-yl)-1H-pyrazol-4-yl]-1-cyclopropanecarbonyl-5-(3,5-di fluorophenoxy)-2-methyl-1,2,3,4-tetrahydroquinoline;
methyl (2S)-5-(3,5-difluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(3,5-difluorophenoxy)-2-methyl-6-[1-(piperidin-4-yl)-1H-pyrazol-4-yl]-1,2,3,4-tetrahydroquinoline;

5-[(2S)-1-cyclopropanecarbonyl-2-methyl-5-phenoxy-1,2,3,4-tetrahydroquinolin-6-yl]-1,3,4-thiadiazol-2-amine;
methyl (2S)-5-(4-fluorophenoxy)-2-methyl-6-[1-(pyrrolidin-3-yl)-1H-pyrazol-4-yl]-1,2,3,4-tetrahydroquinoline-1-carboxylate;
4-{[(2S)-1-acetyl-6-(1-cyclopropyl-1H-pyrazol-4-yl)-2-methyl-1,2,3,4-tetrahydroquinolin-5-yl]oxy}benzamide;
(2S)-1-cyclopropanecarbonyl-2-methyl-5-phenoxy-6-(1H-pyrazol-5-yl)-1,2,3,4-tetrahydroquinoline;
(2S)-1-cyclopropanecarbonyl-2-methyl-6-(1-methyl-1H-1,2,3-triazol-4-yl)-5-phenoxy-1,2,3,4-tetrahydroquinoline;
(2S)-1-cyclopropanecarbonyl-2-methyl-6-(5-methyl-1,3,4-thiadiazol-2-yl)-5-phenoxy-1,2,3,4-tetrahydroquinoline;
(2S)-1-cyclopropanecarbonyl-2-methyl-6-(1-methyl-1H-imidazol-4-yl)-5-phenoxy-1,2,3,4-tetrahydroquinoline;
methyl (2S)-6-[1-(1,1-dioxo-1$\lambda^6$-thian-3-yl)-1H-pyrazol-4-yl]-5-(4-fluorophenoxy)-2-methyl-1,2,3,4-tetrahydroquinoline-1-carboxylate;
methyl (2S)-6-[1-(1,1-dioxo-1$\lambda^6$-thietan-3-yl)-1H-pyrazol-4-yl]-5-(4-fluorophenoxy)-2-methyl-1,2,3,4-tetrahydroquinoline-1-carboxylate;
(2S)-1-cyclopropanecarbonyl-2-methyl-6-(1-methyl-1H-pyrazol-4-yl)-5-phenoxy-1,2,3,4-tetrahydroquinoline;
1-[(2S)-6-(1-cyclopropyl-1H-pyrazol-4-yl)-5-(4-fluorophenoxy)-2-methyl-1,2,3,4-tetrahydroquinolin-1-yl]ethan-1-one;
1-[(2S)-5-(4-chlorophenoxy)-6-(1-cyclopropyl-1H-pyrazol-4-yl)-2-methyl-1,2,3,4-tetrahydroquinolin-1-yl]ethan-1-one;
methyl (2S)-6-(1-cyclopropyl-1H-pyrazol-4-yl)-5-(2-fluorophenoxy)-2-methyl-1,2,3,4-tetrahydroquinoline-1-carboxylate;
1-[(2S)-6-(1-cyclopropyl-1H-pyrazol-4-yl)-5-(2-fluorophenoxy)-2-methyl-1,2,3,4-tetrahydroquinolin-1-yl]ethan-1-one;
(2S)-1-cyclopropanecarbonyl-2-methyl-5-phenoxy-6-(IH-pyrazol-4-yl)-1,2,3,4-tetrahydroquinoline;
3-{4-[(2S)-1-cyclopropanecarbonyl-5-(4-fluorophenoxy)-2-methyl-1,2,3,4-tetrahydroquinolin-6-yl]-1H-pyrazol-1-yl}-1$\lambda^6$-thietane-1,1-dione;
3-{4-[(2S)-1-cyclopropanecarbonyl-2-methyl-5-phenoxy-1,2,3,4-tetrahydroquinolin-6-yl]-1H-pyrazol-1-yl}-1$\lambda^6$-thietane-1,1-dione;
1-[(2S)-5-(2-chlorophenoxy)-6-(1-cyclopropyl-1H-pyrazol-4-yl)-2-methyl-1,2,3,4-tetrahydroquinolin-1-yl]ethan-1-one;
methyl (2S)-6-(1-cyclopropyl-1H-pyrazol-4-yl)-5-(4-fluorophenoxy)-2-methyl-1,2,3,4-tetrahydroquinoline-1-carboxylate;
methyl (2S)-5-(4-cyanophenoxy)-6-(1-cyclopropyl-1H-pyrazol-4-yl)-2-methyl-1,2,3,4-tetrahydroquinoline-1-carboxylate;
methyl (2S)-5-(4-chlorophenoxy)-6-(1-cyclopropyl-1H-pyrazol-4-yl)-2-methyl-1,2,3,4-tetrahydroquinoline-1-carboxylate;
methyl (2S)-5-(2-chlorophenoxy)-6-(1-cyclopropyl-1H-pyrazol-4-yl)-2-methyl-1,2,3,4-tetrahydroquinoline-1-carboxylate;
methyl (2S)-5-(4-carbamoylphenoxy)-6-(1-cyclopropyl-1H-pyrazol-4-yl)-2-methyl-1,2,3,4-tetrahydroquinoline-1-carboxylate;

4-{[(2S)-1-acetyl-6-(1-cyclopropyl-1H-pyrazol-4-yl)-2-methyl-1,2,3,4-tetrahydroquinolin-5-yl]oxy}benzonitrile;

methyl (2S)-5-(4-chloro-2-cyanophenoxy)-2-methyl-6-[1-(1-methylpiperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-{[1-(propan-2-yl)azetidin-3-yl]oxy}-1,2,3,4-tetrahydroquinolin-1-yl]ethan-1-one;

2-{[(2S)-1-acetyl-2-methyl-6-[1-(1-methylpiperidin-4-yl)-1H-pyrazol-4-yl]-1,2,3,4-tetrahydroquinolin-5-yl]oxy}benzonitrile;

methyl (2S)-5-cyclobutoxy-2-methyl-6-[1-(1-methylpyrrolidin-3-yl)-1H-pyrazol-4-yl]-1,2,3,4-tetrahydroquinoline-1-carboxylate;

methyl (2S)-5-cyclobutoxy-2-methyl-6-(1-{2-methyl-octahydrocyclopenta[c]pyrrol-5-yl}-1H-pyrazol-4-yl)-1,2,3,4-tetrahydroquinoline-1-carboxylate;

methyl (2S)-5-(4-fluorophenoxy)-2-methyl-6-[1-(1-methylpyrrolidin-3-yl)-1H-pyrazol-4-yl]-1,2,3,4-tetrahydroquinoline-1-carboxylate;

methyl (2S)-5-(4-fluorophenoxy)-2-methyl-6-(1-{2-methyl-octahydrocyclopenta[c]pyrrol-5-yl}-1H-pyrazol-4-yl)-1,2,3,4-tetrahydroquinoline-1-carboxylate;

methyl (2S)-6-(1-cyclopropyl-1H-pyrazol-4-yl)-5-[(1-ethylazetidin-3-yl)oxy]-2-methyl-1,2,3,4-tetrahydroquinoline-1-carboxylate;

methyl (2S)-6-(1-cyclopropyl-1H-pyrazol-4-yl)-2-methyl-5-{[1-(propan-2-yl)azetidin-3-yl]oxy}-1,2,3,4-tetrahydroquinoline-1-carboxylate;

1-[(2S)-6-(1-cyclopropyl-1H-pyrazol-4-yl)-5-[(1-ethylazetidin-3-yl)oxy]-2-methyl-1,2,3,4-tetrahydroquinolin-1-yl]ethan-1-one;

1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one;

1-[(2S)-6-(1-cyclopropyl-1H-pyrazol-4-yl)-2-methyl-5-[(6-methylpyridin-2-yl)oxy]-1,2,3,4-tetrahydroquinolin-1-yl]ethan-1-one;

1-[(2S)-6-(1-cyclopropyl-1H-pyrazol-4-yl)-5-(isoquinolin-1-yloxy)-2-methyl-1,2,3,4-tetrahydroquinolin-1-yl]ethan-1-one;

1-[(2S)-5-(2-fluorophenoxy)-2-methyl-6-[1-(piperidin-4-yl)-1H-pyrazol-4-yl]-1,2,3,4-tetrahydroquinolin-1-yl]ethan-1-one;

methyl (2S)-5-(2-fluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2-fluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2-fluorophenoxy)-2-methyl-1,2,3,4-tetrahydroquinoline;

methyl (2S)-6-[1-(azetidin-3-yl)-1H-pyrazol-4-yl]-5-(2-fluorophenoxy)-2-methyl-1,2,3,4-tetrahydroquinoline-1-carboxylate;

methyl (2S)-5-(2,4-difluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2,4-difluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2,4-difluorophenoxy)-2-methyl-1,2,3,4-tetrahydroquinoline;

methyl (2S)-6-[1-(azetidin-3-yl)-1H-pyrazol-4-yl]-5-(2,4-difluorophenoxy)-2-methyl-1,2,3,4-tetrahydroquinoline-1-carboxylate;

(2S)-1-cyclopropanecarbonyl-5-(2,3-difluorophenoxy)-2-methyl-6-[1-(piperidin-4-yl)-1H-pyrazol-4-yl]-1,2,3,4-tetrahydroquinoline;

(2S)-6-[1-(azetidin-3-yl)-1H-pyrazol-4-yl]-1-cyclopropanecarbonyl-5-(2,3-difluorophenoxy)-2-methyl-1,2,3,4-tetrahydroquinoline;

methyl (2S)-5-(2,3-difluorophenoxy)-2-methyl-6-[1-(piperidin-4-yl)-1H-pyrazol-4-yl]-1,2,3,4-tetrahydroquinoline-1-carboxylate;

methyl (2S)-6-[1-(azetidin-3-yl)-1H-pyrazol-4-yl]-5-(2,3-difluorophenoxy)-2-methyl-1,2,3,4-tetrahydroquinoline-1-carboxylate;

methyl (2S)-6-[1-(azetidin-3-yl)-1H-pyrazol-4-yl]-5-(2,5-difluorophenoxy)-2-methyl-1,2,3,4-tetrahydroquinoline-1-carboxylate;

(2S)-6-[1-(azetidin-3-yl)-1H-pyrazol-4-yl]-1-cyclopropanecarbonyl-5-(2,5-difluorophenoxy)-2-methyl-1,2,3,4-tetrahydroquinoline;

methyl (2S)-5-(2,5-difluorophenoxy)-2-methyl-6-[1-(piperidin-4-yl)-1H-pyrazol-4-yl]-1,2,3,4-tetrahydroquinoline-1-carboxylate;

(2S)-1-cyclopropanecarbonyl-5-(2,5-di fluorophenoxy)-2-methyl-6-[1-(piperidin-4-yl)-1H-pyrazol-4-yl]-1,2,3,4-tetrahydroquinoline;

1-[(2S)-5-(3,4-difluorophenoxy)-2-methyl-6-[1-(piperidin-4-yl)-1H-pyrazol-4-yl]-1,2,3,4-tetrahydroquinolin-1-yl]ethan-1-one;

1-[(2S)-5-(2,5-difluorophenoxy)-2-methyl-6-[1-(piperidin-4-yl)-1H-pyrazol-4-yl]-1,2,3,4-tetrahydroquinolin-1-yl]ethan-1-one 1-[(2S)-5-{[(E)-2-chloroethenyl]oxy}-6-(1-cyclopropyl-1H-pyrazol-4-yl)-2-methyl-1,2,3,4-tetrahydroquinolin-1-yl]ethan-1-one;

(2S)-5-cyclobutoxy-1-cyclopropanecarbonyl-2-methyl-6-{1H,2H,3H-pyrazolo[1,5-a]imidazol-7-yl}-1,2,3,4-tetrahydroquinoline;

(2S)-5-cyclobutoxy-1-cyclopropanecarbonyl-6-{1-methanesulfonyl-1H,2H,3H-pyrazolo[1,5-a]imidazol-7-yl}-2-methyl-1,2,3,4-tetrahydroquinoline;

methyl (2S)-5-cyclobutoxy-6-[2-(4-hydroxypiperidin-4-yl)-1,3-thiazol-4-yl]-2-methyl-1,2,3,4-tetrahydroquinoline-1-carboxylate;

methyl (2S)-5-cyclobutoxy-6-[2-(4-fluoropiperidin-4-yl)-1,3-thiazol-4-yl]-2-methyl-1,2,3,4-tetrahydroquinoline-1-carboxylate;

methyl (2S)-5-(4-fluorophenoxy)-2-methyl-6-[1-(1-methylazetidin-3-yl)-1H-pyrazol-4-yl]-1,2,3,4-tetrahydroquinoline-1-carboxylate;

methyl (2S)-5-(4-fluorophenoxy)-2-methyl-6-[1-(1-methylpiperidin-4-yl)-1H-pyrazol-4-yl]-1,2,3,4-tetrahydroquinoline-1-carboxylate;

methyl (2S)-5-cyclobutoxy-2-methyl-6-[1-(1-methylazetidin-3-yl)-1H-pyrazol-4-yl]-1,2,3,4-tetrahydroquinoline-1-carboxylate;

methyl (2S)-5-cyclobutoxy-2-methyl-6-[1-(1-methylpiperidin-4-yl)-1H-pyrazol-4-yl]-1,2,3,4-tetrahydroquinoline-1-carboxylate;

1-[(2S)-6-(1-cyclopropyl-1H-pyrazol-4-yl)-2-methyl-5-[(3-methylpyridin-2-yl)oxy]-1,2,3,4-tetrahydroquinolin-1-yl]ethan-1-one;

1-[(2S)-6-(1-cyclopropyl-1H-pyrazol-4-yl)-2-methyl-5-[(5-methylpyridin-2-yl)oxy]-1,2,3,4-tetrahydroquinolin-1-yl]ethan-1-one;

1-[(2S)-5-[(5-chloropyridin-2-yl)oxy]-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(7H-purin-2-yloxy)-1,2,3,4-tetrahydroquinolin-1-yl]ethan-1-one;

methyl (2S)-5-cyclobutoxy-6-[1-(3-methoxypiperidin-4-yl)-1H-pyrazol-4-yl]-2-methyl-1,2,3,4-tetrahydroquinoline-1-carboxylate;

methyl (2S)-5-(4-fluorophenoxy)-6-[1-(3-methoxypiperidin-4-yl)-1H-pyrazol-4-yl]-2-methyl-1,2,3,4-tetrahydroquinoline-1-carboxylate;

methyl (2S)-5-cyclobutoxy-6-[1-(3-methoxy-1-methylpiperidin-4-yl)-1H-pyrazol-4-yl]-2-methyl-1,2,3,4-tetrahydroquinoline-1-carboxylate;

methyl (2S)-5-(4-fluorophenoxy)-6-[1-(3-methoxy-1-methylpiperidin-4-yl)-1H-pyrazol-4-yl]-2-methyl-1,2,3,4-tetrahydroquinoline-1-carboxylate;

3-{4-[(2S)-1-cyclopropanecarbonyl-2-methyl-5-phenoxy-1,2,3,4-tetrahydroquinolin-6-yl]-1H-pyrazol-1-yl}-1$\lambda^6$-thiane-1,1-dione;

3-{4-[(2S)-1-cyclopropanecarbonyl-5-(4-fluorophenoxy)-2-methyl-1,2,3,4-tetrahydroquinolin-6-yl]-1H-pyrazol-1-yl}-1$\lambda^6$-thiane-1,1-dione;

methyl (2S)-5-cyclobutoxy-2-methyl-6-[1-(2-oxopiperidin-4-yl)-1H-pyrazol-4-yl]-1,2,3,4-tetrahydroquinoline-1-carboxylate;

methyl (2S)-5-(4-fluorophenoxy)-2-methyl-6-[1-(2-oxopiperidin-4-yl)-1H-pyrazol-4-yl]-1,2,3,4-tetrahydroquinoline-1-carboxylate;

methyl (2S)-5-(4-fluorophenoxy)-2-methyl-6-{1-[(2S)-2-methylazetidin-3-yl]-1H-pyrazol-4-yl}-1,2,3,4-tetrahydroquinoline-1-carboxylate;

methyl (2S)-5-cyclobutoxy-2-methyl-6-{1-[(2S)-2-methylazetidin-3-yl]-1H-pyrazol-4-yl}-1,2,3,4-tetrahydroquinoline-1-carboxylate;

N-{4-[(2S)-5-cyclobutoxy-1-cyclopropanecarbonyl-2-methyl-1,2,3,4-tetrahydroquinolin-6-yl]-1-cyclopropyl-1H-pyrazol-5-yl}methanesulfonamide;

N-{4-[(2S)-5-cyclobutoxy-1-cyclopropanecarbonyl-2-methyl-1,2,3,4-tetrahydroquinolin-6-yl]-1-cyclopropyl-1H-pyrazol-5-yl}acetamide;

methyl (2S)-5-cyclobutoxy-6-[1-(3-hydroxycyclobutyl)-1H-pyrazol-4-yl]-2-methyl-1,2,3,4-tetrahydroquinoline-1-carboxylate;

methyl (2S)-5-cyclobutoxy-2-methyl-6-[2-(piperidin-4-yl)-1H-imidazol-4-yl]-1,2,3,4-tetrahydroquinoline-1-carboxylate;

methyl (2S)-5-cyclobutoxy-2-methyl-6-[1-methyl-2-(piperidin-4-yl)-1H-imidazol-4-yl]-1,2,3,4-tetrahydroquinoline-1-carboxylate;

2-{[(2S)-1-acetyl-2-methyl-6-[1-(oxetan-3-yl)-1H-pyrazol-4-yl]-1,2,3,4-tetrahydroquinolin-5-yl]oxy}-N-methylacetamide;

1-[(2S)-2-methyl-5-(1,2-oxazol-5-ylmethoxy)-6-[1-(oxetan-3-yl)-1H-pyrazol-4-yl]-1,2,3,4-tetrahydroquinolin-1-yl]ethan-1-one;

N-(2-{[(2S)-1-acetyl-2-methyl-6-[1-(oxetan-3-yl)-1H-pyrazol-4-yl]-1,2,3,4-tetrahydroquinolin-5-yl]oxy}ethyl)methanesulfonamide;

1-[(2S)-6-(1-cyclopropyl-1H-pyrazol-4-yl)-2-methyl-5-(1,2-oxazol-5-ylmethoxy)-1,2,3,4-tetrahydroquinolin-1-yl]ethan-1-one;

N-(2-{[(2S)-1-acetyl-6-(1-cyclopropyl-1H-pyrazol-4-yl)-2-methyl-1,2,3,4-tetrahydroquinolin-5-yl]oxy}ethyl)methanesulfonamide;

2-{[(2S)-1-acetyl-6-(1-cyclopropyl-1H-pyrazol-4-yl)-2-methyl-1,2,3,4-tetrahydroquinolin-5-yl]oxy}-N-methylacetamide;

1-[(2S)-6-(1-cyclopropyl-1H-pyrazol-4-yl)-2-methyl-5-(oxetan-3-yloxy)-1,2,3,4-tetrahydroquinolin-1-yl]ethan-1-one;

1-[(2S)-5-(cyclopentylmethoxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-5-[2-(dimethylamino)ethoxy]-2-methyl-1,2,3,4-tetrahydroquinolin-1-yl]ethan-1-one;

1-[(2S)-6-(1-cyclopropyl-1H-pyrazol-4-yl)-2-methyl-5-propoxy-1,2,3,4-tetrahydroquinolin-1-yl]ethan-1-one;

1-[(2S)-6-(1-cyclopropyl-1H-pyrazol-4-yl)-2-methyl-5-(propan-2-yloxy)-1,2,3,4-tetrahydroquinolin-1-yl]ethan-1-one;

1-[(2S)-5-cyclobutoxy-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-5-(cyclopropylmethoxy)-2-methyl-1,2,3,4-tetrahydroquinolin-1-yl]ethan-1-one;

2-{([(2S)-1-acetyl-6-(1-cyclopropyl-1H-pyrazol-4-yl)-2-methyl-1,2,3,4-tetrahydroquinolin-5-yl]oxy}acetamide;

1-[(2S)-5-(cyclobutylmethoxy)-6-(1-cyclopropyl-1H-pyrazol-4-yl)-2-methyl-1,2,3,4-tetrahydroquinolin-1-yl]ethan-1-one;

1-[(2S)-5-(benzyloxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(2-methylpropoxy)-1,2,3,4-tetrahydroquinolin-1-yl]ethan-1-one;

1-[(2S)-6-(1-cyclopropyl-1H-pyrazol-4-yl)-2-methyl-5-[(3-methyloxetan-3-yl)methoxy]-1,2,3,4-tetrahydroquinolin-1-yl]ethan-1-one;

1-[(2S)-5-(cyclopentyloxy)-6-(1-cyclopropyl-1H-pyrazol-4-yl)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}acetonitrile;

1-[(2S)-6-(1-cyclopropyl-1H-pyrazol-4-yl)-5-(2-methoxyethoxy)-2-methyl-1,2,3,4-tetrahydroquinolin-1-yl]ethan-1-one;

1-[(2S)-6-(1-cyclopropyl-1H-pyrazol-4-yl)-2-methyl-5-(pyridin-3-ylmethoxy)-1,2,3,4-tetrahydroquinolin-1-yl]ethan-1-one;

1-[(2S)-6-(1-cyclopropyl-1H-pyrazol-4-yl)-2-methyl-5-(oxan-4-ylmethoxy)-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}-N,N-dimethylacetamide;

1-[(2S)-5-(cyclohexylmethoxy)-6-(1-cyclopropyl-1H-pyrazol-4-yl)-2-methyl-1,2,3,4-tetrahydroquinolin-1-yl]ethan-1-one;

1-[(2S)-6-(1-cyclopropyl-1H-pyrazol-4-yl)-2-methyl-5-(pyridin-2-ylmethoxy)-1,2,3,4-tetrahydroquinolin-1-yl]ethan-1-one;

1-[(2S)-6-(1-cyclopropyl-1H-pyrazol-4-yl)-5-methoxy-2-methyl-1,2,3,4-tetrahydroquinolin-1-yl]ethan-1-one;

1-[(2S)-6-(1-cyclopropyl-1H-pyrazol-4-yl)-2-methyl-5-[(1-methyl-1H-pyrazol-3-yl)methoxy]-1,2,3,4-tetrahydroquinolin-1-yl]ethan-1-one;

1-[(2S)-6-(1-cyclopropyl-1H-pyrazol-4-yl)-2-methyl-5-(1,3-thiazol-5-ylmethoxy)-1,2,3,4-tetrahydroquinolin-1-yl]ethan-1-one;
1-[(2S)-6-[1-(2-methanesulfonylethyl)-1H-pyrazol-4-yl]-2-methyl-5-propoxy-1,2,3,4-tetrahydroquinolin-1-yl]ethan-1-one;
1-[(2S)-6-[1-(2-hydroxy-2-methylpropyl)-1H-pyrazol-4-yl]-2-methyl-5-propoxy-1,2,3,4-tetrahydroquinolin-1-yl]ethan-1-one;
1-[(2S)-5-cyclobutoxy-6-[1-(2-methanesulfonylethyl)-1H-pyrazol-4-yl]-2-methyl-1,2,3,4-tetrahydroquinolin-1-yl]ethan-1-one;
1-[(2S)-5-cyclobutoxy-6-[1-(2-hydroxy-2-methylpropyl)-1H-pyrazol-4-yl]-2-methyl-1,2,3,4-tetrahydroquinolin-1-yl]ethan-1-one;
1-[(2S)-5-cyclobutoxy-6-[1-(2-hydroxyethyl)-1H-pyrazol-4-yl]-2-methyl-1,2,3,4-tetrahydroquinolin-1-yl]ethan-1-one;
1-[(2S)-5-cyclobutoxy-2-methyl-6-[1-(piperidin-4-yl)-1H-pyrazol-4-yl]-1,2,3,4-tetrahydroquinolin-1-yl]ethan-1-one;
1-[(2S)-6-[1-(2-methanesulfonylethyl)-1H-pyrazol-4-yl]-2-methyl-5-(oxan-4-ylmethoxy)-1,2,3,4-tetrahydroquinolin-1-yl]ethan-1-one;
1-[(2S)-6-[1-(2-hydroxy-2-methylpropyl)-1H-pyrazol-4-yl]-2-methyl-5-(oxan-4-ylmethoxy)-1,2,3,4-tetrahydroquinolin-1-yl]ethan-1-one;
1-[(2S)-6-[1-(2-hydroxyethyl)-1H-pyrazol-4-yl]-2-methyl-5-(oxan-4-ylmethoxy)-1,2,3,4-tetrahydroquinolin-1-yl]ethan-1-one;
1-[(2S)-2-methyl-5-(oxan-4-ylmethoxy)-6-[1-(piperidin-4-yl)-1H-pyrazol-4-yl]-1,2,3,4-tetrahydroquinolin-1-yl]ethan-1-one;
2-{[(2S)-1-acetyl-6-[1-(2-methanesulfonylethyl)-1H-pyrazol-4-yl]-2-methyl-1,2,3,4-tetrahydroquinolin-5-yl]oxy}-N,N-dimethylacetamide;
2-{[(2S)-1-acetyl-6-[1-(2-hydroxy-2-methylpropyl)-1H-pyrazol-4-yl]-2-methyl-1,2,3,4-tetrahydroquinolin-5-yl]oxy}-N,N-dimethylacetamide;
2-{[(2S)-1-acetyl-2-methyl-6-[1-(piperidin-4-yl)-1H-pyrazol-4-yl]-1,2,3,4-tetrahydroquinolin-5-yl]oxy}-N,N-dimethylacetamide;
1-[(2S)-6-[1-(2-methanesulfonylethyl)-1H-pyrazol-4-yl]-2-methyl-5-(2-methylpropoxy)-1,2,3,4-tetrahydroquinolin-1-yl]ethan-1-one;
1-[(2S)-6-[1-(2-hydroxy-2-methylpropyl)-1H-pyrazol-4-yl]-2-methyl-5-(2-methylpropoxy)-1,2,3,4-tetrahydroquinolin-1-yl]ethan-1-one;
1-[(2S)-6-[1-(2-hydroxyethyl)-1H-pyrazol-4-yl]-2-methyl-5-(2-methylpropoxy)-1,2,3,4-tetrahydroquinolin-1-yl]ethan-1-one;
1-[(2S)-2-methyl-5-(2-methylpropoxy)-6-[1-(piperidin-4-yl)-1H-pyrazol-4-yl]-1,2,3,4-tetrahydroquinolin-1-yl]ethan-1-one;
1-[(2S)-5-(cyclopentylmethoxy)-6-[1-(2-methanesulfonylethyl)-1H-pyrazol-4-yl]-2-methyl-1,2,3,4-tetrahydroquinolin-1-yl]ethan-1-one;
1-[(2S)-5-(cyclopentylmethoxy)-6-[1-(2-hydroxy-2-methylpropyl)-1H-pyrazol-4-yl]-2-methyl-1,2,3,4-tetrahydroquinolin-1-yl]ethan-1-one;
1-[(2S)-5-(cyclopentylmethoxy)-6-[1-(2-hydroxyethyl)-1H-pyrazol-4-yl]-2-methyl-1,2,3,4-tetrahydroquinolin-1-yl]ethan-1-one;
1-[(2S)-5-(cyclopentylmethoxy)-2-methyl-6-[1-(piperidin-4-yl)-1H-pyrazol-4-yl]-1,2,3,4-tetrahydroquinolin-1-yl]ethan-1-one;
2-{[(2S)-1-acetyl-6-[1-(2-methanesulfonylethyl)-1H-pyrazol-4-yl]-2-methyl-1,2,3,4-tetrahydroquinolin-5-yl]oxy}-1-(pyrrolidin-1-yl)ethan-1-one;
2-{[(2S)-1-acetyl-6-[1-(2-hydroxy-2-methylpropyl)-1H-pyrazol-4-yl]-2-methyl-1,2,3,4-tetrahydroquinolin-5-yl]oxy}-1-(pyrrolidin-1-yl)ethan-1-one;
2-{[(2S)-1-acetyl-6-[1-(2-hydroxyethyl)-1H-pyrazol-4-yl]-2-methyl-1,2,3,4-tetrahydroquinolin-5-yl]oxy}-1-(pyrrolidin-1-yl)ethan-1-one;
2-{[(2S)-1-acetyl-2-methyl-6-[1-(piperidin-4-yl)-1H-pyrazol-4-yl]-1,2,3,4-tetrahydroquinolin-5-yl]oxy}-1-(pyrrolidin-1-yl)ethan-1-one;
(5R)-5-(({[(2S)-1-acetyl-6-[1-(2-methanesulfonylethyl)-1H-pyrazol-4-yl]-2-methyl-1,2,3,4-tetrahydroquinolin-5-yl]oxy methyl)pyrrolidin-2-one;
(5R)-5-({[(2S)-1-acetyl-6-[1-(2-hydroxy-2-methylpropyl)-1H-pyrazol-4-yl]-2-methyl-1,2,3,4-tetrahydroquinolin-5-yl]oxy}methyl)pyrrolidin-2-one;
(5R)-5-({[(2S)-1-acetyl-6-[1-(2-hydroxyethyl)-1H-pyrazol-4-yl]-2-methyl-1,2,3,4-tetrahydroquinolin-5-yl]oxy}methyl)pyrrolidin-2-one;
(5R)-5-({[(2S)-1-acetyl-2-methyl-6-[1-(piperidin-4-yl)-1H-pyrazol-4-yl]-1,2,3,4-tetrahydroquinolin-5-yl]oxy}methyl)pyrrolidin-2-one;
N-(2-{[(2S)-1-acetyl-6-[1-(2-methanesulfonylethyl)-1H-pyrazol-4-yl]-2-methyl-1,2,3,4-tetrahydroquinolin-5-yl]oxy}ethyl)-N-methylmethanesulfonamide;
N-(2-{[(2S)-1-acetyl-6-[1-(2-hydroxy-2-methylpropyl)-1H-pyrazol-4-yl]-2-methyl-1,2,3,4-tetrahydroquinolin-5-yl]oxy}ethyl)-N-methylmethanesulfonamide;
N-(2-{[(2S)-1-acetyl-6-[1-(2-hydroxyethyl)-1H-pyrazol-4-yl]-2-methyl-1,2,3,4-tetrahydroquinolin-5-yl]oxy}ethyl)-N-methylmethanesulfonamide;
N-(2-{[(2S)-1-acetyl-2-methyl-6-[1-(piperidin-4-yl)-1H-pyrazol-4-yl]-1,2,3,4-tetrahydroquinolin-5-yl]oxy}ethyl)-N-methylmethanesulfonamide;
1-[(2S)-6-[1-(2-hydroxyethyl)-1H-pyrazol-4-yl]-2-methyl-5-[(3S)-pyrrolidin-3-ylmethoxy]-1,2,3,4-tetrahydroquinolin-1-yl]ethan-1-one;
methyl (2S)-6-[1-(2-methanesulfonylethyl)-1H-pyrazol-4-yl]-2-methyl-5-propoxy-1,2,3,4-tetrahydroquinoline-1-carboxylate;
methyl (2S)-6-[1-(2-hydroxy-2-methylpropyl)-1H-pyrazol-4-yl]-2-methyl-5-propoxy-1,2,3,4-tetrahydroquinoline-1-carboxylate;
methyl (2S)-6-[1-(2-hydroxyethyl)-1H-pyrazol-4-yl]-2-methyl-5-propoxy-1,2,3,4-tetrahydroquinoline-1-carboxylate;
methyl (2S)-5-cyclobutoxy-6-[1-(2-methanesulfonylethyl)-1H-pyrazol-4-yl]-2-methyl-1,2,3,4-tetrahydroquinoline-1-carboxylate;
methyl (2S)-5-cyclobutoxy-6-[1-(2-hydroxy-2-methylpropyl)-1H-pyrazol-4-yl]-2-methyl-1,2,3,4-tetrahydroquinoline-1-carboxylate;
methyl (2S)-5-cyclobutoxy-6-[1-(2-hydroxyethyl)-1H-pyrazol-4-yl]-2-methyl-1,2,3,4-tetrahydroquinoline-1-carboxylate;
methyl (2S)-5-cyclobutoxy-2-methyl-6-[1-(piperidin-4-yl)-1H-pyrazol-4-yl]-1,2,3,4-tetrahydroquinoline-1-carboxylate;
methyl (2S)-6-[1-(2-methanesulfonylethyl)-1H-pyrazol-4-yl]-2-methyl-5-(oxan-4-ylmethoxy)-1,2,3,4-tetrahydroquinoline-1-carboxylate;
methyl (2S)-6-[1-(2-hydroxy-2-methylpropyl)-1H-pyrazol-4-yl]-2-methyl-5-(oxan-4-ylmethoxy)-1,2,3,4-tetrahydroquinoline-1-carboxylate;

methyl (2S)-6-[1-(2-hydroxyethyl)-1H-pyrazol-4-yl]-2-methyl-5-(oxan-4-ylmethoxy)-1,2,3,4-tetrahydroquinoline-1-carboxylate;

methyl (2S)-2-methyl-5-(oxan-4-ylmethoxy)-6-[1-(piperidin-4-yl)-1H-pyrazol-4-yl]-1,2,3,4-tetrahydroquinoline-1-carboxylate;

methyl (2S)-5-[(dimethylcarbamoyl)methoxy]-6-[1-(2-methanesulfonylethyl)-1H-pyrazol-4-yl]-2-methyl-1,2,3,4-tetrahydroquinoline-1-carboxylate;

methyl (2S)-5-[(dimethylcarbamoyl)methoxy]-6-[1-(2-hydroxy-2-methylpropyl)-1H-pyrazol-4-yl]-2-methyl-1,2,3,4-tetrahydroquinoline-1-carboxylate;

methyl (2S)-5-[(dimethylcarbamoyl)methoxy]-2-methyl-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-(2-methylpropoxy)-1,2,3,4-tetrahydroquinoline-1-carboxylate;

methyl (2S)-6-[1-(2-hydroxy-2-methylpropyl)-1H-pyrazol-4-yl]-2-methyl-5-(2-methylpropoxy)-1,2,3,4-tetrahydroquinoline-1-carboxylate;

methyl (2S)-6-[1-(2-hydroxyethyl)-1H-pyrazol-4-yl]-2-methyl-5-(2-methylpropoxy)-1,2,3,4-tetrahydroquinoline-1-carboxylate;

methyl (2S)-2-methyl-5-(2-methylpropoxy)-6-[1-(piperidin-4-yl)-1H-pyrazol-4-yl]-1,2,3,4-tetrahydroquinoline-1-carboxylate;

methyl (2S)-5-(cyclopentylmethoxy)-6-[1-(2-methanesulfonylethyl)-1H-pyrazol-4-yl]-2-methyl-1,2,3,4-tetrahydroquinoline-1-carboxylate;

methyl (2S)-5-(cyclopentylmethoxy)-6-[1-(2-hydroxy-2-methylpropyl)-1H-pyrazol-4-yl]-2-methyl-1,2,3,4-tetrahydroquinoline-1-carboxylate;

methyl (2S)-5-(cyclopentylmethoxy)-6-[1-(2-hydroxyethyl)-1H-pyrazol-4-yl]-2-methyl-1,2,3,4-tetrahydroquinoline-1-carboxylate;

methyl (2S)-5-(cyclopentylmethoxy)-2-methyl-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-6-[1-(2-hydroxyethyl)-1H-pyrazol-4-yl]-2-methyl-5-[2-oxo-2-(pyrrolidin-1-yl)ethoxy]-1,2,3,4-tetrahydroquinoline-1-carboxylate;

methyl (2S)-2-methyl-5-[2-oxo-2-(pyrrolidin-1-yl)ethoxy]-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-6-[1-(2-hydroxy-2-methylpropyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-6-[1-(2-hydroxyethyl)-1H-pyrazol-4-yl]-2-methyl-5-{[(2R)-5-oxopyrrolidin-2-yl]methoxy}-1,2,3,4-tetrahydroquinoline-1-carboxylate;

methyl (2S)-2-methyl-5-{[(2R)-5-oxopyrrolidin-2-yl]methoxy}-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[2-(N-methylmethanesulfonamido)ethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[2-(N-methylmethanesulfonamido)ethoxy]-1,2,3,4-tetrahydroquinoline-1-carboxylate;

methyl (2S)-6-[1-(2-hydroxyethyl)-1H-pyrazol-4-yl]-2-methyl-5-[2-(N-methylmethanesulfonamido)ethoxy]-1,2,3,4-tetrahydroquinoline-1-carboxylate;

methyl (2S)-2-methyl-5-[2-(N-methylmethanesulfonamido)ethoxy]-6-[1-(piperidin-4-yl)-1H-pyrazol-4-yl]-1,2,3,4-tetrahydroquinoline-1-carboxylate;

methyl (2S)-6-[1-(2-methanesulfonylethyl)-1H-pyrazol-4-yl]-2-methyl-5-[(3S)-pyrrolidin-3-ylmethoxy]-1,2,3,4-tetrahydroquinoline-1-carboxylate;

methyl (2S)-6-[1-(2-hydroxy-2-methylpropyl)-1H-pyrazol-4-yl]-2-methyl-5-[(3S)-pyrrolidin-3-ylmethoxy]-1,2,3,4-tetrahydroquinoline-1-carboxylate;

methyl (2S)-6-[1-(2-hydroxyethyl)-1H-pyrazol-4-yl]-2-methyl-5-[(3S)-pyrrolidin-3-ylmethoxy]-1,2,3,4-tetrahydroquinoline-1-carboxylate;

methyl (2S)-2-methyl-6-[1-(piperidin-4-yl)-1H-pyrazol-4-yl]-5-[(3S)-pyrrolidin-3-ylmethoxy]-1,2,3,4-tetrahydroquinoline-1-carboxylate;

1-[(2S)-6-(1-cyclopropyl-1H-pyrazol-4-yl)-2-methyl-5-[(5-methyl-1,3-oxazol-2-yl)methoxy]-1,2,3,4-tetrahydroquinolin-1-yl]ethan-1-one;

1-[(2S)-6-(1-cyclopropyl-1H-pyrazol-4-yl)-2-methyl-5-(pyridin-4-ylmethoxy)-1,2,3,4-tetrahydroquinolin-1-yl]ethan-1-one;

1-[(2S)-5-(1,3-benzoxazol-2-ylmethoxy)-6-(1-cyclopropyl-1H-pyrazol-4-yl)-2-methyl-1,2,3,4-tetrahydroquinolin-1-yl]ethan-1-one;

1-[(2S)-6-(4-methanesulfonylphenyl)-2-methyl-5-propoxy-1,2,3,4-tetrahydroquinolin-1-yl]ethan-1-one;

2-{[(2S)-1-acetyl-6-(4-methanesulfonylphenyl)-2-methyl-1,2,3,4-tetrahydroquinolin-5-yl]oxy}-N,N-dimethylacetamide;

1-[(2S)-6-[4-(ethanesulfonyl)phenyl]-2-methyl-5-propoxy-1,2,3,4-tetrahydroquinolin-1-yl]ethan-1-one;

2-{[(2S)-1-acetyl-6-[4-(ethanesulfonyl)phenyl]-2-methyl-1,2,3,4-tetrahydroquinolin-5-yl]oxy}-N,N-dimethylacetamide;

1-[(2S)-6-{4-[2-(dimethylamino)ethoxy]phenyl}-2-methyl-5-propoxy-1,2,3,4-tetrahydroquinolin-1-yl]ethan-1-one;

2-{[(2S)-1-acetyl-6-{4-[2-(dimethylamino)ethoxy]phenyl}-2-methyl-1,2,3,4-tetrahydroquinolin-5-yl]oxy}-N,N-dimethylacetamide;

1-[(2S)-2-methyl-6-[3-(morpholine-4-carbonyl)phenyl]-5-propoxy-1,2,3,4-tetrahydroquinolin-1-yl]ethan-1-one;

2-{[(2S)-1-acetyl-2-methyl-6-[3-(morpholine-4-carbonyl)phenyl]-1,2,3,4-tetrahydroquinolin-5-yl]oxy}-N,N-dimethylacetamide;

N-{3-[(2S)-1-acetyl-2-methyl-5-propoxy-1,2,3,4-tetrahydroquinolin-6-yl]phenyl}methanesulfonamide;

2-{[(2S)-1-acetyl-6-(3-methanesulfonamidophenyl)-2-methyl-1,2,3,4-tetrahydroquinolin-5-yl]oxy}-N,N-dimethylacetamide;

1-[(2S)-6-(3-methanesulfonylphenyl)-2-methyl-5-propoxy-1,2,3,4-tetrahydroquinolin-1-yl]ethan-1-one;

2-{[(2S)-1-acetyl-6-(3-methanesulfonylphenyl)-2-methyl-1,2,3,4-tetrahydroquinolin-5-yl]oxy}-N,N-dimethylacetamide;

N-{4-[(2S)-1-acetyl-2-methyl-5-propoxy-1,2,3,4-tetrahydroquinolin-6-yl]phenyl}methanesulfonamide;

2-{[(2S)-1-acetyl-6-(4-methanesulfonamidophenyl)-2-methyl-1,2,3,4-tetrahydroquinolin-5-yl]oxy}-N,N-dimethylacetamide;
1-[(2S)-2-methyl-6-[4-(morpholine-4-carbonyl)phenyl]-5-propoxy-1,2,3,4-tetrahydroquinolin-1-yl]ethan-1-one;
2-{[(2S)-1-acetyl-2-methyl-6-[4-(morpholine-4-carbonyl)phenyl]-1,2,3,4-tetrahydroquinolin-5-yl]oxy}-N,N-dimethylacetamide;
2-{4-[(2S)-1-acetyl-2-methyl-5-propoxy-1,2,3,4-tetrahydroquinolin-6-yl]phenyl}-1$\lambda^6$,2-thiazolidine-1,1-dione;
2-{[(2S)-1-acetyl-6-[4-(1,1-dioxo-1$\lambda^6$,2-thiazolidin-2-yl)phenyl]-2-methyl-1,2,3,4-tetrahydroquinolin-5-yl]oxy}-N,N-dimethylacetamide;
1-[(2S)-6-(1-methanesulfonyl-2,3-dihydro-1H-indol-5-yl)-2-methyl-5-propoxy-1,2,3,4-tetrahydroquinolin-1-yl]ethan-1-one;
2-{[(2S)-1-acetyl-6-(1-methanesulfonyl-2,3-dihydro-1H-indol-5-yl)-2-methyl-1,2,3,4-tetrahydroquinolin-5-yl]oxy}-N,N-dimethylacetamide;
N-{4-[(2S)-1-acetyl-2-methyl-5-propoxy-1,2,3,4-tetrahydroquinolin-6-yl]phenyl}-N-methylmethanesulfonamide;
2-{[(2S)-1-acetyl-2-methyl-6-[4-(N-methylmethanesulfonamido)phenyl]-1,2,3,4-tetrahydroquinolin-5-yl]oxy}-N,N-dimethylacetamide;
1-[(2S)-6-(1-benzofuran-2-yl)-2-methyl-5-propoxy-1,2,3,4-tetrahydroquinolin-1-yl]ethan-1-one;
1-[(2S)-6-(1H-indol-2-yl)-2-methyl-5-propoxy-1,2,3,4-tetrahydroquinolin-1-yl]ethan-1-one;
methyl (2S)-6-[1-(azetidin-3-yl)-1H-pyrazol-4-yl]-5-cyclobutoxy-2-methyl-1,2,3,4-tetrahydroquinoline-1-carboxylate;
methyl (2S)-6-[1-(azetidin-3-yl)-1H-pyrazol-4-yl]-2-methyl-5-propoxy-1,2,3,4-tetrahydroquinoline-1-carboxylate;
(2S)-5-cyclobutoxy-1-cyclopropanecarbonyl-2-methyl-6-[1-(oxan-4-yl)-1H-pyrazol-4-yl]-1,2,3,4-tetrahydroquinoline;
3-{4-[(2S)-5-cyclobutoxy-1-cyclopropanecarbonyl-2-methyl-1,2,3,4-tetrahydroquinolin-6-yl]-1H-pyrazol-1-yl}-1$\lambda^6$-thiane-1,1-dione;
3-{4-[(2S)-5-cyclobutoxy-1-cyclopropanecarbonyl-2-methyl-1,2,3,4-tetrahydroquinolin-6-yl]-1H-pyrazol-1-yl}-1$\lambda^6$-thietane-1,1-dione;
1-[(2S)-5-[(5-fluoropyrimidin-2-yl)oxy]-2-methyl-6-[1-(piperidin-4-yl)-1H-pyrazol-4-yl]-1,2,3,4-tetrahydroquinolin-1-yl]ethan-1-one;
1-[(2S)-2-methyl-6-[1-(piperidin-4-yl)-1H-pyrazol-4-yl]-5-{[5-(trifluoromethyl)pyridin-2-yl]oxy}-1,2,3,4-tetrahydroquinolin-1-yl]ethan-1-one;
1-[(2S)-2-methyl-6-[1-(piperidin-4-yl)-1H-pyrazol-4-yl]-5-(pyrimidin-2-yloxy)-1,2,3,4-tetrahydroquinolin-1-yl]ethan-1-one;
1-[(2S)-2-methyl-6-[1-(piperidin-4-yl)-1H-pyrazol-4-yl]-5-{[4-(trifluoromethyl)pyrimidin-2-yl]oxy}-1,2,3,4-tetrahydroquinolin-1-yl]ethan-1-one;
1-[(2S)-2-methyl-6-[1-(piperidin-4-yl)-1H-pyrazol-4-yl]-5-{[2-(trifluoromethyl)pyrimidin-4-yl]oxy}-1,2,3,4-tetrahydroquinolin-1-yl]ethan-1-one;
1-[(2S)-2-methyl-5-{[6-(morpholin-4-yl)pyrimidin-4-yl]oxy}-6-[1-(piperidin-4-yl)-1H-pyrazol-4-yl]-1,2,3,4-tetrahydroquinolin-1-yl]ethan-1-one;
1-[(2S)-5-[(6-cyclopropylpyrimidin-4-yl)oxy]-2-methyl-6-[1-(piperidin-4-yl)-1H-pyrazol-4-yl]-1,2,3,4-tetrahydroquinolin-1-yl]ethan-1-one;
1-[(2S)-5-[(5-cyclopropylpyrimidin-2-yl)oxy]-2-methyl-6-[1-(piperidin-4-yl)-1H-pyrazol-4-yl]-1,2,3,4-tetrahydroquinolin-1-yl]ethan-1-one;
1-[(2S)-2-methyl-6-[1-(piperidin-4-yl)-1H-pyrazol-4-yl]-5-{[5-(trifluoromethyl)pyrimidin-2-yl]oxy}-1,2,3,4-tetrahydroquinolin-1-yl]ethan-1-one;
2-1{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxamide;
1-[(2S)-5-{[3-fluoro-5-(trifluoromethyl)pyridin-2-yl]oxy}-2-methyl-6-[1-(piperidin-4-yl)-1H-pyrazol-4-yl]-1,2,3,4-tetrahydroquinolin-1-yl]ethan-1-one;
methyl 6-{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxylate;
6-{[(2S)-1-acetyl-2-methyl-6-[1-(piperidin-4-yl)-1H-pyrazol-4-yl]-1,2,3,4-tetrahydroquinolin-5-yl]oxy}pyridine-3-carboxamide;
methyl (2S)-2-methyl-6-[1-(piperidin-4-yl)-1H-pyrazol-4-yl]-5-{[5-(trifluoromethyl)pyridin-2-yl]oxy}-1,2,3,4-tetrahydroquinoline-1-carboxylate;
methyl (2S)-2-methyl-6-[1-(piperidin-4-yl)-1H-pyrazol-4-yl]-5-(pyrimidin-2-yloxy)-1,2,3,4-tetrahydroquinoline-1-carboxylate;
methyl (2S)-2-methyl-6-[1-(piperidin-4-yl)-1H-pyrazol-4-yl]-5-(pyrazin-2-yloxy)-1,2,3,4-tetrahydroquinoline-1-carboxylate;
methyl (2S)-2-methyl-6-[1-(piperidin-4-yl)-1H-pyrazol-4-yl]-5-{[3-(trifluoromethyl)pyridin-2-yl]oxy}-1,2,3,4-tetrahydroquinoline-1-carboxylate;
methyl (2S)-2-methyl-6-[1-(piperidin-4-yl)-1H-pyrazol-4-yl]-5-{[4-(trifluoromethyl)pyrimidin-2-yl]oxy}-1,2,3,4-tetrahydroquinoline-1-carboxylate;
methyl (2S)-2-methyl-6-[1-(piperidin-4-yl)-1H-pyrazol-4-yl]-5-{[2-(trifluoromethyl)pyrimidin-4-yl]oxy}-1,2,3,4-tetrahydroquinoline-1-carboxylate;
methyl (2S)-2-methyl-5-{[6-(morpholin-4-yl)pyrimidin-4-yl]oxy}-6-[1-(piperidin-4-yl)-1H-pyrazol-4-yl]-1,2,3,4-tetrahydroquinoline-1-carboxylate;
methyl (2S)-5-[(6-cyclopropylpyrimidin-4-yl)oxy]-2-methyl-6-[1-(piperidin-4-yl)-1H-pyrazol-4-yl]-1,2,3,4-tetrahydroquinoline-1-carboxylate;
methyl (2S)-5-[(5-cyclopropylpyrimidin-2-yl)oxy]-2-methyl-6-[1-(piperidin-4-yl)-1H-pyrazol-4-yl]-1,2,3,4-tetrahydroquinoline-1-carboxylate;
methyl (2S)-5-[(5-fluoropyrimidin-2-yl)oxy]-2-methyl-6-[1-(piperidin-4-yl)-1H-pyrazol-4-yl]-1,2,3,4-tetrahydroquinoline-1-carboxylate;
methyl (2S)-2-methyl-6-[1-(piperidin-4-yl)-1H-pyrazol-4-yl]-5-{[5-(trifluoromethyl)pyrimidin-2-yl]oxy}-1,2,3,4-tetrahydroquinoline-1-carboxylate;
methyl (2S)-2-methyl-5-[(5-methylpyrimidin-2-yl)oxy]-6-[1-(piperidin-4-yl)-1H-pyrazol-4-yl]-1,2,3,4-tetrahydroquinoline-1-carboxylate;
methyl (2S)-5-{[3-fluoro-5-(trifluoromethyl)pyridin-2-yl]oxy}-2-methyl-6-[1-(piperidin-4-yl)-1H-pyrazol-4-yl]-1,2,3,4-tetrahydroquinoline-1-carboxylate;
methyl (2S)-5-{[5-(methoxycarbonyl)pyridin-2-yl]oxy}-2-methyl-6-[1-(piperidin-4-yl)-1H-pyrazol-4-yl]-1,2,3,4-tetrahydroquinoline-1-carboxylate;
methyl (2S)-5-[(5-carbamoylpyridin-2-yl)oxy]-2-methyl-6-[1-(piperidin-4-yl)-1H-pyrazol-4-yl]-1,2,3,4-tetrahydroquinoline-1-carboxylate;
(2S)-1-cyclopropanecarbonyl-2-methyl-6-[1-(piperidin-4-yl)-1H-pyrazol-4-yl]-5-{[3-(trifluoromethyl)pyridin-2-yl]oxy}-1,2,3,4-tetrahydroquinoline;

2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}pyridine-3-carbonitrile;
(2S)-1-cyclopropanecarbonyl-2-methyl-6-[1-(piperidin-4-yl)-1H-pyrazol-4-yl]-5-{[5-(trifluoromethyl)pyridin-2-yl]oxy}-1,2,3,4-tetrahydroquinoline;
1-[(2S)-6-[1-(2-hydroxyethyl)-1H-pyrazol-4-yl]-2-methyl-5-([5-(trifluoromethyl)pyrimidin-2-yl]oxy}-1,2,3,4-tetrahydroquinolin-1-yl]ethan-1-one;
1-[(2S)-5-[(5-fluoropyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-5-[(4,6-dimethylpyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-6-[1-(2-hydroxyethyl)-1H-pyrazol-4-yl]-2-methyl-5-{[5-(propan-2-yl)pyrimidin-2-yl]oxy}-1,2,3,4-tetrahydroquinolin-1-yl]ethan-1-one;
1-[(2S)-6-[1-(2-hydroxyethyl)-1H-pyrazol-4-yl]-5-[(5-methoxypyrimidin-2-yl)oxy]-2-methyl-1,2,3,4-tetrahydroquinolin-1-yl]ethan-1-one;
1-[(2S)-5-[(5-cyclopropylpyrimidin-2-yl)oxy]-6-[1-(2-hydroxyethyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-(1-methanesulfonyl-2,3-dihydro-1H-indol-5-yl)-2-methyl-1,2,3,4-tetrahydroquinolin-1-yl]ethan-1-one;
1-[(2S)-5-[(5-fluoropyrimidin-2-yl)oxy]-6-(4-methanesulfonylphenyl)-2-methyl-1,2,3,4-tetrahydroquinolin-1-yl]ethan-1-one;
1-[(2S)-5-[(5-fluoropyrimidin-2-yl)oxy]-6-[1-(2-methanesulfonylethyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-[1-(2-hydroxy-2-methylpropyl)-1H-pyrazol-4-yl]-2-methyl-1,2,3,4-tetrahydroquinolin-1-yl]ethan-1-one;
1-[(2S)-5-[(5-fluoropyrimidin-2-yl)oxy]-6-[1-(1-hydroxy-2-methylpropan-2-yl)-1H-pyrazol-4-yl]-2-methyl-1,2,3,4-tetrahydroquinolin-1-yl]ethan-1-one;
2-{4-[(2S)-1-acetyl-5-[(5-fluoropyrimidin-2-yl)oxy]-2-methyl-1,2,3,4-tetrahydroquinolin-6-yl]phenyl}-1λ⁶,2-thiazolidine-1,1-dione;
methyl (2S)-6-[1-(2-methanesulfonylethyl)-1H-pyrazol-4-yl]-2-methyl-5-([5-(trifluoromethyl)pyridin-2-yl]oxy)-1,2,3,4-tetrahydroquinoline-1-carboxylate;
methyl (2S)-6-[1-(2-hydroxy-2-methylpropyl)-1H-pyrazol-4-yl]-2-methyl-5-{[5-(trifluoromethyl)pyridin-2-yl]oxy}-1,2,3,4-tetrahydroquinoline-1-carboxylate;
methyl (2S)-6-[1-(2-hydroxyethyl)-1H-pyrazol-4-yl]-2-methyl-5-{[5-(trifluoromethyl)pyridin-2-yl]oxy}-1,2,3,4-tetrahydroquinoline-1-carboxylate;
methyl (2S)-6-(1-cyclopropyl-1H-pyrazol-4-yl)-2-methyl-5-{[5-(trifluoromethyl)pyridin-2-yl]oxy}-1,2,3,4-tetrahydroquinoline-1-carboxylate;
methyl (2S)-6-[1-(2-methanesulfonylethyl)-1H-pyrazol-4-yl]-2-methyl-5-(pyrazin-2-yloxy)-1,2,3,4-tetrahydroquinoline-1-carboxylate;
methyl (2S)-6-[1-(2-hydroxy-2-methylpropyl)-1H-pyrazol-4-yl]-2-methyl-5-(pyrazin-2-yloxy)-1,2,3,4-tetrahydroquinoline-1-carboxylate;
methyl (2S)-6-[1-(2-hydroxyethyl)-1H-pyrazol-4-yl]-2-methyl-5-(pyrazin-2-yloxy)-1,2,3,4-tetrahydroquinoline-1-carboxylate;
methyl (2S)-6-(1-cyclopropyl-1H-pyrazol-4-yl)-2-methyl-5-(pyrazin-2-yloxy)-1,2,3,4-tetrahydroquinoline-1-carboxylate;
methyl (2S)-6-[1-(2-methanesulfonylethyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-[1-(2-hydroxy-2-methylpropyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-[1-(2-hydroxyethyl)-1H-pyrazol-4-yl]-2-methyl-5-{[3-(trifluoromethyl)pyridin-2-yl]oxy}-1,2,3,4-tetrahydroquinoline-1-carboxylate;
methyl (2S)-6-(1-cyclopropyl-1H-pyrazol-4-yl)-2-methyl-5-{[3-(trifluoromethyl)pyridin-2-yl]oxy}-1,2,3,4-tetrahydroquinoline-1-carboxylate;
methyl (2S)-5-[(3-cyanopyridin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(3-cyanopyridin-2-yl)oxy]-6-[1-(2-hydroxy-2-methylpropyl)-1H-pyrazol-4-yl]-2-methyl-1,2,3,4-tetrahydroquinoline-1-carboxylate;
methyl (2S)-5-[(3-cyanopyridin-2-yl)oxy]-6-[1-(2-hydroxyethyl)-1H-pyrazol-4-yl]-2-methyl-1,2,3,4-tetrahydroquinoline-1-carboxylate;
methyl (2S)-5-[(3-cyanopyridin-2-yl)oxy]-6-(1-cyclopropyl-1H-pyrazol-4-yl)-2-methyl-1,2,3,4-tetrahydroquinoline-1-carboxylate;
methyl (2S)-5-[(5-cyclopropylpyrimidin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(5-cyclopropylpyrimidin-2-yl)oxy]-6-[1-(2-hydroxy-2-methylpropyl)-1H-pyrazol-4-yl]-2-methyl-1,2,3,4-tetrahydroquinoline-1-carboxylate;
methyl (2S)-5-[(5-cyclopropylpyrimidin-2-yl)oxy]-6-[1-(2-hydroxyethyl)-1H-pyrazol-4-yl]-2-methyl-1,2,3,4-tetrahydroquinoline-1-carboxylate;
methyl (2S)-6-(1-cyclopropyl-1H-pyrazol-4-yl)-5-[(5-cyclopropylpyrimidin-2-yl)oxy]-2-methyl-1,2,3,4-tetrahydroquinoline-1-carboxylate;
methyl (2S)-5-[(5-fluoropyrimidin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(5-fluoropyrimidin-2-yl)oxy]-6-[1-(2-hydroxy-2-methylpropyl)-1H-pyrazol-4-yl]-2-methyl-1,2,3,4-tetrahydroquinoline-1-carboxylate;
methyl (2S)-5-[(5-fluoropyrimidin-2-yl)oxy]-6-[1-(2-hydroxyethyl)-1H-pyrazol-4-yl]-2-methyl-1,2,3,4-tetrahydroquinoline-1-carboxylate;
methyl (2S)-6-(1-cyclopropyl-1H-pyrazol-4-yl)-5-[(5-fluoropyrimidin-2-yl)oxy]-2-methyl-1,2,3,4-tetrahydroquinoline-1-carboxylate;
methyl (2S)-6-[1-(2-methanesulfonylethyl)-1H-pyrazol-4-yl]-2-methyl-5-{[5-(trifluoromethyl)pyrimidin-2-yl]oxy}-1,2,3,4-tetrahydroquinoline-1-carboxylate;
methyl (2S)-6-[1-(2-hydroxy-2-methylpropyl)-1H-pyrazol-4-yl]-2-methyl-5-{[5-(trifluoromethyl)pyrimidin-2-yl]oxy}-1,2,3,4-tetrahydroquinoline-1-carboxylate;
methyl (2S)-6-[1-(2-hydroxyethyl)-1H-pyrazol-4-yl]-2-methyl-5-{[5-(trifluoromethyl)pyrimidin-2-yl]oxy}-1,2,3,4-tetrahydroquinoline-1-carboxylate;
methyl (2S)-6-(1-cyclopropyl-1H-pyrazol-4-yl)-2-methyl-5-{[5-(trifluoromethyl)pyrimidin-2-yl]oxy}-1,2,3,4-tetrahydroquinoline-1-carboxylate;
methyl (2S)-6-[1-(2-methanesulfonylethyl)-1H-pyrazol-4-yl]-2-methyl-5-[(5-methylpyrimidin-2-yl)oxy]-1,2,3,4-tetrahydroquinoline-1-carboxylate;
methyl (2S)-6-[1-(2-hydroxy-2-methylpropyl)-1H-pyrazol-4-yl]-2-methyl-5-[(5-methylpyrimidin-2-yl)oxy]-1,2,3,4-tetrahydroquinoline-1-carboxylate;

methyl (2S)-6-[1-(2-hydroxyethyl)-1H-pyrazol-4-yl]-2-methyl-5-[(5-methylpyrimidin-2-yl)oxy]-1,2,3,4-tetrahydroquinoline-1-carboxylate;
methyl (2S)-6-(1-cyclopropyl-1H-pyrazol-4-yl)-2-methyl-5-[(5-methylpyrimidin-2-yl)oxy]-1,2,3,4-tetrahydroquinoline-1-carboxylate;
methyl (2S)-5-[(3-carbamoylpyridin-2-yl)oxy]-6-[1-(2-methanesulfonylethyl)-1H-pyrazol-4-yl]-2-methyl-1,2,3,4-tetrahydroquinoline-1-carboxylate;
methyl (2S)-5-[(3-carbamoylpyridin-2-yl)oxy]-6-(1-cyclopropyl-1H-pyrazol-4-yl)-2-methyl-1,2,3,4-tetrahydroquinoline-1-carboxylate;
methyl (2S)-5-{[3-fluoro-5-(trifluoromethyl)pyridin-2-yl]oxy}-6-[1-(2-methanesulfonylethyl)-1H-pyrazol-4-yl]-2-methyl-1,2,3,4-tetrahydroquinoline-1-carboxylate;
methyl (2S)-5-{[3-fluoro-5-(trifluoromethyl)pyridin-2-yl]oxy}-6-[1-(2-hydroxy-2-methylpropyl)-1H-pyrazol-4-yl]-2-methyl-1,2,3,4-tetrahydroquinoline-1-carboxylate;
methyl (2S)-5-{[3-fluoro-5-(trifluoromethyl)pyridin-2-yl]oxy}-6-[1-(2-hydroxyethyl)-1H-pyrazol-4-yl]-2-methyl-1,2,3,4-tetrahydroquinoline-1-carboxylate;
methyl (2S)-6-(1-cyclopropyl-1H-pyrazol-4-yl)-5-{[3-fluoro-5-(trifluoromethyl)pyridin-2-yl]oxy}-2-methyl-1,2,3,4-tetrahydroquinoline-1-carboxylate;
methyl (2S)-5-(4-fluorophenoxy)-2-methyl-6-[1-(oxan-4-yl)-1H-pyrazol-4-yl]-1,2,3,4-tetrahydroquinoline-1-carboxylate;
methyl (2S)-6-[1-(azetidin-3-yl)-1H-pyrazol-4-yl]-5-(4-fluorophenoxy)-2-methyl-1,2,3,4-tetrahydroquinoline-1-carboxylate;
1-[(2S)-6-(1-cyclopropyl-1H-pyrazol-4-yl)-2-methyl-5-phenoxy-1,2,3,4-tetrahydroquinolin-1-yl]ethan-1-one;
4-{[(2S)-1-acetyl-6-(1-cyclopropyl-1H-pyrazol-4-yl)-2-methyl-1,2,3,4-tetrahydroquinolin-5-yl]oxy}-N,N-dimethylbenzamide;
methyl (2S)-5-(3-cyanophenoxy)-2-methyl-6-[1-(piperidin-4-yl)-1H-pyrazol-4-yl]-1,2,3,4-tetrahydroquinoline-1-carboxylate;
1-[6-(1-cyclopropyl-1H-pyrazol-4-yl)-2-methyl-5-phenoxy-1,2,3,4-tetrahydroquinolin-1-yl]ethan-1-one;
1-cyclopropanecarbonyl-6-(1-cyclopropyl-1H-pyrazol-4-yl)-2-methyl-5-phenoxy-1,2,3,4-tetrahydroquinoline;
methyl 6-(1-cyclopropyl-1H-pyrazol-4-yl)-2-methyl-5-phenoxy-1,2,3,4-tetrahydroquinoline-1-carboxylate;
1-[(2S)-2-methyl-6-[1-(oxetan-3-yl)-1H-pyrazol-4-yl]-5-[(3R)-pyrrolidin-3-ylmethoxy]-1,2,3,4-tetrahydroquinolin-1-yl]ethan-1-one;
1-[(2S)-2-methyl-6-[1-(oxetan-3-yl)-1H-pyrazol-4-yl]-5-[(3S)-pyrrolidin-3-ylmethoxy]-1,2,3,4-tetrahydroquinolin-1-yl]ethan-1-one;
1-[(2S)-6-(1-cyclopropyl-1H-pyrazol-4-yl)-2-methyl-5-[(3R)-pyrrolidin-3-ylmethoxy]-1,2,3,4-tetrahydroquinolin-1-yl]ethan-1-one;
1-[(2S)-6-(1-cyclopropyl-1H-pyrazol-4-yl)-2-methyl-5-[(3S)-pyrrolidin-3-ylmethoxy]-1,2,3,4-tetrahydroquinolin-1-yl]ethan-1-one;
1-[(2S)-6-[1-(2-hydroxy-2-methylpropyl)-1H-pyrazol-4-yl]-2-methyl-5-[(3S)-pyrrolidin-3-ylmethoxy]-1,2,3,4-tetrahydroquinolin-1-yl]ethan-1-one;
1-[(2S)-2-methyl-5-propoxy-1,2,3,4-tetrahydroquinolin-1-yl]ethan-1-one;
2-{[(2S)-1-acetyl-2-methyl-1,2,3,4-tetrahydroquinolin-5-yl]oxy}-N,N-dimethylacetamide;
1-[(2S)-5-(cyclopentylmethoxy)-2-methyl-1,2,3,4-tetrahydroquinolin-1-yl]ethan-1-one;
1-[(2S)-6-(1-cyclopropyl-1H-pyrazol-4-yl)-2-methyl-5-({1-[(1E)-prop-1-en-1-yl]-1H-1,3-benzodiazol-2-yl}oxy)-1,2,3,4-tetrahydroquinolin-1-yl]ethan-1-one;
1-[(2S)-6-(1-cyclopropyl-1H-pyrazol-4-yl)-2-methyl-5-({1-[(1Z)-prop-1-en-1-yl]-1H-1,3-benzodiazol-2-yl}oxy)-1,2,3,4-tetrahydroquinolin-1-yl]ethan-1-one;
methyl (2S)-5-cyclobutoxy-2-methyl-6-[1-methyl-2-(piperazin-1-yl)-1H-imidazol-4-yl]-1,2,3,4-tetrahydroquinoline-1-carboxylate;
methyl (2S)-5-cyclobutoxy-2-methyl-6-[2-(piperazin-1-yl)-1,3-thiazol-4-yl]-1,2,3,4-tetrahydroquinoline-1-carboxylate;
methyl (2S)-5-cyclobutoxy-6-[2-(3-hydroxyazetidin-1-yl)-1,3-thiazol-4-yl]-2-methyl-1,2,3,4-tetrahydroquinoline-1-carboxylate;
(2S)-5-cyclobutoxy-1-cyclopropanecarbonyl-2-methyl-6-(1,2-oxazol-4-yl)-1,2,3,4-tetrahydroquinoline;
(2S)-1-cyclopropanecarbonyl-2-methyl-6-(1,2-oxazol-4-yl)-5-phenoxy-1,2,3,4-tetrahydroquinoline;
(2S)-5-cyclobutoxy-1-cyclopropanecarbonyl-8-fluoro-2-methyl-6-[1-(piperidin-4-yl)-1H-pyrazol-4-yl]-1,2,3,4-tetrahydroquinoline;
(2S)-5-cyclobutoxy-1-cyclopropanecarbonyl-6-(1-cyclopropyl-1H-pyrazol-4-yl)-8-fluoro-2-methyl-1,2,3,4-tetrahydroquinoline;
(2S)-5-cyclobutoxy-1-cyclopropanecarbonyl-8-fluoro-2-methyl-6-(1H-pyrazol-4-yl)-1,2,3,4-tetrahydroquinoline;
methyl (2S)-5-cyclobutoxy-8-fluoro-2-methyl-6-[1-(piperidin-4-yl)-1H-pyrazol-4-yl]-1,2,3,4-tetrahydroquinoline-1-carboxylate;
methyl (2S)-5-cyclobutoxy-6-(1-cyclopropyl-1H-pyrazol-4-yl)-8-fluoro-2-methyl-1,2,3,4-tetrahydroquinoline-1-carboxylate;
methyl (2S)-5-cyclobutoxy-8-fluoro-2-methyl-6-(1H-pyrazol-4-yl)-1,2,3,4-tetrahydroquinoline-1-carboxylate;
1-[(2S)-5-cyclobutoxy-8-fluoro-2-methyl-6-[1-(piperidin-4-yl)-1H-pyrazol-4-yl]-1,2,3,4-tetrahydroquinolin-1-yl]ethan-1-one;
1-[(2S)-5-cyclobutoxy-6-(1-cyclopropyl-1H-pyrazol-4-yl)-8-fluoro-2-methyl-1,2,3,4-tetrahydroquinolin-1-yl]ethan-1-one;
1-[(2S)-5-cyclobutoxy-8-fluoro-2-methyl-6-(1H-pyrazol-4-yl)-1,2,3,4-tetrahydroquinolin-1-yl]ethan-1-one;
(2S)-1-cyclopropanecarbonyl-8-fluoro-2-methyl-5-phenoxy-6-[1-(piperidin-4-yl)-1H-pyrazol-4-yl]-1,2,3,4-tetrahydroquinoline;
(2S)-1-cyclopropanecarbonyl-6-(1-cyclopropyl-1H-pyrazol-4-yl)-8-fluoro-2-methyl-5-phenoxy-1,2,3,4-tetrahydroquinoline;
(2S)-1-cyclopropanecarbonyl-8-fluoro-2-methyl-5-phenoxy-6-(1H-pyrazol-4-yl)-1,2,3,4-tetrahydroquinoline;
methyl (2S)-8-fluoro-2-methyl-5-phenoxy-6-[1-(piperidin-4-yl)-1H-pyrazol-4-yl]-1,2,3,4-tetrahydroquinoline-1-carboxylate;
methyl (2S)-6-(1-cyclopropyl-1H-pyrazol-4-yl)-8-fluoro-2-methyl-5-phenoxy-1,2,3,4-tetrahydroquinoline-1-carboxylate;
methyl (2S)-8-fluoro-2-methyl-5-phenoxy-6-(1H-pyrazol-4-yl)-1,2,3,4-tetrahydroquinoline-1-carboxylate;
1-[(2S)-8-fluoro-2-methyl-5-phenoxy-6-[1-(piperidin-4-yl)-1H-pyrazol-4-yl]-1,2,3,4-tetrahydroquinolin-1-yl]ethan-1-one;
1-[(2S)-6-(1-cyclopropyl-1H-pyrazol-4-yl)-8-fluoro-2-methyl-5-phenoxy-1,2,3,4-tetrahydroquinolin-1-yl]ethan-1-one;

1-[(2S)-8-fluoro-2-methyl-5-phenoxy-6-(1H-pyrazol-4-yl)-1,2,3,4-tetrahydroquinolin-1-yl]ethan-1-one;
1-[(2S)-5-cyclobutoxy-7,8-difluoro-2-methyl-6-[1-(piperidin-4-yl)-1H-pyrazol-4-yl]-1,2,3,4-tetrahydroquinolin-1-yl]ethan-1-one;
1-[(2S)-5-cyclobutoxy-6-(1-cyclopropyl-1H-pyrazol-4-yl)-7,8-difluoro-2-methyl-1,2,3,4-tetrahydroquinolin-1-yl]ethan-1-one;
(2S)-5-cyclobutoxy-1-cyclopropanecarbonyl-2-methyl-6-(1H-pyrazol-1-yl)-1,2,3,4-tetrahydroquinoline;
(2S)-5-cyclobutoxy-1-cyclopropanecarbonyl-2-methyl-6-(2H-1,2,3-triazol-2-yl)-1,2,3,4-tetrahydroquinoline;
(2S)-1-cyclopropanecarbonyl-2-methyl-5-phenoxy-6-(1H-pyrazol-1-yl)-1,2,3,4-tetrahydroquinoline;
(2S)-1-cyclopropanecarbonyl-2-methyl-5-phenoxy-6-(2H-1,2,3-triazol-2-yl)-1,2,3,4-tetrahydroquinoline;
(2S)-5-cyclobutoxy-1-cyclopropanecarbonyl-2-methyl-6-[1-(piperidin-4-yl)-1H-pyrazol-3-yl]-1,2,3,4-tetrahydroquinoline;
(2S)-5-cyclobutoxy-1-cyclopropanecarbonyl-2-methyl-6-[1-(piperidin-4-yl)-1H-pyrazol-5-yl]-1,2,3,4-tetrahydroquinoline;
(2S)-5-cyclobutoxy-1-cyclopropanecarbonyl-2-methyl-6-[2-(piperidin-4-yl)-2H-1,2,3-triazol-4-yl]-1,2,3,4-tetrahydroquinoline;
(2S)-5-cyclobutoxy-1-cyclopropanecarbonyl-2-methyl-6-[1-(piperidin-4-yl)-1H-1,2,3-triazol-4-yl]-1,2,3,4-tetrahydroquinoline;
(2S)-5-cyclobutoxy-1-cyclopropanecarbonyl-2-methyl-6-[5-(piperidin-4-yl)-1H-imidazol-2-yl]-1,2,3,4-tetrahydroquinoline;
(2S)-1-cyclopropanecarbonyl-2-methyl-5-phenoxy-6-[1-(piperidin-4-yl)-1H-pyrazol-3-yl]-1,2,3,4-tetrahydroquinoline;
(2S)-1-cyclopropanecarbonyl-2-methyl-5-phenoxy-6-[1-(piperidin-4-yl)-1H-pyrazol-5-yl]-1,2,3,4-tetrahydroquinoline;
(2S)-1-cyclopropanecarbonyl-2-methyl-5-phenoxy-6-[2-(piperidin-4-yl)-2H-1,2,3-triazol-4-yl]-1,2,3,4-tetrahydroquinoline;
(2S)-1-cyclopropanecarbonyl-2-methyl-5-phenoxy-6-[1-(piperidin-4-yl)-1H-1,2,3-triazol-4-yl]-1,2,3,4-tetrahydroquinoline;
(2S)-1-cyclopropanecarbonyl-2-methyl-5-phenoxy-6-[5-(piperidin-4-yl)-1H-imidazol-2-yl]-1,2,3,4-tetrahydroquinoline;
(2S)-5-cyclobutoxy-1-cyclopropanecarbonyl-8-fluoro-2-methyl-6-(1-methyl-1H-1,2,3-triazol-4-yl)-1,2,3,4-tetrahydroquinoline;
(2S)-1-cyclopropanecarbonyl-8-fluoro-2-methyl-6-(1-methyl-1H-1,2,3-triazol-4-yl)-5-phenoxy-1,2,3,4-tetrahydroquinoline;
methyl (2S)-5-cyclobutoxy-8-fluoro-2-methyl-6-(1-methyl-1H-1,2,3-triazol-4-yl)-1,2,3,4-tetrahydroquinoline-1-carboxylate;
methyl (2S)-8-fluoro-2-methyl-6-(1-methyl-1H-1,2,3-triazol-4-yl)-5-phenoxy-1,2,3,4-tetrahydroquinoline-1-carboxylate;
1-[(2S)-5-cyclobutoxy-8-fluoro-2-methyl-6-(1-methyl-1H-1,2,3-triazol-4-yl)-1,2,3,4-tetrahydroquinolin-1-yl]ethan-1-one;
1-[(2S)-8-fluoro-2-methyl-6-(1-methyl-1H-1,2,3-triazol-4-yl)-5-phenoxy-1,2,3,4-tetrahydroquinolin-1-yl]ethan-1-one;
(2S)-1-cyclopropanecarbonyl-2-methyl-5-[(6-methylpyridin-2-yl)oxy]-6-[1-(piperidin-4-yl)-1H-pyrazol-4-yl]-1,2,3,4-tetrahydroquinoline;
(2S)-1-cyclopropanecarbonyl-5-[(2,6-dimethylpyridin-3-yl)oxy]-2-methyl-6-[1-(piperidin-4-yl)-1H-pyrazol-4-yl]-1,2,3,4-tetrahydroquinoline;
(2S)-1-cyclopropanecarbonyl-5-[(2,6-dimethylpyridin-4-yl)oxy]-2-methyl-6-[1-(piperidin-4-yl)-1H-pyrazol-4-yl]-1,2,3,4-tetrahydroquinoline;
(2S)-5-[(6-chloropyridin-2-yl)oxy]-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-2-methyl-6-[1-(piperidin-4-yl)-1H-pyrazol-4-yl]-5-(pyridin-2-yloxy)-1,2,3,4-tetrahydroquinoline;
(2S)-1-cyclopropanecarbonyl-5-[(6-fluoropyridin-2-yl)oxy]-2-methyl-6-[1-(piperidin-4-yl)-1H-pyrazol-4-yl]-1,2,3,4-tetrahydroquinoline;
methyl (2S)-2-methyl-5-[(6-methylpyridin-2-yl)oxy]-6-[1-(piperidin-4-yl)-1H-pyrazol-4-yl]-1,2,3,4-tetrahydroquinoline-1-carboxylate;
methyl (2 S)-2-methyl-6-[1-(piperidin-4-yl)-1H-pyrazol-4-yl]-5-(pyridin-2-yloxy)-1,2,3,4-tetrahydroquinoline-1-carboxylate;
1-[(2S)-2-methyl-5-[(6-methylpyridin-2-yl)oxy]-6-[1-(piperidin-4-yl)-1H-pyrazol-4-yl]-1,2,3,4-tetrahydroquinolin-1-yl]ethan-1-one;
(2S)-1-cyclopropanecarbonyl-2-methyl-6-[4-(morpholin-4-yl)-1H-pyrazol-1-yl]-5-phenoxy-1,2,3,4-tetrahydroquinoline;
(2S)-1-cyclopropanecarbonyl-2-methyl-5-phenoxy-6-[4-(piperazin-1-yl)-1H-pyrazol-1-yl]-1,2,3,4-tetrahydroquinoline;
(2S)-1-cyclopropanecarbonyl-2-methyl-5-phenoxy-6-[4-(piperidin-4-yl)-1H-pyrazol-1-yl]-1,2,3,4-tetrahydroquinoline;
methyl (2S)-2-methyl-6-[4-(morpholin-4-yl)-1H-pyrazol-1-yl]-5-phenoxy-1,2,3,4-tetrahydroquinoline-1-carboxylate;
methyl (2S)-2-methyl-5-phenoxy-6-[4-(piperazin-1-yl)-1H-pyrazol-1-yl]-1,2,3,4-tetrahydroquinoline-1-carboxylate;
(2S)-1-cyclopropanecarbonyl-2-methyl-5-phenoxy-1,2,3,4-tetrahydroquinoline-6-carbonitrile;
(2S)-1-cyclopropanecarbonyl-6-ethynyl-2-methyl-5-phenoxy-1,2,3,4-tetrahydroquinoline;
(2S)-1-cyclopropanecarbonyl-2-methyl-5-phenoxy-6-(prop-1-yn-1-yl)-1,2,3,4-tetrahydroquinoline;
methyl (2S)-6-cyano-2-methyl-5-phenoxy-1,2,3,4-tetrahydroquinoline-1-carboxylate;
methyl (2S)-6-ethynyl-2-methyl-5-phenoxy-1,2,3,4-tetrahydroquinoline-1-carboxylate;
methyl (2S)-6-[2-(azetidin-3-yl)-1,3-thiazol-4-yl]-5-cyclobutoxy-2-methyl-1,2,3,4-tetrahydroquinoline-1-carboxylate;
methyl (2S)-5-cyclobutoxy-6-[2-(3-fluoroazetidin-3-yl)-1 3-thiazol-4-yl]-2-methyl-1,2,3,4-tetrahydroquinoline-1-carboxylate;
methyl (2S)-5-cyclobutoxy-6-[2-(3-hydroxyazetidin-3-yl)-1,3-thiazol-4-yl]-2-methyl-1,2,3,4-tetrahydroquinoline-1-carboxylate;
methyl (2S)-5-cyclobutoxy-6-[2-(3-methoxyazetidin-3-yl)-1,3-thiazol-4-yl]-2-methyl-1,2,3,4-tetrahydroquinoline-1-carboxylate;
methyl (2S)-6-(2-carbamoyl-1,3-thiazol-4-yl)-5-cyclobutoxy-2-methyl-1,2,3,4-tetrahydroquinoline-1-carboxylate;
methyl (2S)-5-cyclobutoxy-2-methyl-6-[2-(methylcarbamoyl)-1,3-thiazol-4-yl]-1,2,3,4-tetrahydroquinoline-1-carboxylate;

methyl (2S)-5-cyclobutoxy-6-(2-acetamido-1,3-thiazol-4-yl)-2-methyl-1,2,3,4-tetrahydroquinoline-1-carboxylate;

(2S)-1-cyclopropanecarbonyl-6-cyclopropyl-2-methyl-5-phenoxy-1,2,3,4-tetrahydroquinoline;

methyl (2S)-6-cyclopropyl-2-methyl-5-phenoxy-1,2,3,4-tetrahydroquinoline-1-carboxylate;

(2S)-1-cyclopropanecarbonyl-8-fluoro-5-(3-methoxyphenoxy)-2-methyl-6-[1-(piperidin-4-yl)-1H-pyrazol-4-yl]-1,2,3,4-tetrahydroquinoline;

methyl (2S)-2-methyl-6-(1-methyl-1H-1,2,3-triazol-4-yl)-5-phenoxy-1,2,3,4-tetrahydroquinoline-1-carboxylate;

1-[(2S)-2-methyl-6-(1-methyl-1H-1,2,3-triazol-4-yl)-5-phenoxy-1,2,3,4-tetrahydroquinolin-1-yl]ethan-1-one;

(2S)-1-cyclopropanecarbonyl-5-(3-methoxyphenoxy)-2-methyl-6-(1-methyl-1H-1,2,3-triazol-4-yl)-1,2,3,4-tetrahydroquinoline;

(2S)-1-cyclopropanecarbonyl-5-(2,5-difluorophenoxy)-2-methyl-6-(1-methyl-1H-1,2,3-triazol-4-yl)-1,2,3,4-tetrahydroquinoline;

(2S)-1-cyclopropanecarbonyl-5-(3,4-difluorophenoxy)-2-methyl-6-(1-methyl-1H-1,2,3-triazol-4-yl)-1,2,3,4-tetrahydroquinoline;

2-{[(2S)-1-cyclopropanecarbonyl-2-methyl-6-(1-methyl-1H-1,2,3-triazol-4-yl)-1,2,3,4-tetrahydroquinolin-5-yl]oxy}benzonitrile;

(2S)-1-cyclopropanecarbonyl-5-(3-fluorophenoxy)-2-methyl-6-(1-methyl-1H-1,2,3-triazol-4-yl)-1,2,3,4-tetrahydroquinoline;

(2S)-1-cyclopropanecarbonyl-5-(2-fluorophenoxy)-2-methyl-6-(1-methyl-1H-1,2,3-triazol-4-yl)-1,2,3,4-tetrahydroquinoline;

(2S)-1-cyclopropanecarbonyl-5-(4-fluorophenoxy)-2-methyl-6-(1-methyl-1H-1,2,3-triazol-4-yl)-1,2,3,4-tetrahydroquinoline;

(2S)-1-cyclopropanecarbonyl-5-[(6-methoxypyridin-2-yl)oxy]-2-methyl-6-[1-(piperidin-4-yl)-1H-pyrazol-4-yl]-1,2,3,4-tetrahydroquinoline;

methyl (2S)-5-[(6-methoxypyridin-2-yl)oxy]-2-methyl-6-[1-(piperidin-4-yl)-1H-pyrazol-4-yl]-1,2,3,4-tetrahydroquinoline-1-carboxylate;

1-[(2S)-5-[(6-methoxypyridin-2-yl)oxy]-2-methyl-6-[1-(piperidin-4-yl)-1H-pyrazol-4-yl]-1,2,3,4-tetrahydroquinolin-1-yl]ethan-1-one;

methyl (2S)-5-cyclobutoxy-6-[1-(1,1-dioxo-1λ⁶-thian-4-yl)-1H-pyrazol-4-yl]-2-methyl-1,2,3,4-tetrahydroquinoline-1-carboxylate;

4-{4-[(2S)-5-cyclobutoxy-1-cyclopropanecarbonyl-2-methyl-1,2,3,4-tetrahydroquinolin-6-yl]-1H-pyrazol-1-yl}-1λ⁶-thiane-1,1-dione;

1-[(2S)-6-(1-acetylpiperidin-4-yl)-2-methyl-5-propoxy-1)-2-methyl-5-propoxy-1,2,3,4-tetrahydroquinolin-1-yl]ethan-1-one;

1-[(2S)-6-(1-methanesulfonylpiperidin-4-yl)-2-methyl-5-propoxy-1,2,3,4-tetrahydroquinolin-1-yl]ethan-1-one;

tert-butyl 4-[(2S)-1-acetyl-2-methyl-5-propoxy-1,2,3,4-tetrahydroquinolin-6-yl]-1,2,3,6-tetrahydropyridine-1-carboxylate;

1-[(2S)-2-methyl-6-(piperidin-4-yl)-5-propoxy-1,2,3,4-tetrahydroquinolin-1-yl]ethan-1-one;

4-[(2S)-1-acetyl-2-methyl-5-propoxy-1,2,3,4-tetrahydroquinolin-6-yl]-N-ethylpiperidine-1-carboxamide;

methyl 4-[(2S)-1-acetyl-2-methyl-5-propoxy-1,2,3,4-tetrahydroquinolin-6-yl]piperidine-1-carboxylate;

1-[(2S)-6-(1-ethylpiperidin-4-yl)-2-methyl-5-propoxy-1,2,3,4-tetrahydroquinolin-1-yl]ethan-1-one;

1-[(2S)-2-methyl-5-(phenylamino)-6-[1-(piperidin-4-yl)-1H-pyrazol-4-yl]-1,2,3,4-tetrahydroquinolin-1-yl]ethan-1-one;

methyl (2S)-5-cyclobutoxy-6-{-[(3S,4R)-3-fluoropiperidin-4-yl]-1H-pyrazol-4-yl}-2-methyl-1,2,3,4-tetrahydroquinoline-1-carboxylate;

methyl (2S)-5-cyclobutoxy-6-{1-[(3R,4S)-3-fluoropiperidin-4-yl]-1H-pyrazol-4-yl}-2-methyl-1,2,3,4-tetrahydroquinoline-1-carboxylate;

methyl (2S)-5-cyclobutoxy-6-{1-[(3S,4S)-3-fluoropiperidin-4-yl]-1H-pyrazol-4-yl}-2-methyl-1,2,3,4-tetrahydroquinoline-1-carboxylate;

methyl (2S)-5-(4-fluorophenoxy)-6-{1-[(3S,4S)-3-fluoropiperidin-4-yl]-1H-pyrazol-4-yl}-2-methyl-1,2,3,4-tetrahydroquinoline-1-carboxylate;

methyl (2S)-5-(4-fluorophenoxy)-6-{1-[(3S,4R)-3-fluoropiperidin-4-yl]-1H-pyrazol-4-yl)-2-methyl-1,2,3,4-tetrahydroquinoline-1-carboxylate;

methyl (2S)-5-(4-fluorophenoxy)-6-{1-[(3R,4S)-3-fluoropiperidin-4-yl]-1H-pyrazol-4-yl}-2-methyl-1,2,3,4-tetrahydroquinoline-1-carboxylate;

methyl (2S)-5-cyclobutoxy-6-{1-[(3R,4R)-3-fluoropiperidin-4-yl]-1H-pyrazol-4-yl}-2-methyl-1,2,3,4-tetrahydroquinoline-1-carboxylate;

methyl (2S)-5-(4-fluorophenoxy)-6-{1-[(3R,4R)-3-fluoropiperidin-4-yl]-1H-pyrazol-4-yl)}-2-methyl-1,2,3,4-tetrahydroquinoline-1-carboxylate;

methyl (2S)-5-cyclobutoxy-2-methyl-6-[1-(2-methylpiperidin-4-yl)-1H-pyrazol-4-yl]-1,2,3,4-tetrahydroquinoline-1-carboxylate;

methyl (2S)-5-cyclobutoxy-2-methyl-6-[1-(2-methylpiperidin-4-yl)-1H-pyrazol-4-yl]-1,2,3,4-tetrahydroquinoline-1-carboxylate;

(2S)-5-cyclobutoxy-1-cyclopropanecarbonyl-6-{1-[(3S,4R)-3-fluoropiperidin-4-yl]-1H-pyrazol-4-yl}-2-methyl-1,2,3,4-tetrahydroquinoline;

methyl (2S)-5-cyclobutoxy-6-[5-fluoro-1-(piperidin-4-yl)-1H-pyrazol-4-yl]-2-methyl-1,2,3,4-tetrahydroquinoline-1-carboxylate;

methyl (2S)-5-cyclobutoxy-6-{1-[(3R*,4S*)-4-fluoropyrrolidin-3-yl]-1H-pyrazol-4-yl}-2-methyl-1,2,3,4-tetrahydroquinoline-1-carboxylate; and (2S)-5-cyclobutoxy-1-cyclopropanecarbonyl-6-{1-[(3R*,4S*)-4-fluoropiperidin-3-yl]-1H-pyrazol-4-yl}-2-methyl-1,2,3,4-tetrahydroquinoline.

16. The compound of claim 15 selected from the group consisting:

methyl (2S)-2-methyl-6-[1-(piperidin-4-yl)-1H-pyrazol-4-yl]-5-propoxy-1,2,3,4-tetrahydroquinoline-1-carboxylate;

methyl (2S)-5-cyclobutoxy-2-methyl-6-[1-(piperidin-4-yl)-1H-pyrazol-4-yl]-1,2,3,4-tetrahydroquinoline-1-carboxylate;

1-[(2S)-6-(1-cyclopropyl-1H-pyrazol-4-yl)-5-(2-fluoro-2-methylpropoxy)-2-methyl-1,2,3,4-tetrahydroquinolin-1-yl]ethan-1-one;

2-{[(2S)-1-acetyl-6-(1-cyclopropyl-1H-pyrazol-4-yl)-2-methyl-1,2,3,4-tetrahydroquinolin-5-yl]oxy}benzonitrile;

2-{[(2S)-1-acetyl-2-methyl-6-[1-(piperidin-4-yl)-1H-pyrazol-4-yl]-1,2,3,4-tetrahydroquinolin-5-yl]oxy}benzonitrile;

1-[(2S)-5-(4-fluorophenoxy)-2-methyl-6-[1-(piperidin-4-yl)-1H-pyrazol-4-yl]-1,2,3,4-tetrahydroquinolin-1-yl]ethan-1-one;

1-[(2S)-5-(4-chlorophenoxy)-2-methyl-6-[1-(piperidin-4-yl)-1H-pyrazol-4-yl]-1,2,3,4-tetrahydroquinolin-1-yl]ethan-1-one;
1-[(2S)-5-(2-chlorophenoxy)-2-methyl-6-[1-(piperidin-4-yl)-1H-pyrazol-4-yl]-1,2,3,4-tetrahydroquinolin-1-yl]ethan-1-one;
1-[(2S)-2-methyl-5-phenoxy-6-[1-(piperidin-4-yl)-1H-pyrazol-4-yl]-1,2,3,4-tetrahydroquinolin-1-yl]ethan-1-one;
methyl (2S)-5-(4-methoxyphenoxy)-2-methyl-6-[1-(piperidin-4-yl)-1H-pyrazol-4-yl]-1,2,3,4-tetrahydroquinoline-1-carboxylate;
methyl (2S)-2-methyl-5-phenoxy-6-[1-(piperidin-4-yl)-1H-pyrazol-4-yl]-1,2,3,4-tetrahydroquinoline-1-carboxylate;
methyl (2S)-5-(2-methoxyphenoxy)-2-methyl-6-[1-(piperidin-4-yl)-1H-pyrazol-4-yl]-1,2,3,4-tetrahydroquinoline-1-carboxylate;
methyl (2S)-5-(3-fluorophenoxy)-2-methyl-6-[1-(piperidin-4-yl)-1H-pyrazol-4-yl]-1,2,3,4-tetrahydroquinoline-1-carboxylate;
methyl (2S)-5-(3-chlorophenoxy)-2-methyl-6-[1-(piperidin-4-yl)-1H-pyrazol-4-yl]-1,2,3,4-tetrahydroquinoline-1-carboxylate;
methyl (2S)-5-(3-cyanophenoxy)-2-methyl-6-[1-(piperidin-4-yl)-1H-pyrazol-4-yl]-1,2,3,4-tetrahydroquinoline-1-carboxylate;
1-[(2S)-6-(1-cyclopropyl-1H-pyrazol-4-yl)-5-(2-fluorophenoxy)-2-methyl-1,2,3,4-tetrahydroquinolin-1-yl]ethan-1-one;
methyl (2S)-5-(4-fluorophenoxy)-2-methyl-6-[1-(piperidin-4-yl)-1H-pyrazol-4-yl]-1,2,3,4-tetrahydroquinoline-1-carboxylate;
(2S)-5-cyclobutoxy-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(4-fluorophenoxy)-2-methyl-6-[1-(piperidin-4-yl)-1H-pyrazol-4-yl]-1,2,3,4-tetrahydroquinoline;
1-[(2S)-5-(2-fluorophenoxy)-2-methyl-6-[1-(piperidin-4-yl)-1H-pyrazol-4-yl]-1,2,3,4-tetrahydroquinolin-1-yl]ethan-1-one;
1-[(2S)-5-[(5-chloropyridin-2-yl)oxy]-6-(1-cyclopropyl-1H-pyrazol-4-yl)-2-methyl-1,2,3,4-tetrahydroquinolin-1-yl]ethan-1-one;
methyl (2S)-5-(2-cyano-3-fluorophenoxy)-2-methyl-6-[1-(piperidin-4-yl)-1H-pyrazol-4-yl]-1,2,3,4-tetrahydroquinoline-1-carboxylate;
methyl (2S)-5-(3-chloro-4-fluorophenoxy)-2-methyl-6-[1-(piperidin-4-yl)-1H-pyrazol-4-yl]-1,2,3,4-tetrahydroquinoline-1-carboxylate;
methyl (2S)-5-cyclobutoxy-2-methyl-6-[1-(oxan-4-yl)-1H-pyrazol-4-yl]-1,2,3,4-tetrahydroquinoline-1-carboxylate;
methyl (2S)-5-cyclobutoxy-6-{1-[(3S,4R)-3-fluoropiperidin-4-yl]-1H-pyrazol-4-yl}-2-methyl-1,2,3,4-tetrahydroquinoline-1-carboxylate;
1-[(2S)-6-(1-cyclopropyl-1H-pyrazol-4-yl)-2-methyl-5-[(6-methylpyridin-2-yl)oxy]-1,2,3,4-tetrahydroquinolin-1-yl]ethan-1-one;
(2S)-5-(4-chlorophenoxy)-1-cyclopropanecarbonyl-2-methyl-6-[1-(piperidin-4-yl)-1H-pyrazol-4-yl]-1,2,3,4-tetrahydroquinoline;
4-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;
(2S)-1-cyclopropanecarbonyl-2-methyl-5-phenoxy-6-[1-(piperidin-4-yl)-1H-pyrazol-4-yl]-1,2,3,4-tetrahydroquinoline;
2-{[(2S)-1-cyclopropanecarbonyl-2-methyl-6-[1-(piperidin-4-yl)-1H-pyrazol-4-yl]-1,2,3,4-tetrahydroquinolin-5-yl]oxy}benzonitrile;
methyl (2S)-6-[1-(1,1-dioxo-1$\lambda^6$-thietan-3-yl)-1H-pyrazol-4-yl]-5-(4-fluorophenoxy)-2-methyl-1,2,3,4-tetrahydroquinoline-1-carboxylate;
(2S)-5-(3-chloro-4-fluorophenoxy)-1-cyclopropanecarbonyl-2-methyl-6-[1-(piperidin-4-yl)-1H-pyrazol-4-yl]-1,2,3,4-tetrahydroquinoline;
(2S)-6-[1-(azetidin-3-yl)-1H-pyrazol-4-yl]-1-cyclopropanecarbonyl-5-(4-fluorophenoxy)-2-methyl-1,2,3,4-tetrahydroquinoline;
(2S)-1-cyclopropanecarbonyl-5-(2-fluorophenoxy)-2-methyl-6-[1-(piperidin-4-yl)-1H-pyrazol-4-yl]-1,2,3,4-tetrahydroquinoline;
(2S)-5-(2-chlorophenoxy)-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(3-fluorophenoxy)-2-methyl-6-[1-(piperidin-4-yl)-1H-pyrazol-4-yl]-1,2,3,4-tetrahydroquinoline;
(2S)-1-cyclopropanecarbonyl-5-(3,4-difluorophenoxy)-2-methyl-6-[1-(piperidin-4-yl)-1H-pyrazol-4-yl]-1,2,3,4-tetrahydroquinoline;
methyl (2S)-5-(3,4-difluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(2,4-difluorophenoxy)-2-methyl-6-[1-(piperidin-4-yl)-1H-pyrazol-4-yl]-1,2,3,4-tetrahydroquinoline;
(2S)-1-cyclopropanecarbonyl-2-methyl-6-(1-methyl-1H-1,2,3-triazol-4-yl)-5-phenoxy-1,2,3,4-tetrahydroquinoline;
(2S)-1-cyclopropanecarbonyl-2-methyl-5-phenoxy-6-(1H-pyrazol-4-yl)-1,2,3,4-tetrahydroquinoline;
(2S)-1-cyclopropanecarbonyl-2-methyl-6-(1-methyl-1H-imidazol-4-yl)-5-phenoxy-1,2,3,4-tetrahydroquinoline;
(2S)-5-(3-chlorophenoxy)-1-cyclopropanecarbonyl-2-methyl-6-[1-(piperidin-4-yl)-1H-pyrazol-4-yl]-1,2,3,4-tetrahydroquinoline;
(2S)-1-cyclopropanecarbonyl-5-(2,5-difluorophenoxy)-2-methyl-6-[1-(piperidin-4-yl)-1H-pyrazol-4-yl]-1,2,3,4-tetrahydroquinoline;
methyl (2S)-5-(3,5-difluorophenoxy)-2-methyl-6-[1-(piperidin-4-yl)-1H-pyrazol-4-yl]-1,2,3,4-tetrahydroquinoline-1-carboxylate;
(2S)-1-cyclopropanecarbonyl-5-(3,5-di fluorophenoxy)-2-methyl-6-[1-(piperidin-4-yl)-1H-pyrazol-4-yl]-1,2,3,4-tetrahydroquinoline;
(2S)-1-cyclopropanecarbonyl-5-(3-methoxyphenoxy)-2-methyl-6-[1-(piperidin-4-yl)-1H-pyrazol-4-yl]-1,2,3,4-tetrahydroquinoline;
(2S)-5-cyclobutoxy-1-cyclopropanecarbonyl-6-{1-[(3S,4R)-3-fluoropiperidin-4-yl]-1H-pyrazol-4-yl}-2-methyl-1,2,3,4-tetrahydroquinoline;
(2S)-1-cyclopropanecarbonyl-5-(2-methoxyphenoxy)-2-methyl-6-[1-(piperidin-4-yl)-1H-pyrazol-4-yl]-1,2,3,4-tetrahydroquinoline;
methyl (2S)-5-(3-methoxyphenoxy)-2-methyl-6-[1-(piperidin-4-yl)-1H-pyrazol-4-yl]-1,2,3,4-tetrahydroquinoline-1-carboxylate;
3-{4-[(2S)-1-cyclopropanecarbonyl-5-(4-fluorophenoxy)-2-methyl-1,2,3,4-tetrahydroquinolin-6-yl]-1H-pyrazol-1-yl}-1$\lambda^6$-thietane-1,1-dione;

3-{4-[(2S)-1-cyclopropanecarbonyl-5-(4-fluorophenoxy)-2-methyl-1,2,3,4-tetrahydroquinolin-6-yl]-1H-pyrazol-1-yl}-11$^6$-thiane-1,1-dione;

(2S)-1-cyclopropanecarbonyl-5-(4-methoxyphenoxy)-2-methyl-6-[1-(piperidin-4-yl)-1H-pyrazol-4-yl]-1,2,3,4-tetrahydroquinoline;

(2S)-1-cyclopropanecarbonyl-8-fluoro-2-methyl-5-phenoxy-6-[1-(piperidin-4-yl)-1H-pyrazol-4-yl]-1,2,3,4-tetrahydroquinoline;

methyl (2S)-5-cyclobutoxy-8-fluoro-2-methyl-6-[1-(piperidin-4-yl)-1H-pyrazol-4-yl]-1,2,3,4-tetrahydroquinoline-1-carboxylate;

methyl (2S)-8-fluoro-2-methyl-5-phenoxy-6-[1-(piperidin-4-yl)-1H-pyrazol-4-yl]-1,2,3,4-tetrahydroquinoline-1-carboxylate; and 1-[(2S)-8-fluoro-2-methyl-5-phenoxy-6-[1-(piperidin-4-yl)-1H-pyrazol-4-yl]-1,2,3,4-tetrahydroquinolin-1-yl]ethan-1-one.

17. A pharmaceutical composition comprising the compound of claim 1 and a pharmaceutically acceptable carrier.

18. The pharmaceutical composition of claim 17, further comprising therapeutically effective amounts of one or more additional therapeutic agents.

19. The pharmaceutical composition of claim 18, wherein said additional therapeutic agents are selected from the group consisting of cytotoxic agent, cisplatin, doxorubicin, etoposide, irinotecan, topotecan, paclitaxel, docetaxel, the epothilones, tamoxifen, 5-fluorouracil, methotrexate, temozolomide, cyclophosphamide, Lonafarib, tipifarnib, 4-((5-((4-(3-chlorophenyl)-3-oxopiperazin-1-yl)methyl)-1H-imidazol-1-yl)methyl)benzonitrile hydrochloride, (R)-1-((1H-imidazol-5-yl)methyl)-3-benzyl-4-(thiophen-2-ylsulfonyl)-2,3,4,5-tetrahydro-1H-benzo[e][1,4]diazepine-7-carbonitrile, cetuximab, imatinib , interferon alfa-2b, Peg-Intron®, Pegylated interferon alfa-2b, aromatase combinations, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, leucovorin, oxaliplatin, pentostatine, vinblastine, vincristine, vindesine, bleomycin, dactinomycin, daunorubicin, epirubicin, idarubicin, mithramycin, deoxycoformycin, mitomycin-C, L-asparaginase, teniposide 17a-ethinyl estradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, 17αhydroxyprogesterone, aminoglutethimide, estramustine, medroxyprogesteroneacetate, leuprolide, flutamide, toremifene citrate, goserelin acetate, carboplatin, hydroxyurea, amsacrine, procarbazine, mitotane, mitoxantrone, levamisole, vinorelbine, anastrazole, letrazole, capecitabine, raloxafene, droloxafine, hexamethylmelamine, bevacizumab, trastuzumab, tositumomab, bortezomib, britumomab tiuxetan, arsenic trioxide, porfimer sodium, cetuximab, thioTEPA, altretamine, melphalan, fulvestrant, exemestane, rituximab, alemtuzumab, dexamethasone, bicalutamide, chlorambucil, and valrubicin.

20. A method of inhibiting one or more of BET-family bromodomains in a patient comprising administering to the patient in need thereof an effective amount of the compound of claim 1.

21. A method of inhibiting one or more of BET-family bromodomains in a patient comprising administering to the patient in need thereof an effective amount of the pharmaceutical composition of claim 17.

22. A method of treating or inhibiting a cancer associated with the activity of one or more BET-family bromodomains in a patient comprising administering to said patient in need thereof a therapeutically effective amount of the compound of claim 1, wherein the cancer is selected from the group consisting of lung cancer, cervix cancer, colon cancer, breast cancer, stomach cancers, hematologic cancers, leukemia, lymphoma, multiple myeloma, midline carcinomas, mesenchymal tumors, hepatic tumors, renal tumors, and neurological tumors, melanomas, actinic keratosis, squamous cell carcinoma, and cutaneous T-cell lymphoma.

23. A method of treating, inhibiting, or eliminating an inflammatory disorder associated with the activity of one or more BET-family bromodomains in a patient comprising administering to said patient in need thereof a therapeutically effective amount of the compound of claim 1, wherein the inflammatory disorder is a chronic autoimmune inflammatory condition or an acute inflammatory condition selected from the group consisting of systemic lupus erythematosus, rheumatoid arthritis, atherosclerosis, psoriasis and alopecia.

24. The compound of claim 1, wherein the compound is (S)-1-(6-(1-cyclopropyl-1H-pyrazol-4-yl)-2-methyl-5-(quinazolin-2-yloxy)-3,4-dihydroquinolin-1(2H)-yl)ethanone.

25. The compound of claim 1, wherein the compound is (2S)-5-cyclobutoxy-1-cyclopropanecarbonyl-2-methyl-6-[1-(piperidin-4-yl)-1Hpyrazol-4-yl]-1,2,3,4-tetrahydroquinoline.

26. The compound of claim 1, wherein the compound is (S)-methyl 5-(4-chloro-2-cyanophenoxy)-2-methyl-6-(1-(piperidin-4-yl)-1 Hpyrazol-4-yl)-3,4-dihydroquinoline-1(2H)-carboxylate.

27. The compound of claim 1, wherein the compound is (S)-1-(5-(2-fluorophenoxy)-2-methyl-6-(1-(piperidin-4-yl)-1H-pyrazol-4-yl)-3,4-dihydroquinolin-1(2H)-yl)ethanone.

28. The compound of claim 1, wherein the compound is 1-[(2S)-6-(1-cyclopropyl-1H-pyrazol-4-yl)-2-methyl-5-[(4-methylpyridin-2-yl)oxy]-1,2,3,4-tetrahydroquinolin-1-yl]ethan-1-one.

29. A pharmaceutical composition comprising the compound of claim 24 and a pharmaceutically acceptable carrier.

30. A pharmaceutical composition comprising the compound of claim 25 and a pharmaceutically acceptable carrier.

31. A pharmaceutical composition comprising the compound of claim 26 and a pharmaceutically acceptable carrier.

32. A pharmaceutical composition comprising the compound of claim 27 and a pharmaceutically acceptable carrier.

33. A pharmaceutical composition comprising the compound of claim 28 and a pharmaceutically acceptable carrier.

34. A method of treating leukemia comprising administering to a patient in need thereof a therapeutically effective amount of the compound of claim 24.

35. A method of treating leukemia comprising administering to a patient in need thereof a therapeutically effective amount of the compound of claim 25.

36. A method of treating leukemia comprising administering to a patient in need thereof a therapeutically effective amount of the compound of claim 26.

37. A method of treating leukemia comprising administering to a patient in need thereof a therapeutically effective amount of the compound of claim 27.

38. A method of treating leukemia comprising administering to a patient in need thereof a therapeutically effective amount of the compound of claim 28.

39. A method of treating lymphoma comprising administering to a patient in need thereof a therapeutically effective amount of the compound of claim 24.

40. A method of treating lymphoma comprising administering to a patient in need thereof a therapeutically effective amount of the compound of claim 25.

41. A method of treating lymphoma comprising administering to a patient in need thereof a therapeutically effective amount of the compound of claim 26.

42. A method of treating lymphoma comprising administering to a patient in need thereof a therapeutically effective amount of the compound of claim 27.

43. A method of treating lymphoma comprising administering to a patient in need thereof a therapeutically effective amount of the compound of claim 28.

44. The method of claim 23, wherein the inflammatory disorder is rheumatoid arthritis.

* * * * *